US012303525B2

(12) United States Patent
Kammler et al.

(10) Patent No.: US 12,303,525 B2
(45) Date of Patent: May 20, 2025

(54) NUCLEIC ACID MOLECULE FOR REDUCTION OF PAPD5 AND PAPD7 MRNA FOR TREATING HEPATITIS B INFECTION

(71) Applicant: HOFFMAN-LA ROCHE INC., Little Falls, NJ (US)

(72) Inventors: Susanne Kammler, Horsholm (DK); Anais Lopez, Basel (CH); Henrik Mueller, Basel (CH); Soren Ottosen, Horsholm (DK); Lykke Pedersen, Horsholm (DK)

(73) Assignee: HOFFMAN-LA ROCHE INC., Little Falls, NJ (US)

( * ) Notice: Subject to any disclaimer, the term of this patent is extended or adjusted under 35 U.S.C. 154(b) by 183 days.

(21) Appl. No.: 17/813,576

(22) Filed: Jul. 19, 2022

(65) Prior Publication Data

US 2023/0113497 A1 Apr. 13, 2023

Related U.S. Application Data

(63) Continuation of application No. 16/661,959, filed on Oct. 23, 2019, now Pat. No. 11,484,546, which is a continuation of application No. 16/162,279, filed on Oct. 16, 2018, now Pat. No. 10,953,034.

(30) Foreign Application Priority Data

Oct. 16, 2017 (EP) .................................... 17196554
Dec. 18, 2017 (EP) .................................... 17208056

(51) Int. Cl.

| | |
|---|---|
| ***A61K 31/7105*** | (2006.01) |
| ***A61K 31/712*** | (2006.01) |
| ***A61P 31/20*** | (2006.01) |
| ***C07H 21/02*** | (2006.01) |
| ***C12N 15/113*** | (2010.01) |

(52) U.S. Cl.

CPC ........ *A61K 31/7105* (2013.01); *A61K 31/712* (2013.01); *A61P 31/20* (2018.01); *C07H 21/02* (2013.01); *C12N 15/113* (2013.01); *C12N 15/1137* (2013.01); *C12N 2310/11* (2013.01); *C12N 2310/315* (2013.01); *C12N 2310/3231* (2013.01); *C12N 2310/341* (2013.01); *C12N 2310/343* (2013.01); *C12N 2310/346* (2013.01); *C12N 2310/351* (2013.01); *C12Y 207/07* (2013.01); *C12Y 207/07007* (2013.01)

(58) Field of Classification Search

None

See application file for complete search history.

(56) References Cited

U.S. PATENT DOCUMENTS

| | | | |
|---|---|---|---|
| 4,711,955 | A | 12/1987 | Ward et al. |
| 5,525,711 | A | 6/1996 | Hawkins et al. |
| 5,792,608 | A | 8/1998 | Swaminathan et al. |
| 5,885,968 | A | 3/1999 | Biessen et al. |
| 8,090,542 | B2 | 1/2012 | Khvorova et al. |
| 8,349,809 | B2 | 1/2013 | Brown |
| 8,513,207 | B2 | 8/2013 | Brown |
| 9,458,153 | B2 | 10/2016 | Han et al. |
| 9,637,485 | B2 | 5/2017 | Han |
| 9,920,049 | B2 | 3/2018 | Yang |
| 9,949,966 | B2 | 4/2018 | Han |
| 10,093,671 | B2 | 10/2018 | Han et al. |
| 10,953,034 | B2 | 3/2021 | Kammler et al. |
| 11,104,674 | B2 | 8/2021 | Cheng |
| 11,484,546 | B2 | 11/2022 | Kammler et al. |
| 2004/0157780 | A1 | 8/2004 | Grey et al. |
| 2005/0246794 | A1 | 11/2005 | Khvorova |
| 2005/0272080 | A1 | 12/2005 | Palma et al. |
| 2006/0257851 | A1 | 11/2006 | Bentwich |
| 2010/0173974 | A1 | 7/2010 | Brown |
| 2010/0249219 | A1 | 9/2010 | Hedtjarn et al. |
| 2011/0118337 | A1 | 5/2011 | Chau et al. |
| 2012/0040460 | A1 | 2/2012 | Rigoutsos et al. |
| 2012/0207709 | A1 | 8/2012 | Hamatake |
| 2015/0210682 | A1 | 7/2015 | Han |
| 2015/0232837 | A1 | 8/2015 | Thibonnier et al. |
| 2016/0010093 | A1 | 1/2016 | Javanbakh et al. |
| 2016/0168594 | A1 | 6/2016 | Zhang et al. |
| 2016/0193354 | A1 | 7/2016 | Noe et al. |

(Continued)

FOREIGN PATENT DOCUMENTS

| | | |
|---|---|---|
| CL | 201803561 | 12/2018 |
| CL | 201900945 | 4/2020 |

(Continued)

OTHER PUBLICATIONS

A-fang Ji et al., "Status and research progress in clinical medication of hepatitis B drugs", Anti infect. Pharm., 2019, vol. 16, Issue 12, pp. 2034-2039.

(Continued)

*Primary Examiner* — Brian Whiteman

(74) *Attorney, Agent, or Firm* — McDonnell Boehnen Hulbert & Berghoff LLP

(57) ABSTRACT

The present invention relates to nucleic acid molecules that are complementary to both PAP associated domain containing 5 (PAPD5) and PAP associated domain containing 7 (PAPD7), leading to inhibition of the expression of both PAPD5 and PAPD7 when using a single nucleic acid molecule. The invention also provides for PAPD5 and PAPD7 specific nucleic acid molecules for use in treating and/or preventing a HBV infection, in particular a chronic HBV infection. Also comprised in the present invention is a pharmaceutical composition for use in the treatment and/or prevention of a HBV infection.

41 Claims, 21 Drawing Sheets

Specification includes a Sequence Listing.

(56) References Cited

U.S. PATENT DOCUMENTS

| | | | |
|---|---|---|---|
| 2016/0326167 | A1 | 11/2016 | Cheng et al. |
| 2017/0023568 | A1 | 1/2017 | Brophy et al. |
| 2017/0235368 | A1 | 8/2017 | El-Ouardi et al. |
| 2017/0283496 | A1 | 10/2017 | Pedersen et al. |
| 2019/0111073 | A1 | 4/2019 | Kammler et al. |
| 2019/0194768 | A1 | 6/2019 | Han et al. |
| 2019/0211339 | A1 | 7/2019 | Agarwal et al. |
| 2019/0216846 | A1 | 7/2019 | Javanbakht et al. |
| 2020/0147123 | A1 | 5/2020 | Kammler et al. |

FOREIGN PATENT DOCUMENTS

| | | | |
|---|---|---|---|
| CL | 202001638 | | 6/2020 |
| CL | 202003330 | | 12/2020 |
| CL | 202003329 | | 6/2021 |
| CL | 2020003329 | A1 | 6/2021 |
| CL | 2020003330 | | 6/2021 |
| CN | 101541977 | A | 9/2009 |
| CN | 104080481 | A | 10/2014 |
| CN | 104379765 | | 2/2015 |
| CN | 104955952 | | 9/2015 |
| CN | 107108610 | A | 8/2017 |
| CN | 107624113 | A | 1/2018 |
| CN | 109328237 | A | 2/2019 |
| EP | 0302175 | A2 | 2/1989 |
| EP | 1013661 | A1 | 6/2000 |
| EP | 1152009 | A1 | 11/2001 |
| EP | 1752536 | A1 | 2/2007 |
| EP | 2213738 | B1 | 10/2012 |
| EP | 2890789 | A1 | 7/2015 |
| EP | 3472362 | A1 | 4/2019 |
| JP | 2017-515862 | A | 6/2017 |
| JP | 2018-514575 | A | 6/2018 |
| JP | 2019-523649 | A | 8/2019 |
| RU | 2146706 | C1 | 3/2000 |
| WO | 93/07883 | A1 | 4/1993 |
| WO | 95/27072 | A1 | 10/1995 |
| WO | 98/39352 | A1 | 9/1998 |
| WO | 99/14226 | A2 | 3/1999 |
| WO | 00/47599 | A1 | 8/2000 |
| WO | 00/66604 | A2 | 11/2000 |
| WO | 01/23613 | A1 | 4/2001 |
| WO | 03/22987 | A2 | 3/2003 |
| WO | 2004/046160 | A2 | 6/2004 |
| WO | 2005/014806 | A2 | 2/2005 |
| WO | 2007/031091 | A2 | 3/2007 |
| WO | 2007/090071 | A2 | 8/2007 |
| WO | 2007/106407 | A2 | 9/2007 |
| WO | 2007/134181 | A2 | 11/2007 |
| WO | 2007/146511 | A2 | 12/2007 |
| WO | 2008/049085 | A1 | 4/2008 |
| WO | 2008/082730 | A2 | 7/2008 |
| WO | 2008/113832 | A2 | 9/2008 |
| WO | 2008/150729 | A2 | 12/2008 |
| WO | 2008/154401 | A2 | 12/2008 |
| WO | 2009/006478 | A2 | 1/2009 |
| WO | 2009/067647 | A1 | 5/2009 |
| WO | 2009/090182 | A1 | 7/2009 |
| WO | 2009/124238 | A1 | 10/2009 |
| WO | 2010/036698 | A1 | 4/2010 |
| WO | 2010/040571 | A2 | 4/2010 |
| WO | 2010/077578 | A1 | 7/2010 |
| WO | 2010/093788 | A2 | 8/2010 |
| WO | 2011/017521 | A2 | 2/2011 |
| WO | 2011/108699 | A1 | 9/2011 |
| WO | 2011/156202 | A1 | 12/2011 |
| WO | 2012/024170 | A2 | 2/2012 |
| WO | 2012/055362 | A1 | 5/2012 |
| WO | 2012/109395 | A1 | 8/2012 |
| WO | 2012/145697 | A1 | 10/2012 |
| WO | 2013/003520 | A1 | 1/2013 |
| WO | 2013/022984 | A1 | 2/2013 |
| WO | 2013/033230 | A1 | 3/2013 |
| WO | 2013/036868 | A1 | 3/2013 |
| WO | 2013/113501 | A1 | 8/2013 |
| WO | 2013/154798 | A1 | 10/2013 |
| WO | 2013/159109 | A1 | 10/2013 |
| WO | WO2013/153130 | | 10/2013 |
| WO | 2013/166264 | A2 | 11/2013 |
| WO | 2014/012081 | A2 | 1/2014 |
| WO | 2014/036429 | A1 | 3/2014 |
| WO | 2014/076195 | A1 | 5/2014 |
| WO | 2014/076196 | A1 | 5/2014 |
| WO | WO2014118267 | | 8/2014 |
| WO | 2014/179620 | A1 | 11/2014 |
| WO | 2014/179629 | A2 | 11/2014 |
| WO | 2014/207232 | A1 | 12/2014 |
| WO | 2015/031694 | A2 | 3/2015 |
| WO | 2015/113922 | A1 | 8/2015 |
| WO | 2015/113990 | A1 | 8/2015 |
| WO | 2015/173164 | A1 | 11/2015 |
| WO | 2015/173208 | A2 | 11/2015 |
| WO | 2016004250 | | 1/2016 |
| WO | 2016/051116 | A1 | 4/2016 |
| WO | 2016/055601 | A1 | 4/2016 |
| WO | WO2016/054421 | | 4/2016 |
| WO | 2016/071215 | A1 | 5/2016 |
| WO | 2016/079181 | A1 | 5/2016 |
| WO | WO2016/081941 | | 5/2016 |
| WO | 2016/096938 | A1 | 6/2016 |
| WO | 2016/107832 | A1 | 7/2016 |
| WO | 2016/127002 | A1 | 8/2016 |
| WO | 2016/177655 | A1 | 11/2016 |
| WO | 2017/015175 | A1 | 1/2017 |
| WO | 2017/027350 | A2 | 2/2017 |
| WO | 2017/066712 | A2 | 4/2017 |
| WO | WO2017066796 | | 4/2017 |
| WO | 2017/178656 | A1 | 10/2017 |
| WO | 2017/216390 | A1 | 12/2017 |
| WO | 2017/216391 | A1 | 12/2017 |
| WO | 2018/059718 | A1 | 4/2018 |
| WO | 2019/076842 | A1 | 4/2019 |
| WO | 2019/145543 | A1 | 8/2019 |

OTHER PUBLICATIONS

Altschul, SF et al., "Basic Local Alignment Search Tool," J Mol Biol, 1990, vol. 215, pp. 403-410, 8 pages.
Altschul, SF et al., "Gapped BLAST and PSI-BLAST: a new generation of protein database search programs," Nucleic Acids Research, 1997, vol. 25:17, pp. 3389-3402, 14 pages.
Altschul, SF, "A Protein Alignment Scoring System Sensitive at All Evolutionary Distances," Journal Molecular Evolution, 1993, vol. 36, pp. 290-300; 11 pages.
Ansel's Pharmaceutical Dosage Forms and Drug Delivery Systems, Lippicott Williams & Wilkins, 2004, 4 pgs.
Ansel's Pharmaceutical Dosage Forms and Drug Delivery Systems, Sixth Edition, Williams & Wilkins, 1995, 41 pgs.
Ansel, H.C., Pharmaceutical Dosage Forms and Drug Delivery Systems, 1995, Williams & Wilkins, pp. xi-xii, 105-116, 194-200, 497-514, coverpages.
Atschul: Gapped BLAST and PSI-BLAST—a new generation go protein database search programs, Nucliec Acids Research, 1997, 14 pgs.
Bartel et al., "Cellular interactions in Development: A practical approach." Oxford University Press, pp. 153-179, 28 pages.
Bastin, R.J. et al., Salt Selection and Optimisation Procedures for Pharmaceutical New Chemical Entities, Organic Process Research & Development, (2000), vol. 4, pp. 427-435.
Bergstrom DE, "Unnatural nucleosides with unusual base pairing properties", Current Protocols in Nucleic Acid Chemistry, 2009, Suppl. 37 1.4.1, 32 pgs.
Berry M N and Friend D S, High-yield Preparation of Isolated Rat Liver Parenchymal Cells: A Biochemical and Fine Structural Study , J. Cell Biol., Dec. 1969;43(3):506-20. doi: 10.1083/jcb.43.3.506.
Biessen, E.A.L. et al., "Receptor-Dependent Cell Specific Delivery of Antisense Oligonucleotides," Developments in Cardiovascular Medicine, 1999, 24, pp. 285-299, 15 pages.
Biessen, E.A.L. et al., Synthesis of Cluster Galactosides with High Affinity for the Hepatic Asialoglycoprotein Receptor, J. Med. Chem., 1995, vol. 38(9), pp. 1538-1546.

(56) References Cited

OTHER PUBLICATIONS

Block, Timothy M. et al., "Chronic hepatitis B: A wave of new therapies on the horizon", Antiviral Research, Elsevier BV, NL, vol. 121, Jun. 22, 2015 (Jun. 22, 2015), pp. 69-81.
Boele: PAPD5-mediated 3'adenylation and subsequent degradation of miR-21 is disrupted in proliferative disease, Proc National Academy of Science USA, Aug. 5, 2014, vol. 111, Issue 31, pp. 11467-11472, 6 pgs.
Brutlag et al., "Improved sensitivity of biological sequence database searches," 1990, vol. 6:3, pp. 237-245, 9 pages.
Burroughs: A comprehensive survey of 3' animal miRNA modification events and a possible role fr 3' adenylation in modulating miRNA targeting effectiveness, Genome Research, vol. 20, pp. 1398-1419, 14 pgs.
Buster et al., "Withdrawal Flares After Treatment with Peginterferon Alpha-2b alone or in Combination with Lamivudine in HBeAg-Positive Chronic Hepatitis B," Hepatology, 2007, 46, 1 page.
Buster, E.H. et al., Peginterferon alpha-2b is safe and effective in HBeAg-positive chronic hepatitis B patients with advanced fibrosis, Hepatology, 2007, vol. 46, No. 2, pp. 388-394.
Cahn, R.S., et al., Specification of Molecular Chiralily, Angewandte Chemie International Edition, 1966, vol. 5, No. 4, pp. 385-415.
Caruthers, M.H. et al., Chemical Synthesis of Deoxyoligonucleotides by the Phosphoramidite Method, Methods in Enzymology, 1987, vol. 154, pp. 287-313.
Centers for Disease Control and Prevention, Hepatitis B FAQs for the Public, http://www.cdc.gov/hepatitis/b/bfaq.htm, 7 pgs.
Chan, J. et al., Antisense Oligonucleotides: From Design to Therapeutic Application; Clinical and Experimental Pharmacology and Physiology (2006) 33, pp. 533-540.
Chang, Mei-Hwei, "Hepatitis B virus infection," Elsevier, Seminars in Fetal Neonatal Medicine, 2007, vol. 12, pp. 160-167, 8 pages.
Chen et al., "Immune Tolerance Split between Hepatitis B Virus Precore and Core Proteins", 2005, Journal of Virology, 79: 3016-3027.
Chidley, C. et al., "A yeast-based screen reveals that sulfasalazine inhibits tetrahydrobiopterin biosynthesis", Nature Chemical Biology, 2011, vol. 7, pp. 375-383, 9 pages.
Database EMBL, Aug. 18, 2010, (Aug. 18, 2010) "Sequence 593709 from Patent EP2213738.", XP002787331, retrieved from EBI accession No. EM PAT:HD716993 Database accession No. HD716993 sequence.
Database EMBL, Aug. 18, 2011, (Aug. 18, 2011) 11 Sequence 447635 from Patent EP2213738. 11 XP002787330, retrieved from EBI accession No. EM PAT:HD570919 Database accession No. HD570919 sequence, 1 pg.
Database EMBL, Apr. 19, 2011, (Apr. 19, 2011) WO 2005116204-A/507823: Double strand polynucleotides generating RNA interference., XP002787332, retrieved from EBI accession No. EM PAT:FZ101298 Database ccession No. FZ101298 sequence.
Deleavey, G.F. et al., Designing Chemically Modified Oligonucleotides for Targeted Gene Silencing, Chemistry and Biology, 2012, vol. 19(8), pp. 937-954.
Doudna: CRISPR-Cas: A Laboratory Manual, 2016, ISBN 978-1-621821-31-1, 1 pg.
Duff, R.J. et al., Intrabody Tissue-Specific Delivery of Antisense Conjugates in Animals: Ligand-Linker-Antisense Oligomer Conjugates, Methods in Enzymolology, 2000, vol. 313(17), pp. 297-321.
Examination Report issued in EP Application No. 17732082.7 on Aug. 5, 2020, 6 pages.
Examination Report issued in EP Application No. 17732082.7 on Jan. 22, 2020, 6 pages.
Examination Report issued in EP Application No. 17732082.7 on Mar. 31, 2021, 6 pages.
Examination Report issued in EP Application No. 17732083.5 on Sep. 2, 2020, 5 pages.
Examination Report issued in EP Application No. 17721082.7 on Aug. 5, 2020, 5 pages.
Examination Report issued in EP Application No. 17732083.5 on Jan. 22, 2020, 6 pages.
Fakhr: Precise and efficient siRNA design: a key point in competent gene silencing, Cancer Gene Therapy 2016, 10 pgs.
Fisicaro et al., "Antiviral Intrahepatic T-Cell Responses Can Be Restored by Blocking Programmed Death-1 Pathway in Chronic Hepatitis B," Gastroenterology, 2010, 138, pp. 682-693, 16 pages.
Fluiter, K et al., "Filling the gap in LNA antisense oligo gapmers: the effects of unlocked nucleic acid (UNA) and 4'C-hydroxymethyl-DNA modifications on RNase H recruitment and efficacy of an LNA gapmer," Molecular Biosystems, 2009, vol. 5, pp. 838-843, 6 pages.
Freier, S.M. et al., The ups and downs of nucleic acid duplex stability: structure-stability studies on chemically-modified DNA:RNA duplexes, Nucleic Acids Research, 1997, vol. 25(22), pp. 4429-4443.
Friend: High-yield Preparation of Isolated Rat Liver Parenchymal Cells: A Biochemical and Fine Structrual Study, J. Cell Biol., 1969, 15 pgs.
Geng CA et al: "Small-molecule inhibitors for the treatment of hepatitis B virus documented in patents", Mini Reviews in Medicinal Chem!, Bentham Science Publ, NL, vol. 13, No. 5, Apr. 1, 2013 (Apr. 1, 2013), pp. 749-776, XP009176654.
Gennaro: The Science and Practice of Pharmacy, Philadelphia: Lippincott, Williams & Wilkins, 2000, book details, 1 pg.
Georges: Coordinated Regulation of Cell Cycle Transcripts by p53-InduciblemicroRNAs, miR-192 and miR-215, Cancer Research vol. 68(24) pp. 10105-10112, 9 pgs.
Hadziyannis, "Natural history of chronic hepatitis B in Euro-Mediterranean and African Countries", 2011, Journal of hepatology, 55: 183-191.
Hagedorn: Managing the sequence-specificity of antisense oligonucleotides in drug discovery, Nucleic Acids Research 2017, vol. 45, No. 5, 21 pgs.
Hansen, L.D. et al., Entropy Titration. A calorimetric method for the determination of .Delta.G.degree.(K), .Delta.H.degree. and .Delta.S.degree.1, Chemical Communications, 1965, No. 3, pp. 36-38.
Hantz, O et al., "Persistence of the hepatitis B virus covalently closed circular DNA in HepaRG human hepatocyte-like cells," Journal of General Virology, 2009, vol. 90, Part 1, pp. 127-135, 9 pages.
Heidenreich, M et al., "Applications of CRISPR-Cas systems in neuroscience", Nat Rev Neurosci, 2016, vol. 17(1) pp. 36-44, 23 pages.
Hepatitis B Fact sheet N°204", http://www.who.int/medicalcentre/factsheets/fs204/en/, Jul. 2014, Retrieved Nov. 4, 2014, 4 pgs.
Hirao, I et al., "Natural versus Artificial Creation of Base Pairs in DNA: Origin of Nucleobases from the Perspectives of Unnatural Base Pair Studies," Accounts of Chemical Research, 2012, vol. 45, No. 12, pp. 2055-2065, 11 pages.
Holdgate, GA et al., "Measurements of binding thermodynamics in drug discovery," Drug Discovery Today, 2005, vol. 10, No. 22, pp. 1543-1550, 8 pages.
Hui Wang et al., "Identification of acetyltransferase genes {HAT1 and KAT8) regulating HBV replication by RNAi screening", Cell & Bioscience, vol. 3, No. 9, Dec. 1, 2015 {Dec. 1, 2015), p. 715.
Inan: Hepartitis B Virus: Biology and Life Cycle, Viral Hepatitis Journal, 2015, vol. 1, pp. 1-7, 7 pg.s.
Intention to Grant issued in EP Application No. 17732083.5 on Dec. 17, 2021, 6 pages.
International Preliminary Report on Patentability issued in PCT/EP2017/064980, dated Dec. 18, 2018, 9 pgs.
International Preliminary Report on Patentability issued in PCT/EP2018/078136 dated Apr. 21, 2020, 8 pgs.
International Preliminary Report on Patentability received for PCT Patent Application No. PCT/EP2017/064981, mailed on Dec. 27, 2018, 9 pages.
International Search Report and Written Opinion issued in PCT/EP2017/064980 dated Sep. 15, 2017, 14 pgs.
International Search Report and Written Opinion issued in PCT/EP2018/078136 dated Dec. 18, 2018, 13 pgs.
International Search Report and Written Opinion received for PCT Patent Application No. PCT/EP2017/064981 , mailed on Oct. 2, 2017, 12 pages.

(56) References Cited

OTHER PUBLICATIONS

Iobst et al, "Selective Sugar Binding to the Carbohydrate Recognition Domains of the Rat Hepatic and Macrophage Asialoglycoprotein Receptors," The Journal of Biological Chemistry, vol. 271, Issue 12, 1996, pp. 6686-6693.
Ishida, Y et al., "Novel Robust in Vitro Hepatitis B Virus Infection Model Using Fresh Human Hepatocytes Isolated from Humanized Mice," American Journal of Pathology, 2015, vol. 185, No. 5, pp. 1275-1285, 11 pages.
Janssen et al., "Pegylaled interferon alfa-2b alone or in combination with lamivudine for HBeAg-positive chronic hepatitis B: a randomised trial", Lancet, (2005), 365, 123-9.
Khorev, 0. et al., Trivalent, GaI/GaINAc-containing ligands designed for the asialoglycoprotein receptor, Bioorganic & Medicinal Chemistry, 2008, vol. 16(9), pp. 5216-5231.
Knowles, B.B. et al., Human Hepatocellular Carcinoma Cell Lines Secrete the Major Plasma Proteins and Hepatitis B Surface Antigen, Science, 1980, vol. 209(4455), pp. 497-499.
Ko C et al., "Novel viral and host targets to cure hepatitis B," Current Opinion in Virology, Jun. 2017, vol. 24, pp. 38-45.
Kondo et al., "Hepatitis B Surface Antigen Could Contribute to the Immunopathogenesis of Hepatitis B Virus Infection," ISRN Gasteroenterology, 2013, Article ID 935295, 9 pages.
Kondo et al., "Recovery of Functional Cytotoxic T LymphocytesDuring Lamivudine Therapy by AcquiringMulti-Specificity", Journal of Medical Virology (2004), 74, 425-433.
Kumar et al., "Hepatitis B Virus Regulatory HBx Protein Binds to Adaptor Protein IPS-1 and Inhibits the Activation of Beta Interferon", J Virol, (2011), 85, 987-95.
Lagos-Quintana, M et al. "New microRNAs from mouse and human," RNA, 2003, vol. 9, pp. 175-179, 5 pages.
Laishram, "Poly(A) polymerase (PAP) diversity in gene expression—Star-PAP vs canonical Pap," FEBS Letters, 2014, vol. 588, Issue 14, pp. 2185-2197.
Langer, R, "New Methods of Drug Delivery," Science, 1990, vol. 249, issue 4976, pp. 1527-1533, 7 pages.
Lewis BP et al., "Conserved Seed Pairing, Often Flanked by Adenosines, Indicates that Thousands of Human Genes are MicroRNA Targets," Cell, 2005, vol. 120, pp. 15-20, 6 pages.
Liaw et al., "Hepatitis B e Antigen Seroconversion: A Critical Event in Chronic Hepatitis B Virus Infection," Dig. Dis. Sci., 2010, 55, pp. 2727-2734, 8 pages.
Liaw et al., "Hepatitis B virus infection", Lancet, 2009, 373: 582-592.
Licitra, EJ et al., "A three-hybrid system for detecting small ligand-protein receptor interactions", Proc Nall Academy of Science USA, 1996, vol. 93, pp. 12817-12821, 5 pages.
Mangos, M.M. et al., Efficient RNase H-Directed Cleavage of RNA Promoted by Antisense DNA or 2'F-ANA Constructs Containing Acyclic Nucleotide Inserts, J. Am. Chem. Soc., 2003, vol. 125(3), pp. 654-661.
Manoharan, M., "Oligonucleotide Conjugates in Antisense Technology," Antisense Drug Technology, Marcel Dekker, Inc., 2001, Ch. 16, pp. 391-469, 81 pages.
Marcellin et al., "Peginlerferon Alfa-2a Alone, Lamivudine Alone, and the Two in Combination in Patients with HBeAg-Negative Chronic Hepatitis B", N. Engl. J. Med., (2004), 351, 1206-17.
Mctigue, P.M. et al., Sequence-Dependent Thenrnodynamic Parameters for Locked Nucleic Acid (LNA)-DNA Duplex Formation, Biochemistry, 2004, vol. 43(18), pp. 5388-5405.
Mergny, J.L. et al., Analysis of Thenrnal Melting Curves, Oligonucleotides, 2003, vol. 13(6), pp. 515-537.
Milich et al., "The Secreted Hepatitis B Precore Antigen Can Modulate the Immune Response to the Nucleocapsid: A Mechanism for Persistence", 1998, J. Immunol. 160: 2013-2021.
Milich, D.R., Influence ofT-helper cell subsets and crossregulation in hepatitis B virus infection, Journal of Viral Hepatitis, (1997), vol. 4 {suppl 2), pp. 48-59.
MiRTasBase accession No. MIRT026248 [miRNA, hsa-miR-192-5p: PAPD7, target gene], downloaded Jun. 28, 2019, 4 pages.
MiRTasBase accession No. MIRT026642 [miRNA, hsa-miR-192-5p: PAPD5, target gene], downloaded Jun. 28, 2019, 4 pages.
Mitsuoka, Y et al., "A bridged nucleic acid, 2',4'-BNACOC: synthesis of fully modified oligonucleotides bearing thymine, 5-methylcytosine, adenine and guanine 2',4'-BNACOC monomers and RNA-selective nucleic-acid recognition," Nucleic Acids Research, 2009, vol. 37, No. 4, pp. 1225-1238, 14 pages.
Morita, K. et al., 2'-O,4'-C-ethylene-bridged nucleic acids {ENA): highly nuclease-resistant and thermodynamically stable oligonucleotides for antisense drug, Bioorganic & Medicinal Chemistry Letters, 2002, vol. 12(1), pp. 73-76.
Mueller et al., "PAPD5/7 are novel host factors that are required for Hepatitis B virus RNA stabilization," Hepatology, 2018, XP-002787333, pp. 1527-3350.
N.N: "database entry GS_ NUC Alert:W02015031694.237191", Mar. 5, 2015 (Mar. 5, 2015), pp. 1-1, XP055404257, Retrieved from the Internet: URL:www [retrieved on Sep. 6, 2017].
N.N: "database entry: ATJ17241" , Sep. 20, 2007 (Sep. 20, 2007), pp. 1-1, XP055404262.
N.N: "database entry: GZ986077", Jun. 4, 2013 (Jun. 4, 2013), pp. 1-1, XP055404295, Retrieved from the Internet: URL:file:///C:/Users/TL23249/Documents/Downloads/EM_PAT_GZ986077.pdf [retrieved on Sep. 6, 2017].
N.N: "database entry: miRTarBase—targets for hsa-mir-192-5p", Jun. 3, 2014 (Jun. 3, 2014), XP055404326, Retrieved from the Internet: URL:file:///C:/Users/TL23249/Documents/Downloads/miRNA-Target Interaction Search Results.pdf [retrieved on Sep. 6, 2017].
N.N: database entry GS-NUC-Alert: WO2015031694. 23719111 , Mar. 5, 2015 (Mar. 5, 2015), pp. 1-1.
N.N: Database entry: miRTarBase—targets for hsa-mir-192-5p, Jun. 3, 2014 (Jun. 3, 2014), XP055404326, Retrieved from the Internet: URL:file:///C:/Users/TL23249/Documents/Downloads/miRNA-Target Interaction Search Results.pdf [retrieved on Sep. 6, 2017], 6 pages.
N.N: database entry: mRNA-"EM_EST:AW015126; SV 1; linear; mRNA; EST; HUM; 244 BP," Sep. 13, 1999; Retrieved from the Internet: URL:file:///ibis.inlernal.epo.org/exam/dbfetch.jsp?id=EM_EST:AW015126[retrieved on Jan. 15, 2020], 1 page.
Nayersina, R et al, "HLA A2 restricted cytotoxic T lymphocyte responses to multiple hepatitis B surface antigen epitopes during hepatitis B virus infection," Journal of Immunology, 1993, vol. 150:10, pp. 4659-4671, 14 pages.
Non-Final Office Action dated Jul. 1, 2020, in related U.S. Appl. No. 16/310,789, 20 pages.
Non-final Office Action issued Jul. 1, 2020, in related U.S. Appl. No. 16/310,289, 20 pages.
Non-Final Office Action issued Jun. 25, 2020, in related U.S. Appl. No. 16/310,765, 10 pages.
Notice of Allowance dated May 6, 2020, in related U.S. Appl. No. 16/162,279, 10 pages.
Notice of Reasons for Refusal issued in JP 2018-565394, dated Jul. 30, 2021, 5 pgs.
Notice of Refusal issued in JP 2018-565300, May 26, 2021, 5 pgs.
Ogami, K et al., "Molecular cloning and characterization of a novel isoform of the non-canonical poly(A) polymerase PAPD7", Biochemical and Biophysical Research Communications, 2013, 432.1, pp. 135-140, 6 pages.
Op Den Brouw et al., "Hepatitis B virus surface antigen impairs myeloid dendrilic cellfunclion: a possible immune escape mechanism of hepatitis B virus", Immunology, (2009b), 126, 280-9.
Paterna J C et al., Antioxidant and Cytoprotective Properties ofd-Tagatose in Cultured Murine Hepatocytes, 1998, Toxicol. Appl. Pharmacol., 1998, vol. 148, Issue 1, pp. 117-125.
Ra Palma et al., "database entry: GC056445", Aug. 12, 2005 {Aug. 12, 2005), pp. 1-1, XP055404289, Retrieved from the Internet: URL:file:///C:/UsersfTL23249/Documents/Downloads/EM_PAT_GC056445.pdf [retrieved on Sep. 6, 2017].
Rammelt, C et al., "PAPD5, a noncanonical poly(A) polymerase with an unusual RNA-binding motif", RNA, 2011, vol. 17, pp. 1737-1746, 10 pages.
Remington: The Science and Practice of Pharmacy, Philadelphia; Lippincott, Williams & Wilkins 2000, 1 pg.

(56) References Cited

OTHER PUBLICATIONS

Rowe: Handbook of Pharmaceutical Excipients, Chicago, Pharmaceuitcal Press, 2005, 1 pg.
Rukov, J.L. et al., Dissecting the target specificity of RNase H recruiting oligonucleotides using massively parallel reporter analysis of short RNA motifs, Nucleic Acids Research, 2015, vol. 43(17), pp. 8476-8487.
Russian Office Action; App. No. 2020115761/10(025899); PCT. App. No. PCT/EP2018/078136; dated Mar. 24, 2021; 12 pages.
Santalucia, J Jr., "Unified view of polymer, dumbbell, and oligonucleotide DNA nearest-neighbor thermodynamics," Proc. National Academy Science USA., 1998, vol. 95:4, pp. 1460-1465, 6 pages.
Schulze A. et al., Hepatitis B virus infection initiates with a large surface protein-dependent binding to heparan sulfate proteoglycans, Hepatology, 2007, vol. 46(6), pp. 1759-1768.
Schulze et al., "Detection of CD4+ T Cell Responses in Patients with acute HCV Infection Irrespective of Clinical Outcome," Hepatology, 463, 2007, 1 page.
Sells, M.A. et al., Production of hepatitis B virus particles in Hep G2 cells transfected with cloned hepatitis B virus DNA, Proceedings of National Academy Science USA, 1987, vol. 84(4), pp. 1005-1009.
Seth et al., "Synthesis and Biophysical Evaluation of 2',4'-Constrained 2'0-Methoxyethyl and 2',4'-Constrained 2'0-Ethyl Nucleic Acid Analo!!lles," J. Org. Chem., 2010, 75:1569-1581.
Shi, C.C. et al., Hepatitis B virus suppresses the functional interaction between natural killer cells and plasmacytoid dendritic cells, Journal Viral Hepatitas, 2012, vol. 19(2), e26-e33.
Shin et al., "Prediction of response to entecavir therapy in patients withHBeAg-positive chronic hepatitis B based on ontreatmentHBsAg, HBeAg and HBV DNA levels," Journal of Viral Hepatitis, 2012, 19, pp. 724-731, 8 pages.
Sugimoto, N et al., "Thermodynamic Parameters to Predict Stability of RNA/DNA Hybrid Duplexes," Biochemistry, 1995, vol. 34:35, pp. 11211-11216, 6 pages.
Tavis John E. et al., "The hepatitis B virus ribonuclease H as a drug target", Antiviral Research, vol. 118, Apr. 8, 2015 (Apr. 8, 2015), pp. 132-138.
Thompson, JD et al., "Clustal W: improving the sensitivity of progressive multiple sequence alignment through sequence weighting, position-specific gap penalties and weight matrix choice," Nucleic Acids Res., 1994, vol. 22(22), pp. 4673-4680, 8 pages.
U.S. Centers for Disease Control and Prevention ("CDC"), "Hepatitis B FAQs for the Public", retrieved Jan. 28, 2020, 7 pages.
Uhlmann, "Recent advances in the medicinal chemistry of antisense oligonucleotides," Curr. Opin. Drug Discov. Develop., 2000, 3:203-213.
Uhlmann, E, "Recent advances in the medicinal chemistry of antisense olignonucleotides," Current Opinion in Drug Discovery & Development, 2000, vol. 3:2, pp. 203-213, 12 pages.
Vester, B et al., "Chemically modified oligonucleotides with efficient RNase H response," Bioorganic & Medicinal Chemistry Letters, 2008, vol. 18:7, pp. 2296-2300, 5 pages.
Walsh, R et al., "Targeting the hepatits B virus procore antigen with a novel IgNAR singel variable domain intrabody," Virology, 2011, vol. 411:1, pp. 132-141, 10 pages.
Wang, et al., "Identification of acetyltransferase genes (HAT1 and KATB) regulating HBV replication by RNAi screening," Cell Biosci (2015) 5:66.
Ward, ES et al., "Binding activities of a repertoire of single immunoglobulin variable domains secreted from *Escherichia coli*," Nature, 1989, vol. 341, pp. 544-546, 3 pages.
Wieland, S. F. & F. V. Chisari, "Stealth and Cunning: Hepatitis Band Hepatitis C Viruses", J Virol, (2005), 79, 9369-80.
Winther, TH et al., "Circulating MicroRNAs in Plasma of Hepatitis B e Antigen! Positive Children Reveal Liver-Specifc Target Genes", International Journal of Hepalology, 2014, article ID791045, pp. 1-10, 10 pages.
Woltman et al., "Hepatitis B Virus Lacks Immune Activating Capacity, but Actively Inhibits Plasmacytoid Dendritic Cell Function"; PLoS One, (2011), 6, e15324.
Wooddell, C.I. et al., RNAi-based treatment of chronically infected patients and chimpanzees reveals that integrated hepatitis B virus DNA is a source of HBsAg, Science Translational Medicine, 2017, vol. 9, No. 409, eaan0241.
World Health Organization ("WHO"), "Hepatitis B Fact sheet No. 204", Jul. 2014, retrieved Jan. 28, 2020, 4 pages.
Wu Q et al., "EM_EST:EH352838; SV 1; linear; mRNA; EST; HUM; 105 BP," Mar. 2, 2007; Retrieved from the Internet: URL:file:///ibis.internal.epo.org/exam/dbfelch.jsp?id=EM_EST:EH352838 [retrieved on Jan. 15, 2020], 1 page.
Yan et al., "Molecular Determinants of Hepatitis B and D Virus Entry Restriction in Mouse Sodium Taurocholate Cotransporting Polypeptide," J Virol, 87, 2013, pp. 7977-7991.
Yang, D et al., "A mouse model for HBV immunotolerance and immunotherapy," Cellular & Molecular Immunology, 2014, vol. 11, pp. 71-78, 8 pages.
Zenkova M. A. et al., Imperfectly matched nucleic acid complexes and their biochemical manifestation; Uspekhi Khimii (Russian Chemical Reviews), (1993) vol. 62, No. 4, pp. 414-435.
Zhou, T et al., HBsAg mRNA degradation induced by a dihydroquinolizinone compound depends on the HBV osttranscriplion regulatory element, Antiviral Research, 2018, vol. 149, pp. 191-201, 11 pages.
Burroughs: Genome Research, vol. 20, pp. 1398-1419, 14 pgs.
Fakhr et al. Cancer Gene Therapy 23, 73-82, (Year: 2016).
Hagedorn et al. Nucleic Acid Research vol. 45, pp. 2262-2282 (Year: 2017).
Iobst: Selective Sugar Binding to the Carbohydrate Recognition Domains of the Rat Hepatic and Macrophage Asialoglycoprotein Recptors, 1996, 8 pgs.
Mueller Henrik et al: "PAPD517 are novel host factors that are required for Hepatitis B virus RNA stabilization.", Hepatology, Oct. 26, 2018, pp. 1527-3350.
Ogami et al. Biochemical and Biophysical Research Communications 432, 135-140 (Year: 2013).
Paterna: Antioxidant and Cytoprotective Properties of Tagatose in Cultured Murine Hepatocytes, 1998, Toxiol. Appl. Pharmacol., 1998, 9 pgs.
Bergstrom DE, "Unnatural Nucleosides with Unusual Base Pairing Properties," Current Protocols in Nucleic AcidChemistry, 2001, Suppl. 5, pp. 1.4.1-1.4.13, 13 pages.
Wei, Fen-ju et al., Advances in research on HBV inhibitors based on new targets (2): RNase H and others, Acta Pharmaceutica Sinica, 2020, 55(4), pp. 566-574.

NUCLEIC ACID MOLECULE FOR REDUCTION OF PAPD5 AND PAPD7 MRNA FOR TREATING HEPATITIS B INFECTION

CROSS-REFERENCE TO RELATED APPLICATIONS

This application is a continuation of U.S. patent application Ser. No. 16/661,959 filed 23 Oct. 2019, which is a continuation of U.S. patent application Ser. No. 16/162,279 filed 16 Oct. 2018, issued as U.S. Pat. No. 10,953,034, which claims the benefit of European Patent Application No. 17196554.4 filed 16 Oct. 2017, and European Patent Application No. 17208056.6 filed 18 Dec. 2017, the entire contents of which are fully incorporated by reference herein for all purposes.

SEQUENCE LISTING

The content of the Sequence Listing submitted electronically herewith (name: 103135.0306_Sequence-Listing.xml); size 403,269 bytes; and date of creation: Jul. 19, 2022) is hereby incorporated by reference in its entirety.

FIELD OF THE INVENTION

The present invention relates to nucleic acid molecules that are complementary to both PAP associated domain containing 5 (PAPD5) and PAP associated domain containing 7 (PAPD7), leading to inhibition of the expression of both PAPD5 and PAPD7 when using a single oligonucleotide. The invention also provides for PAPD5 and PAPD7 specific nucleic acid molecules for use in treating and/or preventing a HBV infection, in particular a chronic HBV infection. Also comprised in the present invention is a pharmaceutical composition for use in the treatment and/or prevention of a HBV infection.

BACKGROUND

HBV infection remains a major health problem worldwide which concerns an estimated 350 million chronic carriers. Approximately 25% of carriers die from chronic hepatitis, cirrhosis, or liver cancer. Hepatitis B virus is the second most significant carcinogen behind tobacco, causing from 60% to 80% of all primary liver cancer. HBV is 100 times more contagious than HIV.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, *Hepatology,* 46, (2007), 1759-48) and via the specific binding of HBV surface antigens (HBsAg) to the hepatocyte sodium-taurocholate cotransporting polypeptide (NTCP) receptor (Yan, *J Virol,* 87, (2013), 7977-91). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence.

The secretion of antiviral cytokines in response to a HBV infection by the hepatocytes and/or the intra-hepatic immune cells plays a central role in the viral clearance of the infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signalling system and subsequently the interferon (IFN) antiviral activity. Among these, the excessive secretion of HBV empty sub-viral particles (SVPs, HBsAg) are thought to participate to the maintenance of the immunological tolerant state observed in chronically infected patients (CHB). The persistent exposure to HBsAg and other viral antigens can lead to HBV-specific T-cell deletion or to progressive functional impairment (Kondo, *Journal of Immunology* (1993), 150, 4659-4671; Kondo, *Journal of Medical Virology* (2004), 74, 425-433; Fisicaro, *Gastroenterology*, (2010), 138.682-93;). Moreover HBsAg has been reported to suppress the function of immune cells such as monocytes, dendritic cells (DCs) and natural killer (NK) cells by direct interaction (Op den Brouw, *Immunology*, (2009b), 126, 280-9; Woltman, *PLoS One*, (2011), 6, e15324; Shi. *J Viral Hepet*. (2012), 19, e26-33; Kondo, ISRN *Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains one of the ultimate goals of therapy. Current therapy such as Nucleos(t)ide analogues are molecules that inhibit HBV DNA synthesis but are not directed at reducing HBsAg level. Nucleos(t)ide analogs, even with prolonged therapy, only show weak HBsAg clearance comparable to those observed naturally (between −1%-2%) (Janssen, *Lancet*, (2005), 365, 123-9; Marcellin, *N. Engl. J. Med.*, (2004), 351, 1206-17; Buster, Hepatology, (2007), 46, 388-94). It was recently shown that completely or partially integrated hepatitis B virus DNA is a source of HBsAg expression in chronically infected individuals (see Wooddell et all 2017 Sci. Transl. Med. Vol 9, Issue 409, eaan0241).

Hepatitis B e-antigen (also called HBV envelope antigen or HBeAg) is a viral protein that is secreted by hepatitis B infected cells. HBeAg is associated with chronic hepatitis B infections and is used as a marker of active viral disease and a patient's degree of infectiousness.

The function of the hepatitis B virus precore or HBeAg is not completely known. However HBeAg is well known to play a key role in viral persistence. HBeAg is thought to promote HBV chronicity by functioning as an immunoregulatory protein. In particular, the HBeAg is a secreted accessory protein, which appears to attenuate the host immune response to the intracellular nucleocapsid protein (Walsh, Virology, 2011, 411(1):132-141). The HBeAg acts as an immune tolerogen contributing to HBV persistence, and possibly functions in utero considering that soluble HBeAg traverses the placenta (Walsh, Virology, 2011, 411(1):132-141). Furthermore, HBeAg downregulates: i) cellular genes controlling intracellular signaling; and ii) the Toll-like receptor 2 (TLR-2) to dampen the innate immune response to viral infection (Walsh, Virology, 2011, 411(1):132-141). In the absence of HBeAg, HBV replication is associated with upregulation of the TLR2 pathway (Walsh, Virology, 2011, 411(1):132-141). Accordingly, HBeAg has a significant role in modulating virus/host interactions to influence the host immune response (Walsh, Virology, 2011, 411(1): 132-141). Thus, reducing HBeAg in HBeAg positive patient population may lead to reversal of HBV specific immune dysfunction (Milich, 1997, J. Viral. Hep. 4:48-59; Milich, 1998, J. Immunol. 160: 2013-2021). In addition, the secreted HBeAg is significantly more efficient than the intracellular hepatitis core antigen (HBcAg) at eliciting T-cell tolerance, and the split T-cell tolerance between the HBeAg and the HBcAg and the clonal heterogeneity of HBc/HBeAg-specific T-cell tolerance may have significant implications for natural HBV infection and especially for precore-negative chronic hepatitis (Chen, 2005, Journal of Virology, 79: 3016-3027).

Accordingly, reducing secretion of HBeAg in addition to secretion of HBsAg would lead to an improved inhibition of development of a chronic HBV infection as compared to the inhibition of secretion of HBsAg alone. In addition, the highest rates of transmission of an acute infection to chronic (>80%) have been reported in cases of materno-fetal and neonatal HBV transmission from HBeAg-positive mothers (Liaw, Lancet, 2009, 373: 582-592; Liaw, Dig. Dis. Sci., 2010, 55: 2727-2734; and Hadziyannis, 2011, Journal of hepatology, 55: 183-191). Therefore, reducing HBeAg in an expected mother may not only reduce the patients degree of infectiousness, but may also inhibit the development of a chronic HBV infection of her child.

Therefore, in the therapy of HBV there is an unmet medical need to inhibit viral expression, particularly to inhibit secretion of HBsAg and HBeAg (Wieland, S. F. & F. V. Chisari. J Viral, (2005), 79, 9369-80; Kumar et al. J Viral, (2011), 85, 987-95; Woltman et al. PLoS One, (2011), 6, e15324; Op den Brouw et al. Immunology, (2009b), 126, 280-9).

In WO 2017/066712 down regulation of PAPD5 in relation to the treatment and diagnosis of telomere diseases has been described. Five shRNA structures for this purpose have been described.

PCT/EP2017/064980 discloses targeting PAPD5 or PAPD7 with a nucleic acid molecule and the combination of such molecules to treatment HBV infections.

Objective of the Invention

The present invention identifies novel nucleic acid molecules which are capable of inhibiting the expression of both PAPD5 and PAPD7 in vivo and in vitro. The ability to inhibit two target nucleic acids with a single molecule has distinct advantages in terms of production, simplicity of delivery to the target cell, simplicity of pharmacokinetic/pharmacodynamic (PK/PD) and the concentration needed to achieve a therapeutic benefit. Furthermore the present invention shows that there is a correlation between the PAPD5 and PAPD7 knock down and the HBV antigen inhibition, such as HBsAg inhibition.

BRIEF DESCRIPTION OF THE FIGURES

The Figures show:

In FIGS. 1A and 1B, the oligonucleotide is attached directly to the asialoglycoprotein receptor targeting conjugate moiety without a linker. In the compounds illustrated in FIGS. 1C and 1D, the oligonucleotide is attached to the asialoglycoprotein receptor targeting conjugate moiety via a C6 linker. Compounds illustrated in FIGS. 1E-1I comprise a commercially available trebler brancher molecule and spacers of varying length and structure and three terminal GalNAc carbohydrate moieties.

SUMMARY OF THE INVENTION

Definitions

Nucleic Acid Molecule

Figure 1A:
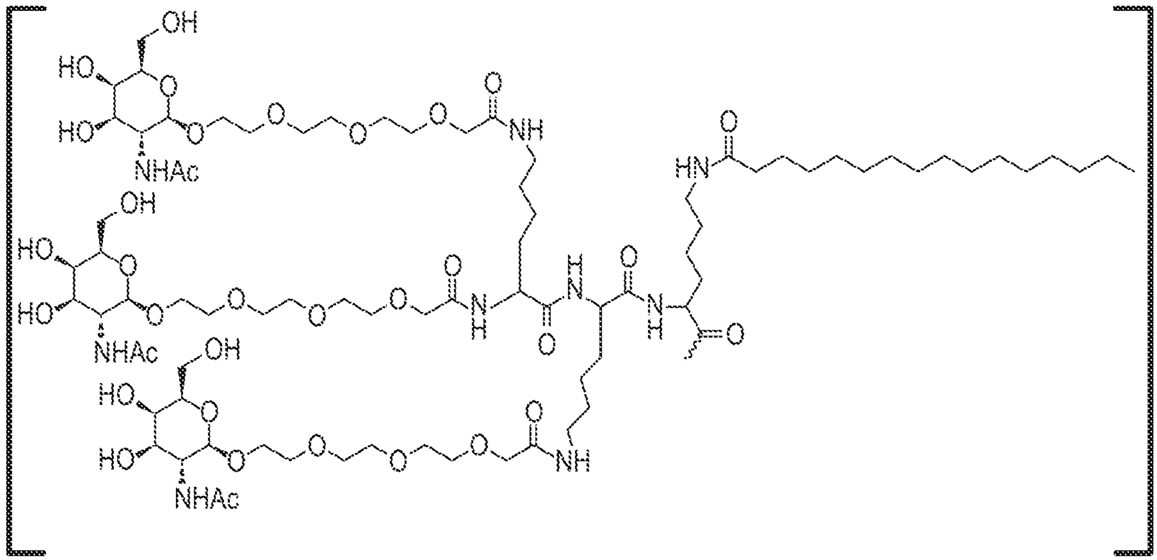
FIGS. 1A-1I: Illustrate exemplary antisense oligonucleotide conjugates, where the oligonucleotide either is represented as a wavy line (FIGS. 1A-1D) or as "oligonucleotide" (FIGS. 1E-1H) or as T2 (FIG. 1I) and the asialoglycoprotein receptor targeting conjugate moieties are trivalent N-acetylgalactosamine moieties. Compounds illustrated in FIGS. 1A-1D comprise a di-lysine brancher molecule, a PEG3 spacer and three terminal GalNAc carbohydrate moieties.
Figure 1B:
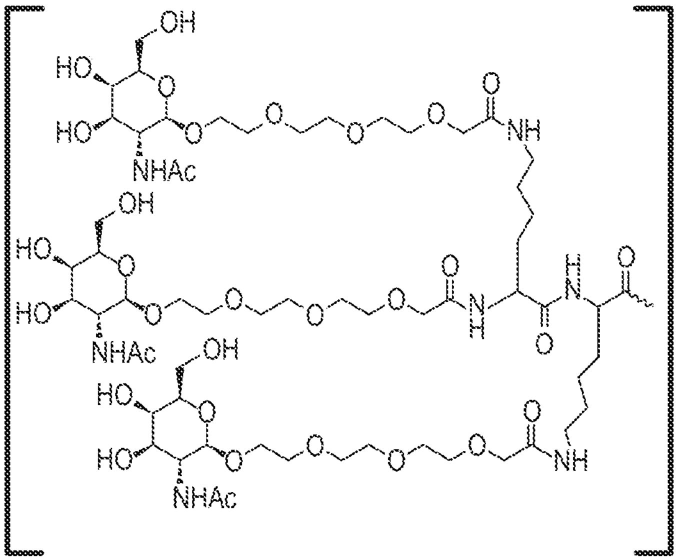
Figure 1C:
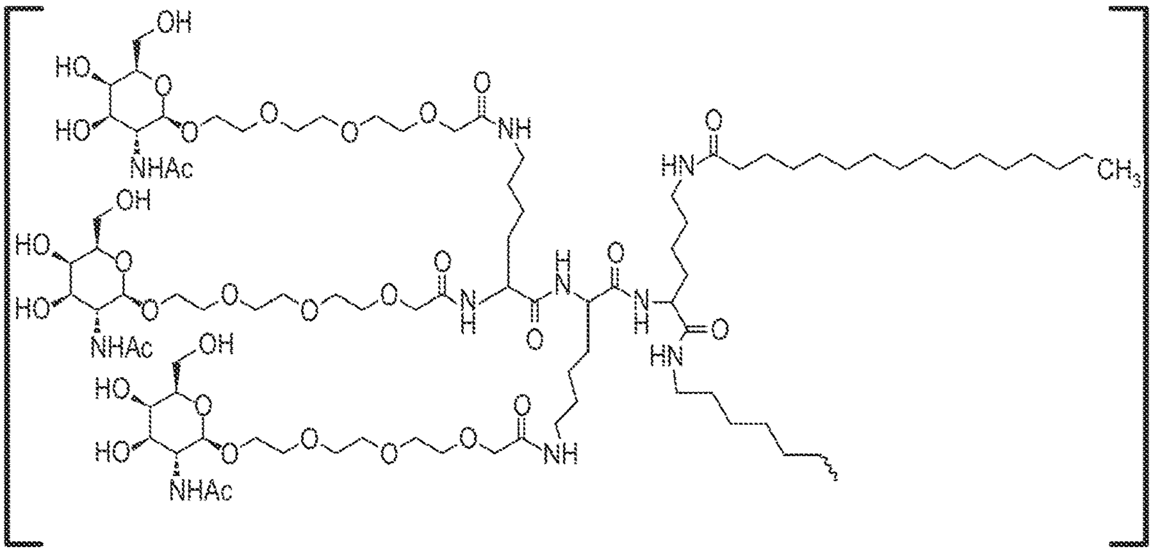

The term "nucleic acid molecule" or "therapeutic nucleic acid molecule" as used herein is defined as it is generally understood by the skilled person as a molecule comprising two or more covalently linked nucleosides (i.e. a nucleotide sequence). The nucleic acid molecule(s) referred to in the method of the invention are generally therapeutic oligonucleotides below 50 nucleotides in length. The nucleic acid molecules may be or comprise an antisense oligonucleotide, or may be another oligomeric nucleic acid molecule, such as a CRISPR RNA, a siRNA, shRNA, an aptamer, or a ribozyme. Nucleic acid molecules are compositions that are commonly made in the laboratory by solid-phase chemical synthesis followed by purification. When referring to a sequence of the nucleic acid molecule, reference is made to the sequence or order of nucleobase moieties, or modifications thereof, of the covalently linked nucleotides or nucleosides. The nucleic acid molecule of the invention is man-made, and is chemically synthesized, and is typically purified or isolated. The nucleic acid molecule of the invention may comprise one or more modified nucleosides or nucleotides.

In some embodiments, the nucleic acid molecule of the Invention comprises or consists of 12 to 50 nucleotides in length, such as from 13 to 40, such as from 14 to 35, such as from 15 to 30, such as from 16 to 22, such as from 16 to 18 or 15 to 17 contiguous nucleotides in length.

In some embodiments, the nucleic acid molecule or contiguous nucleotide sequence thereof comprises or consists of 22 or less nucleotides, such as 20 or less nucleotides, such as 18 or less nucleotides, such as 14, 15, 16 or 17 nucleotides. It is to be understood that any range given herein includes the range endpoints. Accordingly, if a nucleic acid molecule is said to include from 10 to 30 nucleotides, both 10 and 30 nucleotides are included.

In some embodiments, the contiguous nucleotide sequence comprises or consists of 12, 13, 14, 15, 16, 17, 18, 19, 20, 21 or 22 contiguous nucleotides in length The nucleic acid molecule(s) are for modulating the expression of a target nucleic acid in a mammal. In some embodiments the nucleic acid molecules, such as for siRNAs, shRNAs and antisense oligonucleotides, are typically for inhibiting the expression of a target nucleic acid(s).

In one embodiment of the Invention the nucleic acid molecule is selected from a RNAi agent, such as a siRNA or shRNA. In another embodiment the nucleic acid molecule is a single stranded antisense oligonucleotide, such as a high affinity modified antisense oligonucleotide.

In some embodiments the nucleic acid molecule is a phosphorothioate nucleic acid molecule.

In some embodiments the nucleic acid molecule comprises phosphorothioate internucleoside linkages.

In some embodiments the nucleic acid molecule may be conjugated to non-nucleosidic moieties (conjugate moieties).

A library of nucleic acid molecules is to be understood as a collection of variant nucleic acid molecules. The purpose of the library of nucleic acid molecules can vary. In some embodiments, the library of nucleic acid molecules is composed of oligonucleotides with overlapping nucleobase sequence targeting a region in common between the PAPD5 and PAPD7 target nucleic acids with the purpose of identifying the most potent sequence within the library of nucleic acid molecules. In some embodiments, the library of nucleic acid molecules is a library of nucleic acid molecule design variants (child nucleic acid molecules) of a parent or ancestral nucleic acid molecule, wherein the nucleic acid molecule design variants retaining the core nucleobase sequence of the parent nucleic acid molecule.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present Invention are single stranded. The term single stranded is generally understood by the skilled person in the art. Especially it is understood that single stranded oligonucleotides of the present invention can farm hairpins or intermolecular duplex structures (duplex between two molecules of the same oligonucleotide), as long as the degree of intra or inter self complementarity is less than 50% across of the full length of the oligonucleotide.

In one embodiment of the invention the antisense oligonucleotide is an RNaseH recruiting oligonucleotide. Contrary to RNAi molecules antisense oligonucleotides also act in the nucleous of the cell. For targeting pre-mRNA sequences and antisense oligonucleotide is preferable since it acts in the nucleus of the cell.

RNAi

Herein, the term "RNA interference (RNAi) molecule" refers to short double-stranded RNA molecule capable of inducing RNA-dependent gene silencing via the RNA-induced silencing complex (RISC) in a cell's cytoplasm, where they Interact with the catalytic RISC component argonaute. One type of RNAi molecule is a small Interfering RNA (siRNA), which is a double-stranded RNA molecule that, by binding complementary mRNA after transcription, leads to their degradation and loss in translation. A small hairpin RNA (shRNA) is an artificial RNA molecule with a hairpin structure which upon expression is able to reduce mRNA via the DICER and RNA reducing silencing complex (RISC). RNAi molecules can be designed on the base of the RNA sequence of the gene of interest. Corresponding RNAi can then be synthesized chemically or by in vitro transcription, or expressed from a vector or PCR product siRNA and shRNA molecules are generally between 20 and 50 nucleotides in length, such as between 25 and 35 nucleotides in length, and interacts with the endonuclease known as Dicer which is believed to processes dsRNA into 19-23 base pair short interfering RNAs with characteristic two base 3' overhangs which are then incorporated into an RNA-induced silencing complex (RISC). Effective extended forms of Dicer substrates have been described in U.S. Pat. Nos. 8,349,809 and 8,513,207, hereby incorporated by reference. Upon binding to the appropriate target mRNA, one or more endonucleases within the RISC cleave the target to induce silencing. RNAi agents may be chemically modified using modified internucleotide linkages and high affinity nucleosides, such as 2'-4' bicyclic ribose modified nucleosides, including LNA and cET.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention Include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term "modified internucleoside linkage" is defined as generally understood by the skilled person as linkages other than phosphodiester (PO) linkages, that covalently couples two nucleosides together. Nucleotides with modified internucleoside linkage are also termed "modified nucleotides". In some embodiments, the modified internucleoside linkage increases the nuclease resistance of the nucleic acid molecules of the Invention compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides as well as siRNA's for in vivo use, and may serve to protect against nuclease cleavage at regions of DNA or RNA nucleosides in the oligonucleotide or siRNA of the invention, for example within the gap region of a gapmer oligonucleotide, as well as in regions of modified nucleosides.

In an embodiment, the nucleic acid molecule, e.g. antisense oligonucleotide, shRNA or siRNA, comprises one or more internucleoside linkages modified from the natural phosphodiester to a linkage that is for example more resistant to nuclease attack. Nuclease resistance may be determined by Incubating the oligonucleotide in blood serum or by using a nuclease resistance assay (e.g. snake venom phosphodiesterase (SVPD), both are well known in the art. Internucleoside linkages which are capable of enhancing the nuclease resistance of an oligonucleotide are referred to as nuclease resistant internucleoside linkages. In some embodiments at least 50% of the internucleoside linkages in the antisense oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

A phosphorothioate internucleoside linkage is particularly useful due to nuclease resistance, beneficial pharmacokinetics and ease of manufacture. In some embodiments at least 50% of the internucleoside linkages in the oligonucleotide, or contiguous nucleotide sequence thereof, are phosphorothionate, such as at least 60%, such as at least 70%, such as at least 75%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate. In some embodiments at least one of the phosphorothioate internucleoside linkages is stereodefined, such as at least 20%, 30%, 40%, 50%, 60%, such as at least 70%, such as at least 75%, such as at least 80% or such as at least 90% of the internucleoside linkages in the oligonucleotide are stereo defined. The synthesis of stereodefined phosphorothiate linkages are for example described in WO20141012081 and WO2016/079181.

In some embodiments, the oligonucleotide comprises one or more neutral internucleoside linkage, particularly a internucleoside linkage selected from phosphotriester, methylphosphonate, MMI, amide-3, formacetyl or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$O—, —O—P(O,S)—O—, —O—P(S)$_r$O—, —S—P(O)$_r$O—, —S—P(O,S)—O—, —S—P(S)$_2$—, —O—P(O)$_r$S—, —O—P(O,S)—S—, —S—P(O)$_r$S—, —O—PO($R^H$)—O—, O—PO(OCH$_3$)—O—, —O—PO(NRW)—O—, —O—PO(OCH$_2$CH$_2$S—R)—O—, —O—PO(BH$_3$)—O—, —O—PO(NH$R^H$)—O—, —O—P(O)—N$R^H$—, —N$R^H$—P(O)$_r$O—, —N$R^H$—CO—O—, —N$R^H$—CO—N$R^H$—, and/or the internucleoside linker may be selected form the group consisting of: —O—CO—O—, —O—CO—N$R^H$—, —N$R^H$—CO—CH$_2$, —O—CH$_2$CO—N$R^H$—, —O—CH$_2$CH$_2$N$R^H$—, —CO—N$R^H$—CH$_2$—, —CH$_2$—N$R^H$CO—, —O—CH$_2$—CH$_2$S—, —S—CH$_2$—CH$_2$—O—, —S—CH$_2$—CH$_2$—S—, —CH$_2$—SO$_2$—CH$_2$—, —CH$_2$—CO—N$R^H$—, —O—CH$_2$—CH$_2$N$R^H$—CO—, —CH$_2$—NCH$_3$—O—CH$_2$—, where $R^H$ is selected from hydrogen and C1-4-alkyl.

Nuclease resistant linkages, such as phosphothioate linkages, are particularly useful in antisense oligonucleotide regions capable of recruiting nuclease when forming a duplex with the target nucleic acid, such as region G for gapmers, or the non-modified nucleoside region of headmers and tailmers. Phosphorothioate linkages may, however, also be useful in non-nuclease recruiting regions and/or affinity enhancing regions such as regions F and F' for gapmers, or the modified nucleoside region of headmers and tailmers.

Each of the design regions may however comprise internucleoside linkages other than phosphorothioate, such as phosphodiester linkages, in particularly in regions where modified nucleosides, such as LNA, protect the linkage against nuclease degradation. Inclusion of phosphodiester linkages, such as one or two linkages, particularly between or adjacent to modified nucleoside units (typically in the non-nuclease recruiting regions) can modify the bioavailability and/or bio-distribution of an oligonucleotide—see WO2008/113832, incorporated herein by reference.

In an embodiment all the internucleoside linkages in the antisense oligonucleotide are phosphorothioate and/or boranophosphate linkages. Preferably, all the internucleoside linkages in the oligonucleotide are phosphorothioate linkages, Stereorandom Phosphorothioate Linkages Phosphorothioate linkages are internucleoside phosphate linkages where one of the non-bridging oxygens has been substituted with a sulfur. The substitution of one of the non-bridging oxygens with a sulfur introduces a chiral center, and as such within a single phosphorothioate oligonucleotide, each phosphorothioate internucleoside linkage will be either in the S (Sp) or R (Rp) stereoisoforms. Such internucleoside linkages are referred to as "chiral internucleoside lnkages". By comparison, phosphodiester internucleoside linkages are non-chiral as they have two non-terminal oxygen atoms.

The designation of the chirality of a stereocenter is determined by standard Cahn-Ingold-Prelog rules (CIP priority rules) first published in Cahn, R. S.; Ingold. C. K.; Prelog. V. (1966). "Specification of Molecular Chirality". Angewandte Chemie International Edition. 5 (4): 385-415. doi:10.1002/anie.196603851.

During standard oligonucleotide synthesis the stereoselectivity of the coupling and the following sulfurization is not controlled. For this reason the stereochemistry of each phosphorothioate internucleoside linkages is randomly Sp or Rp, and as such a phosphorothioate oligonucleotide produced by traditional oligonucleotide synthesis actually can exist in as many as $2^X$ different phosphorothioate diastereoisomers, where X is the number of phosphorothioate internucleoside linkages. Such oligonucleotides are referred to as stereorandom phosphorothioate oligonucleotides herein, and do not contain any stereodefined internucleoside linkages. Stereorandom phosphorothioate oligonucleotides are therefore mixtures of individual diastereoisomers originating from the non-stereodefined synthesis. In this context the mixture is defined as up to $2^X$ different phosphorothioate diastereoisomers.

Stereodefined Internucleoside Linkages

A stereodefined internucleoside linkage is an internucleoside linkage which introduces a chiral center into the oligonucleotide, which exists in predominantly one stereoisomeric form, either R or S within a population of individual oligonucleotide molecules.

It should be recognized that stereoselective oligonucleotide synthesis methods used in the art typically provide at least about 90% or at least about 95% stereoselectivity at each internucleoside linkage stereocenter, and as such up to about 10%, such as about 5% of oligonucleotide molecules may have the alternative stereo isomeric form.

In some embodiments the stereoselectivity of each stereodefined phosphorothioate stereocenter is at least about 90%. In some embodiments the stereoselectivity of each stereodefined phosphorothioate stereocenter is at least about 95%.

Stereodefined Phosphorothioate Linkages

Stereodefined phosphorothioate linkages are phosphorothioate linkages which have been chemically synthesized in either the Rp or Sp configuration within a population of individual oligonucleotide molecules, such as at least about 90% or at least about 95% stereoselectivity at each stereocenter (either Rp or Sp), and as such up to about 10%, such as about 5% of oligonucleotide molecules may have the alternative stereo isomeric form.

The stereo configurations of the phosphorothioate internucleoside linkages are presented below

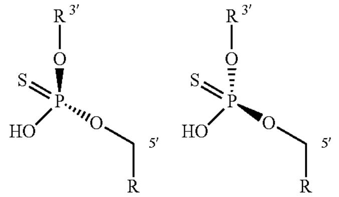

Sp Rp

Where the 3' R group represents the 3' position of the adjacent nucleoside (a 5' nucleoside), and the 5' R group represents the 5' position of the adjacent nucleoside (a 3' nucleoside).

Rp internucleoside linkages may also be represented as srP, and Sp internucleoside linkages may be represented as ssP herein.

In some embodiments the stereoselectivity of each stereodefined phosphorothioate stereocenter is at least about 97%. In some embodiments the stereoselectivity of each stereodefined phosphorothioate stereocenter is at least about 98%. In some embodiments the stereoselectivity of each stereodefined phosphorothioate stereocenter is at least about 99%.

In some embodiments a stereoselective internucleoside linkage is in the same stereoisomeric form in at least 97%, such as at least 98%, such as at least 99%, or (essentially) all of the oligonucleotide molecules present in a population of the oligonucleotide molecule.

Stereoselectivity can be measured in a model system only having an achiral backbone (i.e. phosphodiesters) it is possible to measure the stereoselectivity of each monomer by e.g. coupling a stereodefined monomer to the following model-system "5' t-po-t-po-t-po 3'". The result of this will then give: 5' DMTr-t-srp-t-po-t-po-t-po 3' or 5' DMTr-t-ssp-t-po-t-po-t-po 3' which can be separated using HPLC. The stereoselectivity is determined by integrating the UV signal from the two possible compounds and giving a ratio of these e.g. 98:2, 99:1 or >99:1.

It will be understood that the stereo % purity of a specific single diastereoisomer (a single stereodefined oligonucleotide molecule) will be a function of the coupling selectivity for the defined stereocenter at each internucleoside position, and the number of stereodefined internucleoside linkages to be introduced. By way of example, if the coupling selectivity at each position is 97%, the resulting purity of the stereodefined oligonucleotide with 15 stereodefined internucleoside linkages will be $0.97^{15}$, i.e. 63% of the desired diastereoisomer as compared to 37% of the other diastereoisomers. The purity of the defined diastereoisomer may after synthesis be improved by purification, for example by HPLC, such as ion exchange chromatography or reverse phase chromatography.

In some embodiments, a stereodefined oligonucleotide refers to a population of an oligonucleotide wherein at least about 40%, such as at least about 50% of the population is of the desired diastereoisomer.

Alternatively stated, in some embodiments, a stereodefined oligonucleotide refers to a population of oligonucleotides wherein at least about 40%, such as at least about 50%, of the population consists of the desired (specific) stereodefined internucleoside linkage motif (also termed stereodefined motif).

For stereodefined oligonucleotides which comprise both stereorandom and stereodefined internucleoside stereocenters, the purity of the stereodefined oligonucleotide is determined with reference to the % of the population of the oligonucleotide which retains the defined stereodefined internucleoside linkage motif(s), the stereorandom linkages are disregarded in the calculation.

Nucleobase

The term nucleobase Includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiazolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be Indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide or modified nucleic acid molecule describes an oligonucleotide or nucleic acid molecule comprising one or more sugar-modified nucleosides and/or modified internucleoside linkages. The term "chimeric" is a term that has been used in the literature to describe oligonucleotides or nucleic acid molecules with modified nucleosides, in particular gapmer oligonucleotides.

Stereodefined Oligonucleotide

A stereodefined oligonucleotide is an oligonucleotide wherein at least one of the internucleoside linkages is a stereodefined internucleoside linkage.

A stereodefined phosphorothioate oligonucleotide is an oligonucleotide wherein at least one of the internucleoside linkages is a stereodefined phosphorothioate internucleoside linkage.

Stereodefined Internucleoside Motif

A stereodefined internucleoside motif, also termed stereodefined motif herein, refers to the pattern of stereodefined R and S internucleoside linkages in a stereodefined oligonucleotide, and is written 5'-3'. For example, the stereodefined oligonucleotide (SEQ ID NO 18)

5'-$T_{srP}$ $C_{ssP}$ $A_{ssP}$ $a_{srP}$ $c_{srP}$ $t_{ssP}$ $t_{srP}$ $t_{srP}$ $c_{ssP}$ $a_{srP}$ $c_{ssP}$ $t_{srP}$ $t_{ssP}$ $C_{ssP}$ $A_{ssP}$ G-3', has a stereodefined internucleoside motif of RSSRRSRRSRSRSSS.

With respect to sub-libraries of stereodefined oligonucleotides, these will contain a common stereodefined internucleoside motif in an otherwise stereorandom background (optionally with one or more non chiral internucleoside linkages, e.g. phosphodiester linkages).

For example, the oligonucleotide (SEQ ID NO 18)

5'-$T_s$ $C_s$ $A_s$ $a_s$ $c_{srP}$ $t_{ssP}$ $t_{ssP}$ $t_{srP}$ $c_s$ $a_s$ $c_s$ $t_s$ $t_s$ $C_s$ $A_s$ G-3 has a stereodefined internucleoside motif of XXXXRSSRXXXXXXX, with X representing a stereorandom phosphorothioate internucleoside linkage (shown as subscript s in the compound). It will be noted that in this example the first 5' stereodefined internucleoside linkage is the $5^{th}$ internucleoside linkage from the 5' end (between the nucleosides at position 4 and 5), and as such the above motif is also referred to as a "RSSR" motif at (internucleoside linkage) position 5.

When the stereodefined internucleoside motif (stereodefined motif) is made up on a series of adjacent stereodefined internucleoside linkages (i.e. positioned between contiguous nucleosides), it is referred to herein as a contiguous stereodefined internucleoside motif (a contiguous stereodefined motif). It will be understood that a contiguous stereodefined motif must comprise two or more adjacent stereodefined internucleoside linkages.

In a sub-library mixture, a stereodefined internucleoside motif may also be dis-contiguous, i.e. the stereodefined internucleoside linkages are dispersed with one or more stereorandom internucleoside linkages.

For example the compound (SEQ ID NO 18)

5'-$T_s$ $C_{ssP}$ $A_s$ $a_s$ $c_{srP}$ $t_{ssP}$ $t_s$ $t_s$ $c_s$ $a_s$ $c_s$ $t_s$ $t_{ssP}$ $C_{srP}$ $A_{ssP}$ G-3 has a dis-contiguous motif XSXXRSXXXXXXXSRS.

Parent Oligonucleotide

A parent oligonucleotide is an oligonucleotide which has a defined nucleobase sequence (motif sequence). In the methods of the invention, a parent oligonucleotide is typically an oligonucleotide which is to be Improved by the use of the method of the invention by creating one or more libraries.

Typically a library can vary the nucleoside modifications (design libraries) while maintaining the nucleobase sequence of the parent and the stereochemistry (typically stereorandom).

Alternative a library can vary the stereochemistry of the parent oligonucleotide while maintaining the nucleobase sequence (motif sequence) and nucleoside modification pattern (design). In such a library the stereochemistry of one, or more (2+), of the internucleoside linkages is stereodefined and is different to that of the parent oligonucleotide.

In some embodiments, the parent oligonucleotide is a stereorandom phosphorothioate oligonucleotide. In some embodiments, the parent oligonucleotide is a stereorandom phosphorothioate oligonucleotide gapmer.

In some embodiments, the parent oligonucleotide may be a sub-library which comprises a common stereodefined motif.

Stereodefined Variants (Child Oligonucleotides)

A stereodefined variant of an oligonucleotide is an oligonucleotide which retain the same sequence and nucleoside modifications as a parent oligonucleotide (i.e. the same sequence and nucleoside modification chemistry and design), but differs with respect to one or more stereodefined internucleoside linkages, such as one or more stereodefined phosphorothioate internucleoside linkages (a stereodefined phosphorothioate variant).

A stereodefined variant may be a sub-library, or may be a fully stereodefined oligonucleotide.

Sub-Library of Stereodefined Oligonuclotides

An oligonucleotide which comprises both stereorandom and stereodefined oligonucleotides is referred to herein as a sub-library. Sub-libraries are less complex mixtures of the diastereoisomeric mixture of a fully stereorandom oligonucleotide thus representing a sub-set of all possible diastereoisomers. For example, theoretically, a fully phosphorothioate stereorandom 16mer is a mixture of $2^{15}$ diastereoisomer (32768), whereas a sub-library where one of the phosphorothioate internucleoside linkages is stereodefined will have half the library complexity (16384 diastereoisomer). (2 stereodefined linkages=8192 diastereoisomer; 3 stereodefined linkages=4096 diastereoisomer, 4 stereodefined linkages=2048 diastereoisomer, 5 stereodefined linkages=1024 diastereoisomer) assuming 100% stereoselective coupling efficacy.

Fully Stereodefined Oligonucleotides

A fully stereodefined oligonucleotide is an oligonucleotide wherein all the chiral internucleoside linkages present within the oligonucleotide are stereodefined. A fully stereodefined phosphorothioate oligonucleotide is an oligonucleotides wherein all the chiral internucleoside linkages present within the oligonucleotide are stereodefined phosphorothioate internucleoside linkages.

It will be understood that, in some embodiments, a fully stereodefined oligonucleotide may comprise one or more, non-chiral internucleosides, such as phosphodiester internucleoside linkages, for example phosphodiester linkages can be used within the flanking regions of gapmers, and/or when linking terminal nucleosides, such as between short regions of DNA nucleosides (biocleavable linker) linking a gapmer sequence and a conjugate group.

In some embodiments of fully stereodefined oligonucleotide, all of the internucleoside linkages present in the oligonucleotide, or contiguous nucleotide region thereof, such as an F-G-F' gapmer, are stereodefined internucleoside linkages, such as stereodefined phosphorothioate internucleoside linkages.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol. 45 page 2055 and Bergstrom (2009) Current Protocols in Nucleic Acid Chemistry Suppl. 37 1.4.1).

The term "% complimentary" as used herein, refers to the number of nucleotides in percent of a contiguous nucleotide sequence in a nucleic acid molecule (e.g. oligonucleotide) which, at a given position, are complementary to (i.e. form Watson Crick base pairs with) a contiguous nucleotide sequence, at a given position of a separate nucleic acid molecule (e.g. the target nucleic acid). The percentage is calculated by counting the number of aligned bases that form pairs between the two sequences (when aligned with the target sequence 5'-3' and the oligonucleotide sequence from 3-5), dividing by the total number of nucleotides in the oligonucleotide and multiplying by 100. In such a comparison a nucleobase/nucleotide which does not align (form a base pair) is termed a mismatch. Preferably, insertions and deletions are not allowed in the calculation of % complementarity of a contiguous nucleotide sequence.

The term "fully complementary", refers to 100% complementarity.

The following is an example of an oligonucleotide (SEQ ID NO: 12) that is fully complementary to a region of a target nucleic acid.

```
759 ctgtggatgcagatctgggaga 781 (Pos. 759-781 of SEQ ID NO: 1)
       ||||||||||||||
1-3'-ACCACGTCTAGACCC-5'--- 16  (SEQ ID NO: 12)
```

Identity

The term "Identity" as used herein, refers to the number of nucleotides in percent of a contiguous nucleotide sequence in a nucleic acid molecule (e.g. oligonucleotide) which, at a given position, are identical to (i.e. in their ability to form Watson Crick base pairs with the complementary nucleoside) a contiguous nucleotide sequence, at a given position of a separate nucleic acid molecule (e.g. the target nucleic acid). The percentage is calculated by counting the number of aligned bases that are identical between the two sequences dividing by the total number of nucleotides in the oligonucleotide and multiplying by 100. Percent Identity=(Matches×100)/Length of aligned region. Preferably, insertions and deletions are not allowed in the calculation of % complementarity of a contiguous nucleotide sequence.

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy ΔG° is a more accurate representation of binding affinity and is related to the dissociation constant ($K_d$) of the reaction by ΔG°=−RT ln(K), where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen at al., 1965, *Chem Comm.* 36-38 and Holdgate et al., 2005, *Drug Discov Today. The skilled person will know that commercial equipment is available for ΔG° measurements. ΔG° can also be estimated numerically by using the nearest neighbor model as described by SantaLucia,* 1998. *Proc Natl Acad Sci USA.* 95: 1460-1465 using appropriately derived thermodynamic parameters described by Sugimoto at al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Target Nucleic Acid

According to the present invention, there are two target nucleic acids which are to be modulated by the same oligonucleotide. The target nucleic acids are i) a nucleic acid which encodes mammalian PAPD5 (target nucleic acid 1) and ii) a nucleic acid which encodes mammalian PAPD7 (target nucleic acid 2). The target nucleic acids may for example be a gene, a RNA, a mRNA, and pre-mRNA, a mature mRNA or a cDNA sequence. Suitably, the target nucleic acid encodes a PAPD5 or PAPD7 protein, in particular mammalian PAPD5 or PAPD7, such as human PAPD5 or PAPD7 (See for example table 1 and 2) which provides the pre-mRNA sequences for human, monkey, and mouse PAPD5 and PAPD7).

In some embodiments, the target nucleic acid is selected from the group consisting of SEQ ID NO: 1, 3 and/or 5 naturally occurring variants thereof (e.g. sequences encoding a mammalian PAPD5).

In some embodiments, the target nucleic acid is selected from the group consisting of SEQ ID NO: 2, 4, and/or 6 or 11 or naturally occurring variants thereof (e.g. sequences encoding a mammalian PAPD7).

TABLE 1A

Genome and assembly information for PAPD5 across species.

| | | | | Genomic coordinates | | | |
|---|---|---|---|---|---|---|---|
| Species | Chr. | Band | Strand | Start | End | ensembl_gene_id | Assembly |
| Human | 16 | q12.1 | fwd | 50152918 | 50235310 | ENSG00000121274 | GRCh38.p7 |
| Cynomolgus monkey | 20 | | fwd | 37953893 | 38040642 | RefSeq ID: NC_022291.1 | Macaca_fascicularis_5.0 (GCF_000364345.1) |
| mouse | 8 | C3 | fwd | 88199213 | 88259722 | ENSMUSG00000036779 | GRCm38.p5 |
| Rat | 19 | p11 | rev | 19771677 | 19832812 | ENSRNOG00000024212 | Rnor_6.0 |

TABLE 1B

| Genome and assembly information for PAPD7 across species. | | | | | | | |
|---|---|---|---|---|---|---|---|
| | | | | Genomic coordinates | | | |
| Species | Chr | Band | Strand | Start | End | ensembl_gene_id | Assembly |
| Human | 5 | p15.31 | fwd | 6713007 | 6757048 | ENSG00000112941 | GRCh38.p7 |
| Cynomolgus monkey | 6 | | fwd | 6740764 | 6790723 | RefSeq NC_022277.1 | Macaca_fascicularis_5.0 (GCF_000364345.1) |
| mouse | 13 | B3 | rev | 69497959 | 69534617 | ENSMUSG00000034575 | GRCm38.p5 |
| Rat | 1 | p11 | fwd | 36400443 | 36433238 | ENSRNOG00000017613 | Rnor_6.0 |

Fwd = forward strand.
Rev = reverse strand.
The genome coordinates provide the pre-mRNA sequence (genomic sequence).

If employing the oligonucleotide of the invention in research or diagnostics the target nucleic acid may be a cDNA or a synthetic nucleic acid derived from DNA or RNA.

For in vivo in vitro application, the oligonucleotide of the invention is typically capable of inhibiting the expression of the PAPD5 and PAPD7 target nucleic acid in a cell which is expressing the PAPD5 and PAPD7 target nucleic acid. The contiguous sequence of nucleobases of the oligonucleotide of the Invention Is typically complementary a conserved region of the PAPD5 and PAPD7 target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides (e.g. region D' or D"). Further information on exemplary target nucleotides is provided in table 2.

TABLE 2

| Sequence details for PAPD5 and PAPD7 across species. | | | | |
|---|---|---|---|---|
| Species | Target | RNA type | Length (nt) | SEQ ID NO |
| Human | PAPD5 | Pre-mRNA | 82393 | 1 |
| Human | PAPD7 | Pre-mRNA | 44042 | 2 |
| Cyno monkey | PAPD5 | Pre-mRNA | 86750 | 3 |
| Cyno monkey | PAPD7 | Pre-mRNA | 49960 | 4 |
| Mouse | PAPD5 | Pre-mRNA | 60510 | 5 |
| Mouse | PAPD7 | Pre-mRNA | 36659 | 6 |

Target Sequence

The term "target sequence" as used herein refers to a sequence of nucleotides present in the target nucleic acid which comprises the nucleobase sequence which is complementary to the oligonucleotide or nucleic acid molecule of the invention. In some embodiments, the target sequence consists of a region on the target nucleic acid which is complementary to the contiguous nucleotide sequence of the oligonucleotide of the invention (i.e. a sub-sequence).

In the present invention the target sequence is present both in the human PAPD5 and human PAPD7 target nucleic acid. The target sequence may therefore be referred to as a bispecific target sequence present in both the PAPD5 and PAPD7 target nucleic acid. In advantageous embodiments the target sequence is also present in at least one additional species, such as PAPD5 and PAPD7 from cynomolgus monkey and/or PAPD5 and PAPD7 from mouse. The oligonucleotide or nucleic acid molecule of the invention comprises a contiguous nucleotide sequence which is complementary to or hybridizes to a region on the target nucleic acid, such as a target sequence described herein.

The target nucleic sequence to which the oligonucleotide is complementary to or hybridizes to generally comprises a stretch of contiguous nucleobases of at least 10 nucleotides. The contiguous nucleotide sequence is between 10 to 50 nucleotides, such as 12-30, such as 13 to 25, such as 14 to 20, such as 15 to 18 contiguous nucleotides.

Naturally Occurring Variant

The term "naturally occurring variant" refers to variants of PAPD5 or PAPD7 gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms, and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian PAPD5 target nucleic acid, such as a target nucleic acid selected form the group consisting of SEQ ID NO: 1, 3 or 5. In some embodiments the naturally occurring variants have at least 99% homology to the human PAPD5 target nucleic acid of SEQ ID NO: 1. In some embodiments the naturally occurring variants are the polymorphisms listed in table 3A.

In some embodiments, the naturally occurring variants have at least 95% such as at least 98% or at least 99% homology to a mammalian PAPD5 target nucleic acid, such as a target nucleic acid selected form the group consisting of SEQ ID NO: 2 or 4 or 6. In some embodiments the naturally occurring variants have at least 99% homology to the human PAPD7 target nucleic acid of SEQ ID NO: 2. In some embodiments the naturally occurring variants are the polymorphisms listed in table 36.

Numerous single nucleotide polymorphisms are known in the PAPD5 or PAPD7 gene, for example those disclosed in Table 3A (human PAPD5 premRNA start/reference sequence is SEQ ID NO: 1) and Table 3B human PAPD7 premRNA start/reference sequence is SEQ ID NO: 2).

TABLE 3A

| PAPD5 polymorphisms (naturally occurring variants) | | |
|---|---|---|
| minor allele | Minor allele frequency | Start on SEQ ID NO: 1 |
| G | 0.00399361 | 29 |
| G | 0.000199681 | 34 |

TABLE 3A-continued

PAPD5 polymorphisms (naturally occurring variants)

| minor allele | Minor allele frequency | Start on SEQ ID NO: 1 |
|---|---|---|
| T | 0.000399361 | 39 |
| A | 0 000599042 | 62 |
| A | 0.000599042 | 97 |
| G | 0.000199681 | 141 |
| A | 0.000199681 | 142 |
| T | 0.000199681 | 158 |
| A | 0.0241613 | 235 |
| A | 0.00239617 | 279 |
| — | 0.214058 | 370 |
| G | 0.000798722 | 450 |
| CAGCA | 0.000798722 | 603 |
| A | 0.0223642 | 1028 |
| C | 0.000199681 | 1044 |
| A | 0.0189696 | 1068 |
| T | 0.000199681 | 1181 |
| T | 0.0249601 | 1199 |
| T | 0.000998403 | 1268 |
| A | 0.000199681 | 1261 |
| T | 0.000599042 | 1441 |
| T | 0.000199681 | 1443 |
| C | 0.000599042 | 1469 |
| A | 0.000399361 | 1535 |

TABLE 3B

PAPD7 polymorphisms (naturally occurring variants)

| minor allele | Minor allele frequency | Start on SEQ ID NO: 2 |
|---|---|---|
| A | 0.293331 | 21 |
| T | 0.00119808 | 50 |
| T | 0.000199681 | 64 |
| A | 0.00279553 | 127 |
| A | 0.0597045 | 224 |
| G | 0.000199681 | 234 |
| T | 0.000599042 | 270 |
| A | 0.128994 | 284 |
| C | 0.000399361 | 316 |
| T | 0.000199681 | 349 |
| G | 0.00778754 | 362 |
| A | 0.000199681 | 409 |
| G | 0.000199681 | 425 |
| A | 0.000199681 | 448 |
| T | 0.000199881 | 473 |
| C | 0.000199681 | 491 |
| C | 0.327676 | 564 |
| T | 0.0203674 | 608 |
| — | 0.389577 | 837 |
| — | 0.00139778 | 1317 |
| T | 0.000599042 | 1331 |
| T | 0.000199681 | 1475 |
| T | 0.000399361 | 1483 |
| C | 0.01877 | 1673 |
| A | 0.000199681 | 1682 |
| T | 0.00339457 | 1726 |
| GGTCCTGGCCGGCGCCCGC | 0.258586 | 1736 |
| G | 0.000599042 | 1760 |
| C | 0.000199681 | 1777 |
| G | 0.000399361 | 1780 |
| T | 0.000199681 | 1852 |
| T | 0.000199681 | 1361 |
| T | 0.000199681 | 1889 |
| C | 0.000399361 | 1923 |
| G | 0.000399361 | 1962 |
| T | 0.0147764 | 1987 |
| G | 0.000998403 | 1996 |
| T | 0.000399381 | 2036 |

Modulation of Expression

The term “modulation of expression” as used herein is to be understood as an overall term for a nucleic acid molecules ability to alter the amount of PAPD5 and PAPD7 when compared to the amount of PAPD5 and PAPD7 before administration of the nucleic acid molecule. Alternatively, modulation of expression may be determined by reference to a control experiment. It is generally understood that the control is an Individual or target cell treated with a saline composition or an individual or target cell treated with a non-targeting or nucleic acid molecule (mock). It may however also be an individual treated with the standard of care.

One type of modulation is a nucleic acid molecules, such as an antisense oligonucleotides, ability to inhibit, downregulate, reduce, remove, stop, prevent, lessen, lower, avoid or terminate expression of PAPD5 and PAPD7, e.g. by degradation of mRNA or blockage of transcription.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' sugar modified nucleosides, such as 2' substituted nucleosides like Ome and MOE as well as 2' to 4' bridged nucleic acids such as locked nucleic acids (LNA) 10 (see e.g. Freier & Altmann; Nucl. Acid Res., 1997, 25, 4429-4443 and Uhlmann; Curr. Opinion in Drug Development, 2000, 3(2), 293-213).

Sugar Modifications

The nucleic acid molecule of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of nucleic acid molecules, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the —OH groups naturally found in RNA or DNA nucleosides. Substituents may, for example be introduced at the 2', 3', 4' or 5' positions.

2'Sugar Modified Nucleosides.

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxyl-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000. 3(2), 293-213, and Deleavey and Damha, Chemistry and Biology 2012, 19, 937. Below are illustrations of some 2' substituted modified nucleosides.

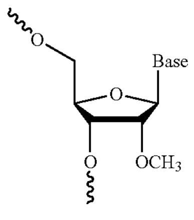

2'-O-Me

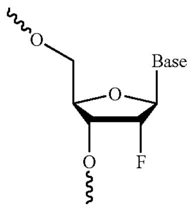

2'F-RNA

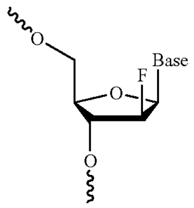

2'F-ANA

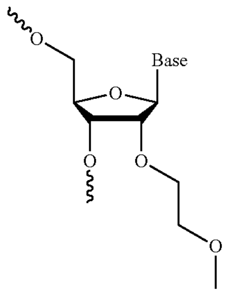

2'-O-MOE

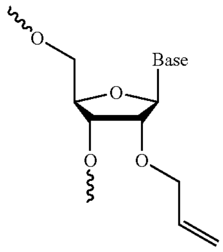

2'-O-Allyl

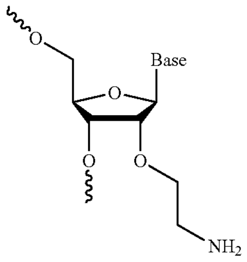

2'-O-Ethylamine

In relation to the present invention 2' substituted does not include 2' bridged molecules like LNA.

Locked Nucleic Acid Nucleosides (LNA).

An "LNA nucleoside" is 2'-sugar modified nucleoside which comprises a biradical Inking the C2' and C4' of the ribose sugar ring of a said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

In some embodiments, the 2'-sugar modified nucleoside(s) or the LNA nucleoside(s) of the oligomer of the invention has a general structure of the formula I or II:

Formula I

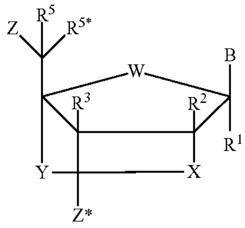

β-D or

Formula II

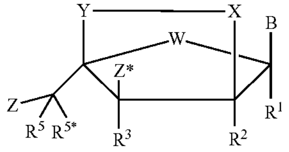

α-L wherein W is selected from —O—, —S—, —N($R^a$)—, —C($R^aR^b$)—, such as, in some embodiments —O—;

B designates a nucleobase or modified nucleobase moiety;

Z designates an internucleoside linkage to an adjacent nucleoside, or a 5'-terminal group;

Z* designates an internucleoside linkage to an adjacent nucleoside, or a 3'-terminal group;

X designates a group selected from the list consisting of —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z In some embodiments, X is selected from the group consisting of: —O—, —S—, NH—, $NR^aR^b$, —$CH_2$—, $CR^aR^b$, —C(═$CH_2$)—, and —C(═$CR^aR^b$)—

In some embodiments, X is —O—

Y designates a group selected from the group consisting of —C($R^aR^b$)—, —C($R^a$)═C($R^b$)—, —C($R^a$)═N—, —O—, —Si($R^a$)$_2$—, —S—, —$SO_2$—, —N($R^a$)—, and >C═Z In some embodiments, Y is selected from the group consisting of: —$CH_2$—, —C($R^aR^b$)—, —$CH_2CH_2$—, —C($R^aR^b$)—C($R^aR^b$)—, —$CH_2CH_2CH_2$—, —C($R^aR^b$)C($R^aR^b$)C($R^aR^b$)—, —C($R^a$)═C($R^b$)—, and —C($R^a$)═N—

In some embodiments, Y is selected from the group consisting of: —$CH_2$—, —$CHR^a$—, —$CHCH_3$—, $CR^aR^b$— or —X—Y— together designate a bivalent linker group (also referred to as a radicle) together designate a bivalent linker group consisting of 1, 2, 3 or 4 groups/atoms selected from the group consisting of —C($R^aR^b$)—, —C($R^a$)═C($R^b$)—, —C($R^a$)═N—, —O—, —Si($R^a$)$_2$, —S—, —$SO_2$—, —N($R^a$)—, and >C═Z, In some embodiments, —X—Y— designates a biradicle selected from the groups consisting of: —X—$CH_2$—, —X—$CR^aR^b$—, —X—$CHR^a$—. —X—C($HCH_3$)—, —O—Y—, —O—$CH_2$—, —S—$CH_2$μ, —NH—CH—, —O—$CHCH_3$—, —$CH_2$—O—$CH_2$, —O—CH($CH_1CH_3$)—, —O—$CH_2$CH—, $OCH_2CH_2CH_2$, —O—$CH_2OCH_2$—, —O—$NCH_2$, —C(═$CH_2$)—$CH_2$—, —$NR^a$—$CH_2$—, N—O—$CH_2$, —S—$CR^aR^b$— and —S—$CHR^a$—.

In some embodiments —X—Y— designates —O—CH or —O—CH($CH_3$)—.

wherein Z is selected from —O—, —S—, and —N($R^a$)—, and $R^a$ and, when present $R^b$, each is independently selected from hydrogen, optionally substituted $C_{1-6}$-alkyl, optionally substituted $C_{2-3}$-alkenyl, optionally substituted $C_{2-6}$-alkynyl, hydroxy, optionally substituted $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alky)amino, carbamoyl, mono- and di($C_{1-6}$-alkyl)-amino-carbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkyl-carbonylamino, carbamido, $C_{1-4}$-alkanoyloxy, sulphono, $C_{1-6}$-alkylsulphonyloxy, nitro, azido, sulphanyl. $C_{1-6}$-alkylthio, halogen, where aryl and heteroaryl may be optionally substituted and where two geminal substituents $R^a$ and $R^b$ together may designate optionally substituted methylene (═$CH_2$), wherein for all chiral centers, asymmetric groups may be found in either R or S orientation.

wherein $R^1$, $R^2$, $R^3$, $R^5$ and $R^{5'}$ are independently selected from the group consisting of: hydrogen, optionally substituted $C_{1-6}$-alkyl, optionally substituted $C_{2-6}$-alkenyl, optionally substituted $C_{2-6}$-alkynyl, hydroxy, $C_{1-6}$-alkoxy, $C_{2-6}$-alkoxyalkyl, $C_{2-6}$-alkenyloxy, carboxy, $C_{1-6}$-alkoxycarbonyl, $C_{1-6}$-alkylcarbonyl, formyl, aryl, aryloxy-carbonyl, aryloxy, arylcarbonyl, heteroaryl, heteroaryloxy-carbonyl, heteroaryloxy, heteroarylcarbonyl, amino, mono- and di($C_{1-6}$-alkyl)amino, carbamoyl, mono- and di($C_{1-6}$-alkyl)-amino-carbonyl, amino-$C_{1-6}$-alkyl-aminocarbonyl, mono- and di($C_{1-6}$-alkylamino-$C_{1-6}$-alkyl-aminocarbonyl, $C_{1-6}$-alkyl-carbonylamino, carbamido, $C_{1-6}$-alkanoyloxy, sulphono, $C_{1-6}$-alkylsulphonyloxy, nitro, azido, sulphanyl, $C_{1-6}$-alkylthio, halogen, where aryl and heteroaryl may be optionally substituted, and where two geminal substituents together may designate oxo, thioxo, imino, or optionally substituted methylene.

In some embodiments $R^1$, $R^2$, $R^3$, $R^5$ and $R^{5'}$ are Independently selected from $C_{1-6}$ alkyl, such as methyl, and hydrogen.

In some embodiments $R^1$, $R^2$, $R^3$, $R^5$ and $R^{5'}$ are all hydrogen.

In some embodiments $R^1$, $R^2$, $R^3$, are all hydrogen, and either $R^5$ and $R^{5'}$ is also hydrogen and the other of $R^5$ and $R^{5'}$ is other than hydrogen, such as $C_{1-6}$ alkyl such as methyl.

In some embodiments, $R^a$ is either hydrogen or methyl. In some embodiments, when present, $R^b$ is either hydrogen or methyl.

In some embodiments, one or both of $R^a$ and $R^b$ is hydrogen

In some embodiments, one of $R^a$ and $R^b$ is hydrogen and the other is other than hydrogen In some embodiments, one of $R^a$ and $R^b$ is methyl and the other is hydrogen In some embodiments, both of $R^a$ and $R^b$ are methyl.

In some embodiments, the biradicle —X—Y— is —$OCH_2$—, W is O, and al of $R^1$, $R^2$, $R^3$, $R^5$ and $R^{5'}$ are all hydrogen. Such LNA nucleosides are disclosed in WO99/014226, WO0066604, WO98/039352 and WO2004/046160 which are all hereby incorporated by reference, and include what are commonly known as beta-D-oxy LNA and alpha-L-oxy LNA nucleosides.

In some embodiments, the biradicle —X—Y— is —S—$CH_2$, W is O, and all of $R^1$, $R^2$, $R^3$, $R^5$ and $R^{5'}$ are all hydrogen. Such thio LNA nucleosides are disclosed in WO99/014226 and WO2004/046160 which are hereby incorporated by reference.

In some embodiments, the biradicle —X—Y— is —NH—$CH_2$. W is O, and all of $R^1$, $R^2$, $R^3$, $R^5$ and $R^{5'}$ are all hydrogen. Such amino LNA nucleosides are disclosed in WO99/014226 and WO2004/046160 which are hereby incorporated by reference.

In some embodiments, the biradicle —X—Y— is —$CH_2CH_2$— or —O—$CH_2$—$CH_2$—$CH_2$—, W is O, and all of $R^1$, $R^2$, $R^3$, $R^5$ and $R^{5'}$ are all hydrogen. Such LNA nucleosides are disclosed in WO00/047599 and Morita et al, Bioorganic & Med. Chem. Lett. 12 73-76, which are hereby incorporated by reference, and include what are commonly known as 2-O-4'C-ethylene bridged nucleic acids (ENA).

In some embodiments, the biradicle —X—Y— is —O—$CH_2$. W is O, and all of $R^1$, $R^2$, $R^3$, and one of $R^5$ and $R^{5'}$ are hydrogen, and the other of $R^5$ and $R^{5'}$ is other than hydrogen such as $C_{1-6}$ alkyl, such as methyl. Such 5' substituted LNA nucleosides are disclosed in WO2007/134181 which is hereby incorporated by reference.

In some embodiments, the biradicle —X—Y— is —O—$CR^aR^b$, wherein one or both of $R^a$ and $R^b$ are other than hydrogen, such as methyl, W is O, and all of $R^1$, $R^2$, $R^3$, and one of $R^5$ and $R^{5'}$ are hydrogen, and the other of $R^5$ and $R^{5'}$ is other than hydrogen such as $C_{1-6}$ alkyl, such as methyl. Such bis modified LNA nucleosides are disclosed in WO2010/077578 which is hereby incorporated by reference.

In some embodiments, the biradicle —X—Y— designate the bivalent linker group —O—$CH(CH_2OCH_3)$— (2' O-methoxyethyl bicyclic nucleic acid—Seth at al., 2010. J. Org. Chem. Vol 75(5) pp. 1569-81). In some embodiments, the biradicle —X—Y— designate the bivalent linker group —O—$CH(CH_2CH_3)$— (2'O-ethyl bicyclic nucleic acid—Seth at al., 2010, J. Org. Chem. Vol 75(5) pp. 1569-81). In some embodiments, the biradicle —X—Y— is —O—$CHR^a$—. W is O, and all of $R^1$, $R^2$, $R^3$, $R^5$ and $R^{5'}$ are all hydrogen. Such 6' substituted LNA nucleosides are disclosed in WO10036698 and WO07090071 which are both hereby incorporated by reference.

In some embodiments, the biradicle —X—Y— is —CH ($CH_2OCH_3$)—, W is O, and all of $R^1$, $R^2$, $R^3$, $R^5$ and $R^{5'}$ are all hydrogen. Such LNA nucleosides are also known as cyclic MOEs in the art (WOE) and are disclosed in WO07090071.

In some embodiments, the biradicle —X—Y— designate the bivalent linker group —O—$CH(CH_3)$—. —in either the R- or S-configuration. In some embodiments, the biradicle —X—Y— together designate the bivalent linker group —O—$CH_2O$—$CH_2$ (Seth at al., 2010, J. Org. Chem). In some embodiments, the biradicle —X—Y— is —O—CH ($CH_3$)—, W is O, and all of $R^1$, $R^2$, $R^3$, $R^5$ and $R^{5'}$ are all hydrogen. Such 6' methyl LNA nucleosides are also known as cET nucleosides in the art, and may be either (S)cET or (R)cET stereoisomers, as disclosed in WO07090071 (beta-D) and WO2010/036698 (alpha-L) which are both hereby incorporated by reference).

In some embodiments, the biradicle —X—Y— is —O—$CR^aR^b$—, wherein in neither $R^a$ or $R^b$ is hydrogen, W is O, and all of $R^1$, $R^2$, $R^3$, $R^5$ and $R^{5'}$ are all hydrogen. In some embodiments, $R^a$ and $R^b$ are both methyl. Such 6' di-substituted LNA nucleosides are disclosed in WO 2009008478 which is hereby Incorporated by reference.

In some embodiments, the biradicle —X—Y— is —S—$CHR^a$—, W is O, and all of $R^1$, $R^2$, $R^3$, $R^5$ and $R^{5'}$ are all hydrogen. Such 6' substituted thio LNA nucleosides are disclosed in WO11156202 which is hereby Incorporated by reference. In some 6' substituted thio LNA embodiments $R^a$ is methyl.

In some embodiments, the biradicle —X—Y— is —C(=$CH_2$)—C($R^aR^b$)—, such as —C(=$CH_2$)—$CH_2$—, or —C(=$CH_2$)—$CH(CH_3)$—W is O, and all of $R^1$, $R^2$, $R^3$, $R^5$ and $R^{5'}$ are all hydrogen. Such vinyl carbo LNA nucleosides are disclosed in WO08154401 and WO09067647 which are both hereby incorporated by reference.

In some embodiments the biradicle —X—Y— is —N(—$OR^a$)—, W is O, and all of $R^1$, $R^2$, $R^3$, $R^5$ and $R^{5'}$ are all hydrogen. In some embodiments $R^a$ is $C_{1-6}$ alkyl such as methyl. Such LNA nucleosides are also known as N substituted LNAs and are disclosed in WO2008/150729 which is hereby incorporated by reference. In some embodiments, the biradicle —X—Y— together designate the bivalent linker group —O—$NR^a$—$CH_3$— (Seth at al., 2010, J. Org. Chem). In some embodiments the biradicle —X—Y— is —N($R^a$)—, W is O, and al of $R^1$, $R^2$, $R^3$, $R^5$ and $R^{5'}$ are all hydrogen. In some embodiments $R^a$ is $C_{1-6}$ alkyl such as methyl.

In some embodiments, one or both of $R^5$ and $R^{5'}$ is hydrogen and, when substituted the other of $R^5$ and $R^{5'}$ is $C_{1-6}$ alkyl such as methyl. In such an embodiment, $R^1$, $R^2$, $R^3$, may all be hydrogen, and the biradicle —X—Y— may be selected from —O—$CH_2$ or —O—C($HCR^a$)—, such as —O—C($HCH_3$)—.

In some embodiments, the biradicle is —$CR^aR^b$—O—$CR^aR^b$—, such as $CH_2O$—$CH_2$, W is O and all of $R^1$, $R^2$, $R^3$, $R^5$ and $R^{5'}$ are all hydrogen. In some embodiments $R^a$ is $C_{1-6}$ alkyl such as methyl. Such LNA nucleosides are also known as conformationally restricted nucleotides (CRNs) and are disclosed in WO2013036868 which is hereby incorporated by reference.

In some embodiments, the biradicle is —O—$CR^aR^b$—O—$CR^aR^b$—, such as O—$CH_2O$—$CH_2$, W is O and all of $R^1$, $R^2$, $R^3$, $R^5$ and $R^{5'}$ are all hydrogen. In some embodiments $R^a$ is $C_{1-6}$ alkyl such as methyl. Such LNA nucleosides are also known as COC nucleotides and are disclosed in Mitsuoka at al., Nucleic Acids Research 2009 37(4). 1225-1238, which is hereby incorporated by reference.

It will be recognized than, unless specified, the LNA nucleosides may be in the beta-D or alpha-L stereoisoform.

Non limiting, exemplary LNA nucleosides are disclosed in WO 99/14226, WO 00/66604, WO 98/039352, WO 20041046160, WO 00/047599, WO 2007/134181, WO 20101077578, WO 2010/036698, WO 2007/090071, WO 20091006478, WO 2011/156202, WO 2008/154401, WO 2009/067647, WO 20081150729, Morkta et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238.

Certain examples of LNA nucleosides are presented in Scheme 1.

Scheme 1

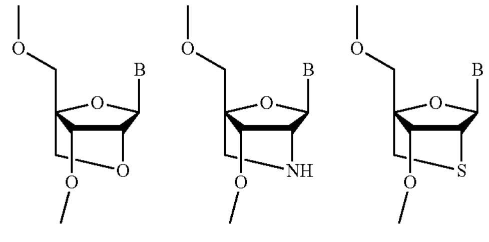

β-D-oxy LNA β-D-amino LNA β-D-thio LNA

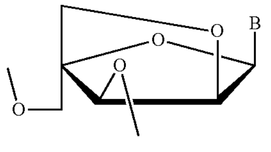

α-L-oxy LNA

-continued

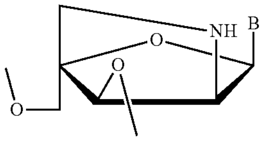

α-L-amino LNA

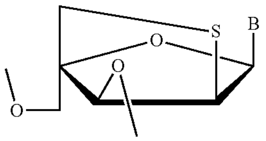

α-L-thio LNA

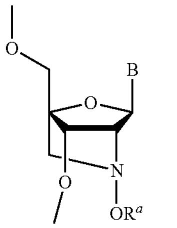

β-D-amino substituted LNA

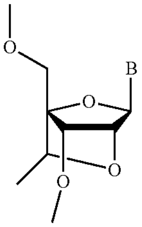

6′methyl β-D-oxy LNA

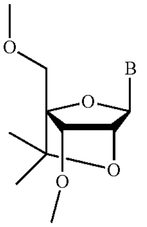

6′dimethylβ-D-oxy LNA

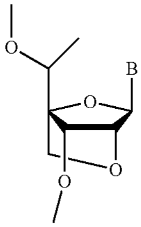

5′ methyl β-D-oxy LNA

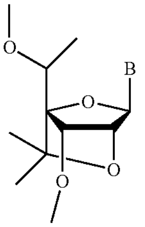

5′methyl, 6′dimethyl β-D-oxy LNA

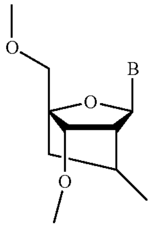

Carbocyclic(vinyl) β-D-LNA

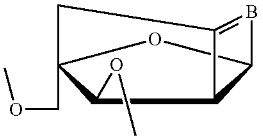

Carbocyclic(vinyl) α-L-LNA

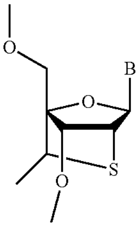

6′ methyl thio β-D LNA

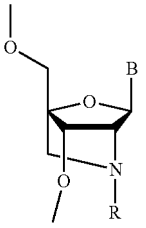

Substituted β-D amino LNA

As illustrated in the examples, in some embodiments of the invention the LNA nucleosides in the oligonucleotides are beta-D-oxy-LNA nucleosides.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers, headmers and tailmers.

RNase H Activity and Recruitment

The RNase H activity of an antisense Oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH, Lucerne, Switzerland Gapmer The antisense oligonucleotide of the invention, or contiguous nucleotide sequence thereof may be a gapmer. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5->3' orientation. The “gap” region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further defined by having at least one sugar modified nucleoside at the end most distant from the gap region. i.e. at the 5' end of the 5' flank and at the 3' end of the 3' flank.

Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, Such as from 14 to 17, such as 16 to 18 nucleosides. By way of example, the gapmer oligonucleotide of the present invention can be represented by the following formulae:

$F_{1-8}$-$G_{5-18}$-$F'_{1-8}$, such as $F_{1-8}$-$G_{7-18}$-$F'_{2-8}$ with the proviso that the overall length of the gapmer regions F-G-F' is at least 12, such as at least 14 nucleotides in length.

Regions F, G and F' are further defined below and can be incorporated into the F-G-F' formula.

Gapmer—Gap, Region G

Region G (gap region) of the gapmer is a region of nucleosides which enables the oligonucleotide to recruit RNaseH, such as human RNase H1. typically DNA nucleosides. RNaseH is a cellular enzyme which recognizes the duplex between DNA and RNA, and enzymatically cleaves the RNA molecule. Suitably gapmers may have a gap region (G) of at least 5 or 6 contiguous DNA nucleosides, such as 5-16 contiguous DNA nucleosides, such as 6-15 contiguous DNA nucleosides, such as 7-14 contiguous DNA nucleosides, such as 8-12 contiguous DNA nucleotides, such as 8-12 contiguous DNA nucleotides in length. The gap region G may, in some embodiments consist of 6, 7, 8, 9, 10, 11, 12, 13, 14, 15 or 16 contiguous DNA nucleosides. Cytosine (C) DNA in the gap region may in some instances be methylated, such residues are either annotated as 5-methyl-cytosine ($^{me}$C or with an a instead of a c). Methylation of Cytosine DNA in the gap is advantageous if cg dinucleotides are present in the gap to reduce potential toxicity, the modification is not expected to have significant impact on efficacy of the oligonucleotides.

In some embodiments the gap region G may consist of 6, 7, 8, 9, 10, 11, 12, 13, 14, 15 or 16 contiguous phosphorothioate linked DNA nucleosides. In some embodiments, all internucleoside linkages in the gap are phosphorothioate linkages.

Whilst traditional gapmers have a DNA gap region, there are numerous examples of modified nucleosides which allow for RNaseH recruitment when they are used within the gap region. Modified nucleosides which have been reported as being capable of recruiting RNaseH when included within a gap region include, for example, alpha-L-LNA, C4' alkylated DNA (as described in PCT/EP2009/050349 and Vaster et al., Bioorg. Med. Chem. Lett. 18 (2008) 2296-2300, both incorporated herein by reference), arabinose derived nucleosides like ANA and 2'F-ANA (Mangos at al. 2003 J. AM. CHEM. SOC. 125, 654-661), UNA (unlocked nucleic acid) (as described in Fluiter et al, Mol. Biosyst., 2009, 10, 1039 incorporated herein by reference). UNA is unlocked nucleic acid, typically where the bond between C2 and C3 of the ribose has been removed, forming an unlocked "sugar" residue. The modified nucleosides used in such gapmers may be nucleosides which adopt a 2' endo (DNA like) structure when introduced Into the gap region, i.e. modifications which allow for RNaseH recruitment). In some embodiments the DNA Gap region (G) described herein may optionally contain 1 to 3 sugar modified nucleosides which adopt a 2' endo (DNA like) structure when Introduced into the gap region.

Region G—"Gap-Breaker"

Alternatively, there are numerous reports of the Insertion of a modified nucleoside which confers a 3' endo conformation into the gap region of gapmers, whist retaining some RNaseH activity. Such gapmers with a gap region comprising one or more 3'endo modified nucleosides are referred to as "gap-breaker" or "gap-disrupted" gapmers, see for example WO2013/022984. Gap-breaker oligonucleotides retain sufficient region of DNA nucleosides within the gap region to allow for RNaseH recruitment. The ability of gapbreaker oligonucleotide design to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA. Modified nucleosides used within the gap region of gap-breaker oligonucleotides may for example be modified nucleosides which confer a 3'endo confirmation, such 2'-O-methyl (OMe) or 2'-O-MOE (MOE) nucleosides, or beta-D LNA nucleosides (the bridge between C2' and C4' of the ribose sugar ring of a nucleoside is in the beta conformation), such as beta-D-oxy LNA or ScET nucleosides.

As with gapmers containing region G described above, the gap region of gap-breaker or gap-disrupted gapmers, have a DNA nucleosides at the 5' end of the gap (adjacent to the 3' nucleoside of region F), and a DNA nucleoside at the 3'end of the gap (adjacent to the 5' nucleoside of region F'). Gapmers which comprise a disrupted gap typically retain a region of at least 3 or 4 contiguous DNA nucleosides at either the 5' end or 3' end of the gap region.

Exemplary designs for gap-breaker oligonucleotides include $F_{1-8}$-[$D_{3-4}$-$E_1$-$D_{3-4}$]$F'_{1-8}$ $F_{1-8}$-[$D_{1-4}$-$E_1$-$D_{3-4}$]-$F'_{1-8}$ $F_{1-4}$-[$D_{3-4}$-$E_1$-$D_{1-4}$]-$F'_{1-8}$ wherein region G is within the brackets [$D_n$~$E_r$-$D_m$], D is a contiguous sequence of DNA nucleosides. E is a modified nucleoside (the gap-breaker or gap-disrupting nucleoside), and F and F' are the flanking regions as defined herein, and with the proviso that the overall length of the gapmer regions F-G-F' is at least 12, such as at least 14 nucleotides in length.

In some embodiments, region G of a gap disrupted gapmer comprises at least 6 DNA nucleosides, such as 6, 7, 8, 9, 10, 11, 12, 13, 14, 15 or 16 DNA nucleosides. As described above, the DNA nucleosides may be contiguous or may optionally be interspersed with one or more modified nucleosides, with the proviso that the gap region G is capable of mediating RNaseH recruitment.

Gapmer—Flanking Regions, F and F'

Region F is positioned immediately adjacent to the 5' DNA nucleoside of region G. The 3' most nucleoside of region F is a sugar modified nucleoside, such as a high affinity sugar modified nucleoside, for example a 2' substituted nucleoside, such as a MOE nucleoside, or an LNA nucleoside.

Region F' is positioned immediately adjacent to the 3' DNA nucleoside of region G. The 5' most nucleoside of region F' is a sugar modified nucleoside, such as a high affinity sugar modified nucleoside, for example a 2' substituted nucleoside, such as a MOE nucleoside, or an LNA nucleoside.

Region F is 1-8 contiguous nucleotides in length, such as 1-6, such as 2-6, such as 3-4 contiguous nucleotides in length. Advantageously the 5' most nucleoside of region F is a sugar modified nucleoside. In some embodiments the two 5' most nucleoside of region F are sugar modified nucleoside. In some embodiments the 5' most nucleoside of region F is an LNA nucleoside. In some embodiments the two 5' most nucleoside of region F are LNA nucleosides. In some embodiments the two 5' most nucleoside of region F are 2' substituted nucleoside nucleosides, such as two 3' MOE nucleosides. In some embodiments the 5' most nucleoside of region F is a 2' substituted nucleoside, such as a MOE nucleoside.

Region F' is 2-8 contiguous nucleotides in length, such as 3-6, such as 4-5 contiguous nucleotides in length. Advantageously, embodiments the 3' most nucleoside of region F' is a sugar modified nucleoside. In some embodiments the two 3' most nucleoside of region F' are sugar modified nucleoside. In some embodiments the two 3' most nucleoside of region F' are LNA nucleosides. In some embodiments the 3'most nucleoside of region F' is an LNA nucleoside. In some embodiments the two 3' most nucleoside of region F' are 2' substituted nucleoside nucleosides, such as two 3' MOE nucleosides. In some embodiments the 3' most nucleoside of region F' is a 2' substituted nucleoside, such as a MOE nucleoside.

It should be noted that when the length of region F or F' is one, it Is advantageously an LNA nucleoside.

In some embodiments, region F and F' independently consists of or comprises a contiguous sequence of sugar modified nucleosides. In some embodiments, the sugar modified nucleosides of region F may be independently selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments, region F and F' independently comprises both LNA and a 2' substituted modified nucleosides (mixed wing design).

In some embodiments, region F and F' consists of only one type of sugar modified nucleosides, such as only MOE or only beta-D-oxy LNA or only ScET. Such designs are also termed uniform flanks or uniform gapmer design.

In some embodiments, all the nucleosides of region F or F', or F and F' are LNA nucleosides, such as Independently selected from beta-D-oxy LNA, ENA or ScET nucleosides. In some embodiments region F consists of 1-5, such as 2-4, such as 3-4 such as 1.2, 3.4 or 5 contiguous LNA nucleosides. In some embodiments, all the nucleosides of region F and F' are beta-D-oxy LNA nucleosides.

In some embodiments, all the nucleosides of region F or F', or F and F' are 2' substituted nucleosides, such as OMe or MOE nucleosides. In some embodiments region F consists of 1, 2, 3, 4, 5, 6, 7, or 8 contiguous OMe or MOE nucleosides. In some embodiments only one of the flanking regions can consist of 2' substituted nucleosides, such as OMe or MOE nucleosides. In some embodiments it is the 5' (F) flanking region that consists 2' substituted nucleosides, such as OMe or MOE nucleosides whereas the 3' (F') flanking region comprises at least one LNA nucleoside, such as beta-D-oxy LNA nucleosides or cET nucleosides. In some embodiments it is the 3' (F') flanking region that consists 2' substituted nucleosides, such as OMe or MOE nucleosides whereas the 5' (F) flanking region comprises at least one LNA nucleoside, such as beta-D-oxy LNA nucleosides or cET nucleosides.

In some embodiments, all the modified nucleosides of region F and F' are LNA nucleosides, such as independently selected from beta-D-oxy LNA, ENA or ScET nucleosides, wherein region F or F, or F and F' may optionally comprise DNA nucleosides (an alternating flank, see definition of these for more details). In some embodiments, all the modified nucleosides of region F and F' are beta-D-oxy LNA nucleosides, wherein region F or F', or F and F' may optionally comprise DNA nucleosides (an alternating flank, see definition of these for more details).

In some embodiments the 5' most and the 3' most nucleosides of region F and F' are LNA nucleosides, such as beta-D-oxy LNA nucleosides or ScET nucleosides.

In some embodiments, the internucleoside linkage between region F and region G is a phosphorothioate internucleoside linkage. In some embodiments, the internucleoside linkage between region F' and region G is a phosphorothioate internucleoside linkage. In some embodiments, the internucleoside linkages between the nucleosides of region F or F', F and F' are phosphorothioate internucleoside linkages.

Further gapmer designs are disclosed in WO20041046160, WO2007/146511 and WO2008/113832, hereby incorporated by reference.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments the LNA gapmer is of formula: $[LNA]_{1-5}$-[region G]-$[LNA]_{1-5}$, wherein region G is as defined in the Gapmer region G definition.

In some embodiments the LNA is beta-D-oxy-LNA and the gapmer has the formula;

$$F_{2-5\ \textit{LNA},\ 0-2\ \textit{DNA}}\text{-}G_{7-11\ \textit{DNA}}\text{-}F'_{3-5\ \textit{LNA},\ 0-2\ \textit{DNA}}$$

MOE Gapmer

A MOE gapmers is a gapmer wherein regions F and F' consist of MOE nucleosides. In some embodiments the MOE gapmer is of design $[MOE]_{1-8}$-[Region G]-$[MOE]_{1-8}$, such as $[MOE]_{2-7}$-$[Region\ G]_{5-19}$-$[MOE]_{2-7}$, such as $[MOE]_{3-6}$-[Region G]-$[MOE]_{3-6}$, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as a MOE nucleosides. In some embodiments wherein at least one of region F and F', or both region F and F' comprise at least one LNA nucleoside, the remaining nucleosides of region F and F' are independently selected from the group consisting of MOE and LNA. In some embodiments wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Mixed wing gapmer designs are disclosed in WO2008/049085 and WO2012/109395, both of which are hereby incorporated by reference.

Alternating Flank Gapmers

Oligonucleotides with alternating flanks are LNA gapmer oligonucleotides where at least one of the flanks (F or F') comprises DNA in addition to the LNA nucleoside(s). In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides.

In some embodiments at least one of region F or F', or both region F and F', comprise both LNA nucleosides and DNA nucleosides. In such embodiments, the flanking region F or F, or both F and F' comprise at least three nucleosides, wherein the 5' and 3' most nucleosides of the F or F' region are LNA nucleosides, and the, Flanking regions which comprise both LNA and DNA nucleoside are referred to as alternating flanks, as they comprise an alternating motif of LNA-DNA-LNA nucleosides. Alternating flank LNA gapmers are disclosed in WO2016/127002.

An alternating flank region may comprise up to 3 contiguous DNA nucleosides, such as 1 to 2 or 1 or 2 or 3 contiguous DNA nucleosides.

The alternating flak can be annotated as a series of integers, representing a number of LNA nucleosides (L) followed by a number of DNA nucleosides (D), for example $[L]_{1-3}$-$[D]_{1-4}$$[L]_{1-3}$ $[L]_{1-2}$-$[D]_{1-2}$$[L]_{1-2}$-$[D]_{1-2}$-$[L]_{1-2}$ In oligonucleotide designs these will often be represented as numbers such that 2-2-1 represents 5' $[L]_2[D]_2$-$[L]_2$-[L] 3', and 1-1-1-1-1 represents 5' [L]-[D]-[L]-[D]-[L] 3'. The length of the flank (region F and F') in oligonucleotides with alternating flanks may independently be 3 to 10 nucleosides, such as 4 to 8, such as 5 to 6 nucleosides, such as 4, 5, 6 or 7 modified nucleosides. In some embodiments only one of the flanks in the gapmer oligonucleotide is alternating while the other is constituted of LNA nucleotides. It may be advantageous to have at least two LNA nucleosides at the 3' end of the 3' flank (F'), to confer additional exonuclease resistance. Some examples of oligonucleotides with alternating flanks are:

$[L]_{1-5}$-$[D]_{1-4}$-$[L]_{1-3}$-$[G]_{5-16}$-$[L]_{2-6}$ $[L]_{1-2}$-$[D]_{1-2}$-$[L]_{1-2}$-$[D]_{1-2}$-$[L]_{1-2}$-$[G]_{5-16}$-$[L]_{1-2}$-$[D]_{1-3}$-$[L]_{2-4}$ $[L]_{1-5}$-$[G]_{5-16}$-[L]-[D]-[L]-[D]-$[L]_2$ with the proviso that the overall length of the gapmer is at least 12, such as at least 14 nucleotides in length.

Region D' or D" in an Oligonucleotide

The oligonucleotide of the invention may in some embodiments comprise or consist of the contiguous nucleotide sequence of the oligonucleotide which is complementary to the target nucleic acid, such as the gapmer F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group. When used for joining the contiguous nucleotide sequence with a conjugate moiety is can serve as a biocleavable linker. Alternatively it may be used to provide exonuclease protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO2014/078195, which include by way of example a phosphodiester linked DNA dinucleotide. The use of biocleavable linkers in poly-oligonucleotide constructs is disclosed in WO2015/113922, where they are used to link multiple antisense constructs (e.g. gapmer regions) within a single oligonucleotide.

In one embodiment the oligonucleotide of the invention comprises a region D' and/or D" in addition to the contiguous nucleotide sequence which constitute the gapmer.

In some embodiments, the oligonucleotide of the present invention can be represented by the following formulae:

F-G-F'; in particular $F_{1-8}$-$G_{5-16}$-$F'_{2-8}$

D'-F-G-F', in particular $D'_{1-3}$-$F_{1-8}$-$G_{5-16}$-$F'_{2-8}$

F-G-F'-D", in particular $F_{1-8}$-$G_{5-18}$-$F'_{2-8}$-$D''_{1-3}$

D'-F-G-F'-D", in particular $D'_{1-3}$-$F_{1-8}$-$G_{5-18}$-$F'_{2-8}$-$D''_{1-3}$ In some embodiments the internucleoside linkage positioned between region D' and region F is a phosphodiester linkage. In some embodiments the internucleoside linkage positioned between region F' and region D" is a phosphodiester linkage.

Conjugate

The term conjugate as used herein refers to an oligonucleotide which is covalently linked to a non-nucleotide moiety (conjugate moiety or region C or third region).

Conjugation of the oligonucleotide of the Invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. A the same time the conjugate may serve to reduce activity of the oligonucleotide in non-target cell types, tissues or organs. e.g., off target activity or activity in non-target cell types, tissues or organs.

WO 93/07883 and WO2013/033230 provides suitable conjugate moieties, which are hereby incorporated by reference. Further suitable conjugate moieties are those capable of binding to the asialoglycoprotein receptor (ASGPR). In particular tri-valent N-acetylgalactosamine conjugate moieties are suitable for binding to the ASGPR, see for example WO 2014/076196. WO 2014/207232 and WO 2014/179620 (hereby incorporated by reference). Such conjugates serve to enhance uptake of the oligonucleotide to the liver while reducing its presence in the kidney, thereby increasing the liver/kidney ratio of a conjugated oligonucleotide compared to the unconjugated version of the same oligonucleotide.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Conjugate Linkers

A linkage or linker is a connection between two atoms that links one chemical group or segment of interest to another chemical group or segment of interest via one or more covalent bonds. Conjugate moieties can be attached to the oligonucleotide directly or through a Inking moiety (e.g. linker or tether). Linkers serve to covalently connect one region, e.g. a conjugate moiety to another region, e.g. an oligonucleotide (e.g. the termini of region A or C).

In some embodiments of the invention the conjugate or oligonucleotide conjugate of the invention may optionally, comprise a linker region which is positioned between the oligonucleotide and the conjugate moiety. In some embodiments, the linker between the conjugate and oligonucleotide is biocleavable. The linker and the oligonucleotide is often attached via a phosphodiester linkage.

Biocleavable linkers (Region B) comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells, Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA.

In one embodiment the linker between the oligonucleotide and the conjugate moiety is a physiologically labile linker composed of 2 to 5 consecutive phosphodiester linked nucleosides at the 5' or 3' terminal of the contiguous nucleotide sequence of the antisense compound. In some embodiments the consecutive phosphodiester linkages are a dinucleotide with a sequence selected from the group consisting of AA, AT, AC, AG, TA, TT, TC, TG, CA, CT, CC, CG, GA, GT, GC, or GG, In some embodiments the consecutive phosphodiester linkages are a trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, or GGG, In specific examples phosphodiester linked CA dinucleotide, with three consecutive phosphodiester linkages, has been used as biocleavable linker between the contiguous nucleotide sequence and the conjugate moiety. Phosphodiester containing biocleavable linkers are described in more detail in WO 2014/076195 (hereby incorporated by reference). In a conjugate compound with a biocleavable linker at least about 50% of the conjugate moiety is cleaved from the oligonucleotide, such as at least about 60% cleaved, such as at least about 70% cleaved, such as at least about 80% cleaved, such as at least about 85% cleaved, such as at least about 90% cleaved, such as at least about 95% of the conjugate moiety is cleaved from the oligonucleotide cleaved when compared against a standard.

Conjugates may also be linked to the oligonucleotide via non-biocleavable linkers, or in some embodiments the conjugate may comprise a non-cleavable linker which is covalently attached to the biocleavable linker. Linkers that are not necessarily biocleavable primarily serve to covalently connect a conjugate moiety to an oligonucleotide or biocleavable linker, and potentially generate some distance between the conjugate moiety and the oligonucleotide. Some example linkers (region Y) include 8-amino-3,6-dioxaoctanoic acid (ADO), succinimidyl 4-(N-maleimidomethyl)cyclohexane-1-carboxylate (SMCC), 6-aminohexanoic acid (AHEX or AHA), 6-aminohexyloxy, 4-aminobutyric acid, 4-aminocyclohexylcarboxylic acid, succinimdyl 4-(N-maleimidomethyl)cyclohexane-1-carboxy-(6-amido-caproate) (LCSMCC), succinimidyl m-maleimido-benzoylate (MBS), succinimidyl N-e-maleimido-caproylate (EMCS), succinimidyl 6-(beta-maleimido-propionamido) hexanoate (SMPH), succinimidyl N-(a-maleimido acetate) (AMAS), succinimidyl 4-(p-maleimidophenyl)butyrate (SMPB). beta-alanine (beta-ALA), phenylglycine (PHG), 4-aminocyclohexanoic acid (ACHC), beta-(cyclopropyl) alanine (beta-CYPR), amino dodecanoic acid (ADC), alylene diols, polyethylene glycols, amino acids, and the like. Non-cleavable linkers may also comprise a chain structure or an oligomer of repeating units such as ethylene glycol, amino acid units or amino alkyl groups. In some embodiments the linker (region Y) is an amino alkyl, such as a $C_2$-$C_{36}$ amino alkyl group, including, for example $C_6$ to $C_{12}$ amino alkyl groups. In some embodiments the linker (region Y) is a $C_6$ amino alkyl group (also termed a C6 linker). Conjugate linker groups may be routinely attached to an oligonucleotide via use of an amino modified oligonucleotide, and an activated ester group on the conjugate group. The linkage group between the amino alkyl and the oligonucleotide may for example be a phosphorothioate or a phosphodiester, or one of the other nucleoside linkage groups referred to herein. A conjugate compound of the present invention may be composed of the following regions C-B-A (Conjugate moiety-biocleavable linker-oligonucleotide/contiguous nucleotide sequence) or C-Y-B-A (conjugate moiety-non-cleavable linker-biocleavable linker-oligonucleotide/contiguous nucleotide sequence).

Treatment

The terms “treatment”, “treating”, “treats” or the like are used herein generally mean obtaining a desired pharmacological and/or physiological effect. This effect is therapeutic in terms of partially or completely curing a disease and/or adverse effect attributed to the disease. The term “treatment” as used herein covers any treatment of a disease in a subject and includes: (a) inhibiting the disease. i.e. arresting its development like the inhibition of increase of HBsAg and/or HBeAg: or (b) ameliorating (i.e. relieving) the disease, i.e. causing regression of the disease, like the repression of HBsAg and/or HBeAg production. Thus, a compound that ameliorates and/or inhibits a HBV infection is a compound that treats a HBV invention. Preferably, the term “treatment” as used herein relates to medical intervention of an already manifested disorder, like the treatment of an already defined and manifested HBV infection.

Prevention

Herein the term "preventing", "prevention" or "prevents" relates to a prophylactic treatment, i.e. to a measure or procedure the purpose of which is to prevent, rather than to cure a disease. Prevention means that a desired pharmacological and/or physiological effect is obtained that is prophylactic in terms of completely or partially preventing a disease or symptom thereof. Accordingly, herein "preventing a HBV infection" includes preventing a HBV infection from occurring in a subject, and preventing the occurrence of symptoms of a HBV infection. In the present invention in particular the prevention of HBV infection in children from HBV infected mothers are contemplated.

Patient

For the purposes of the present invention the "subject" (or "patient") may be a vertebrate. In context of the present invention, the term "subject" includes both humans and other animals, particularly mammals, and other organisms. Thus, the herein provided means and methods are applicable to both human therapy and veterinary applications. Accordingly, herein the subject may be an animal such as a mouse, rat, hamster, rabbit, guinea pig, ferret, cat, dog, chicken, sheep, bovine species, horse, camel, or primate. Preferably, the subject is a mammal. More preferably the subject is human.

HBV Inflection

The term "hepatitis B virus infection" or "HBV infection" is commonly known in the art and refers to an infectious disease that is caused by the hepatitis B virus (HBV) and affects the liver. A HBV Infection can be an acute or a chronic Infection. Some infected persons have no symptoms during the initial infection and some develop a rapid onset of sickness with vomiting, yellowish skin, tiredness, dark urine and abdominal pain ("Hepatitis B Fact sheet No 204". who.int. July 2014. Retrieved 4 Nov. 2014). Often these symptoms last a few weeks and can result in death. It may take 30 to 180 days for symptoms to begin. In those who get infected around the time of birth 90% develop a chronic hepatitis B infection while less than 10% of those infected after the age of five do ("Hepatitis B FAQs for the Public—Transmission", U.S. Centers for Disease Control and Prevention (CDC), retrieved 2011-11-29). Most of those with chronic disease have no symptoms; however, cirrhosis and liver cancer may eventually develop (Chang, 2007, Semin Fetal Neonatal Med, 12: 160-167). These complications result in the death of 15 to 25% of those with chronic disease ("Hepatitis B Fact sheet No 204". who.int. July 2014, retrieved 4 Nov. 2014). Herein, the term "HBV infection" includes the acute and chronic hepatitis 8 infection. The term "HBV infection" also Includes the asymptotic stage of the initial infection, the symptomatic stages, as well as the asymptotic chronic stage of the HBV infection.

Compound

Herein, the term 'compound' means any nucleic acid molecule, such as RNAi molecules or antisense oligonucleotides according to the invention or any conjugate comprising such a nucleic acid molecule. For example, herein the compound may be a nucleic acid molecule targeting PAPD5 and PAPD7, in particular an antisense oligonucleotide.

Composition

The term "composition" may also be used to describe a nucleic acid molecule compound. A nucleic acid molecule composition has less than 20% impurities, preferably less than 15% or 10% impurities, more preferably less than 9, 8, 7 or 6% impurities, most preferably less than 5% impurities. The impurities are typically nucleic acid molecules which are one or two nucleotides shorter (n−1 or n−2) than the primary nucleic acid molecule component. The present invention is further described by reference to the non-limiting figures and examples.

DETAILED DESCRIPTION OF THE INVENTION

PAPD5 and PAPD7 are non-canonical poly(A)-polymerases that belong to the superfamily of polymerase β-like nucleotidyl transferases. In PCT/EP2017/064981 PAPD5 and PAPD7 were identified as relevant targets for inhibition of an HBV infection by inhibiting the production of HBV surface antigen (HBsAg) and the expression of HBV RNA during HBV infection with two small molecules followed by confirmation with pools of siRNA compounds. In PCT/EP2017/064980 antisense oligonucleotides targeting either PAPD5 or PAPD7 were described and combined to achieve in vitro inhibition of an HBV infection.

The present invention has identified target sequences of 12 to 22 nucleotides in length which are shared between human PAPD5 and human PAPD7 mRNA in order to be able to Inhibit both targets with a single nucleic acid molecule. There are around 4500 shared target sites between human PAPD5 and human PAPD7 pre-mRNA. In terms of generating a pharmaceutical acceptable molecule other parameters needs to be taken into account such as the number of off-targets as well as conservation to other species to allow in vivo proof of concept as well as meaningful pharmacokinetic/pharmacodynamic (PK/PD) modelling.

Oligonucleotides of the Invention

The present invention has identified novel antisense oligonucleotides which are capable of inhibiting the expression of both PAPD5 and PAPD7 in vitro and in vivo. The oligonucleotides are complementary to one of three target sites of between 16 and 22 nucleotides in length which are present in both human PAPD5 and human PAPD7.

The inhibition is achieved by hybridizing the antisense oligonucleotide to a target nucleic acid encoding PAPD5 and a target nucleic acid encoding PAPD7. It is understood that the same molecule does not need to hybridize to the two targets simultaneously in order to be effective.

Target nucleic acid 1 may be a mammalian PAPD5 sequence, such as a sequence selected from the group consisting of SEQ ID NO: 1, 3 and 5.

Target nucleic acid 2 may be a mammalian PAPD7 sequence, such as a sequence selected from the group consisting of SEQ ID NO: 2, 4 and 6.

In some embodiments the antisense oligonucleotide of the invention is capable of modulating the expression of target 1 and target 2 by inhibiting or down-regulating them. Preferably, such modulation produces an inhibition of expression of at least 50% compared to the normal expression level of the targets, more preferably at least 60%, 70%, 80%, 90%, 95% or 98% inhibition compared to the normal expression level of the targets. In some embodiments oligonucleotides of the invention are capable of inhibiting expression levels of PAPD5 and PAPD7 mRNA by at least 65%-98%, such as 70% to 95%, in vitro using HeLa cells, this range of target reduction is advantageous in terms of selecting oligonucleotides with good correlation to the HBV antigen reduction, such as HBsAg and/or HBeAg reduction. In some embodiments compounds of the invention may be capable of inhibiting expression levels of PAPD5 and PAPD7 protein by at least 50% in vitro using HeLa cells. The materials and Method section and the Examples herein provide assays which may be used to measure target RNA inhibition in HeLa cells. The target modulation is triggered by the hybridization between a contiguous nucleotide sequence, such as the gapmer region, of the oligonucleotide and the target nucleic acids. In some embodiments the oligonucleotide of the invention comprises mismatches between the oligonucleotide or the contiguous nucleotide sequence and one or both of the target nucleic acids. Despite mismatches hybridization to the target nucleic acid may still be sufficient to show a desired modulation of PAPD5 and PAPD7 expression. Reduced binding affinity resulting from mismatches may advantageously be compensated by increased length of the oligonucleotide and/or an increased number of modified nucleosides capable of increasing the binding affinity to the target within the oligonucleotide sequence. Advantageously, the oligonucleotides of the present invention contain modified nucleosides capable of increasing the binding affinity, such as 2' sugar modified nucleosides, including LNA.

An aspect of the present invention relates to an antisense oligonucleotide of 12 to 32 nucleotides in length, which comprises a contiguous nucleotide sequence of 12 to 22 nucleotides in length which is capable of inhibiting the expression of both PAPD5 and PAPD7.

In some embodiments, the oligonucleotide comprises a contiguous sequence which is at least 90% complementary, such as at least 91%, such as at least 92%, such as at least 93%, such as at least 94%, such as at least 95%, such as at least 96%, such as at least 97%, such as at least 98%, or 100% complementary to the target nucleic acids of SEQ ID NO: 1 and SEQ ID NO: 2, or natural variants thereof.

In one embodiment the antisense oligonucleotide of the invention, or contiguous nucleotide sequence thereof is fully complementary (100% complementary) to a region of the target nucleic acids, or in some embodiments may comprise one or two mismatches between the oligonucleotide and the target nucleic acids.

In some embodiments the antisense oligonucleotide comprises a contiguous nucleotide sequence of 12 to 22 nucleotides in length with at least 93% complementary, such as fully (or 100%) complementary, to a target nucleic acid region present in SEQ ID NO: 1 and SEQ ID NO: 2.

In some embodiments the antisense oligonucleotide or the contiguous nucleotide sequence of the invention is at least 93% complementarity, such as fully (or 100%) complementary, to the target nucleic acid of SEQ ID NO: 1, SEQ ID NO: 2, SEQ ID NO: 3 and SEQ ID NO: 4.

In some embodiments the antisense oligonucleotide or the contiguous nucleotide sequence of the invention is at least 93% complementarity, such as fully (or 100%) complementary, to the target nucleic acid of SEQ ID NO: 1, SEQ ID NO: 2, SEQ ID NO: 5 and SEQ ID NO: 6.

In some embodiments the antisense oligonucleotide or the contiguous nucleotide sequence is 100% complementary to position 64669 to 69429 on SEQ ID NO: 1 and position 29514 to 29530 on SEQ ID NO: 2.

In some embodiments the antisense oligonucleotide or the contiguous nucleotide sequence is 100% complementary to position 6470 to 64685 on SEQ ID NO: 1 and position 29515 to 29530 on SEQ ID NO: 2.

In some embodiments the antisense oligonucleotide or the contiguous nucleotide sequence is 100% complementary to position 69414 to 69429 on SEQ ID NO: 1 and position 30731 to 30746 on SEQ ID NO: 2.

In some embodiments the antisense oligonucleotide or the contiguous nucleotide sequence is 100% complementary to position 759 to 781 on SEQ ID NO: 1 and position 1032 to 1054 on SEQ ID NO: 2.

In some embodiments, the antisense oligonucleotide of the invention comprises or consists of 12 to 32 nucleotides in length, such as from 14 to 25, such as 15 to 22, such as from 18 to 20 contiguous nucleotides in length.

In some embodiments, the contiguous nucleotide sequence of the antisense oligonucleotide which is complementary to the target nucleic acids comprises or consists of 12 to 22, such as from 14 to 20, such as from 18 to 20, such as from 15 to 18, such as from 16 to 18, such as from 16 to 17 contiguous nucleotides in length.

In some embodiments, the antisense oligonucleotide or the contiguous nucleotide sequence thereof comprises or consists of 22 or less nucleotides, such as 20 or less nucleotides, such as 17 or less nucleotides. It is to be understood that any range given herein includes the range endpoints. Accordingly, if an oligonucleotide is said to include from 12 to 32 nucleotides, both 12 and 32 nucleotides are included.

In some embodiments, the antisense oligonucleotide or contiguous nucleotide sequence comprises or consists of 12 to 32 nucleotides in length with at least 93% identity, preferably 100% identity, to a sequence selected from the group consisting of SEQ ID NO: 7 to 16.

In some embodiments, the antisense oligonucleotide or contiguous nucleotide sequence comprises or consists of 12 to 32 nucleotides in length with at least 93% identity, preferably 100% identity, to a sequence selected from the group consisting of SEQ ID NO: 17 to 19.

In some embodiments, the antisense oligonucleotide or contiguous nucleotide sequence comprises or consists of 12 to 32 nucleotides in length with at least 93% identity, preferably 100% identity, to a sequence of SEQ ID NO: 17 or 18.

In some embodiments, the antisense oligonucleotide or contiguous nucleotide sequence comprises or consists of 12 to 32 nucleotides in length with at least 93% identity, preferably 100% identity, to a sequence of SEQ ID NO: 19.

In a further aspect the invention relates to siRNA molecules where the antisense strand has at least 93% identity, preferably 100% identity, to a sequence selected from the group consisting of SEQ ID NO: 17 to 19.

In a further aspect the invention relates to shRNA molecules where a region of the molecule has at least 93% identity, preferably 100% identity, to a sequence selected from the group consisting of SEQ ID NO: 17 to 19.

It is understood that the contiguous nucleobase sequences (motif sequence) can be modified to for example increase nuclease resistance and/or binding affinity to the target nucleic acid.

The pattern in which the high affinity modified nucleotides are incorporated into the oligonucleotide sequence is generally termed oligonucleotide design.

The oligonucleotides of the invention are designed with modified nucleosides and DNA nucleosides. Advantageously, high affinity modified nucleosides are used.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. Suitable modifications are described in the "Definitions" section under "modified nucleoside", "high affinity modified nucleosides". "sugar modifications", "2' sugar modifications' and Locked nucleic acids (LNA)".

In an embodiment, the oligonucleotide comprises one or more sugar modified nucleosides, such as 2' sugar modified nucleosides. Preferably the oligonucleotide of the invention comprise one or more 2' sugar modified nucleoside independently selected from the group consisting of 2'-O-alkyl-RNA, 2-O-methyl-RNA, 2'-alkoxy-RNA, 2'-O-methoxyethyl-RNA, 2'-amino-DNA, 2'-fluoro-DNA, arabino nucleic acid (ANA). 2'-fluoro-ANA and LNA nucleosides. It is advantageous if one or more of the modified nucleoside(s) is a locked nucleic acid (LNA). Often used LNA LNA nucleosides are oxy-LNA, or cET.

In a further embodiment the oligonucleotide comprises at least one modified internucleoside linkage. Suitable internucleoside modifications are described in the "Definitions" section under "Modified internucleoside linkage". It is advantageous if at least 75%, such as all, the internucleoside linkages within the contiguous nucleotide sequence are phosphorothioate or boranophosphate internucleoside linkages. In some embodiments all the internucleotide linkages in the contiguous sequence of the oligonucleotide are phosphorothioate linkages.

In some embodiments, the oligonucleotide of the invention comprises at least one LNA nucleoside, such as 1, 2, 3, 4, 5, 6, 7, or 8 LNA nucleosides, such as from 2 to 6 LNA nucleosides, such as from 3 to 7 LNA nucleosides, 4 to 8 LNA nucleosides or 3, 4, 5, 6, 7 or 8 LNA nucleosides. In some embodiments, at least 75% of the modified nucleosides in the oligonucleotide are LNA nucleosides, such as 80%, such as 85%, such as 90% of the modified nucleosides are LNA nucleosides. In a still further embodiment all the modified nucleosides in the oligonucleotide are LNA nucleosides. In a further embodiment, the oligonucleotide may comprise both beta-D-oxy-LNA, and one or more of the following LNA nucleosides: thio-LNA, amino-LNA, oxy-LNA, ScET and/or ENA in either the beta-D or alpha-L configurations or combinations thereof. In a further embodiment, all LNA cytosine units are 5-methyl-cytosine. It is advantageous for the nuclease stability of the oligonucleotide or contiguous nucleotide sequence to have at least 1 LNA nucleoside at the 5' end and at least 2 LNA nucleosides at the 3' end of the nucleotide sequence.

In an embodiment of the invention the oligonucleotide of the invention is capable of recruiting RNase H.

In the current invention an advantageous structural design is a gapmer design as described in the "Definitions" section under for example "Gapmer", "LNA Gapmer", "MOE gapmer" and "Mixed Wing Gapmer" "Alternating Flank Gapmer". The gapmer design includes gapmers with uniform flanks, mixed wing flanks, alternating flanks, and gapbreaker designs. In the present invention it is advantageous if the oligonucleotide of the invention is a gapmer with an F-G-F' design. In addition to the F-G-F' designs described in the definitions sections one design may be where the F and F' wing regions independently comprise 1-8 2' sugar modified nucleosides and G is a gap region between 5 and 16 nucleosides which are capable of recruiting RNaseH.

In some embodiments the gapmer is an LNA gapmer with uniform flanks or with alternating flanks.

In some embodiments of the invention the LNA gapmer is selected from the following designs uniform flank designs 2-11-3, 2-11-4, 2-12-2, 2-12-3, 2-13-2, 2-9-6, 3-10-3, 3-10-4, 3-11-2, 3-11-3, 3-12-2, 3-9-4, 4-10-2, 4-10-3, 4-11-2, 4-7-5, 4-8-4, 4-9-3, 5-10-2, 5-6-5, 5-7-4, 5-7-5, 5-8-3, 5-8-4, 5-9-2 or 6-9-2.

In some embodiments of the invention the LNA gapmer is selected from the following alternating flanks designs 4-7-1-1-3, 4-9-1-1-2, 1-1-3-7-1-1-2, 1-1-3-9-2, 2-1-1-9-2, 2-1-1-9-3 Table 5 and 7 (Materials and Method section) lists preferred designs of each motif sequence.

In all instances the F-G-F' design may further include region D' and/or D" as described in the "Definitions" section under "Region D' or D" in an oligonucleotide". In some embodiments the oligonucleotide of the invention has 1, 2 or 3 phosphodiester linked nucleoside units, such as DNA units, at the 5' or 3' end of the gapmer region. In some embodiments the oligonucleotide of the Invention consists of two 5' phosphodiester linked DNA nucleosides followed by a F-G-F' gapmer region as defined in the "Definitions" section. In addition to the D'-F-G-F'-D" designs described in the definitions sections one design may be an antisense oligonucleotide wherein a) the F region is between 1 and 6 nucleotides in length and consists of 2-5 identical LNA nucleosides, such as beta-D-oxy LNA or cET, and 0-3 DNA nucleosides; and b) the F' region is between 2 and 6 nucleotides in length and consists of 2-5 identical LNA nucleosides, such as beta-D-oxy LNA or cET, and 0-3 DNA nucleosides; and c) the G region consists of between 5 and 11, such as from 7-10 DNA nucleotides and d) optionally region D' consists of between 1 and 3 phosphodiester linked DNA nucleosides, Oligonucleotides that contain phosphodiester linked DNA units at the 5' or 3' end are suitable for conjugation and may further comprise a conjugate moiety as described herein. For delivery to the liver ASGPR targeting moieties are particular advantageous as conjugate moieties, see the Conjugate section below for further details.

For certain embodiments of the invention, the oligonucleotide is selected from the group of oligonucleotide compounds with CMP ID NO: 7_1 to 7_83 (see oligonucleotides listed in table 5), or pharmaceutically acceptable salts thereof.

For certain embodiments of the invention, the oligonucleotide is selected from the group of oligonucleotide compounds with CMP-ID-NO: 81 to 8_81 (see oligonucleotides listed in table 5, or pharmaceutically acceptable salts thereof.

For certain embodiments of the invention, the oligonucleotide is selected from the group of oligonucleotide compounds with CMP-ID-NO: 9_1 to 9_12 (see oligonucleotides listed in table 5), or pharmaceutically acceptable salts thereof.

For certain embodiments of the invention, the oligonucleotide is selected from the group of oligonucleotide compounds with CMP-ID-NO: 10_1 to 10_18 (see oligonucleotides listed in table 5), or pharmaceutically acceptable salts thereof.

For certain embodiments of the invention, the oligonucleotide is selected from the group of oligonucleotide compounds with CMP-ID-NO: 11_1 to 11_26 (see oligonucleotides listed in table 5), or pharmaceutically acceptable salts thereof.

For certain embodiments of the invention, the oligonucleotide is selected from the group of oligonucleotide compounds with CMP-ID-NO: 12_1 to 12_15 (see oligonucleotides listed in table 5), or pharmaceutically acceptable salts thereof.

For certain embodiments of the invention, the oligonucleotide is selected from the group of oligonucleotide compounds with CMP-ID-NO: 13_1 or 13_2 (see oligonucleotides listed in table 5).

For certain embodiments of the invention, the oligonucleotide is selected from the group of oligonucleotide compounds with CMP-ID-NO: 14_1 to 14_13 (see oligonucleotides listed in table 5), or pharmaceutically acceptable salts thereof.

For certain embodiments of the invention, the oligonucleotide is selected from the group of oligonucleotide compounds with CMP-ID-NO: 15_1 to 15_21 (see oligonucleotides listed in table 5), or pharmaceutically acceptable salts thereof.

For certain embodiments of the invention, the oligonucleotide is selected from the group of oligonucleotide compounds with CMP-ID-NO: 16_1 to 16_5 (see oligonucleotides listed in table 5).

For certain embodiments of the invention, the oligonucleotide is selected from the group of oligonucleotide compounds with CMP-ID-NO: 17_1 to 17_18_3 (see oligonucleotides listed in table 7), or pharmaceutically acceptable salts thereof.

For certain embodiments of the invention, the oligonucleotide is selected from the group of oligonucleotide compounds with CMP-ID-NO: 18_1 to 18_31 or 18_250 to 18_361 (see oligonucleotides listed in table 7), or pharmaceutically acceptable salts thereof.

For certain embodiments of the invention, the oligonucleotide is selected from the group of oligonucleotide compounds with CMP-ID-NO: 18_32 to 18_249 or 18_362 to 18_610 (see oligonucleotides listed in table 7), or pharmaceutically acceptable salts thereof.

For certain embodiments of the invention, the oligonucleotide is selected from the group of oligonucleotide compounds with CMP-ID-NO: 191 to 1922 (see oligonucleotides listed in table 7), or pharmaceutically acceptable salts thereof.

In an embodiment of the invention the oligonucleotide is selected from the group of oligonucleotide with the compound with CMP-ID-NO: 18_1, 18_5, 18_10, 18_15, 18_18, 18_19, 18_24, 18_27, 18_30, 18_346, 18_347, 18_357, 17_10, 17_137 and 17_139.

In an embodiment of the invention the oligonucleotide is selected from the group of oligonucleotide with the compound with CMP-ID-NO: 18_1, 181_5, 18_30, 17_10, 17_137 and 17_139.

In a further embodiment of the invention the oligonucleotide may comprise at least one stereodefined internucleoside linkages, such as a stereodefined phosphorothioate internucleoside linkage.

A key advantage of generating stereodefined oligonucleotide variants is the ability to increase the diversity across a sequence motif, and select stereodefined oligonucleotides including sub-libraries of stereodefined oligonucleotides, which have Improved medicinal chemical properties as compared to a parent oligonucleotide.

In some embodiments, the improved medicinal chemical property (or improved properties) is selected from one or more of enhanced potency, enhanced specific activity, enhanced tissue uptake, enhanced cellular uptake, enhanced efficacy, altered biodistribution, reduced off-target effects, enhanced mismatch discrimination, reduced toxicity, reduced immunogenicity, altered serum protein binding, improved duration of action, and stability. Improvement in one or more property is assessed as compared to the parent oligonucleotide, such as a stereorandom parent oligonucleotide.

In some embodiments the improved property may be the ability of the oligonucleotide to modulate target expression, such as via an improved interaction with the cellular machinery involved in modulating target expression, by way of example, an enhanced RNase H activity, an improved splice modulating activity, or an improved microRNA inhibition.

In some embodiments, the improved property is RNaseH specificity, RNaseH allelic discrimination (i.e. discrimination between single nucleotide polymorphisms (SNPs) and/or RNaseH activity. In some embodiments, the improved property is other than RNaseH specificity, RNaseH allelic discrimination and/or RNaseH activity. In some embodiments the improved property is improved intracellular uptake. In some embodiments the improved property is reduced toxicity, such as cytotoxicity or hepatotoxicity.

A stereodefined oligonucleotide which exhibits one or more Improved property as compared to a parent oligonucleotide, or other stereodefined oligonucleotides, is referred to as an improved phosphorothioate variant.

In an embodiment of the Invention the oligonucleotide is selected from the group of oligonucleotide with the compound with CMP-ID-NO: 18_223, 18_36, 18_196, 18_188, 18_243.

In a further aspect of the invention the nucleic acid molecules, such as the antisense oligonucleotide, of the invention can be targeted directly to the liver by covalently attaching them to a conjugate moiety capable of binding to the asialoglycoprotein receptor (ASGPr), such as divalent or trivalent GalNAc cluster.

Conjugates

Since HBV infection primarily affects the hepatocytes in the liver it is advantageous to conjugate the antisense oligonucleotides of the invention to a conjugate moiety that will increase the delivery of the oligonucleotide to the liver compared to the unconjugated oligonucleotide. In one embodiment liver targeting moieties are selected from moieties comprising cholesterol or other lipids or conjugate moieties capable of binding to the asialoglycoprotein receptor (ASGPR).

In some embodiments the invention provides a conjugate comprising an antisense oligonucleotide of the invention covalently attached to a conjugate moiety.

The asialoglycoprotein receptor (ASGPR) conjugate moiety comprises one or more carbohydrate moieties capable of binding to the asialoglycoprotein receptor (ASPGR targeting moieties) with affinity equal to or greater than that of galactose. The affinities of numerous galactose derivatives for the asialoglycoprotein receptor have been studied (see for example: Jobst, S. T. and Drickamer, K. JB. C. 1996, 271, 6686) or are readily determined using methods typical in the art.

In one embodiment the conjugate moiety comprises at least one asialoglycoprotein receptor targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine. Advantageously the asialoglycoprotein receptor targeting moiety is N-acetylgalactosamine (GalNAc).

To generate the ASGPR conjugate moiety the ASPGR targeting moieties (preferably GalNAc) can be attached to a conjugate scaffold. Generally the ASPGR targeting moieties can be at the same end of the scaffold. In one embodiment the conjugate moiety consists of two to four terminal GalNAc moieties linked to a spacer which links each GalNAc moiety to a brancher molecule that can be conjugated to the antisense oligonucleotide.

In a further embodiment the conjugate moiety is mono-valent, di-valent, tri-valent or tetra-valent with respect to asialoglycoprotein receptor targeting moieties. Advantageously the asialoglycoprotein receptor targeting moiety comprises N-acetylgalactosamine (GalNAc) moieties.

The the ASPGR targeting scaffold which constitute the conjugate moiety can for example be generated by linking the GalNAc moiety to the spacer through its C-I carbon. A preferred spacer is a flexible hydrophilic spacer (U.S. Pat. No. 5,885,968; Biessen et al. J. Med. Chem. 1995 Vol. 39 p. 1538-1546). A preferred flexible hydrophilic spacer is a PEG spacer. A preferred PEG spacer is a PEG3 spacer. The branch point can be any small molecule which permits attachment of two to three GalNAc moieties or other asialoglycoprotein receptor targeting moieties and further permits attachment of the branch point to the oligonucleotide, such constructs are termed GalNAc clusters or GalNAc conjugate moieties. An exemplary branch point group is a di-lysine. A di-lysine molecule contains three amine groups through which three GalNAc moieties or other asialoglycoprotein receptor targeting moieties may be attached and a carboxyl reactive group through which the di-lysine may be attached to the oligomer. Khorev, et al 2008 Bioorg. Med. Chem. Vol 16, pp. 5216 also describes the synthesis of a suitable trivalent brancher. Other commercially available branchers are 1,3-bis-[5-(4,4'-dimethoxytrityloxy)pentylamido]propyl-2-[(2-cyanoethyl)-(N,N-diisopropyl)] phosphoramidite (Glen Research Catalogue Number: 10-1920-xx); tris-2,2,2-[3-(4,4'-dimethoxytrityloxy)propyloxymethyl]ethyl-((2-cyanoethyl)-(N,N-diisopropyl)]-phosphoramidite (Glen Research Catalogue Number: 10-1922-xx); and tris-2,2,2-[3-(4,4'-dimethoxytrityloxy)propyloxymethyl]methyenoxypropy-[(2-cyanoethyl)-(N,N-diisopropyl)]-phosphoramidite; and 1-[5-(4,4'-dimethoxy-trityloxy)pentylamido]-3-[5-fluorenomethoxy-carbonyl-oxy-pentylamido]-propy-2-[(2-cyanoethyl)-(N,N-disopropyl)]-phosphoramidite (Glen Research Catalogue Number: 10-1925-xo).

Other GalNAc conjugate moieties can include, for example, those described in WO 2014/179620 and WO 2016/055601 and PCT/EP2017/059080 (hereby incorporated by reference), as well as small peptides with GalNAc moieties attached such as Tyr-Glu-Glu-(aminohexyl GalNAc)3 (YEE(ahGalNAc)3; a glycotripeptide that binds to asialoglycoprotein receptor on hepatocytes, see, e.g., Duff, at al., Methods Enzymol. 2000, 313, 297); lysine-based galactose clusters (e.g., L3G4; Blessen, et al., Cardovasc. Med., 1999, 214); and cholane-based galactose clusters (e.g., carbohydrate recognition motif for asialoglycoprotein receptor).

The ASGPR conjugate moiety, in particular a trivalent GalNAc conjugate moiety, may be attached to the 3'- or 5'-end of the oligonucleotide using methods known in the art. In one embodiment the ASGPR conjugate moiety is linked to the 5'-end of the oligonucleotide.

One or more linkers may be inserted between the conjugate moiety (such as at the brancher molecule) and the oligonucleotide. It is advantageous to have a biocleavable linker between the conjugate moiety and the antisense oligonucleotide, optionally in combination with a non-cleavable linker such as a C6 linker. The linker(s) may be selected from the linkers described in the "Definitions" section under "Conjugate linkers" in particular biocleavable region D' or D" linkers are advantageous.

Figure 1D:
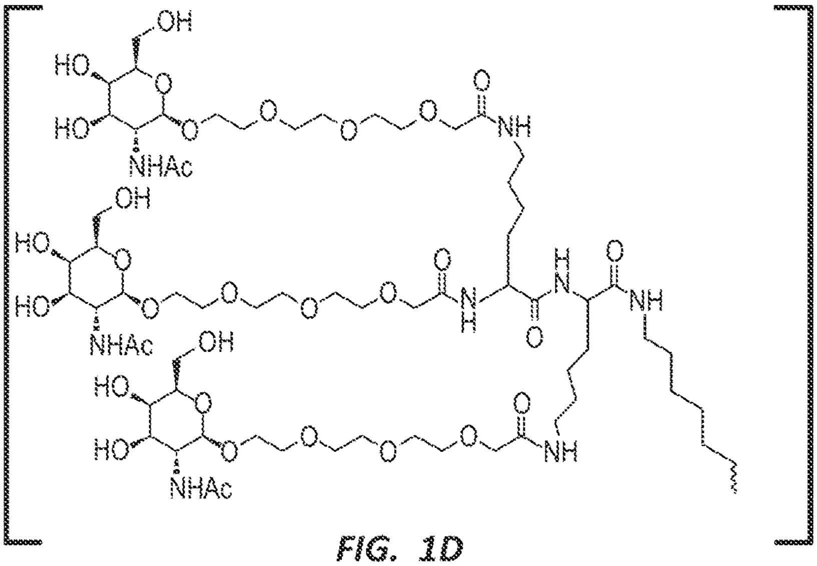
Figure 1E:
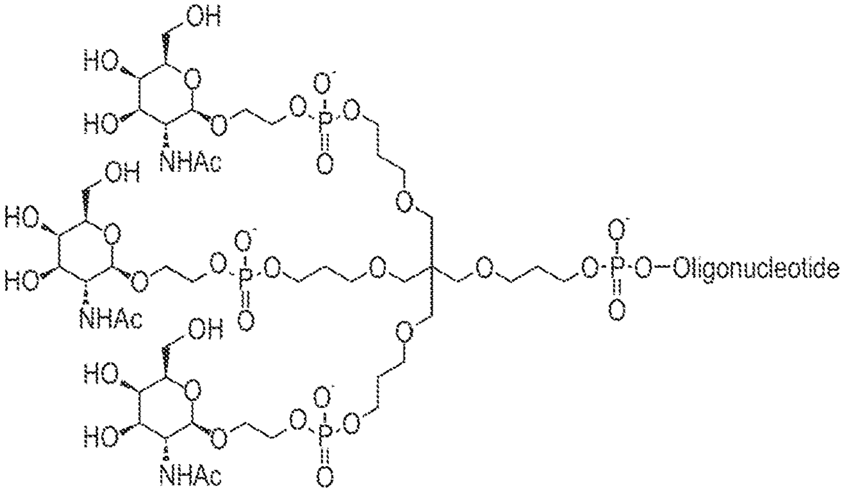
Figure 1F:
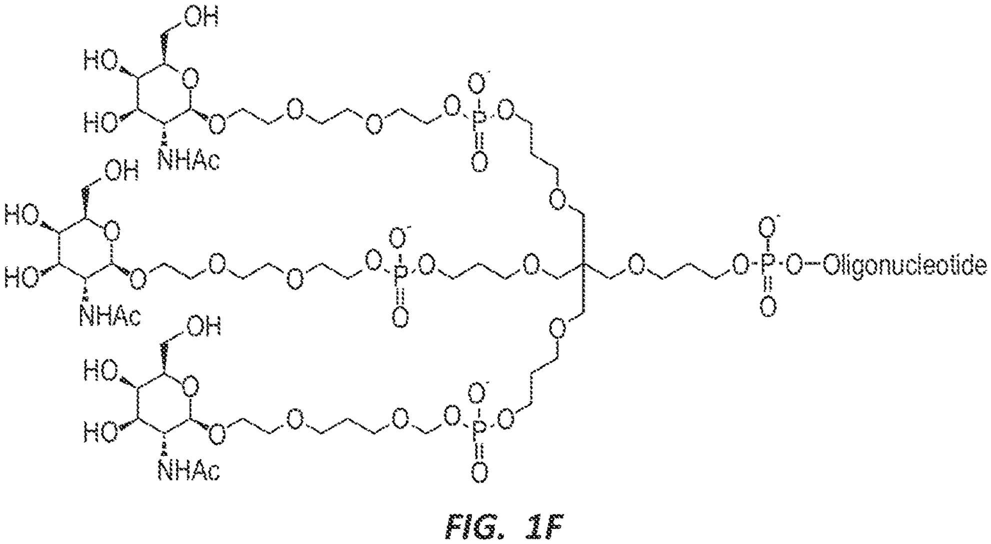
Figure 1G:
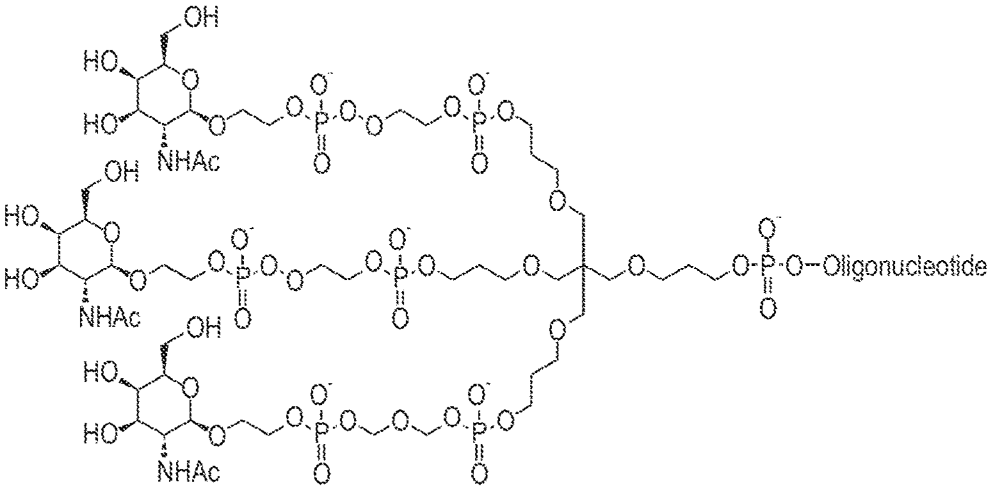
Figure 1H:
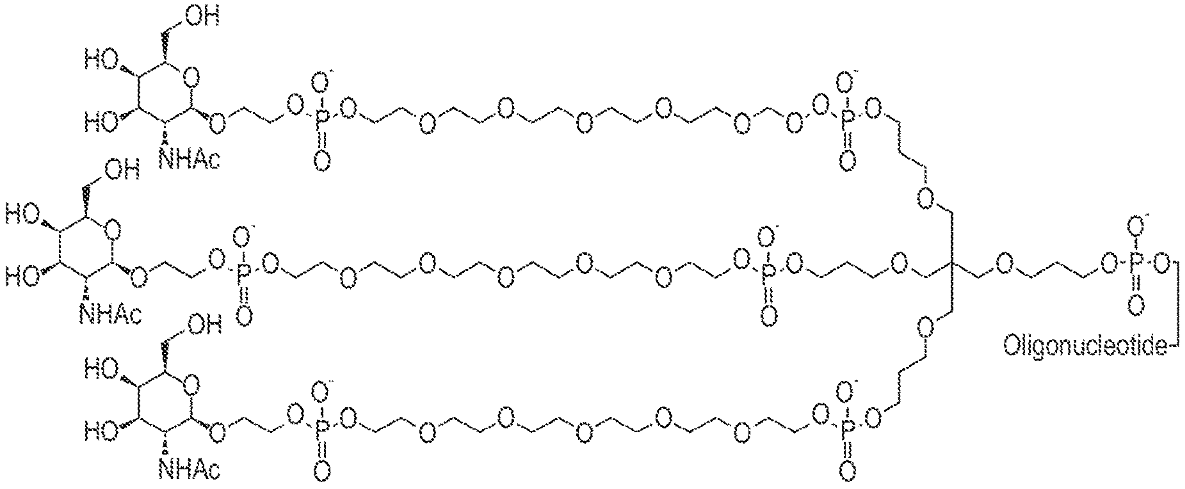
Figure 1I:
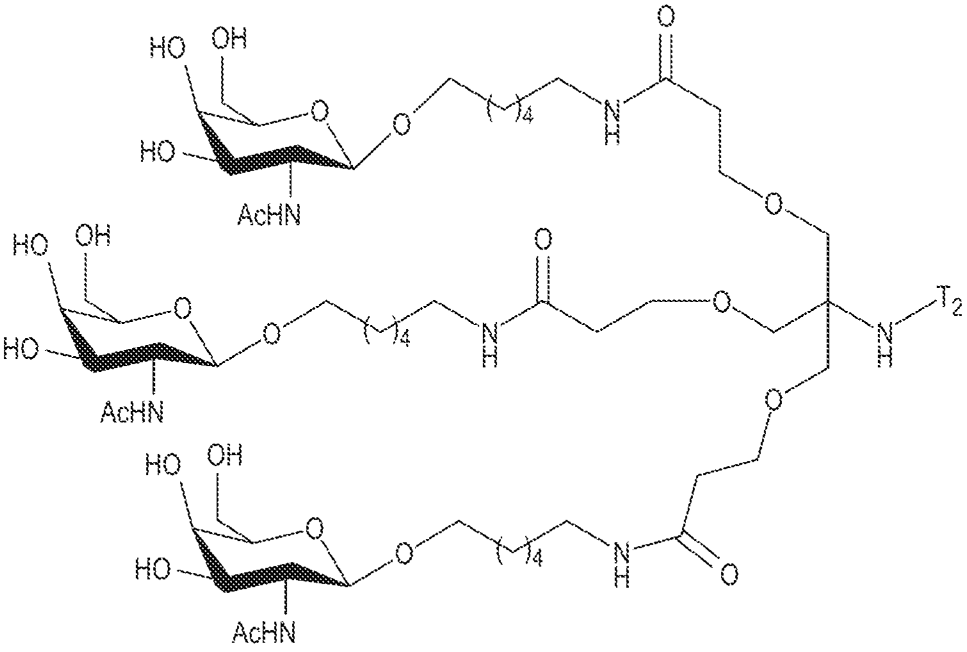

In one embodiment the conjugate moiety is a tri-valent N-acetylgalactosamine (GalNAc), such as those shown in FIG. 1, in particular as shown in FIG. 1D.

In an embodiment of the invention the conjugate compound Is selected from the group of compounds in table 9 in the Material and Method section.

In an embodiment of the Invention the conjugate compound is CMP-ID-NO: 20_12.

In an embodiment of the invention the conjugate compound is CMP-ID-NO 20_13.

In an embodiment of the invention the conjugate compound is CMP-ID-NO 20_14.

In an embodiment of the Invention the conjugate compound is CMP-ID-NO 20_15.

In an embodiment of the invention the conjugate compound is CMP-ID-NO 20_16.

In an embodiment of the Invention the conjugate compound is CMP-ID-NO 20_18.

In an embodiment of the invention the conjugate compound is CMP-ID-NO 20_20.

In an embodiment of the Invention the conjugate compound is CMP-ID-NO 20_21.

In an embodiment of the invention the conjugate compound is CMP-ID-NO 20_22.

In an embodiment of the invention the conjugate compound is CMP-ID-NO 20_30.

In an embodiment of the invention the conjugate compound is CMP-ID-NO 20_35.

In an embodiment of the invention the conjugate compound is CMP-ID-NO 20_36.

In an embodiment of the invention the conjugate compound is CMP-ID-NO 21_2.

In an embodiment of the invention the conjugate compound is CMP-ID-NO 21_33.

In an embodiment of the invention the conjugate compound is CMP-ID-NO 21_34.

Method of Manufacture

In a further aspect, the invention provides methods for manufacturing the antisense oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Compositions

In a further aspect, the Invention provides pharmaceutical compositions comprising an antisense oligonucleotides and/or conjugate compounds of the invention or salts thereof and a pharmaceutically acceptable diluent, carrier, salt and/or adjuvant. A typical pharmaceutical composition is prepared by mixing antisense oligonucleotide or conjugate compound of the invention and a diluent, carrier, or excipient.

A pharmaceutically acceptable diluent includes phosphate-buffered saline (PBS). In some embodiments the pharmaceutically acceptable diluent is sterile phosphate buffered saline. In some embodiments the oligonucleotide is used in the pharmaceutically acceptable diluent at a concentration of 50-300 μM solution.

For nucleic acid molecules, antisense oligonucleotides and conjugate compound comprising these suitable formulations are found in Remington's Pharmaceutical Sciences, Mack Publishing Company, Philadelphia. Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby Incorporated by reference). Suitable dosages, formulations, administration routes, compositions, dosage forms, combinations with other therapeutic agents, pro-drug formulations are also provided in WO2007/031091.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesufonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin. Organic Process Research & Development 2000, 4, 427-435 or in Ansel, In: Pharmaceutical Dosage Forms and Drug Delivery Systems, 6th ed. (1995), pp. 196 and 1458-1457. For example, the pharmaceutically acceptable salt of the compounds provided herein may be a sodium salt or potassium salt.

Applications

The oligonucleotides of the invention may be utilized as research reagents for, for example, diagnostics, therapeutics and prophylaxis.

In research, such oligonucleotides may be used to specifically modulate the synthesis of PAPD6 and PAPD7 protein in cells (e.g. in vitro cell cultures) and experimental animals thereby facilitating functional analysis of the target or an appraisal of its usefulness as a target for therapeutic intervention. Typically the target modulation is achieved by degrading or inhibiting the mRNA producing the protein, thereby prevent protein formation or by degrading or inhibiting a modulator of the gene or mRNA producing the protein.

If employing the oligonucleotide of the invention in research or diagnostics the target nucleic acid may be a cDNA or a synthetic nucleic acid derived from DNA or RNA.

Also encompassed by the present invention is an in vivo or in vivo method for modulating PAPD5 and PAPD7 expression in a target cell which is expressing PAPD5 and PAPD7, said method comprising administering an antisense oligonucleotide, conjugate compound or pharmaceutical composition of the invention in an effective amount to said cell.

In some embodiments, the target cell, Is a mammalian cell in particular a human cell. The target cell may be an in vitro cell culture or an in vivo cell forming part of a tissue in a mammal. In preferred embodiments the target cell is present in in the liver. The target cell may be a hepatocyte.

One aspect of the present invention is related the antisense oligonucleotides, conjugate compounds or pharmaceutical compositions of the invention for use as a medicament.

In an aspect of the invention the antisense oligonucleotide, conjugate compound or pharmaceutical composition of the invention is capable of inhibiting the propagation of HBV. In particular the antisense oligonucleotide is capable of affecting one or more of the following parameters i) reduce the expression of viral RNA; ii) reduce the production of viral DNA (HBV DNA) derived from viral RNA (HBV RNA), iii) reduce the production of new viral particles (HBV particles); iv) reduce production of HBV antigens, in particular HBsAg and/or HBeAg.

For example, an antisense oligonucleotide that inhibits propagation of HBV may reduce i) the expression of viral RNA (HBV RNA) by at least 40% such as 50%, 60%, 70%, 80%, or 90% reduction compared to controls; ii) the production of viral DNA (HBV DNA) by at least 40% such as 50%, 60%, 70%, 80%, or 90% reduction compared to controls: iii) the production of new viral particles (HBV particles) by at least 40% such as 50%, 60%, 70%, 80%, or 90% reduction compared to controls; or iv) the production and/or secretion of HBsAg and/or HBeAg by at least 50%, such as at least 60%, 70%, 80%, 90% or even up to complete depletion of one or both of the antigens compared to controls. The controls may be untreated cells or animals or cell or animal treated with an appropriate control.

Inhibition of propagation of HBV may be measured in vitro using HBV infected dHepaRG cells or ASGPR-dHepaRG cells or in vivo for oligonucleotides complementary to mouse PAPD5 and PAPD7 using the AAV/HBV mouse model as described in the Materials and Methods section. Inhibition of secretion of HBsAg and/or HBeAg may be measured by ELISA, e.g. by using the CLIA ELISA Kit (Autobio Diagnostic) according to the manufacturers' instructions. Inhibition of production of intracellular HBV mRNA may be measured by real-time PCR, e.g. as described in the Materials and Methods section. Further methods for evaluating whether a test compound inhibits propagation of HBV are measuring secretion of HBV DNA by RT-qPCR e.g. as described in WO 2015/173208 or as described in Materials and method section; Northern Blot; in-situ hybridization, or immuno-fluorescence.

Due to the reduction of HBsAg secretion the antisense oligonucleotides, conjugate compounds or pharmaceutical compositions of the present invention can be used to inhibit development of or in the treatment of HBV infection. In particular, due to Inhibition of HBeAg secretion, the antisense oligonucleotides, conjugate compounds or pharmaceutical compositions of the present invention more efficiently inhibits development of or treats a chronic HBV infection as compared to a compound that only reduces secretion of HBsAg. In addition, reducing HBeAg in an expecting mother may also inhibit the development of a chronic HBV infection of her child. Thus, due to the reduction of HBeAg secretion the antisense oligonucleotides, conjugate compounds or pharmaceutical compositions of the present Invention inhibits development of a chronic HBV infection (such as development of a chronic HBV infection in the offspring of an HBV infected mother) and reduces the infectiousness of a HBV infected person.

Accordingly, one aspect of the present invention is related to use of the antisense oligonucleotides, conjugate compounds or pharmaceutical compositions of the invention to reduce secretion of HBsAg and HBeAg in an HBV infected individual. It is advantageous if the antisense oligonucleotides, conjugate compounds or pharmaceutical compositions of the invention are capable of reducing HBsAg expression from HBV DNA integrated into the host genome.

A further aspect of the invention relates to the use of the antisense oligonucleotides, conjugate compounds or pharmaceutical compositions of the invention to inhibit development of or treat a chronic HBV infection.

A further aspect of the Invention relates to the use of the antisense oligonucleotides, conjugate compounds or pharmaceutical compositions of the invention to and reduces the infectiousness of a HBV infected person. In a particular aspect of the invention, the antisense oligonucleotides, conjugate compounds or pharmaceutical compositions of the invention inhibits development of a chronic HBV infection in the offspring of a HBV infected mother. This mother is preferably HBeAg positive.

The subject to be treated with the antisense oligonucleotides, conjugate compounds or pharmaceutical compositions of the invention (or which prophylactically receives antisense oligonucleotides, conjugate compounds or pharmaceutical compositions of the present invention) is preferably a human, more preferably a human patient who is HBsAg positive and/or HBeAg positive, even more preferably a human patient that is HBsAg positive and HBeAg positive. Said human patient may be an expected mother. e.g. an expected mother who is HBeAg positive and/or HBsAg positive, more preferably an expected mother who is HBeAg positive and HBsAg positive.

Accordingly, the present invention relates to a method of treating and/or preventing a HBV infection, wherein the method comprises administering an effective amount of the antisense oligonucleotides, conjugate compounds or pharmaceutical compositions of the invention.

The invention also provides for the use of a nucleic acid molecule, an antisense oligonucleotide, a conjugate compound or a pharmaceutical composition of the invention for the manufacture of a medicament, in particular a medicament for use in the treatment or prevention of HBV infection or chronic HBV infection or reduction of the infectiousness of a HBV infected person. In preferred embodiments the medicament is manufactured in a dosage form for subcutaneous administration.

The invention also provides for the use of a nucleic acid molecule, an antisense oligonucleotide, a conjugate compound, the pharmaceutical composition of the invention for the manufacture of a medicament wherein the medicament is in a dosage form for intravenous administration.

The nucleic acid molecule, antisense oligonucleotide or the pharmaceutical composition of the invention may be used in a combination therapy. For example, nucleic acid molecule, antisense oligonucleotide, or the pharmaceutical composition of the invention may be combined with other anti-HBV agents such as interferon alpha-2b, Interferon alpha-2a, and interferon alphacon-1 (pegylated and unpegylated), ribavirin, lamivudine (3TC), entecavir, tenofovir, telbivudine (LdT), adefovir, or other emerging anti-HBV agents such as a HBV RNA replication inhibitor, a HBsAg secretion inhibitor, a HBV capsid inhibitor, an antisense oligomer (e.g. as described in WO20121145697 and WO 2014/179629), a siRNA (e.g. described in WO 2005/014806, WO 2012/024170, WO 2012/2055362, WO 2013/003520, WO 2013/159109, WO 2017/027350 and WO2017/015175), a HBV therapeutic vaccine, a HBV prophylactic vaccine, a HBV antibody therapy (monoclonal or polyclonal), or TLR 2, 3, 7, 8 or 9 agonists for the treatment and/or prophylaxis of HBV.

Administration

The antisense oligonucleotides, conjugate compounds or pharmaceutical composition of the invention is formulated, dosed, and administered in a fashion consistent with good medical practice. Factors for consideration in this context include the particular mammal being treated, the clinical condition of the individual patient, the site of delivery of the agent, the method of administration, the scheduling of administration, the age and sex of the patients and other factors known to medical practitioners. Herein, an "effective amount" (also known as "(therapeutically) effective dose") means the amount of a compound that will elicit the biological or medical response of a subject that is being sought by a medical doctor or other clinician. The "effective amount" of an antisense oligonucleotide, conjugate compound or pharmaceutical composition of the invention, will be governed by such considerations, and is the minimum amount necessary to inhibit HBsAg and/or HBeAg. For example, such amount may be below the amount that is toxic to the cells of the recipient, or to the mammal as a whole.

In some embodiments, the oligonucleotide, oligonucleotide conjugate or pharmaceutical composition of the invention is administered at a dose of 0.1-15 mg/kg, such as from 0.2-10 mg/kg, such as from 0.25-5 mg/kg. The administration can be once a week, every $2^{nd}$ week, every third week or even once a month.

The nucleic acid molecules or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, intramuscular, intracerebral, intracerebroventricular or intrathecal).

In a preferred embodiment the nucleic acid molecule, antisense oligonucleotide, conjugate compounds or pharmaceutical compositions of the present invention are administered by a parenteral route including intravenous, intraarterial, subcutaneous, intraperitoneal or intramuscular injection or infusion. In one embodiment the active oligonucleotide or oligonucleotide conjugate is administered intravenously. With GalNAc conjugated compounds it may be advantageous to administer subcutaneously in order to delay saturation of the ASGP receptor.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above.

By way of example, the oligomer or the oligomer conjugate of the present invention may be used in combination with other actives, such as oligonucleotide-based antivirals—such as sequence specific oligonucleotide-based antivirals—acting either through antisense (including other LNA oligomers), siRNAs (such as ARC520), aptamers, morpholinos or any other antiviral, nucleotide sequence-dependent mode of action.

By way of further example, the oligomer or the oligomer conjugate of the present Invention may be used in combination with other actives, such as immune stimulatory antiviral compounds, such as Interferon (e.g. pegylated interferon alpha), TLR7 agonists (e.g. GS-9620), or therapeutic vaccines.

By way of further example, the oligomer or the oligomer conjugate of the present Invention may be used in combination with other actives, such as small molecules, with antiviral activity. These other actives could be, for example, nucleoside/nucleotide inhibitors (eg entecavir or tenofovir disoproxil fumarate), encapsidation inhibitors, entry inhibitors (eg Myrcludex B).

In certain embodiments, the additional therapeutic agent may be an HBV agent, an Hepatitis C virus (HCV) agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, or an immunosuppressant agent.

In particular related embodiments, the additional HBV agent may be interferon alpha-2b, interferon alpha-2a, and interferon alphacon-1 (pegylated and unpegylated), ribavirin; an HBV RNA replication inhibitor, a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In other particular related embodiments, the additional HCV agent may be interferon alpha-2b, interferon alpha-2a, and interferon alphacon-1 (pegylated and unpegylated); ribavirin; pegasys; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

Embodiments of the Invention

The following embodiments of the present invention may be used in combination with any other embodiments described herein.

1. A nucleic acid molecule of 12 to 32 nucleotides in length, which comprises a contiguous nucleotide sequence of 12 to 22 nucleotides in length which is capable of inhibiting the expression of both PAPD5 and PAPD7.

2. The nucleic acid molecule of embodiment 1, wherein the contiguous nucleotide sequence is at least 93% complementarity to target nucleic acid of SEQ ID NO: 1 and SEQ ID NO: 2.

3. The nucleic acid molecule of embodiment i or 2, wherein the contiguous nucleotide sequence is at least 100% complementarity to target nucleic acid of SEQ ID NO: 1 and SEQ ID NO: 2.

4. The nucleic acid molecule of embodiment 1 or 3, wherein the contiguous nucleotide sequence is complementary to target nucleic acid of SEQ ID NO: 1, SEQ ID NO: 2, SEQ ID NO: 3 and SEQ ID NO: 4.

5. The nucleic acid molecule of embodiment 1 or 3, wherein the contiguous nucleotide sequence is complementary to target nucleic acid of SEQ ID NO: 1, SEQ ID NO: 2, SEQ ID NO: and SEQ ID NO: 8.

6. The nucleic acid molecule of embodiment 1 to 3 or 5, wherein the nucleic acid molecule is complementary to position 759 to 781 on SEQ ID NO: 1 and position 1032 to 1054 on SEQ ID NO: 2.

7. The nucleic acid molecule of embodiment 1 to 4, wherein the nucleic acid molecule is complementary to position 64669 to 69429 on SEQ ID NO: 1 and position 29514 to 29530 on SEQ ID NO: 2.

8. The nucleic acid molecule of embodiment 1 to 4, wherein the nucleic acid molecule is complementary to position 69414 to 69429 on SEQ ID NO: 1 and position 30731 to 30746 on SEQ ID NO: 2.

9. The nucleic acid molecule of embodiment 1 to 8 is capable of hybridizing to a target nucleic acid of SEQ ID NO: 1 and SEQ ID NO: 2 with a ΔG° below −15 kcal.

10. The nucleic acid molecule of embodiment 2 to 9, wherein the target nucleic acid is RNA.

11. The nucleic acid molecule of embodiment 10, wherein the RNA is pre-mRNA.

12. The nucleic acid molecule of embodiment 1-11, wherein the nucleic acid molecule is selected from antisense oligonucleotide, siRNA or shRNA.

13. The nucleic acid molecule of embodiment 1-11, wherein the nucleic acid molecule is a single stranded antisense oligonucleotide.

14. The antisense oligonucleotide of embodiment 12 or 13, wherein the contiguous nucleotide sequence comprises or consists of at least 14 contiguous nucleotides, particularly 15, 16, 17, 18, 19 or 20 contiguous nucleotides.

15. The antisense oligonucleotide of embodiment 12 or 13, wherein the contiguous nucleotide sequence comprises or consists of from 14 to 20 nucleotides.

16. The antisense oligonucleotide of embodiment 15, wherein the contiguous nucleotide sequence comprises or consists of from 16 to 18 nucleotides.

17. The antisense oligonucleotide of embodiment 1 to 16, wherein the oligonucleotide comprises or consists of 14 to 25 nucleotides in length.

18. The antisense oligonucleotide of embodiment 17, wherein the antisense oligonucleotide comprises or consists of 15 to 22 nucleotides in length.

19. The antisense oligonucleotide of embodiment 17 or 18, wherein the antisense oligonucleotide comprises or consists of 16 to 20 nucleotides in length.

20. The antisense oligonucleotide of embodiment 12-19, wherein the contiguous nucleotide sequence comprises or consists of a sequence selected from the group consisting of SEQ ID NO: 7, 8, 9, 10, 11, 12, 13, 14, 15, 16, 17, 18 and 19.

21. The antisense oligonucleotide of embodiment 12-20, wherein the contiguous nucleotide sequence comprises or consists of a sequence selected from the group consisting of SEQ ID NO: 7, 8, 9, 10, 11, 12, 13, 14, 15 and 16.

22. The antisense oligonucleotide of embodiment 12-20, wherein the contiguous nucleotide sequence comprises or consists of a sequence selected from SEQ ID NO: 17 or SEQ 10 NO: 18.

23. The antisense oligonucleotide of embodiment 12-20, wherein the contiguous nucleotide sequence comprises or consists of SEQ ID NO: 19.

24. The antisense oligonucleotide of embodiment 12-23, wherein the contiguous nucleotide sequence has zero to three mismatches compared to the target nucleic acids it is complementary to.

25. The antisense oligonucleotide of embodiment 24, wherein the contiguous nucleotide sequence has one mismatch compared to the target nucleic adds.

26. The antisense oligonucleotide of embodiment 24, wherein the contiguous nucleotide sequence has two mismatches compared to the target nucleic adds.

27. The antisense oligonucleotide of embodiment 24, wherein the contiguous nucleotide sequence is fully complementary to both target nucleic acid sequences.

28. The antisense oligonucleotide of embodiment 12-27, comprising one or more modified nucleosides.

29. The antisense oligonucleotide of embodiment 28, wherein the one or more modified nucleoside is a high-affinity modified nucleosides.

30. The antisense oligonucleotide of embodiment 28 or 29, wherein the one or more modified nucleoside is a 2' sugar modified nucleoside.

31. The antisense oligonucleotide of embodiment 30, wherein the one or more 2' sugar modified nucleoside is independently selected from the group consisting of 2'-O-alkyl-RNA, 2'-O-methyl-RNA, 2'-alkoxy-RNA, 2'-O- methoxyethyl-RNA, 2'-amino-DNA, 2'-fluoro-DNA, 2'-fluoro-ANA and LNA nucleosides.

32. The antisense oligonucleotide of embodiment 28-31, wherein the one or more modified nucleoside is a LNA nucleoside.

33. The antisense oligonucleotide of embodiment 32, wherein the modified LNA nucleoside is selected from oxy-LNA, amino-LNA, thio-LNA, cET, and ENA.

34. The antisense oligonucleotide of embodiment 32 or 33, wherein the modified LNA nucleoside is oxy-LNA with the following 2'-4' bridge —O—$CH_2$.

35. The antisense oligonucleotide of embodiment 34, wherein the oxy-LNA is beta-D-oxy-LNA.

36. The antisense oligonucleotide of embodiment 32 or 33, wherein the modified LNA nucleoside is cET with the following 2'-4' bridge —O—$CH(CH_3)$—.

37. The antisense oligonucleotide of embodiment 36, wherein the cET is (S)cET. i.e. 6'(S)methyl-beta-D-oxy-LNA.

38. The antisense oligonucleotide of embodiment 32 or 33, wherein the LNA is ENA, with the following 2'-4' bridge —O—$CH_2CH_2$.

39. The antisense oligonucleotide of any one of embodiments 12-33, wherein the antisense oligonucleotide comprises at least one modified internucleoside linkage.

40. The antisense oligonucleotide of embodiment 39, wherein the modified internucleoside linkage is nuclease resistant.

41. The antisense oligonucleotide of embodiment 39 or 40, wherein at least 75% of the internucleoside linkages within the contiguous nucleotide sequence are phosphorothioate internucleoside linkages or boranophosphate internucleoside linkages.

42. The antisense oligonucleotide of embodiment 39 or 40, wherein all the internucleoside linkages within the contiguous nucleotide sequence are phosphorothioate internucleoside linkages.

43. The antisense oligonucleotide of embodiment 41 or 42, wherein at least one of the phosphorothioate Internucleoside linkages are stereodefined 44. The antisense oligonucleotide of embodiment 12-43, wherein the antisense oligonucleotide is capable of recruiting RNase H.

45. The antisense oligonucleotide of embodiment 44, wherein the antisense oligonucleotide or the contiguous nucleotide sequence is a gapmer.

46. The antisense oligonucleotide of embodiment 45, wherein the gapmer has the formula 5'-F-G-F'-3', where the F and F' wing regions independently comprise or consist of 1-7 2' sugar modified nucleosides in accordance with embodiments 31 to 38 and G is a region between 5 and 16 nucleosides which are capable of recruiting RNaseH.

47. The antisense oligonucleotide of embodiment 46, wherein each wing (F and F') is characterized by having at least one 2' sugar modified nucleoside at the 5' terminal and the 3' terminal of the wing and the G region has at least one DNA nucleoside adjacent to the wing regions (e.g. 5' and 3' terminal of the G region).

48. The antisense oligonucleotide of embodiment 46 or 47, wherein all the 2' sugar modified nucleosides in region F and F' are Identical LNA nucleosides.

49. The oligonucleotide of embodiment 46-48, wherein a. the F region is between 1 and 6 nucleotides in length and consists of 1-5 Identical LNA nucleosides and 0-3 DNA nucleosides; and b. the F' region is between 2 and 6 nucleotides in length and consists of 2-5 identical LNA nucleosides and 0-3 DNA nucleosides; and c. the G region is between 5 and 11 nucleotides which are capable of recruiting RNaseH, and d. optionally a D' region with 1 to 3 phosphodiester linked DNA nucleosides are positioned at the 5' end of the F region 50. The antisense oligonucleotide of embodiment 47, wherein region F and F' consist of identical LNA nucleosides.

51. The antisense oligonucleotide of embodiment 46-48, wherein all the 2' sugar modified nucleosides in region F and F' are oxy-LNA nucleosides.

52. The antisense oligonucleotide of embodiment 46 or 47, wherein at least one of region F or F' further comprises at least one 2' substituted modified nucleoside independently selected from the group consisting of 2'-O-alkyl-RNA, 2'-O-methyl-RNA, 2'-alkoxy-RNA, 2'-O-methoxyethyl-RNA, 2'-amino-DNA and 2'-fluoro-DNA.

53. The antisense oligonucleotide of embodiment 46-52, wherein the RNaseH recruiting nucleosides in region G are independently selected from DNA, alpha-L-LNA. C4' alkylated DNA, ANA and 2' F-ANA and UNA.

54. The antisense oligonucleotide of embodiment 53, wherein the nucleosides in region G is DNA and/or alpha-L-LNA nucleosides.

55. The antisense oligonucleotide of embodiment 46 or 53 or 54, wherein region G consists of at least 75% DNA nucleosides.

56. The antisense oligonucleotide of embodiment 55, where all the nucleosides in region G are DNA nucleosides.

57. The antisense oligonucleotide of embodiment 12-56, wherein the antisense oligonucleotide is selected from CMP ID NO: 71 to 7_83, or pharmaceutically acceptable salts thereof.

58. The antisense oligonucleotide of embodiment 12-56, wherein the antisense oligonucleotide is selected from CMP ID NO: 81 to 8_81, or pharmaceutically acceptable salts thereof.

59. The antisense oligonucleotide of embodiment 12-55, wherein the antisense oligonucleotide is selected from CMP ID NO: 91 to 9_12, or pharmaceutically acceptable salts thereof.

60. The antisense oligonucleotide of embodiment 12-55, wherein the antisense oligonucleotide is selected from CMP ID NO: 10_1 to 10_18, or pharmaceutically acceptable salts thereof.

61. The antisense oligonucleotide of embodiment 12-55, wherein the antisense oligonucleotide is selected from CMP ID NO: 11_1 to 11_26, or pharmaceutically acceptable salts thereof.

62. The antisense oligonucleotide of embodiment 12-55, wherein the antisense oligonucleotide is selected from CMP ID NO: 12_1 to 12_15, or pharmaceutically acceptable salts thereof.

63. The antisense oligonucleotide of embodiment 12-55, wherein the antisense oligonucleotide is selected from CMP ID NO: 13_1 or 13_2, or pharmaceutically acceptable salts thereof.

64. The antisense oligonucleotide of embodiment 12-56, wherein the antisense oligonucleotide is selected from CMP ID NO: 14_1 to 14_13, or pharmaceutically acceptable salts thereof.

65. The antisense oligonucleotide of embodiment 12-55, wherein the antisense oligonucleotide is selected from CMP ID NO: 151 to 15_21, or pharmaceutically acceptable salts thereof.

66. The antisense oligonucleotide of embodiment 12-55, wherein the antisense oligonucleotide is selected from CMP ID NO: 16_1 to 16_5, or pharmaceutically acceptable salts thereof.

67. The antisense oligonucleotide of embodiment 12-55, wherein the antisense oligonucleotide is selected from CMP ID NO: 17_1 to 17_183, or pharmaceutically acceptable salts thereof.

68. The antisense oligonucleotide of embodiment 12-55, wherein the antisense oligonucleotide is selected from CMP ID NO: 18_1 to 18_31 or 18_250 to 18_361, or pharmaceutically acceptable salts thereof.

69. The antisense oligonucleotide of embodiment 68, wherein the antisense oligonucleotide is selected from CMP ID NO: 18_1, 18_5, 18_10, 18_15, 18_18, 18_19, 18_24, 18_27, 18_30, 18_346, 18_347, 18_357, 17_10, 17_137 and 17_139, or pharmaceutically acceptable salts thereof.

70. The antisense oligonucleotide of embodiment 69, wherein the antisense oligonucleotide is selected from CMP ID NO: 18_1, 18_15, 18_27, 18_30, 17_10, 17_137 and 17_139.

71. The antisense oligonucleotide of embodiment 12-55, wherein the antisense oligonucleotide is selected from CMP ID NO: 18_32 to 18_249 or 18_362 to 18_610, or pharmaceutically acceptable salts thereof.

72. The antisense oligonucleotide of embodiment 71, wherein the antisense oligonucleotide is selected from CMP ID NO: 18_223, 18_36, 18_196, 18_188 and 18_243.

73. The antisense oligonucleotide of embodiment 12-55, wherein the antisense oligonucleotide is selected from CMP ID NO: 19_1 to 19_22, or pharmaceutically acceptable salts thereof.

74. A conjugate compound comprising a nucleic acid molecule according to any one of claims 1 to 11 or an antisense oligonucleotide according to any one of embodiments 12-57, and at least one conjugate moiety covalently attached to said antisense oligonucleotide.

75. The conjugate compound of embodiment 74, wherein the conjugate moiety is selected from carbohydrates, cell surface receptor ligands, drug substances, hormones, lipophilic substances, polymers, proteins, peptides, toxins, vitamins, viral proteins or combinations thereof.

76. The conjugate compound of embodiment 74 or 75, wherein the conjugate moiety is capable of binding to the asialoglycoprotein receptor.

77. The conjugate compound of embodiment 76, wherein the conjugate moiety comprises at least one asialoglycoprotein receptor targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine.

78. The conjugate compound of embodiment 77, wherein the asialoglycoprotein receptor targeting moiety is N-acetylgalactosamine (GalNAc).

79. The conjugate compound of embodiment 77 or 78, wherein the conjugate moiety is mono-valent, di-valent, tri-valent or tetra-valent with respect to asialoglycoprotein receptor targeting moieties.

80. The conjugate compound of embodiment 79, wherein the conjugate moiety consists of two to four terminal GalNAc moieties and a spacer linking each GalNAc moiety to a brancher molecule that can be conjugated to the antisense compound.

81. The conjugate compound of embodiment 80, wherein the spacer is a PEG spacer.

82. The conjugate compound of embodiment 76 to 81, wherein the conjugate moiety is a tri-valent N-acetylgalactosamine (GalNAc) moiety.

83. The conjugate compound of embodiment 76 to 82, wherein the conjugate moiety is selected from one of the trivalent GalNAc moieties in FIG. 1.

84. The conjugate compound of embodiment 83, wherein the conjugate moiety is the trivalent GaINAc moiety in FIG. 1D.

85. The conjugate compound of embodiment 74-84, comprising a linker which is positioned between the nucleic acid molecule or the antisense oligonucleotide and the conjugate moiety.

86. The conjugate compound of embodiment 85, wherein the linker is a physiologically labile linker.

87. The conjugate compound of embodiment 86, wherein the physiologically labile linker is nuclease susceptible linker.

88. The oligonucleotide conjugate of embodiment 86 or 87, wherein the physiologically labile linker is composed of 2 to 5 consecutive phosphodiester linkages.

89. The conjugate compound of embodiment 86 to 88, wherein the antisense oligonucleotide has the formula D'-F-G-F' or F-G-F'-D", wherein F, F and G are as defined in embodiments 48-56 and D' or D" comprises 1, 2 or 3 DNA nucleosides with phosphodiester internucleoside linkages.

90. The oligonucleotide conjugate of embodiment 88 or 89, wherein at least two consecutive phosphodiester internucleoside linkages are associated with a CA dinucleotide.

91. The conjugate compound of embodiment 76-90, which display improved cellular distribution between liver vs. kidney or improved cellular uptake into the liver of the conjugate compound as compared to an unconjugated nucleic acid molecule or antisense oligonucleotide.

92. The conjugate compound of embodiment 76-91, where in the conjugate compound is selected from the group consisting of CPM ID NO 20_12, 20_13, 20_14, 20_15, 20_16, 20_18, 20_20, 20_21, 20_22, 20_30, 20_35, 20_36, 21_2, 21_33 and 21_34.

93. A pharmaceutical composition comprising a nucleic acid molecule according to any one of embodiments 1 to 11, an antisense oligonucleotide of embodiment 12-73, a conjugate compound of embodiment 74-92 or acceptable salts thereof and a pharmaceutically acceptable diluent, carrier, salt and/or adjuvant.

94. A method for manufacturing the antisense oligonucleotide of embodiment 12-73, comprising reacting nucleotide units thereby forming covalently linked contiguous nucleotide units comprised in the antisense oligonucleotide.

95. The method of embodiment 94, further comprising reacting the contiguous nucleotide sequence with a non-nucleotide conjugation moiety as described in any one of embodiments 76-84.

96. A method for manufacturing the composition of embodiment 93, comprising mixing the antisense oligonucleotide with a pharmaceutically acceptable diluent, carrier, salt and/or adjuvant.

97. An in vivo or in vitro method for modulating PAPD5 and PAPD7 expression in a target cell which is expressing PAPD5 and PAPD7, said method comprising administering the nucleic acid molecule of any one of embodiments 1 to 11, the antisense oligonucleotide of any one of embodiments 12-73 or the conjugate compound of any one of embodiment 74-92 or the pharmaceutical composition of embodiment 93 in an effective amount to said cell.

98. The method of embodiments 97, wherein the PAPD5 and PAPD7 expression is reduced by at least 30%, or at least or at least 40%, or at least 50%, or at least 60%, or at least 70%, or at least 80%, or at least 90%, or at least 95% in the target cell compared to the level without any treatment.

99. A method for treating or preventing a disease comprising administering a therapeutically or prophylactically effective amount of the nucleic acid molecule any one of embodiments 1 to 11, the antisense oligonucleotide of any one of embodiments 12-73 or the conjugate compound of any one of embodiments 74-92 or the pharmaceutical composition of embodiment 93 to a subject suffering from or susceptible to the disease.

100. The nucleic acid molecule anyone of embodiments 1 to 11, the antisense oligonucleotide of any one of embodiments 12-57 or the conjugate compound of any one of embodiments 74-92 or the pharmaceutical composition of embodiment 93, for use as a medicament for treatment or prevention of a disease in a subject.

101. Use of the nucleic acid molecule anyone of embodiments 1 to 11, the antisense oligonucleotide of any one of embodiment 12-73 or the conjugate compound of any one of embodiment 74-92 for the preparation of a medicament for treatment or prevention of a disease in a subject.

102. The method, the nucleic acid molecule, or the use of embodiments 99-101, wherein the disease is HBV infection or chronic HBV infection.

103. The method, the nucleic acid molecule or the use of embodiments 102, wherein the secretion of HBsAg and/or HBeAg and/or intracellular HBV mRNA and/or HBV DNA is reduced.

104. The method, the nucleic acid molecule or the use of embodiments 102 or 103, wherein HBsAg is reduced by at least 30%, or at least or at least 40%, or at least 50%, or at least 80%, or at least 70%, or at least 80%, or at least 90%, or at least 95% compared to the level without any treatment.

105. The method, the antisense oligonucleotide or the use of embodiments 99-104 wherein the subject is a mammal.

106. The method, the antisense oligonucleotide or the use of embodiment 105, wherein the mammal is human.

EXAMPLES

The Examples illustrate the invention.

Material and Methods

Oligonucleotide Motif Sequences and Oligonucleotide Compounds

TABLE 4

List of oligonucleotide motif sequences targeting human and mouse transcripts
Sequences are indicated by SEQ ID NO, the motif sequence and the position they target on the human PAPD5 transcript (SEQ ID NO: 1) and the human PAPD7 transcript (SEQ ID NO: 2).

| SEQ ID NO | Motif Sequence | Start ID NO: 1 | End ID NO: 1 | Start ID NO: 2 | End ID NO: 2 |
|---|---|---|---|---|---|
| 7 | AGATCTGCATCCACAG | 759 | 774 | 1032 | 1047 |
| 8 | CAGATCTGCATCCACAG | 759 | 775 | 1032 | 1048 |
| 9 | CCAGATCTGCATCCACAG | 759 | 776 | 1032 | 1040 |
| 10 | CCAGATCTGCATCCACA | 760 | 776 | 1033 | 1049 |
| 11 | CCCAGATCTGCATCCAC | 761 | 777 | 1034 | 1050 |

TABLE 4-continued

List of oligonucleotide motif sequences targeting human and mouse transcripts
Sequences are indicated by SEQ ID NO, the motif sequence and the position they target on the human PAPD5 transcript (SEQ ID NO: 1) and the human PAPD7 transcript (SEQ ID NO: 2).

| SEQ ID NO | Motif Sequence | Start ID NO: 1 | End ID NO: 1 | Start ID NO: 2 | End ID NO: 2 |
|---|---|---|---|---|---|
| 12 | CCCAGATCTGCATCCA | 762 | 777 | 1035 | 1050 |
| 13 | TCCCAGATCTGCATCCA | 762 | 778 | 1035 | 1051 |
| 14 | GTCTCCCAGATCTGCAT | 765 | 781 | 1038 | 1054 |
| 15 | TCTCCCAGATCTGCAT | 765 | 780 | 1038 | 1053 |
| 16 | GTCTCCCAGATCTGCA | 766 | 781 | 1039 | 1054 |

Motif sequences represent the contiguous sequence of nucleobases present in the oligonucleotide.

TABLE 5

Lists oligonucleotides designs and specific antisense oligonucleotide compounds
Compounds are indicated by CMP ID NO, and based on the on the motif sequence in table 4.

| SEQ ID NO | Design | Oligonucleotide Compound | CMP ID NO | dG |
|---|---|---|---|---|
| 7 | 1-1-1-7-3-1-2 | AgAtctgcatCCAcAG | 7_1 | -23 |
| 7 | 1-9-3-1-2 | AgatctgcatCCACAG | 7_2 | -22 |
| 7 | 1-9-2-1-3 | AgatctgcatCCaCAG | 7_3 | -23 |
| 7 | 1-1-2-6-2-2-2 | AgATctgcatCCacAG | 7_4 | -23 |
| 7 | 1-1-1-7-2-2-2 | AgAtctgcatCCacAG | 7_5 | -21 |
| 7 | 1-3-1-5-2-2-2 | AgatCtgcatCCacAG | 7_6 | -22 |
| 7 | 1-9-2-2-2 | AgatctgcatCCacAG | 7_7 | -21 |
| 7 | 2-8-1-1-4 | AGatctgcatCcACAG | 7_8 | -23 |
| 7 | 1-1-1-7-1-1-4 | AgAtctgcatCcACAG | 7_9 | -22 |
| 7 | 1-3-1-5-1-14 | AgatCtgcatCcACAG | 7_10 | -22 |
| 7 | 1-9-1-1-4 | AgatctgcatCcACAG | 7_11 | -21 |
| 7 | 3-7-1-1-1-1-2 | AGAtctgcatCcAcAG | 7_12 | -22 |
| 7 | 2-2-1-5-1-1-1-1-2 | AGatCtacatCcACAG | 7_13 | -21 |
| 7 | 2-8-1-1-1-1-2 | AGatctgcatCcAcAG | 7_14 | -20 |
| 7 | 1-1-3-5-1-1-1-1-2 | AgATCtgcatCcAcAG | 7_15 | -22 |
| 7 | 1-1-1-1-1-5-1-1-1-1-2 | AgAtCtgcatCcAcAG | 7_16 | -20 |
| 7 | 1-1-1-7-1-1-1-1-2 | AgAtctacatCcAcAG | 7_17 | -19 |
| 7 | 1-2-2-5-1-1-1-1-2 | AgaTCtgcatCcAcAG | 7_18 | -21 |
| 7 | 1-3-1-5-1-1-1-1-2 | AgatCtgcatCcAcAG | 7_19 | -20 |
| 7 | 1-9-1-1-1-1-2 | AgatCtgcatCcAcAG | 7_20 | -19 |
| 7 | 1-1 2-5-1-2-3 | AgATctgcatCcaCAG | 7_21 | -23 |

TABLE 5-continued

Lists oligonucleotides designs and specific anti-sense oligonucleotide compounds
Compounds are indicated by CMP ID NO, and based on the on the motif sequence in table 4.

| SEQ ID NO | Design | Oligonucleotide Compound | CMP ID NO | dG |
|---|---|---|---|---|
| 7 | 1-1-1-7-1-2-3 | AgAtctgcatCcaCAG | 7_22 | -21 |
| 7 | 1-3-1-5-1-2-3 | AgatCtgcatCcaCAG | 7_23 | -22 |
| 7 | 1-9-1-2-3 | AgatctgcatCcaCAG | 7_24 | -21 |
| 7 | 3-7-1-3-2 | AGAtctgcatCcacAG | 7_25 | -22 |
| 7 | 2-2-1-51-3-2 | AGatCtgcatCcacAG | 7_26 | -21 |
| 7 | 2-8-1-3-2 | AGatctgcatCcacAG | 7_27 | -20 |
| 7 | 1-1-3-5-1-3-2 | AgATCtgcatCcacAG | 7_28 | -22 |
| 7 | 1-1-1-1 1-5-1 3-2 | AgAtCtgcatCcacAG | 7_29 | -20 |
| 7 | 1-1-1-7-1-3-2 | AgAtctgcatCcacAG | 7_30 | -19 |
| 7 | 1-2-2-5-1-3-2 | AgaTCtacatCcacAG | 7_31 | -21 |
| 7 | 1-3-1-5-1-3-2 | AgatCtgcatCcacAG | 7_32 | -20 |
| 7 | 1-9-1-3-2 | AgatCtgcatCcacAG | 7_33 | -19 |
| 7 | 1-1-1-8-5 | AgAtctgcatcCACAG | 7_34 | -23 |
| 7 | 1-10-5 | AgatctgcatcCAcAG | 7_35 | -23 |
| 7 | 2-2-1-6-21-2 | AGatCtgacatCAcAG | 7_36 | -22 |
| 7 | 2-9-2-1-2 | AGatctgcatcCAcAG | 7_37 | -21 |
| 7 | 1-1-2-7-2-1-2 | AgATctgcatcCAcAG | 7_38 | -22 |
| 7 | 1-1-1-1-1-6-2-1-2 | AgAtCtgcatcCAcAG | 7_39 | -22 |
| 7 | 1-1-18-2-1-2 | AgAtctgcatcCAcAG | 7_40 | -21 |
| 7 | 1-3-1-6-2-1-2 | AgatctgcatcCAcAG | 7_41 | -21 |
| 7 | 1-10-2-1-2 | AgatctgcatcCAcAG | 7_42 | -20 |
| 7 | 1-1-1-8-1-1-3 | AgAtctgcatcCaCAG | 7_43 | -21 |
| 7 | 1-3-1-6-1-13 | AgatCtgcatcCaCAG | 7_44 | -22 |
| 7 | 1-10-1-1-3 | AgatctgcatcCaCAG | 7_45 | -21 |
| 7 | 3-1-1-6-1-2-2 | AGAtCtgcatcCacAG | 7_46 | -22 |
| 7 | 2-2-1-6-1-2-2 | AGatCtgcatcCacAG | 7_47 | -21 |
| 7 | 1-1-3-6-1-2-2 | AgATCtgcatcCacAG | 7_48 | -22 |
| 7 | 1-1-1-1-1-6-1-2-2 | AgAtCtgcatcCacAG | 7_49 | -20 |
| 7 | 1-1-1-8-1-2-2 | AgAtctgcatcCacAG | 7_50 | -19 |
| 7 | 1-2-2-6-1-2-2 | AgaTCtgcatcCacAG | 7_51 | -21 |
| 7 | 1-3-1-6-1-2-2 | AgatCtgcatcCacAG | 7_52 | -20 |
| 7 | 1-10-1-2-2 | AgatctgcatcCacAG | 7_53 | -19 |
| 7 | 1-1-1-1-1-7-4 | AgAtCtgcatccACAG | 7_54 | -22 |
| 7 | 1-1-1-9-4 | AgAtctgcatccACAG | 7_55 | -21 |
| 7 | 1-2-2-7-4 | AgaTCtgcatccACAG | 7_56 | -23 |
| 7 | 1-3-1-7-4 | AgatCtgcatccACAG | 7_57 | -22 |
| 7 | 1-11-4 | AgatctqcatccACAG | 7_58 | -21 |
| 7 | 3-1-1-7-1-1-2 | AGAtCtgcatccAcAG | 7_59 | -22 |
| 7 | 3-9-1-1-2 | AGAtctgcatccAcAG | 7_60 | -21 |
| 7 | 2-2-1-7-1-1-2 | AGatCigcatccAcAG | 7_61 | -20 |
| 7 | 1-1-3-7-1-1-2 | AgATCtgcatccAcAG | 7_62 | -22 |
| 7 | 1-1-1-1-1-7-1-1-2 | AgAtCtgcatccAcAG | 7_63 | -20 |
| 7 | 1-1-1-9-1-1-2 | AgAtctgcatccAcAG | 7_64 | -19 |
| 7 | 1-2-2-7-1-1-2 | AgaTCtgcatccAcAG | 7_65 | -20 |
| 7 | 1-3-1-7-1-1-2 | AgatCtgcatccAcAG | 7_66 | -19 |
| 7 | 1-11-1-1-2 | AgatctgcatccAcAG | 7_67 | -18 |
| 7 | 3-10-3 | AGAtctgcatccaCAG | 7_68 | -23 |
| 7 | 1-1-1-1-1-8-3 | AgAtCtgcatccaCAG | 7_69 | -22 |
| 7 | 1-1-1-10-3 | AgAtctgcatccaCAG | 7_70 | -21 |
| 7 | 1-2-2-8-3 | AgaTCtacatccaCAG | 7_71 | -22 |
| 7 | 1-3-1-8-3 | AgatCtgcatccaCAG | 7_72 | -21 |
| 7 | 1-12-3 | AgatctgcatccaCAG | 7_73 | -20 |
| 7 | 3-1-1-9-2 | AGAtCtgcatccacAG | 7_74 | -22 |
| 7 | 3-11-2 | AGAtctacatccaCAG | 7_75 | -21 |
| 7 | 2-1 2-9-2 | AGaTCtgcatccacAG | 7_78 | -21 |
| 7 | 2-2-1-9-2 | AGatCtgcatccacAG | 7_77 | -20 |
| 7 | 1-1-3-9-2 | AgATCtgcatccacAG | 7_78 | -21 |
| 7 | 1-1-1-1-1-9-2 | AgAtCtgcatccacAG | 7_79 | -19 |
| 7 | 1-1-1-11-2 | AgAtCtgcatccacAG | 7_80 | -18 |
| 7 | 1-2-2-9-2 | AgaTCtgcatecacAG | 7_81 | -20 |
| 7 | 1-3-1-9-2 | AgatCtgcatccacAG | 7_82 | -19 |
| 7 | 1-13-2 | AgatctgcatccacAG | 7_83 | -18 |
| 8 | 1-2-1-7-2-2-2 | CagAtctgcatCCacAG | 8_1 | -23 |
| 8 | -3-1-6-2-2-2 | CagaTctgcatCCacAG | 8_2 | -23 |
| 8 | 1-10-2-2-2 | CagatctgcatCCacAG | 8_3 | -22 |
| 8 | 1-2-1-7-1-1-4 | CagAtctgcatCcACAG | 8_4 | -23 |
| 8 | 1-10-1-1-4 | CagatctgcatCcACAG | 8_5 | -23 |
| 8 | 2-1-1-7-1-1-1-1-2 | CAgAtctgcatCcAcAG | 8_5 | -23 |
| 8 | 2-3-1-5 1-1-1-1-2 | CAgatCtgcatCcAcAG | 8_7 | -23 |
| 8 | 2-9-1-1-1-1-2 | CAgatctgcatCcAcAG | 8_8 | -22 |
| 8 | 1-1-2 7_1-1-1 1-2 | CaGAtctacatCcAcAG | 8_9 | -23 |

TABLE 5-continued

Lists oligonucleotides designs and specific anti-sense oligonucleotide compounds
Compounds are indicated by CMP ID NO, and based on the on the motif sequence in table 4.

| SEQ ID NO | Design | Oligonucleotide Compound | CMP ID NO | dG |
|---|---|---|---|---|
| 8 | 1-1-1-2-1-5-1-1-1-1-2 | CaGatCtgcatCcAcAG | 8_10 | -22 |
| 8 | 1-1-1-8-1-1-1-1-2 | CaGatctgcatCcAcAG | 8_11 | -21 |
| 8 | 1-2-1-1-1-5-1-1-1-1-2 | CagAtCtgcatCcAcAG | 8_12 | -22 |
| 8 | 1-2-1-7-1-1-1-1-2 | CagAtctacatCcAcAG | 8_13 | -21 |
| 8 | 1-3-2-5-1-1-1-1-2 | CagaTCtgcatCcACAG | 8_14 | -22 |
| 8 | 1-4-1-5-1-1-1-1-2 | CagatCtgcatCcAcAG | 8_15 | -21 |
| 8 | 1-10-1-1-1-1-2 | CagatctgcatCcAcAG | 8_16 | -20 |
| 8 | 1-2-1-7-1-2-3 | CagAtctgcatCcaCAG | 8_17 | -23 |
| 8 | 1-10-1-2-3 | CagatetgcatCcaCAG | 8_18 | -22 |
| 8 | 2-1-1-7-1-3-2 | CAgAtctgcatCcacAG | 8_19 | -23 |
| 8 | 2-3-1-5-1-3-2 | CAgatCtgcatCcacAG | 8_20 | -23 |
| 8 | 2-9-1-3-2 | CAgatctgcatCcacAG | 8_21 | -22 |
| 8 | 1-1-2-7-1-3-2 | CaGAtctgcatCcacAG | 8_22 | -23 |
| 8 | 1-1-1-2-1-5-1-3-2 | CaGatCtgcatCcacAG | 8_23 | -22 |
| 8 | 1-1-1-8-1-3-2 | CaGatctgcatCcacAG | 8_24 | -21 |
| 8 | 1-2-1-1-1-5-1-3-2 | CagAtCtgcatCcacAG | 8_25 | -22 |
| 8 | 1-2-1-7-1 3-2 | CagAtctgcatCcacAG | 8_26 | -21 |
| 8 | 1-3-2-51-3-2 | CagaTCtgcatCcacAG | 8_27 | -22 |
| 8 | 1-4-1-5-1-3-2 | CagatCtgcatCcacAG | 8_28 | -21 |
| 8 | 1-10-1-3-2 | CagatctgcatCcacAG | 8_29 | -20 |
| 8 | 1-2-1-8-5 | CagAtctgcatcCACAG | 8_30 | -24 |
| 8 | 1-2-1-11-6-2-1-2 | CagAtCtgcatcCAcAG | 8_31 | -23 |
| 8 | 1-2-1-8-2-1-2 | CagAtctgcatcCAcAG | 8_32 | -22 |
| 8 | 1-4-1-6-2-1-2 | CagatCtgcatcCAcAG | 8_33 | -22 |
| 8 | 1-11-2-1-2 | CagatctgcatcCAcAG | 8_34 | -21 |
| 8 | 1-2-1-8-1-1-3 | CagAtctgcatcCaCAG | 8_35 | -22 |
| 8 | 1-4-1-6-1-1-3 | CagatCtgcatcCaCAG | 8_36 | -23 |
| 8 | 1-11-1-1-3 | CagatctgcatcCaCAG | 8_37 | -22 |
| 8 | 2-1-1-8-1 2-2 | CAgAtctgcatcCacAG | 8_38 | -22 |
| 8 | 2-3-1-8-1-2-2 | CAgatCtgcatcCacAG | 8_39 | -23 |
| 8 | 2-10-1-2-2 | CAgatctgcatcCacAG | 8_40 | -22 |
| 8 | 1-1-2-1-1-6-1-2-2 | CaGAtCtgcatcCacAG | 8_41 | -23 |
| 8 | 1-1-1-2-1-6-1-2-2 | CaGatCtgcatcCacAG | 8_42 | -22 |
| 8 | 1-2-3-6-1-2-2 | CagATCtgcatcCacAG | 8_43 | -23 |
| 8 | 1-2-1-1-1-6-1-2-2 | CagAtCtgcatcCacAG | 8_44 | -21 |

TABLE 5-continued

Lists oligonucleotides designs and specific anti-sense oligonucleotide compounds
Compounds are indicated by CMP ID NO, and based on the on the motif sequence in table 4.

| SEQ ID NO | Design | Oligonucleotide Compound | CMP ID NO | dG |
|---|---|---|---|---|
| 8 | 1-2-1-8-1-2-2 | CagAtctgcatcCacAG | 8_45 | -20 |
| 8 | 1 3-2-6-1-2-2 | CagaTCtgcatcCacAG | 8_48 | -22 |
| 8 | 1-4-1-6-1-2-2 | CagatCtgcatcCacAG | 8_47 | -21 |
| 8 | 1-11-1-2-2 | CagatctgcatcCacAG | 8_48 | -20 |
| 8 | 2-1-1-9-4 | CAgAtctgcatccACAG | 8_49 | -24 |
| 8 | 1-2-1-1-1-7-4 | CagAtCtgcatccACAG | 8_50 | -23 |
| 8 | 1-4-1-7-4 | CagatCtgcatccACAG | 8_51 | -23 |
| 8 | 1-12-4 | CagatctgcatccACAG | 8_52 | -22 |
| 8 | 2-1-1-1-1-7-1-1-2 | CAgAtCtgcatccAcAG | 8_53 | -23 |
| 8 | 2-1-1-9-1-1-2 | CAgAtctgcatccAcAG | 8_54 | -22 |
| 8 | 2-3-1-7-1-1-2 | CAgatCtgcatccAcAG | 8_55 | -22 |
| 8 | 2-11-1-1-2 | CAgatctgcatccAcAG | 8_56 | -21 |
| 8 | 1-1-2-1-1-7-1-1 2 | CaGAtCtgcatccAcAG | 8_57 | -23 |
| 8 | 1-1-1-2-1-7-1-1-2 | CaGatCtgcatccAcAG | 8_58 | -21 |
| 8 | 1-2-3-7-1-1-2 | CagATCtacatccAcAG | 8_59 | -23 |
| 8 | 1-2-1-1-1-7-1-1-2 | CagAtCtgcatccAcAG | 8_60 | -21 |
| 8 | 1-2-1-9-1-1-2 | CagAtctgcatccAcAG | 8_61 | -20 |
| 8 | 1 3-2-7_1-1-2 | CagaTCtgcatccAcAG | 8_62 | -22 |
| 8 | 1-4-1-7-1-1-2 | CagatCtacatccAcAG | 8_83 | -20 |
| 8 | 1-12-1-1-2 | CagatctgcatccAcAG | 8_64 | -19 |
| 8 | 2-1-1-10-3 | CAgAtctgcatccaCAG | 8_85 | -24 |
| 8 | 1 2-1-1-1-8-3 | CagAtCtacatccaCAG | 8_66 | -23 |
| 8 | 1-2-1-10-3 | CagAtctgcatccaCAG | 8_67 | -22 |
| 8 | 1-4-1-8-3 | CagatCtgcatccaCAG | 8_68 | -22 |
| 8 | 1-13-3 | CagatctgcatccaCAG | 8_89 | -21 |
| 8 | 2-1-1-1-1-9-2 | CAgAtCtgcatccacAG | 8_70 | -23 |
| 8 | 2-1-1-11-2 | CAgAtctgcatccacAG | 8_71 | -22 |
| 8 | 2-2-2-9-2 | CAgaTCtgcatccacAG | 8_72 | -23 |
| 8 | 2-3-1-9-2 | CAgatCtgcatccacAG | 8_73 | -22 |
| 8 | 2-13-2 | CAgatctgcatccacAG | 8_74 | -21 |
| 8 | 1-1-2-1-1-9-2 | CaGAtCtgcatccacAG | 8_75 | -23 |
| 8 | 1-1-1-2-1-9-2 | CaGatCtgcatccacAG | 8_76 | -21 |
| 8 | 1-2-1-1-1-9-2 | CagAtCtgcatccacAG | 8_77 | -21 |
| 8 | 1-2-1-11-2 | CagAtctgcatccacAG | 8_78 | -20 |
| 8 | 1-3-2-9-2 | CagaTCtgcatccacAG | 8_79 | -21 |

TABLE 5-continued

Lists oligonucleotides designs and specific anti-sense oligonucleotide compounds
Compounds are indicated by CMP ID NO, and based on the on the motif sequence in table 4.

| SEQ ID NO | Design | Oligonucleotide Compound | CMP ID NO | dG |
|---|---|---|---|---|
| 8 | 1-4-1-9-2 | CagatCtgcatccacAG | 8_80 | −20 |
| 8 | 1-14-2 | CagatctgcatccacAG | 8_81 | −19 |
| 9 | 1-3-1-7-1-1-1-1-2 | CcagAtctgcatCcAcAG | 9_1 | −24 |
| 9 | 1-1-1-1-1-7-1-3-2 | CcAgAtctgcatCcacAG | 9_2 | −24 |
| 9 | 1-1-1-10-1-2-2 | CcAgatctgcatcCacAG | 9_3 | −23 |
| 9 | 1-12-1-2-2 | CcagatctgcatcCacAG | 9_4 | −23 |
| 9 | 1-1-1-1-1-9-1-1-2 | CcAgAtctgcatccAcAG | 9_5 | −23 |
| 9 | 1-1-1-11-1-1-2 | CcAgatctgcatccAcAG | 9_6 | −23 |
| 9 | 1-3-1-9-1-1-2 | CcagAtctgcatccAcAG | 9_7 | −23 |
| 9 | 1-13-1-1-2 | CcagatctgcatccAcAG | 9_8 | −22 |
| 9 | 1-3-1-10-3 | CcagAtctgcatccaCAG | 9_9 | −25 |
| 9 | 2-2-1-11-2 | CCagAtctgcatccacAG | 9_10 | −25 |
| 9 | 1-1-1-13-2 | CcAgatctgcatccacAG | 9_11 | −23 |
| 9 | 1-2-2-11-2 | CcaGAtctgcatccacAG | 9_12 | −25 |
| 10 | 1-3-1-8-1-3-2 | CcagAtctgcaTccaCA | 10_1 | −23 |
| 10 | 1-3-1-7-1-1-3 | CeagAtctgcatCcACA | 10_2 | −24 |
| 10 | 1-1-1-9-1-2-2 | CcAgatctgcatCcaCA | 10_3 | −23 |
| 10 | 1-3-1-7-1-2-2 | CcagAtctgcatCcaCA | 10_4 | −23 |
| 10 | 1-11-1-2-2 | CcagatctgcatCcaCA | 10_5 | −23 |
| 10 | 1-3-1-8-4 | CcagAtctgcatcCACA | 10_6 | −25 |
| 10 | 1-1-1-10-1-1-2 | CcAgatctgcatcCaCA | 10_7 | −23 |
| 19 | 1-3-1-8-1-1-2 | CcagAtctgcatcCaCA | 10_8 | −23 |
| 10 | 1-12-1-1-2 | CcagatctgcatcCaCA | 10_9 | −22 |
| 19 | 1-1-1-1-1-9-3 | CcAgAtctgcatccACA | 10_10 | −23 |
| 10 | 1-1-1-11-3 | CcAgatctgcatccACA | 10_11 | −23 |
| 10 | 1-3-1-9-3 | CcagAtctgcatccACA | 10_12 | −23 |
| 10 | 1-13-3 | CcagatctgcatccACA | 10_13 | −22 |
| 10 | 1-1-1-1-1-10-2 | CcAgAtctgcatccaCA | 10_14 | −23 |
| 10 | 1-1-1-12-2 | CcAgatctgcatccaCA | 10_15 | −22 |
| 10 | 1-2-2-10-2 | CcaGAtctgcatccaCA | 10_16 | −24 |
| 10 | 1-3-1-10-2 | CcagAtctgcatccaCA | 10_17 | −22 |
| 10 | 1-14-2 | CcagatctgcatccaCA | 10_18 | −22 |
| 11 | 1-1-1-8-1-1-1-1-2 | CcCagatctgcAtCcAC | 11_1 | −23 |
| 11 | 1-2-1-7-1-1-1-1-2 | CccAgatctgcAtCcAC | 11_2 | −23 |
| 11 | 1-10-1-1-1-1-2 | CccagatctgCAtCcAC | 11_3 | −23 |
| 11 | 1-1-1-8-1-2-3 | CcCagatctgcAtcCAC | 11_4 | −25 |
| 11 | 1-2-1-7-1-2-3 | CccAgatctgcAtcCAC | 11_5 | −25 |
| 11 | 1-10-1-2-3 | CccagatctgCAtcCAC | 11_6 | −24 |
| 11 | 2-1 1-7-1-3-2 | CCcAgatctgcAtccAC | 11_7 | −25 |
| 11 | 2-9-1-3-2 | CCcagatctgcAtccAC | 11_8 | −24 |
| 11 | 1-1-2-7-1-3-2 | CcCAgatctaCAtccAC | 11_9 | −25 |
| 11 | 1-1-1-1-1-6-1-32 | CcCaGatctgcAtccAC | 11_10 | −23 |
| 11 | 1-1-1-8-1-3-2 | CcCagatctgcAtccAC | 11_11 | −23 |
| 11 | 1-2-2-6-1-3-2 | CccAGatctgcAtccAC | 11_12 | −24 |
| 11 | 1-2-1-1-1-5-1-3-2 | CCCAgAtctgcAtccAC | 11_13 | −23 |
| 11 | 1-2-1-71-3-2 | CccAgatctgcAtccAC | 11_14 | −23 |
| 11 | 1-10-1-3-2 | CccagatctgCAtccAC | 11_15 | −22 |
| 11 | 1-2-1-1-1-7-1-1-2 | CccAgAtctgcatCcAC | 11_16 | −24 |
| 11 | 1-12-1-1-2 | CccagatctgcatCcAC | 11_17 | −23 |
| 11 | 1-2-1-1-1-8-3 | CccAgAtctgcatcCAC | 11_18 | −25 |
| 11 | 1-4-1-8-3 | CccagAtctgcatcCAC | 11_19 | −24 |
| 11 | 2-3-1-9-2 | CCcagAtctgcatccAC | 11_20 | −25 |
| 11 | 1-1-2-1-1-9-2 | CcCAgAtctgcatccAC | 11_21 | −25 |
| 11 | 1-1-1-1-2-9-2 | CcCaGAtctgcatccAC | 11_22 | −25 |
| 11 | 1-1-1-12-2 | CcCagatctgcatccAC | 11_23 | −23 |
| 11 | 1-2-1-1-1-9-2 | CccAgAtctgcatccAC | 11_24 | −23 |
| 11 | 1-2-1-11-2 | CccAgatctgcatccAC | 11_25 | −23 |
| 11 | 1-14-2 | CccagatctgcatccAC | 11_26 | −22 |
| 12 | 1-9-2-2-2 | CccagatctgCAtcCA | 12_1 | −24 |
| 12 | 1-1-1-7-1-3-2 | CcCatatctgCatcCA | 12_2 | −23 |
| 12 | 1-2-1-6-1-3-2 | CccAgatctgCatcCA | 12_3 | −23 |
| 12 | 1-9-1-3-2 | CccagatctgCatcCA | 12_4 | −23 |
| 12 | 1-2-1-7-1-1-3 | CccAgatctgcAtCCA | 12_5 | −25 |
| 12 | 1-10-1-1-3 | CccagatctgcAtCCA | 12_6 | −24 |
| 12 | 2-9-1-2-2 | CCcagatctgcAtcCA | 12_7 | −24 |
| 12 | 1-1-1-8-1-2-2 | CcCagatctgcAtcCA | 12_8 | −23 |
| 12 | 1-2-1-7-1-2-2 | CccAgatctgcAtcCA | 12_9 | −23 |
| 12 | 1-3-1-6-1-2-2 | CccaGatctgcAtcCA | 12_10 | −23 |
| 12 | 1-10-1-2-2 | CccagatctgcAtcCA | 12_11 | −22 |
| 12 | 2-1-1-10-2 | CCcAgatctgcatcCA | 12_12 | −25 |
| 12 | 1-1-1-11-2 | CcCagatctgcatcCA | 12_13 | −22 |

TABLE 5-continued

Lists oligonucleotides designs and specific anti-sense oligonucleotide compounds
Compounds are indicated by CMP ID NO, and based on the on the motif sequence in table 4.

| SEQ ID NO | Design | Oligonucleotide Compound | CMP ID NO | dG |
|---|---|---|---|---|
| 12 | 1-2-1-10-2 | CccAgatctgcatcCA | 12_14 | -22 |
| 12 | 1-13-2 | CccagatctgcatcCA | 12_15 | -22 |
| 13 | 2-10-1-2-2 | TCccagatctgcAtcCA | 13_1 | -24 |
| 13 | 2-2-1-10-2 | TCccAgatctgcatcCA | 13_2 | -25 |
| 14 | 1-3-1-6-1-1-1-1-2 | GtctCccagatCtGcAT | 14_1 | -24 |
| 14 | 1-4-1-5-1-3-2 | GtctcCcagatCtgcAT | 14_2 | -23 |
| 14 | 1-10-1-3-2 | GtctcccagatCtgcAT | 14_3 | -23 |
| 14 | 1-1-1-2-1-6-1-2-2 | GtCtcCcagatcTgcAT | 14_4 | -24 |
| 14 | 1-4-1-6-1-2-2 | GtctcCcagatcTgcAT | 14_5 | -23 |
| 14 | 1-1-1-1-1-8-1-1-2 | GtCtCccagAtctGcAT | 14_6 | -24 |
| 14 | 1-2-2-8-1-1-2 | GtcTCccagatctGcAT | 14_7 | -24 |
| 14 | 1-4-1-7-1-1-2 | GtctcCcagatctGcAT | 14_8 | -23 |
| 14 | 1-4-1-8-3 | GtctcCcagatctgCAT | 14_9 | -25 |
| 14 | 1-1-1-2-1-9-2 | GtCtcCcagatctgcAT | 14_10 | -23 |
| 14 | 1-1-1-12-2 | GtCtcccagatctgcAT | 14_11 | -23 |
| 14 | 1-3-1-10-2 | GtctCccagatctgcAT | 14_12 | -22 |
| 14 | 1-4-1-9-2 | GtctcCcagatctgcAT | 14_13 | -22 |
| 15 | 2-8-1-1-1-1-2 | TCtcccagatCtGcAT | 15_1 | -22 |
| 15 | 1-3-1-5-1-2-3 | TctcCcagatCtgCAT | 15_2 | -23 |
| 15 | 2-1-1-6-1-3-2 | TCtCccagatCtgcAT | 15_3 | -23 |
| 15 | 2-2-1-5-1 3-2 | TCtcCcagatCtgcAT | 15_4 | -23 |
| 15 | 2-8-1-3-2 | TCtcccagatCtgcAT | 15_5 | -22 |
| 15 | 1-3-1-5-1-3-2 | TctcCcagatCtgcAT | 15_6 | -21 |
| 15 | 2-9-2-1-2 | TCtcccagatcTGcAT | 15_7 | -23 |
| 15 | 2-1-1-7-1 2-2 | TCtCccagatcTgcAT | 15_8 | -23 |
| 15 | 2-2-1-6-1-2-2 | TCtcCcagatcTgcAT | 15_9 | -23 |
| 15 | 2-9-1-2-2 | TCtcccagatcTgcAT | 15_10 | -22 |
| 15 | 4-8-1-12 | TCTCccagatctGcAT | 15_11 | -24 |
| 15 | 3-9-1-1-2 | TCTcccagatctGcAT | 15_12 | -23 |
| 15 | 2-2-1-7-1-1-2 | TCtcCcagatctGcAT | 15_13 | -22 |
| 15 | 2-10-1-1-2 | TCtcccagatctGcAT | 15_14 | -21 |
| 15 | 2-2-1-8-3 | TCtcCcagatctgCAT | 15_15 | -24 |
| 15 | 1-3-1-8-3 | TctcCcagatctgCAT | 15_16 | -22 |
| 15 | 3-11-2 | TCTcccagatctgcAT | 15_17 | -22 |
| 15 | 2-1-1-10-2 | TCtCccagatctgcAT | 15_18 | -22 |
| 15 | 2-2-1-9-2 | TCtcCcagatctgcAT | 15_19 | -22 |
| 15 | 2-12-2 | TCtcccagatctgcAT | 15_20 | -21 |
| 15 | 1-2-2-9-2 | TctCCcagatctgcAT | 15_21 | -23 |
| 16 | 1-3-1-6-1-2-2 | GtctCccagatCtgCA | 16_1 | -24 |
| 16 | 1-10-1-2-2 | GtctcccagatCtgCA | 16_2 | -23 |
| 16 | 1-1-1-1-1-9-2 | GtCtCccagatctgCA | 16_3 | -24 |
| 16 | 1-1-1-11-2 | GtCtcccagatctgCA | 16_4 | -23 |
| 16 | 1-3-1-9-2 | GtctCccagatctgCA | 16_5 | -23 |

Designs refer to the gapmer design, F-G-F'. in classic gapmer design e.g. 3-10-3 all the nucleotides in the flanks (F and F') are constituted of the same 2-sugar modified nucleoside, e.g. LNA, cET, or MOE, and a stretch of DNA in the middle forming the gap (G). In gapmers with alternating flank designs the flanks of oligonucleotide is annotated as a series of integers, representing a number of 2' sugar modified nucleosides (M) followed by a number of DNA nucleosides (D). For example a flank with a 2-2-1 motif represents 5' $[M]_2$-$[D]_2$-[M] 3' and a 1-1-1-1-1 motif represents 5' [M]-[D]-[M]-[D]-[M] 3'. Both flanks have a 2' sugar modified nucleoside at the 5' and 3' terminal. The gap region (G). which is constituted of a number of DNA nucleosides (typically between 5 and 16), is located between the flanks. The heading "Oligonucleotide compound" in the table represents specific designs of a motif sequence. Capital letters represent beta-D-oxy LNA nucleosides, lowercase letters represent DNA nucleosides, all LNA C are 5-methyl cytosine, and 5-methyl cytosine DNA are presented by "e", all internucleoside linkages are phosphorothioate internucleoside linkages.

TABLE 6 list of oligonucleotide motif sequences targeting human and cyno
Sequences are indicated by SEQ ID NO, the sequence (nucleobase sequence) and the position motif target on the human PAPD5 transcript (SEQ ID NO: 1) and the human PAPD7_ transcript (SEQ ID NO: 2).

| SEQ ID NO | Motif Sequence | Start ID NO: 1 | End ID NO: 1 | Start ID NO: 2 | End ID NO: 2 |
|---|---|---|---|---|---|
| 17 | TCAACTTTCACTTCAGT | 64669 | 64885 | 29514 | 29530 |
| 18 | TCAACTTTCACTTCAG | 64870 | 64685 | 29515 | 29530 |
| 19 | TGTTTCAATACTAAAA | 69414 | 69429 | 30731 | 30746 |

Motif sequences represent the contiguous sequence of nucleobases present in the oligonucleotide.

TABLE 7

Lists oligonucleotides designs and specific anti-sense oligonucleotide compounds
Compounds are indicated by CMP ID NO. and based on the on the motif sequence in table 6.

| SEQ ID NO | Design | Oligonucleotide Compound | CMP ID NO | dG |
|---|---|---|---|---|
| 17 | 2-12-3 | TCaactttcacttcAGT | 17_1 | -19 |
| 17 | 2-2-1-6-1-2-3 | TCaaCtttcacTtcAGT | 17_2 | -21 |

TABLE 7-continued

Lists oligonucleotides designs and specific anti-sense oligonucleotide compounds
Compounds are indicated by CMP ID NO. and based on the on the motif sequence in table 6.

| SEQ ID NO | Design | Oligonucleotide Compound | CMP ID NO | dG |
|---|---|---|---|---|
| 17 | 2-9-1 2-3 | TCaactttcacTtcAGT | 17_3 | -20 |
| 17 | 1-3-1-6-1-2-3 | TcaaCtttcacTtcAGT | 17_4 | -20 |
| 17 | 2-9-1-3-2 | TCaactttcacTtcaGT | 17_5 | -19 |
| 17 | 2-2-1-7-2-1-2 | TCaaCtttcactTCaGT | 17_6 | -21 |
| 17 | 1-1-1-9-1-1-3 | TcAactttcactTcAGT | 17_7 | -19 |
| 17 | 1-1-2-8-1-2-2 | TcAActttcactTcaGT | 17_8 | -18 |
| 17 | 5-8-1-1-2 | TCAACtttcacttCaGT | 17_9 | -23 |
| 17 | 4-9-1-1-2 | TCAActttcacttCaGT | 17_10 | -21 |
| 17 | 2-2-1-8-1-1-2 | TCaaCtttcacttCaGT | 17_11 | -20 |
| 17 | 2-11-1-1-2 | TCaactttcacttCaGT | 17_12 | -19 |
| 17 | 1-1-2-9-1-1-2 | TcAActttcacttCaGT | 17_13 | -18 |
| 17 | 3-11-3 | TCAactttcacttcAGT | 17_14 | -21 |
| 17 | 2-2-1-9-3 | TCaaCtttcacttcAGT | 17_15 | -20 |
| 17 | 2-13-2 | TCaactttcacttcaGT | 17_16 | -18 |
| 17 | 3-1-1-6-6 | TCAaCtttcacTTCAGT | 17_17 | -26 |
| 17 | 2-1-2-6-6 | TCaACtttcacTTCAGT | 17_18 | -25 |
| 17 | 2-2-1-6-6 | TCaaCtttcacTTCAGT | 17_19 | -25 |
| 17 | 2-9-6 | TCaactttcacTTCAGT | 17_20 | -24 |
| 17 | 1-1-3-6-6 | TcAACtttcacTTCAGT | 17_21 | -24 |
| 17 | 1-1-2-1-1-5-6 | TcAAcTttcacTTCAGT | 17_22 | -23 |
| 17 | 1-3-1-6-6 | TcaaCtttcacTTCAGT | 17_23 | -23 |
| 17 | 5-6-3-1-2 | TCAACtttcacTTCaGT | 17_24 | -25 |
| 17 | 4-7-3-1-2 | TCAActttcacTTCaGT | 17_25 | -23 |
| 17 | 3-1-1-6-3-1-2 | TCAaCtttcacTTCaGT | 17_26 | -24 |
| 17 | 3-2-1-5-3-1-2 | TCAacTttcacTTCaGT | 17_27 | -23 |
| 17 | 3-8-3-1-2 | TCAactttcacTTCaGT | 17_28 | -23 |
| 17 | 2-1-2-6-3-1-2 | TCaACtttcacTTCaGT | 17_29 | -23 |
| 17 | 2-1-1-1-1-5-3-1-2 | TCaAcTttcacTTCaGT | 17_30 | -22 |
| 17 | 2-1-1-7-3-1-2 | TCaActttcacTTCaGT | 17_31 | -21 |
| 17 | 2-2-1-6-3-1-2 | TCaaCtttcacTTCaGT | 17_32 | -22 |
| 17 | 2-3-1-5-3-1-2 | TCaacTttcacTTCaGT | 17_33 | -22 |
| 17 | 2-9-3-1-2 | TCaactttcacTTCaGT | 17_34 | -21 |
| 17 | 1-1-3-6-3-1-2 | TcAACtttcacTTCaGT | 17_35 | -22 |
| 17 | 5-6-2-1-3 | TCAACtttcacTTCAGT | 17_36 | -24 |
| 17 | 4-1-1-5-2-1-3 | TCAAcTttcacTTCAGT | 17_37 | -23 |
| 17 | 2-1-1-1-1-5-2-1-3 | TCaAcTttcacTTcAGT | 17_38 | -22 |
| 17 | 1-1-2-1-1-5-2-1-3 | TcAAcTttcacTTcAGT | 17_39 | -21 |
| 17 | 1-2-1-1-1-5-2-1-3 | TcaAcTttcacTTcAGT | 17_40 | -20 |
| 17 | 1-3-1-6-2-1-3 | TcaaCtttcacTTcAGT | 17_41 | -21 |
| 17 | 1-4-1-5-2-1-3 | TcaacTttcacTTcAGT | 17_42 | -20 |
| 17 | 1-1-3-6-2-2-2 | TcAACtttcacTTcaGT | 17_43 | -21 |
| 17 | 1-1-1-1-1-6-2-2-2 | TcAaCtttcacTTcaGT | 17_44 | -20 |
| 17 | 1-3-1-6-2-2-2 | TcaaCtttcacTTcaGT | 17_45 | -19 |
| 17 | 5-6-1-1-4 | TCAACtttcacTtCAGT | 17_46 | -26 |
| 17 | 3-1-1-6-1-1-4 | TCAaCtttcacTtCAGT | 17_47 | -25 |
| 17 | 2-1-1-7-1-1-4 | TCaActttcacTtCAGT | 17_48 | -22 |
| 17 | 2-2-1-6-1-1-4 | TCaaCtttcacTtCAGT | 17_49 | -23 |
| 17 | 2-3-1 5-1-1-4 | TCaacTttcacTtCAGT | 17_50 | -23 |
| 17 | 2-9-1-1-4 | TCaactttcacTtCAGT | 17_51 | -22 |
| 17 | 1-3-1-6-1-1-4 | TcaaCtttcacTtCAGT | 17_52 | -22 |
| 17 | 5-6-1-1-1-1-2 | TCAACtttcacTtCaGT | 17_53 | -23 |
| 17 | 4-1-1-5-1-1-1-1-2 | TCAAcTttcacTtCaGT | 17_54 | -22 |
| 17 | 4-7-1-1 1-1-2 | TCAActttcacTtCaGT | 17_55 | -22 |
| 17 | 3-1-1-6-1-1-1-1-2 | TCAactttcacTtCaGT | 17_56 | -22 |
| 17 | 3-8-1-11-1-2 | TCAaCtttcacTtCaGT | 17_57 | -21 |
| 17 | 2-1 2-6-1-1-1-1-2 | TCaActttcacTtCaGT | 17_58 | -21 |
| 17 | 2-1-1-1-1-5-1-1-1-1-2 | TCaAcTttcacTtCaGT | 17_59 | -20 |
| 17 | 2-1-1-7-1-1-1-1-2 | TCaActttcacTtCaGT | 17_60 | -20 |
| 17 | 2-2-2-5-1-1-11-2 | TCaaCTttcacTtCaGT | 17_61 | -22 |
| 17 | 2-2-1-6-1-1-1-1-2 | TCaaCtttcacTtCaGT | 17_62 | -21 |
| 17 | 2-3-1-5-1-1-1-1-2 | TCaacTttcacTtCaGT | 17_63 | -20 |
| 17 | 2-9-1-1-1-1-2 | TCaactttcacTtCaGT | 17_64 | -20 |
| 17 | 5-6-1-2-3 | TCAACtttcacTtCAGT | 17_65 | -23 |
| 17 | 4-1-1-5-1-2-3 | TCAAcTttcacTtcAGT | 17_66 | -23 |
| 17 | 4-7-1-2-3 | TCAActttcacTtcAGT | 17_67 | -22 |
| 17 | 3-1-1-6-1-2-3 | TCAaCtttcacTtcAGT | 17_68 | -22 |
| 17 | 3-2-1-5-1-2-3 | TCAacTttcacTtcAGT | 17_69 | -22 |
| 17 | 2-1-2-6-1-2-3 | TCaACtttcacTtcAGT | 17_70 | -22 |
| 17 | 2-1-1-1-1-5-1-2-3 | TCaAcTttcacTtcAGT | 17_71 | -21 |
| 17 | 1-1-2-1-1-5-1-2-3 | TcAAcTttcacTtcAGT | 17_72 | -20 |
| 17 | 5-6-1-3-2 | TCAACtttcacTtcaGT | 17_73 | -22 |

TABLE 7-continued

Lists oligonucleotides designs and specific anti-sense oligonucleotide compounds
Compounds are indicated by CMP ID NO. and based on the on the motif sequence in table 6.

| SEQ ID NO | Design | Oligonucleotide Compound | CMP ID NO | dG |
|---|---|---|---|---|
| 17 | 4-7-1-3-2 | TCAActttcacTtcaGT | 17_74 | −21 |
| 17 | 3-1-2-5-1-3-2 | TCAaCTttcacTtcaGT | 17_75 | −23 |
| 17 | 3-1-1-6-1-3-2 | TCAaCtttcacTtcaGT | 17_76 | −21 |
| 17 | 3-2-1-5-1-3-2 | TCAacTttcacTtcaGT | 17_77 | −21 |
| 17 | 2-1-2-6-1-3-2 | TCaACtttcacTtcaGT | 17_78 | −21 |
| 17 | 2-1-1-1-1-5-1-3-2 | TCaAcTttcacTtcaGT | 17_79 | −20 |
| 17 | 2-2-1-6-1-3-2 | TCaaCtttcacTtcaGT | 17_80 | −20 |
| 17 | 2-3-1-5-1-3-2 | TCaacTttcacTtcaGT | 17_81 | −19 |
| 17 | 1-1-3-6-1-3-2 | TCAACtttcacTtcaGT | 17_82 | −20 |
| 17 | 1-1-1-1-1-6-1-3-2 | TcAaCtttcacTtcaGT | 17_83 | −19 |
| 17 | 1-3-1-6-13-2 | TcaaCtttcacTtcaGT | 17_84 | −19 |
| 17 | 5-7-5 | TCAACtttcactTCAGT | 17_85 | −26 |
| 17 | 2-1-1-8-5 | TCaActttcactTCAGT | 17_86 | −23 |
| 17 | 2-2-1-7-5 | TCaaCtttcactTCAGT | 17_87 | −23 |
| 17 | 2-3-1-6-5 | TCaacTttcactTCAGT | 17_88 | −23 |
| 17 | 2-10-5 | TCaactttcactTCAGT | 17_89 | −23 |
| 17 | 1-1-2-8-5 | TcAActttcactTCAGT | 17_90 | −22 |
| 17 | 1-1-1-1-1-7-5 | TcAaCtttcactTCAGT | 17_91 | −22 |
| 17 | 1-3-1-7-5 | TcaaCtttcactTCAGT | 17_92 | −22 |
| 17 | 1-11-5 | TcaactttcactTCAGT | 17_93 | −21 |
| 17 | 5-7-2-1-2 | TCAACtttcactTCaGT | 17_94 | −24 |
| 17 | 4-1-1-6-2-1-2 | TCAAcTttcactTCaGT | 17_95 | −23 |
| 17 | 4-8-2-1-2 | TCAActttcactTCaGT | 17_96 | −22 |
| 17 | 3-1-1-7-2-1-2 | TCAaCtttcactTCaGT | 17_97 | −22 |
| 17 | 3-2-1-6-2-1-2 | TCAacTttcactTCaGT | 17_98 | −22 |
| 17 | 3-9-2-1-2 | TCAactttcactTCaGT | 17_99 | −22 |
| 17 | 2-1-1-6-2-1-2 | TCaActttcactTCaGT | 17_100 | −20 |
| 17 | 2-10-2-1-2 | TCaactttcactTCaGT | 17_101 | −20 |
| 17 | 1-1-3-7-2-1-2 | TCAACtttcactTCaGT | 17_102 | −21 |
| 17 | 1-1-2-8-2-1-2 | TcAActttcactTCaGT | 17_103 | −19 |
| 17 | 1-1-1-1-1-7-2-1-2 | TcAaCtttcactTCaGT | 17_104 | −20 |
| 17 | 1-1-1-2-1-6-2-1-2 | TcAacTttcactTCaGT | 17_105 | −19 |
| 17 | 1-1-1-9-2-1-2 | TcAactttcactTCaGT | 17_106 | −19 |
| 17 | 1-3-1-7-2-1-2 | TcaaCtttcactTCaGT | 17_107 | −20 |
| 17 | 1-11-2-1-2 | TcaactttcactTCaGT | 17_108 | −19 |
| 17 | 4-8-1-1-3 | TCAActttcactTcAGT | 17_109 | −22 |
| 17 | 3-1-1-7-1-1-3 | TCAaCtttcactTCAGT | 17_110 | −22 |
| 17 | 2-10-1-1-3 | TCaactttcactTcAGT | 17_111 | −20 |
| 17 | 1-1-3-7-1-1-3 | TCAACtttcactTCAGT | 17_112 | −21 |
| 17 | 1-1-2-8-1-1-3 | TcAActttcactTCAGT | 17_113 | −19 |
| 17 | 1-1-1-1-1-7-1-1-3 | TcAaCtttcactTCAGT | 17_114 | −20 |
| 17 | 1-2-1-8-1-1-3 | TcaActttcactTCAGT | 17_118 | −19 |
| 17 | 1-3-1-7-1-1-3 | TcaaCtttcactTcAGT | 17_116 | −20 |
| 17 | 1-11-1-1-3 | TcaactttcactTcAGT | 17_117 | −19 |
| 17 | 5-7-1 2-2 | TCAACtttcactTcaGT | 17_118 | −22 |
| 17 | 4-8-1-2-2 | TCAActttcactTcaGT | 17_119 | −21 |
| 17 | 3-1-1-7-1-2-2 | TCAaCtttcactTcaGT | 17_120 | −21 |
| 17 | 3-9-1-2-2 | TCAactttcactTcaGT | 17_121 | −20 |
| 17 | 2-2-1-7-1-2-2 | TCaaCtttcactTcaGT | 17_122 | −20 |
| 17 | 2-10-1-2-2 | TCaactttcactTcaGT | 17_123 | −19 |
| 17 | 1-1-1-1-1-7-1-2-2 | TcAaCtttcactTcaGT | 17_124 | −19 |
| 17 | 1-1-1-8-1-2-2 | TcAactttcactTcaGT | 17_125 | −18 |
| 17 | 1-2-1-8-1-2-2 | TcaActttcactTcaGT | 17_126 | −18 |
| 17 | 1-11-1-2-2 | TcaactttcactTcaGT | 17_127 | −17 |
| 17 | 5-8-4 | TCAACtttcacttCAGT | 17_128 | −25 |
| 17 | 3-10-4 | TCAactttcacttCAGT | 17_129 | −23 |
| 17 | 2-1-2-8-4 | TCaACtttcacttCAGT | 17_130 | −23 |
| 17 | 2-1-1-1-1-7-4 | TCaAcTttlcactCAGT | 17_131 | −22 |
| 17 | 2-1-1-9-4 | TCaActttcacttCAGT | 17_132 | −22 |
| 17 | 2-2-1-8-4 | TCaaCtttcacttCAGT | 17_133 | −23 |
| 17 | 2-3-1-7-4 | TCaacTttcacttCAGT | 17_134 | −22 |
| 17 | 2-11-4 | TCaactttcacttCAGT | 17_135 | −22 |
| 17 | 1-1-3-8-4 | TcAACtttcacttCAGT | 17_138 | −22 |
| 17 | 1-1-2-9-4 | TcAActttcacttCAGT | 17_137 | −21 |
| 17 | 1-1-1-1-1-8-4 | TcAaCtttcacttCAGT | 17_138 | −21 |
| 17 | 1-1-1-10-4 | TcAactttcacttCAGT | 17_139 | −20 |
| 17 | 4-1-1-7-1-1-2 | TCAAcTttcacttCaGT | 17_140 | −22 |
| 17 | 3-1-2-7-1-1-2 | TCAaCTttcacttCaGT | 17_141 | −23 |
| 17 | 3-1-1-8-1-1-2 | TCAaCtttcacttCaGT | 17_142 | −22 |
| 17 | 3-2-1-7-1-1-2 | TCAacTttcacttCaGT | 17_143 | −21 |
| 17 | 3-10-1-1-2 | TCAactttcacttCaGT | 17_144 | −21 |

TABLE 7-continued

Lists oligonucleotides designs and specific anti-sense oligonucleotide compounds
Compounds are indicated by CMP ID NO. and based on the on the motif sequence in table 6.

| SEQ ID NO | Design | Oligonucleotide Compound | CMP ID NO | dG |
|---|---|---|---|---|
| 17 | 2-1-3-7-1-1-2 | TCaACTttcacttCaGT | 17_145 | -22 |
| 17 | 2-1-2-8-1-1-2 | TCaACtttcacttCaGT | 17_146 | -21 |
| 17 | 2-1-1-1-1-7-1-1-2 | TCaAcTttcacttCaGT | 17_147 | -20 |
| 17 | 2-2-2-7-1-1-2 | TCaaCTttcacttCaGT | 17_148 | -21 |
| 17 | 2-3-1-7-1-1-2 | TCaacTttcacttCaGT | 17_149 | -20 |
| 17 | 1-1-3-8-1-1-2 | TcAACtttcacttCaGT | 17_150 | -20 |
| 17 | 1-1-1-1-1-8-1-1-2 | TcAaCtttcacttCaGT | 17_151 | -19 |
| 17 | 1-1-1-10-1-1-2 | TcAactttcacttCaGT | 17_152 | -18 |
| 17 | 1-2-1-9-1-1-2 | TcaActttcacttCaGT | 17_153 | -18 |
| 17 | 1-3-2-7-1-1-2 | TcaaCTttcacttCaGT | 17_154 | -20 |
| 17 | 1-12-1-1-2 | TcaactttcacttCaGT | 17_155 | -18 |
| 17 | 4-1-1-8-3 | TCAACTttcacttcAGT | 17_156 | -22 |
| 17 | 4-10-3 | TCAActttcacttcAGT | 17_157 | -22 |
| 17 | 3-1-2-8-3 | TCAaCTttcacttcAGT | 17_158 | -23 |
| 17 | 3-1-1-9-3 | TCAaCtttcacttcAGT | 17_159 | -22 |
| 17 | 2-2-2-8-3 | TCaaCTttcacttcAGT | 17_160 | -22 |
| 17 | 2-3-1-8-3 | TCaacTttcacttcAGT | 17_161 | -20 |
| 17 | 1-1-1-1-1-9-3 | TcAaCtttcacttcAGT | 17_162 | -19 |
| 17 | 1-1-1-11-3 | TcAactttcacttcAGT | 17_163 | -18 |
| 17 | 1-2-1-10-3 | TcaActttcacttcAGT | 17_164 | -19 |
| 17 | 1-13-3 | TcaactttcacttcAGT | 17_165 | -18 |
| 17 | 6-9-2 | TCAACTttcacttcaGT | 17_166 | -23 |
| 17 | 5-10-2 | TCAACtttcacttcaGT | 17_167 | -22 |
| 17 | 4-1-1-9-2 | TCAAcTttcacttcaGT | 17_168 | -21 |
| 17 | 4-11-2 | TCAActttcacttcaGT | 17_169 | -20 |
| 17 | 3-1-2-9-2 | TCAaCTttcactteaGT | 17_170 | -22 |
| 17 | 3-1-1-10-2 | TCAaCtttcacttcaGT | 17_171 | -21 |
| 17 | 3-12-2 | TCAactttcacttcaGT | 17_172 | -20 |
| 17 | 2-1-3-9-2 | TCaACTttcacttcaGT | 17_173 | -21 |
| 17 | 2-1-2-10-2 | TCaACtttcacttcaGT | 17_174 | -20 |
| 17 | 2-1-1-11-2 | TCaActttcacttcaGT | 17_175 | -19 |
| 17 | 2-2-1-10-2 | TCaaCtttcacttcaGT | 17_176 | -19 |
| 17 | 2-3-1-9-2 | TCaacTttcacttcaGT | 17_177 | -19 |
| 17 | 1-1-2-11-2 | TcAActttcacttcaGT | 17_178 | -18 |
| 17 | 1-1-1-1-1-10-2 | TcAaCtttcacttcaGT | 17_179 | -18 |
| 17 | 1-1-1-12-2 | TcAactttcacttcaGT | 17_180 | -17 |
| 17 | 1-2-1-11-2 | TcaActttcacttcaGT | 17_181 | -17 |
| 17 | 1-3-1-10-2 | TcaaCtttcacttcaGT | 17_182 | -18 |
| 17 | 1-14-2 | TcaactttcacttcaGT | 17_183 | -17 |
| 18 | 3-10-3 | TCAactttcacttCAG | 18_1 | -19 |
| 18 | 2-2-1-8-5 | TCaaCtttcacTTCAG | 18_2 | -21 |
| 18 | 1-1-3-6-2-1-2 | TcAACtttcacTTcAG | 18_3 | -18 |
| 18 | 5-6-1-1-3 | TCAACtttcacTtCAG | 18_4 | -22 |
| 18 | 4-7-1-1-3 | TCAActttcacTtCAG | 18_5 | -20 |
| 18 | 2-9-1-1-3 | TCaactttcacTtCAG | 18_6 | -18 |
| 18 | 1-3-1-6-11-3 | TcaaCtttcacTtCAG | 18_7 | -18 |
| 18 | 2-1-1-7-1-2-2 | TCaActttcacTtcAG | 18_8 | -17 |
| 18 | 5-7-4 | TCAACtttcactTCAG | 18_9 | -22 |
| 18 | 4-8-4 | TCAActttcactTCAG | 18_10 | -21 |
| 18 | 3-1-1-7-4 | TCAaCtttcactTCAG | 18_11 | -21 |
| 18 | 3-9-4 | TCAactttcactTCAG | 18_12 | -20 |
| 18 | 2-2-1-7-4 | TCaaCtttcactTCAG | 18_13 | -20 |
| 18 | 2-10-4 | TCaactttcactTCAG | 18_14 | -19 |
| 18 | 1-1-3-7-1-1-2 | TCAACtttcactTcAG | 18_15 | -17 |
| 18 | 1-1-1-1-1-7-1-1-2 | TcAaCtttcactTcAG | 18_16 | -16 |
| 18 | 3-1-7.1-1-2 | TcaaCtttcactTcAG | 18_17 | -16 |
| 18 | 5-8-3 | TCAACtttcacttCAG | 18_18 | -21 |
| 18 | 4-9-3 | TCAActttcacttCAG | 18_19 | -20 |
| 18 | 3-1-1-8-3 | TCAaCtttcacttCAG | 18_20 | -20 |
| 18 | 2-2-1-8-3 | TCaaCtttcacttCAG | 18_21 | -19 |
| 18 | 2-11-3 | TCaactttcacttCAG | 18_22 | -18 |
| 18 | 5-9-2 | TCAACtttcacttcAG | 18_23 | -19 |
| 18 | 4-10-2 | TCAActttcacttcAG | 18_24 | -18 |
| 18 | 3-1-1-9-2 | TCAaCtttcacttcAG | 18_25 | -18 |
| 18 | 3-11-2 | TCAactttcacttcAG | 18_26 | -17 |
| 18 | 2-1-2-9-2 | TCaACtttcacttcAG | 18_27 | -17 |
| 18 | 2-2 1-9-2 | TCaaCtttcacttcAG | 18_28 | -17 |
| 18 | 2-12-2 | TCaactttcacttcAG | 18_29 | -16 |
| 18 | 1-1-3-9-2 | TcAACtttcacttcAG | 18_30 | -18 |
| 18 | 1-3-1-9-2 | TcaaCtttcacttcAG | 18_31 | -15 |
| 18 | 3-10-3 | TCAactttcacttCAG | 18_249 | -19 |

TABLE 7-continued

Lists oligonucleotides designs and specific anti-sense oligonucleotide compounds
Compounds are indicated by CMP ID NO. and based on the on the motif sequence in table 6.

| SEQ ID NO | Design | Oligonucleotide Compound | CMP ID NO | dG |
|---|---|---|---|---|
| 18 | 5-5-6 | TCAACtttcaCTTCAG | 18_250 | −25 |
| 18 | 4-6-6 | TCAActttcaCTTCAG | 18_251 | −24 |
| 18 | 3-1-1-5-6 | TCAaCtttcaCTTCAG | 18_252 | −24 |
| 18 | 2-1-2-5-6 | TCaACtttcaCTTCAG | 18_253 | −23 |
| 18 | 2-2-1-5-6 | TCaaCtttcaCTTCAG | 18_254 | −22 |
| 18 | 1-3-1-5-6 | TcaaCtttcaCTTCAG | 18_255 | −21 |
| 18 | 1-9-6 | TcaactttcaCTTCAG | 18_256 | −20 |
| 18 | 1-1-1-1-1-5-3-1-2 | TcAaCtttcaCTTcAG | 18_257 | −19 |
| 18 | 1-3-1-5-3-1 2 | TcaaCtttcaCTTcAG | 18_258 | −18 |
| 18 | 1-9-3-1-2 | TcaactttcaCTTcAG | 18_259 | −17 |
| 18 | 3-1-1-5-2-1-3 | TCAaCtttcaCTtCAG | 18_260 | −22 |
| 18 | 3-7-2-1-3 | TCAactttcaCTtCAG | 18_261 | −21 |
| 18 | 2-2-1-5-2-1-3 | TCaaCtttcaCTtCAG | 18_282 | −21 |
| 18 | 2-8-2-1-3 | TCaactttcaCTtCAG | 18_263 | −20 |
| 18 | 1-1-3-5-2-1-3 | TcAACtttcaCTtCAG | 18_264 | −21 |
| 18 | 1-3-1-5-2-1-3 | TcaaCtttcaCTtCAG | 18_265 | −20 |
| 18 | 1-9-2-1-3 | TcaactttcaCTtCAG | 18_286 | −19 |
| 18 | 5-5-2-2-2 | TCAACtttcaCTtcAG | 18_267 | −21 |
| 18 | 4-6-2-2-2 | TCAActttcaCTtcAG | 18_268 | −20 |
| 18 | 3-1-1-5-2-2-2 | TCAaCtttcaCTtcAG | 18_269 | −20 |
| 18 | 3-7-2-2-2 | TCAactttcaCTtcAG | 18_270 | −19 |
| 18 | 2-1-2-5-2-2-2 | TCaACtttcaCTtcAG | 18_271 | −20 |
| 18 | 2-1-1-6-2-2-2 | TCaActttcaCTtcAG | 18_272 | −18 |
| 18 | 1-11-1-1-5-2-2-2 | TcAaCtttcaCTtcAG | 18_273 | −18 |
| 18 | 1-3-1-5-2-2-2 | TcaaCtttcaCTtcAG | 18_274 | −18 |
| 18 | 5-5-1-1-4 | TCAACtttcaCtTCAG | 18_275 | −23 |
| 18 | 4-6-1-1-4 | TCAActttcaCtTCAG | 18_276 | −22 |
| 18 | 3-1-1-5-1-1-4 | TCAactttcaCtTCAG | 18_277 | −22 |
| 18 | 3-7-1-1-4 | TCAactttcaCtTCAG | 18_278 | −21 |
| 18 | 2-1-2-5-1-1-4 | TCaACtttcaCtTCAG | 18_279 | −22 |
| 18 | 2-1-1-6-1-1-4 | TCaActttcaCtTCAG | 18_280 | −20 |
| 18 | 2-2-1-5-1-1-4 | TCaaCtttcaCtTCAG | 18_281 | −21 |
| 18 | 2-8-1-1-4 | TCaactttcaCtTCAG | 18_282 | −20 |
| 18 | 2-2-1-5-1-1-1-1-2 | TCaaCtttcaCtTcAG | 18_283 | −18 |
| 18 | 2-8-1-1-1-1 2 | TCaactttcaCtTCAG | 18_284 | −17 |
| 18 | 1-1-3-5-1-1-1-1-2 | TCAACtttcaCtTcAG | 18_285 | −18 |
| 18 | 1-1-2-6-1-1-1-1-2 | TcAActttcaCtTCAG | 18_286 | −16 |
| 18 | 1-1-1-1-1-5-1-1-1-1-2 | TcAaCtttcaCtTCAG | 18_287 | −17 |
| 18 | 1-1-1-7-1-1-1-1-2 | TcAactttcaCtTcAG | 18_288 | −16 |
| 18 | 1-2-1-6-1-1-1-1-2 | TcaActttcaCtTcAG | 18_289 | −16 |
| 18 | 1-3-1-5-1-1-1-1-2 | TcaaCtttcaCtTCAG | 18_290 | −17 |
| 18 | 1-9-1-1-1-1-2 | TcaactttcaCtTcAG | 18_291 | −18 |
| 18 | 5-5-1-2-3 | TCAACtttcaCttCAG | 18_292 | −22 |
| 18 | 4-6-1-2-3 | TCAActttcaCttCAG | 18_293 | −21 |
| 18 | 3-1-1-5-1-2-3 | TCAaCtttcaCttCAG | 18_294 | −21 |
| 18 | 3-7-1-2-3 | TCAactttcaCttCAG | 18_295 | −20 |
| 18 | 2-1-2-5-1-2-3 | TCaACtttcaCttCAG | 18_296 | −21 |
| 18 | 2-1-1-6-1-2-3 | TCaActttcaCttCAG | 18_297 | −19 |
| 18 | 2-2-1 5-1-2-3 | TCaaCtttcaCttCAG | 18_298 | −20 |
| 18 | 2-8-1-2-3 | TCaactttcaCttCAG | 18_299 | −10 |
| 18 | 1-1-3-5-1-2-3 | TcAACtttcaCttCAG | 18_300 | −20 |
| 18 | 1-2-2-5 1-2-3 | TcaACtttcaCttCAG | 18_301 | −19 |
| 18 | 1-2-1-6-1-2-3 | TcaActttcaCttCAG | 18_302 | −18 |
| 18 | 5-5-1-3-2 | TCAACtttcaCttcAG | 18_303 | −20 |
| 18 | 4-6-1-3-2 | TCAActttcaCttcAG | 18_304 | −19 |
| 18 | 3-1-1-5-1-3-2 | TCAaCtttcaCttcAG | 18_305 | −19 |
| 18 | 3-7-1-3-2 | TCAactttcaCttcAG | 18_306 | −18 |
| 18 | 2-1-2-5-1-3-2 | TCaACtttcaCttcAG | 18_307 | −18 |
| 18 | 2-1-1-6-1 3-2 | TCaActttcaCttcAG | 18_308 | −17 |
| 18 | 2-2-1-5-1-3-2 | TCaaCtttcaCttcAG | 18_309 | −18 |
| 18 | 2-8-1-3-2 | TCaactttcaCttcAG | 18_310 | −17 |
| 18 | 1-1-3-5-1-3-2 | TcAACtttcaCttcAG | 18_311 | −17 |
| 18 | 1-1 2-6-1-3-2 | TcAActttcaCttcAG | 18_312 | −16 |
| 18 | 1-1-1-1-1-5-1-3-2 | TcAaCtttcaCttcAG | 18_313 | −16 |
| 18 | 1-1-1-7-1-3-2 | TcAactttcaCttcAG | 18_314 | −15 |
| 18 | 1-2-2-5-1-3-2 | TcaACtttcaCttcAG | 18_315 | −17 |
| 18 | 1-3-1-5-1-3-2 | TcaaCtttcaCttcAG | 18_316 | −16 |
| 18 | 1-9-1-3-2 | TcaactttcaCttcAG | 18_317 | −15 |
| 18 | 4-7-5 | TCAActttcacTTCAG | 18_318 | −22 |
| 18 | 3-1-1-6-5 | TCAaCtttcacTTCAG | 18_319 | −22 |

TABLE 7-continued

Lists oligonucleotides designs and specific anti-sense oligonucleotide compounds
Compounds are indicated by CMP ID NO. and based on the on the motif sequence in table 6.

| SEQ ID NO | Design | Oligonucleotide Compound | CMP ID NO | dG |
|---|---|---|---|---|
| 18 | 2-1-2-6-5 | TCaACtttcacTTCAG | 18_320 | -22 |
| 18 | 1-1-3-6-5 | TCAACtttcacTTCAG | 18_321 | -21 |
| 18 | 1-1-1-1-1-6-5 | TcAaCtttcacTTCAG | 18_322 | -20 |
| 18 | 1-3-1-6-5 | TcaaCtttcacTTCAG | 18_323 | -19 |
| 18 | 5-6-2-1-2 | TCAACtttCacTTCAG | 18_324 | -21 |
| 18 | 3-1-1-5-2-1-2 | TCAaCtttcacTTcAG | 18_325 | -20 |
| 18 | 2-2-1-6-2-1-2 | TCaaCtttcacTTcAG | 18_326 | -18 |
| 18 | 1-1-2-7-2-1-2 | TcAActttcacTTcAG | 18_327 | -16 |
| 18 | 1-1-1-1-1-6-2-1-2 | TcAaCtttcacTTcAG | 18_328 | -17 |
| 18 | 1-1-1-8-2-1-2 | TcAactttcacTTcAG | 18_329 | -16 |
| 18 | 1-3-1-6-2-1-2 | TcaaCtttcacTTcAG | 18_330 | -17 |
| 18 | 1-10-2-1-2 | TcaaCtttcacTTcAG | 18_331 | -16 |
| 18 | 3-1-1-6-1-1-3 | TCAaCtttcacTtCAG | 18_332 | -21 |
| 18 | 2-1-1-7-1-1-3 | TCaActttcacTtCAG | 18_333 | -19 |
| 18 | 2-2-1-6-1-1-3 | TCaaCtttcacTtCAG | 18_334 | -19 |
| 18 | 1-1-2-7-1-1-3 | TcAActttcacTtCAG | 18_335 | -18 |
| 18 | 1-10-1-1-3 | TcaactttcacTtCAG | 18_336 | -17 |
| 18 | 5-6-1-2-2 | TCAACtttcacTtcAG | 18_337 | -20 |
| 18 | 4 7-1-2-2 | TCAActttcacTtcAG | 18_338 | -18 |
| 18 | 3-1-1-6-1-2-2 | TCAaCtttcacTtcAG | 18_339 | -19 |
| 18 | 2-2-1-6-1-2-2 | TCaaCtttcacTtcAG | 18_340 | -17 |
| 18 | 2-9-1-2-2 | TCaactttcacTtcAG | 18_341 | -16 |
| 18 | 1-1-3-6-1-2-2 | TcAACtttcacTtcAG | 18_342 | -17 |
| 18 | 1-1-1-1-1-6-1-2-2 | TcAaCtttcacTtcAG | 18_343 | -16 |
| 18 | 1-3-1-6-1 2-2 | TcaaCtttcacTtcAG | 18_344 | -16 |
| 18 | 2-1-2-7-4 | TCaACtttcactTCAG | 18_345 | -21 |
| 18 | 2-1-1-8-4 | TCaActttcactTCAG | 18_346 | -19 |
| 18 | 1-1-2-8-4 | TcAActttcactTCAG | 18_347 | -18 |
| 18 | 1-2-1-8-4 | TcaActttcactTCAG | 18_348 | -18 |
| 18 | 1-11-4 | TcaactttcactTCAG | 18_349 | -17 |
| 18 | 4-8-1-1-2 | TCAActttcactTcAG | 18_350 | -18 |
| 18 | 2-2-1-7-1-1-2 | TCaaCtttcactTcAG | 18_351 | -17 |
| 18 | 2-10-1-1-2 | TCaactttcactTcAG | 18_352 | -16 |
| 18 | 1-1-2-8-1-1-2 | TcAActttcactTcAG | 18_353 | -15 |
| 18 | 1-2-2-7-1-1-2 | TcaACtttcactTcAG | 18_354 | -17 |
| 18 | 1-2-1-8-1-1-2 | TcaActttcactTcAG | 18_355 | -15 |
| 18 | 2-1-2-S-3 | TCaACtttcacttCAG | 18_356 | -20 |
| 18 | 2-1-1-9-3 | TCaActttcacttCAG | 18_357 | -18 |
| 18 | 1-2-2-8-3 | TcaACtttcacttCAG | 18_358 | -18 |
| 18 | 1-2-1-9-3 | TcaActttcacttCAG | 18_359 | -17 |
| 18 | 1-12-3 | TcaactttcacttCAG | 18_360 | -18 |
| 18 | 1-1-1-1-1-9-2 | TcAaCtttcacttcAG | 18_361 | -15 |
| 19 | 5-6-5 | TGTTTcaatacTAAAA | 19_1 | -16 |
| 19 | 4-7-5 | TGTTtcaatacTAAAA | 19_2 | -15 |
| 19 | 5-6-2-1-2 | TGTTTcaatacTAaAA | 19_3 | -16 |
| 19 | 5-5-6 | TGTTTcaataCTAAAA | 19_4 | -18 |
| 19 | 4-6-6 | TGTTtcaataCTAAAA | 19_5 | -17 |
| 19 | 3-1-1-5-6 | TGTtTcaataCTAAAA | 19_6 | -17 |
| 19 | 3-7-6 | TGTttcaataCTAAAA | 19_7 | -18 |
| 19 | 2-1-2-5-6 | TGtTTcaataCTAAAA | 19_8 | -16 |
| 19 | 2-2-1-5-6 | TGttTcaataCTAAAA | 19_9 | -15 |
| 19 | 1-1-3-5-6 | TgTTTcaataCTAAAA | 19_10 | -16 |
| 19 | 5-5-3-1-2 | TGTTTcaatacTAaAA | 19_11 | -17 |
| 19 | 4-6-3-1-2 | TGTTtcaataCTAaAA | 19_12 | -16 |
| 19 | 3-1-1-5-3-1-2 | TGTtTcaataCTAaAA | 19_13 | -16 |
| 19 | 3-7-3-1-2 | TGTttcaataCTAaAA | 19_14 | -16 |
| 19 | 2-1-2-5-3-1-2 | TGtTTcaataCTAaAA | 19_15 | -15 |
| 19 | 1-1-3-5-3-1-2 | TgTTTcaataCTAaAA | 19_16 | -15 |
| 19 | 5-5-2-1-3 | TGTTTcaataCTaAAA | 19_17 | -17 |
| 19 | 4-6-2-1-3 | TGTTtcaataCTaAAA | 19_18 | -16 |
| 19 | 3-1-1-5-2-1-3 | TGTtTcaataCTaAAA | 19_19 | -15 |
| 19 | 5-5-2-2-2 | TGTTTcaataCTaaAA | 19_20 | -16 |

TABLE 7-continued

Lists oligonucleotides designs and specific anti-sense oligonucleotide compounds
Compounds are indicated by CMP ID NO. and based on the on the motif sequence in table 6.

| SEQ ID NO | Design | Oligonucleotide Compound | CMP ID NO | dG |
|---|---|---|---|---|
| 19 | 4-6-2-2-2 | TGTTtcaataCTaAAA | 19_21 | −15 |
| 19 | 5-5-1-1-4 | TGTTTcaataCtAAAA | 19_22 | −15 |

Designs refer to the gapmer design, F-G-F'. In classic gapmer design e.g. 3-10-3 all the nucleotides in the flanks (F and F') are constituted of the same 2'-sugar modified nucleoside, e.g, LNA, cET, or MOE, and a stretch of DNA in the middle forming the gap (G) in gapmers with alternating flank designs the flanks of oligonucleotide is annotated as a series of integers representing a number of 2' sugar modified nucleosides (M) followed by a number of DNA nucleosides (D) For example a flank with a 2-2-1 motif represents 5'$[M]_2$-$[D]_2$-[M]3' and a 1-1-1-1-1 motif represents 5' [M]-[D]-[M]-[D]-[M] 3'. Both flanks have a 2' sugar modified nucleoside at the 5' and 3" terminal. The gap region (G) which is constItuted of a number of DNA nucleosides (typically between 5 and 16), is located between the flanks. The heading "Oligonucleotide compound" in the table represents specific designs of a motif sequence. Capital letters represent beta-D-oxy LNA nucleosides, lowercase letters represent DNA nucleosides, alt LNA C are 5-methyl cytosine, and 5-methyl cytosine DNA are presented by "e", all internucleoside linkages are phosphorothioate internucleoside linkages.

TABLE 8

List of stereodefined variants.
The parent oligonucleotide compound is indicated with its sequence motif and design. The stereo-definition motif of the internucleoside linkages of the parent compound is indicated below the sequence and design, and reflects a fully stereo-random phosphorthioate gapmer. The stereodefined variants of the parent are listed by CMP ID NO and stereodefined motifs below the parent compound. The table contain three parent compounds CMP ID NO: 18_1, 18_347_and 18_12.

| SEQ ID NO | Design | CMP ID NO | Parent Compound/ stereodefinition |
|---|---|---|---|
| 18 | 3-10-3 | 18_1 | TCAactttcacttcag<br>XXXXXXXXXXXXXXXH |

| CMP ID NO | Stereodefined motif | CMP ID NO | Stereodefined motif |
|---|---|---|---|
| 18_32 | RSSRXXXXXXXXXxXH | 18_365 | SSSSSRSRRXXXXXXH |
| 18_33 | XRSSRXXXXXXXXXXH | 18_366 | SSSSSSRRRXXXXXXH |
| 18_34 | XXRSSRXXXXXXXXXH | 18_367 | SSSRSRRRRXXXXXXH |
| 18_35 | XXXRSSRXXXXXXXXH | 18_368 | SSRSSRRRRXXXXXXH |
| 18_36 | XXXXRSSRXXXXXXXH | 18_369 | SSRRSSRRRXXXXXXH |
| 18_37 | XXXXXRSSRXXXXXXH | 18_370 | SSRRSRSRRXXXXXXH |
| 18_38 | XXXXXXRSSRXXXXXH | 18_371 | SSRRSSSRRXXXXXXH |
| 18_39 | XXXXXXXRSSRXXXXH | 18_372 | SSSRSRSRRXXXXXXH |
| 18_40 | XXXXXXXXRSSRXXXH | 18_373 | SSSSSRRRRXXXXXXH |
| 18_41 | XXXXXXXXXRSSRXXH | 18_374 | SSRSSSRRRXXXXXXH |
| 18_42 | XXXXXXXXXXRSSRXH | 18_375 | SSRSSRSRRXXXXXXH |
| 18_43 | XXXXXXXXXXXRSSRH | 18_376 | SSSRSSRRRXXXXXXH |

TABLE 8-continued

List of stereodefined variants.
The parent oligonucleotide compound is indicated with its sequence motif and design. The stereo-definition motif of the internucleoside linkages of the parent compound is indicated below the sequence and design, and reflects a fully stereo-random phosphorthioate gapmer. The stereodefined variants of the parent are listed by CMP ID NO and stereodefined motifs below the parent compound. The table contain three parent compounds CMP ID NO: 18_1, 18_347_and 18_12.

| | | | |
|---|---|---|---|
| 18_44 | XXXXXXXXXSSSSSRH | 18_377 | SSRRSRRRRXXXXXXH |
| 18_45 | XXXXXXXXXRRRRRRH | 18_378 | RSSRRSSSSRRRRSSH |
| 18_46 | XXXXXXXXXSSRRSRH | 18_379 | SRSRRSSSSRRRRSSH |
| 18_47 | XXXXXXXXXSSSRSRH | 18_380 | SSRRRSSSSRRRRSSH |
| 18_48 | XXXXXXXXXSSSRRSH | 18_381 | SSSSRSSSSRRRRSSH |
| 18_49 | XXXXXXXXXSRSSSSH | 18_382 | SSSRSSSSSRRRRSSH |
| 18_50 | XXXXXXXXXRSRSRSH | 18_383 | SSSRRRSSSRRRRSSH |
| 18_51 | XXXXXXXXXSSSSRSH | 18_384 | SSSRRSRSSRRRRSSH |
| 18_52 | XXXXXXXXXSSRRSSH | 18_385 | SSSRRSSRSRRRRSSH |
| 18_53 | XXXXXXXXXRRSSSSH | 18_386 | SSSRRSSSRRRRRSSH |
| 18_54 | XXXXXXXXXRSSRRRH | 18_387 | SSSRRSSSSSRRRSSH |
| 18_55 | XXXXXXXXXSRRRRSH | 18_388 | SSSRRSSSSSSRRSSH |
| 18_56 | XXXXXXXXXSSRSRRH | 18_389 | SSSRRSSSSRRSRSSH |
| 18_57 | XXXXXXXXXRRRSRRH | 18_390 | SSSRRSSSSRRRSSSH |
| 18_58 | XXXXXXXXXRRSRSRH | 18_391 | SSSRRSSSSRRRRRSH |
| 18_59 | XXXXXXXXXSSRRRSH | 18_392 | SSSRRSSSSRRRRSRH |
| 18_60 | XXXXXXXXXSRRSSSH | 18_393 | SRSSRSSSSRRRRSSH |
| 18_61 | XXXXXXXXXRRRRRSH | 18_394 | SSRSSRSSSRRRRSSH |
| 18_62 | XXXXXXXXXRRSSRRH | 18_395 | SSSRSSRSSRRRRSSH |
| 18_63 | XXXXXXXXXRSRRRRH | 18_396 | SSSRRRSSRRRRRSSH |
| 18_64 | XXXXXXXXXSRRRSSH | 18_397 | SSSRRSSRSSRRRSSH |
| 18_65 | XXXXXXXXXSRSRSRH | 18_398 | SSSRRSSSRSSRRSSH |
| 18_86 | XXXXXXXXXRSSSSRH | 18_399 | SSSRRSSSSRSSRSSH |
| 18_67 | XXXXXXXXXSSSSRRH | 18_400 | SSSRRSSSSRRSSRSH |
| 18_68 | XXXXXXXXXRRSSSRH | 18_401 | SSSRRSSSSRRRSSRH |
| 18_69 | XXXXXXXXXRSSRRSH | 18_402 | RSSRRSSSSRRRSSRH |
| 18_70 | XXXXXXXXXRSSSRRH | 18_403 | SRSSRSSSSRRSSRSH |
| 18_71 | XXXXXXXXXSRRRRRH | 18_404 | SSRSSRSSSRSSRSSH |
| 18_72 | XXXXXXXXXRRSRSSH | 18_405 | SSSRSSRSRSSRRSSH |
| 18_73 | XXXXXXXXXRSRSSRH | 18_406 | SSSRRSSRRSSRRSSH |
| 18_74 | XXXXXXXXXRSRSRRH | 18_407 | RSSRRRSSRRRRSSRH |
| 18_75 | XXXXXXXXXSRRRSRH | 18_408 | SSSRSSSRRRRRXXXH |
| 18_76 | XXXXXXXXXRRSRRSH | 18_409 | SSSSSSSRRRRRXXXH |
| 18_77 | XXXXXXXXXSSSRRRH | 18_410 | SSSRSSSRRSRRXXXH |

TABLE 8-continued

List of stereodefined variants. The parent oligonucleotide compound is indicated with its sequence motif and design. The stereo-definition motif of the internucleoside linkages of the parent compound is indicated below the sequence and design, and reflects a fully stereo-random phosphorthioate gapmer. The stereodefined variants of the parent are listed by CMP ID NO and stereodefined motifs below the parent compound. The table contain three parent compounds CMP ID NO: 18_1, 18_347_and 18_12.

| | | | |
|---|---|---|---|
| 18_78 | XXXXXXXXXRSRRSRH | 18_411 | SSSRSSSRRRSRXXXH |
| 18_79 | XXXXXXXXXSRRSRSH | 18_412 | SSSSSSSRRSSRXXXH |
| 18_80 | XXXXXXXXXRRSRRRH | 18_413 | SSSSSSSRRSRRXXXH |
| 18_81 | XXXXXXXXXSRRSSRH | 18_414 | SSSSSSSRRRSRXXXH |
| 18_82 | XXXXXXXXXSRSSSRH | 18_415 | SSSRSSSRRSSRXXXH |
| 18_83 | XXXXXXXXXRSRRRSH | 18_416 | SSRRSRRRRXXRXXXH |
| 18_84 | XXXXXXXXXSSSRSSH | 18_417 | SSSRSRRRRXXRXXXH |
| 18_85 | XXXXXXXXXSSRSSRH | 18_418 | SSRSSRRRRXXRXXXH |
| 18_86 | XXXXXXXXXRSSRSSH | 18_419 | SSRRSSRRRXXRXXXH |
| 18_87 | XXXXXXXXXSRSSRSH | 18_420 | SSRRSRSRRXXRXXXH |
| 18_88 | XXXXXXXXXSSSSSSH | 18_421 | SSSSSSSRRXXRXXXH |
| 18_89 | XXXXXXXXXRSRRSSH | 18_422 | SSRSSSSRRXXRXXXH |
| 18_90 | XXXXXXXXXRRRRSRH | 18_423 | SSSSSSSRRXXRXXXH |
| 18_91 | XXXXXXXXXSSRSRSH | 18_424 | SSSSSSSRRXXRXXXH |
| 18_92 | XXXXXXXXXRSRRSSH | 18_425 | SSSSSRSRRXXRXXXH |
| 18_93 | XXXXXXXXXRSRSSSH | 18_426 | SSSSSSSRRXXRXXXH |
| 18_94 | XXXXXXXXXRSSRSRH | 18_427 | SSSSSRSRRXXRXXXH |
| 18_95 | XXXXXXXXXRRRSRSH | 18_428 | SSSRSSRRRXXRXXXH |
| 18_96 | XXXXXXXXXRRSSRSH | 18_429 | SSRSSSSRRXXRXXXH |
| 18_97 | XXXXXXXXXSRSSRSH | 18_430 | SSRSSSSRRXXRXXXH |
| 18_98 | XXXXXXXXXSSRSRRH | 18_431 | SSSSSRSRRXXRXXXH |
| 18_99 | XXXXXXXXXSRSRSSH | 18_432 | SSSRRSSSSRSRRSSH |
| 18_100 | XXXXXXXXXSSSRRRH | 18_433 | XXXXRSSRXSSSRXXH |
| 18_101 | XXXXXXXXXSSSSSSH | 18_434 | XXXXRSSRXSSRRXXH |
| 18_102 | XXXXXXXXXSSSSSSH | 18_435 | XXXXRSSRXRSSRXXH |
| 18_103 | XXXXXXXXXRSSSRSH | 18_438 | XXXXRSSRXSRSSXXH |
| 18_104 | XXXXXXXXXRSRSSRH | 18_437 | XXXXRSSRXRRRRXXH |
| 18_105 | XXXXXXXXXRRRSSSH | 18_438 | XXXXRSSRXRRSRXXH |
| 18_106 | XXXXXXXXXSRSSRSH | 18_439 | XXXXRSSRXSRRRXXH |
| 18_107 | XXXXXXXXXSSRRRRH | 18_440 | XXXXRSSRXSRSSXXH |
| 18_108 | XXXXXXXXXXSSRSSH | 18_441 | XXXXRSSRXRSRRXXH |
| 18_109 | XXXXXXXXXXRRRSSH | 18_442 | XXXXRSSRXRSSSXXH |
| 18_110 | XXXXXXXXXXRRSSRH | 18_443 | XXXXRSSRXRRRSXXH |
| 18_111 | XXXXXXXXXXRSSSRH | 18_444 | XXXXRSSRXRSRSXXH |

TABLE 8-continued

List of stereodefined variants. The parent oligonucleotide compound is indicated with its sequence motif and design. The stereo-definition motif of the internucleoside linkages of the parent compound is indicated below the sequence and design, and reflects a fully stereo-random phosphorthioate gapmer. The stereodefined variants of the parent are listed by CMP ID NO and stereodefined motifs below the parent compound. The table contain three parent compounds CMP ID NO: 18_1, 18_347_and 18_12.

| | | | |
|---|---|---|---|
| 18_112 | XXXXXXXXXXRRSRRH | 18_445 | XXXXRSSRXSRSSXXH |
| 18_113 | XXXXXXXXXXSSSSRH | 18_446 | XXXXRSSRXSSSSXXH |
| 18_114 | XXXXXXXXXXRRSRRH | 18_447 | XXXXRSSRXSRSRXXH |
| 18_115 | XXXXXXXXXXSRSSSH | 18_448 | XXXXRSSRXSSRSXXH |
| 18_116 | XXXXXXXXXXSSSSRH | 18_449 | SSSRRSSSRRSSRSSH |
| 18_117 | XXXXXXXXXXRSSRSH | 18_450 | RSSRRSSSRRRRRSSH |
| 18_118 | XXXXXXXXXXRSRRRH | 18_451 | SRSRRSSSRRRRRSSH |
| 18_119 | XXXXXXXXXXSRRRRH | 18_452 | SSRRRSSSRRRRRSSH |
| 18_120 | XXXXXXXXXXSRSRSH | 18_453 | SSSSRSSSRRRRRSSH |
| 18_121 | XXXXXXXXXXSSSRSH | 18_484 | SSSRSSSSRRRRRSSH |
| 18_122 | XXXXXXXXXXRSRSSH | 18_455 | SSSRRSRSRRRRRSSH |
| 18_123 | XXXXXXXXXXSSSSSH | 18_456 | SSSRRSSRRRRRRSSH |
| 18_124 | XXXXXXXXXXSRRSSH | 18_457 | SSSRRSSSRSRRRSSH |
| 18_125 | XXXXXXXXXXRSRRSH | 18_458 | SSSRRSSSRRSRRSSH |
| 18_126 | XXXXXXXXXXSSRRSH | 18_459 | SSSRRSSSRRRSRSSH |
| 18_127 | XXXXXXXXXXRRRSRH | 18_460 | SSSRRSSSRRRRSSSH |
| 18_128 | XXXXXXXXXXSRSRRH | 18_461 | SSSRRSSSRRRRRRSH |
| 18_129 | XXXXXXXXXXRRSRSH | 18_462 | SSSRRSSSRRRRRSRH |
| 18_130 | XXXXXXXXXXRRSSSH | 18_463 | SSSRRSSSRRRSSSRH |
| 18_131 | XXXXXXXXXXRSSSSH | 18_464 | SSSRRSSSRRRSRRSH |
| 18_132 | XXXXXXXXXXRSSRRH | 18_465 | XXXXRSSRXRRSRRSH |
| 18_133 | XXXXXXXXXXSRRSRH | 18_466 | XXXXRSSRXXRSSSRH |
| 18_134 | XXXXXXXXXXSSRRRH | 18_467 | SSXXSXXRRXXRXXXH |
| 18_135 | XXXXXXXXXXSRSSRH | 18_468 | SSXXSXXRRXXXXXXH |
| 18_136 | XXXXXXXXXXRRRRSH | 18_469 | SSSXSSSRRXXRXXXH |
| 18_137 | XXXXXXXXXXRSRSRH | 18_470 | SXXXSXXXXXXXXXXH |
| 18_138 | XXXXXXXXXXSSSRRH | 18_497 | RRRSSRSSRSSRSRRH |
| 18_139 | XXXXXXXXXXSRSRSH | 18_498 | SSSRRSRRSRRSRSSH |
| 18_140 | SSRRRRSSSSSRSSRH | 18_499 | SRRSRSRSRRRSRRRH |
| 18_141 | SSSSSRRRRRRSRRSH | 18_500 | SRRRSSRRSSRSSSSH |
| 18_142 | SRSSRSSSRRRSRSRH | 18_501 | SRRRSSRSSRSRSSSH |
| 18_143 | SRRSSSSRRSRRRRRH | 18_502 | RRRSSRSRSSSRRRRH |
| 18_144 | SSRRSRSRSSSRSRRH | 18_503 | SRRRSSSRRRRSSSSH |
| 18_145 | SSSRRRRSRRRSSRRH | 18_504 | RRSSRSRSRSSRRSSH |

TABLE 8-continued

List of stereodefined variants. The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347_and 18_12.

| | | | |
|---|---|---|---|
| 18_146 | RRSRSSRRSSSRRSSH | 18_505 | RRSRSRSRSSSRRSRH |
| 18_147 | RSSRRRSSSRSSSRSH | 18_506 | RSSSRRSSSRSRRSRH |
| 18_148 | SSSSRRRSRSSSRRSH | 18_507 | SRRSRSSSSSSRRRSH |
| 18_149 | SSSRSSSSSSSRRRRH | 18_508 | RRSSRSRRSRSRRRRH |
| 18_150 | SSSSRSSSSSSSSSSH | 18_509 | RRRRSRRRRSSSSRSH |
| 18_151 | RRSRRRRRSSSSSSSH | 18_510 | SSRRSRSRRSSSRRRH |
| 18_152 | RRRRSRSSRRRRSSSH | 18_511 | SSRRRRSRSSSRRRRH |
| 18_153 | RRRRRSSRRRSRSSRH | 18_512 | RRRRRSSSRSRSSSSH |
| 18_154 | SSRRRRSRSRSSRRSH | 18_513 | SRSRSSRRRSSSSSSH |
| 18_155 | RSSSSSRSSRRSSSSH | 18_514 | RSRSRSRSSRSRRRRH |
| 18_156 | RRRSSSSSRSRSRRSH | 18_515 | SSRRSRSSSSSRSSRH |
| 18_157 | RSSSRSRSRRRSRRRH | 18_516 | RSRRSRSSSSRRSSSH |
| 18_158 | RRSRRSSSRRRRRRSH | 18_517 | RRSSRSRRRSRRRSRH |
| 18_159 | RRSSSSRSRSSSRSRH | 18_518 | SRSRSSSSSSSSSSSH |
| 18_160 | RSSRSRSRSRSRSRRH | 18_519 | RSSSSSRSRSSSRSSH |
| 18_161 | SRRRSSSSRSRSRSRH | 18_520 | SRSSSSRSRSSSSRSH |
| 18_162 | SRSSSRRSRRRRSSRH | 18_521 | RRSRRSRRRSRRRSSH |
| 18_163 | RSSRRRSRRSRSSRRH | 18_522 | SRRSRSRSRSRSRRRH |
| 18_164 | SSRRRSSRSSRRRRSH | 18_523 | SRRRRSSSSRRSSRSH |
| 18_165 | RSRSSRRSRRRSSSRH | 18_524 | RSSSRRRRRSSSRRRH |
| 18_166 | RRRRSRRRSSRSRRSH | 18_525 | RRSSRRRRSSSSRRSH |
| 18_167 | SRRRSSSRSRSSRRRH | 18_526 | SSSSRSRRSRSSSRSH |
| 18_168 | SRSSRSSSSSRSRSSH | 18_527 | RRRRSRRSSSSSRSSH |
| 18_169 | SSRRSRSSSSSRSSSH | 18_528 | SRRSRSRRRRSSRRSH |
| 18_170 | SSRRRRRSRSRRSSSH | 18_529 | RSRSSRRRRRSSRSSH |
| 18_171 | SSSRRSSRSRRRRRSH | 18_530 | RRRSRSRSSRSRSSSH |
| 18_172 | RSSSSSSSRSRRRRRH | 18_531 | RRSSRSSSSSRSSSRH |
| 18_173 | SSRSRSSRSSRRSRRH | 18_532 | RRRSSSSSRSSSRSSH |
| 18_174 | SRSRSSSRRRSRRRSH | 18_533 | RRSSSSSRRSSRSRRH |
| 18_175 | RRRRRRRSSRRSSSRH | 18_534 | RSSRSRRSRSSSSRRH |
| 18_176 | SSRSRRRRRSRRSRSH | 18_535 | SSSSRSSSSRRSRRSH |
| 18_177 | RRSRRRRRRSSRRRSH | 18_536 | RRSSRRSSRSRRSSRH |
| 18_178 | SSSSRRRRRRRRRSRH | 18_537 | RRRSRRRRSSSRSSSH |
| 18_179 | SRRRSSRRRSSRRRSH | 18_538 | SSSRSSRRSRRRSSSH |

TABLE 8-continued

List of stereodefined variants. The parent oligonucleotide compound is indicated with its sequence motif and design. The stereodefinition motif of the internucleoside linkages of the parent compound is indicated below the sequence and design, and reflects a fully stereorandom phosphorthioate gapmer. The stereodefined variants of the parent are listed by CMP ID NO and stereodefined motifs below the parent compound. The table contain three parent compounds CMP ID NO: 18_1, 18_347_and 18_12.

| | | | |
|---|---|---|---|
| 18_180 | SSSRRRRRSRRSSRRH | 18_539 | RSRRRRRRRSSSRRSH |
| 18_181 | RRSRRSSSSRRRSSRH | 18_540 | SSRSRSSSSRSRSRRH |
| 18_182 | SSRRSRSSRRRSSSSH | 18_541 | SSSRRSSSRSRRRRSH |
| 18_183 | SSRSRRRRSSRSSSRH | 18.542 | SSRRSSSSSRSRRSSH |
| 18_184 | RRRSRRSRSSRSRRRH | 18_543 | SSSRRRSRRRSSRSRH |
| 18_185 | RSRSSRSRSRRSRSRH | 18_544 | SRSSSSSRSSRSRRSH |
| 18_186 | SSSRRRRSSRRSRRRH | 18_545 | SRSSSSSSRRSSRRRH |
| 18_187 | RSSRRSRRRRSRRRSH | 18_546 | SRRSSSSRRRRRRSRH |
| 18_188 | SSSRRSSRSRSRSSSH | 18_547 | RSRSRRRSSSRSRRSH |
| 18_189 | RSRSSSSRSSRRRSSH | 18_548 | RRSRRSSSSSSSRSSH |
| 18_190 | SSSRSSSRSRRSRSSH | 18_549 | RSSRRRSSRRSSSSSH |
| 18_191 | RSSRSSSSRSSSSSRH | 18_550 | RSSRRSRSSRRSSRSH |
| 18_192 | RSSRRSSRSSSRRSRH | 18_551 | RRSSRSRRRRRRRRSH |
| 18_193 | RSSRRSRSRRSSSSRH | 18_552 | SRSSSRSRRRSSRSSH |
| 18_194 | RRSSSRRSRRRRSSSH | 18_553 | RSSRRRRRSRSRRRRH |
| 18_195 | RRRRRSSRSRRSSSRH | 18_554 | RSRSSSSRRSSSSSRH |
| 18_196 | SSSSRSRRRSSRRRSH | 18_555 | RRRRSSRRRSSRSSRH |
| 18_197 | RSRRRRRRRRSSRSRH | 18_556 | SSRSSRRSSSSRSRSH |
| 18_198 | RSRRSSSSRSSRSSRH | 18_557 | SRRRSSSSRRRSSRRH |
| 18_199 | SSRRSRSSRRRSSSRH | 18_558 | SRRSSSSRRSRRSRRH |
| 18_200 | RRRRSSSRRSRSRSSH | 18_559 | SSRRRSSRSSRSRRRH |
| 18_201 | RSRRRRRRSRRSSRSH | 18_560 | RSSRRRRSRSRRSRSH |
| 18_202 | SRRSRRRRRSRSSSSH | 18_561 | RSSRRRRSRRRRRRRH |
| 18_203 | SRRSRRSSSRSSSSSH | 18_562 | RRRRRRSRSRSRSSRH |
| 18_204 | SSSRRRRSRSRRRSSH | 18_563 | SSSRSSSSRRSSSRRH |
| 18_205 | SSRSRSRSSSRSRSRH | 18_564 | SRRSRSSSSSRSRRRH |
| 18_206 | SSSRRSRRSRRRSRSH | 18_565 | SSSSSRRSRSRSSRSH |
| 18_207 | SRSSRRRSSSSSRRRH | 18_566 | SSRSSRRSRRSSSRRH |
| 18_208 | RRSSRSSSSSSRSSRH | 18_567 | SSRSRSRRRSRSRRSH |
| 18_209 | SRSSRRSSRSRRSRRH | 18_568 | SRRSSRSRSRRRRSSH |
| 18_210 | RSRRSSRSRSSRRSSH | 18_569 | SRSRSRSRRSSSSRRH |
| 18_211 | RSSSRRSRSSSRSSSH | 18_570 | SRSSSRRRSRSSSSSH |
| 18_212 | SSSSSSSSRSRRRSSH | 18_571 | SRRSRSSSSSRSRSSH |
| 18_213 | RRSSSSSSSRSSSRRH | 18_572 | RSSRSRSRRSRSRRRH |

TABLE 8-continued

List of stereodefined variants. The parent oligonucleotide compound is indicated with its sequence motif and design. The stereo-definition motif of the internucleoside linkages of the parent compound is indicated below the sequence and design, and reflects a fully stereo-random phosphorthioate gapmer. The stereodefined variants of the parent are listed by CMP ID NO and stereodefined motifs below the parent compound. The table contain three parent compounds CMP ID NO: 18_1, 18_347_and 18_12.

| | | | |
|---|---|---|---|
| 18_214 | SSSRRSSSSRRRRSSH | 18_573 | SSRSRRRRRRRSSSSH |
| 18_215 | SSSRRRRRRSSSSRRH | 18_574 | RRSSRRSSSSSSSSSH |
| 18_216 | RSRSRRRSSSRRRSRH | 18_575 | SRSSSRRRRRSSRSRH |
| 18_217 | SSSSRRSRRRSSRRRH | 18_576 | SSSSRSRRSSRRSRRH |
| 18_218 | RSSRRSSRSRRRSSSH | 18_577 | RSSSRSSRSRRRSSRH |
| 18_219 | RRSSSSSRRRRSRRSH | 18_578 | RRSRSRSRRRRSRRSH |
| 18_220 | RXXXXXXXXXXXXXXH | 18_579 | SRSRSSRSSSSSRRSH |
| 18_221 | SXXXXXXXXXXXXXXH | 18_580 | RRRSRRSSSSSSSRRH |
| 18_222 | XRXXXXXXXXXXXXXH | 18_581 | RRRSRSRSRSSRRRSH |
| 18_223 | XSXXXXXXXXXXXXXH | 18_582 | SSRRSRSSRRRRSSRH |
| 18_224 | XXRXXXXXXXXXXXXH | 18_583 | RRSSSSSRRRRSSRSH |
| 18_225 | XXSXXXXXXXXXXXXH | 18_584 | SRSSRRSRSSSSRRSSH |
| 18_226 | XXXRXXXXXXXXXXXH | 18_585 | RSSSSSSRRSSSSRRH |
| 18_227 | XXXSXXXXXXXXXXXH | 18_586 | SRRRSSSSRRRSSSSH |
| 18_228 | XXXXRXXXXXXXXXXH | 18_587 | RRSRRRSRSSSSRSSH |
| 18_229 | XXXXSXXXXXXXXXXH | 18_588 | SSSSRSSSRSRSSSSH |
| 18_230 | XXXXXRXXXXXXXXXH | 18_589 | RRSRRRRRSRSSRSRH |
| 18_231 | XXXXXSXXXXXXXXXH | 18_590 | RRSSSRSRRRSRSSSH |
| 18_232 | XXXXXXRXXXXXXXXH | 18_591 | RRSRSRSSSRSSSSSH |
| 18_233 | XXXXXXSXXXXXXXXH | 18_592 | RRSSRSSSSRSRRSRH |
| 18_234 | XXXXXXXRXXXXXXXH | 18_593 | RRRRSSRSRSRSRSRH |
| 18_235 | XXXXXXXSXXXXXXXH | 18_594 | SRRSSRSSRRSRSSSH |
| 18_236 | XXXXXXXXRXXXXXXH | 18_595 | SRRSRRSRRRSSRSRH |
| 18_237 | XXXXXXXXSXXXXXXH | 18_596 | SSSSSRRRSSRRSSSH |
| 18_238 | XXXXXXXXXRXXXXXH | 18_597 | RRSRRRSRSSRSRRRH |
| 18_239 | XXXXXXXXXSXXXXXH | 18_598 | RSRSSRRSSRRSSRSH |
| 18_240 | XXXXXXXXXXRXXXXH | 18_599 | SSSRRRRSSRSRSSSH |
| 18_241 | XXXXXXXXXXSXXXXH | 18_600 | RRRRRSSRSRRRSRSH |
| 18_242 | XXXXXXXXXXXRXXXH | 18_601 | SSSRRSSRSRRSSRRH |
| 18_243 | XXXXXXXXXXXSXXXH | 18_602 | RRRSRSRSSRRSRRSH |
| 18_244 | XXXXXXXXXXXXRXXH | 18_603 | SRSSSSSRRSSRSRSH |
| 18_245 | XXXXXXXXXXXXSXXH | 18_604 | SSSRSSRSSSSSSSRH |
| 18_246 | XXXXXXXXXXXXXRXH | 18_605 | SSRSRSSRSSSSRRRH |
| 18_247 | XXXXXXXXXXXXXSXH | 18_606 | SRSRRSRRSRSRRRRH |
| 18_248 | XXXXXXXXXXXXXXRH | 18_607 | SRSRRRRSRSSRSSSH |
| 18_249 | XXXXXXXXXXXXXXSH | 18_608 | SRSRRRRRSSSRRSRH |
| 18_362 | SSSSSSSRRXXXXXXH | 18_609 | RRRSSSSRSSRRSSRH |
| 18_363 | SSRSSSSRRXXXXXXH | 18_610 | RRRSSSSSRRSRSRRH |
| 18_364 | SSSRSSSRRXXXXXXH | | |

| SEQ ID NO | Design | CMP ID NO | Parent Oligonucleotide Cmp/stereodefinition |
|---|---|---|---|
| 18 | 1-1-2-8-4 | 18_347 | TcAActttcactTCAG<br>XXXYXXXZXXXXXXXH |

| CMP ID NO | Stereodefined motif | CMP ID NO | Stereodefined motif |
|---|---|---|---|
| 18_471 | SSSRRSSSRRRRRSSH | 18_478 | SSSRSSSRSRRSRSSH |
| 18_472 | XXXXRSSRXXXXXXXH | 18_479 | SRRSRSRSRRRSRRRH |
| 18_473 | XXXXXXXXXXRSSSRH | 18_480 | SRRRSSRRSSRSSSSH |
| 18_474 | XXXXXXXXXRRSRRSH | 18_481 | SRRRSSRSSRSRSSSH |
| 18_475 | SSSSRSRRRSSRRRSH | 18_482 | RRRSSRSRSSSRRRRH |
| 18_476 | RRSRSSRRSSSRRSSH | 18_483 | SRRRSSSRRRRSSSSH |
| 18_477 | RSRSSSSRSSRRRSSH | | |

| SEQ ID NO | Design | CMP ID NO | Parent Oligonucleotide Cmp/stereodefinition |
|---|---|---|---|
| 18 | 3-9-4 | 1812 | TCAactttcactTCAG<br>XXXXXXXXXXXXXXXH |

| CMP ID NO | Stereodefined motif | CMP ID NO | Stereodefined motif |
|---|---|---|---|
| 18_484 | SSSRRSSSRRRRRSSH | 18_491 | SSSSRSRRRSSRRRSH |
| 18_485 | XXXXRSSRXXXXXXXH | 18_492 | SRRSRSRSRRRSRRRH |
| 18_486 | XXXXXXXXXXRSSSRH | 18_493 | SRRRSSRRSSRSSSSH |
| 18_487 | XXXXXXXXXRRSRRSH | 18_494 | SRRRSSRSSRSRSSSH |
| 18_488 | RRSRSSRRSSSRRSSH | 18_495 | RRRSSRSRSSSRRRRH |

TABLE 8-continued

List of stereodefined variants. The parent oligonucleotide compound is indicated with its sequence motif and design. The stereo-definition motif of the internucleoside linkages of the parent compound is indicated below the sequence and design, and reflects a fully stereo-random phosphorthioate gapmer. The stereodefined variants of the parent are listed by CMP ID NO and stereodefined motifs below the parent compound. The table contain three parent compounds CMP ID NO: 18_1, 18_347_and 18_12.

| | | | |
|---|---|---|---|
| 18_489 | RSRSSSSRSSRRRSSH | 18_496 | SRRRSSSRRRRSSSSH |
| 18_490 | SSSRSSSRSRRSRSSH | | |

In relation to the parent oligonucleotide CMP: Capital letters represent beta-D-oxy LNA nucleosides, lowercase letters represent DNA nacleosides, all LNA C are 5-methyl cytosine, all internucleoside linkages are phosphorothioate internacleoside linkages.

TABLE 8-continued

List of stereodefined variants. The parent oligonucleotide compound is indicated with its sequence motif and design. The stereo-definition motif of the internucleoside linkages of the parent compound is indicated below the sequence and design, and reflects a fully stereo-random phosphorthioate gapmer. The stereodefined variants of the parent are listed by CMP ID NO and stereodefined motifs below the parent compound. The table contain three parent compounds CMP ID NO: 18_1, 18_347_and 18_12.

In relation to the stereodefinition/stereodefined motifs: X represent a stereorandom phosphorothioate internucleoside linkage. R represents one stereoisomeric form and S represents the other stereoisomeric form as defined in the a description, H represents the hydrogen atom at the 3' terminus of the oligonucleotide. The first letter (X, R or S) in the stereo-defined motif correspond to the internucleoside linkage between nucleoside 1 and 2 from the 5' end of the oligonucleotide.

TABLE 9

Oligonucleotide motif sequences and antisense compounds with 5'ca biocleavable linker

| SEQ ID NO | motif sequence | oligonucleotide compound with a C6 alkyl ca biocleavable linker | CMP ID NO |
|---|---|---|---|
| 20 | CATCAACTTTCACTTCAG | C6$_o$c$_o$a$_o$TCAactttcacttCAG | 20_1 |
| 20 | CATCAACTTTCACTTCAG | C6$_o$c$_o$a$_o$TCAActttcactTCAG | 20_2 |
| 20 | CATCAACTTTCACTTCAG | C6$_o$c$_o$a$_o$TCAActttcacttCAG | 20_3 |
| 20 | CATCAACTTTCACTTCAG | C6$_o$c$_o$a$_o$TCAActttcacTtCAG | 20_4 |
| 20 | CATCAACTTTCACTTCAG | C6$_o$c$_o$a$_o$TCAACtttcacttCAG | 20_5 |
| 20 | CATCAACTTTCACTTCAG | C6$_o$c$_o$a$_o$TCAACtttcacttcAG | 20_6 |
| 20 | CATCAACTTTCACTTCAG | C6$_o$c$_o$a$_o$TCAActttcacttcAG | 20_7 |
| 20 | CATCAACTTTCACTTCAG | C6$_o$c$_o$a$_o$TCAactttcactTCAG | 20_8 |
| 20 | CATCAACTTTCACTTCAG | C6$_o$c$_o$a$_o$TcAACtttcactTcAG | 20_9 |
| 20 | CATCAACTTTCACTTCAG | C6$_o$c$_o$a$_o$TcAACtttcacttcAG | 20_10 |
| 20 | CATCAACTTTCACTTCAG | C6$_o$c$_o$a$_o$TCaACtttcacttcAG | 20_11 |
| 20 | CATCAACTTTCACTTCAG | C6$_o$c$_o$a$_o$TCaActttcacttCAG | 20_23 |
| 20 | CATCAACTTTCACTTCAG | C6$_o$c$_o$a$_o$TCaactttcactTCAG | 20_24 |
| 20 | CATCAACTTTCACTTCAG | C6$_{0o}$c$_o$aTCAaCtttcacttCAG | 20_25 |
| 20 | CATCAACTTTCACTTCAG | C6$_o$c$_o$a$_o$TCaaCtttcacttCAG | 20_26 |
| 20 | CATCAACTTTCACTTCAG | C6$_o$c$_o$a$_o$TCAaCtttcacttcAG | 20_27 |
| 20 | CATCAACTTTCACTTCAG | C6$_o$c$_o$a$_o$TCaActttcactTCAG | 20_28 |
| 20 | CATCAACTTTCACTTCAG | C6$_o$c$_o$a$_o$TcAActttcactTCAG | 20_29 |
| 20 | CATCAACTTTCACTTCAG | C6$_o$c$_o$a$_o$TCAActttcactTcAG | 20_37 |
| 20 | CATCAACTTTCACTTCAG | C6$_o$c$_o$a$_o$TcaACtttcacttCAG | 20_38 |
| 21 | CATCAACTTTCACTTCAGT | C6$_o$c$_o$a$_o$TCAActttcacttCaGT | 21_1 |
| 21 | CATCAACTTTCACTTCAGT | C6$_o$c$_o$a$_o$TcAactttcactTcAGT | 21_3 |
| 21 | CATCAACTTTCACTTCAGT | C6$_o$c$_o$a$_o$TcAActttcacttCaGT | 21_4 |
| 21 | CATCAACTTTCACTTCAGT | C6$_o$c$_o$a$_o$TCAactttcacttcAGT | 21_5 |
| 21 | CATCAACTTTCACTTCAGT | C6$_o$c$_o$a$_o$TCaactttcacTtCAGT | 21_6 |

TABLE 9-continued

| Oligonucleotide motif sequences and antisense compounds with 5′ca biocleavable linker | | | |
|---|---|---|---|
| SEQ ID NO | motif sequence | oligonucleotide compound with a C6 alkyl ca biocleavable linker | CMP ID NO |
| 21 | CATCAACTTTCACTTCAGT | C6$_o$c$_o$a$_o$TCAactttcacTtCaGT | 21_7 |
| 21 | CATCAACTTTCACTTCAGT | C6$_o$c$_o$a$_o$TCaActttcactTCAGT | 21_8 |
| 21 | CATCAACTTTCACTTCAGT | C6$_o$c$_o$a$_o$TcAActttcactTCAGT | 21_9 |
| 21 | CATCAACTTTCACTTCAGT | C6$_o$c$_o$a$_o$TCAActttcactTCaGT | 21_10 |
| 21 | CATCAACTTTCACTTCAGT | C6$_o$c$_o$a$_o$TCAactttcactTCaGT | 21_11 |
| 21 | CATCAACTTTCACTTCAGT | C6$_o$c$_o$a$_o$TCAActttcactTCaGT | 21_12 |
| 21 | CATCAACTTTCACTTCAGT | C6$_o$c$_o$a$_o$TCaactttcactTcAGT | 21_13 |
| 21 | CATCAACTTTCACTTCAGT | C6$_o$c$_o$a$_o$TCAactttcacttCAGT | 21_14 |
| 21 | CATCAACTTTCACTTCAGT | C6$_o$c$_o$a$_o$TCaactttcacttCAGT | 21_15 |
| 21 | CATCAACTTTCACTTCAGT | C6$_o$c$_o$a$_o$TcAActttcacttCAGT | 21_16 |
| 21 | CATCAACTTTCACTTCAGT | C6$_o$c$_o$a$_o$TcAactttcacttCAGT | 21_17 |
| 21 | CATCAACTTTCACTTCAGT | C6$_o$c$_o$a$_o$TCAactttcacttCaGT | 21_18 |
| 21 | CATCAACTTTCACTTCAGT | C6$_o$c$_o$a$_o$TCAActttcacttcAGT | 21_19 |
| 21 | CATCAACTTTCACTTCAGT | C6$_o$c$_o$a$_o$TCaactttcactTCAGT | 21_37 |
| 21 | CATCAACTTTCACTTCAGT | C6$_o$c$_o$a$_o$TCaActttcactTCaGT | 21_38 |
| 21 | CATCAACTTTCACTTCAGT | C6$_o$c$_o$a$_o$TCAActttcactTcaGT | 21_39 |
| 21 | CATCAACTTTCACTTCAGT | C6$_o$c$_o$a$_o$TCaActttcacttCAGT | 21_40 |

C6 represents an amino alkyl group with 6 carbons, capital Setters represent beta-D-oxy LNA nucleosides, towercase letters represent DNA nucleosides, all LNA Care 5-methyl cytosine, subscript o represent a phosphodiester internucleoside linkage and unless otherwise indicated other inte-mucleoside linkages are phosphorothioate intemucleoside linkages.

TABLE 10

| GalNAc conjugated antisense oligonucleotide compounds. | | | |
|---|---|---|---|
| SEQ ID NO | CMP ID NO | antisense oligonucleotide conjugate | Corre-sponding CMP ID of naked compound |
| 20 | 20_12 | GN2-C6$_o$c$_o$a$_o$TCAactttcacttCAG | 18_1 |
| 20 | 20_13 | GN2-C6$_o$c$_o$a$_o$TCAActttcactTCAG | 10_10 |
| 20 | 20_14 | GN2-C6$_o$c$_o$a$_o$TCAActttcacttCAG | 18_19 |
| 20 | 20_15 | GN2-C6$_o$c$_o$a$_o$TCAACtttcacTtCAG | 18_5 |
| 20 | 20_16 | GN2-C6$_o$c$_o$a$_o$TCAACtttcacttCAG | 18_18 |
| 20 | 20_17 | GN2-C6$_o$c$_o$a$_o$TCAACtttcacttCAG | 18_23 |
| 20 | 20_18 | GN2-C6$_o$c$_o$a$_o$TCAActttcacttcAG | 18_24 |
| 20 | 20_19 | GN2-C6$_o$c$_o$a$_o$TCAactttcactTCAG | 18_12 |
| 20 | 20_20 | GN2-C6$_o$c$_o$a$_o$TcAACtttcactTCAG | 18_15 |
| 20 | 20_21 | GN2-C6$_o$c$_o$a$_o$TcAACtttcacttcAG | 18_30 |
| 20 | 20_22 | GN2-C$_o$c$_o$a$_o$6TCaACtttcacttcAG | 18_27 |

TABLE 10-continued

| GalNAc conjugated antisense oligonucleotide compounds. | | | |
|---|---|---|---|
| SEQ ID NO | CMP ID NO | antisense oligonucleotide conjugate | Corre-sponding CMP ID of naked compound |
| 20 | 20_30 | GN2-C$_o$c$_o$a$_o$6TCaActttcacttCAG | 18_357 |
| 20 | 20_31 | GN2-C6$_o$c$_o$a$_o$TCaactttcactTCAG | 18_14 |
| 20 | 20_32 | GN2-C6$_o$c$_o$a$_o$TCAaCtttcacttCAG | 18_20 |
| 20 | 20_33 | GN2-C6$_o$c$_o$a$_o$TCaaCtttcacttCAG | 18_21 |
| 20 | 20_34 | GN2-C6$_o$c$_o$a$_o$TCAaCtttcacttcAG | 18_25 |
| 20 | 20_35 | GN2-C6$_o$c$_o$a$_o$TCaActttcactTCAG | 18_346 |
| 20 | 20_36 | GN2-C6$_o$c$_o$a$_o$TcAActttcactTCAG | 18_347 |
| 20 | 20_39 | GN2-C6$_o$c$_o$a$_o$TCAActttcactTcAG | 18_350 |
| 20 | 20_40 | GN2-C6$_o$c$_o$a$_o$TcaACtttcacttCAG | 18_358 |
| 21 | 21_2 | GN2-C6$_o$c$_o$a$_o$TCAActttcacttCaGT | 17_10 |
| 21 | 21_20 | GN2-C6$_o$c$_o$a$_o$TcAactttcactTcAGT | 17_7 |

TABLE 10-continued

GalNAc conjugated antisense oligonucleotide compounds.

| SEQ ID NO | CMP ID NO | antisense oligonucleotide conjugate | Corre-sponding CMP ID of naked compound |
|---|---|---|---|
| 21 | 21_21 | GN2-C6$_o$c$_o$a$_o$TcAActttcacttCaGT | 17_13 |
| 21 | 21_22 | GN2-C6$_o$c$_o$a$_o$TCAactttcacttcAGT | 17_14 |
| 21 | 21_23 | GN2-C6$_o$c$_o$a$_o$TCaactttcacTtCAGT | 17_51 |
| 21 | 21_24 | GN2-C6$_o$c$_o$a$_o$TCAactttcacTtCaGT | 17_57 |
| 21 | 21_25 | GN2-C6$_o$c$_o$a$_o$TCaActttcactTCAGT | 17_86 |
| 21 | 21_26 | GN2-C6$_o$c$_o$a$_o$TCAActttcactTCAGT | 17_90 |
| 21 | 21_27 | GN2-C6$_o$c$_o$a$_o$TCAActttcactTCaGT | 17_96 |
| 21 | 21_28 | GN2-C6$_o$c$_o$a$_o$TCAactttcactTCaGT | 17_99 |
| 21 | 21_29 | GN2 C6$_o$c$_o$a$_o$TcAActttcactTCaGT | 17_103 |
| 21 | 21_30 | GN2-C6$_o$c$_o$a$_o$TCaactttcactTcAGT | 17_111 |
| 21 | 21_31 | GN2-C6$_o$c$_o$a$_o$TCAactttcacttCAGT | 17-129 |
| 21 | 21_32 | GN2-C6$_o$c$_o$a$_o$TCaactttcacttCAGT | 17_135 |
| 21 | 21_33 | GN2-C6$_o$c$_o$a$_o$TcAActttcacttCAGT | 17-137 |
| 21 | 21_34 | GN2-C6$_o$c$_o$a$_o$TcAactttcacttCAGT | 17_139 |
| 21 | 21_35 | GN2-C6$_o$c$_o$a$_o$TCAActttcacttCaGT | 17-144 |
| 21 | 21_36 | GN2-C6$_o$c$_o$a$_o$TCAActttcacttcAGT | 17-157 |
| 21 | 21_41 | GN2-C6$_o$c$_o$a$_o$TCaactttcactTCAGT | 17-89 |
| 21 | 21_42 | GN2-C6$_o$c$_o$a$_o$TCaActttcactTCaGT | 17_100 |
| 21 | 21_43 | GN2-C6$_o$c$_o$a$_o$TCAActttcactTcaGT | 17-119 |
| 21 | 21_44 | GN2-C6$_o$c$_o$a$_o$TCaActttcacttCAGT | 17_132 |

Figure 2:
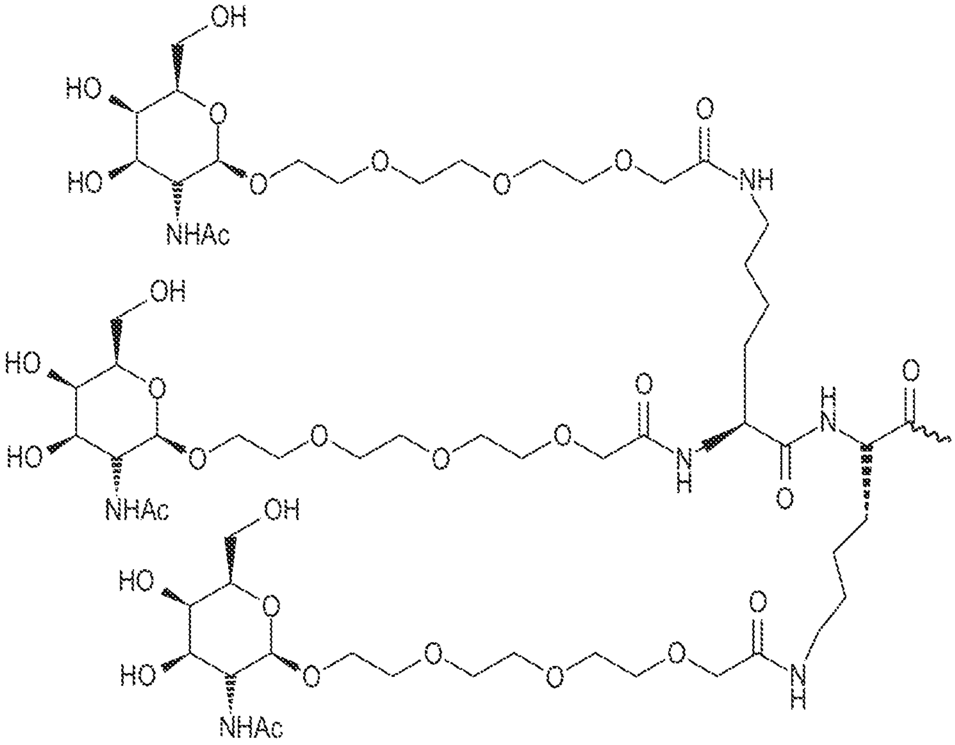
FIG. 2: Structural formula of the trivalent GalNAc cluster (GN2). GN2 is useful as conjugation moiety in the present invention. The wavy line illustrates the site of conjugation of the duster to e.g. a C6 amino linker or directly to the oligonucleotide

GN2 represents the trivalent GalNAC cluster shown in Figure 2, C6 represents an amino alkyl group with 6 carbons, capital letters represent beta-D-oxy LNA nucleosides, lowercase letters represent DNA nucleosides, all LNA C are 5-methyl cytosine, subscript o represent a phosphodiester nucleoside linkage and unless otherwise indicated internucleoside linkages are phosphorothioate intemucleoside linkages. Chemical drawings representing some of the molecules are shown in FIGS. 4 to 17.

AAV/HBV Mouse Models

In the AAV/HBV mouse model mice are infected with a recombinant adeno-associated virus (AAV) carrying the HBV genome (AAV/HBV) maintains stable viremia and antigenomia for more than 30 weeks (Dan Yang, et al. 2014 Cellular&8 Molecular Immunology 11, 71-78).

Male C57BL/6 mice (4-6 weeks old), specific pathogen free, are purchased from SLAC (Shanghai Laboratory Animal Center of Chinese Academy of Sciences) and housed in an animal care facility in individually ventilated cages. Guidelines are followed for the care and use of animals as indicated by WuXi IACUC (Institutional Animal Care and Use Committee, WUXI IACUC protocol number R20131126-Mouse). Mice are allowed to acclimate to the new environment for 3 days and are grouped according to the experimental design.

Recombinant AAV-HBV is diluted in PBS, 200 μL per injection. This recombinant virus carries 1.3 copies of the HBV genome (genotype D, serotype ayw).

On day 0, all mice are injected through tail vein with 200 μl-AAV-HBV ($1\times10^{11}$ vector genome). On Pre-dose Day 23 (23 days post AAV-HBV injection), animals were distributed to in groups based on serum levels of HBV markers and body weight. Each group was housed (up to 5/cage) in polycarbonate cages with comcob bedding. Low, medium, and high HBV titer values were spread, ensuring group means to be similar across groups. The animal groups can be treated with oligonucleotides which can be unconjugated or GalNAc conjugated. All serum collections (0.1 ml blood/mouse) were performed by retro-orbital bleeding after animals were anesthetized with isoflurane inhalation.

HeLa Cell Lines

HeLa cell line was purchased from European Collection of Authenticated Cell Cultures (ECACC, #93021013) and maintained as recommended by the supplier in a humidified incubator at 37° C. with 5% CO2. For assays, 2,500 cells/well were seeded in a 96 multi well plate in Eagle's Minimum Essential Medium (Sigma, M2279) with 10% fetal bovine serum (FBS), 2 mM Glutamin AQ, 1% NEAA, 25 μg/ml Gentamicin.

Differentiated HepaRG Cell Culture (no HBV Infection)

HepaRG cells (Biopredics International, Rennes, France, Cat #HPR101) were cultured at 37° C. In a humidified atmosphere with 5% C02 in complete HepaRG growth medium consisting of William's E Medium (Sigma W4128), Growth Medium Supplement (Biopredics, Cat #ADD710) and 1% (v/v) GlutaMAX-I (Gibco #32551) for 2 weeks.

To initiate differentiation cells were grown in complete HepaRG growth medium for 2 weeks until they were fully confluent. Half of the medium was exchanged by HepaRG differentiation medium consisting of William's E Medium (Sigma W4128), Growth Medium Supplement (Biopredics. Cat #ADD720) and 1% (v/v) GlutaMAX-I (Gibco #32551), final concentration of DMSO was 0.9% (wv)). After 3 days, medium was fully replaced by complete differentiation medium (final concentration of DMSO 1.8% (v)) in which cells were maintained for approximately 2 weeks with differentiation medium renewal every 7 days. Differentiated HepaRG cells (dHepaRG), displayed hepatocyte-like cell islands surrounded by monolayer of biliary-like cells. Prior to compound treatment, dHepaRG cells were seeded into collegen I coated 96-well plates (Corning BioCoat REF354407) at 80,000 cells per well in 100 μL of complete differentiation medium. Cells were allowed to recover their differentiated phenotype in 96-well plates for approximately 1 week after plating prior to oligonucleotide treatment. RNA was isolated 6 days after treatment.

HBV Infected dHepaRG Cells

HepaRG cells (Biopredics International, Rennes, France, Cat #HPR101) were cultured at 37° C. in a humidified atmosphere with 5% C02 in complete HepaRG growth medium consisting of William's E Medium (GIBCO), Growth Medium Supplement (Biopredics, Cat #ADD711C) and 1% (v/v) GlutaMAX-1 (Gibco #32551) and 1×Pen/Strep (Gibco, #15140) for 2 weeks.

To initiate differentiation, 0.9% (v/v) DMSO (Sigma-Aldrich, D2650) was added to the growth medium on confluent cells. After one week, medium was replaced by complete differentiation medium (HepaRG growth medium supplemented with 1.8% (v/v) DMSO) in which cells were maintained for approximately 4 weeks with differentiation medium renewal every 7 days. Differentiated HepaRG cells (dHepaRG), displayed hepatocyte-like cell islands surrounded by monolayer of biliary-like cells.

Prior to HBV infection and compound treatment, dHepaRG cells were seeded into collagen I coated 96-well plates (Gibco, Cat #A11428-03) at 60,000 cells per well in 100 μL of complete differentiation medium. Cells were allowed to recover their differentiated phenotype in 96-well plates for approximately 1 week after plating prior to HBV infection.

The dHepaRG cells were infected with HBV particles at an MOI of 30. The HBV particles were produced from HBV-producing HepG2.2.15 cells (Sells et al 1987 Proc Natl Aced Sci USA 84, 1005-1009). dHepaRG culture conditions, differentiation and HBV infection have been described previously (Hantz, 2009, J. Gen. Virol., 2009, 90: 127-135). In brief complete differentiation medium (HepaRG growth medium consisting of William's E Medium (GIBCO). Growth Medium Supplement (Biopredics, Cat #ADD711C) and 1% (v/v) GlutaMAX-I (Gibco #32551) and 1×Pen/Strep (Gibco. #15140), supplemented with 1.8% (v/v) DMSO), containing 4% PEG-8000 and virus stock (20 to 30 GE/cell) was added (120 μL/well). One day post-infection, the cells were washed four times with phosphate-buffered saline and medium (complete differentiation medium) was replaced on day 4 and day 7 during the experiment.

HBV Infected ASGPR-dHepaRG

From the HepaRG cell line (Biopredics International, Rennes, France, Cat #HPR101) a cell line stably overexpressing human ASGPR1 and ASGPR2 was generated using a lentiviral method. Proliferating HepaRG cells were transduced at MOI 300 with a lentivirus produced on demand by Sirion biotech (CLV-CMV-ASGPR1-T2a_ASGPR2-IRES-Puro) coding for Human ASGPR1 and 2 under the control of a CMV promoter and a puromycin resistance gene. Transduced cells were selected for 11 days with 1 μg/ml puromycin and then maintained in the same concentration of antibiotic to ensure stable expression of the transgenes. ASGPR1/2 overexpression was confirmed both at mRNA level by RT-qPCR (ASGPR1: 8560 fold vs non-transduced, ASGPR2: 2389 fold vs non-transduced), and at protein level by flow cytometry analysis. The differentiated cells are termed ASGPR-dHepaRG cells.

The ASGPR-HepaRG cells were differentiated using 1.8% DMSO for at least 2 weeks before infection. HBV infection was performed as for the dHepaRG cells described above.

Primary mouse hepatocytes (PMH)

Primary mouse hepatocytes were isolated from livers of C57BL/6J mice anesthetized with Pentobarbital after a 2 step perfusion protocol according to the literature (Berry and Friend, 1969, J. Cell Biol; Paterna et al., 1998. Toxicol. Appl. Pharmacol.). The first step was 5 min with HBSS+15 mM HEPES+0.4 mM EGTA followed by 12 min HBSS+20 mM $NaHCO_3$+0.04% BSA (Sigma #A7979)+4 mM $CaCL_2$ (Sigma #21115)+0.2 mg/ml Collagenase Type 2 (Worthington #4176). The Hepatocytes were captured in 5 ml cold Williams medium E (WME) (Sigma #W1878, complemented with 1×Pen/Strep/Glutamine, 10% (v/v) FBS (ATCC #30-2030)) on ice.

The crude cell suspension was filtered through a 70 μm followed by a 40 μm cell strainer (Falcon #352350 and #352340), filled up to 25 ml with WME and centrifuged at room temperature for 5 min at 50×g to pellet the hepatocytes. The supernatant was removed and the hepatocytes were resuspended in 25 ml WME. After adding 25 ml 90% Percoli solution (Sigma #P4937; pH=8.5-9.5) and centrifugation for 10 min at 25° C., 50×g the supernatant and floating cells were removed. To remove the remaining Percoll the pellet was resuspended again in 50 mL WME medium, centrifuged 3 min. 25° C. at 50×g and the supernatant discarded. The cell pellet was resuspended in 20 mL WME and cell number and viability determined (Invitrogen, Cellcount) and diluted to 250,000 cells/ml. 25,000 cells/well were seeded on collagen-coated 96-well plates (PD Biocoat Collagen I #356407) and incubated at 37° C., 5% $CO_2$. After 3-4 h, the cells were washed with WME to remove unattached cells and the medium was replaced. 24 h after seeding the oligonucleotides were added in the desired concentration and the cells were incubated at 37° C., 5% CO2 for 72 hours. RNA isolation (Qiagen, RNeasy 96) was followed by one-step RT-QPCR (Quanta Bioscience, qScript XLT 1-Step RT-qPCR ToughMix) using TaqMan assays for the target genes (PAPD5:Mm01244121_m1 FAM-MGB, PAPD7: Mm01349513_m1 FAM-MGB) and a house keeping gene (GusB Mm_01197698_m1, VIC-MGB) according to the manufacturers protocols.

Primary Human Hepatocyte (PHH) Natural Infection Assay

Primary human hepatocytes (PHH) isolated by collagenase perfusion method from chimeric uPA/SCID mice with humanized livers were obtained from PhoenixBio (Hiroshima, Japan). The cells were plated on type I collagen coated 96-well plates at a concentration of 7×104 cells per well in culture media provided by Phoenix Bio (See Ishida at al 2015 Am J Pathol. Vol 185 page 1275-1285 for further details). HBV genotype D was derived from HepG2.2.15 cell culture supernatant and concentrated using PEG precipitation. PHHs were infected in PHH medium containing 4% PEG 8000 at MOI 10 for 20 h at 37° C. before cells were washed 4 times with PBS. One day 1 post-infection, oligonucleotide was delivered to the cells in a final volume of 125 μl of PHH medium. The cells were retreated on day 4 and 7 post-infection. At day 11 post-infection, supernatants and cells were harvested. HBsAg and HBeAg levels in the supernatants were assessed using the CLIA ELISA assay (see Materials and Method section; HBV antigen measurements). mRNA was extracted from the cells using a MagNA Pure robot and the MagNA Pure 96 Cellular RNA Large Volume Kit (Roche. #05467535001) according to the manufacturer's protocol. The relative PAPD5 and PAPD7 mRNA expression levels were analyzed using Real-time PCR as described in Materials and Methods section.

HBV Antigen Measurements

To evaluate the impact on HBV antigen expression and secretion, supernatants were collected on Day 11. The HBV propagation parameters, HBsAg and HBeAg levels, were measured using CLIA ELISA Kits (Autobio Diagnostic #CL0310-2, #CL0312-2), according to the manufacturer's protocol. Briefly, 25 μL of supernatant per well were transferred to the respective antibody coated microtiter plate and 25 μL of enzyme conjugate reagent were added. The plate was Incubated for 60 min on a shaker at room temperature before the wells were washed five times with washing buffer using an automatic washer. 25 μL of substrate A and B were added to each well. The plates were incubated on a shaker for 10 min at room temperature before luminescence was measured using an Envision luminescence reader (Perkin Elmer).

Real-Time PCR for Intracellular HBV mRNA from HBV Infected Cee

HBV mRNA was quantified in technical duplicate by qPCR using a QuantStudio 12K Flex (Applied Biosystems), the TaqMan RNA-to-CT 1-Step Kit (Applied Biosystems, #4392938). Human ACTB endogenous control (Applied Biosystems, #4310881E). Taqman reagents were used together with the following commercial ThermoFisher Scientific primers (HBV Pa03453406_s1, ACTB 4310881E). The mRNA expression was analyzed using the comparative cycle threshold 2-ΔΔCt method normalized to the reference gene ACTB and to PBS treated cells.

Real-Time PCR for PAPD5 and PAPD7 mRNA Expression

QPCR was conducted on RNA extracted from treated cells or homogenized tissue samples. After RNA/LNA duplex denaturation (90° C., 40 sec) Real-time PCR was done with a one-step protocol (qScript™ XLT One-Step RT-qPCR ToughMix®, Low ROX™ from Quanta Bioscience, #95134-500) in a duplex set up with the following TaqMan primer assays (ThermoFisher Scientific):

PAPD5 (Hs00223727_m1, FAM-MGB)

PAPD7 (Hs00173159_m1, FAM-MGB),

House keeping gene GUSB (Hu_4326320E, VIC-MGB) following the recommendations of the provider.

HBV DNA Quantification Viral Particle Titer

HBV DNA extraction is performed using the QIAamp UltraSens Virus kit (Qiagen, #53704) according to the manufacturer's protocol with the following optimizations. 30 μL and 3 μL of the virus sample are diluted into 1 mL of PBS before adding buffer AC. The first centrifugation step is done for 45 min at full speed and 4° C. HBV DNA is quantified in duplicate by qPCR using a QuantStudio 12K Flex (Applied Biosystems), the TaqMan Gene Expression Master Mix (Applied Biosystems, #4369016) and a premix 1:1:0.5 of the primers Indicated in Table 9 above and probe reconstituted at 100 μM. The qPCR is performed using the following settings: UDG incubation (2 min, 50° C.), enzyme activation (10 min, 95° C.) and qPCR (40 cycles with 15 sec, 95° C. for denaturation and 1 min, 60° C. for annealing and extension). Genomes equivalent calculation is based on a standard curve generated from HBV genotype D plasmid dilutions with known concentrations.

The HBV particle titer can be determined using HBV core-specific primer (Integrated DNA Technologies) (Table 11) in a QPCR on isolated intracellular mRNA from treated cells.

TABLE 11

HBV core specific TaqMan probes

| | Name | Dye | Sequence | SEQ ID NO |
|---|---|---|---|---|
| HBV core Primer | Forward (F3 HBVcore) | | CTG TGC CTT GGG TGG CTT T | 24 |
| | Reverse (R3 HBVcore) | | AAG GAA AGA AGT CAG AAG GCA AAA | 25 |
| | Probe (P3 HBVcore) | FAM-MGB | AGC TCC AAA/ZEN/TTC TTT ATA AGG GTC GAT GTC CAT G | 26 |

ZEN is an internal quencher

Oligonucleotide Synthesis

Oligonucleotide synthesis is generally known in the art. Below is a protocol which may be applied. The oligonucleotides of the present Invention may have been produced by slightly varying methods in terms of apparatus, support and concentrations used.

Oligonucleotides are synthesized on uridine universal supports using the phosphoramidite approach on an Oligomaker 48 at 1 μmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of p-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle, a phosphoramidite with desired modifications can be used. e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphodiester linkages can be introduced using 0.02 M iodine in THF/Pyridine/water 7:2:1. The rest of the reagents are the ones typically used for oligonucleotide synthesis.

For post solid phase synthesis conjugation a commercially available C6 amino linker phosphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C 18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations

DCI: 4,5-Dicyanoimidazole

DCM: Dichloromethane

DMF: Dimethylformamide

DMT: 4,4'-Dimethoxytrityl

THF: Tetrahydrofurane

Bz: Benzoyl

Ibu: Isobutyryl

RP-HPLC: Reverse phase high performance liquid chromatography $T_m$ Assay:

Oligonucleotide and RNA target (phosphate linked, PO) duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Example 1: Screening for In Vitro Efficacy of Antisense Oligonucleotides Targeting PAPD5 and PAPD7 (Bispecific) in HeLa Cells An oligonucleotide screen was done using 16 to 18mer gapmers targeting SEQ ID NO: 17, 18 and 19. Efficacy testing was performed in an in vitro experiment in HeLa cells expressing both PAPD5 and PAPD7.

HeLa cells were cultured as described in the Materials and Method section. The cells were incubated for 24 hours before addition of oligonucleotides dissolved in PBS. Final concentration of oligonucleotides was 5 and 25 μM, the final culture volume was 100 μl/well. The cells were harvested 3 days after addition of oligonucleotide compounds and RNA was extracted using the PureLink Pro 96 RNA Purification kit (Ambion), according to the manufacturer's instructions.

PAPD5 and PAPD7 mRNA levels were analysed by Real-time PCR as described in the Materials and Method section.

The relative PAPD5 mRNA and PAPD7 mRNA expression levels are shown in table 12 as % of average control samples (PBS-treated cells) i.e. the lower the value the larger the inhibition.

TABLE 12 in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| | % PAPD5 mRNA of control | | | | % PAPD7 mRNA of control | | | | |
|---|---|---|---|---|---|---|---|---|---|
| CMP ID | 25 µM | | 5 µM | | 25 µM | | 5 µM | | |
| NO | Avg | sd | Avg | sd | Avg | sd | Avg | sd | Compound (CMP) |
| 17_2 | 35.36 | 0.58 | 69.86 | 3.08 | 31.55 | 0.88 | 89.02 | 14.48 | TCaaCtttcacTtcAGT |
| 17_3 | 13.78 | 1.40 | 35.71 | 3.94 | 11.56 | 1.63 | 56.65 | 11.86 | TCaactttcacTtcAGT |
| 17_4 | 39.72 | 2.23 | 51.51 | 4.97 | 83.29 | 11.18 | 117.6 | 14.81 | TcaaCtttcacTtcAGT |
| 17_5 | 24.87 | 2.09 | 53.56 | 8.57 | 62.21 | 2.96 | 27.92 | 2.32 | TCaactttcacTtcaGT |
| 17_6 | 19.50 | 1.22 | 34.68 | 0.37 | 14.51 | 0.16 | 82.74 | 26.43 | TCaaCtttcactTCaGT |
| 17_7 | 6.17 | 1.04 | 22.09 | 0.01 | 13.47 | 3.64 | 20.41 | 3.12 | TcAactttcactTcAGT |
| 17_8 | 9.85 | 1.44 | 28.15 | 4.60 | 25.29 | 4.47 | 26.39 | 3.48 | TcAActttcactTcaGT |
| 17_9 | 18.73 | 2.57 | 47.62 | 3.48 | 31.00 | 3.51 | 58.02 | 6.32 | TCAACtttcacttCaGT |
| 17_10 | 6.13 | 1.18 | 23.39 | 0.44 | 5.88 | 0.34 | 31.76 | 3.25 | TCAActttcacttCaGT |
| 17_11 | 14.64 | 2.09 | 31.58 | 4.40 | 42.82 | 6.50 | 86.43 | 11.95 | TCaaCtttcacttCaGT |
| 17_12 | 15.33 | 0.62 | 29.82 | 1.07 | 34.94 | 5.35 | 51.77 | 3.89 | TCaactttcacttCaGT |
| 17_13 | 6.63 | 0.34 | 23.62 | 9.01 | 8.49 | 0.51 | 20.44 | NA | TcAActttcacttCaGT |
| 17_14 | 4.61 | 1.98 | 22.51 | 5.00 | 6.19 | 0.36 | 44.27 | 6.69 | TCAactttcacttcAGT |
| 17_15 | 17.99 | 2.76 | 32.73 | 4.87 | 26.59 | 2.61 | 38.30 | 4.15 | TCaaCtttcacttcAGT |
| 17_16 | 42.29 | 1.06 | 75.49 | 6.32 | 26.91 | 1.57 | 46.19 | 0.88 | TCaactttcacttcaGT |
| 18_2 | 41.16 | 0.15 | 65.30 | 5.51 | 48.83 | 6.29 | 63.37 | 10.84 | TCaaCtttcacTTCAG |
| 18_3 | 54.39 | 3.08 | 71.95 | 2.89 | 69.99 | 0.89 | 66.50 | 3.56 | TCAACtttcacTTcAG |
| 18_4 | 40.86 | 1.32 | 64.99 | 4.39 | 78.13 | 1.60 | 109.0 | 0.49 | TCAACtttcacTtCAG |
| 18_5 | 9.30 | 0.76 | 27.26 | 0.91 | 7.32 | 1.32 | 14.80 | 1.92 | TCAActttcacTtCAG |
| 18_6 | 7.49 | 0.75 | 21.64 | 2.49 | 10.32 | 0.39 | 14.16 | 0.82 | TCaactttcacTtCAG |
| 18_7 | 25.02 | 0.30 | 47.25 | 4.07 | 37.93 | 10.34 | 68.66 | 5.11 | TcaaCtttcacTtCAG |
| 18_8 | 22.93 | 8.09 | 44.18 | 1.59 | 33.95 | 7.34 | 39.70 | 5.06 | TCaActttcacTtcAG |
| 18_9 | 15.21 | 2.21 | 39.74 | 0.32 | 12.21 | 1.80 | 23.08 | 0.01 | TCAACtttcaCtTCAG |
| 18_10 | 3.99 | 0.67 | 20.53 | 4.40 | 7.81 | 0.52 | 23.89 | 2.49 | TCAActttcactTCAG |
| 18_11 | 13.84 | 3.93 | 35.46 | 1.52 | 28.39 | 1.96 | 56.56 | 11.43 | TCAaCtttcactTCAG |
| 18_12 | 5.13 | 0.14 | 20.21 | 0.24 | 3.40 | 0.29 | 41.51 | 7.20 | TCAactttcactTCAG |
| 18_13 | 11.90 | 1.05 | 26.20 | 0.47 | 26.51 | 0.82 | 20.79 | 5.61 | TCaaCtttcactTCAG |
| 18_14 | 5.42 | 0.33 | 20.05 | 2.62 | 8.85 | 1.46 | 66.72 | 8.16 | TCaactttcactTCAG |
| 18_15 | 7.16 | 0.03 | 20.84 | 1.94 | 6.17 | 0.05 | 46.67 | 1.26 | TcAACtttcactTcAG |
| 18_16 | 14.28 | 2.44 | 33.79 | 1.00 | 29.49 | 1.95 | 16.87 | 2.38 | TcAaCtttcactTcAG |
| 18_17 | 27.49 | 2.66 | 61.62 | 9.21 | 55.71 | 3.61 | 36.14 | 0.32 | TcaaCtttcactTcAG |

TABLE 12-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control | | | | % PAPD7 mRNA of control | | | | |
|---|---|---|---|---|---|---|---|---|---|
| | 25 µM | | 5 µM | | 25 µM | | 5 µM | | |
| NO | Avg | sd | Avg | sd | Avg | sd | Avg | sd | Compound (CMP) |
| 18_18 | 5.43 | 0.81 | 26.45 | 0.75 | 3.16 | 0.61 | 35.64 | 2.03 | TCAACtttcacttCAG |
| 18_19 | 4.85 | 1.04 | 17.24 | 1.69 | 12.48 | 0.60 | 13.12 | 0.88 | TCAActttcacttCAG |
| 18_20 | 5.51 | 0.05 | 20.28 | 1.07 | 12.76 | 1.24 | 14.83 | 0.13 | TCAaCtttcacttCAG |
| 18_21 | 10.64 | 0.32 | 23.88 | 1.67 | 12.61 | 0.50 | 14.50 | 1.05 | TCaaCtttcacttCAG |
| 18_22 | 10.66 | 1.95 | 34.29 | 7.33 | 16.22 | 1.84 | 25.81 | 7.43 | TCaactttcacttCAG |
| 18_23 | 5.50 | 1.99 | 24.63 | 0.61 | 10.97 | 0.12 | 27.22 | 1.51 | TCAACtttcacttcAG |
| 18_24 | 8.37 | 0.44 | NA | NA | 12.02 | 1.77 | NA | NA | TCAActttcacttcAG |
| 18_25 | 7.58 | 0.80 | 23.71 | 3.32 | 9.03 | 0.05 | 19.79 | 1.14 | TCAaCtttcacttcAG |
| 18_26 | 12.94 | 0.46 | 35.03 | 2.99 | 25.90 | 0.06 | 28.01 | 0.45 | TCAactttcacttcAG |
| 18_27 | 7.21 | 1.46 | 21.24 | 2.15 | 19.27 | 2.92 | 72.92 | 25.73 | TCaACtttcacttcAG |
| 18_28 | 15.47 | 4.10 | 39.98 | 4.60 | 14.60 | 0.36 | 43.25 | 5.37 | TCaaCtttcacttcAG |
| 18_29 | 32.76 | 9.83 | 43.53 | 4.96 | 21.47 | 5.16 | 34.84 | 0.17 | TCaactttcacttcAG |
| 18_30 | 4.45 | 0.12 | 20.61 | 5.21 | 10.94 | 1.63 | 24.09 | 0.58 | TCAACtttcacttcAG |
| 18_31 | 55.81 | 9.87 | 71.92 | 22.31 | 50.86 | 4.18 | 60.22 | 0.42 | TcaaCtttcacttcAG |
| 19_1 | 101.9 | 10.60 | 89.66 | 13.79 | 59.35 | 6.51 | 160.6 | 2.10 | TGTTTcaatacTAAAA |
| 19_2 | 90.94 | 1.54 | 68.65 | 6.91 | 59.66 | 1.75 | 60.33 | 1.98 | TGTTtcaatacTAAAA |
| 19_3 | 104.6 | 13.82 | 86.79 | 12.54 | 80.71 | 0.60 | 68.25 | 5.99 | TGTTTcaatacTAaAA |

Example 2: In Vitro EC50 and Efficacy in HBV Infected HepaRG Cells

All the oligonucleotides from Example 1 were tested for their effect on HBV propagation parameters in HBV infected dHepaRG cells.

For comparative purposes the antisense oligonucleotides of the invention were compared to antisense oligonucleotides targeting HBV mRNA directly. The HBV targeting oligonucleotides are shown in table 13.

TABLE 13

Comparative HBV targeting oligonucleotides

| Description | Compound | SEQ ID NO | Reference |
|---|---|---|---|
| HBV targeting 1 (HBV1) | AGCgaagtgcacaCGG | 27 | WO2015/173208 |
| HBV targeting 2 (HBV2) | GCGtaaagagaGG | 28 | WO2015/173208 |

HBV infected dHepaRG cells (described in the Materials and Methods section. HBV infected dHepaRG cells) were cultured in 96-well plates. One day post HBV infection the oligonucleotides were added to the cells in three-fold serial dilutions (20.00, 6.67, 2.22, 0.74, 0.25, 0.08, 0.03, 0.01 µM oligonucleotide) using unassisted uptake (gymnosis). A total of 49 oligonucleotides were tested. The experiment was conducted in triplicate, with PBS controls. The oligonucleotide treatment was repeated at day 4 and 7.

At day 11 post-infection, supernatants and cells were harvested.

HBsAg and HBeAg levels in the supernatants were assessed using the CLIA ELISA assay (see Materials and Methods, HBV antigen measurements).

EC 50, max KD (efficacy) of the HBV propagation parameters HBsAg and HBeAg was calculated using the R-function drm( ) from the drc package (v3.0-1) a four-parameter log-logistic function is fitted to the expression of the gene of interest as a function of oligonucleotide concentration to obtain a value for EC50 and maximum knockdown. The results are shown in table 14 and are % of average control samples (PBS control and Non Infected (NIF), calculated as follows [(Test Value−meanPBS)/(meanNIF−meanPBS)]*100)).

TABLE 14

EC50 and Max KD of anti-PAPD5/PAPD7 compounds on HBsAg and HBeAg (average of 3) in HBV infected dHepaRG cells.

| CMP ID | HBsAg | | | | HBeAg | | | | |
|---|---|---|---|---|---|---|---|---|---|
| | Max KD % of saline | | EC50 µM | | Max KD % of saline | | EC50 µM | | |
| NO | Avg | sd | Avg | sd | Avg | sd | Avg | sd | Compound |
| 17_7 | 57.18 | 6.67 | 7.36 | 20.66 | 33.61 | 10.44 | 7.07 | 15.94 | TcAactttcacTcCAGT |
| 17_8 | 28.29 | 13.46 | 4.75 | 1.59 | 23.75 | 11.32 | 5.14 | 1.69 | TcAActttcactTcaGT |
| 17_10 | 19.10 | 4.81 | 6.73 | 15.00 | 2.28 | 11.52 | 6.63 | 2.67 | TCAActttcacttCaGT |
| 17_13 | 22.07 | 8.55 | 5.74 | 1.01 | 4.09 | 15.51 | 4.40 | 1.52 | TcAActttcacttCaGT |
| 17_14 | 0.00 | 855.97 | 24.07 | 61.33 | 1.04 | NA | 21.37 | NA | TCAactttcacttcAGT |
| 18_1 | 5.42 | 9.05 | 4.67 | 0.71 | 5.88 | 14.10 | 4.12 | 1.22 | TCAactttcacttCAG |
| 18_5 | 4.70 | 9.40 | 6.67 | 1.20 | 0.30 | 7.04 | 4.86 | 0.80 | TCAActttcacTtCAG |
| 18_6 | 26.99 | 12.22 | 6.66 | 1.39 | 22.14 | 9.60 | 6.40 | 3.64 | TCaactttcacTtCAG |
| 18_10 | 0.00 | 10.01 | 4.94 | 0.88 | 2.68 | 10.92 | 4.40 | 1.09 | TCAActttcactTCAG |
| 18_12 | 14.01 | 8.21 | 6.52 | 0.60 | 3.86 | 14.96 | 6.12 | 1.14 | TCAactttcactTCAG |
| 18_15 | 15.87 | 25.90 | 6.22 | 3.82 | 32.23 | 7.88 | 2.10 | 4.75 | TcAACtttcactTCAG |
| 18_18 | 8.11 | 11.24 | 7.21 | 1.14 | 8.75 | 6.36 | 6.58 | 5.28 | TCAACtttcacttCAG |
| 18_19 | 3.43 | 3.49 | 2.32 | 0.18 | 3.75 | 5.69 | 2.16 | 3.09 | TCAActttcacttCAG |
| 18_20 | 36.72 | 4.45 | 7.05 | 17.16 | 0.00 | 74.91 | 8.07 | 9.71 | TCAaCtttcacttCAG |
| 18_21 | 26.03 | 51.79 | 9.16 | 9.36 | 0.00 | 92.94 | 10.13 | 14.18 | TCaaCtttcacttCAG |
| 18_23 | 11.13 | 7.74 | 5.53 | 0.76 | 6.33 | 9.42 | 4.82 | 0.99 | TCAACtttcacttcAG |
| 18_24 | 11.95 | 8.90 | 3.64 | 0.82 | 13.90 | 10.15 | 2.36 | 0.62 | TCAActttcacttcAG |
| 18_25 | 25.93 | 17.79 | 7.90 | 2.60 | 19.84 | 10.18 | 6.78 | 4.08 | TCAaCtttcacttcAG |
| 18_30 | 16.85 | 5.93 | 2.51 | 0.38 | 12.47 | 8.12 | 2.22 | 0.27 | TcAACtttcacttcAG |
| 17_3 | 93.91 | 127.26 | 32.39 | 329.47 | 89.14 | 8.47 | 0.91 | 10.00 | TCaactttcacTtcAGT |
| 17_5 | 90.80 | 7.82 | 1.31 | 10.00 | 95.11 | 10.13 | 0.10 | 10.00 | TCaactttcacTtcaGT |
| 17_6 | 92.43 | NA | 0.57 | NA | 89.80 | NA | 0.00 | NA | TCaaCtttcactTCaGT |
| 17_9 | 54.71 | 6.03 | 7.08 | 14.69 | 15.37 | 35.83 | 8.44 | 3.80 | TCAACtttcacttCaGT |
| 17_11 | 83.26 | 7.52 | 3.61 | 10.00 | 62.66 | 9.37 | 0.58 | 10.00 | TCaaCtttcacttCaGT |
| 17_12 | 97.35 | 7.36 | 19.89 | 10.00 | 78.78 | 8.65 | 0.35 | 10.00 | TCaactttcacttCaGT |
| 17_15 | 91.43 | NA | 0.67 | NA | 78.81 | 8.76 | 0.46 | 10.00 | TCaaCtttcacttcAGT |
| 18_7 | 90.45 | NA | 11.53 | NA | 85.05 | 8.27 | 0.34 | 10.00 | TcaaCtttcacTtCAG |
| 18_8 | 63.76 | 12.80 | 5.22 | 1.98 | 52.50 | 9.20 | 4.77 | 1.14 | TCaActttcacTtAG |
| 18_9 | 23.40 | 156.35 | 12.06 | 23.00 | 26.07 | 11.37 | 7.57 | 16.01 | TCAACtttcactTCAG |
| 18_11 | 0.00 | 236.59 | 23.95 | 50.46 | 0,05 | NA | 18.25 | NA | TCAaCtttcactTCAG |
| 18_13 | 53.81 | 6.31 | 7.16 | 11.60 | 42.15 | 8.15 | 7.31 | 13.89 | TCaaCtttcactTCAG |
| 18_14 | 32.71 | 11.10 | 5.13 | 1.25 | 24.27 | 14.19 | 4.20 | 1.31 | TCaactttcactTCAG |
| 18_16 | 81.65 | 6.89 | 7.15 | 17.43 | 72.67 | 8.30 | 7.01 | 9.77 | TcAaCtttcactTcAG |
| 18_22 | 29.19 | 5.87 | 6.40 | 7.22 | 16.60 | 18.52 | 4.54 | 1.31 | TCaactttcacttCAG |
| 18_26 | 40.75 | 8.16 | 5.35 | 0.90 | 36.63 | 6.43 | 5.34 | 1.09 | TCAactttcacttcAG |

TABLE 14-continued

EC50 and Max KD of anti-PAPD5/PAPD7 compounds on HBsAg and HBeAg (average of 3) in HBV infected dHepaRG cells.

| | HBsAg | | | | HBeAg | | | | |
|---|---|---|---|---|---|---|---|---|---|
| CMP ID | Max KD % of saline | | EC50 µM | | Max KD % of saline | | EC50 µM | | |
| NO | Avg | sd | Avg | sd | Avg | sd | Avg | sd | Compound |
| 18_27 | 20.92 | 10.83 | 4.61 | 1.10 | 13.89 | 13.63 | 4.03 | 1.20 | TCaACtttcacttcAG |
| 18_28 | 67.96 | 9.83 | 8.11 | 77.37 | 47.21 | 2274.28 | 18.70 | 138.89 | TCaaCtttcacttcAG |
| 17_2 | 84.70 | 14.17 | 0.28 | 10.00 | 61.86 | 9.52 | 0.21 | 10.00 | TCaaCtttcacTtcAGT |
| 17_4 | 85.48 | 10.18 | 0.31 | 10.00 | 55.95 | 9.53 | 0.13 | 10.00 | TcaaCtttcacTtcAGT |
| 17_16 | 68.31 | 10.41 | 0.10 | 10.00 | 39.65 | 9.69 | 0.27 | 10.00 | TCaactttcacttcaGT |
| 18_2 | 94.41 | 8.20 | 0.47 | 10.00 | 61.03 | 9.43 | 0.28 | 10.00 | TCaaCtttcacTTCAG |
| 18_3 | 68.72 | 9.16 | 0.24 | 10.00 | 51.03 | 9.02 | 0.14 | 10.00 | TcAACtttcacTTcAG |
| 18_4 | 92.84 | 8.61 | 0.12 | 10.00 | 85.97 | 8.77 | 0.18 | 10.00 | TCAACtttcacTtCAG |
| 18_17 | 71.76 | 8.21 | 0.59 | 10 00 | 49.14 | 8.82 | 0.83 | 10.00 | TcaaCtttcactTcAG |
| 18_29 | 81.88 | 9.30 | 1.00 | 10.00 | 72.13 | 9.16 | 0.24 | 10.00 | TCaactttcacttcAG |
| 18_31 | 73.12 | 9.07 | 0.43 | 10.00 | 73.76 | 8.47 | 0.47 | 10.00 | TcaaCtttcacttcAG |
| 19_1 | 82.69 | 9.37 | 0.20 | 10.00 | 96.30 | 10.43 | 0.06 | 10.00 | TGTTTcaatacTAAAA |
| 19_2 | 85.50 | 16.76 | 0.27 | 10.00 | 83.38 | 8.96 | 0.24 | 10.00 | TGTTtcaatacTAAAA |
| 19_3 | 103.91 | NA | 0.30 | NA | 108.39 | 8.81 | 0.09 | 10.00 | TGTTTcaatacTAaAA |
| HBV1 | 0.00 | 16.32 | 2.44 | 1.22 | 0.00 | 23.37 | 1.33 | 1.09 | AGCgaagtgcacaCGG |
| HBV2 | 0.00 | 55.69 | 16.80 | 19.97 | 0.00 | NA | 20.73 | NA | GCGtaaagagaGG |

From these data it can be seen that a significant number of the compounds have a good effect on HBsAg and HBeAg. Compounds with the oligonucleotide motif of SEQ ID NO 17 and 18 seem more efficient than the compounds that have been made with the motif of SEQ ID NO: 19

Figure 3:
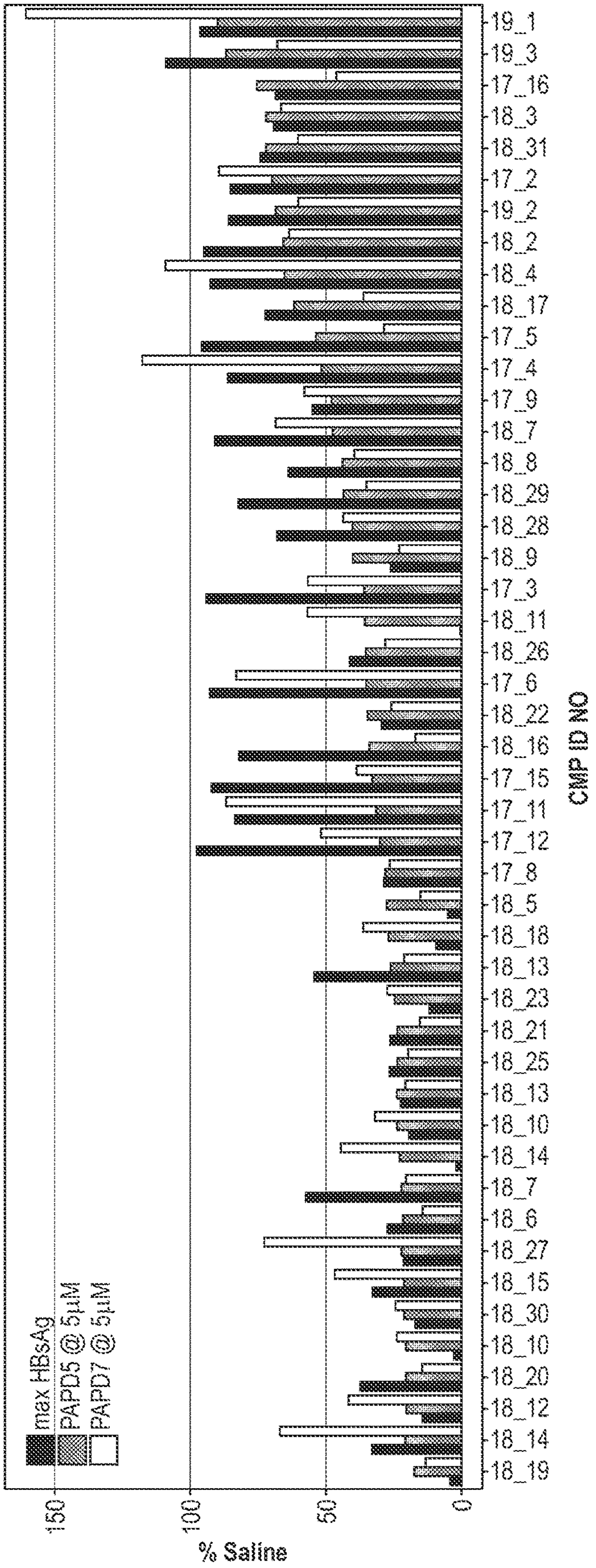
FIG. 3: Shows the correlation between PAPD5 and PAPD7 knock down in Hela cells from example 1 with HBsAg reduction in dHepRG cells from example 2.
Figure 4:
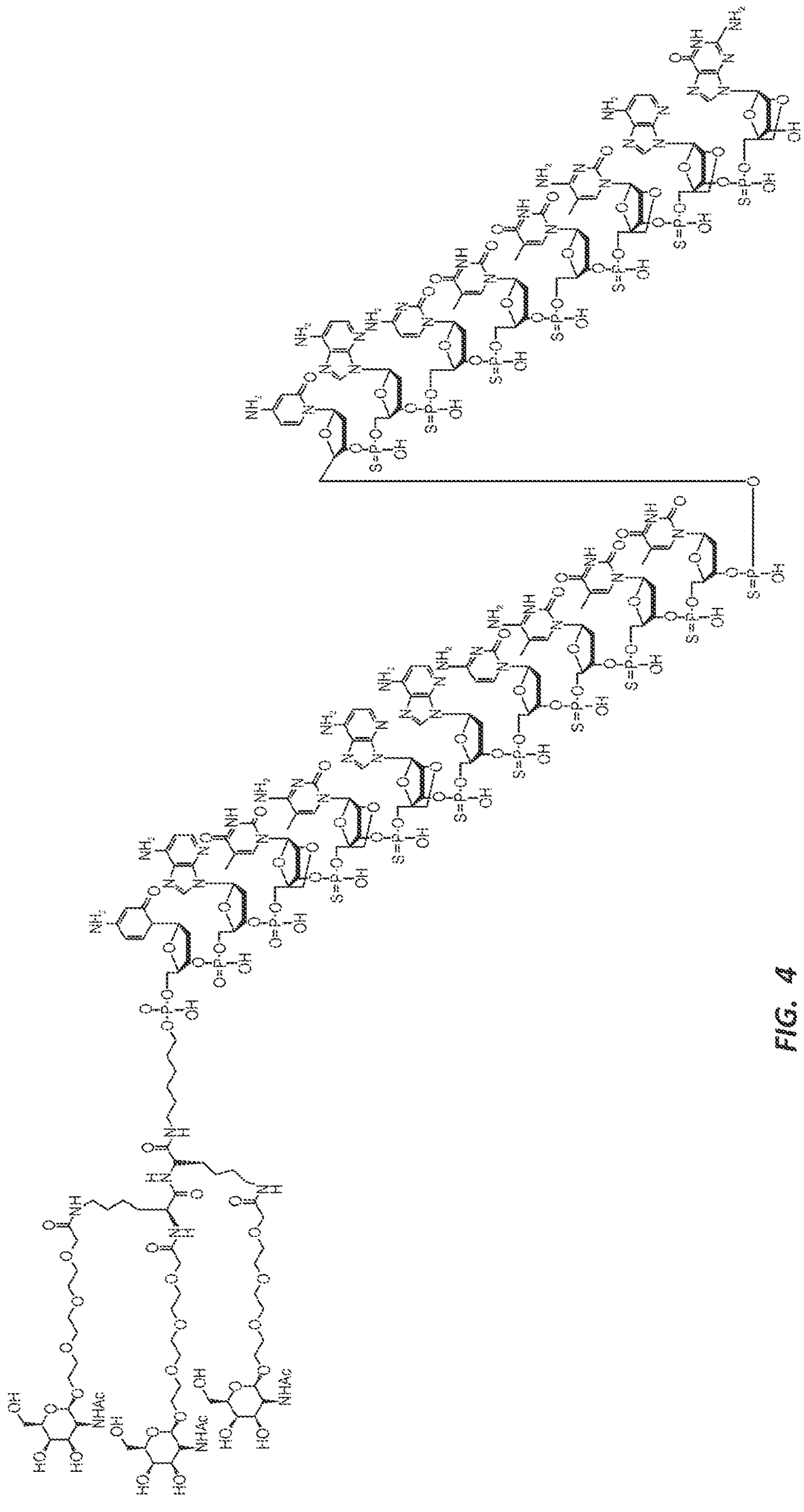
FIG. 4: Structural formula of CMP ID NO: 20_ 12. Pharmaceutical salts thereof include monovalent or divalent cations, such as Na+, K+, and Ca2+ or a mixture of these being associated with the compound.
Figure 5:
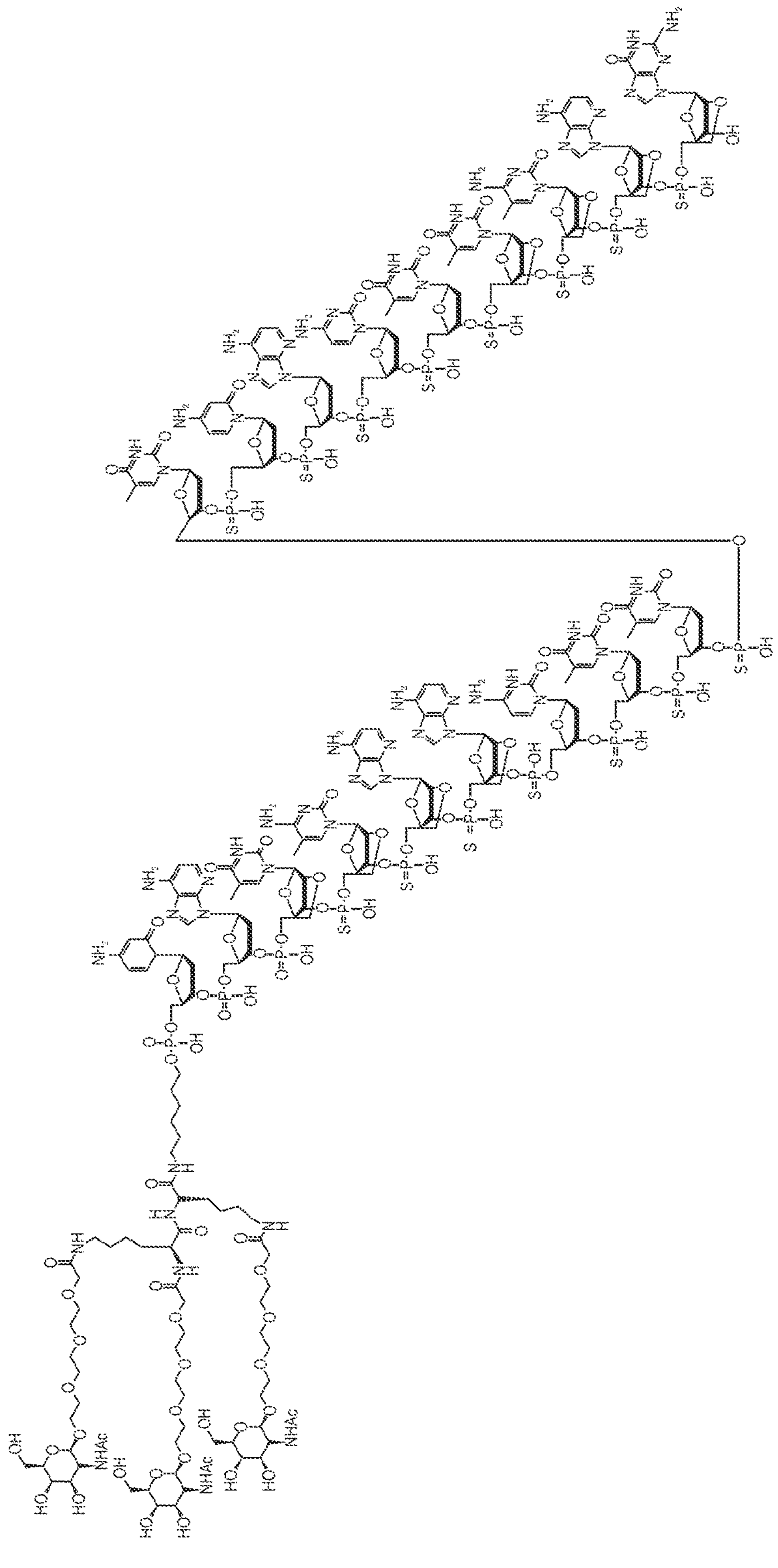
FIG. 5: Structural formula of CMP ID NO: 20_ 13. Pharmaceutical salts thereof include monovalent or divalent cations, such as Na+, K+, and Ca2+ or a mixture of these being associated with the compound.
Figure 6:
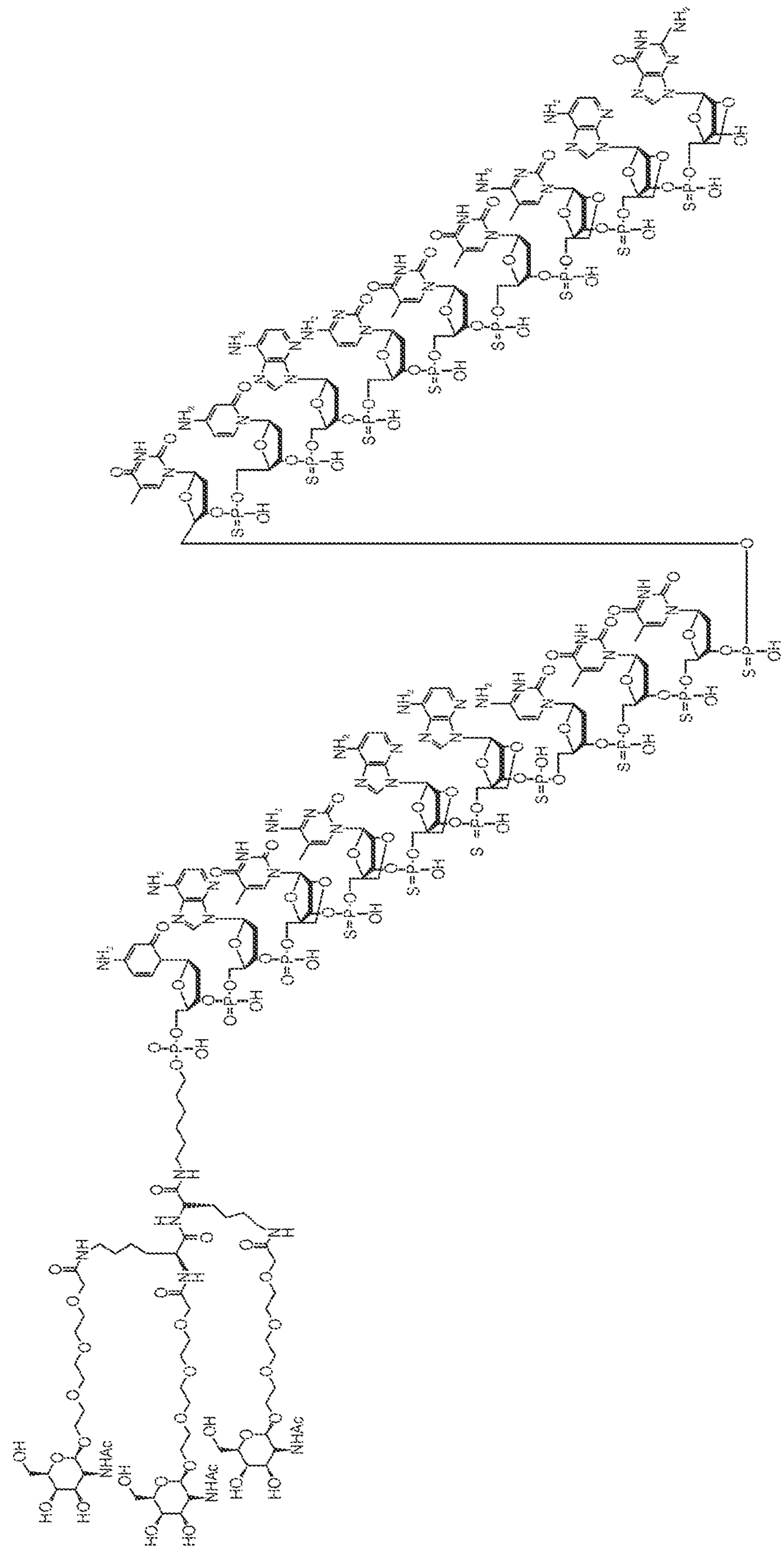
FIG. 6: Structural formula of CMP ID NO: 20_ 14. Pharmaceutical salts thereof include monovalent or divalent cations, such as Na+, K+, and Ca2+ or a mixture of these being associated with the compound.
Figure 7:
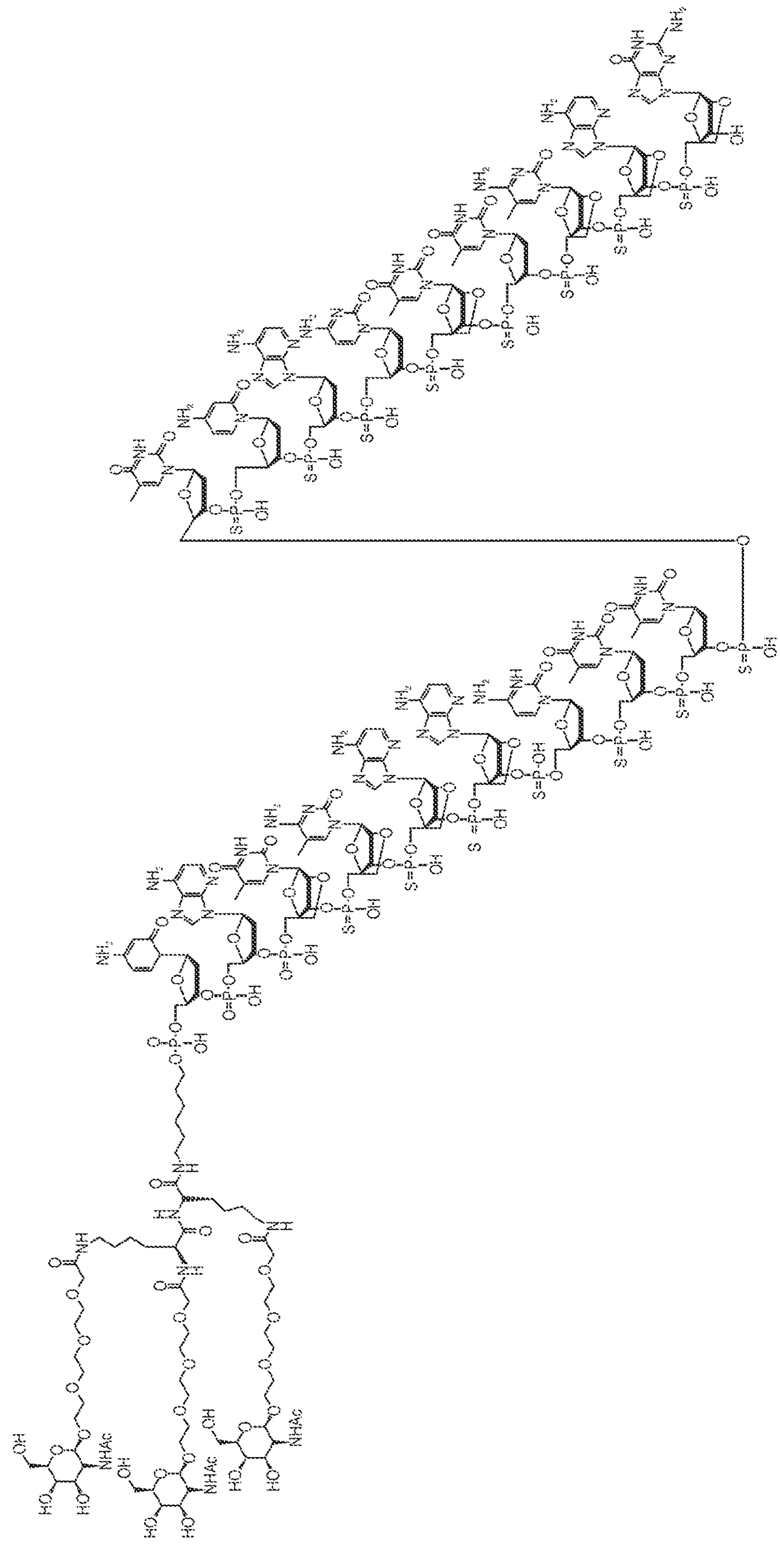
FIG. 7: Structural formula of CMP ID NO: 20_ 15. Pharmaceutical salts thereof include monovalent or divalent cations, such as Na+, K+, and Ca2+ or a mixture of these being associated with the compound.
Figure 8:
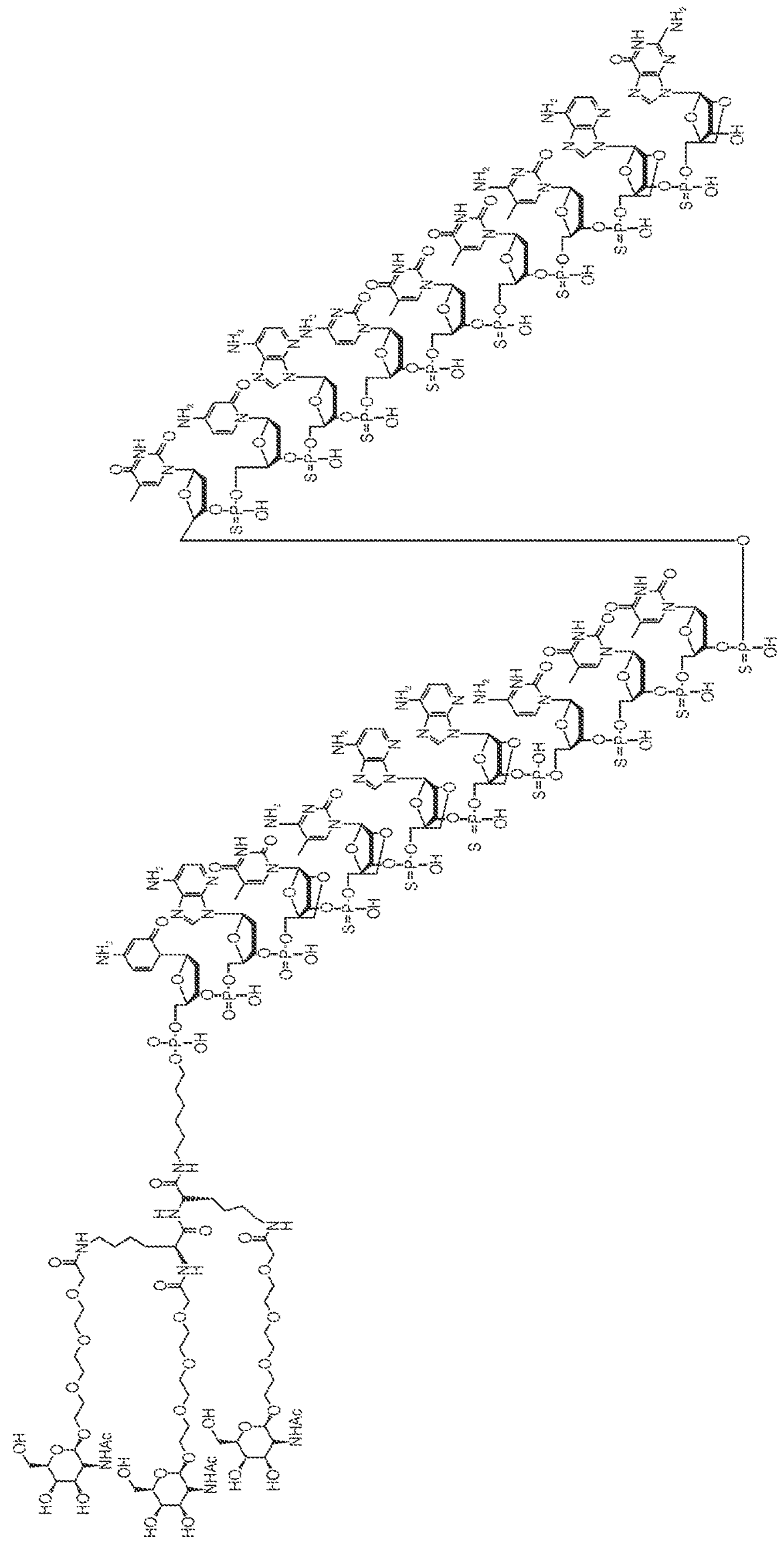
FIG. 8: Structural formula of CMP ID NO: 20_ 18. Pharmaceutical salts thereof include monovalent or divalent cations, such as Na+, K+, and Ca2+ or a mixture of these being associated with the compound.
Figure 9:
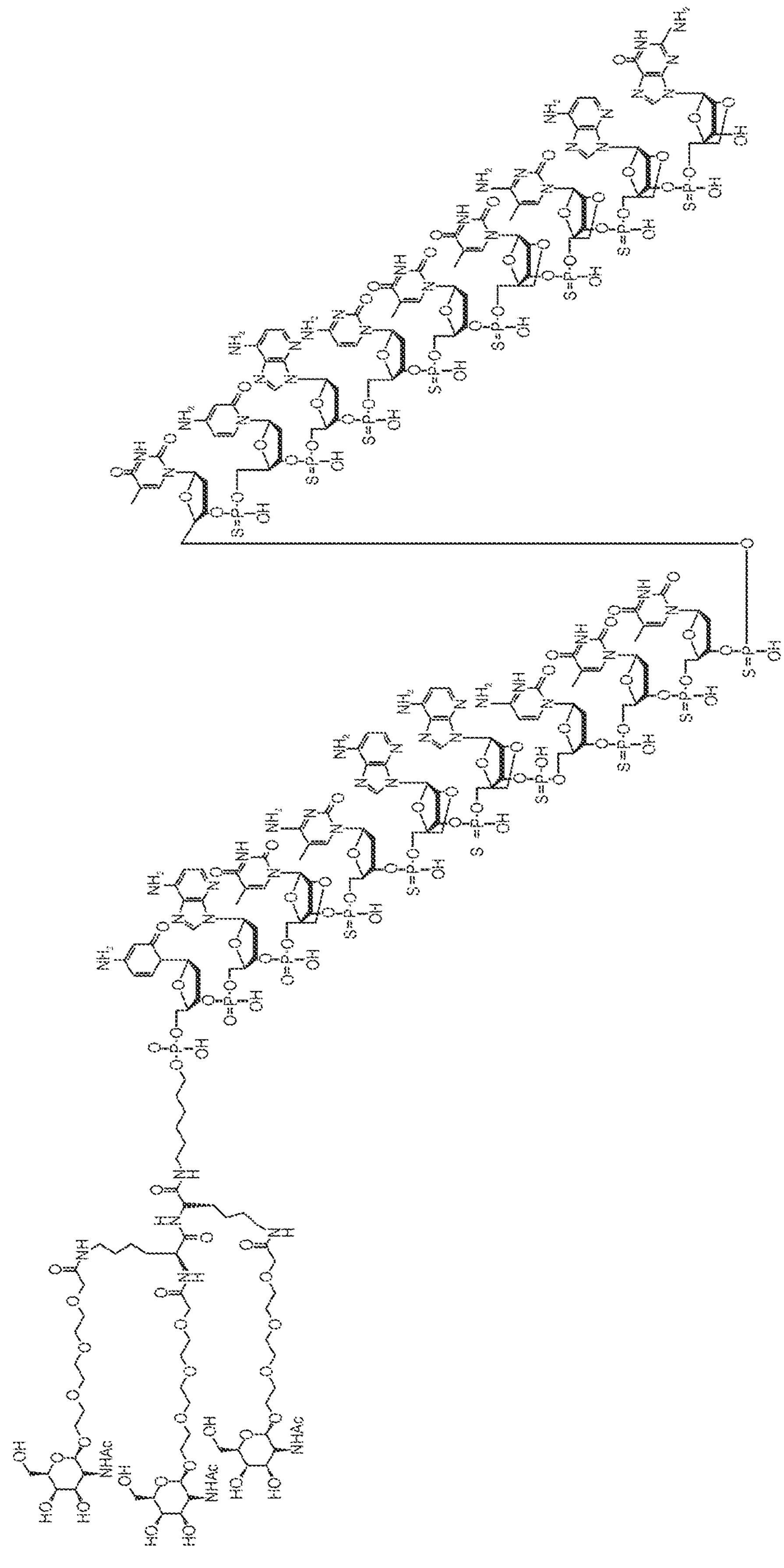
FIG. 9: Structural formula of CMP ID NO: 20_36. Pharmaceutical salts thereof include monovalent or divalent cations, such as Na+, K+, and Ca2+ or a mixture of these being associated with the compound.
Figure 10:
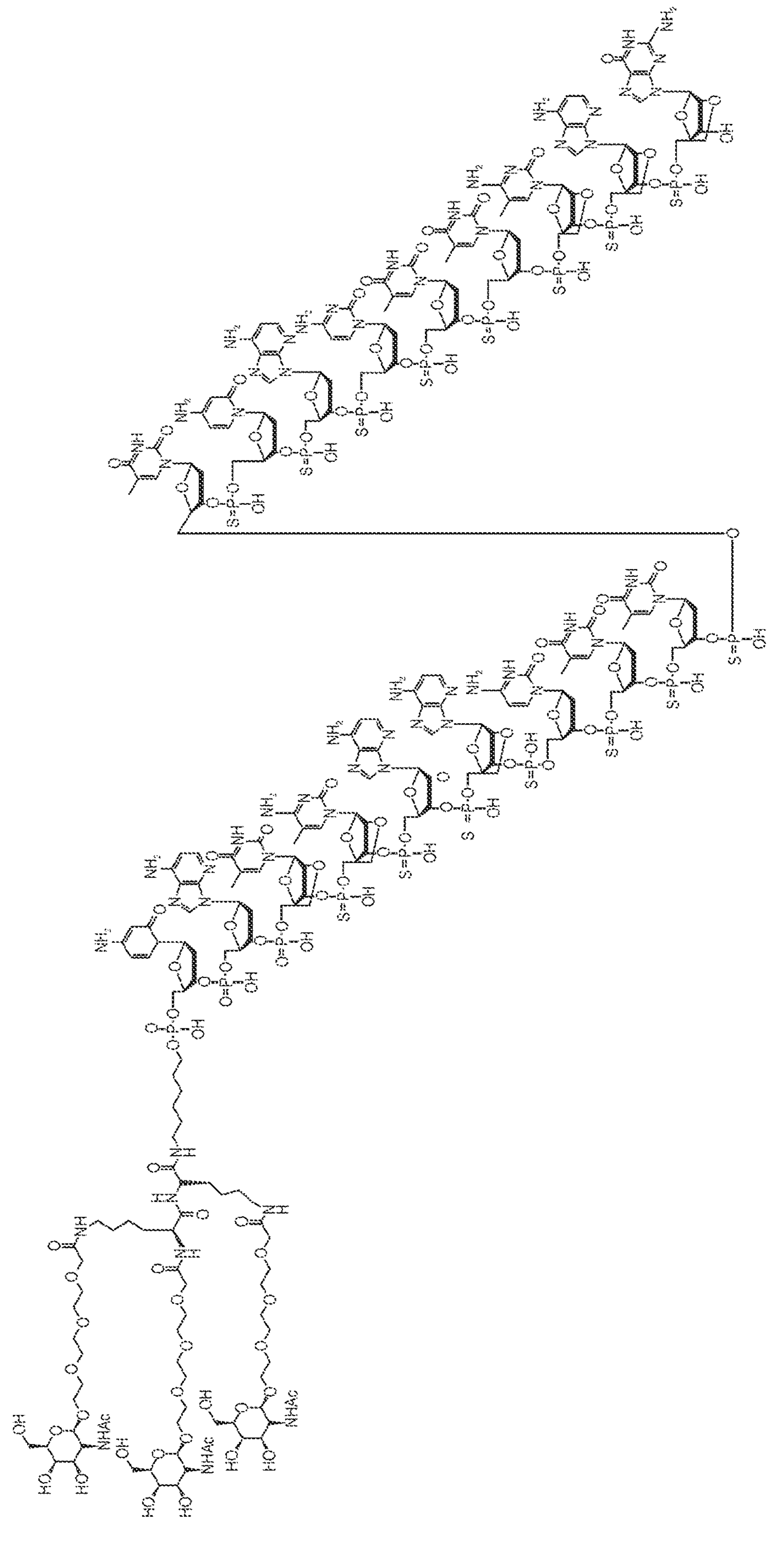
FIG. 10: Structural formula of CMP ID NO: 20_30. Pharmaceutical salts thereof include monovalent or divalent cations, such as Na+, K+, and Ca2+ or a mixture of these being associated with the compound.

In FIG. 3, it can also be seen that for oligonucleotides that reduce PAPD5 and PAPD7 in HeLa cells with more than 70% there is a high correlation with respect to these oligonucleotides ability to reduce HBsAg in HBV infected dHepaRG cells.

Example 3 Screening for In Vitro Efficacy of Antisense Oligonucleotides Targeting PAPD5 and PAPD7 in HeLa Cells A further library of 298 oligonucleotides expanding the diversity of the oligonucleotide motifs of SEQ ID NO: 17, 18 and 19 using different designs was generated. Efficacy testing was performed in an in vivo experiment as described in Example 1, with the exception that the screening was only conducted at 5 NM.

The relative PAPD5 mRNA and PAPD7 mRNA expression levels are shown in table 15 as % of average control samples (PBS-treated cells) i.e. the lower the value the larger the inhibition.

TABLE 15 in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control 5 uM | | % PAPD7 mRNA of control 5 uM | | |
|---|---|---|---|---|---|
| NO | Avg | sd | Avg | sd | Compound (CMP) |
| 17_17 | 97.74 | 7.10 | 88.55 | 3.38 | TCAaCtttcacTTCAGT |
| 17_18 | 86.48 | 5.52 | 81.81 | 1.73 | TCaACtttcacTTCAGT |
| 17_19 | 66.13 | 13.83 | 78.41 | 1.05 | TCaaCtttcacTTCAGT |
| 17_20 | 62.79 | 2.79 | 61.90 | 1.55 | TCaactttCacTTCAGT |
| 17_21 | 86.77 | 5.77 | 84.45 | 2.79 | TcAACtttcacTTCAGT |
| 17_22 | 83.56 | 9.69 | 76.97 | 2.27 | TcAAcTttcacTTCAGT |
| 17_23 | 75.81 | 5.73 | 73.23 | 5.44 | TcaaCtttcacTTCAGT |
| 17_24 | 97.11 | NA | 88.80 | 2.14 | TCAACtttcacTTCaGT |
| 17_25 | 62.02 | 5.46 | 64.52 | 2.73 | TCAActttcacTTCaGT |
| 17_26 | 90.95 | 11.41 | 92.31 | 2.78 | TCAaCtttcacTTCaGT |
| 17_27 | 75.23 | 6.15 | 75.70 | 3.92 | TCAacTttcacTTCaGT |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control 5 uM | | % PAPD7 mRNA of control 5 uM | | |
|---|---|---|---|---|---|
| NO | Avg | sd | Avg | sd | Compound (CMP) |
| 17_28 | 57.34 | 11.56 | 51.15 | 2.33 | TCAactttcacTTCaGT |
| 17_29 | 86.07 | 8.22 | 79.21 | 4.63 | TCaACtttcacTTCaGT |
| 17_30 | 82.66 | 3.99 | 82.55 | 7.92 | TCaAcTttcacTTCaGT |
| 17_31 | 63.66 | 7.08 | 58.10 | 6.16 | TCaActttcacTTCaGT |
| 17_32 | 70.24 | 8.96 | 74.38 | 4.15 | TCaaCtttcacTTCaGT |
| 17_33 | 62.01 | 4.54 | 66.85 | 2.18 | TCaacTttcacTTCaGT |
| 17_34 | 47.04 | 1.05 | 53.40 | 3.12 | TCaactttcacTTCaGT |
| 17_35 | 77.50 | 7.79 | 79.78 | 1.36 | TcAACtttcacTTCaGT |
| 17_36 | 100.06 | 11.65 | 81.00 | 3.56 | TCAACtttcacTTcAGT |
| 17_37 | 85.23 | 8.93 | 80.34 | 2.60 | TCAAcTttcacTTcAGT |
| 17_38 | 68.09 | 6.84 | 70.24 | 2.54 | TCaAcTttcacTTcAGT |
| 17_39 | 75.83 | 14.88 | 74.95 | 1.29 | TcAAcTttcacTTcAGT |
| 17_40 | 60.89 | 6.53 | 69.40 | 1.14 | TcaAcTttcacTTcAGT |
| 17_41 | 67.33 | 12.02 | 73.92 | 1.59 | TcaaCtttcacTTcAGT |
| 17_42 | 55.60 | 7.22 | 68.28 | 1.86 | TcaacTttcacTTcAGT |
| 17_43 | NA | NA | 73.73 | 6.69 | TcAACtttcacTTcaGT |
| 17_44 | 78.69 | 9.83 | 69.98 | 3.35 | TcAaCtttcacTTcaGT |
| 17_45 | 76.31 | 5.75 | 77.93 | 6.73 | TcaaCtttcacTTcaGT |
| 17_46 | 82.77 | 4.94 | 88.62 | 3.06 | TCAACtttcacTtCAGT |
| 17_47 | 75.09 | 3.28 | 75.56 | NA | TCAaCtttcacTtCAGT |
| 17_48 | 41.87 | 3.23 | 46.58 | 4.31 | TCaActttcacTtCAGT |
| 17_49 | 65.39 | 83.03 | 73.12 | 4.72 | TCaaCtttcacTtCAGT |
| 17_50 | 44.54 | 7.92 | 58.99 | 1.91 | TCaacTttcacTtCAGT |
| 17_51 | 38.28 | 4.62 | 49.61 | 11.12 | TCaactttcacTtCAGT |
| 17_52 | 72.04 | 11.74 | 67.18 | 1.56 | TcaaCtttcacTtCAGT |
| 17_53 | 77.11 | 6.61 | 80.39 | 4.87 | TCAACtttcacTtCaGT |
| 17_54 | 68.58 | 5.17 | 81.14 | 9.92 | TCAAcTttcacTtCaGT |
| 17_55 | 54.70 | NA | 55.71 | 7.63 | TCAActttcacTtCaGT |
| 17_56 | 73.62 | 8.99 | 77.13 | 4.24 | TCAaCtttcacTtCaGT |
| 17_57 | 37.11 | 4.10 | 45.26 | 2.67 | TCAactttcacTtCaGT |
| 17_58 | 75.70 | 7.51 | 79.77 | 3.37 | TCaACtttcacTtCaGT |
| 17_59 | 62.77 | 7.89 | 67.67 | 2.31 | TCaAcTttcacTtCaGT |
| 17_60 | 59.08 | 5.30 | 53.75 | 3.07 | TCaActttcacTtCaGT |
| 17_61 | 58.34 | 2.53 | 66.25 | 3.04 | TCaaCTttcacTtCaGT |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control 5 uM | | % PAPD7 mRNA of control 5 uM | | |
|---|---|---|---|---|---|
| NO | Avg | sd | Avg | sd | Compound (CMP) |
| 17_62 | 69.33 | 5.17 | 72.06 | 2.78 | TCaaCtttcacTtCaGT |
| 17_63 | 61.54 | NA | 64.88 | 2.78 | TCaacTttcacTtCaGT |
| 17_64 | 49.47 | 3.41 | 50.89 | 2.55 | TCaactttcacTtCaGT |
| 17_65 | 80.85 | 11.35 | 81.88 | 4.86 | TCAACtttcacTtcAGT |
| 17_66 | 65.22 | NA | 68.32 | 2.12 | TCAAcTttcacTtcAGT |
| 17_67 | 54.53 | 4.81 | 53.80 | 1.98 | TCAActttcacTtcAGT |
| 17_68 | 74.51 | 6.00 | 76.56 | 0.65 | TCAaCtttcacTtcAGT |
| 17_69 | 56.83 | NA | 57.20 | 4.10 | TCAacTttcacTtcAGT |
| 17_70 | 76.86 | NA | 76.34 | 2.03 | TCaACtttcacTtcAGT |
| 17_71 | 63.44 | 10.55 | 64.68 | 5.87 | TTCaAcTttcacTCAGT |
| 17_72 | 62.56 | 5.79 | 61.72 | 1.34 | TcAAcTttcacTtcAGT |
| 17_73 | 60.51 | 6.25 | 67.89 | 3.45 | TCAACtttcacTtcaGT |
| 17_74 | 54.17 | NA | 56.84 | 3.66 | TCAActttcacTtcaGT |
| 17_75 | 66.76 | 4.71 | 62.81 | 3.26 | TCAaCTttcacTtcaGT |
| 17_76 | 66.23 | 5.60 | 53.07 | 13.10 | TCAaCtttcacTtcaGT |
| 17_77 | 59.39 | 8.21 | 63.25 | 4.95 | TCAacTttcacTtcaGT |
| 17_78 | 56.02 | 5.00 | 64.25 | 3.27 | TCaACtttcacTtcaGT |
| 17_79 | 45.91 | 4.00 | 56.13 | 3.45 | TCaAcTttcacTtcaGT |
| 17_80 | 69.86 | 6.08 | 69.85 | 3.93 | TCaaCtttcacTtcaGT |
| 17_81 | 65.32 | 5.73 | 70.58 | 4.02 | TCaacTttcacTtcaGT |
| 17_82 | 63.33 | 8.83 | 70.99 | 4.18 | TcAACtttcacTtcaGT |
| 17_83 | 68.96 | 8.36 | 74.25 | 5.87 | TcAaCtttcacTtcaGT |
| 17_84 | 63.62 | 7.64 | 81.25 | 4.70 | TcaaCtttcacTtcaGT |
| 17_85 | 83.30 | 4.59 | 84.25 | 2.62 | TCAACtttcactTCAGT |
| 17_86 | 37 09 | 7.98 | 43.15 | 2.13 | TCaActttcactTCAGT |
| 17_87 | 50.48 | 4.81 | 60.27 | 6.81 | TCaaCtttcactTCAGT |
| 17_88 | 53.38 | 5.35 | 56.84 | 5.09 | TCaacTttcactTCAGT |
| 17_89 | NA | NA | 43.67 | 3.84 | TCaactttcactTCAGT |
| 17_90 | 29.17 | 3.73 | 37.06 | 3.81 | TcAActttcactTCAGT |
| 17_91 | 61.71 | 7.15 | 71.61 | 3.90 | TcAaCtttcactTCAGT |
| 17_92 | 56.04 | 3.53 | 65.82 | 5.45 | TcaaCtttcactTCAGT |
| 17_93 | 45.09 | 4.71 | 56.40 | 2.59 | TcaactttcactTCAGT |
| 17_94 | 69.38 | 7.28 | 70.95 | 4.84 | TCAACtttcactTCaGT |
| 17_95 | 64.57 | 3.46 | 70.96 | 2.87 | TCAAcTttcactTCaGT |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control 5 uM | | % PAPD7 mRNA of control 5 uM | | |
|---|---|---|---|---|---|
| NO | Avg | sd | Avg | sd | Compound (CMP) |
| 17_96 | 34.51 | 2.38 | 39.62 | 1.63 | TCAActttcactTCaGT |
| 17_97 | 55.05 | 10.06 | 57.09 | 1.62 | TCAaCtttcactTCaGT |
| 17_98 | 64.97 | 7.46 | 63.11 | 2.12 | TCAacTttcactTCaGT |
| 17_99 | 36.70 | 4.12 | 39.75 | 1.43 | TCAactttcactTCaGT |
| 17_100 | 39.06 | NA | 41.61 | 1.24 | TCaActttcactTCaGT |
| 17_101 | 41.26 | 2.45 | 49.05 | 3.40 | TCaactttcactTCaGT |
| 17_102 | 78.96 | 10.63 | 60.35 | 2.12 | TcAACtttcactTCaGT |
| 17_103 | 32.50 | 2.83 | 36.44 | 1.34 | TcAActttcactTCaGT |
| 17_104 | 60.36 | 6.41 | 58.67 | 0.78 | TcAaCtttcactTCaGT |
| 17o105 | 58.78 | 3.01 | 65.37 | 2.47 | TcAacTttcactTCaGT |
| 17_106 | 41.78 | 7.71 | 45.57 | 2.93 | TcAactttcactTCaGT |
| 17_107 | 68.24 | 10.65 | 68.52 | 2.11 | TcaaCtttcactTCaGT |
| 17_108 | 63.66 | 6.15 | 69.87 | 1.49 | TcaactttcactTCaGT |
| 17_109 | 43.39 | 6.06 | 44.03 | 1.22 | TCAActttcactTcAGT |
| 17_110 | 67.71 | 3.99 | 68.24 | 2.49 | TCAaCtttcactTcAGT |
| 17_111 | 38.72 | 5.67 | 45.18 | 4.37 | TCaactttcactTcAGT |
| 17_112 | 74.81 | 8.54 | 82.12 | 2.07 | TcAACtttcactTcAGT |
| 17113 | 45.61 | 3.48 | 49.46 | 3.00 | TcAActttcactTcAGT |
| 17_114 | 75.79 | 7.63 | 72.29 | 2.16 | TcAaCtttcactTcAGT |
| 17_115 | 75.42 | 15.41 | 74.41 | 3.07 | TcaActttcactTcAGT |
| 17_116 | 65.82 | 10.42 | 71.11 | 2.68 | TcaaCtttcactTcAGT |
| 17_117 | 59.41 | 10.07 | 62.29 | 5.94 | TcaactttcactTcAGT |
| 17_118 | 52.64 | NA | 52.72 | 2.61 | TCAACtttcactTcaGT |
| 17_119 | 39.63 | NA | 40.24 | 1.12 | TCAActttcactTcaGT |
| 17_120 | 59.98 | 2.92 | 50.20 | 0.85 | TCAaCtttcactTcaGT |
| 17_121 | 43.88 | 11.36 | 47.72 | 4.55 | TCAactttcactTcaGT |
| 17_122 | 64.88 | 13.05 | 60.50 | 3.00 | TCaaCtttcactTcaGT |
| 17_123 | 63.11 | 5.97 | 66.33 | 6.52 | TCaactttcactTcaGT |
| 17_124 | 56.82 | 7.60 | 52.41 | 2.44 | TcAaCtttcactTcaGT |
| 17_125 | 53.85 | 8.06 | 61.73 | 4.31 | TcAactttcactTcaGT |
| 17_126 | 81.50 | 15.86 | 84.13 | 4.80 | TcaActttcactTcaGT |
| 17_127 | 78.91 | 10.65 | 82.69 | 2.51 | TcaactttcactTcaGT |
| 17_128 | 81.11 | 11.24 | 78.80 | 1 05 | TCAACtttcacttCAGT |
| 17_129 | 32.28 | 2.57 | 39.12 | 1.07 | TCAactttcacttCAGT |
| 17_130 | 70.27 | 8.13 | 72.06 | 1.44 | TCaACtttcacttCAGT |
| 17_131 | 52.53 | 5.34 | 51.48 | 1.51 | TCaAcTttcacttCAGT |
| 17_132 | 39.54 | 5.34 | 40.49 | 2.90 | TCaActttcacttCAGT |
| 17_133 | 49.75 | 8.73 | 51.25 | 2.19 | TCaaCtttcacttCAGT |
| 17_134 | 40.11 | 4.72 | 46.40 | 3.25 | TCaacTttcacttCAGT |
| 17_135 | 32.68 | 5.78 | 44.12 | 1.28 | TCaactttcacttCAGT |
| 17_136 | 73.83 | 11.05 | 64.31 | 14.71 | TcAACtttcacttCAGT |
| 17_137 | 27.45 | 3.58 | 37.37 | 0.87 | TcAActttcacttCAGT |
| 17_138 | 52.94 | 2.36 | 52.33 | 6.75 | TcAaCtttcacttCAGT |
| 17_139 | 33.04 | 3.96 | 41.18 | 2.84 | TcAactttcacttCAGT |
| 17_140 | 51.65 | 1.57 | 52.29 | 3.62 | TCAAcTttcacttCaGT |
| 17_141 | 61.72 | 2.80 | 58.93 | 0.97 | TCAaCTttcacttCaGT |
| 17_142 | 46.19 | NA | 52.83 | 5.45 | TCAaCtttcacttCaGT |
| 17_143 | 43.84 | 1.08 | 45.66 | 0.98 | TCAacTttcacttCaGT |
| 17_144 | 37.39 | 2.38 | 43.74 | 1.32 | TCAactttcacttCaGT |
| 17_145 | 67.26 | 7.35 | 74.40 | 4.87 | TCaACTttcacttCaGT |
| 17_146 | 56.45 | 2.94 | 56.68 | 0.48 | TCaACtttcacttCaGT |
| 17_147 | 47.22 | 1.68 | 54.43 | 1.21 | TCaAcTttcacttCaGT |
| 17_148 | 43.18 | 2.71 | 56.05 | 1.42 | TCaaCTttcacttCaGT |
| 17_149 | 45.97 | NA | 53.84 | 3.68 | TCaacTttcacttCaGT |
| 17_150 | 59.24 | 6.22 | 60.59 | 3.40 | TcAACtttcacttCaGT |
| 17_151 | 51.93 | NA | 61.55 | 5.08 | TcAaCtttcacttCaGT |
| 17_152 | 47.41 | 5.67 | 52.89 | 3.10 | TcAactttcacttCaGT |
| 17_153 | 65.27 | 4.09 | 69.29 | 7.55 | TcaActttcacttCaGT |
| 17_154 | 53.74 | NA | 62.46 | 1.61 | TcaaCTttcacttCaGT |
| 17_155 | 66.62 | 5.23 | 74.14 | 3.90 | TcaactttcacttCaGT |
| 17_156 | 48.09 | 0.70 | 49.14 | 1.49 | TCAAcTttcacttcAGT |
| 17_157 | 38.49 | 2.92 | 43.72 | 1.30 | TCAActttcacttcAGT |
| 17_158 | 59.33 | 3.81 | 63.90 | 1.94 | TCAaCTttcacttcAGT |
| 17_159 | 56.79 | 9.47 | 55.56 | 2.69 | TCAaCtttcacttcAGT |
| 17_160 | 50.32 | 7.20 | 48.93 | 2.20 | TCaaCTttcacttcAGT |
| 17_161 | 40.36 | 4.00 | 45.81 | 1.30 | TCaacTttcacttcAGT |
| 17_162 | 64.11 | 4.76 | 62.08 | 1.69 | TcAaCtttcacttcAGT |
| 17_163 | 58.28 | NA | 59.97 | 2.18 | TcAactttcacttcAGT |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control 5 uM | | % PAPD7 mRNA of control 5 uM | | |
|---|---|---|---|---|---|
| NO | Avg | sd | Avg | sd | Compound (CMP) |
| 17_164 | 76.29 | 13.13 | 77.15 | 3.83 | TcaActttcacttcAGT |
| 17_165 | 78.09 | 15.89 | 72.59 | 8.69 | TcaactttcacttcAGT |
| 17_166 | 62.49 | 3.63 | 64.37 | 5.16 | TCAACTttcacttcaGT |
| 17_167 | 50.03 | 8.03 | 54.73 | 1.30 | TCAACtttcacttcaGT |
| 17_168 | 51.60 | 9.81 | 52.08 | 4.48 | TCAAcTttcacttcaGT |
| 17_169 | 46.17 | 5.15 | 51.40 | 2.49 | TCAActttcacttcaGT |
| 17_170 | 52.75 | 11.01 | 54.83 | 2.69 | TCAaCTttcacttcaGT |
| 17_171 | 53.33 | 9.21 | 54.36 | 2.78 | TCAaCtttcacttcaGT |
| 17_172 | 58.21 | 6.31 | 58.05 | 1.23 | TCAaCtttcacttcaGT |
| 17_173 | 53.76 | 2.90 | 58.61 | 1.13 | TCaACTttcacttcaGT |
| 17_174 | 50.25 | 5.79 | 50.99 | 7.67 | TCaACtttcacttcaGT |
| 17_175 | 51.82 | 4.61 | 54.72 | 1.85 | TCaActttcacttcaGT |
| 17_176 | 53.43 | NA | 58.36 | 6.34 | TCaaCtttcacttcaGT |
| 17_177 | 57.85 | 3.78 | 63.73 | 2.53 | TCaacTttcacttcaGT |
| 17_178 | 62.40 | 7.11 | 60.69 | 2.19 | TcAActttcacttcaGT |
| 17_179 | 58.09 | 9.19 | 57.23 | 4.50 | TcAaCtttcacttcaGT |
| 17_180 | 74.45 | 11.02 | 75.46 | 4.00 | TcAactttcacttcaGT |
| 17_181 | 90.80 | 14.30 | 82.83 | 2.65 | TcaActttcacttcaGT |
| 17_182 | 74.91 | NA | 75.31 | 4.39 | TcaaCtttcacttcaGT |
| 17_183 | 88.59 | 4.23 | 85.23 | 2.44 | TcaactttcacttcaGT |
| 18_1 | 32.92 | 3.39 | 35.69 | 3.82 | TCAactttcacttCAG |
| 18_250 | 100.08 | 10.66 | 88.51 | 4.20 | TCAACtttcaCTTCAG |
| 18_251 | 84.40 | 7.39 | 80.86 | 4.12 | TCAActttcaCTTCAG |
| 18_252 | 91.54 | 3.68 | 89.30 | 5.79 | TCAaCtttcaCTTCAG |
| 18_253 | 91.81 | 6.31 | 89.37 | 3.90 | TCaACtttcaCTTCAG |
| 18_254 | 85.25 | 10.05 | 84.67 | 2.91 | TCaaCtttcaCTTCAG |
| 18_255 | 86.24 | 2.27 | 87.98 | 0.91 | TCaaCtttcaCTTCAG |
| 18_256 | 78.51 | 4.22 | 82.48 | 9.24 | TcaactttcaCTTCAG |
| 18_257 | 89.59 | 11.37 | 90.01 | 5.75 | TcAaCtttcaCTTcAG |
| 18_258 | 95.95 | 14.37 | 92.27 | 12.06 | TcaaCtttcaCTTcAG |
| 18_259 | 81.62 | 8.01 | 75.93 | 5.23 | TcaactttcaCTTcAG |
| 18_260 | 89.34 | 4.48 | 92.90 | 6.69 | TCAaCtttcaCTtCAG |
| 18_261 | 54.74 | NA | 59.78 | 4.39 | TCAactttcaCTtCAG |
| 18_262 | 91.32 | 12.46 | 85.83 | 4.88 | TCaaCtttcaCTtCAG |
| 18_263 | 53.49 | 6.41 | 55.73 | 1.72 | TCaactttcaCTtCAG |
| 18_264 | 77.00 | 7.13 | 83.85 | 2.44 | TcAACtttcaCTtCAG |
| 18_265 | 82.71 | 2.41 | 80.20 | 3.21 | TcaaCtttcaCTtCAG |
| 18_266 | 65.50 | 14.42 | 63.32 | 7.76 | TcaactttcaCTtCAG |
| 18_267 | 88.30 | 14.79 | 88.12 | 2.67 | TCAACtttcaCTtcAG |
| 18_268 | 85.83 | 5.66 | 80.25 | 1.37 | TCAActttcaCTtcAG |
| 18_269 | 84.52 | 3.17 | 89.90 | 6.04 | TCAactttcaCTtcAG |
| 18_270 | 57.28 | 7.24 | 62.34 | NA | TCAactttcaCTtcAG |
| 18_271 | 84.49 | 8.06 | 91.51 | 3.02 | TCaACtttcaCTtcAG |
| 18o272 | 76.13 | 4.46 | 79.90 | NA | TCaActttcaCTtcAG |
| 18_273 | 85.88 | 7.38 | 97.42 | 4.00 | TcAaCtttcaCTtcAG |
| 18_274 | 95.40 | 13.18 | 95.86 | 1.55 | TcaaCtttcaCTtcAG |
| 18_275 | 95.60 | 10.21 | 92.33 | 2.77 | TCAACtttcaCtTCAG |
| 18_276 | 83.72 | 6.59 | 80.77 | 2.02 | TCAACtttcaCtTCAG |
| 18_277 | 90.13 | 10.30 | 96.27 | 13.83 | TCAaCtttcaCtTCAG |
| 18_278 | 55.67 | 8.13 | 62.46 | 6.54 | TCAactttcaCtTCAG |
| 18_279 | 87.22 | 13.33 | 88.16 | 8.73 | TCaACtttcaCtTCAG |
| 18_280 | 76.65 | 3.97 | 79.84 | 12.72 | TCaActttcaCtTCAG |
| 18_281 | 81.18 | 8.97 | 84.87 | 7.12 | TCaaCtttcaCtTCAG |
| 18_282 | 61.04 | 7.74 | 61.76 | 1.66 | TCaactttcaCtTCAG |
| 18_283 | 84.65 | 3.34 | 80.88 | 2.96 | TCaaCtttcaCtTcAG |
| 18_284 | 61.02 | 6.86 | 62.10 | 2.82 | TCaactttcaCtTcAG |
| 18_285 | 86.61 | 3.69 | 95.03 | 18.61 | TcAACtttcaCtTcAG |
| 18_286 | 84.98 | 9.65 | 85.00 | 14.32 | TcAActttcaCtTcAG |
| 18_287 | 86.45 | 4.35 | 88.69 | 7.72 | TcAaCtttcaCtTcAG |
| 18_288 | 57.67 | 1.82 | 61.38 | NA | TcAactttcaCtTcAG |
| 18_289 | 79.05 | 6.07 | 83.92 | 4.10 | TcaActttcaCtTcAG |
| 18_290 | 87.52 | 9.96 | 91.14 | 2.20 | TcaaCtttcaCtTcAG |
| 18_291 | 73.29 | 5.03 | 69.25 | 5.43 | TcaactttcaCtTcAG |
| 18_292 | 72.78 | 7.03 | 68.16 | 1.00 | TCAACtttcaCttCAG |
| 18_293 | 59.43 | 5.50 | 58.08 | 2.89 | TCAActttcaCttCAG |
| 18_294 | 75.84 | 3.56 | 63.66 | 3.73 | TCAaCtttcaCttCAG |
| 18_295 | 46.89 | 3.57 | 49.06 | 2.63 | TCAactttcaCttCAG |
| 18_298 | 65.42 | 3.75 | 63.31 | 3.08 | TCaACtttcaCttCAG |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control 5 uM | | % PAPD7 mRNA of control 5 uM | | |
|---|---|---|---|---|---|
| NO | Avg | sd | Avg | sd | Compound (CMP) |
| 18_297 | 58.20 | 6.79 | 55.76 | 1.22 | TCaActttcaCttCAG |
| 18_298 | 66.88 | 4.87 | 66.09 | 3.03 | TCaaCtttcaCttCAG |
| 18_299 | 57.00 | 3.54 | 52.43 | 0.96 | TCaactttcaCttCAG |
| 18_300 | 67.40 | 4.43 | 64.15 | 3.50 | TcAACtttcaCttCAG |
| 18_301 | 76.29 | 2.94 | 66.61 | 0.93 | TcaACtttcaCttCAG |
| 18_302 | 79.40 | 6.94 | 75.09 | 2.40 | TcaActttcaCttCAG |
| 18_303 | 80.86 | 2.61 | 67.53 | 3.70 | TCAACtttcaCttcAG |
| 18_304 | 67.19 | 3.65 | 64.77 | 2.65 | TCAActttcaCttcAG |
| 18_05 | 79.81 | 7.90 | 76.61 | 4.75 | TCAaCtttcaCttcAG |
| 18_306 | 65.48 | 4.30 | 60.08 | 1.89 | TCAactttcaCttcAG |
| 18_307 | 70.08 | 6.13 | 70.40 | 2.08 | TCaACtttcaCttcAG |
| 18_308 | 70.99 | 2.21 | 71.46 | 3.87 | TCaActttcaCttcAG |
| 18_309 | 69.43 | 6.30 | 81.14 | 12.38 | TCaaCtttcaCttcAG |
| 18_310 | 73.04 | 7.86 | 73.31 | 4.69 | TCaactttcaCttcAG |
| 18_311 | 72.32 | 9.45 | 78.61 | 8.91 | TcAACtttcaCttcAG |
| 18_312 | 67.82 | 11.23 | 78.05 | 7.27 | TcAActttcaCttcAG |
| 18_313 | 75.81 | 10.76 | 78.01 | 7.76 | TcAaCtttcaCttcAG |
| 18_314 | 66.04 | 5.65 | 75.33 | 8.56 | TcAactttcaCttcAG |
| 18_315 | 78.82 | 5.66 | 75.34 | 2.78 | TcaACtttcaCttcAG |
| 18_316 | 87.37 | 14.72 | 95.41 | 6.94 | TcaaCtttcaCttcAG |
| 18_317 | 79.19 | 4.27 | 94.13 | 12.76 | TCaactttcaCttcAG |
| 18_318 | 59.57 | 10.72 | 63.41 | 2.62 | TCAActttcacTTCAG |
| 18_319 | 84.55 | 4.72 | 81.60 | 3.53 | TCAaCtttcacTTCAG |
| 18_320 | 72.74 | 2.03 | 79.32 | 10.24 | TCaACtttcacTTCAG |
| 18_321 | 72.73 | 6.17 | 74.90 | 3.78 | TcAACtttcacTTCAG |
| 18_322 | 70.71 | 12.19 | 72.65 | 3.47 | TcAaCtttcacTTCAG |
| 18_323 | 63.05 | 4.68 | 64.11 | 2.23 | TcaaCtttcacTTCAG |
| 18_324 | 90.00 | 7.49 | 79.94 | 4.07 | TCAACtttcacTTCAG |
| 18_325 | 79.21 | 4.73 | 75.34 | 2.42 | TCAaCtttcacTTcAG |
| 18_326 | 68.92 | NA | 67.74 | 4.83 | TCaaCtttcacTTcAG |
| 18_327 | 56.44 | 4.90 | 56.48 | 2.86 | TcAActttcacTTcAG |
| 18_328 | 75.87 | 4.14 | 71.99 | 4.42 | TcAaCtttcacTTcAG |
| 18_329 | 61.35 | 2.64 | 57.83 | 2.46 | TcAactttcacTTcAG |
| 18_330 | 82.34 | 3.56 | 78.64 | 4.39 | TcaaCtttcacTTcAG |
| 18_331 | 75.40 | 6.43 | 72.02 | 3.95 | TcaactttcacTTcAG |
| 18_332 | 72.69 | 7.00 | 73.99 | 3.23 | TCAaCtttcacTtCAG |
| 18_333 | 47.08 | 4.26 | 45.64 | 2.17 | TCaActttcacTtCAG |
| 18_334 | 63.55 | 2.17 | 61.47 | 5.18 | TCaaCtttcacTtCAG |
| 18_335 | 45.43 | 2.17 | 43.67 | 0.51 | TcAActttcacTtCAG |
| 18_336 | 62.16 | 1.68 | 63.10 | 4.22 | TcaactttcacTtCAG |
| 18_337 | 68.12 | 1.83 | 69.62 | 5.48 | TCAACtttcacTtcAG |
| 18_338 | 58.66 | 3.79 | 55.57 | 3.90 | TCAActttcacTtcAG |
| 18_339 | 64.78 | 3.20 | 67.31 | 4.73 | TCAaCtttcacTtcAG |
| 18_340 | 73.84 | 12.62 | 70.76 | 2.66 | TCaaCtttcacTtcAG |
| 18_341 | 63.86 | 1.31 | 62.80 | 2.97 | TCaactttcacTtcAG |
| 18_342 | 63.62 | 7.33 | 62.67 | 3.14 | TcAACtttcacTtcAG |
| 18_343 | 77.34 | 8.12 | 76.95 | 8.74 | TcAaCtttcacTtcAG |
| 18_344 | 77.52 | 4.63 | 72.61 | 19.40 | TcaaCtttcacTtcAG |
| 18_345 | 44.88 | 5.16 | 44.48 | 2.03 | TCaACtttcactTCAG |
| 18_346 | 33.58 | 3.96 | 33.46 | 0.75 | TCaActttcactTCAG |
| 18_347 | 25.34 | 3.90 | 27.48 | 1.20 | TcAActttcactTCAG |
| 18_348 | 72.22 | 13.10 | 69.54 | 2.55 | TcaActttcactTCAG |
| 18_349 | 60.34 | 3.62 | 62.20 | 3.43 | TcaactttcactTCAG |
| 18_350 | 42.64 | 7.75 | 39.08 | 1.64 | TCAActttcactTcAG |
| 18_351 | 64.87 | 4.90 | 60.46 | 2.58 | TCaaCtttcactTcAG |
| 18_352 | 60.50 | 8.75 | 58.85 | NA | TCaactttcactTcAG |
| 18_353 | 46.91 | 7.66 | 48.41 | 2.35 | TcAActttcactTcAG |
| 18_354 | 56.92 | 5.54 | 55.90 | 3.41 | TcaACtttcactTcAG |
| 18_355 | 83.71 | 14.79 | 81.27 | 2.26 | TcaActttcactTcAG |
| 18_356 | 39.74 | 8.56 | 46.46 | NA | TCaACtttcacttCAG |
| 18_357 | 38.75 | 4.00 | 38.86 | 1 61 | TCaActttcacttCAG |
| 18_358 | 38.88 | 4.61 | 43.88 | 5.77 | TcaACtttcacttCAG |
| 18_359 | 77.53 | 8.61 | 72.87 | 3.73 | TcaActttcacttCAG |
| 18_360 | 78.21 | NA | 75.73 | 4.38 | TcaactttcacttCAG |
| 18_361 | 57.41 | NA | 51.70 | 2.51 | TcAaCtttcacttcAG |
| 19_4 | 101.90 | 8.84 | 105.29 | 4.25 | TGTTTcaataCTAAAA |
| 19_5 | 105.24 | 11.89 | 100.23 | 3.22 | TGTTtcaataCTAAAA |
| 19_6 | 99.75 | 6.33 | 104.03 | 3.46 | TGTtTcaataCTAAAA |

TABLE 15-continued in vitro efficacy of anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control 5 uM | | % PAPD7 mRNA of control 5 uM | | |
|---|---|---|---|---|---|
| NO | Avg | sd | Avg | sd | Compound (CMP) |
| 19_7 | 91.29 | NA | 91.20 | 2.56 | TGTttcaataCTAAAA |
| 19_8 | 106.37 | NA | 100.46 | 3.70 | TGtTTcaataCTAAAA |
| 19_9 | 108.42 | 11.96 | 101.59 | 4.05 | TGttTcaataCTAAAA |
| 19_10 | 100.39 | 8.50 | 102.93 | 6.06 | TgTTTcaataCTAAAA |
| 19_11 | 90.83 | 3.68 | 92.38 | 3.27 | TGTTTcaataCTAaAA |
| 19_12 | 90.86 | 3.89 | 91.69 | 3.53 | TGTTtcaataCTAaAA |
| 19_13 | 89.85 | 3.87 | 91.34 | 2.59 | TGTtTcaataCTAaAA |
| 19_14 | 94.01 | 8 75 | 94.66 | 2.33 | TGTttcaataCTAaAA |
| 19_15 | 92.12 | 2.54 | 91.25 | 2.22 | TGtTTcaataCTAaAA |
| 19_16 | 97.86 | 5.30 | 93.85 | 1.92 | TgTTTcaataCTAaAA |
| 19_17 | 105.50 | 15.59 | 99.75 | 4.80 | TGTTTcaataCTaAAA |
| 19_18 | 102.61 | 5.30 | 96.26 | 2.40 | TGTTtcaataCTaAAA |
| 19_19 | 94.76 | 5.45 | 94.05 | 2.41 | TGTtTcaataCTaAAA |
| 19_20 | 97.80 | 9.88 | 102.61 | 9.09 | TGTTTcaataCTaaAA |
| 19_21 | 95.95 | 9.14 | 89.84 | 2.06 | TGTTtcaataCTaaAA |
| 19_22 | 101.79 | 7.29 | 95.45 | 3.90 | TGTTTcaataCtAAAA |

From these data it can be seen that the LNA-gapmer designs based on the motif sequence with SEQ ID NO: 19 have very low (between 0 and 10%) PAPD5 and PAPD7 knock down.

Example 4: In Vitro EC50 and Efficacy of Selected Antisense Oligonucleotides in HeLa Cells The EC50 and efficacy (KD) of the best performing oligonucleotides from Example 1 and 3 was determined using the same assay with the following oligonucleotide concentrations 50, 15.81, 5.00, 1.58, 0.50, 0.16, 0.05, and 0.016 μM.

EC 50, max KD (efficacy) of the PAPD5 and PAPD7 mRNA expression was calculated using the R-function drm( ) from the drc package (v3.0-1) a four-parameter log-logistic function is fitted to the expression of the gene of interest as a function of oligonucleotide concentration to obtain a value for EC50 and maximum knock-down. The results are shown in Table 16.

TABLE 16

EC50 and Max KD of anti-PAPD5/PAPD7 compounds on PAPD5 and PAPD7 mRNA expression in HeLa cells.

| CMP | PAPD5 | | | | PAP D7 | | | | |
|---|---|---|---|---|---|---|---|---|---|
| | Max KD % of saline | | EC50 μM | | Max KD % of saline | | EC50 μM | | |
| ID NO | Avg | sd | Avg | sd | Avg | sd | Avg | sd | Compound |
| 17_7 | 1.45 | 7.29 | 2.40 | 0.55 | 8.00 | 6.58 | 3.13 | 0.65 | TcAactttcactTcAGT |
| 17_8 | 7.66 | 4.14 | 3.08 | 0.42 | 5.37 | 5.16 | 4.00 | 0.62 | TcAActttcactTcaGT |
| 17_10 | 0.00 | 2.40 | 2.30 | 0.19 | 3.31 | 5.90 | 3.79 | 0.68 | TCAActttcacttCaGT |
| 17_12 | 6.52 | 3.37 | 2.72 | 0.31 | 11.14 | 4.37 | 3.32 | 0.49 | TCaactttcacttCaGT |
| 17_13 | 0.68 | 5.12 | 2.43 | 0.42 | 2.29 | 4.83 | 3.64 | 0.55 | TcAActttcacttCaGT |
| 17_14 | 0.19 | 5.00 | 2.51 | 0.42 | 3.13 | 4.54 | 3.69 | 0.52 | TCAactttcacttcAGT |
| 17_51 | 3.29 | 3.89 | 1.41 | 0.21 | 5.81 | 1.20 | 1.78 | 0.08 | TCaactttcacTtCAGT |
| 17_57 | 2.61 | 7.96 | 1.54 | 0.47 | 3.07 | 3.45 | 1.76 | 0.21 | TCAactttcacTtCaGT |
| 17_86 | 0.00 | 3.77 | 1.19 | 0.17 | 0.00 | 3.32 | 2.01 | 0.22 | TCaActttcactTCAGT |
| 17_89 | 6.03 | 2.64 | 1.02 | 0.11 | 9.23 | 3.65 | 1.44 | 0.21 | TCaactttcactTCAGT |
| 17_90 | 2.43 | 5.44 | 1.38 | 0.29 | 1.87 | 5.63 | 1.95 | 0.40 | TcAActttcactTCAGT |
| 17_96 | 3.27 | 2.62 | 1.85 | 0.18 | 0.00 | 3.44 | 1.99 | 0.24 | TCAActttcactTCaGT |
| 17_99 | 0.00 | 3.61 | 1.42 | 0.18 | 0.55 | 5.03 | 1.57 | 0.28 | TCAactttcactTCaGT |

TABLE 16-continued

EC50 and Max KD of anti-PAPD5/PAPD7 compounds on PAPD5 and PAPD7 mRNA expression in HeLa cells.

| CMP | PAPD5 | | | | PAP D7 | | | | |
|---|---|---|---|---|---|---|---|---|---|
| | Max KD % of saline | | EC50 µM | | Max KD % of saline | | EC50 µM | | |
| ID NO | Avg | sd | Avg | sd | Avg | sd | Avg | sd | Compound |
| 17_100 | 1.01 | 2.65 | 1.66 | 0.16 | 3.81 | 3.46 | 1.89 | 0.24 | TCaActttcactTCaGT |
| 17_103 | 0.00 | 2.69 | 1.09 | 0.12 | 0.00 | 3.70 | 1.46 | 0.21 | TcAActttcactTCaGT |
| 17_111 | 3.45 | 3.62 | 1.39 | 0.20 | 2.65 | 5.82 | 2.03 | 0.41 | TCaactttcactTcAGT |
| 17_119 | 0.00 | 6.24 | 1.75 | 0.39 | 0.30 | 3.81 | 1.86 | 0.25 | TCAActttcactTcaGT |
| 17_129 | 0.00 | 2.62 | 1.02 | 0.11 | 2.60 | 2.44 | 1.41 | 0.13 | TCAactttcacttCAGT |
| 17_132 | 1.71 | 2.02 | 1.27 | 0.10 | 0.00 | 4.17 | 1.74 | 0.26 | TCaActttcacttCAGT |
| 17_135 | 0.00 | 3.23 | 1.24 | 0.14 | 8.56 | 4.86 | 2.04 | 0.38 | TCaactttcacttCAGT |
| 17_137 | 0.00 | 2.80 | 1.07 | 0.12 | 1.34 | 3.94 | 1.64 | 0.23 | TcAActttcacttCAGT |
| 17_139 | 0.00 | 3.62 | 1.43 | 0.20 | 2.48 | 5.82 | 1.89 | 0.39 | TcAactttcacttCAGT |
| 17_144 | 0.91 | 2.35 | 1.40 | 0.12 | 1.53 | 1.58 | 1.95 | 0.11 | TCAactttcacttCaGT |
| 17_157 | 2.94 | 2.87 | 1.27 | 0.14 | 2.32 | 3.12 | 1.62 | 0.18 | TCAActttcacttcAGT |
| 18_1 | 2.74 | 1.41 | 1.82 | 0.09 | 5.06 | 2.24 | 2.03 | 0.16 | TCAactttcacttCAG |
| 18_5 | 4.25 | 6.93 | 4.08 | 0.82 | 6.91 | 4.42 | 3.35 | 0.47 | TCAActttcacTtCAG |
| 18_6 | 5.49 | 4.00 | 2.97 | 0.39 | 8.16 | 4.67 | 2.93 | 0.45 | TCaactttcacTtCAG |
| 18_10 | 0.00 | 6.55 | 1.60 | 0.38 | 0.00 | 3.59 | 2.17 | 0.26 | TCAActttcactTCAG |
| 18_12 | 1.34 | 3.34 | 1.69 | 0.20 | 0.84 | 4.01 | 2.37 | 0.32 | TCAactttcactTCAG |
| 18_15 | 5.89 | 2.84 | 2.92 | 0.28 | 6.85 | 3.64 | 3.10 | 0.39 | TCAACtttcactTcAG |
| 18_18 | 4.23 | 4.44 | 2.71 | 0.41 | 2.40 | 10.93 | 2.76 | 0.88 | TCAACtttcacttCAG |
| 18_19 | 2.22 | 3.25 | 2.04 | 0.23 | 1.66 | 5.12 | 2.53 | 0.44 | TCAActttcacttCAG |
| 18_20 | 0.00 | 3.21 | 2.56 | 0.27 | 0.00 | 4.96 | 2.81 | 0.47 | TCAaCtttcacttCAG |
| 18_21 | 2.13 | 3.08 | 2.52 | 0.25 | 5.72 | 2.45 | 2.73 | 0.23 | TCaaCtttcacttCAG |
| 18_23 | 0.49 | 4.56 | 2.65 | 0.39 | 0.53 | 3.28 | 3.02 | 0.31 | TCAACtttcacttcAG |
| 18_24 | 0.29 | 6.14 | 2.82 | 0.54 | 0.00 | 6.27 | 2.95 | 0.61 | TCAActttcacttcAG |
| 18_25 | 2.22 | 5.75 | 2.55 | 0.49 | 0.00 | 3.68 | 3.13 | 0.36 | TCAaCtttcacttcAG |
| 18_27 | 0.00 | 4.13 | 2.30 | 0.30 | 1.21 | 2.04 | 2.87 | 0.19 | TCaACtttcacttcAG |
| 18_28 | 10.11 | 3.82 | 4.52 | 0.56 | 12.26 | 11.67 | 5.13 | 1.78 | TCaaCtttcacttcAG |
| 18_30 | 1.60 | 3.21 | 2.56 | 0.27 | 0.00 | 3.47 | 3.10 | 0.34 | TcAACtttcacttcAG |
| 18_346 | 0.56 | 3.27 | 1.27 | 0.17 | 1.43 | 1.58 | 1.49 | 0.09 | TCaActttcactTCAG |
| 18_347 | 0.16 | 3.81 | 0.87 | 0.14 | 0.00 | 1.55 | 1.17 | 0.07 | TcAActttcactTCAG |
| 18_350 | 0.00 | 3.12 | 1.54 | 0.17 | 1.43 | 1.29 | 2.10 | 0.09 | TCAActttcactTcAG |
| 18_357 | 0.00 | 2.87 | 1.61 | 0.18 | 0.00 | 1.97 | 2.18 | 0.15 | TCaActttcacttCAG |
| 18_358 | 0.00 | 2.30 | 1.54 | 0.13 | 0.15 | 1.91 | 2.31 | 0.14 | TcaACtttcacttCAG |

Example 5: In Vitro Effect on HBV Infected ASGPR-dHepaRG Cells Using Selected Antisense Oligonucleotides Targeting PAPD5 and PAPD7

A selection of the oligonucleotides screened in example 3 was screened in ASGPR-dHepaRG essentially using the assay of example 2 with the following changes. The screening was conducted in HBV infected ASGPR-dHepaRG at the following concentrations 20, 6.67 and 2.22 μM of oligonucleotide and with the comparative molecules in table 17.

For comparative purposes combinations of a single targeting PAPD5 and a single targeting PAPD7 oligonucleotide in table 17 were tested together with the oligonucleotides of the invention.

TABLE 17

Combination of single targeting PAPD5 and PAPD7 oligonucleotide

| Description | Compound | SEQ ID NO | Reference |
|---|---|---|---|
| PAPD5 and PAPD7 single | CAAaggttgttgtacTCT | 31 | PCT/EP2017/064980 |
| targeting combination 1 (combo1) | CAGTtttatgctaatCA | 32 | PCT/EP2017/064980 |
| PAPD5 and PAPD7 single | GTAttcttattcttgCT | 33 | PCT/EP2017/064980 |
| targeting combination 2 (combo2) | CATTgcttttataatccTA | 34 | PCT/EP2017/064980 |

The reduction of HBsAg and HBeAg levels are shown in table 18 and 19, the larger the value the larger the inhibition.

TABLE 18 in vitro efficacy on HBsAg of anti-PAPD5/PAPD7 compounds in three concentrations (average of 3) in HBV infected ASGPR-dHepaRG cells.

| CMP ID | 20 μM | | 6.67 μM | | 2.22 μM | | |
|---|---|---|---|---|---|---|---|
| NO | Avg | sd | Avg | sd | Avg | sd | Compound |
| 17_51 | -9.61 | 19.93 | -30.60 | 9.19 | -33.16 | 6.96 | TCaactttcacTtCAGT |
| 17_57 | 9.44 | 6.27 | -18.18 | 8.10 | -33.24 | 6.19 | TCAactttcacTtCaGT |
| 17_86 | 20.58 | 5.80 | -5.34 | 4.43 | -8.03 | 5.54 | TCaActttcactTCAGT |
| 17_89 | 2.66 | 3.48 | -12.71 | 2.14 | -7.18 | 7.05 | TCaactttcactTCAGT |
| 17_90 | 40.07 | 6.93 | 3.05 | 14.90 | -11.67 | 7.22 | TcAActttcactTCAGT |
| 17_96 | 58.09 | 7.77 | 36.82 | 3.53 | 4.92 | 4.06 | TCAActttcactTCaGT |
| 17_99 | 25 54 | 6.97 | 5.75 | 8.72 | -7.25 | 5.93 | TCAactttcactTCaGT |
| 17_100 | 43.85 | 7.30 | 15.20 | 12.19 | -10.24 | 9.46 | TCaActttcactTCaGT |
| 17_103 | 41.44 | 9.31 | 25.07 | 2.93 | 9.98 | 3.98 | TcAActttcactTCaGT |
| 17_111 | -5.59 | 7.25 | -7.04 | 3.62 | -8.11 | 6.03 | TCaactttcactTcAGT |
| 17_119 | 73.06 | 2.91 | 51 21 | 3.44 | 13.11 | 9.33 | TCAActttcactTcaGT |
| 17_129 | 37.17 | 10.95 | 9.73 | 10.63 | 2.19 | 14.92 | TCAactttcacttCAGT |
| 17_132 | 41.31 | 5.57 | 11.54 | 5.29 | -10.07 | 4.00 | TCaActttcacttCAGT |
| 17_135 | 3.24 | 6.43 | 2.61 | 10.50 | -13.05 | 2.27 | TCaactttcacttCAGT |
| 17_137 | 60.37 | 4.60 | 44.00 | 4.51 | 13.77 | 1.76 | TcAActttcacttCAGT |
| 17_139 | 51.89 | 6.99 | 25.28 | 5.62 | -9.98 | 3.81 | TcAactttcacttCAGT |
| 17_144 | 15.51 | 9.49 | 2.98 | 11.13 | -14.47 | 6.57 | TCAactttcacttCaGT |
| 17__157 | 60.44 | 2.21 | 43.72 | 7.14 | -0.43 | 5.64 | TCAActttcacttcAGT |
| 18_1 | 90.68 | 1.23 | 75.99 | 2.96 | 17.58 | 8.44 | TCAactttcacttCAG |
| 18_346 | 87.27 | 1.42 | 51.65 | 5.99 | -0.36 | 6.52 | TCaActttcactTCAG |
| 18_347 | 88.09 | 2.70 | 66.31 | 4.12 | 1.27 | 11.46 | TcAActttcactTCAG |

TABLE 18-continued in vitro efficacy on HBsAg of anti-PAPD5/PAPD7 compounds in three concentrations (average of 3) in HBV infected ASGPR-dHepaRG cells.

| CMP ID | 20 µM | | 6.67 µM | | 2.22 µM | | |
|---|---|---|---|---|---|---|---|
| NO | Avg | sd | Avg | sd | Avg | sd | Compound |
| 18_350 | 82.82 | 2.94 | 68.17 | 3.68 | 25.39 | 3.40 | TCAActttcactTcAG |
| 18_357 | 91.46 | 1.63 | 77.08 | 2.24 | 35.54 | 3.18 | TCaActttcacttCAG |
| 18_358 | 83.98 | 3.39 | 63.78 | 6.55 | 26.29 | 5.45 | TcaACtttcacttCAG |
| Combo 1 | 72.08 | 0.75 | 58.03 | 2.25 | 21.27 | 8.25 | |
| Cambo2 | 71.77 | 4.54 | 67.54 | 3.72 | 50.53 | 5.82 | |

TABLE 19 in vitro efficacy on HBeAg of anti-PAPD5/PAPD7 compounds in three concentrations (average of 3) in HBV infected ASGPR-dHepaRG cells,

| CMP | 20 µM | | 6.67 µM | | 2.22 µM | | |
|---|---|---|---|---|---|---|---|
| ID NO | Avg | sd | Avg | sd | Avg | sd | Compound |
| 17_51 | -39.37 | 39.73 | -71.52 | 24.98 | -89.89 | 24.95 | TCaactttcacTtCAGT |
| 17_57 | 2.88 | 4.42 | -38.92 | 11.07 | -76.67 | 6.90 | TCAactttcacTtCaGT |
| 17_86 | 22.69 | 5.54 | -20.63 | 5.70 | -42.45 | 4.40 | TCaActttcactTCAGT |
| 17_89 | -11.41 | 3.45 | -36.53 | 9.77 | -34.92 | 9.69 | TCaactttcactTCAGT |
| 17_90 | 50.40 | 8.09 | -4.45 | 25.09 | -36.73 | 16.16 | TcAActttcactTCAGT |
| 17_96 | 68.32 | 9.42 | 47.89 | 5.53 | 2.93 | 16.50 | TCAActttcactTCaGT |
| 17_99 | 34.82 | 8.81 | 15.96 | 21.39 | -13.36 | 13.51 | TCAactttcactTCaGT |
| 17_100 | 55.17 | 5.99 | 20.03 | 20.34 | -25.12 | 18.75 | TCaActttcactTCaGT |
| 17_103 | 48.08 | 14.67 | 28.80 | 9.35 | 7.18 | 12.00 | TcAActttcactTCaGT |
| 17_111 | -5.24 | 15.62 | -10.26 | 3.22 | -18.78 | 9.24 | TCaactttcactTcAGT |
| 17_119 | 83.29 | 3.11 | 69.67 | 1.75 | 24.17 | 9.29 | TCAActttcactTcaGT |
| 17_129 | 47.32 | 8.81 | 19.21 | 17.51 | -6.65 | 24.28 | TCAactttcacttCAGT |
| 17_132 | 59.04 | 4.63 | 21.83 | 1.86 | -14.91 | 0.44 | TCaActttcacttCAGT |
| 17_135 | 8.35 | 11.28 | 2.09 | 13.51 | -25.60 | 9.12 | TCaactttcacttCAGT |
| 17_137 | 73.77 | 2.83 | 58.40 | 3.45 | 18.22 | 1.27 | TcAActttcacttCAGT |
| 17_139 | 64.19 | 7.67 | 39.45 | 5.57 | -17.73 | 3.08 | TcAactttcacttCAGT |
| 17_144 | 24.74 | 7.77 | 12.21 | 16.40 | -31.19 | 11.36 | TCAactttcacttCaGT |
| 17_157 | 75.79 | 1.10 | 61.26 | 4.35 | 9.64 | 7.17 | TCAActttcacttcAGT |
| 18_1 | 97.88 | 1.00 | 89.38 | 2.73 | 39.44 | 12.14 | TCAactttcacttCAG |
| 18_346 | 90.95 | 3.99 | 61.25 | 4.11 | -4.13 | 6.95 | TCaActttcactTCAG |
| 18_347 | 91.45 | 3.48 | 78.72 | 2.03 | 9.18 | 8.96 | TcAActttcactTCAG |
| 18_350 | 92.56 | 3.36 | 80.54 | 6.12 | 41.46 | 7.29 | TCAActttcactTcAG |
| 18_357 | 96.37 | 1.27 | 87.86 | 2.94 | 51.94 | 2.98 | TCaActttcacttCAG |
| 18_358 | 89.92 | 0.54 | 76.73 | 7.28 | 37.70 | 9.45 | TcaACtttcacttCAG |

TABLE 19-continued in vitro efficacy on HBeAg of anti-PAPD5/PAPD7 compounds in three concentrations (average of 3) in HBV infected ASGPR-dHepaRG cells,

| CMP | 20 μM | | 6.67 μM | | 2.22 μM | | |
|---|---|---|---|---|---|---|---|
| ID NO | Avg | sd | Avg | sd | Avg | sd | Compound |
| Combo 1 | 79.37 | 2.03 | 68.47 | 2.04 | 25.24 | 12.68 | |
| Combo 2 | 75.26 | 2.05 | 72.07 | 3.78 | 59.69 | 2.36 | |

From these data it Can be seen that the best performing bispecific PAPD5/PAPD7 oligonucleotides have better effect in terms of HBsAg and HBeAg reduction with half the oligonucleotide concentration (20 μM) when compared to the combination treatments (2×20 μM).

Example 6 Screening for In Vitro Efficacy of Stereodefined Antisense Oligonucleotides Targeting PAPD5 and PAPD7 in HeLa Cells To expand the diversity around the motif sequences of SEQ ID NO: 18 even further, a library of stereodefined oligonucleotides was made based on the stereorandom parent compound with CMP ID NO 18_1.

Efficacy testing was performed in an in vitro experiment as described in Example 1, with the exception that the screening was conducted with 1 μM and some with 5 μM.

The relative PAPD5 mRNA and PAPD7 mRNA expression levels are shown in table 20 as % of the parent oligonucleotide i.e. the larger the value the better the Inhibition.

TABLE 20 in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| | % PAPD5 mRNA of control | | | | % PAPD7 mRNA of control | | | | |
|---|---|---|---|---|---|---|---|---|---|
| CMP ID | 1 μM | | 5 μM | | 1 μM | | 5 μM | | |
| NO | Avg | sd | Avg | sd | Avg | sd | Avg | sd | Stereodefinition |
| 18_1 | 100.0 | 6.3 | | | 100.0 | 3.4 | | | TCAactttcacttCAG XXXXXXXXXXXXXXXH |
| 18_32 | 87.0 | 5.1 | | | 94.7 | 0.9 | | | RSSRXXRRRRXXXXXH |
| 18_33 | 76.4 | NA | | | 89.7 | 1.7 | | | XRSSRXXXXXXXXXXH |
| 18_34 | 79.8 | 6.7 | | | 91.5 | 2.3 | | | XXRSSRXSSSSXXXXH |
| 18_35 | 70.0 | 10.8 | | | 86.7 | 3.8 | | | XXXRSSRXXXXXXXXH |
| 18_36 | 102.5 | 7.8 | | | 107.4 | 3.1 | | | XXXXRSSRXXXXXXXH |
| 18_37 | 88.8 | 7.6 | | | 95.1 | 4.5 | | | XXXXXRSSRXXXXXXH |
| 18_38 | 68.3 | 6.5 | | | 82.0 | 3.6 | | | XXXXXXRSSRXXXXXH |
| 18_39 | 87.2 | 5.7 | | | 93.8 | 5.0 | | | XXXXXXXRSSRXXXXH |
| 18_40 | 92.2 | 3.5 | | | 96.3 | 5.5 | | | XXXXXXXSRSSRXXXH |
| 18_41 | 81.1 | 1.3 | | | 95.2 | 7.6 | | | XXXXXXXXXRSSRXXH |
| 18_42 | 78 0 | 3.8 | | | 92.0 | 9.4 | | | XXXXXXXXXXRSSRXH |
| 18_43 | 80.4 | 3.4 | | | 92.7 | 3.6 | | | XXXXXXXXXXXRSSRH |
| 18_44 | 79.4 | 3.5 | | | 89.7 | 3.4 | | | XXXXXXXXXSSSSSRH |
| 18_45 | 75.2 | 8.2 | | | 88.7 | 2.4 | | | XXXXXXXXXRRRRRRH |
| 18_46 | 86.2 | 6.5 | | | 9 0 | 6.7 | | | XXXXXXXXXSSRRSRH |
| 18_47 | 79.7 | 8.2 | | | 85.7 | 1.5 | | | XXXXXXXXXSSSRSRH |
| 18_48 | 80.6 | 1.6 | | | 87.5 | 1.5 | | | XXXXXXXXXSSSRRSH |
| 18_49 | 79.9 | 3.2 | | | 101.8 | 6.5 | | | XXXXXXXXXSRSSSSH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control | | | | % PAPD7 mRNA of control | | | | |
|---|---|---|---|---|---|---|---|---|---|
| | 1 µM | | 5 µM | | 1 µM | | 5 µM | | |
| NO | Avg | sd | Avg | sd | Avg | sd | Avg | sd | Stereodefinition |
| 18_50 | 82.7 | 3.1 | | | 88.9 | 2.2 | | | XXXXXXXXXRSRSRSH |
| 18_51 | 78.0 | 5.7 | | | 90.2 | 2.9 | | | XXXXXXXXXSSSSRSH |
| 18_52 | 90.1 | 6.0 | | | 93.7 | 1.1 | | | XXXXXXXXXSSRRSSH |
| 18_53 | 82.7 | 8.7 | | | 90.7 | 3.2 | | | XXXXXXXXXRRSSSSH |
| 18_54 | 63.3 | 13.2 | | | 77 8 | 6.4 | | | XXXXXXXXXRSSRRRH |
| 18_55 | 73.9 | 6.2 | | | 90.9 | 1.6 | | | XXXXXXXXXSRRRRSH |
| 18_56 | 83.1 | 5.6 | | | 98.5 | 6.4 | | | XXXXXXXXXSSRSRRH |
| 18_57 | 73.4 | 6.8 | | | 89.6 | 8.2 | | | XXXXXXXXXRRRSRRH |
| 18_58 | 89.1 | 2.2 | | | 98.7 | 2.8 | | | XXXXXXXXXRRSRSRH |
| 18_59 | 73.2 | 8.5 | | | 91.7 | 2.5 | | | XXXXXXXXXSSRRRSH |
| 18_60 | 88.8 | 4.2 | | | 93.3 | 3.4 | | | XXXXXXXXXSRRSSSH |
| 18_61 | 77.0 | 13.6 | | | 81.6 | 13.7 | | | XXXXXXXXXRRRRRSH |
| 18_62 | 75 6 | 8.7 | | | 87.8 | 8.5 | | | XXXXXXXXXRRSSRRH |
| 18_63 | 74.8 | 5.0 | | | 85.5 | 1.4 | | | XXXXXXXXXRSRRRRH |
| 18_64 | 86 9 | 7.3 | | | 92.2 | 2.5 | | | XXXXXXXXXSRRRSSH |
| 18_65 | 77.8 | 10.3 | | | 89.0 | 7.4 | | | XXXXXXXXXSRSRSRH |
| 18_66 | 81 7 | 10.2 | | | 88.9 | 6.1 | | | XXXXXXXXXRSSSSRH |
| 18_67 | 77.6 | 7.4 | | | 81.1 | 4.7 | | | XXXXXXXXXSSSSRRH |
| 18_68 | 88.9 | 9.2 | | | 91.3 | 2.7 | | | XXXXXXXXXRRSSSRH |
| 18_69 | 77.8 | 3.8 | | | 89.9 | 4.0 | | | XXXXXXXXXRSSRRSH |
| 18_70 | 75.9 | 11.7 | | | 83.9 | 7.8 | | | XXXXXXXXXRSSSRRH |
| 18_71 | 84.2 | 6.7 | | | 86.7 | 1.4 | | | XXXXXXXXXSRRRRRH |
| 18_72 | 93.6 | 2.3 | | | 95.0 | 1.7 | | | XXXXXXXXXRRSRSSH |
| 18_73 | 90.5 | 4.3 | | | 92.4 | 2.9 | | | XXXXXXXXXRSRSSRH |
| 18_74 | 88.3 | 10.5 | | | 88.2 | 3.0 | | | XXXXXXXXXRSRSRRH |
| 18_75 | 85.2 | 7.1 | | | 89.0 | 3.1 | | | XXXXXXXXXSRRRSRH |
| 18_76 | 99.6 | 2.7 | | | 99.5 | 2.2 | | | XXXXXXXXXRRSRRSH |
| 18_77 | 87.4 | 1.5 | | | 87.2 | 1.8 | | | XXXXXXXXXSSSRRRH |
| 18_78 | 80.6 | 10.4 | | | 83.5 | 5.2 | | | XXXXXXXXXRSRRSRH |
| 18_79 | 89.3 | 6.8 | | | 98.7 | 3.4 | | | XXXXXXXXXSRRSRSH |
| 18_80 | 85.9 | 2.0 | | | 83.2 | 2.8 | | | XXXXXXXXXRRSRRRH |
| 18_81 | 92.4 | 5.0 | | | 84.1 | NA | | | XXXXXXXXXSRRSSRH |
| 18_82 | 86.8 | 3.4 | | | 39.8 | 3.0 | | | XXXXXXXXXSRSSSRH |
| 18_83 | 93.1 | 4.7 | | | 92.4 | 3.3 | | | XXXXXXXXXRSRRRSH |
| 18_84 | 91.1 | 4.9 | | | 93.4 | 5.2 | | | XXXXXXXXXSSSRSSH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| | % PAPD5 mRNA of control | | | | % PAPD7 mRNA of control | | | | |
|---|---|---|---|---|---|---|---|---|---|
| CMP ID | 1 µM | | 5 µM | | 1 µM | | 5 µM | | |
| NO | Avg | sd | Avg | sd | Avg | sd | Avg | sd | Stereodefinition |
| 18_85 | 84.3 | 3.9 | | | 87.9 | 1.6 | | | XXXXXXXXXSSRSSRH |
| 18_86 | 86.2 | 8.1 | | | 84.6 | 2.2 | | | XXXXXXXXXRSSRSSH |
| 18_87 | 77.3 | 9.7 | | | 90.5 | 0.9 | | | XXXXXXXXXSRSSRSH |
| 18_88 | 85.8 | 5.4 | | | 92.4 | 3.0 | | | XXXXXXXXXSSSSSSH |
| 18_89 | 94.9 | 5.7 | | | 95.8 | 7.3 | | | XXXXXXXXXRSRRSSH |
| 18_90 | 91.2 | 6.3 | | | 92.9 | 2.3 | | | XXXXXXXXXRRRRSRH |
| 18_91 | 85.9 | 4.1 | | | 90.4 | 5.0 | | | XXXXXXXXXSSRSRSH |
| 18_92 | 84.7 | 6.5 | | | 90.1 | 9.3 | | | XXXXXXXXXRRRRSSH |
| 18_93 | 81.7 | 6.5 | | | 90.6 | 4.0 | | | XXXXXXXXXRSRSSSH |
| 18_94 | 82.2 | 7.7 | | | 82.9 | 8.0 | | | XXXXXXXXXRSSRSRH |
| 18_95 | 89.4 | 1.9 | | | 84.9 | 7.5 | | | XXXXXXXXXRRRSRSH |
| 18_96 | 80.1 | 3.7 | | | 85.0 | 5.9 | | | XXXXXXXXXRRSSRSH |
| 18_97 | 68.9 | 7.5 | | | 82.3 | 4.8 | | | XXXXXXXXXSRSSRRH |
| 18_98 | 81.7 | 4.1 | | | 93.9 | 6.9 | | | XXXXXXXXXSRRSRRH |
| 18_99 | 97.7 | 5.4 | | | 97.7 | 8.7 | | | XXXXXXXXXSRSRSSH |
| 18_100 | 77.5 | 3.7 | | | 85.4 | 4.1 | | | XXXXXXXXXSRSRRRH |
| 18_101 | 77.9 | 7.1 | | | 88.3 | 4.3 | | | XXXXXXXXXSSRSSSH |
| 18_102 | 77.3 | 6.3 | | | 93.0 | 2.8 | | | XXXXXXXXXRSSSSSH |
| 18_103 | 74.8 | 3.7 | | | 86.4 | 1.2 | | | XXXXXXXXXRSSSRSH |
| 18_104 | 90.3 | 6.1 | | | 91.5 | 2.3 | | | XXXXXXXXXRRRSSRH |
| 18_105 | 95.7 | 7.2 | | | 102.9 | 1.7 | | | XXXXXXXXXRRRSSSH |
| 18_106 | 79.7 | 5.4 | | | 85.7 | 1.2 | | | XXXXXXXXXSRSRRSH |
| 18_107 | 87.6 | 4.4 | | | 89.0 | 2 2 | | | XXXXXXXXXSSRRRRH |
| 18_108 | 86.4 | 10.6 | | | 95.3 | 4.0 | | | XXXXXXXXXXSSRSSH |
| 18_109 | 99.1 | 2.5 | | | 99.0 | 6.6 | | | XXXXXXXXXXRRRSSH |
| 18_110 | 91.1 | 5.4 | | | 93.1 | 3.5 | | | XXXXXXXXXXRRSSRH |
| 18_111 | 103.1 | 2.9 | | | 99.1 | 6.2 | | | XXXXXXXXXXRSSSRH |
| 18_112 | 96.5 | 2.7 | | | 90.7 | 2.5 | | | XXXXXXXXXXRRSRRH |
| 18_113 | 78.0 | 17.5 | | | 90.4 | 3.7 | | | XXXXXXXXXXSSSSRH |
| 18_114 | 86 9 | 3.4 | | | 88.8 | 4 5 | | | XXXXXXXXXXRRRRRH |
| 18_115 | 94.7 | 8.1 | | | 94.1 | 3.8 | | | XXXXXXXXXXSRSSSH |
| 18_116 | 79.8 | 4.1 | | | 83 7 | 2.6 | | | XXXXXXXXXXSSRSRH |
| 18_117 | 88.3 | 8.6 | | | 95.6 | 4.1 | | | XXXXXXXXXXRSSRSH |
| 18_118 | 83 6 | 7.9 | | | 88 8 | 2.1 | | | XXXXXXXXXXRSRRRH |
| 18_119 | 85.2 | 2.3 | | | 88.7 | 2.5 | | | XXXXXXXXXXSRRRRH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control | | | | % PAPD7 mRNA of control | | | | |
|---|---|---|---|---|---|---|---|---|---|
| | 1 µM | | 5 µM | | 1 µM | | 5 µM | | |
| NO | Avg | sd | Avg | sd | Avg | sd | Avg | sd | Stereodefinition |
| 18_120 | 86.2 | 6.8 | | | 91.9 | 0.7 | | | XXXXXXXXXXSRRRSH |
| 18_121 | 90.4 | 5.9 | | | 86.9 | 0.7 | | | XXXXXXXXXXSSSRSH |
| 18_122 | 74.2 | 8.8 | | | 79.5 | 7.8 | | | XXXXXXXXXXRSRSSH |
| 18_123 | 82.2 | 1.0 | | | 87.6 | 1.5 | | | XXXXXXXXXXSSSSSH |
| 18_124 | 91.0 | 12.7 | | | 111.4 | 11.9 | | | XXXXXXXXXXSRRSSH |
| 18_125 | 87.8 | 6.7 | | | 85.7 | 4.4 | | | XXXXXXXXXXRSRRSH |
| 18_126 | 81.5 | 7.1 | | | 85.5 | 1.9 | | | XXXXXXXXXXSSRRSH |
| 18_127 | 82.9 | 3.7 | | | 96.0 | 2.3 | | | XXXXXXXXXXRRRSRH |
| 18_128 | 79.0 | 3.7 | | | 83.5 | 4.3 | | | XXXXXXXXXXSRSRRH |
| 18_129 | 98.4 | NA | | | 91.7 | 6.2 | | | XXXXXXXXXXRRSRSH |
| 18_130 | 90.7 | 5.4 | | | 89.8 | 2.3 | | | XXXXXXXXXXRRSSSH |
| 18_131 | 82.2 | 6.1 | | | 89.6 | 1.0 | | | XXXXXXXXXXRSSSSH |
| 18_132 | 81.6 | 6.9 | | | 84.2 | 2.3 | | | XXXXXXXXXXRSSRRH |
| 18_133 | 88.9 | 4.1 | | | 94.5 | 4.0 | | | XXXXXXXXXXSRRSRH |
| 18_134 | 73.6 | 7.5 | | | 83.3 | 4.3 | | | XXXXXXXXXXSSRRRH |
| 18_135 | 86.6 | 10.3 | | | 91.0 | 7.1 | | | XXXXXXXXXXSRSSRH |
| 18_136 | 93.8 | 4.5 | | | 85.0 | 8.1 | | | XXXXXXXXXXRRRRSH |
| 18_137 | 100.6 | 8.4 | | | 83.2 | 7.2 | | | XXXXXXXXXXRSRSRH |
| 18_138 | 83.1 | 9.5 | | | 86.5 | 4.0 | | | XXXXXXXXXXSSSRRH |
| 18_139 | 82.4 | 10.8 | | | 87.3 | 2.9 | | | XXXXXXXXXXSRSRSH |
| 18_140 | 83.9 | 5.6 | | | 78.9 | 5.1 | | | SSRRRRSSSSSRSSRH |
| 18_141 | 96.7 | 9.9 | | | 83.2 | 13.8 | | | SSSSSRRRRRRSRRSH |
| 18_142 | 81.7 | 13.0 | | | 83.7 | 7.7 | | | SRSSRSSSRRRSRSRH |
| 18_143 | 86.4 | 11.5 | | | 80.3 | 11.7 | | | SRRSSSSRRSRRRRRH |
| 18_144 | 88.5 | 7.1 | | | 78 5 | 8.5 | | | SSRRSRSRSSSRSRRH |
| 18_145 | 75.2 | 12.2 | | | 78.4 | 3.9 | | | SSSRRRRSRRRSSRRH |
| 18_146 | 109.4 | 6.8 | | | 105.6 | 8.1 | | | RRSRSSRRSSSRRSSH |
| 18_147 | 82.8 | 7.1 | | | 80.3 | 2.9 | | | RSSRRRSSSRSSSRSH |
| 18_148 | 78.2 | 7.1 | | | 73.3 | 9.6 | | | SSSSRRRSRSSSRRSH |
| 18_149 | 78.5 | 3.9 | | | 77.1 | 14.5 | | | SSSSRSSSSSSRRRRH |
| 18_150 | 80.2 | 5.3 | | | 75.0 | 8.5 | | | SSSSRSSSSSSSSSSH |
| 18_151 | 65.6 | 21.5 | | | 73.0 | 9.1 | | | RRSPRRRRSSSSSSSR |
| 18_152 | 98.9 | 5.4 | | | 92.9 | 3.3 | | | RRRRSASSRRRRSSSH |
| 18_153 | 92.1 | 9.5 | | | 93.2 | 3.1 | | | RRRRRSSRRRSRSSRH |
| 18_154 | 98.3 | 4.0 | | | 92.3 | 2.7 | | | SSRRRRSRSRSSRRSH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control | | | | % PAPD7 mRNA of control | | | | |
|---|---|---|---|---|---|---|---|---|---|
| | 1 µM | | 5 µM | | 1 µM | | 5 µM | | |
| NO | Avg | sd | Avg | sd | Avg | sd | Avg | sd | Stereodefinition |
| 18_155 | 77.4 | 8.1 | | | 82.0 | 3.8 | | | RSSSSSRSSRRSSSSH |
| 18_156 | 79.9 | 7.8 | | | 81.8 | 5.9 | | | RRRSSSSSRSRSRRSH |
| 18_157 | 76.8 | 4.3 | | | 82.6 | 3.5 | | | RSSSRSRSRRRSRRRH |
| 18_158 | 81.8 | 12.8 | | | 86.8 | 4.1 | | | RRSRRSSSSRRRRRRSS |
| 18_159 | 76.4 | 12.4 | | | 77.9 | 2.8 | | | RRSSSSRSRSSSRSRH |
| 18_160 | 82.2 | 16.3 | | | 88.8 | 4.2 | | | RSSRSRSRSRSRSRRH |
| 18_16 | 76.4 | 14.9 | | | 77.9 | 4.9 | | | SRRRSSSSRSRSRSRH |
| 18_162 | 66.6 | 15.9 | | | 80.4 | 4.1 | | | SRSSSRRSRRRRSSRH |
| 18_163 | 76.8 | 14.0 | | | 85.3 | 2.9 | | | RSSRRRSRRSRSSRRH |
| 18_164 | 88.4 | 9.4 | | | 97.5 | 5.2 | | | SSRRRSSRSSRRRPSH |
| 18_165 | 75.1 | 14.9 | | | 85.2 | 3.0 | | | RSRSSRRSRRRSSSRH |
| 18_166 | 81.6 | 6.7 | | | 83.9 | 5.8 | | | RRRRSRRRSSPSPRSH |
| 18_167 | 74.4 | 11.7 | | | 77.5 | 4.5 | | | SRRRSSSRSRSSRRRH |
| 18_168 | 73 9 | 9.7 | | | 77.3 | 1.9 | | | SRSSRSSSSSRSRSSH |
| 18_169 | 73.7 | 15.1 | | | 86.2 | 1.1 | | | SSRRSRSSSSSRSSSH |
| 18_170 | 75 8 | 7.0 | | | 82 4 | 2.0 | | | SSRRRRRSRSRRSSSH |
| 18_171 | 97.4 | 2.3 | | | 98.5 | 3.3 | | | SSSRRSSRSRRRRRSH |
| 18_172 | 85.3 | 10.9 | | | 81.0 | 2.0 | | | RSSSSSSSRSRRRRRH |
| 18_173 | 88.5 | 10.9 | | | 92.5 | 1.4 | | | SSRSRSSRSSRRSRRH |
| 18_174 | 84.1 | 11.1 | | | 81.5 | 17.2 | | | SRSRSSSSRRRSRRRSH |
| 18_175 | 72.7 | 6.6 | | | 79.1 | 1.1 | | | RRRRRRRSSRRSSSRH |
| 18_176 | 77.0 | 14.4 | | | 81.9 | 4.8 | | | SSRSRRRRRSRRSRSH |
| 18_177 | 81.9 | 5.6 | | | 79.9 | 10 1 | | | RRSRRRRRRSSRRRSH |
| 18_178 | 88.9 | 3.9 | | | 94.4 | 3.1 | | | SSSSRRRRRRRRRSRR |
| 18_179 | 87.8 | 11.8 | | | 81.5 | 8.6 | | | SRRRSSRRRSSRRRSN |
| 18_180 | 75.9 | 2.9 | | | 72.9 | 11.0 | | | SSSRRRRRSRRSSRRH |
| 18_181 | 85.3 | 11.1 | | | 86.7 | 1.9 | | | RRSRRSSSSRRRSSRH |
| 18_182 | 93.0 | 9.2 | | | 95.4 | 7.3 | | | SSRRSRSSRRRSSSSH |
| 18_183 | 83.8 | 12.3 | | | 80.5 | 5.2 | | | SSRSRRRRSSRSSSRH |
| 18_184 | 87.0 | 15.0 | | | 79.3 | 4.5 | | | RRRSRRSRSSRRRRSH |
| 18_185 | 98.7 | 4.6 | | | 96.8 | 1.7 | | | RSRSSRSRSRRSRSRH |
| 18_186 | 87.9 | 3.7 | | | 87.7 | 5.2 | | | SSRSRRRRSSRSSSRH |
| 18_187 | 99.1 | 3.5 | | | 99.8 | 2.3 | | | RSSRRSRRRRSRRRSH |
| 18_188 | 101.1 | 5.9 | | | 92.8 | 6.6 | | | SSSRRSSRSRSRSSSH |
| 18_189 | 106.9 | 4.2 | | | 105.0 | 3.1 | | | RSRSSSSRSSRRRSSH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control | | | | % PAPD7 mRNA of control | | | | |
|---|---|---|---|---|---|---|---|---|---|
| | 1 µM | | 5 µM | | 1 µM | | 5 µM | | |
| NO | Avg | sd | Avg | sd | Avg | sd | Avg | sd | Stereodefinition |
| 18_190 | 104.0 | 3.5 | | | 96.7 | 2.2 | | | SSSRSSSRSRRSRSSH |
| 18_191 | 87.7 | 10.4 | | | 84.9 | 7.8 | | | RSSRSSSSRSSSSSRH |
| 18_192 | 86.5 | 7.9 | | | 96.1 | 1.6 | | | RSSRRSSRSSSRRSRH |
| 18_193 | 76.5 | 8.0 | | | 80.4 | 3.2 | | | RSSRRSRSRRSSSSRH |
| 18_194 | 80.0 | 4.8 | | | 86.4 | 3.3 | | | RRSSSRRSRSRRRRSSSH |
| 18_195 | 100.4 | 8.3 | | | 99.3 | 1.6 | | | RRRRRSSRSRRSSSRH |
| 18_196 | 109.5 | 2.6 | | | 113.5 | 4.2 | | | SSSSRSRRRSSRRRSH |
| 18_197 | 82.6 | 1.9 | | | 81.0 | 4.8 | | | RSRRRRRRRRSSRSRH |
| 18_198 | 87.2 | 4.6 | | | 87.4 | 6.4 | | | RSRRSSSSRSSRSSRH |
| 18_199 | 80.9 | 2.8 | | | 91.5 | 1.0 | | | SSRRSRSSRRRSSSRH |
| 18_200 | 74.7 | 11.4 | | | 84.8 | 2.1 | | | RRRRSSSRRSRSRSSH |
| 18_201 | 73.5 | 13.7 | | | 82.0 | 1.3 | | | RSRRRRRRSRRSSRSH |
| 18_202 | 70.6 | 8.6 | | | 81.4 | 1.4 | | | SRRSRRRRRSRSSSSH |
| 18_203 | 69.8 | 9.5 | | | 73.8 | 1.4 | | | SRRSRRSSSRSSSSSH |
| 18_204 | 77.8 | 6.8 | | | 86.3 | 2.7 | | | SSSRRRRSRSRRRSSH |
| 18_205 | 73.4 | 4.2 | | | 77.8 | 2.6 | | | SSRSRSRSSSRSRSRH |
| 18_206 | 80.6 | 12.7 | | | 90.4 | 3.6 | | | SSSRRSRRSRRRSRSH |
| 18_207 | 67.8 | 7.5 | | | 74.3 | 2.6 | | | SRSSRRRSSSSSRRRH |
| 18_208 | 71.9 | 12.0 | | | 83.0 | 4.9 | | | RRSSRSSSSSSRSSRH |
| 18_209 | 74.0 | 5.5 | | | 83.7 | 3.4 | | | SRSSRRSSRSRRSRRH |
| 18_210 | 55.6 | 14.6 | 48.5 | 5.4 | 84.2 | 7.2 | 66.2 | 4.5 | RSRRSSRSRSSRRSSH |
| 18_211 | 60.5 | 11.1 | 52.4 | 6.7 | 84.4 | 6.7 | 76.4 | 6.8 | RSSSRRSRSSSRSSSH |
| 18_212 | 53.3 | 3.3 | 47.3 | 3.5 | 93.4 | 8.0 | 60.5 | 5.6 | SSSSSSSSRSRRRSSH |
| 18_213 | 43.0 | 8.3 | 26.1 | 6.0 | 72.4 | 10.7 | 38.3 | 8.4 | RRSSSSSSSRSSSRRH |
| 18_214 | 66.6 | 8.9 | 97.1 | 4.2 | 108.3 | 7.0 | 106.6 | 7.8 | SSSRRSSSSRRRRSSH |
| 18_215 | 61.0 | 11.2 | 59.9 | 8.2 | 98.3 | 10.7 | 76.0 | 11.9 | SSSRRRRRRSSSSRRH |
| 18_216 | 35.6 | 9.3 | 42.2 | 5.4 | 56.2 | 6.8 | 53.1 | 12.8 | RSRSRRRSSSRRRSRH |
| 18_217 | 37.6 | 8.9 | 73.8 | 8.8 | 65.0 | 6.4 | 79.6 | 8.0 | SSSSRRSRRRSSRRRH |
| 18_218 | 101.7 | 11.6 | 90.1 | 1.6 | 162.0 | 9.8 | 100.5 | 2.4 | RSSRRSSRSRRRSSSH |
| 18_219 | 70.9 | 10.8 | 75.5 | 3.7 | 97.0 | 9.1 | 93.3 | 4.9 | RRSSSSSRRRRSRRSH |
| 18_220 | 58.0 | 11.3 | 62.5 | 4.0 | 92.0 | 8.6 | 79.5 | 6.3 | RXXXXXXXXXXXXXXH |
| 18_221 | 66.8 | 8.8 | 89.8 | 4.1 | 101.2 | 11.1 | 109.1 | 6.9 | SXXXXXXXXXXXXXXH |
| 18_222 | 73.2 | 6.2 | 79.4 | 3.4 | 106.4 | 8.8 | 95.1 | 4.2 | XRXXXXXXXXXXXXXH |
| 18_223 | 84.1 | 9.0 | 98.4 | 4.9 | 134.3 | 6.6 | 134.7 | 5.5 | XSXXXXXXXXXXXXXH |
| 18_224 | 73.3 | 7.0 | 91.9 | 4.7 | 117.0 | 6.4 | 131.4 | 5.2 | XXRXXXXXXXXXXXXH |

TABLE 20-continued in vitro efficacy of stereodefined anti-PAPD5/PAPD7 compounds (single experiment with duplex QPCR). PAPD5 and PAPD7 mRNA levels are normalized to GUSB in HeLa cells and shown as % of control (PBS treated cells).

| CMP ID | % PAPD5 mRNA of control | | | | % PAPD7 mRNA of control | | | | |
|---|---|---|---|---|---|---|---|---|---|
| | 1 µM | | 5 µM | | 1 µM | | 5 µM | | |
| NO | Avg | sd | Avg | sd | Avg | sd | Avg | sd | Stereodefinition |
| 18_225 | 76.5 | 9.3 | 94.3 | 7.7 | 110.1 | 6.0 | 108.4 | 7.6 | XXSXXXXXXXXXXXXH |
| 18_226 | 74.4 | 11.6 | 92.4 | 6.7 | 102.3 | 7.6 | 108.8 | 6.3 | XXXRXXXXXXXXXXXH |
| 18_227 | 83.1 | 11.6 | 109.9 | 8.4 | 99.1 | 14.1 | 111.2 | 6.9 | XXXSXXXXXXXXXXXH |
| 18_228 | 56.4 | 7.2 | 55.0 | 5.5 | 87.4 | 3.7 | 74.5 | 7.5 | XXXXRXXXXXXXXXXH |
| 18_229 | 69.4 | 6.2 | 81.4 | 4.4 | 113.1 | 4.6 | 104.9 | 7.4 | XXXXSXXXXXXXXXXH |
| 18_230 | 66.6 | 5.8 | 84.6 | 3.3 | 109.3 | 6.6 | 106.4 | 6.7 | XXXXXRXXXXXXXXXH |
| 18_231 | 80.7 | 2.7 | 109.0 | 1.1 | 114.1 | 5.6 | 120.8 | 4.9 | XXXXXSXXXXXXXXXH |
| 18_232 | 63.74 | 4.4 | 66.6 | 6.3 | 101.7 | 5.2 | 88.0 | 8.2 | XXXXXXRXXXXXXXXH |
| 18_233 | 68.3 | 3.1 | 96.4 | 8.0 | 102.4 | 6.5 | 120.3 | 6.6 | XXXXXXSXXXXXXXXH |
| 18_234 | 69.9 | 10.7 | 98.7 | 8.9 | 113.0 | 5.2 | 124.2 | 7.1 | XXXXXXXRXXXXXXXH |
| 18_235 | 68.6 | 16.7 | 82.3 | 7.5 | 91.1 | 12.4 | 90.3 | 9.2 | XXXXXXXSXXXXXXXH |
| 18_236 | 114.6 | 7.6 | 90.5 | 2.8 | 187.8 | 9.9 | 113.0 | 4.6 | XXXXXXXXRXXXXXXH |
| 18_237 | 66.4 | 13.5 | 66.6 | 7.3 | 117.3 | 12.3 | 93.2 | 7.3 | XXXXXXXXSXXXXXXH |
| 18_238 | 72.5 | 5.3 | 90.1 | 3.9 | 122.5 | 6.6 | 126.8 | 4.3 | XXXXXXXXXRXXXXXH |
| 18_239 | 39.8 | 3.0 | 20.9 | 5.7 | 67.2 | 6.4 | 29.2 | 2.1 | XXXXXXXXXSXXXXXH |
| 18_240 | 63.0 | 12.0 | 92.7 | 2.0 | 116.2 | 7.9 | 117.7 | 1.6 | XXXXXXXXXXRXXXXH |
| 18_241 | 65.1 | 15.1 | 75.4 | 4.4 | 105.9 | 19.9 | 104.8 | 5.0 | XXXXXXXXXXXSXXXH |
| 18_242 | 65.0 | 12.7 | 85.0 | 3.2 | 106.0 | 12.5 | 114.3 | 2.4 | XXXXXXXXXXXRXXXH |
| 18_243 | 145.2 | 7.8 | 112.0 | 6.0 | 180.8 | 6.0 | 118.8 | 6.5 | XXXXXXXXXXXSXXXH |
| 18_244 | 75.3 | 9.9 | 87.8 | 2.8 | 110.4 | 8.1 | 91.2 | 4.8 | XXXXXXXXXXXXRXXH |
| 18_245 | 81.7 | 8.6 | 63.6 | 5.6 | 100.3 | 5.9 | 79.2 | 1.9 | XXXXXXXXXXXXSXXH |
| 18_246 | 60.3 | 7.4 | 71.7 | 6.2 | 90.4 | 8.0 | 80.8 | 8.1 | XXXXXXXXXXXXXRXH |
| 18_247 | 70.3 | 8.0 | 90.4 | 6.4 | 108.4 | 7.5 | 94.4 | 8.1 | XXXXXXXXXXXXXSXH |
| 18_248 | 74.0 | 7.7 | 77.4 | 5.1 | 87.4 | 19.5 | 86.7 | 7.3 | XXXXXXXXXXXXXXRH |
| 18_249 | 74.8 | 4.9 | 88.2 | 5.4 | 114.8 | 5.6 | 109.7 | 6.4 | XXXXXXXXXXXXXXSH |

Example 7: In Vitro EC50 and Efficacy of Selected Stereodefined Antisense Oligonucleotides in HeLa Cells The EC50 and efficacy (KD) of the best performing oligonucleotides from Example 6 was determined using the same assay with the following oligonucleotide concentrations 33, 10.44, 3.33, 1.044, 0.33, 0.104, 0.033 and 0.01 µM.

EC 50, max KD (efficacy) of the PAPD5 and PAPD7 mRNA expression was calculated using R-function drm( ) from the drc package (03.0-1) a four-parameter log-logistic function is fitted to the expression or the gene of interest as a function of oligonucleotide concentration to obtain a value for EC50 and maximum knock-down. The results are shown in Table 21.

TABLE 21

EC50 and Max KD of anti-PAPD5/PAPD7 compounds on PAPD5 and PAPD7 mRNA expression in HeLa cells. CMP ID NO 18_1 is the stereorandom parent compound.

| CMP | PAPD5 Max KD % of saline | | PAPD5 EC50 µM | | PAPD7 Max KD % of saline | | PAPD7 EC50 µM | | |
|---|---|---|---|---|---|---|---|---|---|
| ID NO | Avg | sd | Avg | sd | Avg | sd | Avg | sd | Stereodefined motif |
| 18_1 | 2.74 | 1.41 | 1.82 | 0.09 | 5.06 | 2.24 | 2.03 | 0.16 | TCAactttcacttCAG XXXXXXXXAXXXXXXH |
| 18_36 | 0.49 | 2.00 | 1.19 | 0.08 | 0.00 | 2.77 | 1.57 | 0.14 | XXXXRSSRXXXXXXXH |
| 18_76 | 1.83 | 5.88 | 3.18 | 0.54 | 1.12 | 7.32 | 3.38 | 0.69 | XXXXXXXXXRRSRRSH |
| 18_99 | 0.12 | 7.43 | 2.87 | 0.63 | 4.53 | 13.63 | 3.39 | 1.30 | XXXXXXXXXSRSRSSH |
| 18_109 | 2.46 | 3.84 | 1.59 | 0.20 | 2.66 | 4.77 | 2.04 | 0.32 | XXXXXXXXXXRRRSSH |
| 18_111 | 0.36 | 8.02 | 2.41 | 0.59 | 5.64 | 3.86 | 2.88 | 0.34 | XXXXXXXXXXRSSSRH |
| 18_124 | 0.00 | 8.02 | 1.76 | 0.45 | 0.00 | 4.30 | 2.27 | 0.28 | XXXXXXXXXXSRRSSH |
| 18_146 | 0.00 | 4.37 | 1.59 | 0.22 | 0.00 | 5.67 | 2.27 | 0.40 | RRSRSSRRSSSRRSSH |
| 18_171 | 0.00 | 3.47 | 1.44 | 0.17 | 0.00 | 5.90 | 2.24 | 0.41 | SSSRRSSRSRRRRRSH |
| 18_185 | 2.94 | 4.54 | 1.57 | 0.23 | 2.34 | 5.97 | 2.10 | 0.40 | RSRSSRSRSRRSRSRH |
| 18_187 | 0.00 | 2.50 | 1.73 | 0.14 | 0.00 | 6.11 | 2.27 | 0.40 | RSSRRSRRRRSRRRSH |
| 18_188 | 0.00 | 3.88 | 1.66 | 0.21 | 3.63 | 6.56 | 1.94 | 0.38 | SSSRRSSRSRSRSSSH |
| 18_190 | 3.56 | 5.01 | 2.59 | 0.41 | 7.41 | 6.38 | 3.11 | 0.62 | SSSRSSSRSRRSRSSH |
| 18_196 | 0.00 | 2.00 | 1.31 | 0.09 | 1.40 | 5.30 | 1.71 | 0.28 | SSSSRSRRRSSRRRSH |
| 18_223 | 0.00 | 3.36 | 1.40 | 0.16 | 1.15 | 4.84 | 1.83 | 0.28 | XSXXXXXXXXXXXXXH |
| 18_227 | 0.00 | 6.48 | 1.75 | 0.37 | 0.45 | 6.48 | 2.20 | 0.39 | XXXSXXXXXXXXXXXH |
| 18_231 | 0 00 | 3.57 | 1.37 | 0.17 | 0.00 | 4.34 | 2.13 | 0.28 | XXXXXSXXXXXXXXXH |
| 18_236 | 2.37 | 3.44 | 1.82 | 0.21 | 4.69 | 3.90 | 2.22 | 0.27 | XXXXXXXXRXXXXXXH |
| 18_243 | 0.15 | 5.38 | 2.38 | 0.37 | 5.18 | 8.67 | 2.52 | 0.66 | XXXXXXXXXXXSXXXH |

From these data it can be seen that improvements in EC50 and efficacy in relation to PAPD5 and PAPD7 knock down can be achieved both with stereodefined sub-libraries and with fully stereodefined compounds.

Example 8: In Vitro Effect on HBV Infected ASGPR-dHepaRG Cells Using Selected Stereodefined Antisense Oligonucleotides Targeting PAPD5 and PAPD7

A selection of the most efficacious oligonucleotides from example 86 was tested for their effect on HBV propagation parameters in HBV infected dHepaRG-ASGPR cells.

The experiment was conducted as described in example 5.

The reduction of HBsAg and HBeAg levels are shown in table 22 and 23, the larger the value the larger the inhibition.

TABLE 22 in vitro efficacy on HBsAg of anti-PAPD5/PAPD7 compounds in three concentrations (average of 3) in HBV Infected ASGPR-dHepaRG cells. CMP ID NO 18_1 is the stereorandom parent compound

| CMP ID | 20 µM | | 6.67 µM | | 2.22 µM | | |
|---|---|---|---|---|---|---|---|
| NO | Avg | sd | Avg | sd | Avg | sd | Stereodefined motif |
| 18_1 | 97.88 | 1.00 | 89.38 | 2.73 | 39.44 | 12.14 | TCAactttcacttCAG XXXXXXXXXXXXXXXH |
| 18_36 | 72.64 | 1.45 | 37.85 | 8.05 | 10.98 | 8.04 | XXXXRSSRXXXXXXXH |
| 18_76 | 40.85 | 34.07 | 2.07 | 19.39 | -15.02 | 23.15 | XXXXXXXXXRRSRRSH |
| 18_99 | 34.94 | 6.39 | -13.21 | 12.32 | -42.74 | 12.83 | XXXxXxXXXSRSRSSH |
| 18_105 | 82.12 | 2.60 | 74.93 | 3.30 | 19.30 | 7.25 | XXXXXXXXXRRRSSSH |
| 18_109 | 57.43 | 14.41 | 18.19 | 9.25 | 7.15 | 16.09 | XXXXXXXXXXRRRSSH |
| 18_111 | 28.98 | 6.10 | -10.71 | 7.93 | -30.92 | 15.15 | XXXXXXXXXXRSSSRH |
| 18_124 | 59.86 | 4.12 | 27.17 | 15.97 | -3.69 | 18.85 | XXXXXXXXXXSRRSSH |
| 18_146 | 62.69 | 6.93 | 44.31 | 4.08 | -19.52 | 12.39 | RRSRSSRRSSSRRSSH |
| 18_171 | 38.32 | 2.10 | -11.53 | 3.85 | -28.30 | 10.51 | SSSRRSSRSRRRRRSH |
| 18_185 | -20.73 | 17.60 | -19.59 | 14.46 | -4.32 | 7.01 | RSRSSRSRSRRSRSRH |
| 18_187 | 56.84 | 6.44 | 17.42 | 10.77 | -49.55 | 11.42 | RSSRRSRRRRSRRRSH |
| 18_188 | 59.41 | 12.82 | 25.09 | 16.54 | 6.76 | 20.56 | SSSRRSSRSRSRSSSH |
| 18_189 | 32.87 | 6.69 | 3.52 | 16.56 | -50.76 | 34.50 | RSRSSSSRSSRRRSSH |
| 18_190 | -53.00 | 16.64 | -57.27 | 12.78 | -69.75 | 14.40 | SSSRSSSRSRRSRSSH |
| 18_195 | 32.58 | 3.42 | -12.74 | 45.18 | -16.33 | 18.72 | RRRRRSSRSRRSSSRH |
| 18_196 | -17.72 | 3.29 | -36.50 | 9.00 | -49.29 | 11.33 | SSSSRSRRRSSRRRSH |
| 18_218 | 53.86 | 6.46 | 42.40 | 3.88 | 9.55 | 20.41 | RSSRRSSRSRRRSSSH |
| 18_223 | 83.06 | 2.73 | 62.17 | 11.58 | 15.29 | 11.02 | XSXXXXXXXXXXXXXH |
| 18_227 | 79.92 | 1.95 | 49.95 | 6.87 | 11.69 | 7.50 | XXXSXXXXXXXXXXXH |
| 18_231 | 83.13 | 1.45 | 69.70 | 3.35 | 37.16 | 11.77 | XXXXXSXXXXXXXXXH |
| 18_236 | 64.19 | 2.58 | 38.47 | 5.37 | -19.29 | 5.10 | XXXXXXXXRXXXXXXH |
| 18_243 | 82.96 | 1.85 | 67.55 | 3.06 | 26.96 | 10.36 | XXXXXXXXXXXSXXXH |
| Combo 1 | 79.37 | 2.03 | 68.47 | 2.04 | 25.24 | 12.68 | |
| Combo 2 | 75.26 | 2.05 | 72.07 | 3.78 | 59.69 | 2.36 | |

TABLE 23 in vitro efficacy on HBeAg of anti-PAPD5/PAPD7 compounds in three concentrations (average of 3) in HBV infected ASGPR-dHepaRG cells. CMP ID NO 18_1 is the stereorandom parent compound

| CMP | 20 µM | | 6.67 µM | | 2.22 µM | | |
|---|---|---|---|---|---|---|---|
| ID NO | Avg | sd | Avg | sd | Avg | sd | Compound |
| 18_ 1 | 90.68 | 1.23 | 75.99 | 2.96 | 17.58 | 8.44 | TCAactttcacttCAG XXXXXXXXXXXXXXXH |
| 18_36 | 61.56 | 2.27 | 32.88 | 7.00 | 13.90 | 2.63 | XXXXRSSRXXXXXXXH |
| 18_76 | 42.45 | 24.97 | 12.44 | 4.58 | 5.05 | 11.65 | XXXXXXXXXRRSRRSH |
| 18_99 | 29.44 | 4.44 | -5.01 | 7.61 | -15.22 | 8.54 | XXXXXXXXXSRSRSSH |

TABLE 23-continued in vitro efficacy on HBeAg of anti-PAPD5/PAPD7 compounds in three concentrations (average of 3) in HBV infected ASGPR-dHepaRG cells. CMP ID NO 18_1 is the stereorandom parent compound

| CMP | 20 µM | | 6.67 µM | | 2.22 µM | | |
|---|---|---|---|---|---|---|---|
| ID NO | Avg | sd | Avg | sd | Avg | sd | Compound |
| 18_105 | 77.20 | 2.93 | 63.83 | 3.75 | 17.89 | 6.08 | XXXXXXXXXRRRSSSH |
| 18_109 | 50.97 | 12.79 | 18.65 | 7.96 | 18.34 | 10.47 | XXXXXXXXXXRRRSSH |
| 18_111 | 26.62 | 5.65 | 5.57 | 6.76 | -5.32 | 8.48 | XXXXXXXXXXRSSSRH |
| 18_124 | 52.84 | 6.90 | 26.44 | 13.62 | 8.76 | 13.32 | XXXXXXXXXXSRRSSH |
| 18_146 | 57.25 | 5.51 | 32.84 | 4.19 | -5.83 | 9.16 | RRSRSSRRSSSRRSSH |
| 18_171 | 31.41 | 2.24 | -0.52 | 0.38 | -5.55 | 4.51 | SSSRRSSRSRRRRRSH |
| 18_185 | 3.01 | 9.20 | 0.38 | 6.33 | 6.86 | 2.17 | RSRSSRSRSRRSRSRH |
| 18_187 | 45.26 | 5.54 | 14.19 | 7.61 | -7.36 | 5.03 | RSSRRSRRRRSRRRSH |
| 18_188 | 51.94 | 10.97 | 26.12 | 10.92 | 15.12 | 17.90 | SSSRRSSRSRSRSSSH |
| 18_189 | 32.71 | 4.45 | 3.59 | 7 73 | -20 18 | 13.54 | RSRSSSSRSSRRRSSH |
| 18_190 | -8.26 | 5.56 | -19.34 | 5.60 | -23.56 | 3.06 | SSSRSSSRSRRSRSSH |
| 18_195 | 33.37 | 4.40 | 6.47 | 23.36 | -3.00 | 7.16 | RRRRRSSRSRRSSSRH |
| 18_196 | 8.16 | 3.13 | -5.42 | 9.08 | -16.04 | 9.21 | SSSSRSRRRSSRRRSH |
| 18_218 | 52.20 | 7.32 | 38.24 | 6.77 | 9.85 | 11.45 | RSSRRSSRSRRRSSSH |
| 18_223 | 79.06 | 3.79 | 53.28 | 3.42 | 15.60 | 12.30 | XSXXXXXXXXXXXXXH |
| 18_227 | 76.98 | 5.26 | 39.75 | 9.09 | -0.96 | 3.34 | XXXSXXXXXXXXXXXH |
| 18_231 | 72.79 | 4.62 | 54.88 | 2.74 | 25.58 | 8.29 | XXXXXSXXXXXXXXXH |
| 18_236 | 59.69 | 3.81 | 33.06 | 7.16 | -0.33 | 4.37 | XXXXXXXXRXXXXXXH |
| 18_243 | 79.05 | 1.15 | 53.54 | 2.97 | 21.12 | 7.39 | XXXXXXXXXXXSXXXH |
| Combo 1 | 72.08 | 0.75 | 58.03 | 2.25 | 21.27 | 8.25 | |
| Combo 2 | 71.77 | 4.54 | 67.54 | 3.72 | 50.53 | 5.82 | |

Example 9: In Vitro Effect on HBV Infected ASGPR-dHepaRG Cells Using Selected GalNAc Conjugated Antisense Oligonucleotides Targeting PAPD5 and PAPD7

A selection of the most efficacious oligonucleotides from Example 1 were conjugated to a GalNAc conjugate moiety and tested for their effect on HBV propagation parameters in HBV infected ASGPR-dHepaRG cells.

The assessment of the EC50 and efficacy (KD) on HBsAg and HBeAg of the GalNAc conjugated oligonucleotides was performed as described in Example 2 using HBV infected ASGPR-dHepaRG cells and without comparative oligonucleotides. The results are shown in Table 24.

In addition to the procedure n example 2 the harvested cells were washed once in PBS and lysed in MagNA Pure lysis buffer (Roche #05467535001) and stored at −80° C. RNA was extracted using MagNA Pure "96 Cellular RNA Large Volume Kit" (Roche #05467535001) and PAPD26 and PAPD7 mRNA expression levels were determined as described in Materials and Methods seton, Real-time PCR for PAPD5 and PAPD7. EC5 and efficacy (KD) was calculated using the R-function drm( ) from the drc package (v3.0-1) a four-parameter log-logistic function is fitted to the expression of the gene at interest as a function of oligonucleotide concentration to obtain a value for EC50 and maximum knock-down. The results are shown in Table 24A

TABLE 24

EC50 and Max KD of anti-PAPD5/PAPD7 compounds on HBSAg and HBeAg (average of 3) in HBV infected ASGPR-dHepaRG cells.

| CMP ID | HBeAg | | | | HBsAg | | | | |
|---|---|---|---|---|---|---|---|---|---|
| | Max KD % of saline | | EC50 nM | | Max KD % of saline | | EC50 nM | | |
| NO | Avg | sd | Avg | sd | Avg | sd | Avg | sd | Compound |
| 20_12 | 6.1 | 1.0 | 127.7 | 10.1 | 7.7 | 1.6 | 87.0 | 17.4 | GN2-C6$_o$c$_o$a$_o$TCAactttcacttCAG |
| 20_13 | 0.8 | 0.3 | 65.1 | 1.3 | 2.5 | 1.0 | 72.4 | 3.5 | GN2-C6$_o$c$_o$a$_o$TCAActttcactTCAG |
| 20_14 | 0.3 | 1.1 | 43.2 | 3.4 | 1.2 | 1.3 | 58.5 | 5.1 | GN2-C6$_o$c$_o$a$_o$TCAActttcactTCAG |
| 20_15 | 0.0 | 0.7 | 45.3 | 6.1 | 0.4 | 1.7 | 37.8 | 11.2 | GN2-C6$_o$c$_o$a$_o$TCAActttcacTtCAG |
| 20_16 | 3.9 | 2.9 | 58.2 | 6.6 | 1.9 | 2.4 | 84.2 | 11.6 | GN2-C6$_o$c$_o$a$_o$TCAACtttCacttCAG |
| 20_17 | 5.9 | 1.9 | 83.8 | 11.8 | 11.2 | 1.7 | 110.4 | 14.3 | GN2-C6$_o$c$_o$a$_o$TCAACtttcacttcAG |
| 20_18 | 6.5 | 2.1 | 75.6 | 34.3 | 13.9 | 2.4 | 77.8 | 33.2 | GN2-C6$_o$c$_o$a$_o$TCAActttcacttcAG |
| 20_19 | 0.0 | 7.3 | 76.3 | 81.9 | 11.4 | 4.2 | 106.9 | 26.9 | GN2-C6$_o$c$_o$a$_o$TCAactttcactTCAG |
| 20_20 | 0.0 | 6.1 | 79.6 | 59.4 | 9.2 | 2.4 | 135.0 | 16.2 | GN2-C6$_o$c$_o$a$_o$TCAACtttcaCtTCAG |
| 20_21 | 1.8 | 2.4 | 41.5 | 8.7 | 7.8 | 2.6 | 74.9 | 17.6 | GN2-C6$_o$c$_o$a$_o$TCAACtttcacttcAG |
| 20_22 | 7.2 | 1.2 | 60.6 | 6.8 | 10.7 | 0.7 | 126.7 | 6.9 | GN2-C6$_o$c$_o$a$_o$TCaACtttcacttcAG |
| 21_2 | 14.6 | 5.5 | 79.2 | 40.8 | 18.8 | 3.3 | 125.9 | 23.6 | GN2-C6$_o$c$_o$a$_o$TCAActttcacttCaGT |

From these data it can be seen that by conjugating a GalNAc moiety to the oligonucleotide the EC50 values are Improved at least 40 fold (note the current table is in nM whereas table 14 is in μM). For example is the HBsAg reduction of compound 20_15 (GalNAc conjugated) improved 176 fold over compound 18_05 (naked version of 20_15).

TABLE 24A in vitro efficacy and potency (EC50) of GalNAc conjugated anti-PAPD5/PAPD7 compounds. PAPD5 and PAPD7 mRNA levels are normalized to GUSB in ASGPR-dHepaRG cells and shown as % of control (PBS treated cells).

| CMP ID | PAPD5 | | | | PAPD7 | | | |
|---|---|---|---|---|---|---|---|---|
| | Max KD % of saline | | EC50 μM | | Max KD % of saline | | EC50 μM | |
| NO | Avg | sd | Avg | sd | Avg | sd | Avg | sd |
| 20_12 | 1.9 | 0.95 | 0.032 | 0.002 | 1.6 | 1.59 | 0.030 | 0.003 |
| 20_13 | 17 | 1.93 | 0.045 | 0.009 | 17 | 1.57 | 0.038 | 0.006 |
| 20_14 | 5.2 | 1.24 | 0.024 | 0.008 | 2.9 | 1.47 | 0.003 | 0.002 |
| 20_15 | 11 | 1.45 | 0.002 | 0.002 | 8.5 | 0.99 | 0.001 | 0.001 |
| 20_16 | 10 | 1.20 | 0.046 | 0.006 | 11 | 1.18 | 0.041 | 0.005 |
| 20_17 | 5.2 | 2.29 | 0.022 | 0.012 | 4.3 | 2.05 | 0.037 | 0.013 |
| 20_18 | 5.4 | 1.14 | 0.047 | 0.006 | 2 | 1.27 | 0.014 | 0.007 |
| 20_19 | 4.7 | 1.68 | 0.048 | 0.009 | 6.5 | 1.54 | 0.041 | 0.009 |
| 20_20 | 9.3 | 1.33 | 0.047 | 0.005 | 4.7 | 2.17 | 0.019 | 0.012 |
| 20_21 | 6.2 | 1.30 | 0.043 | 0.006 | 4.4 | 2.78 | 0.020 | 0.008 |
| 20_22 | 4.7 | 1.29 | 0.044 | 0.008 | 5.4 | 2.68 | 0.048 | 0.010 |
| 21_2 | 12 | 1.12 | 0.075 | 0.005 | 12 | 3.41 | 0.052 | 0.013 |

From these data it can be seen that the majority of the selected GalNAc conjugated oligonucleotides targeting PAPD5 and PAPD7 are capable of reducing the mRNA levels to below 10%.

Example 10: Screening for In Vitro Efficacy of Antisense Oligonucleotides Targeting PAPD5 and PAPD7 in dHepaRG Cells The oligonucleotides screened for PAPD5 and PAPD7 knock down in HeLa cells (Example 1 and 3) were screened in dHepaRG cells to demonstrate efficient knock down in a liver cell line.

dHepaRG cells were cultured as described in the Materials and Method Section. The following oligonucleotide concentrations 50, 15.81, 5.00, 1.58, 0.50, 0.16, 0.05, and 0.016 μM were used in a final culture volume of 100 μl/well. The cells were harvested 6 days after addition of oligonucleotide compounds and RNA was extracted using the PureLink Pro 96 RNA Purification kit (Ambion) according to the manufacturer's instructions.

PAPD5 and PAPD7 mRNA levels were analysed by Real-time PCR as described in the Materials and Method section. EC 50, max KD (efficacy) of the PAPD5 and PAPD7 mRNA expression was calculated using the R-function drm( ) from the drc package (v3.0-1) a four-parameter log-logistic function is fitted to the expression of the gene of interest as a function of oligonucleotide concentration to obtain a value for EC50 and maximum knock-down. The results are shown in table 25.

TABLE 25

EC50 and Max KD of anti-PAPD5/PAPD7 compounds on PAPD5 and PAPD7 mRNA expression in dHepaRG cells.

| | PAPD5 | | | | PAP D7 | | | | |
|---|---|---|---|---|---|---|---|---|---|
| CMP | Max KD % of saline | | EC50 μM | | Max KD % of saline | | EC50 μM | | |
| ID NO | Avg | sd | Avg | sd | Avg | sd | Avg | sd | Compound |
| 17_103 | 11.0 | 6.1 | 1.7 | 0.4 | 2.2 | 39.9 | 7.6 | 13.3 | TcAActttcactTCaGT |
| 17 111 | 7.5 | 8.7 | 2.2 | 0.8 | 0.0 | 38.7 | 6.4 | 11.7 | TCAActttcactTCAGT |
| 17_119 | 5.3 | 16.1 | 1.8 | 1.1 | 2.1 | 16.7 | 3.8 | 2.2 | TCAactttcactTcaGT |
| 17_129 | 11.5 | 5.5 | 1.5 | 0.4 | 0.0 | 31.2 | 5.0 | 6.2 | TCAactttcacttCAGT |
| 17_132 | 9.8 | 10.0 | 3.2 | 1.3 | 13.2 | 13.2 | 6.6 | 3.5 | TCaActttcacttCAGT |
| 17_135 | 4.1 | 3.6 | 1.1 | 0.1 | 0.0 | 32.7 | 4.0 | 4.3 | TCaactttcacttCAGT |
| 17_137 | 0.0 | 7.5 | 3.5 | 0.9 | 16.6 | 8.2 | 5.0 | 1.5 | TcAActttcacttCAGT |
| 17_139 | 5.3 | 8.3 | 2.3 | 0.7 | 5.7 | 19.1 | 7.7 | 4.9 | TeAactttcacttCAGT |
| 17_144 | 6.0 | 8.0 | 1.4 | 0.4 | 0.0 | 12.7 | 2.8 | 1.3 | TCAactttcacttCaGT |
| 17_157 | 8.2 | 4.6 | 3.1 | 0.5 | 0.0 | 16.2 | 8.8 | 4.9 | TCAActttcacttcAGT |
| 18_1 | 0.0 | 7.8 | 1.6 | 0.4 | 0.0 | 8.7 | 3.8 | 1.2 | TCAactttcacttCAG |
| 18_6 | 10.1 | 9.2 | 2.5 | 0.9 | 0.0 | 19.8 | 5.8 | 4.2 | TCaactttcacTtCAG |
| 18_10 | 13.4 | 15.6 | 1.5 | 1.0 | 10.1 | 15.1 | 4.1 | 2.3 | TCAActttcactTCAG |
| 18_12 | 8.8 | 7.4 | 1.9 | 0.6 | 13.3 | 8.9 | 4.6 | 1.6 | TCAactttcactTCAG |
| 18_15 | 0.0 | 35.4 | 4.7 | 6.0 | 34.8 | 11.8 | 4.8 | 2.3 | TcAACtttcactTCAG |
| 18_8 | 0.0 | 27.1 | 2.6 | 2.7 | 25.0 | 7.3 | 5.4 | 1.5 | TCAACtttcacttCAG |
| 18_19 | 0.0 | 7.0 | 2.8 | 0.7 | 0.0 | 18.1 | 1.2 | 1.0 | TCAActttcacttCAG |
| 18_20 | 11.9 | 10.6 | 4.2 | 1.8 | 0.0 | 64.2 | 9.3 | 22.5 | TCAaCtttcacttCAG |
| 18_21 | 21.9 | 7.0 | 4.4 | 1.3 | 0.0 | 40.5 | 16.0 | 25.6 | TCaaCtttcacttCAG |
| 18_23 | 8.8 | 10.8 | 3.0 | 1.2 | 0.0 | 32.5 | 3.5 | 4.1 | TCAACtttcacttcAG |
| 18_24 | 13.5 | 5.9 | 3.3 | 0.8 | 23.3 | 6.2 | 3.4 | 1.0 | TCAActttcacttcAG |
| 18_25 | 13.0 | 11.4 | 3.0 | 1.3 | 9.4 | 18.7 | 5.0 | 3.3 | TCAaCtttcacttcAG |
| 18_27 | 7.9 | 9.2 | 2.7 | 0.9 | 19.2 | 7.5 | 3.3 | 1.0 | TCaACtttcacttcAG |
| 18_28 | 13.4 | 11.3 | 4.7 | 2.1 | 19.1 | 5.8 | 4.6 | 1.1 | TCaaCtttcacttcAG |
| 18_30 | 9.9 | 7.4 | 5.1 | 1.2 | 0.0 | 14.4 | 7.1 | 3.5 | TcAACtttcacttcAG |
| 18_346 | 8.1 | 8.9 | 1.5 | 0.6 | 0.0 | 19.1 | 3.9 | 2.5 | TCaActttcactTCAG |
| 18_347 | 9.2 | 15.0 | 1.6 | 1.0 | 0.0 | 24.0 | 4.3 | 3.6 | TcAActttcactTCAG |

TABLE 25-continued

EC50 and Max KD of anti-PAPD5/PAPD7 compounds on PAPD5 and PAPD7 mRNA expression in dHepaRG cells.

| CMP | PAPD5 Max KD % of saline | | PAPD5 EC50 µM | | PAP D7 Max KD % of saline | | PAP D7 EC50 µM | | |
|---|---|---|---|---|---|---|---|---|---|
| ID NO | Avg | sd | Avg | sd | Avg | sd | Avg | sd | Compound |
| 18_350 | 8.5 | 6.3 | 1.8 | 0.5 | 0.0 | 24.4 | 3.4 | 2.6 | TCAActttcactTcAG |
| 18_357 | 0.0 | 10.0 | 4.5 | 1.6 | 0.0 | 25.5 | 8.1 | 6.5 | TCaActttcacttCAG |
| 18_358 | 0.0 | 19.3 | 3.9 | 2.5 | 29.9 | 9.2 | 4.3 | 1.8 | TcaACtttcacttCAG |

From these data it can be seen that an effective target reduction can also be archived in a hepatocyte derived cell line.

Example 11: Screening for In Vitro Efficacy of Stereodefined Antisense Oligonucleotides Targeting PAPD5 and PAPD7 in dHepaRG Cells The stereodefined oligonucleotides screened for PAPD5 and PAPD7 knock down in Hela cells (Example 7) were screened in dHepaRG calls to demonstrate efficient knock down in a liver cell line.

The Screening was conducted as described in example 10 with the following oligonucleotide concentrations 33, 10.44, 3.33, 1.044, 0.33, 0.104, 0.033 and 0.01 PM.

PAPD5 and PAPD7 mRNA levels were analysed by Real-time PCR as described in the Materials and Method section. EC 50, max KD (efficacy) of the PAPD5 and PAPD7 mRNA expression was calculated using the R-function drm( ) from the drc package (v3.0-1) a four-parameter log-logistic function is fitted to the expression of the gene of Interest as a function of oligonucleotide concentration to obtain a value for EC50 and maximum knock-down. The results are shown in table 26.

TABLE 26

EC50 and Max KD of anti-PAPD5/PAPD7 stereodefined compounds on PAPD5 and PAPD7 mRNA expression in dHepaRG cells

| CMP | PAPD5 Max KD % of saline | | PAPD5 EC50 µM | | PAPD7 Max KD % of saline | | PAPD7 EC 50 µM | | |
|---|---|---|---|---|---|---|---|---|---|
| ID NO | Avg | sd | Avg | sd | Avg | sd | Avg | sd | Stereodefined motif |
| 18_1 | 0.0 | 7.75 | 1.6 | 0.43 | 0.0 | 8.71 | 3.8 | 1.16 | TCAactttcacttCAG XXXXXXXXXXXXXXXH |
| 18_36 | 3.6 | 2.33 | 1.3 | 0.11 | 0.0 | 7.23 | 1.6 | 0.34 | SXXXRSSRXXXXXXZH |
| 18_76 | 0.0 | 18.65 | 6.3 | 3.60 | 11.6 | 11.23 | 6.5 | 2.36 | XXXXXXXXXRRSRRSH |
| 18_99 | 9.4 | 6.99 | 5.7 | 1.40 | 13.7 | 18.67 | 7.2 | 4.94 | KXZAXXXXASRSRSSH |
| 18_109 | 4.0 | 9.74 | 2.3 | 0.75 | 6.4 | 15.14 | 3.4 | 1.73 | XXXXXXXXXXRRRSSH |
| 18_111 | 7.4 | 16.00 | 3.0 | 1.61 | 12.6 | 14.95 | 4.4 | 2.12 | XXXXXXXXXXRSSSRH |
| 18_124 | 7.0 | 29.13 | 1.7 | 1.61 | 6.3 | 14.24 | 3.7 | 1.55 | XXXXXXXXXXSRRSSH |
| 18_146 | 1.7 | 19.93 | 1.8 | 1.19 | 12.3 | 20.51 | 4.9 | 3.39 | RRSRSSRRSSSRRSSH |
| 18_171 | 3.9 | 6.86 | 1.7 | 0.40 | 0.0 | 16.12 | 3.0 | 1.52 | SSSRRSSRSRRRRRSH |
| 18_185 | 0.0 | 14.48 | 2.6 | 1.19 | 10.4 | 9.76 | 4.1 | 1.28 | RSRSSRSRSRRSRSRH |
| 18_187 | 5.2 | 8.79 | 1.5 | 0.45 | 2.9 | 5.11 | 2.0 | 0.35 | RSSRRSRSRRRSRRSH |
| 18_188 | 7.5 | 4.82 | 1.5 | 0.28 | 12.2 | 10.13 | 1.7 | 0.63 | SSSRRSSRSRSRSSSH |
| 18_190 | 0.0 | 27.66 | 8.1 | 8.27 | 30.4 | 10.66 | 4.1 | 1.95 | SSSRSSSRSRRSRSSH |
| 18_196 | 9.0 | 8.92 | 1.8 | 0.62 | 19.7 | 8.01 | 1.5 | 0.51 | SSSSRSRRRSSRRRSH |
| 18_223 | 11.2 | 10.00 | 1.4 | 0.62 | 19.9 | 6.90 | 2.5 | 0.75 | XSXXXXXXXXXXXXXH |
| 18_227 | 6.4 | 20.21 | 1.7 | 1.19 | 10.8 | 10.55 | 3.2 | 1.15 | XXXSXXXXXXXXXXXH |

TABLE 26-continued

EC50 and Max KD of anti-PAPD5/PAPD7 stereodefined compounds on PAPD5 and PAPD7 mRNA expression in dHepaRG cells

| CMP | PAPD5 | | | | PAPD7 | | | | |
|---|---|---|---|---|---|---|---|---|---|
| | Max KD % of saline | | EC50 µM | | Max KD % of saline | | EC 50 µM | | |
| ID NO | Avg | sd | Avg | sd | Avg | sd | Avg | sd | Stereodefined motif |
| 18_231 | 10.2 | 5.89 | 1.3 | 0.30 | 9.9 | 6.10 | 2.1 | 0.44 | XXXXXSXXXXXXXXXH |
| 18_236 | 10.8 | 6.26 | 3.1 | 0.59 | 15.3 | 6.47 | 3.3 | 0.64 | XXXXXXXXRXXXXXXH |
| 18_243 | 6.0 | 9.15 | 1.8 | 0.52 | 26.9 | 3.26 | 1.9 | 0.24 | XXXXXXXXXXXSXXXH |

From these data it can be seen that stereo defined oligonucleotides also are effective in target reduction in a hepatocyte derived cell fie.

Example 12: In Vitro Effect on HBV Infected ASGPR-dHepaRG Cells Using Selected GalNAc Conjugated Antisense Oligonucleotides Targeting PAPD5 and PAPD7

A selection of the most efficacious oligonucleotides from example 5 were conjugated to a GalNAc conjugate moiety and tested for their effect on HBV propagation parameters in HBV infected ASGPR-dHepaRG cells.

For comparative purposes the antisense oligonucleotides of the invention were compared to GalNAc conjugated versions of the he HBV targeting oligonucleotides shown in table 13 the GalNAc conjugated versions are shown in Table 13A.

TABLE 13A

Comparative HBV targeting oligonucleotides

| Description | Compound | SEQ ID NO | Reference |
|---|---|---|---|
| HBV targeting 1 | GN2$_o$c$_o$a$_o$AGCgaagtgcacaCGG | 29 | WO2015/173208 |

TABLE 13A-continued

Comparative HBV targeting oligonucleotides

| Description | Compound | SEQ ID NO | Reference |
|---|---|---|---|
| HBV targeting 2 | GN2$_o$c$_o$a$_o$GCGtaaagagaGG | 30 | WO2015/173208 |

The assessment of the EC50 and efficacy (KID) on HBsAg and HBeAg of the GalNAc conjugated oligonucleotides was performed as described in Example 2 using HBV Infected ASGPR-dHepaRG cells. The results are shown in Table 27.

In addition to the procedure in example 2 the harvested cells were washed once in PBS and lysed in MagNA Pure lysis buffer (Roche #0567535001) and stored at −80° C. RNA was extracted using MagNA Pure "98 Cellular RNA Large Volume Kit" (Roche #05467535001) and PAPD5 and PAPD7 mRNA expression levels were determined as described in Materials and Methods section, Real-time PCR for PAPD5 and PAPD7. EC50 and efficacy (KD) was calculated using the R-function drm( ) from the drc package (v3.0-1) a four-parameter log-logistic function is fitted to the expression of the gene of interest as a function of oligonucleotide concentration to obtain a value for EC50 and maximum knock-down. The results are shown in Table 27A.

TABLE 27

EC50 and Max KD of anti-PAPD5/PAPD7 compounds on HBsAg and HBeAg (average of 3) in HBV infected ASGPR-dHepaRG cells.

| CMP ID | HBeAg | | | | HBsAg | | | | |
|---|---|---|---|---|---|---|---|---|---|
| | Max KD % of saline | | EC50 µM | | Max KD % of saline | | EC50 µM | | |
| NO | Avg | sd | Avg | sd | Avg | sd | Avg | sd | Compound |
| HBV1 | 26.4 | 3.6 | 0.124 | 0.026 | 39.6 | 7.3 | 0.220 | 0.104 | GN2-C6caAGCgaagtgcacaCGG |
| HBV2 | 31.3 | 4.2 | 0.233 | 0.373 | 33.2 | 4.8 | 0.391 | 0.119 | GN2-C6caGCGtaaagagaGG |
| 21_26 | 11.4 | 15.7 | 0.175 | 0.113 | 18.1 | 8.9 | 0.201 | 0.070 | GN2-C6caTcAActttcactTCAGT |
| 21_27 | 18.5 | 6.2 | 0.128 | 0.041 | 23.3 | 8.1 | 0.192 | 0.068 | GN2-C6caTCAActttcactTCaGT |

TABLE 27-continued

EC50 and Max KD of anti-PAPD5/PAPD7 compounds on HBsAg and HBeAg (average of 3) in HBV infected ASGPR-dHepaRG cells.

| | HBeAg | | | | HBsAg | | | | |
|---|---|---|---|---|---|---|---|---|---|
| CMP ID | Max KD % of saline | | EC50 µM | | Max KD % of saline | | EC50 µM | | |
| NO | Avg | sd | Avg | sd | Avg | sd | Avg | sd | Compound |
| 21_33 | 28.4 | 19.3 | 0.247 | 0.133 | 33.2 | 10.5 | 0.242 | 0.106 | GN2-C6caTcAActttcacTtCAGT |
| 21_34 | 17.6 | 5.5 | 0.083 | 0.037 | 27.3 | 3.7 | 0.085 | 0.091 | GN2-C6caTcAactttcactTCAGT |
| 21_36 | 13.8 | 6.0 | 0.086 | 0.156 | 20.6 | 9.6 | 0.193 | 0.086 | GN2-C6caTCAAcTtTcacTtcAGT |
| 20_12 | 0.0 | 2.6 | 0.073 | 0.088 | 9.9 | 1.9 | 0.057 | 0.005 | GN2-C6caTCAactttcacTtCAG |
| 20_35 | 3.2 | 10.4 | 0.080 | 0.166 | 9.7 | 6.6 | 0.085 | 0.143 | GN2-C6caTCaAcTttcactTCAG |
| 20_36 | 3.7 | 4.0 | 0.062 | 0.001 | 3.9 | 3.1 | 0.082 | 0.014 | GN2-C6caTCAActttcactTCAG |
| 20_30 | 4.8 | 5.6 | 0.107 | 0.031 | 2.3 | 4.2 | 0.137 | 0.032 | GN2-C6caTCaActttcacTtCAG |

The compounds indicated in the table have phosphodiester linkages in the ca dinucleotide following the C8 linker as it is indicated in table 10.

TABLE 27A in vitro efficacy and potency (EC50) of GalNAc conjugated anti-PAPD5/PAPD7 compounds. PAPD5 and PAPD7 mRNA levels are normalized to GUSB in ASGPR-dHepaRG cells and shown as % of control (PBS treated cells).

| | PAPD5 | | | | PAPD7 | | | |
|---|---|---|---|---|---|---|---|---|
| | Max KD % of saline | | EC50 µM | | Max KD % of saline | | EC50 µM | |
| CMP ID NO | Avg | sd | Avg | sd | Avg | sd | Avg | sd |
| HBV1 | 58 | 9.26 | Inf | 10.00 | 76 | 11.5 | 0.780 | 10.000 |
| HBV2 | 59 | 43.5 | Inf | 24000 | 82 | 7.47 | Inf | 10.000 |
| 21_26 | 11 | 2.01 | 0.080 | 0.010 | 14 | 2.01 | 0.059 | 0.010 |
| 21_27 | 7.8 | 1.04 | 0.056 | 0.004 | 14 | 3.4 | 0.076 | 0.018 |
| 21_33 | 8.4 | 1.2 | 0.050 | 0.005 | 14 | 2.16 | 0.075 | 0.009 |
| 21_34 | 4.8 | 1.05 | 0.065 | 0.004 | 9.4 | 1.75 | 0.047 | 0.006 |
| 21_36 | 3.9 | 1.04 | 0.087 | 0.005 | 2.4 | 5.85 | 0.033 | 0.025 |
| 20_12 | 1.6 | 1.05 | 0.034 | 0.004 | 3.6 | 1.79 | 0.040 | 0.006 |
| 20_35 | 6.7 | 1.51 | 0.038 | 0.006 | 8.4 | 1.81 | 0.054 | 0.008 |
| 20_36 | 3.4 | 1.48 | 0.037 | 0.004 | 6.9 | 4.35 | 0.082 | 0.018 |
| 20_30 | 1.9 | 1.06 | 0.035 | 0.003 | 4.9 | 5.8 | 0.040 | 0.019 |

Inf = EC50 could not be calculated due to lack in dose response.

As expected the two HBV targeting molecules had very insignificant effect on PAPD5 and PAPD7, their HBsAg and HBeAg effects are therefore not connected to their ability to reduce PAPD5 or PAPD7. The reminder of the tested compound show target reduction below 85% and EC50 values below 0.09 µM, which correlate well with the effects seen on HBsAg and HBeAg in table 27.

Example 13 In Vitro Effect on HBV Infected PHH Cells Using Selected GalNAc Conjugated Antisense Oligonucleotides Targeting PAPD5 and PAPD7

A selection of GalNAc conjugated oligonucleotides were further tested in HBV infected primary human hepatocytes (see materials and method section; PHH natural infection assay) to Illustrate efficacy in an in vitro system with a natural ASGPR expression. The oligonucleotide concentrations used were three-fold serial dilutions (20.00, 6.67, 2.22, 0.74, 0.25, 0.08, 0.03, 0.01 μM oligonucleotide).

EC 50, max KD (efficacy) of the HBV propagation parameters HBsAg and HBeAg was calculated using the R-function drm( ) from the drc package (v3.0-1) a four-parameter log-logistic function is fitted to the expression of the gene of interest as a function of oligonucleotide concentration to obtain a value for EC50 and maximum reduction. The results are shown in Table 28.

EC 50, max KD (efficacy) of the PAPD5 and PAPD7 mRNA expression was calculated using the same algorithm. The results are shown in Table 28A.

TABLE 28A in vitro efficacy and potency (EC50) of GalNAc conjugated anti-PAPD5/PAPD7 compounds. PAPD5 and PAPD7 mRNA levels are normalized to GUSB in PPH cells and shown as % of control (PBS treated cells).

| CMP ID | PAPD5 Max KD % of saline | | PAPD5 EC50 μM | | PAPD7 Max KD % of saline | | PAPD7 EC50 μM | |
|---|---|---|---|---|---|---|---|---|
| NO | Avg | sd | Avg | sd | Avg | sd | Avg | sd |
| 20_13 | 0 | 6.28 | 0.030 | 0.028 | 0 | 10.4 | 0.018 | 0.034 |
| 20_14 | 3.6 | 1.92 | 0.026 | 0.007 | 0 | 8.63 | 0.011 | 0.020 |
| 20_12 | 4.2 | 3.41 | 0.033 | 0.009 | 2.9 | 5.31 | 0.007 | 0.012 |
| 20_15 | 0 | 6.37 | 0.001 | 0.001 | 0 | 8.93 | 0.033 | 0.061 |
| 20_16 | 11 | 2.67 | 0.094 | 0.016 | 1.8 | 6.2 | 0.016 | 0.016 |
| 20_17 | 91 | 4.6 | 4.200 | 0.270 | 13 | 6.05 | 0.039 | 0.022 |
| 20_18 | NA | NA | NA | NA | 6.7 | 7.11 | 0.015 | 0.016 |
| 20_20 | 11 | 3.19 | 0.045 | 0.012 | 13 | 7.9 | 0.004 | 0.015 |

NA = not assessed due to technical error

TABLE 28

EC50 and Max KD of anti-PAPD5/PAPD7 compounds on HBsAg and HBeAg (average of 3) in HBV infected PHH cells.

| CMP ID | HBsAg Max KD % of saline | | HBsAg EC50 μM | | HBeAg MaxKD % OF saline | | HBeAg EC50 μM | | |
|---|---|---|---|---|---|---|---|---|---|
| NO | Avg | sd | Avg | sd | Avg | sd | Avg | sd | Compound |
| 20_13 | 11.8 | 4.1 | 0.078 | 0.179 | 9.0 | 2.3 | 0.078 | 0.010 | GN2-C6caTCAActttcactTCAG |
| 20_14 | 11.8 | 1.9 | 0.062 | 0.006 | 13.1 | 1.8 | 0.063 | 0.006 | GN2-C6caTCAActttcacttCAG |
| 20_12 | 17.0 | 2.1 | 0.054 | 0.006 | 24.4 | 1.3 | 0.075 | 0.005 | GN2-C6caTCAactttcacttCAG |
| 20_15 | 9.5 | 1.4 | 0.017 | 0.003 | 11.2 | 2.4 | 0.029 | 0.006 | GN2-C6caTCAActttcacTtCAG |
| 20_16 | 16.7 | 1.9 | 0.098 | 0.010 | 19.5 | 3.4 | 0.180 | 0.031 | GN2-CBcaTCAACtttcacttCAG |
| 20_17 | 10.9 | 2.1 | 0.068 | 0.011 | 26.0 | 3.0 | 0.119 | 0.024 | GN2-C6caTCAACtttcacttcAG |
| 20_18 | 13 2 | 1.9 | 0.066 | 0.008 | 19.2 | 1.0 | 0.070 | 0.004 | GN2-C6caTCAActttcacttcAG |
| 20_20 | 14.8 | 5.9 | 0.087 | 0.022 | 18.8 | 4.3 | 0.168 | 0.043 | GN2-C6caTcAACtttcactTcAG |

The compounds indicated in the the have phosphodiester linages in the ca dinucleotide following the C6 linker as it is indicated in table 10.

From these data it can be seen that the selected GalNAc conjugated oligonucleotides targeting PAPD5 and PAPD7 are capable of reducing HBV antigen secretion in infected primary human hepatocytes.

From these data it can be seen that the selected GalNAc conjugated oligonucleotides targeting PAPD5 and PAPD7 are capable of reducing their targets to 11% or lower, with the exception of compound 20_17 that appears to have very little effect on PAPD5 mRNA, while maintain the effect on PAPD7 mRNA.

Example 14 Screening for In Vitro Efficacy of Antisense Oligonucleotides Targeting Human and Mouse PAPD5 and PAPD7 (Bispecific) in HeLa Cells and PMH Cells An oligonucleotide screen was performed using gapmer oligonucleotides targeting the human and mouse transcripts of PAPD5 and PAPD7 (table 5) in the human HeLa cell line and in primary mouse hepatocytes (PMH).

The screening in HeLa cells was conducted as described in Example 1 with a 25 μM concentration.

The screening in PMH cells was conducted as described in the "Materials and methods" section under "Primary mouse Hepatocytes" using 5 μM oligonucleotide.

Figure 11A:
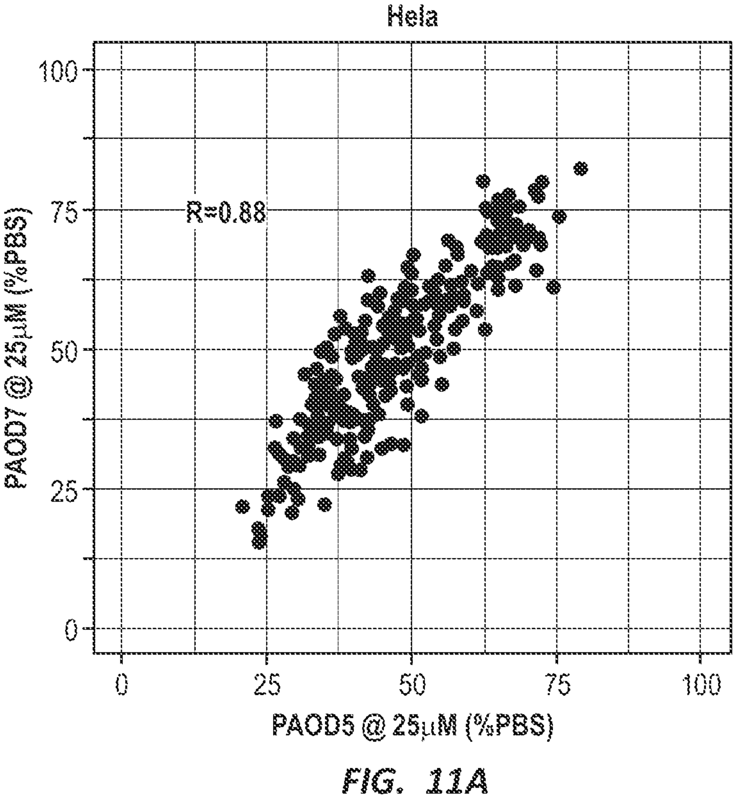
FIGS. 11A and 11B: Representation of in vitro PAPD5 and PAPD7 reduction achieved with oligonucleotides targeting the human and mouse transcripts (table 5) in the human Hela cell line (FIG. 11A) and in primary mouse hepatocytes (PMH) (FIG. 11B).

FIG. 11 shows the results of the screen, each dot represents a compound from table 5 and it's ability to reduce PAPD7 mRNA (Y axis) and PAPD5 mRNA (X axis). In the HeLa cells (human) there is a good correlation between PAPD5 and PAPD7 mRNA reduction, whereas in the PMH (mouse) cells it appears that the reduction of PAPD7 mRNA is not very efficient compared to the PAPD5 mRNA reduction.

A plausible explanation of the modest inhibition of PAPD7 mRNA in the mouse hepatocytes is that the primary spliced mRNA transcript of PAPD7 expressed in primary mouse hepatocytes has a transcription start site downstream of the binding site of the oligonucleotides. This was not identified unto a whole transcriptome shotgun sequencing (RNAseq) was performed on the primary mouse hepatocytes.

Example 15: In Vitro Effect on HBV Infected ASGPR-dHepaRG Cells Using Selected GalNAc Conjugated Antisense Oligonucleotides Targeting PAPD5 and PAPD7

A further selection of oligonucleotides from example 2 and 5 were conjugated to a GalNAc conjugate moiety and tested for their effect on HBV propagation parameters in HBV infected ASGPR-dHepaRG cags.

The assessment of the EC50 and efficacy (KD) on HBsAg and HBeAg of the GalNAc conjugated oligonucleotides was performed as described in Example 2 using HBV infected ASGPR-dHepaRG cells. The results are shown in Table 29.

In addition to the procedure in example 2 the harvested cells were washed once in PBS and lysed in MagNA Pure lysis buffer (Roche #05467535001) and stored at −80° C. RNA was extracted using MagNA Pure "96 Cellular RNA Large Volume Kit" (Roche #05467535001) and PAPD5 and PAPD7 mRNA expression levels were determined as described in Materials and Methods section, Real-time PCR for PAPD3 and PAPD2. EC50 and efficacy (KD) was calculated using the R-function drm( ) from the drc package (v3.0-1) a four-parameter log-logistic function is fitted to the expression of the gene of interest as a function of oligonuclotides concentration to obtain a value for EC50 and maximum knock-down. The results are shown in Table 29A.

TABLE 29

EC50 and Max KD of anti-PAPD5/PAPD7 compounds on HBSAg and HBeAg (average of 3) in HBV infected ASGPR-dHepaRG cells.

| | HBeAg | | HBsAg | | |
|---|---|---|---|---|---|
| CMP ID NO | Max KD % of saline Avg | EC50 μM Avg | Max KD % of saline Avg | EC50 μM Avg | Compound |
| 20_12 | 8.12 | 0.05 | 9.59 | 0.05 | GN2-C6ocoaoTCAactttcacttCAG |
| 21_20 | 26.60 | 0.32 | 27.25 | 0.32 | GN2-C6ocoaoTcAactttcactTcAGT |
| 21_21 | 21.08 | 0.12 | 24.20 | 0.17 | GN2-C6ocoaoTcAActttcacttCaGT |
| 21_22 | 42.22 | 0.52 | 40.26 | 1.43 | GN2-C6ocoaoTCAactttcacttcAGT |
| 20_31 | 17.80 | 0.18 | 17.19 | 0.29 | GN2-C6ocoaoTCaactttcactTCAG |
| 20_32 | 1.20 | 0.07 | 10.25 | 0.08 | GN2-C6ocoaoTCAaCtttcacttCAG |
| 20_33 | 15.30 | 0.13 | 22.90 | 0.17 | GN2-C6ocoaoTCaaCtttcacttCAG |
| 20_34 | 12.51 | 0.07 | 14.65 | 0.07 | GN2-C6ocoaoTCAaCtttcacttcAG |
| 21_41 | 26.52 | 4.25 | 37.88 | 4.84 | GN2-C6ocoaoTCaactttcactTCAGT |
| 21_44 | 35.05 | 0.11 | 37.69 | 0.23 | GN2-C6ocoaoTCaActttcacttCAGT |
| 20_40 | 0.00 | 0.06 | 6.26 | 0.09 | GN2-C6ocoaoTcaACttcacttCAG |
| 20_39 | 0.00 | 0.05 | 16.47 | 0.07 | GN2-C6oCoaoTCAActttcactTCAG |
| 21_42 | 23.75 | 0.13 | 26.69 | 0.17 | GN2-C6ocoaoTCaActttcactTCaGT |
| 21_43 | 8.92 | 0.08 | 16.60 | 0.16 | GN2-C6ocoaoTCAActttcactTcaGT |

TABLE 29A in vitro efficacy and potency (EC50) of GalNAc conjugated anti-PAPD5/PAPD7 compounds. PAPD5 and PAPD7 mRNA levels are normalized to GUSB in ASGPR-dHepaRG cells and shown as % of control (PBS treated cells).

| | PAPD5 | | | | PAPD7 | | | |
|---|---|---|---|---|---|---|---|---|
| CMP ID | Max KD % of saline | | EC50 µM | | Max KD % of saline | | EC50 µM | |
| NO | Avg | sd | Avg | sd | Avg | sd | Avg | sd |
| 20_12 | 1.8 | 1.31 | 0.043 | 0.005 | 1.5 | 1.42 | 0.027 | 0.005 |
| 21_20 | 6.8 | 1.48 | 0.076 | 0.009 | 12 | 3.21 | 0.096 | 0.018 |
| 21_21 | 12 | 1.38 | 0.035 | 0.007 | 16 | 4.3 | 0.009 | 0.019 |
| 21_22 | 4.7 | 0.723 | 0.044 | 0.003 | 5.1 | 2.2 | 0.044 | 0.009 |
| 20_31 | 5.9 | 1.55 | 0.056 | 0.009 | 6.3 | 1.57 | 0.048 | 0.008 |
| 20_32 | 8 | 1.37 | 0.058 | 0.007 | 6.2 | 2.09 | 0.027 | 0.020 |
| 20_33 | 11 | 1.28 | 0.084 | 0.008 | 5.4 | 3.57 | 0.001 | 0.002 |
| 20_34 | 6.8 | 1.87 | 0.046 | 0.011 | 8.2 | 2.2 | 0.044 | 0.007 |
| 21_41 | 35 | 4.51 | 0.097 | 0.045 | 37 | 5.74 | 0.220 | 0.096 |
| 21_44 | 10 | 1.79 | 0.120 | 0.016 | 21 | 2.2 | 0.140 | 0.024 |
| 20_40 | 4.2 | 1.38 | 0.041 | 0.006 | 7.3 | 1.11 | 0.047 | 0.004 |
| 20_39 | 5.4 | 1.98 | 0.026 | 0.011 | 8 | 3.15 | 0.025 | 0.014 |
| 21_42 | 16 | 1.8 | 0.098 | 0.011 | 16 | 2.46 | 0.063 | 0.010 |
| 21_43 | 5.8 | 1.31 | 0.059 | 0.008 | 11 | 2.31 | 0.044 | 0.010 |

Example 16 Effect on HBsAg Expression from Chromosomally Integrated HBV DNA Using Selected Bispecific PAPD5 and PAPD7 Targeting Oligonucleotides In the current experiment it was tested whether a selection of GalNAc conjugated anti-PAPD5/7 oligonucleotides with good potency towards PAPD5 and PAPD7 were capable of reducing HBs antigen and mRNA expression from the human hepatocellular carcinoma cell line Hep3B which secrete HBs antigen from chromosomally integrated HBV DNA.

Hep3B cells (Knowles et al. 1980. Science 209 pp. 497-499) were purchased from ATCC (ATCC HB-8064) and cultured in Eagle's minimum essential medium (EMEM) supplemented with 10% FBS. The cells were plated on collagen coated 96-well plates at a concentration of $1.5\times10^5$ cells per well and cultured at 37° C. in a humidified atmosphere with 5% $CO_2$. One day after seeding the cells oligonucleotide was added to the cells using concentrations starting at 20 µM and three-fold serial dilutions thereof (20.00, 6.67, 2.22, 0.74, 0.25, 0.08, 0.03, 0.01 µM oligonucleotide). The treatment was repeated with a medium change on day 4 and day 7. At day 11 the supernatants were harvested for HBsAg measurement (performed as described in the Materials and Method section under HBV antigen measurements) and the cells were washed once with PBS and 2001 MagNA Pure lysis buffer was added to each well and plates were stored at −80° C. for RNA extraction.

Intracellular mRNA was extracted from lysed Hep3B cells using a MagNA Pure robot and the MagNA Pure 96 Cellular RNA Large Volume Kit (Roche. #05467535001) according to the manufacturer's protocol. PAP 2, and PAPD7 mRNA was quantified in technical duplicate by separate RT qPCRs using a QuantStudio 12K Flex (Applied Biosystems), the TaqMan RNA-to-CT 1-Step Kit (Applied Biosystems, #4392938), Human ACTB endogenous control (Applied Biosystems, #4310881E), and PAPD5 and PAPD7 mRNA Taqman primers and reagents (Life Technologies, assay ID Hs00900790_m1 (PAPD5) and Hs00173159 ml (PAPD7) and custom assay ID APMFW4G (Small HBs)). The qPCR was performed using the following settings: UDG incubation (15 min, 48° C.), enzyme activation (10 min, 95'C) and qPCR (40 cycles with 15 sec, 95° C. for denaturation and 1 min, 60° C. for annealing and extension).

EC 50 and max KD (Max efficacy in % of saline) of the HBsAg, HBs mRNA, PAPD5 and PAPD7 reductions was calculated using using GraphPad Prism 7.02 non line fit. The results are shown in Table 30 and 31.

TABLE 30

EC50 and Max KD of anti-PAPD5/PAPD compounds on chromosomal integrated HBs mRNA and HBsAg expressed from the chromosomal integrant (average of 3 biological replicates and 2 technical duplicates) in Hep3B cells.

| | HBsAg | | HBs mRNA | | |
|---|---|---|---|---|---|
| CMP ID NO | Max KD % Avg | EC50 µM Avg | Max KD % of saline Avg | EC50 µM Avg | Compound |
| 20_12 | 26.51 | 0.37 | 49.94 | 0.33 | GN2-C6ocoaoTCAactttcacttCAG |
| 20_21 | 45.17 | 1.55 | 52.85 | 0.27 | GN2-C6ocoaoTcAACtttcacttCAG |
| 20_20 | NA | >20 | 67.68 | 0.13 | GN2-C6ocoaoTcAACtttcactTcAG |
| 21_34 | 82.3 | NA | 86.73 | NA | GN2-C6ocoaoTcAactttcacttCAGT |
| 20_13 | 14.25 | 0.43 | 27.67 | 0.19 | GN2-C6ocoaoTCAActttcactTCAG |
| 20_14 | 19.60 | 0.30 | 35.97 | 0.15 | GN2-C6ocoaoTCAActttcacttCAG |
| 21_33 | 56.68 | 5.33 | 68.22 | 0.02 | GN2-C6ocoaoTcAActttcacttCAGT |

NA = not applicable

TABLE 31

EC50 and Max KD of anti-PAPD5/PAPD7 compounds on on PAPD5 and PAPD7 mRNA expression (average of 3 biological replicates and 2 technical duplicates) in Hep3B cells.

| | PAPD5 mRNA | | PAPD7 mRNA | | |
|---|---|---|---|---|---|
| CMP ID NO | Max KD % of saline Avg | EC50 µM Avg | Max KD % of saline Avg | EC50 µM Avg | Compound |
| 20_12 | 10.83 | 0.16 | 14.08 | 10.18 | GN2-C6oCoaoTcAactttcacttCAG |
| 20_21 | 15.57 | 0.33 | 15.72 | 0.35 | GN2-C6ocoaoTcAACtttcacttcAG |
| 20_20 | 27.34 | 0.17 | 33.46 | 0.22 | GN2-C6ocoaoTcAACtttcactTcAG |
| 21_34 | 21.51 | 0.43 | 33.83 | 0.46 | GN2-C6ocoaoTcAactttcacttCAGT |
| 20_13 | 9.76 | 0.11 | 12.31 | 0 17 | GN2-C6ocoaoTCAActttcactTCAG |
| 20_14 | 5.17 | 0.15 | 7.78 | 0.17 | GN2-C6ocoaoTCAACtttcacttCAG |
| 21_33 | 21.19 | 0.16 | 30.13 | 0.31 | GN2-C6ocoaoTcAActttcacttCAGT |

From these data it can be seen that 4 out of the 7 tested oligonucleotides are capable of reducing HBsAg and HBs mRNA expression from an intergrated HBs fragment to less than 55% of the saline control.

Example 17 Effect of a Selected Bispecific PAPD5 and PAPD7 Targeting Oligonucleotide in Non-Human Primates Inhibition of PAPD5 and PAPD7 mRNA expression in the liver of cynomolgus macaques was quantified by RNA-sequencing. The animals were treated once-weekly with either saline or 1, 3, or 10 mg/kg/week with compound ID NO 2012 for 4 weeks (6 animals per group, 5 doses total at days 1, 8, 15, 22 and 29) and sacrificed on day 29 (4 weeks post dosing). In parallel, animals were treated once-weekly with either saline or 10 mg/kg/week of compound ID NO 2012), again for 4 weeks, for a total of 5 doses, but with a 4 week recovery period and sacrificed at day 56 (4 week dosing+4 weeks recovery).

Liver samples were collected in RNA-Later (Qiagen cat. 76104) within 20 min after exsanguination. Approximately 10 mg of tissue were lysed in 800 microL Magnapure lysis buffer (Roche) using the Tissue Lyser II (Qiagen). 350 microL aliquots of lysates were then transferred into the Magnapure 96 Deep Well Plate and processed automatically. RNA was quantified by absorption spectroscopy (Nanodrop. ThermoFischer) and RNA integrity (as per RNA integrity number, RIN) was controlled by microfluidic capillary array electrophoresis using the Agilent Bioanalyzer 2100 with RNA 6000 Nanochips (Agilent cat. 5067-1511).

For the construction of barcoded cDNA libraries, 400 ng total RNA aliquots were used as input for the TruSeq™ Stranded Total RNA kit (Illumina cat. 20020598) in conjunction with the Ribo-Zero™ Gold rRNA Removal Kit (Illumina cat. MRZG12324). The size distribution of the libraries was estimated by electrophoresis using the Agilent High Sensitivity DNA kit (cat. 5067-4627). The libraries were quantified using the KAPA Library Quantification qRT-PCR kit (Kapa Biosystems cat. KK4824). The libraries were pooled at equimolar concentrations and diluted to 11 pM prior to loading onto a flow cell of the Illumina HiSeq 4000 sequencer as follows The libraries were extended using the HiSeq PE Rapid Cluster Kit v2 (Illumina cat. PE-402-4002). The flow cells carrying amplified clusters were sequenced using paired-end reads (50-base pairs) with the TruSeq Rapid SBS Kit-HS (illumina cat. FC-402-4001). Real time image analysis and base calling were performed using the HISeq Sequencing Control Software (HCS). CASAVA software version 1.8 was used for production of FASTQ files of sequence read pairs.

The lowest library size obtained was 17 million read pairs and the highest was 114 million read pairs. On average there were 50 million read pairs per sample and the median was at 47 million read pairs per sample. Read pairs of each library were aligned to the Cynomolgus transcripts from the RefSeq/NCBI database using the GSNAP program to generate gene-level raw counts. These were normalized to the respective library size (for inter-samples comparisons) and for each transcript the data were further normalized to the respective transcript length (for inter-transcript comparisons). For all samples this generated transcript-level expression in normalized units RPKMs (Reads Per Kilobase of transcript, per Million mapped reads). The values for PAPD5 and PAPD7 in the treated animals were normalized to the saline-treated animals, at the corresponding timepoint the results are shown in table 32.

TABLE 32

PAPD5 and PAPD7 mRNA expression in liver of cynomolgus monkeys treated with CMP ID NO 20_12.

| CMP ID NO 20_12 | Dose | PAPD5 mRNA % of saline*, geometric mean | PAPD5 mRNA geometric SD factor | PAPD7 mRNA % of saline*, geometric mean | PAPD7 mRNA geometric SD factor |
|---|---|---|---|---|---|
| After 4 wk dosing | Saline | 100 | 1.35 | 100 | 1.24 |
| | 1 mg/kg | 24.2 | 1.31 | 46.4 | 1.30 |
| | 3 mg/kg | 18.2 | 1.23 | 37.1 | 1.40 |
| | 10 mg/kg | 19.3 | 1.34 | 33.8 | 1.22 |
| After 4 wk dosing + 4 wk follow up | Saline | 100 | 1.13 | 100 | 1.26 |
| | 10 mg/kg | 21.8 | 1.65 | 45.5 | 1.31 |

*normalized to control animals for same time-point

Relatively to the respective vehicle control group, the results show down-regulation of PAPD5 and PAPD7 mRNAs in liver, both in the main group animals and in recovery animals, at all tested dose levels of CMP ID NO 20_12. The down-regulation of PAPD5 mRNA appeared saturated in the liver with around 80% at 3 and 10 mg/kg. The down-regulation of PAPD7 mRNA was dose-related, reaching 66% reduction of mRNA at 10 mg/kg. In the recovery animals dosed with 10 mg/kg/week, the down-regulation of PAPD5 mRNA was 78%. For PAPD7 mRNA, the down-regulation reached 55%. The latter data Indicates that the PAPD5 and PAPD7 mRNA inhibition persisted in the liver at least for 4 weeks after last dose.

Example 18 Effect on HBsAg and HBeAg in HBV Infected Mice Following Administration of PAPD5 and PAPD7 Targeting Oligonucleotides The present study sets out to show an in vivo effect on the HBV propagation parameters when reducing the PAPD5 and PAPD7 transcripts in the AAV/HBV mouse model.

Figure 11B:
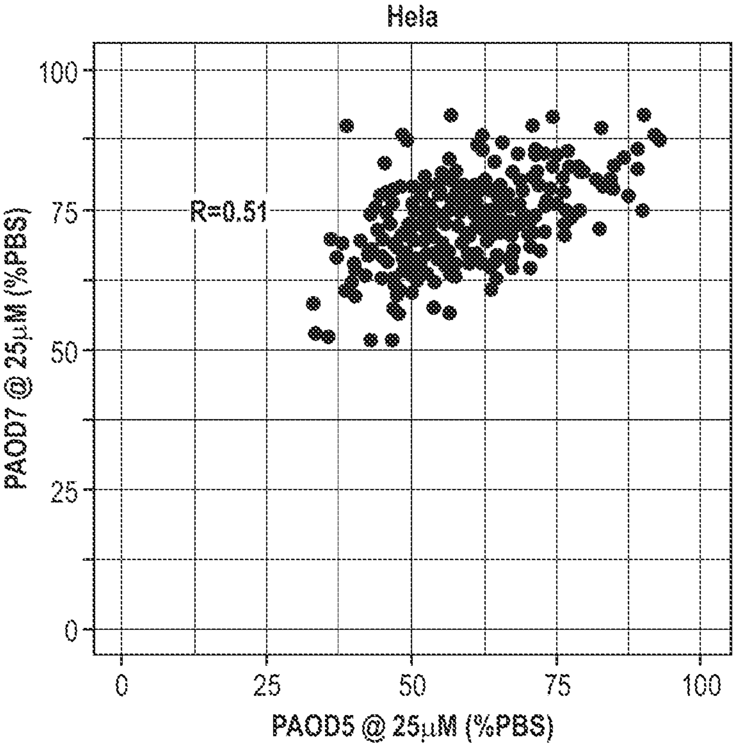
Figure 12:
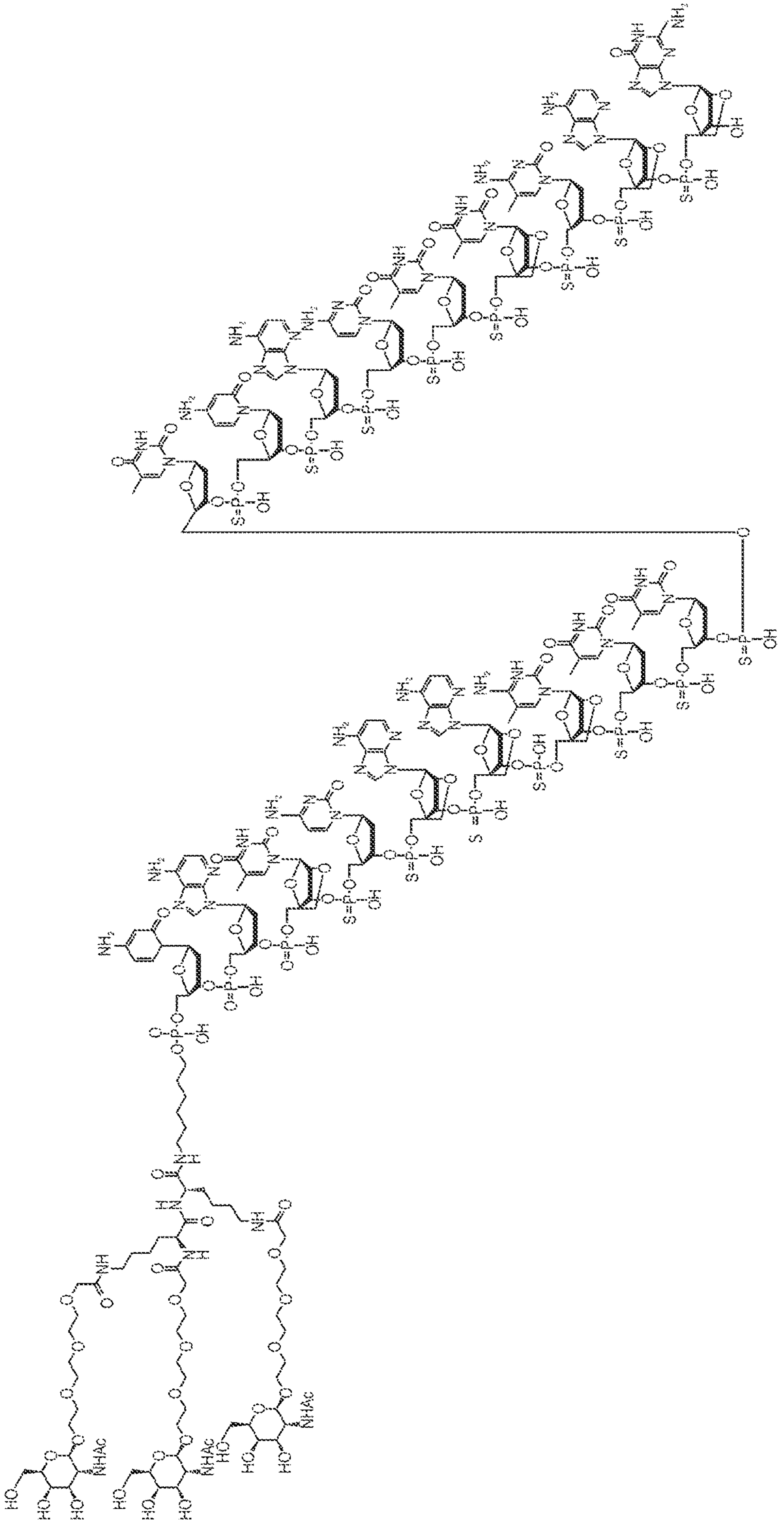
FIG. 12: Structural formula of CMP ID NO: 20_20. Pharmaceutical salts thereof include monovalent or divalent cations, such as Na+, K+, and Ca2+ or a mixture of these being associated with the compound.
Figure 13:
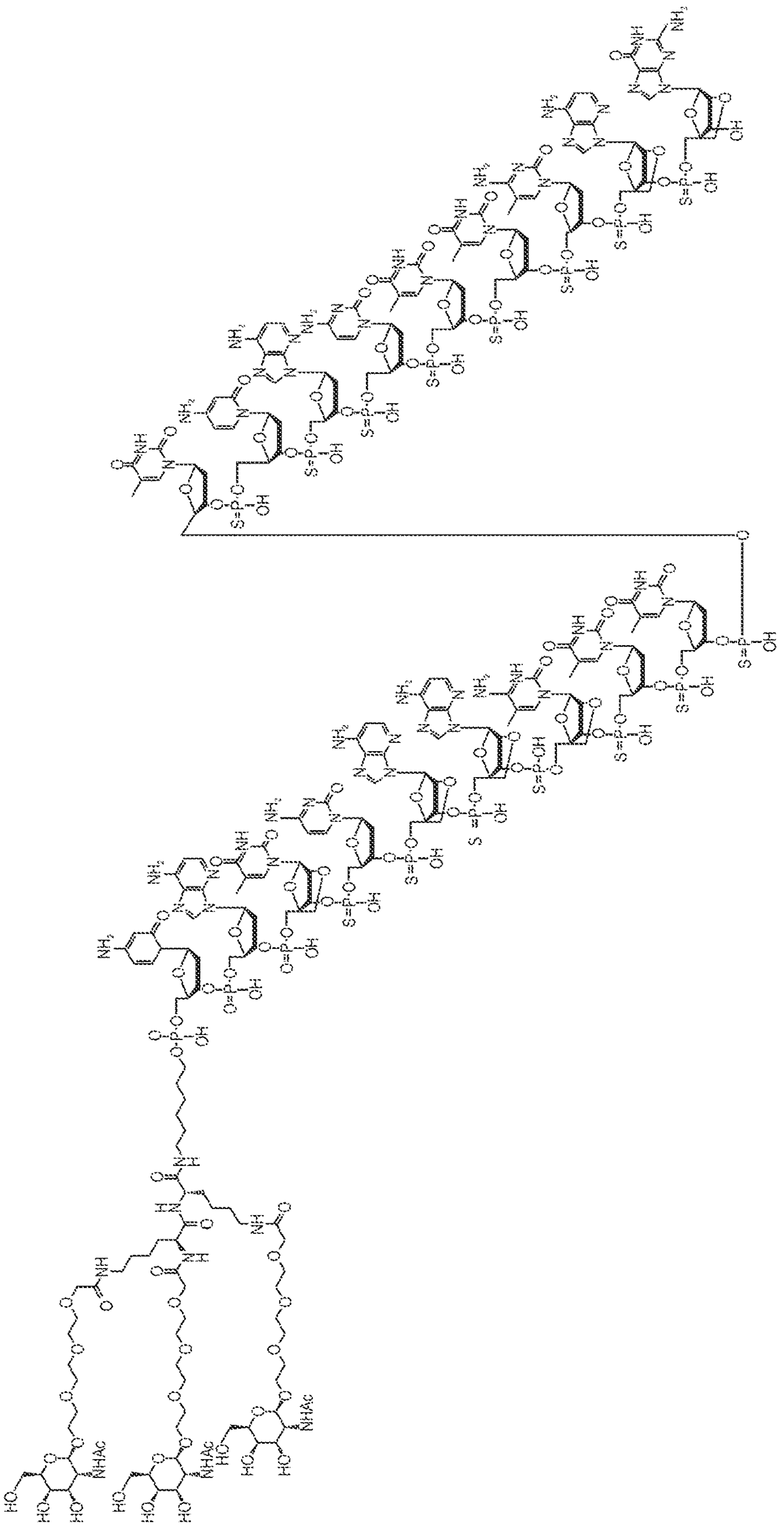
FIG. 13: Structural formula of CMP ID NO: 20_21. Pharmaceutical salts thereof include monovalent or divalent cations, such as Na+, K+, and Ca2+ or a mixture of these being associated with the compound.
Figure 14:
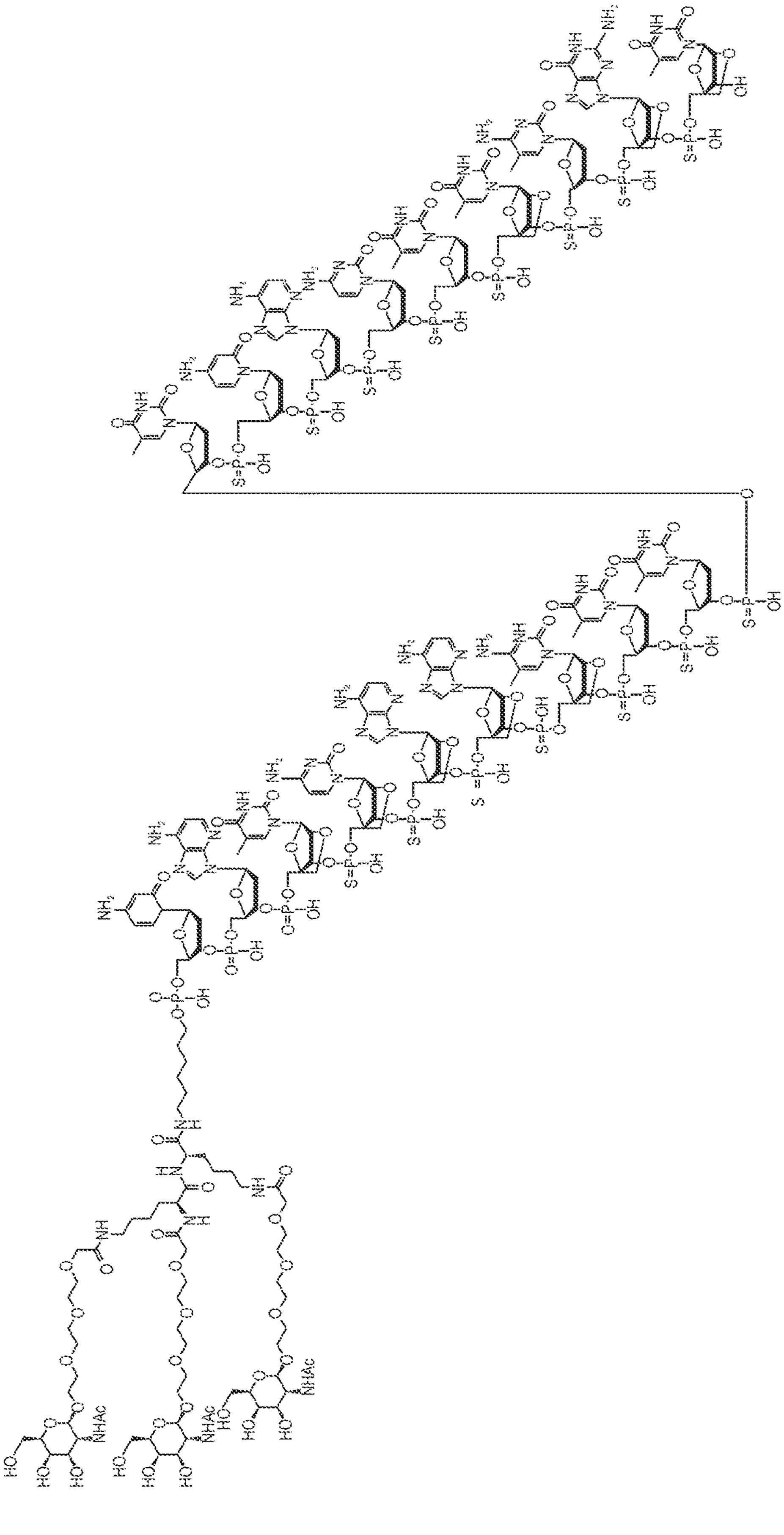
FIG. 14: Structural formula of CMP ID NO: 21_2. Pharmaceutical salts thereof include monovalent or divalent cations, such as Na+, K+, and Ca2+ or a mixture of these being associated with the compound.
Figure 15:
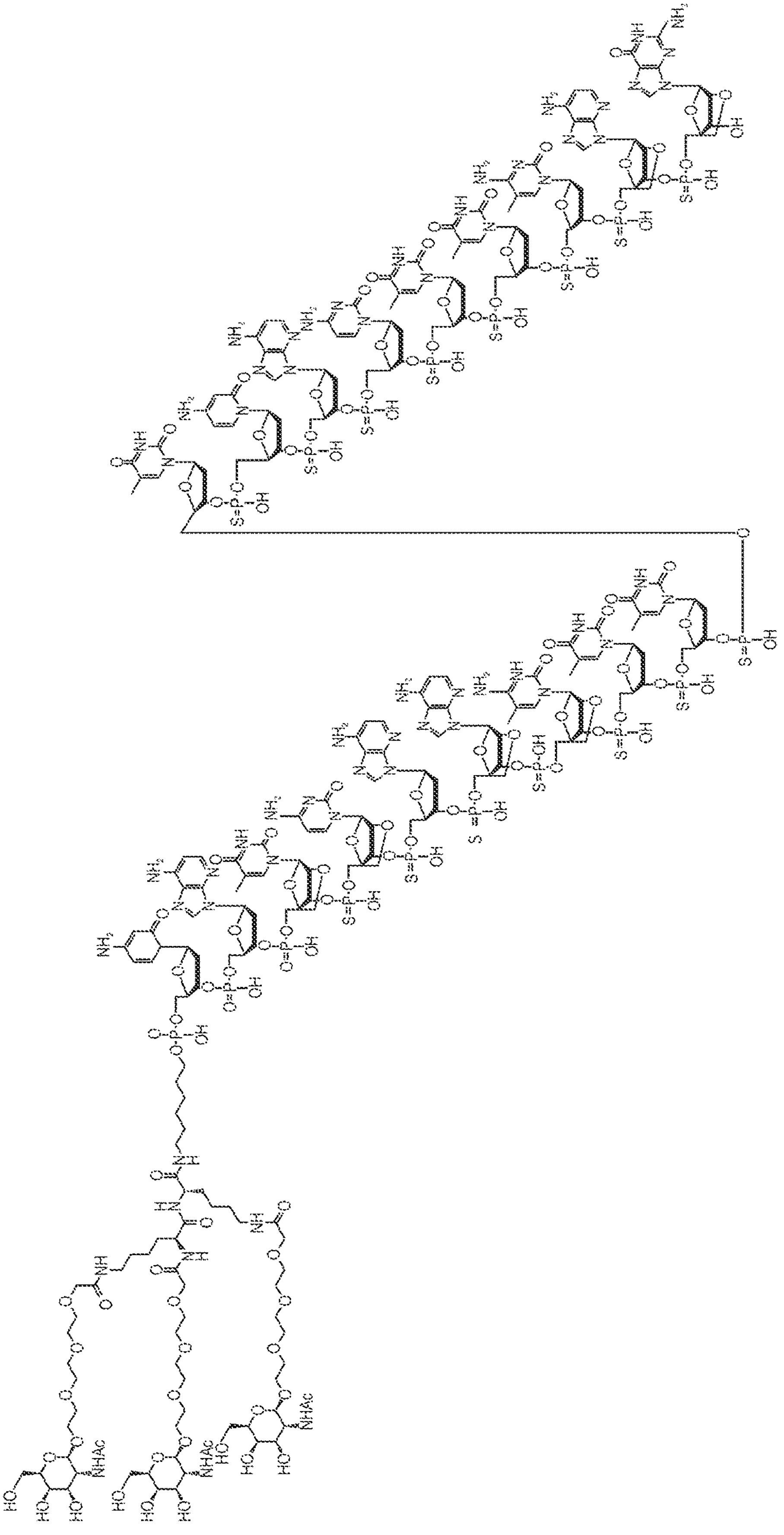
FIG. 15: Structural formula of CMP ID NO: 20_22. Pharmaceutical salts thereof include monovalent or divalent cations, such as Na+, K+, and Ca2+ or a mixture of these being associated with the compound.
Figure 16:
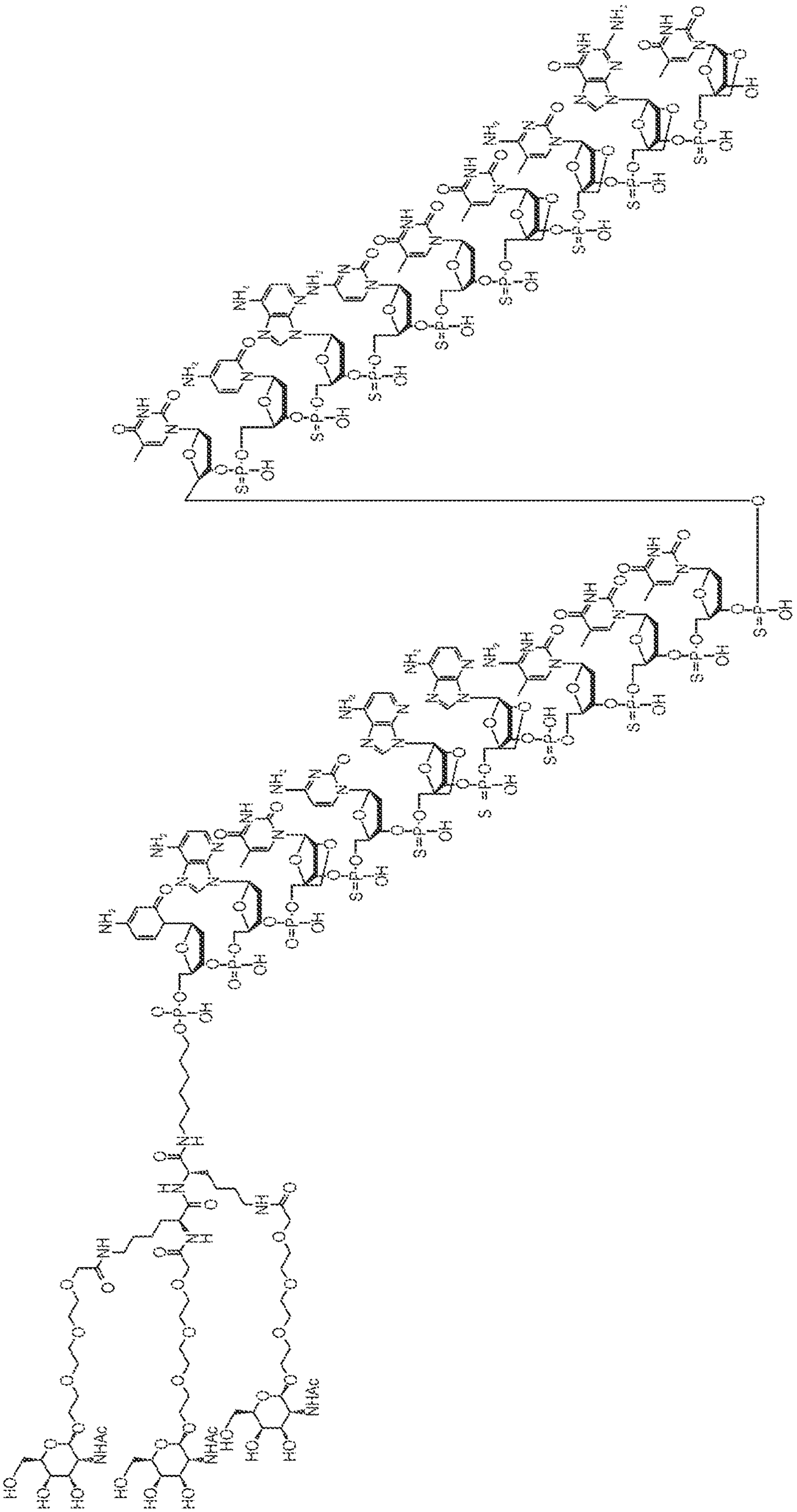
FIG. 16: Structural formula of CMP ID NO: 21_33. Pharmaceutical salts thereof include monovalent or divalent cations, such as Na+, K+, and Ca2+ or a mixture of these being associated with the compound.
Figure 17:
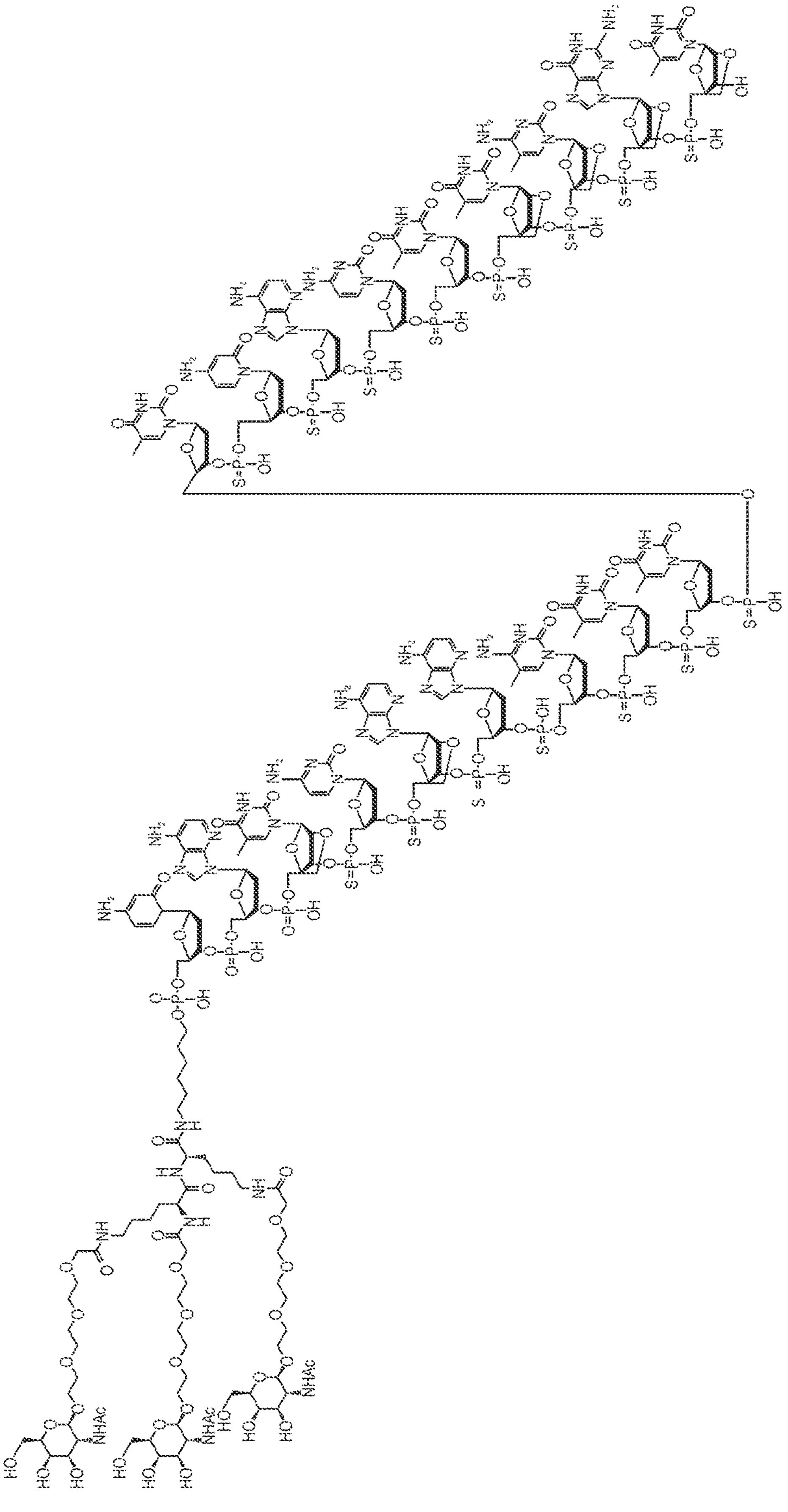
FIG. 17: Structural formula of CMP ID NO: 21_34. Pharmaceutical salts thereof include monovalent or divalent cations, such as Na+, K+, and Ca2+ or a mixture of these being associated with the compound.

Example 14 and FIG. 11B showed that it was challenging to target both PAPD5 and PAPD7 in a mouse cell line using a single oligonucleotide. In the present study a combination of two oligonucleotides, one targeting mouse PAPD5 (CMP ID NO: 22_1) and one targeting mouse PAPD7 CMP ID NO: 22_1) listed in table 33, has therefore been used.

The AAV/HBV mouse model described in the Materials and Method section was used. Mice (3 pr. group) were dosed subcutaneously with a single dose of 10 mg/kg of each of compounds 22_1 and 23_1 (two separate injections 6 hours apart) or with 5 ml/kg saline (control) on day 0. HBsAg and HBeAg in serum was measured every 3 days using the methods described in the "Materials and Methods" section. To measure target knockdown two Intermediate groups of mice were sacrificed on day 3 and day 14 and the remaining mice were sacrificed on day 27. After scarification their liver was removed following PBS perfusion. The perfused liver was cut in smaller pieces and directly frozen.

mRNA was extracted from the frozen liver pieces by adding them to 2 ml tubes containing ceramic beads and 1 ml MagNA Pure lysis buffer (Roche #05467535001). The liver pieces were homogenized using the TissueLyser (Qiagen). RNA was isolated from the tissue homogenates using MagNA Pure "96 Cellular RNA Large Volume Kit" (Roche #05467535001). The lysates may be stored at −80° C. PAPD5 and PAPD7 mRNA was measured essentially using qPCR as described in the Materials and Method section, with the following change in the TaqMan primer assay, which was performed with the following two assay (ThermoFisher Scientific):

| | |
|---|---|
| Mouse GUSB | Mm1197698_m1 |
| Mouse PAPD5 | Mm1244121_m1 |
| Mouse PAPD7 | Mm1349513_m1 |
| Mouse TBP | Mm00446971_m1 |

TABLE 33

Oligonucleotides targeting mouse PAPD5 (SEQ ID NO: 5) or mouse PAPD7 (SEQ ID NO: 6)

| SEQ ID NO | Motif sequence | Start | End | CMP ID NO | Compound |
|---|---|---|---|---|---|
| 22 | caacataagtctacacatcc | SEQ ID NO: 5 60034 | 60051 | 22_1 | 5'-GN2-C6$_o$c$_o$a$_o$ACataagtctacacATCC |
| 23 | cagttttaccgattcatca | SEQ ID NO. 6 10684 | 10700 | 23_1 | 5'-GN2-C6$_o$c$_o$a$_o$GTtttaccgattcATCA |

GN2 represents the trivalent GalNAc cluster shown in FIG. 2. C6 represents an amino alkyl group with 6 carbons, capital letters represent beta-D-oxy LNA nucleosides, lowercase letters represent DNA nucleosides, all LNA C are 5-methyl cytosine, subscript o represent a phosphodiester nucleoside linkage and unless otherwise indicated internucleoside linkages are phosphorothioate internucleoside linkages.

-continued

| | |
|---|---|
| Mouse PAPD5 | Mm_011244125m1 |
| Mouse PAPD7 | Mm1349513_m1 |

GUSB and TBP are housekeeping genes used for normalization of the PAPD5 and PAPD7 mRNA measured with the primer assay indicated below the housekeeping gene.

Figure 18A:
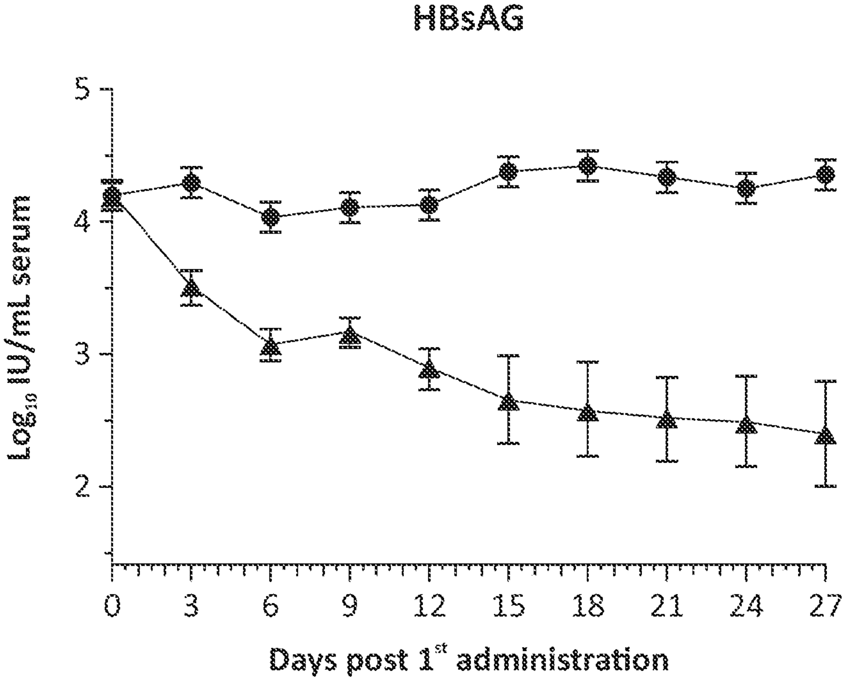
FIGS. 18A and 18B: Effect on HBsAg (FIG. 18A) and HBeAg (FIG. 18B) over time in vivo in the AAV/HBV mouse model following a single treatment with 10 mg/kg of two oligonucleotides one targeting PAPD5 and one targeting PAPD7.
Figure 18B:
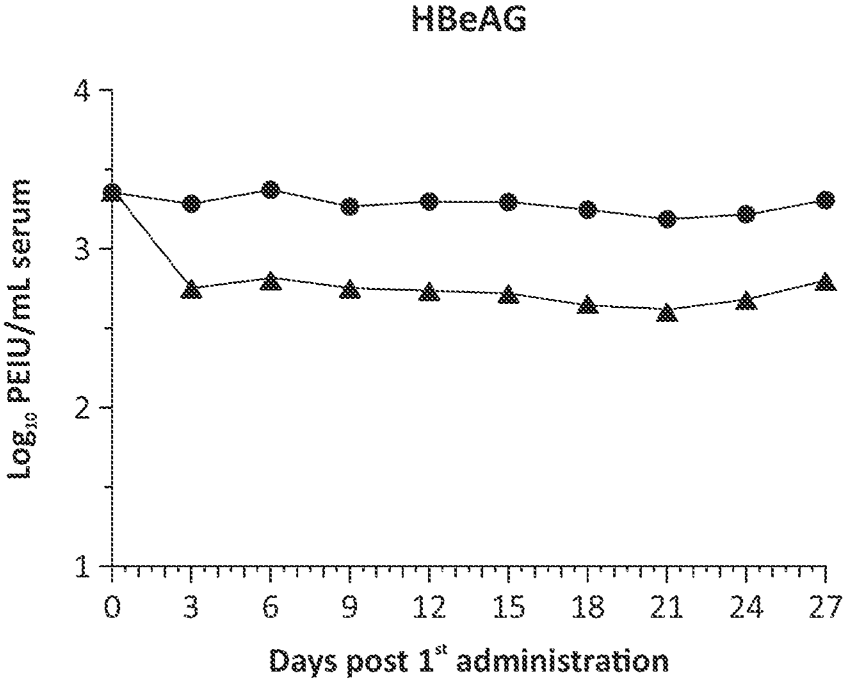

The results are shown in the table 34, 35 and 36 below. The data in table 34 are furthermore presented in FIGS. 18A and B.

TABLE 34

HBsAg (Log10 IU/mL serum) in AAV/HBV mice treated with PAPD5 and PAPD7 targeting oligonucleotides

| | Control (5 ml/kg saline) | | | PAPD5 and PAPD7 oligonucleotide (10 mg/kg each) | | |
|---|---|---|---|---|---|---|
| Day | HBsAg Mean (Log10 IU/mL) | SD | No of animals | HBsAg Mean (Log10 IU/mL) | SD | No of animals |
| 0 | 4.21 | 0.19 | 10 | 4.23 | 0.31 | 11 |
| 3 | 4.30 | 0.19 | 10 | 3.50 | 0.43 | 11 |
| 6 | 4.05 | 0.29 | 7 | 3.08 | 0.36 | 8 |
| 9 | 4.12 | 0.29 | 7 | 3.17 | 0.35 | 8 |
| 12 | 4.15 | 0.32 | 7 | 2.89 | 0.44 | 8 |
| 15 | 4.39 | 0.12 | 4 | 2.67 | 0.75 | 5 |
| 18 | 4.45 | 0.23 | 4 | 2.59 | 0.80 | 5 |
| 21 | 4.36 | 0.14 | 4 | 2.51 | 0.73 | 5 |
| 24 | 4.27 | 0.11 | 4 | 2.50 | 0.77 | 5 |
| 27 | 4.37 | 0.06 | 4 | 2.41 | 0.90 | 5 |

The data show that targeting PAPD5 and PAPD7 in the AAV/HBV mouse model with a single treatment resulted in a sustained 2 log reduction in HBsAg up to 27 days after treatment.

TABLE 35

HBeAg (Log10 IU/mL serum) in AAV/HBV mice treated with PAPD5 and PAPD7 targeting oligonucleotides

| | Control (5 ml/kg saline) | | | PAPD5 and PAPD7 oligonucleotide (10 mg/kg each) | | |
|---|---|---|---|---|---|---|
| Day | HBeAg Mean (Log10 IU/mL) | SD | No of animals | HBeAg Mean (Log10 IU/mL) | SD | No of animals |
| 0 | 3.39 | 0.06 | 10 | 3.40 | 0.05 | 11 |
| 3 | 3.31 | 0.06 | 10 | 2.75 | 0.07 | 11 |
| 6 | 3.39 | 0.05 | 7 | 2.83 | 0.03 | 8 |
| 9 | 3.29 | 0.05 | 7 | 2.77 | 0.04 | 8 |
| 12 | 3.33 | 0.03 | 7 | 2.75 | 0.05 | 8 |
| 15 | 3.32 | 0.06 | 4 | 2.74 | 0.05 | 5 |
| 18 | 3.28 | 0.04 | 4 | 2.67 | 0.02 | 5 |
| 21 | 3.22 | 0.03 | 4 | 2.63 | 0.01 | 5 |
| 24 | 3.24 | 0.04 | 4 | 2.70 | 0.03 | 5 |
| 27 | 3.32 | 0.05 | 4 | 2.80 | 0.04 | 5 |

TABLE 36

PAPD5 and PAPD7 mRNA in AAV/HBV mice (3 animals on day 3 and 14 and 5 on day 27) and ALT levels (11 animals day 0, 8 on day 14 and 5 on day 27) following a single dose treatment with PAPD5 and PAPD7 targeting oligonucleotides (10 mg/kg of each).

| | % PAPD5 mRNA of control | | % PAPD7 mRNA of control | | ALT (U/L) Control | | ALT (U/L) Treated | |
|---|---|---|---|---|---|---|---|---|
| Day | Avg | sd | Avg | sd | Avg | sd | Avg | sd |
| 0 | NA | NA | NA | NA | 30.91 | 6.95 | 27.27 | 7.55 |
| 3 | 14.47 | 4.20 | 24.82 | 3.43 | NA | NA | NA | NA |
| 14 | 21.995 | 5.13 | 20.37 | 1.75 | 37.50 | 14.49 | 47.00 | 26.51 |
| 27 | 37.543 | 7.65 | 27.52 | 8.08 | 28.80 | 9.55 | 28.00 | 18.97 |

From these data it can be seen that the PAPD5 and PAPD7 targeting oligonucleotides leads to reduction in PAPD5 and PAPD7 mRNA levels, respectively, and are well tolerated in the AAV/HBV mouse model.

The invention claimed is:

1. An antisense oligonucleotide selected from the group of:

```
(i)
                                  (SEQ ID NO: 18)
TCaACtttcacttcAG

(ii)
                                  (SEQ ID NO: 18)
TcAACtttcacttcAG

(iii)
                                  (SEQ ID NO: 17)
TCAActttcacttCaGT

(iv)
                                  (SEQ ID NO: 17)
TcAActttcacttCAGT;
and

(v)
                                  (SEQ ID NO: 17)
TcAactttcacttCAGT;
```

or a pharmaceutically acceptable salt thereof;

wherein capital letters represent beta-D-oxy LNA nucleosides; lowercase letters represent DNA nucleosides; all cytosine LNA nucleosides are 5-methyl cytosine; and all internucleoside linkages are phosphorothioate internucleoside linkages.

2. The antisense oligonucleotide of claim 1, wherein the antisense oligonucleotide is TCaACtttcacttcAG (SEQ ID NO: 18) or a pharmaceutically acceptable salt thereof.

3. The antisense oligonucleotide of claim 1, wherein the antisense oligonucleotide is TcAACtttcacttcAG (SEQ ID NO: 18) or a pharmaceutically acceptable salt thereof.

4. The antisense oligonucleotide of claim 1, wherein the antisense oligonucleotide is TCAActttcacttCaGT (SEQ ID NO: 17) or a pharmaceutically acceptable salt thereof.

5. The antisense oligonucleotide of claim 1, wherein the antisense oligonucleotide is TcAActttcacttCAGT (SEQ ID NO: 17) or a pharmaceutically acceptable salt thereof.

6. The antisense oligonucleotide of claim 1, wherein the antisense oligonucleotide is TcAactttcacttCAGT (SEQ ID NO: 17) or a pharmaceutically acceptable salt thereof.

7. A conjugate compound comprising the antisense oligonucleotide of claim 1 and a conjugate moiety attached to said antisense oligonucleotide.

8. The conjugate compound of claim 7, wherein the conjugate moiety is capable of binding to an asialoglycoprotein receptor.

9. The conjugate compound of claim 8, wherein the conjugate moiety is a tri-valent N-acetyl-galactosamine (GalNAc) moiety.

10. The conjugate compound of claim 7, wherein the conjugate moiety is covalently attached to said antisense oligonucleotide.

11. The conjugate compound of claim 7, wherein a linker is positioned between the antisense oligonucleotide and the conjugate moiety.

12. The conjugate compound of claim 11, wherein the linker is a physiologically labile linker.

13. The conjugate compound of claim 12, wherein the physiologically labile linker is a S1 nuclease susceptible linker.

14. The conjugate compound of claim 12, wherein the physiologically labile linker is a phosphodiester linked cytidine-adenosine dinucleotide with three consecutive phosphodiester linkages.

15. The conjugate compound of claim 12, wherein a C6 amino alkyl group is positioned between the conjugate moiety and the physiologically labile linker.

16. The conjugate compound of claim 7, wherein the conjugate moiety is capable of binding to an asialoglycoprotein receptor and wherein the conjugate moiety is a tri-valent N-acetyl-galactosamine (GalNAc) moiety;

wherein the conjugate moiety is covalently attached to said antisense oligonucleotide;

wherein a phosphodiester linked cytidine-adenosine dinucleotide with three consecutive phosphodiester linkages is positioned between the antisense oligonucleotide and the conjugate moiety; and wherein a C6 amino alkyl group is positioned between the conjugate moiety and the phosphodiester linked cytidine-adenosine dinucleotide with three consecutive phosphodiester linkages.

17. The conjugate compound of claim 7, that has a formula selected from the group of:

(i) (SEQ ID NO: 20)

$GN2\text{-}C6_{o}c_{o}a_{o}$ TCaACtttcacttcAG;

(ii) (SEQ ID NO: 20)

$GN2\text{-}C6_{o}c_{o}a_{o}$ TcAACtttcacttcAG;

(iii) (SEQ ID NO: 21)

$GN2\text{-}C6_{o}c_{o}a_{o}$ TCAActttcacttCaGT;

(iv) (SEQ ID NO: 21)

$GN2\text{-}C6_{o}c_{o}a_{o}$ TcAActttcacttCAGT;
and (v) (SEQ ID NO: 21)

$GN2\text{-}C6_{o}c_{o}a_{o}$ TcAactttcacttCAGT wherein capital letters represent beta-D-oxy LNA nucleosides;

all cytosine LNA nucleosides are 5-methyl cytosine;

lowercase letters represent DNA nucleosides; subscript o represents a phosphodiester nucleoside linkage; and all other internucleoside linkages are phosphorothioate internucleoside linkages;

wherein C6 represents an amino alkyl group with 6 carbons; and wherein GN2 represents a trivalent GalNAc cluster shown in FIG. 2;

wherein the wavy bond line in FIG. 2 indicates the site of conjugation of the trivalent GalNAc cluster to the C6 amino alkyl group.

18. A pharmaceutically acceptable salt of the antisense oligonucleotide of claim 1.

19. A pharmaceutically acceptable sodium salt of the antisense oligonucleotide of claim 1.

20. A pharmaceutically acceptable potassium salt of the antisense oligonucleotide of claim 1.

21. A pharmaceutical composition comprising the antisense oligonucleotide of claim 1 or a pharmaceutically acceptable salt thereof, and a pharmaceutically acceptable diluent, solvent, carrier, salt and/or adjuvant.

22. The pharmaceutical composition of claim 21 wherein the pharmaceutically acceptable diluent is sterile phosphate buffered saline.

23. An in vitro method for modulating PAPD5 and PAPD7 expression in a target cell which is expressing PAPD5 and PAPD7, the method comprising administering the antisense oligonucleotide of claim 1 or a pharmaceutically acceptable salt thereof to said target cell in an effective amount.

24. The antisense oligonucleotide of claim 1 or a pharmaceutically acceptable salt thereof; or a pharmaceutical composition thereof, for use in treating an HBV infection in a subject.

25. The antisense oligonucleotide of claim 1 or a pharmaceutically acceptable salt thereof, or a pharmaceutical composition thereof for use in treating chronic HBV infection in a subject.

26. The antisense oligonucleotide of claim 1, a pharmaceutically acceptable salt thereof, or a pharmaceutical composition thereof, for use in reducing the infectiousness of a HBV-infected subject.

27. A method for treating HBV infection in a subject suffering from HBV infection, the method comprising administering a therapeutically effective amount of the antisense oligonucleotide of claim 1, a pharmaceutically acceptable salt thereof, or a pharmaceutical composition thereof to the subject suffering from HBV infection.

28. A method for treating chronic HBV infection in a subject suffering from chronic HBV infection, the method comprising administering a therapeutically effective amount of the antisense oligonucleotide of claim 1, a pharmaceutically acceptable salt thereof, or a pharmaceutical composition thereof to the subject suffering from chronic HBV infection.

29. A method for reduction of the infectiousness of a HBV-infected subject, the method comprising administering a therapeutically effective amount of the antisense oligonucleotide of claim 1, a pharmaceutically acceptable salt thereof, or a pharmaceutical composition thereof to the HBV-infected subject.

30. A pharmaceutically acceptable salt of the conjugate compound of claim 17.

31. A pharmaceutically acceptable sodium salt of the conjugate compound of claim 17.

32. A pharmaceutically acceptable potassium salt of the conjugate compound of claim 17.

33. A pharmaceutical composition comprising the conjugate compound of claim 17 or a pharmaceutically acceptable salt thereof, and a pharmaceutically acceptable diluent, solvent, carrier, salt and/or adjuvant.

34. The pharmaceutical composition of claim 33 wherein the pharmaceutically acceptable diluent is sterile phosphate buffered saline.

35. An in vitro method for modulating PAPD5 and PAPD7 expression in a target cell which is expressing PAPD5 and PAPD7, the method comprising administering the conjugate compound of claim 17 or a pharmaceutically acceptable salt thereof to said target cell in an effective amount.

36. The conjugate compound of claim 17 or a pharmaceutically acceptable salt thereof; or a pharmaceutical composition thereof, for use in treating an HBV infection in a subject.

37. The conjugate compound of claim 17 or a pharmaceutically acceptable salt thereof, or a pharmaceutical composition thereof for use in treating chronic HBV infection in a subject.

38. The conjugate compound of claim 17, a pharmaceutically acceptable salt thereof, or a pharmaceutical composition thereof, for use in reducing the infectiousness of a HBV-infected subject.

39. A method for treating HBV infection in a subject suffering from HBV infection, the method comprising administering a therapeutically effective amount of the conjugate compound of claim 17, a pharmaceutically acceptable salt thereof, or a pharmaceutical composition thereof to the subject suffering from HBV infection.

40. A method for treating chronic HBV infection in a subject suffering from chronic HBV infection, the method comprising administering a therapeutically effective amount of the conjugate compound of claim 17, a pharmaceutically acceptable salt thereof, or a pharmaceutical composition thereof to the subject suffering from chronic HBV infection.

41. A method for reduction of the infectiousness of a HBV-infected subject, the method comprising administering a therapeutically effective amount of the conjugate compound of claim 17, a pharmaceutically acceptable salt thereof, or a pharmaceutical composition thereof to the HBV-infected subject.

* * * * *

SEQUENCE LISTING

```
Sequence total quantity: 34
SEQ ID NO: 1            moltype = DNA  length = 82393
FEATURE                 Location/Qualifiers
source                  1..82393
                        mol_type = unassigned DNA
                        organism = Homo sapiens
SEQUENCE: 1
acaacgcgct ccctgcgggg cgggcggcaa cctccatgcg gcctcgtcca cgctcagcac  60
cggggaagcc gaggcggaga agccgcgcgc gcctcagaag ctcccggacg cccaggtacg  120
tgggagcact ccacagatgg cgcaagtacg gttgggccag gcggttgcgg ccccgtcgcg  180
ccgcggcctc tgtgacgcac ggcgaggcct cccgggctgc tgcgcggcgc agcgggggcg  240
gggcgagcgc gtgagggcgg ggcggtgggg gggggggcg gagcgagagg ggcggagccg  300
```

-continued gcagaggccc cgccccgggg ccggaggagc gaggacgcta cggagcaggc gcgtctcgct 360
gccgccgctg ccgccgccgc cgctcgctct tctgtggagc cgccgccgcc gccgccgcca 420
tttgcacggg gaccccagtg acaggggctc ggcggagggg cggaggggcg gagggagggg 480
gggagggccc gcggagcccc cgagggcggg agcgacgccg ccggcgccgg ccgggctccc 540
tgcgcgaccg cgccgcccgc ggcgggcccc gagcagcagc agcagcagca gcggcagcag 600
cggcagcagc agcagcagcc gaggccgggc gtgcgcctga ggcggcggcg gcggcggccc 660
tgcgggcggc cgggaggggc gggggcagcg gccgccgccg tttgatggat ccgaggatcg 720
cctggtttca gccagagcag ctcggaccgt ccaacagtct gtggatgcag atctgggaga 780
cgacccaggg gctgaggaac ctctacttca accaccactg tcacagcagc ggcggcgcga 840
gcggcggcgg cggcagcagc agcagcagca gcacggccac cggcgggagc ggcagcagca 900
ccggcagccc cggcggcgcg gcctcggccc cggccccggc cccggccggc atgtatcgct 960
ccggggagcg cctgctgggc agccacgcgc tgcccgcgga gcagcgggac ttcctgcccc 1020
tagagacgac caacaacaac aacaaccacc accagcccgg ggcctgggcc cgccgggcgg 1080
gctcctcggc gtcctcgcct ccctcggcgt cctcgtcccc gcacccttcg gccgccgtcc 1140
ccgccgccga tccagccgat tcggcctcgg gcagcagcaa caagaggaag cgcgacaaca 1200
aggccagcac gtatggactc aactacagcc tgctgcagcc cagcggaggg cgggccgcgg 1260
ggggcggccg agcagacggc ggcggggtcg tgtacagcgg gaccccgtgg aaacggagga 1320
actacaacca gggagtcgtg gggtgagtgc tggctctgcg gcccgatggc ctggccggtg 1380
cgaatgcgca gccgggcaca cgcccacaga ggggggttgt gagggtctag gagcggccac 1440
ccccacggcc tgccttcgct gctgttgcac gggggtgctg ctggccatcc ccaacccccc 1500
agtcgttcac acctttcccc aagcctcctt agccgtccac accctccgtc tcctgtcctc 1560
ccttagtcgt ccacaccttc ctcccctccc tcttaaccgt ccacaccttc cccaggcccc 1620
cccctttatc cattcactct cctcccatcc cccttagtta aacacatcta cccttgacca 1680
ccaccccgcc tccagccctc cacacctttt tccccatcat cacaactcaa gatgagaccg 1740
cttagcacgg gcctatcatt cattccctga gaacattggt gtgtgagtgt tttttgatgg 1800
tgcaggaccc ggaggtgctt tccttgccaa gaatagaaac atccagaatg ctcctcccca 1860
tcccccaatc ccagacagca attatgtcag ccctgtaagg cattgcctgc tcttgaccct 1920
ttggcccatc tttttatttt taaaaaattc ccatgtcaca gatgccctgt ctatgcagag 1980
ggtggcgtgg gatgggtgac cactaagttt aggctggtga aggtggtgag cccttctgag 2040
gccctgatag aactttccag gagttcatgg tccgcggctc cagcttctca ctgtaaagtt 2100
gtcatcctgg cagaggcagc caatgctttt cattctaggg ggtagagatt tatgctaatg 2160
agtgaatatt gcaccactag tgactttctg tttaaagttc agctcttaga aaatggaatc 2220
ttacctgacc cctagtgaat tatgtacata agcagggaat gtttccaact agatctccct 2280
tcagaagagt ccctgtgctg gaataggtca ctgaatctta tttgttttgt aaaacaaagc 2340
ttttgggtct cgtgggtgtg tgtgtgtgtg tgtgtgtgtg tgtgtgtgtg tgtgtagctt 2400
gagtatggag aaccggcttt caaattgctt ttcatttttc aggttgtgtt ttacattgag 2460
ggctttagca tgcaaatgaa attaccaatt agtaatccca tgtgaacctt ttcctggatt 2520
tattcattca gatctgccct gctttggctg agagagagag ttctgtgtac ctttttgaag 2580
gtctggataa aatgagttgg tgggttccat ctgcttccag tgggctggtg tctgctctat 2640
gctactatta caactcctac cttttgtgga aaatgcagtc aagcgttcta ggactggtgc 2700
tgtggtacat gtcaaacctg ccctcacatt ccagaaaggg aaccctttta gggttgagtc 2760
ctctgttgct aagcttcaag ggtgctctcc atggtcatca cgttttatta aaggcttgtg 2820
gttccatcct gttagcattt ccaagtctac gcgtaaacct gtggtttagt gacaagcaaa 2880
ttgatgttga gggtttctgg tagtttcatt tcacaggagt aagctccagt taggtaatca 2940
ctgtcaacga aaaccttgaa gttccttaat tgcattttac tgaagcctct ttgcatgtgt 3000
ctagcaaaag atataagtcc aagatgctta tttttttttt gataaattag aaattgtcct 3060
ctcctctact tgctatttaa tgcagaagat actctaaaag gttcatattt atacttagaa 3120
gcaagatgtt cttgttcctg attcaaatat attgccctca aagggattag gagaggaatt 3180
ttcatttccc ggagggatta ctgtttaaaa actggttgta aacctcttta aaaactgctt 3240
atcacttcac cagattttcc attcttttgc ctcctccctt agaggatgtc agcagttaat 3300
ttttttttta aattaaaaaa agttcaattc tgagacctcc tagtttcaaa aaatacatta 3360
aacaattccc aagagtgtta agagtgtctg ggtgcttaga aattcttgct ttgattcatg 3420
tattctgatt tttttttttt ttttgagacg gagtttcgct cttgttgccc aggctggagt 3480
gcagtggctc gatctcagct caccgcaacc tctgcctccc aggttcaagc gattctgctg 3540
cctcagcctc ccgagtagct gggattacag gcgcttgcca ccacgcctgg ctaatttttt 3600
atttttagta gagacggggt ttcttcatgt tggtcaggct ggtctcgaac tcctgacctc 3660
aggtgatctg cccgtcttgg cctcccaaag gactgggatt acaggcatga gccaccgtgc 3720
ccggcctcat tatcctgatt tctttttttt cttttgagac tgggtctcac tctgctgcct 3780
aggctggagt ggagtgacgt gatcatagct cactgtatcc tctaactctt gggctcaagt 3840
gatcctcctg ccttagcttc ctggagtagc tgggactaca ggcacatgtc accacacctg 3900
cctaattttt ttatttttac tttttgtaga gatggggcct ccatttgttg cctaggctgg 3960
tcttcaaccg gcctcaagca gtcctcccac cttggcctca cagagtgctg ggattatagg 4020
catgagccac cattctcgcc agtatcctta tttcttaact ttagaaagtt tttctatttt 4080
taatataggt atttaaaaaa atctgaattc agagtgcacc tcgatgttat gctgttctga 4140
gattaaatat actaaaactg ttaccattgt ttttctgaatt cttaagatgt gactgatagt 4200
tagctaatag gttaacacat tgtggtggtt cttggcctct gaactgatag tccagatggg 4260
gagaggagac cagaaagcat gtgaaaatgg actagaacca tgggacagct atatagtctc 4320
tcgcagctgt cttttgtgtt ctctgcttcc accaaattgg ttgatttatt tagaatgctg 4380
acctcttgca ttgcctaagt ccttgatgtt tttggtttct cctctgaact ctcaaaggta 4440
ctcacttcat gctcttggta tagcccactt atgtttaact ttccttttat tatgtgttcc 4500
ctcttacaca tgacatggac atttctttaa tatgtagagt aagatattgg atttcatcct 4560
aaagtcttca aaataaaact cttgagctca tcatctcaga cttcttcatg tacccacaga 4620
ccagggattt tgtttgcttt ttaaaacatt tttttatttt gtgttttatt atttttaaat 4680
tttaatttaa ttttatggag acagggtctc gctctgttgc ccaggctgga gtgcagtggt 4740
gtgatctcgg ctcactgcag cctttgcctg ggctcaagcc atccacatgc cttggcctcc 4800
cagtgtgctg ggattacagg tgtgagccac tgtgcctggc ctaaatttat tttttttaatt 4860
tttttgaga cagggtcttg ctctgtcgct caggctggag tgcagtgtca taatcatggg 4920
tcacagcagc cttggcctcc caggctgaag tgaacttccc acctcagcct cctgagtagt 4980
tgggactaca ggcgagtgcc accatgcctg gctcattttg gttttttttg taaagatggg 5040

-continued

```
gtcttgtcat gttgcccatg aaggtctcca actcctggtc caagtgatcc tcccgcctcc  5100
gcctagcaaa atgttgggat tacaggtgtg agccaccatg cctggcctta tttatttatt  5160
taattatgaa tgaatgaatg aattaatgag agggagtctt gctctcttgc ccaggctgga  5220
gtgtggtggc acaatcttgg cccactgcaa cctccgtctc ccaggttcga gcaattctcc  5280
tgcctcagcc tcccgagtaa ctgggattac aggcgcccgc caccatgccc aggtaatttt  5340
tgtattttta gtagagatgg ggtctcacca tgttggccag actggtttcg aacttctgac  5400
ctcaagtgat ctgcccacct tggcttccca aagtgtcagg attacaggca tgagccacca  5460
tgcctggcct ggccttttat gttttaagtt gcttccactg attctcttgg gctttgctcc  5520
cctccagaac tggccatggt ttaggatgct gtccacctgc tgctgcttgt ccatgaaaac  5580
gagccataaa cccttttctt ttgaaagact taattgttta tcactatgga gaaagagggg  5640
atggcaagaa gtagcaaata cagggaattt gcagaacttg gtcttgagcc ctgggtccag  5700
aaacttcttc tggaaggtgc ttggtgtttg tccaagctca tgataggttt ctgttggctg  5760
tactgccaga tctgtagatg ctttttttaag gcttggatga cttgttcaaa acaatgtttt  5820
ggagtacaaa tttggctgtg gggacatcaa gaccttgttg ggaaacttgg gtttaaggta  5880
caatttctta aactaggatg gtgggaatgg ggatgtgaag ggagaatgaa tgtgagaggt  5940
attacagggt aaggatggag atgattcaga ttccttaagt ggatttaata atcacactgt  6000
agctttgaac ttgagtgact ggggaaatat ttgtggtgtt tttggaaata agggccagaa  6060
ggactattgg tttgggtaag aagatagtag ggggatgtat aggtggacct gctagtgggg  6120
agctgagatt tggagggctg agatgtagtg ctcttcactg ccgtagggca gtatcctctt  6180
gtatgtgcca tcctctagtg cccattgttc atcatgtcat agtaagccca agatgttcat  6240
gcctttttc agcactgcat tagggcttat atctgcttct ctttctctct ctctctcgct  6300
ctcgctccct ccctctctct ctctttctgt tttttttttt tttttagacg gagtttcact  6360
tgtgttgccc aggttggagt gcagtggcgc gatcttggct cattgcaacc tctgactccc  6420
gggttcaagc aattctcctg cctcagcctc ccaagtagct gggattacag gcatgtgcca  6480
ccatgcctaa ttttgtatct ttagtagaga tggggtttct ccatgttggt caggctggtg  6540
tcaaactccc aacatcaggt gatctacctg cctcggccgc ccaaagtgct gggattacag  6600
gcatgagcca ccgcgcccgg cctctctctg cttatttcta cacagtgtta ccaatgagat  6660
tggtgttact gctgggctcc aaagcaatca gacagattaa agtagattga atatgaaaga  6720
atttagaggc ctttttccaa gtgatttgtg ctctatttaa tttctgtgca tttgcagata  6780
tagcccacag taattcttag tgaactagaa ccttcaggtt attgaatttt actgatttgg  6840
gtactgacat gcgcttttaa gaagacatta ggttttctat agtgtagatt gtacactaac  6900
aatataattc atatttaaga atgtctcaaa atttagtata ctgtgttcaa ctaacttaac  6960
tttctttgtt tttttgttt tgttttgttt ttgtttttg agacggagtc ttgctatgcc  7020
acccaggctg gagtgcagtg gcgtgatctt ggcttactgc aacttcaaca ctcctgggtt  7080
caagtgattt tcctgcctca gcctcctgag tagctgggat tacaggcacc cgccaccaca  7140
ccggctaatt tttgtatttt tagtagagac ggggtttcgc cgtgttggcc aggctggtct  7200
tggactcctg actcaaatga tctgcctgcc ttggcctccc acagtgctag gattacagac  7260
atgagccact gcgcccggcc gctaacttaa ctttcattcc acaacttcca tcttttatcc  7320
aaaatctgtg atcattgaat actgtcacca ttaatcattg gcatttcagt gtttggactt  7380
tttttttccc ccttcgtctt tgtggactct tttttaacac tcataaagtt ttaactattg  7440
aaaagcaaag gaaacggtga gtgacttttt ggagtctgtc tacccagtgg tcacacaaaa  7500
ggcttactac attacaggaa agataggatg ggaaagggat actagaaaat tctaagtcag  7560
gaacgggggt gtgtattaga aaaattctga tcctggcatg ccagatggcc ttacatctca  7620
atttcttccg tgaaattcct gccaacaaat catagtgtta gaagtacaga agggtccatg  7680
ggaacagaat ttaagggctc cgttggtgat acggaactga tcagatggtt ctcacttgtt  7740
ctcagataac ctgtatactg aatatcacag gaagggtata gacgtcatgg cagtggttag  7800
atattcttgc acctgctgaa gctgagaaaa ttaaagtaat tttttttcct gtggaaagta  7860
gaaaatcaag cttttgtatg atttcacaca gctttctatt ctctcttttg ttgactctgt  7920
taagagtaac atttagtggt ggaaactatt tcaggatcac acccacaaca ctagagactg  7980
tattaatcac ttacacacac ataggtatag agtaatcttg aaggggctgt aggccaaaga  8040
taatgctttt ttgaagaatt agagactagt taccagcacc tggtatttgc tgtttcctac  8100
agagctgact ggacagccta gagtctgctg aggaattcag aggatggcca gtagaatgtt  8160
ctttccaccc cagaatattt ggtagggact cagctgctgt ggaatgccaa aaaggctttg  8220
agtttgtttc actattctta agattacacg taattgtttt tttgtaagag attatatata  8280
ttcaagttga ggatggcttt gagttagact ttccttaatt tggaatcaca cagcagatga  8340
tacatttatt tccatctgat aagttacttg atgatgtaaa aagacatttg agttaaagat  8400
ttttgggaaa aaagctgaat gttgagccat ttatgttgtg tactggttcc ctattcactt  8460
ggacaatttt aagtcttaaa acaatcttaa ccatgtgcac aagagatttc acatagtatt  8520
tggtaattaa attaaggaat tctagctcaa gtcatgcttt ttgctgaaat agttgtatat  8580
atttagtgcg gaaacctgtg ttttcaaatt aatgtaataa aagtttcaat aaaatggaag  8640
cctttattac cgtgtttcaa atgctatgct aaacctttc catttgttat tatattaacc  8700
tcctcataca tagccctact aatttttta ctttctattt tgaaataatt acagatttat  8760
aggaagttgt gaaaaatagt acagagccca tgttcccttc accaagtttc acctaatggt  8820
agtagctcac ataacgataa tttaatgtca agaaccagga aattgtcatc gttgcaatcc  8880
ataagccttt tttagatttc accagtttca catgtatttg tgtgtgtgtg tatatatata  8940
attgtatgca attttatcat gtgtagatct ggatagccac tgtaacagtc tatagttcta  9000
tatacagagc tactccatca cctcagggct ccctatgcta ccactttata gccgcacgca  9060
cccttccagc aaccactaat ctgtttgcat ctctgtaatt ttgccatttt gagaatgtta  9120
tataaatgga atcatacaga atgtaacttt ggcttttttt cttttaccat acttcctttg  9180
agagccatcc aaattgctgc atgtatcagt agttcatttc tttttactat tgagtagtag  9240
tccatagtat ggctgaacca cacaatttgt ttaaccattt acttattgaa ggacatacca  9300
gaagggtggt ttccagtttt ttggctattg caaataaagc tgctataaac attcatgtat  9360
ataaatattt ttatgtgaat ataaagtttt cattttgggg gaataaatgc ccaaatgttt  9420
ggattgtatg gtaagtgcat gtttggtttt tagagaaact gctgaactat ttattttcta  9480
gaatgactat atcctcttat attcctatca acaatatatg agatatccag tttctctgca  9540
tccttgctag catttagtgt taccactttt ttatttgagc ggttctaata tgtgtagtga  9600
tagcctgttt tgccttatat taatcaataa aaatagcctc atctaatctt aacttttttt  9660
attttaaaac atcttggcag tattgaactt tctcaatgaa aaatctctaa aattgtgact  9720
tgaaaggctt taattttcca gtttttcttt ggttttactc ttagcagtaa cattttaact  9780
```

-continued

```
ttttttgtc tttgaagtaa ttttcagtgt ttcctttaca tgttgctttt tcttagaaac  9840
tagttactag catgaagtag atctttagcc tcgttttcta aaaacataaa aaagtaaaac  9900
tgtggggttt atttcaaaat tgagagtcct gtcttttcat atgaggatat tttatagtct  9960
gttggcttgg ctatatttta gggagtaaac ctgtggttag tggtttgttg ttggtggtgg  10020
taaagttttc ttacagtatt tttatacctg aataatacct ttagactcta tagaatagat  10080
acttgatctt caaatctatc ctagaataaa ttgttttatc taaacagctt tgtgacctga  10140
gaattgggac ttagtccctt agttttccct tactggccct ttgtagtcac tgttttgatt  10200
ttgtgaaagt aacttaactc ttagcactgt caggtattgt acattcctgc caaagcaaga  10260
ataagaatac ataggattgt gttttaattc tataattagg tgacttttgg ctaatttcca  10320
ggaacttgga cttaataaag tactagtgat aagtttggaa attttagtgt ccttgttctt  10380
tgaagttatt caccctttac tttcttgttt gtttggggtg tttatactac tgtccctaaa  10440
tatagctgaa ataaaggaag aaaaataacc cctgtaatat cactaccagg atataatttc  10500
tttttttttt tttttttga gatggagtct cgctctgtcg cccaccatct cggctcactg  10560
caagctctgc ctcctgggtt cacgccattc tcctgcctca tcctcccgag tagctgggac  10620
tacaggcgcc cgccaccaca cccggcttat tttttgtatt tttagtagag acggggtttc  10680
actgtgttag ccaggatggt cttgatctcc tgatcttgtg atccacctgc ctcggcctcc  10740
caaagtactg ggattacagg catgagccac cgcgcccggc ctgatataat ttctgttaac  10800
agtttgatgt aaatattttt tgacttttta gtgtttttat atatatatat attttatgtt  10860
tttcttttat caatacgcac tcttactgtg ggaataattt taatgttttt aaagagttgg  10920
gttttatttg tttattttat tttatagaaa tggggtctcg ccgggtgcga tggctcacgc  10980
ctgtaatccc agtactttgg gaggccaagg caggagcatc acctgaggtc gggagttcga  11040
gaccagcctg accaacatgg ataaaccgcc tctctactaa aaatacaaaa ttagccgggc  11100
gtggtggcac gtgcctgtaa ttccagctac ttgggaggct gaggcaggag aatcacttga  11160
acccggccgg tggaggttgc agtgagcaaa gattgtgcca ttgcactcca tcctgggcag  11220
caagagtgaa acttcatctc aaaaaaaata aaaaataaaa aagaaagaaa gaaagaaatg  11280
ggatctcacc attttggctg gttttgaact tgtggtctca agcagtcttc ctacctcagc  11340
atcccaaagt attgggatta caggtgtgag cccatcctgt ttgttgttgt tcttttgttg  11400
ttgttgtttt tagatgaagt ctccctctgt cacccaggct ggagtgcagt ggcgctatct  11460
tggctcactg caagccccgc cacccaagtt caagcaattt tctgcctcag cctcccgagt  11520
agctgggatt acaggcgccc accaccatac ctggctaatt tttgtatttt tagtggagac  11580
gaggtttcac catattggcc aggctagtct tgagctcctg acctcgtgat ccacctgcct  11640
cggcctccca aagtgctggg attacaggtg tgagccactg cgcctggcct gttgttgttt  11700
aaataaaaga aatttattct cttacagtcg aggccagaac ttagaactgg ttttcaatct  11760
aaattttttt tcttctttgg gagaagggca tcagaatatt gtggatatac ttttttgact  11820
taaaaaaaaa ggttttactg ggctgggcat ggtggctcac ctgggattaa ctgcctgtaa  11880
ccttggcact ttgggaggct gaggcaggtg gatcgcttga gtccaggagt tcaagagcag  11940
cttgggtgac atggtgaaac tccgtctcta ccaaaaaaaa aaaattagcc aggcatggtg  12000
atggcgtgcc cttgaagtcc cagctacttg ggaggcttag ctgggaggat cgcttgagac  12060
caagaggcag aggttgcagt gagctaagtt catgccactg cactccagcc tgggtgacag  12120
agcgagacct cgtctgaaaa attttttttt tttttacta atatgacaaa catcttttca  12180
tttcaaatat atttctatac catttttaat atctcattgc ctttagaatg accttgtatt  12240
catagtacat atgtatgtga tattccattt atttattttt tttcttttgt ctttttttgg  12300
ttatattcca ttgatttaat gtaccttaat ttatcttacc aatttcttgt tgaccatttt  12360
gtttccagtc ttttgttttt ttaccagaca tggattaagc tgagcctttg ccccagacga  12420
cattatttct tttttatcag caaaatatgc gtgtaatgaa attagaatta aaaggcaaaa  12480
aaggttatcc tttattttc tacttatttt tattgagata gtaattcaca taccataaat  12540
ttaacccttt taaagtgtac agttcagtgg ttttcatata ttagaaggtt gtacaaccat  12600
cgcaactaat tccagaacat tttcatcacc ccagaaagaa actctgaacc cattatcact  12660
ccccactccc tcacacaccc taaccctggc agtcacatat agactctctg tctctgtgga  12720
tttgtttact ctggaccttt catataagtg gaatcataac agtttgtggc cttttgtgct  12780
tggcttctca aacttatctg tttccaaagg ttatctgtgt cgtagcatgt gtcagtactt  12840
cattcctttt tatggctgaa tattttattg catgtatatg ccacattttg tttatccatt  12900
cacctgtaga aggacattta ggttgtttcc attttttggc tgttatgaat attactgctg  12960
tagacgttca tgtacaagtt tttatgtgaa cgtgttttca tttttcttgg gtatatactt  13020
aagtgaggaa ttcctgggtc ttaagttaac tctctgttta acattttgag gaactgccaa  13080
attatttttt aaagtggctg tgacatttta tattctacca gcagtgaatg aaatttccaa  13140
tttctccaca tacttgacag cacttttttt tttttttttt tttgaggtga agtcttgctt  13200
tattgcccag gctggagtgc agtagcatga tcttggctca ctgcaacctc cacctcccag  13260
gttcaagcaa ttcttgtatc tctcagcctc ccgagtagct gggattacag gcgcatgtca  13320
ccatgcctgg ctaatttttg tatttttat agagacaggg ttttgccatg ttggtcaggc  13380
tggtcttgaa ctcctgattt caagtgatcc acctgcctta gcctcccaga gttctgggat  13440
tacaggcgtg agccactgca cccagtctgc actttcttta ttatctgtct tctttattat  13500
agccaatcta gtgggtatga agtaagtgtg tcatttgtga ttttgattgt tagtggtgac  13560
taaaaatgtt gaatatcttt acatgagctt gttggccatg tgcacatctt tgttggagaa  13620
atatctattc aaatcttttg actattttaa aattgggtta tttatctttt tattgttgag  13680
ctataggagt tctttatttt attttactga gacagggtct tgctctgtca cctaggctgg  13740
agtgtagtga tgccatcttg actcactgca acctctgccc ccaccccagg ctcaagtgat  13800
cctcccacct cagtcagcat cccacagctg ggaccacagg cgcatgccac catgcctggc  13860
taattttttt tttttttttt tttttgtatt ttagtataga cagagtctca ccttattgcc  13920
caggctggtc tcaaactcct gagctgaagc aatccgccca tctcagcttc ccaaagtgct  13980
ggaattagag gcatgagcca ctgtgcctgg cctattttat tttaaagatg aggcctcact  14040
ttgtcaccca ggttggagtg cagtggcgtg atcatagttc actgccattt tgccctcctg  14100
ggctcaaaca gtactcacga ctcatcttcc tgagtagcta ggactgcagg catgtcgcta  14160
gcatgcccag ctaaaacagt tctttatatt ctagatcggg gtgtccaatc ttttgacttc  14220
cctgggccac attagaagaa gaagaattgt cttgggccac acataaaata cactaacagt  14280
aatgacagct gatgagctaa aaaaagaatt accaaaacat ctcataatgt tttaagaaag  14340
tttacaagtt tatgttgggc cacattcaaa gccatcgtgg gcctctggcc gtgggttgga  14400
tgagcttgtt ctaaatgcta gacccttatc agatggatgg tttgtagata tttatcgcat  14460
gctgtgggtt ttttttttt actttctttt aggttttttt ttttcttaaa taattaaact  14520
```

-continued

```
gattaaaagc tttaatcttt tcattttctt gataatgtct tttaaagcac aaagttttgt 14580
ttcaatgatg tctaatttgt ctattttttt ttctttggtt gcttgtcata cgtaagaaac 14640
tgttgctaaa tccagaatgc tgaagattta cttgtgaact ttgtttcctt ctatgagttt 14700
tatagtttta gctcttgtat ttaggtcttt gatacatttt gaggtttttt tgttgttgtt 14760
gagacagtct tgctctgtcg cccaggctgg agtgcagtgg tgtgatcttg gcttactgca 14820
ccctctgcct cctcggttca agcaattctc atgcttcagc acccgagtag ctcggattac 14880
aggcgtgcac caccaagcct ggctaatttt tgtattttta gtaaagaggg ggcttcacca 14940
tgtttgtcag gttggtcttg aactcctggg ctcaagcaat cctctcatct cggcctcccc 15000
aagtgctggg attacaggca tgagccacca cgcccagcct gttttgagtt catttttaaa 15060
atatggtgtg aggtagaggt cccatttcat tcctttgcct gtgggtatcc agttgtccca 15120
gaaccatttg ttgaaatgac tcttgtttcc tcattgagca atgtcgtgag accctatctc 15180
cataaaaaat aattaaaaaa aaaaaagaat gcagaaggaa acagttttgc caattttgta 15240
gtatttactg acaatttgca tatgtcttta cattctttag ctatttattt ttcttttgaa 15300
ttactgcctt tgttcatttt tcttttggag ttgtttgtct ttttcttatt aatttgtaag 15360
agattttgca aatatataca atttcttttc tctttttttt gagatggagt tttgctcttc 15420
ttgcccaggc tggagtgcag tggcatgatc ttggcttact gcagcctctg cctcctggtt 15480
tcaagagatt cttctgcctc agcttcctga gtagctggga ttacaggtgc ccaccaccac 15540
acccagctaa tttttttttt tttttttttgt atttttagta gagactcggt ttcatcatgt 15600
tggccagact ggtctcaaac tcctcacctc agttgatcca cccaccttgg cctcccaaag 15660
tgctgggatt acagttgtga gccaccgtgc ctggacctcc cacattattt tgaaacaaat 15720
tccatatcac ataatttctt ttttttgaga cagagtctcg ctctgtcacc caggctggaa 15780
tgctgtggcg tgacctgtgc ttactgtacc ttctgcctcc taggttcaag cgattctcct 15840
gcctcagtct cctgagtagc tgggattaca ggcacgcacc accacacctg gctagttttt 15900
gtatttttag tagagatggg gtttcaacat gttggccagg ctggtcttga actcctggcc 15960
tcaggtggtc cgtccacttc ggcctcccaa agtgctggga ttacaggctt gagccactgc 16020
acccagccaa tatcatataa tttcatataa atagttcttt gtgtatcttt agataaggac 16080
ttaaaagaag gcataatcgt aacaccatta ttaatacccta aaagaagtga gcaataaata 16140
attcatttgc cgtatcaaat atccaatgtt catatttcct ccattgtccc ataataattt 16200
ttaaaagttt gctcaaatca aaatccaaac aagattattt caaagcattg tttgaggtac 16260
attttaaatc ttaatttata gatttctctg ctgtctcttt tcccccatat ttatttgttg 16320
aagaaaccaa gcgttgtttc ctgtggactt tcctactctc tggattttgc tggttatatt 16380
cctctggtat cagtttacta tgatcccttt ttcccctgta ttttctgtaa atttgtaact 16440
agatctagag atttgtttag attttgtggg tttttttttt tttttttttt ttttttgcaa 16500
aaatgcatca taaatggtgg tgtgtacatc tctcagaaga cacatatctt aatgtctttt 16560
tgtggtatta gttattaatg attactgcct atatttatta attcattatt tggattgtaa 16620
gtttatgata gtctcttgat gctttttctg ttgttagctg gaatgcttct aaaaggagaa 16680
ggctttcctc ttcaagctac ttggttgtct tgagggtttg cttcttatag ggaaagcagg 16740
ctaagggtga aaaaggaaat agtttctaac tgggtctgtt aatgagctgt caccccaggc 16800
aaagagaagc aaggcaggtc acaggaaagt gaagtgggct tgggatgatt ggtgccccat 16860
gcgtgcatgc atgaagggaa gttaatcctc cctgtagtga actctactgg gcttttggtc 16920
agtagccaag actgtcaagg aagacctttg tcagaagcca tacctggcct ttgcttttag 16980
ctgttggtag ctgaaggaaa ccagaacaga cctatgacct gtgaacttct gctcagtaga 17040
caaagttctc tcagcctaaa ttcagtaagc aggagtaaga tgcttgcttt cccttgaagt 17100
gaaacgtgaa ttatatgttt cttcaacttg tgctaatatt cttttttttt ttgagatgga 17160
gtctcacact gtctcccagg ctggagtgca gtggtgcaat ctccgctcac tgcaacctca 17220
gcctcccgag tagctgggat tacaggcgcc tgccaccacg cctggctaat tttttgtatt 17280
tttagcagag atggggtttc actatgttgg ccaggctgga cttgaactcc tgacctcacg 17340
atctgcctgc ctcggtctcc caaagtgctg ggattacagg cgtgagccac cacacctggg 17400
caacttgtgc taatattctt aaccttcatg tgaatcattc ctgccctcag gctagcataa 17460
cccatacagc cttccttata ggaagatttc ctactgggag tgaatttgtc cagtgattcc 17520
cccaagatat cccccaatca aatattttaa aagtcatcat ttacatgtaa aaactatgta 17580
acaagcatgg tagcagcagc gttaaagaaa tggcagtatg gcccctgtaa gggaaggctc 17640
cagaagatga gccgcactca gcctctaggt cacagctacc ttaggagttt gcagttgttc 17700
ctggggaagt cagtagacaa agctatctct caggcctggg caagataggg attttttttt 17760
tttctttgag atggagtctc accctgtcat ccaggctgga gtgcagcagc atgatctcgg 17820
ttcaccacaa cctccacctc ctgggttcaa gtgattttac tgcctcagcc tcctgagtag 17880
ctgggactac aggtgcgggc catcatgcct ggctcatttt tgtattttta gtagagatgg 17940
ggtttcacca tgttggctag gctagtctca aactcctgac ctcaggtgat ccacctgcct 18000
cccagagtgc tgggattata ggcatgagcc actgtgccca gtgttttttt ttttttaatt 18060
gtagtgacag gatctcactt tgtttcctgg gctattccca aactccaggc ctcaagccgt 18120
cctcctacct tagcctccca gagtgctggg gttacaggtt tgacccactg tgcctagtct 18180
cagaattcat gtttttaaaa gtcactctgt gccaggctca tgcctgtaat cctaatactt 18240
tgggaggctg aggcaggagg gttgcttgag cccaggagtt tgagaccagc ctggaaacca 18300
tagcaaaatc ctaactctac aaaaaaataca aaaaatagcc aggtgtggtg gcatgcacct 18360
gtagtcccgg ttacttggga ggctgaagtg caaggatcgc ttgagcctag gaagttgagg 18420
ctgcagtgag ctgtgatcat gccactgcac aacagcctgg gcaacagagt gagaagtaac 18480
tctggctgtg gtggggaaag tggattagtg gagaatggaa gctgggaaac atggtggttc 18540
ttgctaagtc agtatcaagg gatcacagat gagggggcta tttcgtccta ataagggcct 18600
tggtctccca gatagtcatg gatttttcta tttagaagct ccttctcagt ttttcttgcc 18660
caaggcatat acggttgata tttgtacaac acaggctgga tctgtatggg tccacttata 18720
tgtggatttt ttttcaacca aacttggatt aaaaatatag ttgtaggcca ggcacagtga 18780
cttatgcctg taagcctagc actttgggag cccaaggcag gcggatcagc tgaggtcagg 18840
agtttgagac cagcctggcc aatgtggtga aaccatgtgc ctactaaaaa tacaaaaaat 18900
agctgggtgt ggtggtgtgc acttgtaatc ccagctactc aggaggctga agccagagaa 18960
ttgcttgaac ccgggaggtg gaggttgcag tgagctaacg cagcagaggt tgcagtgagc 19020
taacgcagca gaggttgcag tgagccaacg gggtggaggt tgcagtgagc caagattgca 19080
ccaccacact ctagcctgtg tgacagagca agactctgtc tcaaaaaataa ataaataaaa 19140
atacagtgta ggccaggtat agtggctcat gcctataatc ccagaacttt gagaggccaa 19200
ggcaggcaga tcagttgaag ccaggagttt gagaccaacc tggctaacat ggtagaaccc 19260
```

-continued

```
cacctctact aaacagaagt acagaaatta accaggcata ggtggtgcat gcctgtaatc  19320
ccagctgctt gctaaactga ggcaggagaa ttgggaggca gaggttgcag tgagctacga  19380
ttgtgccact ggactccaga ctgggtgaca gagcgagact ctgtctccaa gagaaaaaaa  19440
aaaattgtac ttacaggaca tgaaacccac ctgtacggtg tgctgactgg gagactggag  19500
tatgcatagt tcttggtaaa caaggggatt cctgaaacca atcccctgag tatatggagg  19560
gttgactata tattttaata gaatttatta cttttttttt tttttttagc agttttaggt  19620
ttatggaaaa attgagcagg agtacatagt ttctctatct ccctcacatt tccccattac  19680
tagcatcttg aaatagtgtg gtacatttgt tacaactgaa gagccaaata ttgatacatt  19740
actgttaact aaggtccgta atttacttta gagttcactc ttggtgttgc agtttctatg  19800
agtgttggca aatatatcat gacatgtatc tagcattata gtatcatatt gagtagtttc  19860
actgccctaa aaatcccctt tgttccacct tttcatccct ccatctacct gaacccctga  19920
taaccactga tccttttaca gtctctatag ttttaccttt tacagaatgt catatagttg  19980
gaatcataca gattggcttc tttccatgtt ccttcctggc ttgatagctc ttttcttttt  20040
tttgagatgg agtctcgctc tcgcccaggc tggagtgcag tggcgcaatc ttggctcact  20100
gcaaactctc cgcctcctgg gttcaagcaa ttctcctgtc tcagcctccc aagtagcttg  20160
gactacaggc gcatacctcc cctgcctggc taatgtttgt atttttggta aaggtggggt  20220
tttaccatat tggtcaggct ggtctcaaac acctgtcctc aggtgatcca cccacctcgg  20280
cctcccaaag tgctgggatt acaggcgtga gccaccctgc cctgccagct cttttttttg  20340
tactgctgaa taatactcca ttgtataggt gtatgagttt atctattcac cttctgaagg  20400
acattttggt tgctcctaag ttttggcaat tatgcatgaa gttactataa acatctgtgt  20460
gtaggttttt gtgtggtcat gtttttagct catttggata aataccaagg agcacgattg  20520
ttggatcgta tggtaagagt atgtttagtt ttgtaagaaa ctgccaaact gtctttcagg  20580
gtgactgtac cattttgcat tcccaccagc aatgaatcaa gttcctgtcg ctccacatcc  20640
tcgttagcat ttggtgttgt cagtgttttg gcttttcacc attctaatag atatgtagtg  20700
atatcttgtc ttactttgca gttctctaat gacgtatgat gttgagcatc ttttcatctg  20760
cttatttgtt gttgttgttg ttgtgttgtt cattgaaatg gaatctcgct ctattgccca  20820
ggctggagtg caatggtaca atcttggctc actgcaacct ctgcctcctg ggttcaagtg  20880
attctcctgc ctcagctccc caggtagctg ggattacagg cgcccgccac catgcccggc  20940
tagtttttgt atttttagta gagacaggat ttcaccatgt tggccaggct ggtcttgaac  21000
tcctgacctt aggtgatctg cccgcctcgg cctcccaaag tgctgggatt acaggcgtga  21060
gccactgcgc ctggctttca tctgcttatt tgatatgtgt atatgttatt tggcaaagta  21120
tctgttctga tcttttgccc atttttttaat cagattgttc ttttattgct tctggggttc  21180
tttttgtttg cttttttttga gacagagtct tgctctgtcg cccagtctgg aatgcagtgg  21240
catgatctca gctcactgcg acctctgctt cctgggttca agtgattctt gtgccttagc  21300
ctcccaaata gctgggatta caagcatgtg ccactgcacc tggctaattt ttgtatttat  21360
agtagggaca gggttttgcc atgttggcca ggctggtctt ggactcctgg tcttcagtga  21420
tccacccacc tttgcctccc aaagtaatga gattacaggc gtgagccacc atgcccggct  21480
tattgttaag ttttaagagt tctttgtata tgtgtatttt ttgattcttt taaaattaat  21540
acttaataaa ataattgtac atatttatgg gatgcatgtg atattttgat acatgcatac  21600
aatgtggatc aaatcaaggt aattagagta ttacctcaaa catttgtcat ttctttatgt  21660
tgggaacatt tcaaaatgtc tagctatttt gaaatataca ataaattatt atctataagt  21720
cacctcattg tgctgtcaaa cattagaact tattctttct acctggcttt atttttttta  21780
ccccttaacc aaccattctt catcagctcc ccgtctcccc tactcttttt tttttttttt  21840
ttttttgata cggagtcgct ctgttaccca ggctagagta cagtggcaca atctcgactc  21900
actgcagctt ccgcctccca ggtttaagca attctctgcc tcagcctccc gagtagctgg  21960
gattacaggc gaatgctacc acacccgact aatttttata tttttagtag agatggggtt  22020
tcaccatctt agccagactg gtcttgaact cttgacctcc tgatccaccc gcctcagcct  22080
cccaaagtgc cgggattaca ggggtgagcc accatgcctg gcccctctta ctcttttctt  22140
agcctctggt atctatcatt ctactctcta cttctatgag atcaactttt ttttagctcc  22200
cacatatgag taagaacatg taatatttct ctttctgggt ctggcttctt tgtatatttt  22260
ggataataag tcttttatta gatacgtgtt ttgcaaatat tttttccgag tccgtgactt  22320
atcttttcat tctcttaaat agtgtctttt gcagagcaca cattatacat tttagtgcag  22380
tccagtttac caattctttc tttgatggat tttgcttttg gtattgtgtc tagaaagtct  22440
tcgccaaacc acagtcatct agagttcccc ttatattatc ttacaggagt tttatagttt  22500
ttgttttaca tttaggtctg tgatctattt taagttaatt tttatgtgaa agatataaga  22560
tctatgtctg gattctctct ttttttgaga tggagtctcg ctttgtcgcc aggctgaagt  22620
gcagtggcgc gatctcggct cactgcaacc tctgactccc tggttcaagg gattctcctg  22680
cctcagcctc ccgagtagca catgacacca cgcccagcta atttttgtat tttgagtaga  22740
gacggggttg caccatgttg gccaggatgg tcttgatctc ttgacctcgt gatccgcccg  22800
cctcagcctc ccaaagtgct gagattacag gcatgagcca ccacgtccgg ccagtttttt  22860
tgttttattt atttatttat ttgaaacagg gtcttgttct gttgcccagg ctgcagtata  22920
gtgacaccat caaggcttcg ttgcagcctt gacctcctag ggtcaagtta tcttcttgct  22980
tcagcctcct gagtagctgg gactacaggt gagcaccact ctgaccaggt actttttaaa  23040
tttattttag agacagggtt ttaccatgtt gcccaggctg gtcttgaact cctgggctga  23100
aatgcccctc ctaccttggc ctcccaaagt gttgggatta cagacatgag gcactcagcc  23160
cagccaatat aattcttttt tttttttttg agacagtctt actctgttgc ccaggctgga  23220
gtgcagtggc atgatcacag ctcactgcaa cctctgcctc ctggactcaa gctgtcctcc  23280
cacctcagcc tcccaagcag ctgggattat gggtgcccat gaccacaccc agctaagttt  23340
ttaaattttt ttagagattg aatctttctt tttctcagcc tggtctcaaa ctcctgagct  23400
catatgatct gcccgcctcc gtctcccaaa gtgctgcgat tacaggcatg aaccactacg  23460
cccagcctac aatttatttg taatccaagt tttattgaaa aaaaaatcca catataagtg  23520
gacatatgta gatccaacct gtgttgttcc agtgtcaacc atatatacca ataattcttt  23580
tttttttttt tttttttttt tttttttgag atggagtctt gctctgtcgc ccaggctgga  23640
gtgcagcggt gcaatctcat ctcactgcaa cctctgcctc ccgggttcaa gtaattctcc  23700
tgcctcagcc tcctgagcag ctgggactac aggcatgcac caccacgccc agataatttt  23760
tgtattttta gtagagatgg ggtttcacca tattggccag gctggtctca aactcctgac  23820
ctcaagtgat ccacccgcct tggcctccca aagtgttggg attacaggag tgagccactg  23880
tgcctggcct ataattcttt acgtatattg ttagattcag tttgctagta ttttatttag  23940
catttgtgta tctgtgttca tgagaggtat tgttctgtag ttttctttgg tttcttttct  24000
```

-continued

```
gtctggttta gggtaatgct ggcctcatag aataggttag gaaatatttc ctctgcttct  24060
gtttctgaaa gagaattgag gtaatatcta tttttttttt tttgagatgg aatcttgctc  24120
tgtcgcctag gctggagtgt agtggcgcaa tcttggttca ctgcaacctc tgcctcccag  24180
gttcaagtga ttctcctgcc tcagtctcct gagtagctag aattacaggc atgcaccacc  24240
atgcctggct aatttttgta tttttagtag agatggggtt tcactatgtg gccaggctg   24300
gtcttgaact tctgatctca ggtgatccac ctgtcttgtc ctcccaatgt gctgggatta  24360
caggcgtgag tcactgtgcc tggcccgaga taatatctaa tttaacagtt tggtagaatt  24420
caccagtgaa cccatctggg cctggtgcct tttgctttag aaggttattg attattgatt  24480
caatttcctt aatagataaa ggtgcattga gattgtcttt tcttcttggg taagttttaa  24540
tacattgtgt ctttcaagaa attgttccat ttcatctagg ttatcaaatt tgtgggatta  24600
gagtccttca taatatttct ttgttttgct tttggtgtcc ataggttcag aagtgatggc  24660
cctttttcat tttttctatt agtaatttgt gtctttgccc ttttttttct ttgttaatct  24720
ggctagaagc ttatcaattt tgttgatctt ttcaaagaac cagtttttgg tttcactgat  24780
ttttctctat taattttgtt ttcaatttaa ttgatttctg ctctaattgg ttttcttctg  24840
ctcactttgg atttaatttt ttttagtttt tctagaaaac taagttttta agtgaaaact  24900
gagattattg atttttagat cttttttcta atgtttacag ttaacactgt acaatttcct  24960
gtaagcactg ctttctctat atcttacaaa ttttgatgtc atattttcat tttcatttag  25020
ttagaaatat ctcttgagac ttctttgacc catctgttat ttagaagtgt attgtttaat  25080
ctccaagtat gtattttggg atttttctgg ctatcttttct gctgttgatt tctagtttaa  25140
ttacatgtgg tctgagagca taccttgtat gctttctatt cttttcaatt tgttaaggtg  25200
ctctttgtgg ctcaaggtgg tctactttt ttttttttt tttttaaag aaaagctggc  25260
caggtgcagt ggcttatgcc tgtactccag cactttggga ggcgtaagtg ggaggatcac  25320
ttgaggtcag gagtttgaga ccagcctggg caacatatag agacttcact tgcacaacaa  25380
atttttaaaa tattagttgg gtatggtggc atatacctgt atatggctga agtgggagga  25440
ttgcttgagc cctggaggtt gaggctacat gagccatgat cgcaccactg tactccagcc  25500
tgggcaacag agtgaaattt tgttctctct tgaaaagaaa aaaaaagttg atgacataaa  25560
gttcattcat cttttttgta tgtgacttca aaataactac tgatggttaa aaaaaaaatc  25620
agaatgatgc aacccaagtg tccatcaatg gatgaataga taatatgtgg tgtatgaata  25680
caatgggcta ctattattca gcctttaaaa ataagaaaat gctgacactg ctgtaacatg  25740
gatgaacgtt cagatcatta tgctaaatga gaaaagccag acacaaaagg acaaatattg  25800
catgattgca cttatatgag gtatctggaa tataagagtc atagaaacag taattcagta  25860
attagaataa tgcttgccag ggcctgtggg gaggagggaa tgaggaattc atgtttaatg  25920
ggtacagagt ttcatttgga aaagattaaa aagttatgga ggtggatggt ggtgaggatt  25980
gcacaacagt gtgaatgtac ttaataccac tgaactgtac acctaaaaat gattaaaatg  26040
gtacatttta tgttacatat gttttacaac aatttttaca gatggaaaaa aattataaaa  26100
aacatcagga tggtgttgac agtgaaaagg ttaaagagtt actttaaaaa tttactttat  26160
tccagccggg tgcggtggct cacacctgta atcccagcac tttgggagac cgaggcgggt  26220
ggatcacctg aggtcaggag tttgagacca gcctgaccaa catggagaaa ccccgtctct  26280
actaaaaata caaaattagc caggtgtggt ggcgcatgcc tgtaatccca gctacttggg  26340
aggctgaggc aggagaatcg cttgaacccg ggtggtggag gttgcagtga gccgagatct  26400
tgccattgca ctccagcctg ggcaacaaag cgcaactccg tctcaaaaga aaattttttt  26460
tttttacttt atcccaaatg tttatattta ctttggggct tatgtgacca gtttaatttt  26520
catttgtaat tgacttgata gaacacacta atgttcagtt aagatttctt atggtgtggt  26580
gaggagtagg atttttatgt aaataagccc aaaattgtat atatgaggtt aatctgatat  26640
ttgcagaaga tattcatgca ttactgtaag gaccactctg cttattcatt tgaccgattt  26700
gttacaacat ggttagaaat catcaaggtg tttgagatca aaggatcttc agaggtgatt  26760
tactccaatc ctttttttaaa aaattaataa cttgagcctc agagaagtta agtgacatta  26820
ccaagttctg ctgttagtat agtgacttta tctttacctg aatccagggt ttcttagccc  26880
tagtctgtaa tgtgtcctag tgtgcctcta gaatctggtc ctgtcagccc aagtctgtta  26940
aatcaaataa aaccagggct tggtgcttca ccttgtcttc tgccataccg ttgggtttcc  27000
tgtggaccat gcagataatg atgatgggct cagtgggctt gatagtgata actcctaaag  27060
cagctccttc taagtgcggt tctcaatctg aggaagttaa aaaaaaaatt agtgactaga  27120
acccacttct caggtactct gataaaatac atttgtaggg gagtgatagt tttcactttc  27180
ttttttttctt tttcttttt ttttgagatg gcgtctcgct cttttgccca ggctggagtg  27240
caatggtgcg atctcagctt actgcaacct ctgcctccca gtttcaagtg attcttctgc  27300
cttagcttcc tgagtagctg agattacagg tgtgtgccac catgcctggc taatttttgt  27360
atttttatta gagacgggat ttcaccatgg ttggtcaggt tggtctcgaa ctcctaacct  27420
tgtgatctgc ctgcctcagc ctcccagagt gctgggatta caggcatgag ccactgtgcc  27480
cagccttcac atatttttg aaataatagg ccagttgcgg tggttcatgc ctgtaatctc  27540
acactttggg aggccgaggt gggcagatca cttgaggcca ggagttcaag gccaccctgg  27600
ccaacatggc gaaaccctgt ttctactaaa aatacaaaaa aattagccgg gtatgatggc  27660
atgtgcctgt ggtcccagct actctggaag ttgaggcatg agaatcgctt taacttagga  27720
ggtggaggtt gcagtgaggc aagatcgtgc ccctgcactc cagcctgggt gacagagcga  27780
gactccatct caaaaaaaaa aaaaaaaatc gtatgcagta aaggttgaaa actgctgccc  27840
aaaggcgcta ttaaactata ggttcccaaa cctggccaat tgtcaaaatc cctcaagaag  27900
gggcagtggg gtctaaggga ccccattgct gtagaggaga ttagtagtcc aagagtgaga  27960
tgaactgttg gaagtcctca aacttccaaa ctattaaaat agaatagttt tgcttcctta  28020
aaatagaata gttttcttcc tcactgattt ttctgtattg attagaacca taacaagtga  28080
attaaacaac tacaaaatag ttatgtgggc cacagacatt attgtaatga agtgaagttt  28140
ggctcaggcc ttgtaacaca attgcttttt ggattaaaag taaaaatatt aaattgtgaa  28200
attatgtgta agttttaaaa aattggtctt gtacaaaagt gttgggtttt tctttgtttt  28260
taactggatt tgtttttaag caagacagaa tatttatatt gttggagagt cacaaaggag  28320
gtgtgtttgt ggatttaaat gtggagacag tgtgccttga aatgcccttt atcagtctga  28380
ttcaagccac ctgcaatcat ggatttgaac tttttttttt ttttcccctg agatagggtt  28440
gcctaggctg gggtgcagtg gtgtgatctt ggctcactgc aacctctggc tcagcctctt  28500
ggagtacctg ggactatagg cacacaacat catatccagc tattgtattt tttttttttt  28560
ttttttttat agagacagag tttcaccatg ttgtccaggc tggtcttgaa ctcctgagct  28620
caagcaactc acctgcctcg gccttccaga gtgctgagat tataggtgtg agccaccatg  28680
cccagccttc actttattta aaaaccatag tttttaaaag ccacattcct actgatgaac  28740
```

```
acagaggttg tttccagtgt tttcatttgc agggctgtag tgattgtttt tgcacatgcc  28800
tctttatgta catgtgctgt gtcttctggg acagagagtg gacattttaa gtgttttatt  28860
ggtcctgcta aattgtcttt cagccaaact gctgcagagg tgatggagat gaggtgggta  28920
ctcaggagaa ttatgctcag tgcttgtgtg ctagtcactg acctggaaac attttattaa  28980
aaatgctaga ttaggttagt gatgtaaata ccaggtgata gtaaccagaa taattgtgtc  29040
aaaacatcaa gaatcatcaa gagatgccag gcatggtggc tcatgcctgt aatctcagcc  29100
ctttagtagg aggccgaggt gggcagattg cttgagctca ggagttcaag accagcctag  29160
gcaacatggt gaaaccctgt ctctaccaaa aatacaaaaa tttgctggat gcagtggtac  29220
gtgcatgtgg tcccagctac tcagtaggct gaggcgggag gatcgcttga gcctgggagg  29280
cagaggttgc agtgagccaa gactacacta cagcccgggc aacagagtga aaccctgcca  29340
taaaaaaagg agaaaaagaa tcatcaagag aaaacttaat ttgatgtgct ctgcgttttc  29400
tttggtgctt catgtcagtg ttagaaacta taggttgtat atttattaat ttttctccta  29460
catttgttca acttgactaa aatattaact ccaaatgcct agaatttcaa aatacctctt  29520
cgttataaag tatcaactat ttcttagtcc ccttaagctg atagtattgt gtcattgtaa  29580
aagatccctt gtgaaaaata atttttgtca acatgaaagg tcttaatgtg tctcctagtt  29640
tacattttac atggtctttt ccatgtattt atatagttga catatatagc tttttttgta  29700
aatacacttt cctatgtgaa catgccaagg tttacttaag cattctctta ttcttggaca  29760
tctaaattgc ttcttatttt ctattgtaaa taaagtgcta gaagcttctt tcctgaaaag  29820
ttatttactt ttcacctagt atttccatct gtgttcctca aaataagatt gctgagattc  29880
atgtatgttg ccagaaagat tgtgaggttt aacagtgaat gaggaaaact tttaacactc  29940
aaggtctacc aagtacagca agttttattt taccttttt tttttttttt tttttttttt  30000
tttttgagtt aggccaagtt gcctaggctg ggctcaagca atccttctgc ctcagcctcc  30060
ggagtagctg ggattatagg tgtgcagcac cacacccggc tttcttgtat ttttttttta  30120
tttttattta tttatttatt tttgagatgg agtttcactc ttgtcaccca ggctggagtg  30180
caatggccca atctcgactc accgcaacct ctgcctccca ggttcaagcg attcttctgc  30240
ctcagcctcc caagtagctg ggattacagg catgtgccac cacacccggc taatttttct  30300
atttttagta gagacggggt tcctccatgt tggtcaggct ggtctcaaac tcccgacctc  30360
aggtgatcca cccacctgag cctcccaaag tgctgggatt acaggtgtga gccaccgtgc  30420
ctggctgctt tcttgtattt tatcttgctg tagcggttgt gggatttttg cctggtgtgt  30480
tcattggagt gtgtgtgtgt gttttgagat gtatgactgt gttggttgtg ttgtcatact  30540
ttgaaggttc attaatgtgc tggtctttct atttttcttg ttatacttag tcacttaaaa  30600
accctttttt tttttttttt ggaattctta tttttacagt actttgaatt cctgttttat  30660
taatcacctt cttatctgaa agtgaagtaa tagtgtactt ggcaccattg aattagaaaa  30720
ttgtgtgtcc ttggccagaa gatcacatac acaggaactc gataagttga gagatttagc  30780
cgtttcagaa atgggcattt gtgtcttcca gtggagaagc atctgcaaaa gaattgggca  30840
gatttggcca ggcgcggtag ctcatgcctg taatcccagc actttgggag gccgaggtgg  30900
gcagatcacc tgaggtcagg agtttgagac cagcctggcc aacatggtga aaccccgtct  30960
ctactaaaaa tacaaaatta gccaggcgtg gtggctaacc catttaaagt gggtgaatta  31020
tatcttttat gttttaatgt attcctagag ttgtgcaacc atcaccagaa taagttgtag  31080
aacattttca tcaacccaaa aagaaacttt gtattcatta gtcgttcctc ctcatttctc  31140
ccctaacctc ccagcactag gcaaccatca gaatactttt tgtctccacg gatttgactg  31200
ttttggacat ttcatattaa tggaatgcac aatacagtag tataatacat taattttgga  31260
aggccaaaat taatggcttt tgatgtctgc ctttttcac ttagaataat gtcttccagg  31320
tccatctgtg ttatagcatg tatcattact ttatccttta tgtggctggg taatattcca  31380
ttgtatggtt ataccatgtt ttgtttatct attcatcagt tgatggacat ttaggttgtt  31440
ttccattgac tattaagagt aatgctgccg gccgggcgcg gtggctcacg cctgtaatcc  31500
cagcactttg ggaggctgag gcgggtggat acgagggtca ggagatcgag accatcctgg  31560
ctaacacggt gaaaccccgt ctctactaaa aaacaaaaaa ttagccgggc gtggtggcgg  31620
gcgcctatag tcccagctac gcaggaggct gaggcaggag aatggcgtaa acccgggagg  31680
cggagctggc agtgagccga gatggcgcca ctgcactcca gcctgggcga cagagcgaga  31740
ctccatctca aaaagaaaaa aaaaagagaa taatgctgcc atcatgcttg agggtttttt  31800
tttattttgt tttgttttgt ttgtgggggg agcggagggc acagtctcac tctgttacgc  31860
aggctggagt gtagtaggct tactgcagcc tcctccgccc cctggttcta gtgattcttg  31920
tgcctcaggc tcctgagtat catgctgcaa tttttgtgtg agcatacatt tttcatttct  31980
cttgggtcaa tatctaggag tatccccact tttggttctg agtgttaatt gagcctgttg  32040
tgttctcaca ttccctgtac ttagatggaa atagtgcttt gcctaaaaag aaaataaaag  32100
acctgattgt gcaggcgagt gagaaagaga gagaggcgct agggttattt ccaccctgat  32160
actctttggg tagtcttggt atgactagca aagaagcaag ctccaagttg tagtttgctt  32220
ccaagtttct ggcttctgtg ggaatttctg catctaagta atgacaattt tcagttactt  32280
gcagtaagta aattatcaac caatcttact gtgtattact agcctagtag gaatttactt  32340
gtatatcgag aggaatgctg cagctttcac cttacttcta atggggatta atgcttactt  32400
aacttgcagt tttggaggca agtacaaagt acaggaccaa ttatggtcat gaagtgagag  32460
agaagtctgg ctagtgaatg gtgattggca actccagttg actgttcatg gcatcttaga  32520
tctgtgagga gggaggaggg aaggaaagtt caagctggtc tttatggtaa gttctggaac  32580
atttccctgt gtcaatgggt catctgttca ttcactgtgt aaaatggttg agggaagttt  32640
taatttacat gcttccttat tgtgtaaacc tttgattttt agtgatttca gagtttgttt  32700
ttataattac ttaacacgtg aagaggatgc agagtaacgt atcgaagctc tggttacctt  32760
ccactgggat ttgacacatt tgatttcctt tattccctcc ttccttccct tcctccctct  32820
ctcttttctt aaggaatgca actactcaga ttcacctgca cacccttggc atacctctca  32880
ctccccctta cccccacttc ctcagaggtg acctgtcctc agaggcaaat gtgtgccctt  32940
tccatccgta cttttatgct ctcatctatg tttacatcta ttagtacact attgtctgta  33000
tttttaaaca ttacataaat ggtgtaattt ttacttttaa ttctgtagtg gtgtttctca  33060
aattaagttc tgcacaaaac atttttatag atatccagtg ttagcttaac gtttttctta  33120
ttgtggtaaa atatacataa gataaaattt accattttag ccatttttaa gtttacaagt  33180
cagtggcatt aagtacattc acagtgttgt ataaccatca ccattgtcca ttgccagaac  33240
ttttcatcat cctaaacaga aactctgtac tcattaaaca atagtttatc actccttccc  33300
tgcaactaga tgctggcaat caccattcta ctttctatct ctatcaattt gcctcttcca  33360
tctaagtgga atcctacata tttgtcgctt tgtttctggc tttttttct tcttgtgatg  33420
ctttgtttta attatgttcc tggctttcat catctagcag gctgattcca aggtttgtcc  33480
```

-continued

```
atgtggtagc ttgtatcact ttaatgtttt tagagatagt taatattaca ttgtttatat  33540
ataccacatt ttgttttttc attcaacctt gatggacatt tgaattgttt ccccctttac  33600
ctgttgtgaa taatgctgcc gtgaacattg ataaccaaat atttgtttga atctctgatt  33660
tcagttcttt tggttccata cctaggagtg gaattgctgg atcatatgat aattctatgt  33720
ttaactcttt gagggatggc cagacttttc caccatagct aaatcatttt accttcccac  33780
aagcaaagtt caagggctcc agtctctccc cataaggtcc tttgcacttt tttttttgag  33840
acggaatctc actctgttgc ccaggctgga gaacagtggc accatcttgc ctgacctcaa  33900
gtggcacctg ccttggcctc ccaaagtgct aggattgtag gcgtgggcca ctgcactctg  33960
ccaatttttt aatttttatt ttcatttatt tttctttttt taatttttaa tttttttatt  34020
ttttgaaggg ataaggtctc actttgttgc ccaggctggt cttgaactcc tggcttcaag  34080
caatcctcct acctcggctt ctcagagtgc tgagattata ggtgtaagcc cctgcacatg  34140
gcctttactc tcttgatagt gtcctttgat gcacaaaagc tttcaatttt gatgaagttt  34200
attttttatc ttgttacctg tacatttggt gtcatatatc taagagacca ttgccaaatg  34260
cagtgtcatg aagctttccc tcagtgtttt ctttctgcag ttttatgatt ttagctccta  34320
agtttaggtc tttgatccat tttgagttaa tttttgtata cagtttgaga gtcacacttg  34380
aggctctggg cgcagtggct cacgcctgta atcccactac ttggggaggc cgaggcggat  34440
ggatcacctg aggtcaggag tttgagacca gcctggccaa catgccgaaa ccctgtctct  34500
actaaaaata caaaaattag ccaggcatgg tgatgcatac ctgtggtccc agctacttgg  34560
gaggctgagg caggagaatt gcttgaacac aggaggcgga ggttgcagtg agccgagatt  34620
gtgccactgc actccagcct gggcgacaga gcgagactcc atcgtgcggg gtggggggta  34680
aaagtcaaac ttgagtcttt tgcctgtgga tatccagttt tcccatcact atttgttgaa  34740
aagactatcc tttctcaact gtgaatggtc ttggtaccct agctgaagtt atttttatta  34800
ttatgttact taggaatgca cataaggcct ggcacggtgg ctcatgcttg taattgcagc  34860
actttgagag gtcaaggtgg gaggattcct tgagccgagg agtttgagac cagcctgggc  34920
aatatagcag caagacccca tctctatatt ttaaaaaaag aagaaaaaaa aacctctgat  34980
gcataaaata tttaaacttg tatgcattct tttctttctt tattttttaa aaattgagac  35040
agcagcttac tctgttgtcc aggctggtct tgaactcctg ggctcaagca gttcctctca  35100
ccttggcctg cagtgctgag atgacaggtg tgaaccacta cacctggcct gcttacagat  35160
tataaaaaga aaataagttt acaagttaaa gacagataaa atgacaaaat cagtaaaatt  35220
aaaattactt ttatggagcc gatgatgttt attccagttg ctcctctcat tgtgaatatg  35280
gtattgttgc tgtggcagat ttggaggccg tggcagattt ggaggctttg gcaatggctt  35340
ctgttacctt gccatgaggt aactcagttc cctcatcact tttctctgag aactataaaa  35400
ccttggaggg gtgccttctg cccttcgctt ggcatgtata ttatgcaggg atcaggtctt  35460
actccgttct tgattgttag tacaaattag ttaaaattgt attgtttggc cttagcctga  35520
tggtaaacac aacagcacac gtgggctgtg aaatctctgg gcagctctgt gtttctaggg  35580
aagcatctcg atgatccaga acaggcttat actaatgttt tagtgtaatt ttgaaatgaa  35640
aacacagcat ttaaaaattc ttatagagaa tgtatagacc ttgagaagtg ttagcagacc  35700
cagtttacga catgtctcaa tattatgaaa cattgcttta ttccctatcc tgcttgtaca  35760
tttaattttt tcatccagtt ttaaacaact tgggtactgt ggcctgtgcc tgtattccca  35820
gctactaggg aggctgaggc aggaggattg cttgagcaca ggacttttgag ggctgtagtg  35880
agctgtgatt gtgcctgtga atagccattg tgctccagcc tgggcaacat agcaagaccc  35940
tgataccttg ggtttttaaa aaacaaaaca agatacatgc tgacatttct ggtttggcag  36000
gcagagcttg ttctgctccc caccctccct tttcccatag taaccattta taggacatct  36060
cactgttgtc tactctgtgt tgcctctgct tccctgcgtg gtagatctag gaatcttagg  36120
atttcttagt tttagctggt gatccgtatc tttttcttaa ttccattgta acttcagctt  36180
ttcttattgc ttgtaggaag gctgtttcca ttgaatacaa acaaaataaa agcttttatt  36240
cttaatctta gagataggat gtttgtattt aaaaataatt gtgctgtcaa aattctgtca  36300
agttggcttt taccacatta gttttttttta atgtggttta tatgaccctg gagtaccttg  36360
tcttctcact gttaaattct caactgagtt gtccctattt aaagtgtgag actgtgccag  36420
tttgatttta aaatattgca agtgcgttat ggcaagataa aactgcaaag aaagaacctt  36480
catgtccctt tgattataaa tgcttttggc acttgtttct actttttcct aatgtttttt  36540
gaggaaagaa cctccaactc tccagacagg tctgggggca aatgactaaa acatgaactg  36600
aggccctggg ctgtctctgt gaggatatcc cctctattct ctctgaaatg tcccagcatg  36660
tggtgcattt cttgttagtg tggactcctc tgtatataac acatcttatt tatcttctgt  36720
gcataacatg aagtagtgcc ctaatgcaat tccaggatgt aattcagcat ttctataaaa  36780
atacagtgtt tttctacatt tgcatcaaaa aataaccaga taattatatt tattaagaaa  36840
atagcatttt tggctgggtg tggtagctca cgtaatccca gcactttggg aggccgaggc  36900
aggcagatca cttgaggtca ggagtgaggc aggcagatca cttgagatca ggagttcgag  36960
accagcctgg ccaacatggt gaaaccccat ctctactaaa aatgcaaaat tagcctggcg  37020
tagtggtgca tgcctgtaat cctagctact caggagactg aggcaggaga atcacttgaa  37080
cttgggaagg ggagattgca gtgagctgag attgtgccac tgcactccag cctaggcaac  37140
agagtgagac tctgtttcaa aaaaaaaaaa aaaaaacaaa gaaaagaaaa gaaagaaaga  37200
aatgtatttt tggtatttgt tttcacaaac tagagcattt atgtgaaata acattgctag  37260
tattgatatt ataccatagt ataatactta gttcttcagc gatgtatctc tgctgatcag  37320
ctacatgata tctacttgag ctgttggatt ttttttaaga acagtgcatt tttgaatgct  37380
tttgaaaaat tgtagtaaaa tacataaaac aacatttacc ttgtaagcat tttaattggt  37440
acaattcagt gacattaagt acagtcccag tttagtgcaa ccactgttac tgtctagttt  37500
cagaacgttt ttgccccaga tggatactct gtacctgttg aacattcagt cctcatggcc  37560
caataatctt tatgtctgta tagatttgcc tattctgcat attttatata aatggaatca  37620
tgtcttttgt gtctggcttc ttttacctag catagtattt tcaaggttca tccatgttgc  37680
agcatgtttc aatactttgt tcctttttat gtccattgta tggatatgcc acatttcgtt  37740
aatgacaatt cttttgggta gctacatttt aaaacattat agtagaatac atatagcata  37800
caatttacta tcttaaccat ttaagcctgc agttcagtgg cattaaatac attcacgtta  37860
ctgtgcaatt atcaccacca tctgtttgca gaaacttttc atctcctcca tttgaaactc  37920
tgtatacatt aaacatgaac tctcccttct cccttcctc cagccctggc agccaccgtt  37980
ctacattttt atctttctga cagagatttt actactctag gtacctcaca taagtgaaat  38040
caaccagtat ttatcctttt gtgaccagct tatttcatta gcttaatgtc ctcaaggttc  38100
atccatgttg tagcatatgt caacatgact ttcctttttaa ggttgaataa tattccattg  38160
tatgtatatg tcacaatttg tttctccatt tatccatcac tggacatttg ggttgctttt  38220
```

-continued

```
acctatcggc tgtcttgaat catgttgcta tagctgtaca agtatctatt tgagtttctg  38280
ctatcaattc tttaagtata tgcccagaag tggaattgct ggatcatatg gtaattccgt  38340
gtctggtttt ttttttgagg aagtgccatg ctgttttcca cacagctgta ccattgtaca  38400
ttccccccag caatgtacga gggctctgat ttcttcacat ccttgctaac acttagtatt  38460
tttttgata gaatagccat cctaatggct acttttaaag tatgtttaac attatttatt  38520
tatttttaat tttttttgta gagatggcat cttactgtgt tgcccaggct ggtcatgaac  38580
tcctgggctc aagcagtcct cctgcttcag cctcccaaag tgttcggatt ataggcgtga  38640
gccaccatgc ccagcccaaa tttaaatata taactaaaca catagcagct aacaccaagc  38700
ctttaaaaat atcattaata ggccaggcgc agtggctcat gcctgtaatc ccagcacttt  38760
gggaggccga ggcgggcaga tcacctgagg tcgcgagttc gagaccagcc tgaccaacat  38820
ggagaaaccc tgtctctact aaaaatacaa aattagccgg gcatggtggc acatgcctgt  38880
aatcccagct actggggagg ctgaggcagg agaatcactt gaacctggga ggcggaggtt  38940
gcggtgagtc gagatcgcac cattgccctc cagcctgggc aacaagagca aaactccatc  39000
tcaaaaaaac aaacaaacaa acaaaatata tatatcatta ataggccggg catggtgtct  39060
cacgcttgta atcccagtgc tttgagaggc cgaggtgggc agatcactgg ggtcaggagt  39120
tcgataccag cctgggcaac atggtgaaac cctgtctctg ctaaaaatac aaaaattagc  39180
cacgcatggt ggtaagcacc tgtaatccca gctactcagg aggctgaggc tggagaatgc  39240
ttggacctgg gaggtggagg ctacagtgag ctgagatcac actccagcct gggtgacaga  39300
gcaagactct gtctcaaaaa aaaaaaaaaa aatcattaat aaatgtgatc tttttcttc  39360
ctatacaaca agttgtcaag caagtatgac cttcttaatt gaccctttga catgaactgg  39420
gatgagatcg tggaggatgt tgaggagaca gttgttacca tagtgcactt ctaaaaactt  39480
taattctata gatttcttta aaatttttt taaaattatt atgagtacac aataggtgca  39540
tctatagatt tcattaccct caaataaatg tacaaggcaa tgcagagaaa tgcacagtgt  39600
aacttggtag acttgaccta tcaagttact gttgaatata ttatggagcc tgtgtattac  39660
caggggcagc agacttttcc tgtaaagata gttgttttca gctttgttga atctgtggtc  39720
tctgtcttaa ctacaactga gaaagccatt gacaatatat agatgaatgt acatgactat  39780
tctaataaaa ctgtgtacac tgtaatttga attgcacata attttcatgt gtctcctgta  39840
taattcttct tttgacttct tttcaaccat taaaaaatgt aaaaacaggc caggcgtggt  39900
ggctcatgct tgtaatccca gcactttggg aggctgggtg gattgctgga gcccaggagc  39960
ttgagatcag cctgagcaat gtgatgaaac cctgtctcta caaaaaaatta gctgggcatg  40020
gtgttatgtg cctgtggtcc cagctacttg ggaggctgag gtaggaggat tgcctgaacc  40080
cgaggaagtc aaggctacag tggtttgtgc cactgcactc tagcctaggt gacagagtga  40140
gaccctgtct cagtgaatga atgaatacat tattagcttg tggactatac aaaaatcaga  40200
ggctggaggt gagctgggta tggccattgg gtgtggtttg ctgacttctg gtagagagga  40260
attaggagat gttaaaggtg gtggaactgt cagatacttg cattctttta gaaatacttt  40320
ggagttagct ttttggttca ggcaaaggac caaagggtta ggagagtcag gccggtaaag  40380
aggagtggtg ggcccatagc agcagttcct ggagtttttt tttttttttt ttttttgtga  40440
gacggagttt tgctctgtcg cccaggctgg agtgcagtgg cacgatctcg gctcactgca  40500
acctctgcct cctgggctca agcaattctc ctgcctcagc ctcccgagta gctgggacta  40560
caggtgccca ccgccacgcc cggccaattt ttttctattt ttagtagaga tgggatttca  40620
ccgtgtttgc taggatggtc tcgatctcct gacctcgtga tccacctgcc tcggcctccc  40680
aaagtgttgg gattacaggt gtgagtcacc gcgcctggcc aggtcctgga gtctttaaga  40740
ggaggtttgt ctgatggttg gttggacaaa agcctgggca tgttgtcacc ttccataagt  40800
gtttgtggga atgtaggtaa tgaggaggag taaaggattc ctgaaggatg aggaggaggg  40860
ctggtggctg ccataggaag tgatcactgt tttggcagac ctgtcttaga gtaatgaccg  40920
tcatactctc tcattgccct tgtgaactca tgaaatccca tggctgctaa agctgaaggt  40980
caagtgggga cttcccggcc actgggctta gcaccccaca gagctgtgga gtgggcatta  41040
atgtcccttt tttatagatg cggagactga gaatgaggac tgttggtaac ttttgaaagg  41100
gcactcagct agaaaagtct gagccaggat ttcaagtccc atggctttac ctctgtggtc  41160
ctaatatttg gtgtgttcaa gtgagatctg tttttttcct atttcatttt gattattgat  41220
tttcataaat ttttttctct tttgagatag tatcttctct ctcttttctt ttttctgttc  41280
tttctttctc ttttctttct tttttttttt ttctctgaga cggagtcttg ctctgtcgcc  41340
caggctggag tgcaatggtg caatctcagt tcactgcaac ctctgcctct cgggttcaag  41400
cgattctccc atctcagcct cctgagttgc tgagattaca ggcacctgcc atcttgcctg  41460
gctagttttt gtatttttgt agagacgggg tttcatcacg ttggccaggc tggtcttgaa  41520
cttctgacct caggcgatcc acccgcctct gcctcccaaa gcgctgtgat tatatgcatg  41580
agccaccatg cctggccatt atttctttct ttctttcttt ttcttttttt caggttcatt  41640
gaatttgctt tgagacaggg tcttgctctg ttgcccaggc tgaagcgcag tggtgcagtc  41700
atggctcact ggagcatcaa tttcctgggc tcaagcgata cttgcacttc agcacccctc  41760
cacccccacc cgctcctttc ccccacagta gctggaacta caggcgctag ccaccgtgct  41820
tggctaattt tttttttttt tttttttttg agacggagtc tcgctctgtc acccaggctg  41880
gagtgcagtg gcgcgatctc ggctcactgc aagctctgcc tcccaggttc acatcattct  41940
cctgcctcag cctcccaagt agctgggact acaggcgccc gccaccatgc ccggctaatt  42000
ttttgtattt tttagtagag acggggtttc accgtgttag ccaggatggt ctcgatctcc  42060
tgaccttgtg atccgcctgc ctcggcctcc caaagtgctg ggattacagg catgagccac  42120
tgcacccggc ctggctaatt tttaaatttt tttttgtaga ctgcccaggc ttgtttaatt  42180
gattttctat gtgatcttag ggaaatcgat tatttcccat aaacattttt ttaattagaa  42240
gttaaattct gcctagtttg attcacagga ttattgtgga tgactgaaac agagaatagg  42300
taagagcttc tttgaaaaat atgaggtacc atacagaagt tagatgcttt gtcctggtga  42360
tacccccctcc aaagcacagc taaggaaatg tggaaggcac tcttatctca tcatatagct  42420
ttgaaagcct agcattgaaa gtacgaactt gattcttttg gagaaatcct ttggctctca  42480
gtgagtttac tttctattaa tgactgtgtt aagcggaatg aaaactgaaa gaggaaaggg  42540
gaggaagtca gaattaagca ggaagagtga gcccatagca gagtccagat ttagacccca  42600
agctacttgg aatgatactg gacaattatg ggtgtgttta atgatggtcc tgagtcatga  42660
aaacaaaagg aggctttaaa ttatgtctgg cttagtgtac agcatatttt tgtcattatt  42720
caagttttag catgtaaaga ggaaagtgtg cagtacttat gcatatcatt ttcattaatg  42780
aaactaaatg aggcctcttt aaaattatca gtgttcacag tatcttccaa aagacatgta  42840
aatgtataaa ggtataaaaa atatacatat aaattttaca attttgtgag ctatatagta  42900
gatctcttat tttgtccata ggtcttaaag atcttatact gtattcagga ataaagataa  42960
```

-continued

```
cttcagtggg aggcctttac agggctaatg agtaagcatt attttgataa agttctgtgt  43020
tgtctacaat agatatagta gaaatactct tggaatggta atcatcccag gccctgcttt  43080
ggagcggaag aaatagtcaa tgtagaactt tacagtatat tgtacacaga tgtgcctgct  43140
aataacttct gtagacagca aagtttaaga gaaattaggt ggtaaatgca acatatgtat  43200
ctaaataaat ttggtctgag ggatttgata agatgaaaca gtacatagtc cagaaaattt  43260
ttatactcaa agaattatag aaaatatctg aaatgttttc agttttgtgc atatccagaa  43320
aatgtcatcc tgtgatctgc tggttggcag cccaatggca gtattagatg tattgttttt  43380
attttgtttt gtttgctatt tatttggtta agagagttac ctaattagga gtgtgaaaaa  43440
aaagatttat tatagtagtg ggcttttgtt tgacttaaaa catttttgtt gttaccacag  43500
tatgagtgcc ttgtttgtga aatttgttta ccgggaagcc atatacttag agtagctttt  43560
agtttatcat tatcatcatc atcatcatca tcatcatcat catcatcatc tccttcatca  43620
tgaaaggaag aagctaccaa tgttgcttta ttctgcaaaa aatacaatag atgcttgttg  43680
aaagtatgga gtgaaatctt aaatatgtct gttaaaaaga gtacaactgg ccaggggtag  43740
tgcctcatgc ctgtaatccc agcactttgg gaggccaagg cgggcagatc gcttgagcca  43800
ggagtttgag accagcctgg gcaacatggt gaaatcctgt ctctacaaaa aaaaaaaaaa  43860
tagacaaaaa ttagctgggt gtgatggcat gcagctgtag tcccagctac agtggggctg  43920
aggcaggggg attgcttgag cccaggaagt aaaggctgca gtgagctatg gttgtgccac  43980
tgcattccag tgtgggtaac agaacgaaac cctgtctcaa aaaaaaaaaa atagtacaac  44040
tttaagcagg atgtgggcac atgcctgtag tctcagctac ttgggaggct aagtcaggag  44100
agtcacttga gcccaggagc ttgatgctgc agtgagatgt gattgtgcca ctgccttcca  44160
gcctggggat gatagcaaga ccccatctct aaaaaaaaaa caaaaaacaa aaaaaaaaca  44220
gagtacaaca acctttggta aacttggaat ataaaggtgt ttccttaacc tgttaaagag  44280
ctgataaaga gtggtacttt caaaccagta cacattatgt gaaacactag agacacttcc  44340
catttgttaa aagaaaaacc ttagccaaat taaatttaag tttttttgg agacagagtc  44400
ttgctttgtc acccaggctg gagtgcagtg gtgcaagcac agctcactgc aacctccgcc  44460
ttctgggttc aagtgatttt cctgcctcag cctcctgcgt agctgggact acaggtgtgc  44520
accaccacgc ctgggtgatt tttgtatttt ttgtagacat ggggttttgc catgttgccc  44580
agtctggtct tgaactcctg ggctcaagca atctgcctgc ctgggcctct gaaagtgctg  44640
ggattacagg cgtgagccac catgccattt aatggtttaa ttgagcaaag aatgatttgc  44700
aaattgggca gcctcccgag ccagagtagg ttcagagact ccagcacagc catgtcgtgg  44760
aaaaagattt atgaatggaa agaggaaagt gatgtaccga aaacggaagt gaggtacaga  44820
aacagccgga ttggttacag ctctgaattt gccttatttg aacacaagtt gaggtttgta  44880
cagttggcca cctttgattg gccaaaactc ggtgattggc acaagagcag gttatagtct  44940
gtttacatct ccattttggt tatagttcat tatggacaga aaaacctgta ggtcaaactt  45000
aaaatatgta aggagacagt tttaggctaa acttgattta acacattaaa tccgtaacaa  45060
gacaggatgc ctgccctcac catgttattt gatcttattt tagtaattct agccaatgta  45120
gtagggcaag aaaactgcct gcttggctac aaaataaaca cacaaaagtc agtatctgta  45180
atatgtgaca gaaaatataa ttaaaaaaaa aaaaaaaagc cgggcacagt ggcccatgac  45240
tgtaatccta gcactttggg aggccaacgt gggtggatct cttgagctca ggagttcaag  45300
accatcctag gcaacatggc aaaaccccgt ctctacaaaa aatacaaaaa aattagccac  45360
gtgtggtggt gagctcctat agtcccagct actttggagg ctgaggttgg aggatcattt  45420
gaacctgaga agcacaggtt atagtgagct gagatcacgc cactgcactc cagcctgggt  45480
gacaaagtga gactctgtct aaaaaaaaaa aaaaaagaag aaaaggaaag gaaagtaaaa  45540
gaaaaaataa tttcacttac tagagcatca aatccctaag ataatttaga gcaaagccag  45600
aaaagtgaag aaaatataaa aatctttaca gtgggttgca ttttaaaaaa aaacttgaag  45660
atatcagatc aactcactaa tgtattaatt aatataattt aaattaaaat cccactgatt  45720
tttttgtggg gagggtggga gagtcatttg ttaaaatgat tctaaagagc atctggaaga  45780
ataagcaggc aagaatagcc aagaacattt tgaaaactaa agatgagttt ggaagacgat  45840
tggttttgta ctgtcaacta cttatagatt ttacatgaat tttaaagggt aatctgagcc  45900
ctcgaataga cagaaatagc catagatctg aaagaacact taagacctga tccagctatc  45960
catgagagta tatataatca aagtctttgt gtgtgaatca ggagtctttc aggtgcaagg  46020
taaataaact cataattgct tacgcaaagg tggtatttgc tttagtgact ccagagaaag  46080
ctcaagtgcc tatctctccc ctgactttga ttctttttgg ggttggctcc attctctcct  46140
gttgctaatg gcttcctttg tgcagccaga ggaaaggagg tgtggttttt tgatacttcc  46200
aggcttctat ttttatagct tgagatcaaa gagggaagtg accttcctta gagtcagtgt  46260
gtaaagtcct aaggaagata ccacgtgggg tgctggggcc atgtgcccat ccctggccca  46320
tgaccatggg gatgctacac taactggggg ccacgcatgg ctgttcctgc cctgaactgc  46380
cagctggctt tgcagtgcag cctcaccaga atcacatgga atagtaggga tatgaattgt  46440
ttcccaaaga aagtgtgtgg ggtggtagaa ttactagtgg gggagtaagg ggacaggcca  46500
ttgggcatac tggagcagca tttactcagt cattgagaaa aggatggaac attcaataaa  46560
gggtgctgga cacatttgtg ctctaaaaat tttgtgtttc acctattaat ttatccctcc  46620
ccttagcccc tggcaaacac tgatctgttt actgtctcca tagttttgcc tttcccagaa  46680
tgtcacaccc ttggaatcat acagcatgta accttttcag attggcttct tttacgtagt  46740
aatatgcatt taggattcct tcatgccttt tcctggattg atagctcatt tctttttagt  46800
cctgaataat attccattct atggatatac cacaattgat ccattcacct actgaaggtc  46860
attttgattg cttccaagtt ttgataattt aaaaaatttt ttaagacagg gtgtcattgt  46920
gttttccata ctggtctcct gaacacctgg gctgatgtga acccctctcc tcagcctcct  46980
gggtaactgg gattacagct atacaccact gtgcccagtg tgacaattat gaataaggct  47040
gctgtaaact tctgtgtagg tttttttgtg tgtggacatt ggttttcagt tcattatggt  47100
aaataccaag gagtgcagtt gctggattgt atggtaaaag tatgtttagt ttgctaagga  47160
actgccagct gggtgtggtg gctcatgcct gtaatcctag cataatggga ggctgagaca  47220
ggaggatccc ttgaagccag gagttcgaga ctagcctggg caacatagtg agacctcatc  47280
tctacaaaaa atttaaaaat tagctgggcg tggtcttatg tgcctatagt cctaactgct  47340
tgggagactg aggtgggagg atcacttgag cccaggagct ggaggtggca gtaaactgtg  47400
atcataccac tgcactgctg cctgggtgac aaagcaagac cctgacttaa aaaaaaaaag  47460
agaaaagaaa aaaagatgag tcagagggta aggaagcaaa aataagtaaa taaataaata  47520
gaagagaaaa gaaaaaagaa aaaactgtct ttcaaagtgg ctgcgccatt ttgcattcct  47580
accagcaatg aatgagagtc tgttgttgca catcctcacc agcatttggt gttgtcagtg  47640
ttctggattt tgaatattct attaggtata taatgctgtc tcacttgttt taatcaatga  47700
```

-continued

```
tatatgacat tgagcatctt tttaatatgt ttacttctca tctatgtatc ttctttagtg  47760
aggcctttgt ttaggtcttc tgcccatttt aaaaaatggg ttcattttct tattgttgaa  47820
tatcatgagt tctttgtcta ttttgaatac ctgcctttttg ctttattttt gtgtttttta  47880
ttttttttt ttattgagac aagttctcac tctgttgccc aggctagagt gcagtggcat  47940
gaacatggct cactgcagcc tcaacttctc ccagcctcaa gcaatcctct tgcctcagcc  48000
ttccgagtag ctgggactat aggcacacac caccatgccc tgctaattta aaagagtttt  48060
tttttgtaga ggtgggatct cgccatgtta cccaggtggt cttgaactcc tggcctcagg  48120
caatcttcca gccctcagcc tcccaaagtg ctgattatag gcctgagcca cttagcctag  48180
ctcagaattt atttttattt tgttaatttt gaaaaaatat aggacctcat aaaagtcagt  48240
ctacatttgt acacattatg tttttggtga atatgtaaat ggattctttg tgaatcaatt  48300
tggttttgtt tttttgcttt taaaaatacc agccctgggc tggatgcggt ggctcacgcc  48360
tgtaatccta gcactttggg aggctgaggc aggtggatct cctgaggtca ggagtttgag  48420
accagcctgg ccaacatggt gaaacgctgt ctctactaaa aatacaaaaa ttagctgggc  48480
gtggtggcgc atgtcagtaa tcccagctac ttaggaggct gaggcatgag aatcgattga  48540
acctgggagg cagaggttgc agtgagccga gatcgcgcca ctgcactcca accttggcga  48600
tagagcaaga ctctgtctca agaaaaaaaa aaatgccagc agtggctggc tgaggtggct  48660
cacacctata atcccagcac tttgggaagc caaggcaggt agatctcttg tggtcaggag  48720
ttcaagacca gcctggcgaa catggcgaaa ccccatctct accaaaaata caaaaattag  48780
ctggatgtgg tagtgcgcac ctgtaatttc agctgctggg gaggctgaga catgagaatc  48840
acttggaccc tggaggcaga ggttggagtg agccactgta ttccagcctg ggtgaaagag  48900
ggatactcta tttaaaaaaa aaaaaaaaaa aagcgggctg gatacagtgg tgcacacctg  48960
taaccctagc actttgggag gctgaggtgc tcagattgct tgagctcagg agtttgagac  49020
cagcctagac aacatagtga gacatcgtcc ctaaagaaaa aaaaaaaata ccagcactta  49080
gccaaaagat ttcaacagtg cagaaaaaga aagttgtgat atcttttctc caaattagtc  49140
ttgttttcag tttcattatc caagtaacca ctactaatag ttaaaacatt tgaaatacgt  49200
gtgggagctt gtcctattta atataaatta tttattgagc aaataatcac cactagtatg  49260
ttttggatac tggaattttc atatgtagga gtccttgaat gtaaggtgcc cctttggtag  49320
ttctgtgctt cttttacctg tactgtaaca tagggaaaga tgttacaaat ggttgtattt  49380
ttaacagagc agtatctatt cttaaacacc agcccttcca ctaaaggtaa acaacaaatg  49440
aatacataaa tgaagttttg gtattgggat tatgtgggtt aaacacatcc atatttcatt  49500
attaatattt aagaatataa caaacttttt attggcattt ggaccttgta gctaaggaaa  49560
gattaaactt tgtttatttg tgctttgttt tttttcttca ctcagatatt tgaggatttc  49620
ccatttgagg aatacattta ttaatcaagc tttagtttca agatccttga tcttagggaa  49680
taccatcaac cgttcttctt taagcttcct aactttgccc aaatttggtt agaactactc  49740
aagagtagtt tgggtaattc agaaatttta ttggaagggg aaagaatttt tgacccaaat  49800
tagataaagc aactcttggg taatgatttc ttttcttgtt ctctctttat aatcaattga  49860
aagtagtagt aaggctgggt ggcaaaagaa agaggcctgg ggagaatcgc gtggttttca  49920
ttatctcttt tcatagcagc aaagtgggaa gggaccaaga ggaaatcaac tgaaaaacca  49980
tccttctgaa acattggcct aaaaaactgt agtccagaaa ttgagtgcaa ctggcagtgg  50040
catttaaaag gaatgctcta atttctagga aagcaggcac gagtacctct taaaagaaga  50100
aaaaaatgaa aactgtaatt taggacacat agacgagtat ccattccctg tacttttact  50160
ctcatgtcct aaccaaggaa gggttgccat agcaaatatg gcattcctta gccatgattc  50220
actgttgtaa atgcctgcag cattcataaa agtaagatat atgggctctt ctttttcctt  50280
ttaaatcttt atttctgtat ttaaatctgt atgtcatcat ctgtattttc tctcttgttt  50340
tttttaaatc ttgggagatg gtacaaatta tttaggggag ggaatgagtt tcttgtccac  50400
aaatagagga gagagagggc tttttgtctt tctgctttgg aactggagag cttcctattt  50460
aggcatggcc tttttcaagt gaccttgtat tgttatcagt actgtagaag gtaggcacgt  50520
tgtgtaaact ttaaaattga aagccattag gcattccact tgtaaacctt ggctttttaa  50580
agaaaattac atgttcattg tgaatatttt cttatcgacc tatctctgtg cacatgcaga  50640
cttcctttgc ctacattctg aaaggtgtaa ttgccttctt taaggacagc ggacatctat  50700
agttcttggg tcaaattgtc ctccttctgg ttttgtcagt tctcagccac actgtgtgag  50760
catccatttt cttggattct ggttcggagc tcattttaag gaacatcatg tccctttttga  50820
gactctgtgg acattggggt gggtagatgt ccccctgtga acagaaggtc cctccctaag  50880
gaggtgcttc tctgtgttga gtcctgcatc tgggcacaca gagcccgaag caggaagagt  50940
tgagtctgaa tagggaggcc tgtaagcctg actgctctgc cacgggtagg cctggtctgc  51000
catgctccag gagcccccag gaggctctga agtcattctg cctctgggaa ttttacagag  51060
gagctaatat ttgagctgag tgagaaggtg attcttgaaa aagcaaggcg tgccctggtc  51120
cagttctgtg gggctgtcgt agaagagggc tcggaagctc ttgggagtga ggctagaaag  51180
gtaggcagtg ttaccataag gaggttggaa gtgacacaga taggctaagg aaggggactt  51240
cagtaatcat gcagcaatgg cctggaaaag ggagaggctc atagtaggga gaccagtttg  51300
gaggctgcca tagtgttcta ctgagagaga aaaagacttg aactcagagc acggtcaggg  51360
aaggtggagg ggcagggtct gatttggaag tgttttgttt tttggttttg ggaacaagga  51420
tttggaaacc tcttggctcc gtagatgaag aaaggtgaac caaggaagac tgaagtttcc  51480
actcaaggaa acagtaactc agggaagaaa acacaggagt aggaataggt ttaagagaat  51540
gacaagcagt tgtgttttgg acttgtttag ttcgaggtga catctttgta gggatgtcta  51600
gctggtagct gcaagtatag gaggaggctg gatgtgtgca tgagtttctt ggtaaagatc  51660
catctgcagt ctcctgaaga tgtcacccag attgccctgc catcacccca gggccttgag  51720
tcactcgctt ctcttggtgt ctaggcaggc ttgaagaaaa tcaaacagta caaaatcatg  51780
caaattcaga cctctattcc accccagagg aaagtcctgc tagcagtttt tgtgtattct  51840
tccagaaatt tgccttgcaa cgcgtttgag tatataaata atcccagaaa ggatgggcca  51900
gacactagca gaaactcacc acacacactg cactgggcat gcagaaactt tgcaaaatgt  51960
actggtgtgt gctgtcactg cattcctggg tttggaggtc ttctgtgtcc ccagctgtca  52020
gtattgccca caggctgacc actgagctcc ttccacagcc ggcccatatc accctctttc  52080
gaagtgtgtc tgcaaggcta gattattaga gtaatttaag tgtttctgct ttgtgttttc  52140
tttaatgaat ttttttatga tgaagttctt gttttaaaaa tatacagtgg taattaacat  52200
gtatgcattt ttcttaaaat gacccccccca gtccctcttc ggatgtgatc actgttaaca  52260
gtatcgtata tagaccctgt tctgtgtggg gcgggcagag ggctggttag tgggtggaac  52320
atgcatactc acaaccatat ttttcacatg ggaaaatata aaggtgacaa caaatctcct  52380
ggactataat ctcatcaagc agacaataat ctctgtttca aaagtggaca aatacatgct  52440
```

-continued

```
gatttttaa aaaaaattat aatagtacag aaagatacaa aaataagtta aagtcttcct  52500
aactctcctg cctgtgccct ccactgggca aaagtccctg tccctaaggt aatatctgtt  52560
aacagttctc cttccagaaa acttgcaatg caaataggaa cattttgtgt gtctgcctct  52620
gtgtgtatgt gtttacatgt cttttttttt tttttttttt tttttttttt tttttttttt  52680
tttttttttt tgagacagag tcttgctctg ttatccaggc tggagtgcag tggcatgatc  52740
tcagcttgct gtgatctctg cctcctgggt tcaagtgatt ctcatgcctc agcctcccga  52800
gtagctggaa ttacaggcgc ctgccaccac acccagctaa tttttgtatt tttagtagag  52860
atggggtttc gccatgttgg ccaggctggt ctgaaactcc tgacatcaag tgatctaccc  52920
gcctcagcct cccaaagtgc tgggattaca ggtgtgagcc actgcttctg cccctgcaca  52980
tgtctaacgc acacaaaaga gattctgctg aacacatttt ttatgctttt tctttccaat  53040
ttaacatatt tgacatcttt atcagcttat atagctttat ttttttaaga ggttattggc  53100
tataaaggga aagtgcttta tgggtgcttc tgttgttatt taattggatc ctgttgatgg  53160
acattgatat catttctaaa ttttttagta tcctaattaa tcctgtggtg agcatcctta  53220
tacagatatc cttgttccct catgaaaata tttctggagg atggaaagaa gggaaatttt  53280
aaaaattatt tgtgtaaaca ttatcgtttg ttagtagaat gacctcagga gagattgtag  53340
taatttatac ttccccacat gcatatgaat gccttttcaa tatattgttt caaaattgga  53400
tatcatgaac cttaagagat aaatatatat gtatgtattt tttttttttt tttttttttg  53460
gtgggggcat gtcctgttat tgacagtttg ttttggtgga gggatgtcct gttattgaca  53520
gttatcgaat agaactttgt cagttccttc atgtaaggga tgaatttggt aataaaacag  53580
gtctgacttc agttatggaa ctgggaaagc tggaccttga tgtggaggtg ggctcagaca  53640
tgctgtgtct gggcaggtat ctcttgggaa gcagtgtcat ccctgaacag aaacatggat  53700
gagccgcagg ggacggtgct gagcagaggg gctggccgtg ggtcatctgc ctcccttggc  53760
ctagaaggca caagggagct ttccaccttg cctttggttt tgagaatgca gaagctacta  53820
agcaactcac agtgtgccca gggtggtcca gctgaaggat gcgaaatggt tcttcctttt  53880
ccagccaaag atcttgaacc tcccacccca tgacaagcat tataaaattc acataatttt  53940
gataggctgg attcctttttc tgtagcagat ctttcctcag aacagaagtt tgttttttttt  54000
ttttaaccta aattacctgt gagttttatt ttttaaatat ggaatctgtt ttttggacac  54060
ctccttgtca tattaaatgt tctgttatta attttgagat tttaatgtaa attttacccc  54120
agcaaattaa ttttgtttct cttgctctct cttttttttt ttttggcatc ctttcccgtt  54180
gtatagtggt gctcatttta tcatactgct tttatatgac ttttcttttg tgaacaggga  54240
tcttgttcac ttttcctttt ttaaaaattt ttttattttt ttgagacgga gtcttgctct  54300
gttgcccagg ctggagaaca gaggcacaat ctcagcccac tgcaagtttt gtcttccggg  54360
ctcaagcgat tctcccacct tagcctcttg agtagctggg attacaggcg tgcaccatca  54420
cgcctggcta atttttttgt atttttgtag agatggggtt tcactatgtc atccaggctg  54480
gtctcgaact cctggactca agcgatccac ccgcctcagc ctcacaaaat gctagggtta  54540
caggcgtgag ccactgtgcc cgagccactt ttccttttaa cataaaaaca ttgatatcct  54600
agagagggca ctgtattttg ggtacataca ggttcagatc acggaagagt tgtattctat  54660
actttttttc atcattctta gttcagtatg atgtatttta taatttcata tgagaaactg  54720
taacaatggg catgtgtcat ccagcaatac ctactcataa atcatattaa attttgatcc  54780
aaacatggga gaaactgaag ttttctctgt gtacttggat gctttcagag gcataaaatt  54840
atattaccat gtgaaagcaa gcctacaaaa ttcctcaggt ggtccactct gccactcaaa  54900
tgagagccag acttacagtg cacactctac aaacggactt ccagctcgtc agggtatttt  54960
aagtgcctga atatgcaagg cactgtgcca gtaaaattac tcagtcctga ggatagagcc  55020
tgttagaatt attttaaaat ctgtacttga agtttatttc ctcagtattc caagatattt  55080
tatctggttg ttctctgagt atttcacacg tagctagtta catataggtg agatggtgat  55140
gcttgtgcct ggtgtggatg agaaactgag cctggcagac ccgagattgg atttcctctt  55200
ctgactttgc aagtgtggct ttgctttaat aatagccctc ctctttttct gtattcctct  55260
tttctccttc cagtgtggca aatatgcatc aatcaaaata caataacctg tggaaccatt  55320
ttttctaaaa taggaaggtg gtgccatggg ctattgattg ttgagggtag tcttcagagc  55380
ctgtcttata aatctataat aattcccccc aaattaatgt gctagttaga accctagaat  55440
tgcagcactg aaagtgaatt ttagaatctt ttccaacttt ttaccaagct cagaaagccc  55500
ttttattgga cctttgtttg cctcatggtc atctggtttc tttatgctgg tagtaacagg  55560
aaccttacta acctacaagg tgacccagtc catcctgggc agctgtgatc attggaaagc  55620
tctgaatcat tcatctggaa gctgcctgtg gcagaatagt acagaacata tgcattgcac  55680
acactacaaa actgctttaa ataagtgttc cttttcattg ttagatggaa gtgacccagg  55740
gcaaggatca tgttttatga gccagttttc tcctagtgcc ttgaacatag gcacttggta  55800
gtgtttagag aatgaattgt cttttttttt tttgagacaa agtctcactc cattgcccag  55860
gctggattgc agtggcacgg tgtcagctca ctgcagcctc cacctcccaa gttgaagtga  55920
tttttgtgcc tcatcctccc gaggagctgg aattacaggc atgcgccacc acacccagct  55980
aatttttata tttttagtag agatggggtt ttgcgtgttg gccagatggt ctccaactcc  56040
tggcctcagg cgatctgcct gcctcagcct cccaaagtgc tgggattaca ggcgtgagcc  56100
actgcgcctg gccagagaat gaattcttaa taagtttctt atgacttcag attgactggc  56160
agttgtgcta aatatttttt gcctttattt gaattagaaa attcgtaagg gggccttgag  56220
agtagatgca gtcacattta ggagattttt cccccccatt ggttaaaatg cagtttttct  56280
atggatctgc tttagaacta caaataaact ccgatcactc acagcagact acgcaatgag  56340
ataagaagca gtccatttgt tctgtcgttt attcatggcc ctcatctttg ccagccaacc  56400
tgtgcagaag agcacagcaa agcataagct tcctaacagc tattcccatt cagctgctgt  56460
cttcaagaag cagaagggtt tagataacct tagagaacat aatcaaacct gggaaactca  56520
aatcaaaaca aaacttcgaa acggaagttg aaggtcctga ggtacccaga ggcatagcaa  56580
ggaaaacgtc cccactggga tatcttctgg attcacctac agacctctct ggagttttaa  56640
gatccacgtt ttatgacata ttgcatagca aacaggccga acgctgttgt aaatcatcct  56700
ctacgaaagg cccaggtttt gaaactgaag gcctgaaaag gctcctgctt accagctgtg  56760
tgctgtacct gacacactga agcctgagag tgccagtcac ctgtcagagg gaacacagct  56820
gccctcaggc agaacctgag tctagaactc aaggtttttg actcttaggc taaaaataaa  56880
aaatcagaag gaggaactat ggattgctta atcagtcaca ttttcacttt ctaaggtttc  56940
ttgtagcaaa agttatagtc tttggggatt gggatgtaga cacttttttt tccttcccta  57000
aaacaatttt tggcctgcca gtttttcgag cttcctgctc tggaccctga agttgccatg  57060
cagttgcaga catgctcctc cttcaaggct ctgttaagct gtggctgccc ttccttacca  57120
ctgctgtgcc ccaggccaaa ccccctgccc ctccttcccc taaggcactt tgcacctgtt  57180
```

-continued

```
gctccgagcc ttctggtcta tcccagttgg tagagtccct gtgcttacct ctgtggctca  57240
gtcctcgtgg gtggtcagtg ctctagggaa ggtgagctga ccacttcact ttcccttccc  57300
agccatagct cttcacagcc tcaccaactt agaaaggaat gctgcttttc tctctgtccc  57360
ccgtcctgac tatgttcaag tcattgctca gcccagtgag tttgtccttt cttccagacc  57420
agtagttttc ccccagtccc tcaggcttca gcccttgaag gcatccttag ccccccacca  57480
ccatgatagt caggcgctgc gcctatccgc agggtgtggg tatgtgtgtg tcttttgttt  57540
ctggagccca ttcctttcct tccaccagcc tctaggcctt catccaatcc ttttgcaact  57600
cagtgattca tgacttttcc ctgcatccag tctagtctct ttgctggtcc attgtttcca  57660
tagttgccag tttaatcttc ttaaaatgct gcatttttga agtcagtctc ttttggtccc  57720
tctcagaaac atttaaatag ctatctgttg ccacaggggg aaagcttgaa cctcttagcc  57780
agtcattcag agcctgccct ctgctggggc ctgctttcct ctacagatgc ttctcccact  57840
ctgcctgcca cagcccttgt agctggctga ttgccctgta cctcgcaggc tctggaagtc  57900
ttcagctcct tcatggagcc tttgccagcc attcttttca agactttgct gttgttcact  57960
gcctgatttg ttcatttgac acttaattca ctgagcaaac attatgaaag atgtactgtt  58020
tgctactgtg aggaatggat ccccaagaga taagagggtc agtccctact gccaggaaac  58080
ttgcctgtgt cacctgggtt cagtatcttg tgtctattag atcagaagtg gaaaggcaga  58140
ggccagcccg tatgcttgtt ttattttatt taaatcacca gcaccccagc aagtgttttg  58200
cacaggaaat ttctcattat ttaattattt tgggtttttt gattaaattc tgtacattcc  58260
cattttagct tatcttgagt tataacatta aaattaaggt agtcatcagc tgaattataa  58320
gacttaatta gataagatta tttaagatag tgatttctca ttagattggc cctgttcata  58380
ttaacttttc tgttttttttc ttcagtctgc atgaagaaat cagtgatttt tatgaataca  58440
tgtctccaag acctgaggag gagaagatgc ggatggaggt ggtgaacagg atcgagagtg  58500
taattaagga gctctggccc agcgctgacg tgagtccctt cctgggtagc ttatgcttcg  58560
gacagtcctt gtccacgggc tagaagccta tctgctggta tctcatgcta gtcctcacat  58620
gcaagtagaa gtgctctgta gagttgtggt ctaattaaat tttaaaggca aacaattttc  58680
tgcagtcttt agaattgagg cttcctaact attttcattg gattggatga ctaacaacta  58740
ttttttttt gtagtgctaa tagcaactac taaaggcaag ctatccttag aaattattag  58800
tgtaaagaga agaaagacaa atcaaacctc attgttgtag tggtctgtta ttggatatga  58860
tatatcaaaa cctcattact acttagttcc agcctgccag ggtaaacatt atataattgt  58920
ttacagctaa atgaaaatgt caagtaagaa cttttgtcac ttgaagttca tttcctttgg  58980
ctaatgcacg cataagtctt ttcttatttc tttcctgaaa ttgccatttt tcatctctct  59040
cagaccagct aattgccttt tagacagctc ccagtcagtg aacaaaatga ttactcagga  59100
tttcttcttg gcttatttgt cgtttttgtt actggtacta agtcttttgt tttttgtttt  59160
tgagatgggg tctcactctg ttgctgaggc tggagtgcaa tagtgcgatc acgacttact  59220
gcagcctcga tttcctgggc tcaggtgatc cacctcagca tcccgagtag ctgggactgc  59280
aggtgcacgc caccacactt agctaatttt tgtatttttt tgtagagact gagtctcact  59340
atgttgccca ggttggtctt gaactcctgg gttcaagcaa tgtgcccgcc ttggcctccc  59400
aaagtgctag gattacaggt gtgagccacc acacttggcc tgttactggt actaagttaa  59460
tacgtcactt tttagggcac tttgagggcc tgttctacaa ttttgtgtat gcaaagaagt  59520
acacaaaata atactaataa aatccattac tttgtgtttg tagcttttct tcaggcactg  59580
tcctgggtgg tggtgggaag ctagggaagg ttttttttcca attggcaaaa caaagaagtt  59640
tcattgtatg taaaacttgc aagtatatga cagtatgtat atgacactgt aggtaaaggg  59700
aaaaggcaag ggtactaatg ttttatgagc aatgaccata catcgcattc tttctcctat  59760
gtgatccaaa tcagtggttc tcagctagtg gctattttgt tctccagggg gcatttggca  59820
atgtccgaga catatttgat tgtcctgact gggtacgcac tgctagtacc tagtgggtag  59880
aggccatgga tgccatcagc cattctatga tgaacagtat aggcccttac aacaaagaat  59940
tatccacccc caaatgccaa tgttgagaag ccgtgatcta acttaaccct tatctttctt  60000
aggtggaggt tgattatcta tctatctctt tctctccagc cagccaggca gccatcatct  60060
gtctacctac agatgaggaa catgagcttg tggttaggtt cccaggtcca tctcgcctca  60120
gaggttgaac tggtttcact gtttatcatt tttttccccc gagatggagt ctcgctctgt  60180
cgcccaggct ggagtgcagt gacatgatct cagctcactg cagcctttgc ctcccaggtt  60240
caagaaattt tcctgtctca gcctcccaag tagctggggt tcaggcgccc gtcaccacac  60300
ctggctgatt tttgtaattt tagtagaggt gggatttcat catgttggcc aggctggtct  60360
tgaactcctg acatcaggtg acccacctgc cttggcctcc caaagtgctg ggattacagg  60420
cgtgagccac tgtgcccggc ctatcctttt tttattacaa ttacctgcat acatatttct  60480
gcctgagttc caccgttctc catgggttga gatggaatgc atcccagttt tatgccacag  60540
catgatgtta cctgatgttc tttgtggaat tgacctaaag gccctcactt gccctacagt  60600
taaagtagtc tgatcccaat ttagtaatct attcgaagac tcctgcttag agaacaaaaa  60660
tgaaggattt gtgattgtgt ctctggataa tgagggaaca ttagtgatct gaactgcttc  60720
tgaaagtttc ctgtggttgg ctttctgtat ccacaggtac cacacctcca tattaaacca  60780
acaatggatt gaaaatattc agaaaaaaact ataaaaataa caatgtacca ataaaaacaa  60840
tacaaattat tttaaaaata cagtataaca actatttagg tagcatttac atcatacttg  60900
gtattatagg tattataagt aatctaaaga tgatgtaaag tacatgggag gactagcata  60960
ggttgcatgc aaatactcta ccattttata gcagggactc aagcatcttc agattttggc  61020
atggtgggac tggaaccaat ctcctgccga taccaaggga caactgtatt ttggtctatg  61080
tgtttcatat tgaaccagat aagtttaaat tatattcaga atgtctgctt gtgaaacaga  61140
atccccgctt catgaagctt ggggttagaa aaaaatgctc ttgtcatacc aaaaagtacc  61200
agtagagggt agcaaaaact gacatttctc catatcttgg tgactcaata tgataacaac  61260
ttctgataac tcaatataat aacaacttct ttttctgttt caggtccaga tatttggaag  61320
ttttaaaact ggactttatt tacctactag gttagtacac tcatgaatct ttcaaaggac  61380
ttttcttaga gtgtattcat tttggctgtc aaatttgtaa ggagtagaaa caaaacaaat  61440
ttataaaaca aaatggggct gggcatggtg gctcatgcct gtaatcctag cacttcggga  61500
ggccaaggag ggtggatcat ttgaggtcag gagttcaaga ccagcctggc caacatggta  61560
aaaccccatc tctactagaa atacaagaat tagccaggcg tagcagtgcg cacctgtaat  61620
cccagctact caggaggctg aggcaggaga attgcttgaa cccgggaggt gaaggttgca  61680
gtgagccgag atcgcgccac tgcactccag cctgggcgac agagcaagac tctgtctcaa  61740
aaaataagta agtaaataaa taaaggattt accagcattt aatttgattt accttgaagt  61800
agaatatcac ttcacatcat cttaccaaga catagatggt acagagagat ggaaaaggga  61860
tcatgttgca atggaatcaa ttagttacta attttagaaa ttgactgcct ggcagagtat  61920
```

-continued

```
tgctcagtcc cataacttaa cccactgaca cagatgttaa tgtagtatca tgataaaatg  61980
tctgattata tatcctcttg aatgtgagtt cccgctgtct tgctcactca ctcttacact  62040
caccctcgct ttcaaattaa gaactcattc tactagttat ggctccagca tcctgatcca  62100
gaaattcagg gtacagatct cttctctgag aaagatcttg gcctttcagg actgttgttc  62160
agtttcagtc ttctcaaatg agacctcttg tgacgcacag ccttggaggc tctcttttgg  62220
gaaatgataa tgtttctcca aagggtgaat acttgctctc taagaattga aattgtttga  62280
acattccatc atggttatta ttattattac cttaaatttt aatctctcca gaataaagtc  62340
agcatcatgt ttttccattt gagcttgatt tggtatactt taccccaact taaagtgtgc  62400
tgaagtggat ggaccctggc aatttccgtt cttctcatag atgcccttgg cctgcaaaag  62460
tcataaaata ctcaacttcg agttaatatt tcttatttag gttgtcagca tcagtaaaac  62520
atgaaaaatc accttttctta aaaaatttaa ttaaatttta tgaataggta gtacattcac  62580
atagttcaca tttggaaaag gcacaaaaat caatacaggg aaaagtctca gtcccacctc  62640
tgccccctgg ttctccttgg aacagccgct tttaccagtt tctcacatat cctttcagag  62700
atatctgtgc atataaaagg acatgtgtgt atattaacac aaatggtagc atgctggata  62760
cctgttctgc atccagctta aagcacttca taatatttct gagttgcaat taatctcatc  62820
cggataggaa aatcattatg tctagtacca caagcgttta ttaaagaaaa tacatgaagt  62880
gctttttgtt tttttttctt tgaggtttta cttctttcaa aatcacccta tttcctgagg  62940
cctgaattct gtgaaatgac tgagaggagg agtttgttaa aatcaacaac tactatttcc  63000
cttctccaca aaaccattat caccaacaca tttagtcttc gttggccagg gtgggaaata  63060
ggttttaatt gtactaatga agtctataag catgagtgtc agttaaaaca agtttccaac  63120
ttcttccgac cctcttgtat atgtattctg tgttcagtga catcgaccta gtggtgtttg  63180
ggaagtggga gaacctaccc ctctggactc tggaagaagc tcttcggaaa cacaaagtcg  63240
cagatgagga ttcggtgaaa gttttagaca aagcaactgt aagttctgca gcatttcata  63300
ttaaaatcct tagttattta cctatgaaac ttgaattaaa attaaagttt ggtgagcaca  63360
gttgcattgc aagtgagtga ttctttcatt ttgttaatgt caccgtgctt gcacataaaa  63420
agttttctgg ttgtccacac tggagtgtga ccatacaatc tcggctcact acaacctgtg  63480
cctcctcggc tcaagtgatc cttctacctc agcctcttgg ggagctgtac tacaaacaca  63540
acctgccatg cctggctaat tttgttgtat tttttgtaga gacggggttt caccgtgtta  63600
cccagactga tctccaactc ctgggctcaa gtgatccacc cacctctgcc tcccaaaatg  63660
ctgggattac aggcgtgagc cactgcacct ggtctgcatt tcttttcaca gcagcaaaat  63720
atgcaatttt attatacaca gtactcactg tagagatttt tgtttgtttt attcattttt  63780
tttagagaga tacagtctca ctatgttgcc caggctggtc tctaactcct ggactcaagt  63840
gatcctccca cctcagcctt atgtgtatct gggactaagg cgcaccctac cacgccctgc  63900
ttatttaaaa aattttttttt tgtagagata gggtctccct gtgttgccca agttaggcca  63960
tttttgaaa agaactgctg atagctcatg taaataatcc tgtcagcttt ttagaataat  64020
ttttatattt tatcttgtca ggttgttttt tgggctattt gcaaaactga ccagtaatgc  64080
aagtgggttg tagtgtacac cttaagaatc cagcaatttt cttattagaa acagtttgat  64140
gatacaaaac atttaatacc tggcattcct agttcttcat cttatactca gaaagtgttc  64200
tccaaattat tgaggaaggt ttttgttcat tttaaaatta tcattataac tatatgtcaa  64260
ctaataaatg agatgatggg catattaatt tatttaactg tagtaatcac ttcagtatgt  64320
atatcaagat aagtatatca aaacatgtac accttaaata taaacaataa aaataaataa  64380
taaaaaattg gacaccaaac aaaattctcg gttgatagaa attatactgt aatatactgt  64440
atgggaccca gtgctaaata tgcagcatat agtatttgta gcagaccagg tttactgggg  64500
tgtgccatat ttagaatact cagtgttctt atgctctcat gagatgatgg agacctcatg  64560
tctagtaggc ttccatcccc tgattttatc atttaatctg gttaaagcat ttacatttta  64620
cctttcttct ctttataggt acctattatt aaattaacag attcttttac tgaagtgaaa  64680
gttgatatca gctttaatgt acagaatggc gtgagagcag ctgacctcat caaagatttt  64740
accaaggtca gagaatttag cgtttataca acaaaactat tagaaacgta attttaagat  64800
tctgttgtgg tggtgttcta atatttttat atgcatgttg ctgtctctct ctctctcttt  64860
taaatagagc tagggtctca ctctgtcacc taggctggag tgcagtggct ggatcatggc  64920
ccgctgcagc ctcaaactcc tgggttcaag tggtcatctc acctcagcct cccaagtagc  64980
tgggactaca gacgtgagcc actacacctg gctatttttt gtattttttt ttttttttta  65040
gtgttggggt ctcgctgtgt tggccaggct ggtctcttaa ctcctggcct tagcctccca  65100
aagcactggg attacaggca tgagccacca tgctcagcct gcaccttact tttgtatgca  65160
acggttttgc tttctttgaa tctgcttgta atgatcagtg attaacttat aatgtgacct  65220
caagtaagaa ttaaaagttg agaaagcttt tgaagaaatt gtctgctcta gatccttcct  65280
tgtagagaca gaagagatgg aattctacta cacagttgat tccatctgtt tttaaccttc  65340
aggagttcag attaagaacc tttcctttaa cccatttccc atatgcccca agaatactgt  65400
gcgggcagtg agctgcactt tttttttttc ttttttcgag gcagagtctc tctctgtcac  65460
ccgggctgga gtgcagtggc acgatcttgg ttcactgcca cctccgcctc ccgggttcaa  65520
gcaattcttc tgcctcagtc tcatgagtac ctgggactcg tgcctgggac gagtaccagg  65580
cacctgccac catgcctggc taatttttgt atttttatta gagatggggt ttcaccatat  65640
tggccaggct ggtctcgaac tcctgacctt gtgatccgcc tacctcggcc tcccaaagtg  65700
cccggattac aggcgtgagc caccgtgccc agctgtactt tttttttcc taaacaggaa  65760
ataggttaag agttttaaga gccttttcta gatttcaatc cctaaattac ctttaaggtg  65820
tttcctacag gcttccttac ttctgttttg aaattattta agtttatttc tattctgttt  65880
tcttccaaga tagagaataa tttgtcacca tcatctgtgg aacattttac atacttaggt  65940
agttgtcagc tttctcacct ctaacctaag ccattaactc ctttggcttc tgttagaata  66000
ttcacaattt ttttttctg tagcagctct aaagtttcta tttcttcttt tttgtttttt  66060
aagaaaaaaa tgttaactac ttgatgttac aagcattatc atcttgcata aatgtatgga  66120
agacagaaaa gcagaaaaat aaaagaaaga ttatccataa tcgcactata ttgggggtgt  66180
gtgtgtgtgt gtctgtctaa tattttcttt ttctggaaaa aactttttaaa aattgaaatt  66240
catatgcatg ataacattca tcagtataaa gagacagtgt aaagtgagtc acccttacac  66300
catagatact tagatcattt ttacagaatt tctcattgcc aattattgtt ttttgcgttg  66360
ctttttttatg ttctttaaaa ttataagcaa aaggagtagc acattataca cacattgtct  66420
tataacttca taaaaactta atgttttgga ggtttcttcc atattagcac atacaggctt  66480
gctttattct ttttgttggt tacacaggca gtagtctttt ataaggctgt gactgcttga  66540
tttagcagtt cttcagtatt gttccagttt tcttttgcta ttagaaaaag ggattgatga  66600
atatacttcc atacatgcat cttgctttac acatgcaaaa tgtttgtaga aagattccca  66660
```

aaagcaaaat tttgaggtcg aagggtatat ccagataaaa ttctgttgga tatttcccta 66720
attatttatt ctttcatatt ctcattttct ctctctccct ccccctttc ttctccctcc 66780
ccctcttcct ctatccctcc ctttcccttt tctctctttt tctttccctc ccttttcttt 66840
tctcttttct cttcttcctt tttcttcctt cccctttccc ttttccttcc ttctgcttcc 66900
ttttttcct ttctttcatt ttttgacacc gagtctcact ctgttaccca ggctagagcg 66960
cagtgatcat ggctcactgc agcctcggct tcttgggctc aagtgatcct cccaccttgg 67020
cctgagtatc tgggatcaca ggcttgccca ccacacctgg ctaacttttt ttttaatttt 67080
tttttttttg agatggagtc tcactctgtt gcccaggctg gagtgcagtg gcgcgatctt 67140
ggctcactgc aacctccgtc tcccaggttc aagcgattct cctgccttag cctcctgagt 67200
agctgggatt agaggcgcac accaccacgc tcagctaatt tttgtatttg tagtagagat 67260
gtggttgcac catgttggcc agggtggtct caaaccctga cctcaggtga tccgccctcc 67320
tcagcctccc gcagtgctgg gattacaggc gtgagccact gagcccggcc actttttat 67380
tttatttttt aagtagagat gaggtcttgc tatgtggcca cttttttttt tcttttttt 67440
taagtagaga taaggtcttg ctatgttgcc caagctgttc ttaaactcct gggctcaagc 67500
agtcctcctt ccttgacctc ccaaagtgtt gggattacag gcatgaacca ccacacctga 67560
cccctaattg ttctttgaaa gggaactgta tctagactga cttaaccacc atgttttgtt 67620
ttgtttttg agacagagtc ttgctctgtc actcaggctg gagtgcaatg gtgcgatcat 67680
ggctcattgt accctccgcc tcctgagttc aaacgattct tgtgcctcag cctccagaat 67740
agctgggact acatatgtgt gccaccacgc tgggctaatt tttgtatttt tagtagagat 67800
ggggtttctc catgttggcc aggctggtct tgaactcctg acctcaagag atccacccgc 67860
ctcagcctcc cagagtgctg ggattacaga tatgagccac cgtgcccagc ccacaatgtt 67920
taaaaatact tatttctcca tatttttgtt ctttcctatg cttgcttagt ttgatacaat 67980
ttgcaaaagt ataagctttt ttttcttttt tatagaagcc atgcgtgttc attgtaggac 68040
atctagaaaa cagagataag agtaaagaaa aaaaaatgga aatcaccggc caggtgctat 68100
gtttcacacc tgtaatccca acactttggg aggcccagac aggcagatca tttgagctta 68160
ggagttcaag accagcccgg gcaatgtggt gaaaccctgt ctctacaaaa atacaaaaat 68220
tagctgggca tggtgggctg aggtcggagg atcacttgag cccaggagct ggagattgca 68280
atgagccaag attgtgctac tgtactccag cctgggtgac agaatgaggg ggaaaaaaat 68340
ggaaatcact agtaatttta ccaccctaag taataatagc tgttaagact tctttgaaga 68400
tgttgtgcct gctttgtttc cctccgtggc cccagcctat ggcatggttt acagaggagt 68460
gaatgaatat gtgcacagca aaaggtggac tcattctgta catacttgcc cactcaggtg 68520
ttctctcggg tagccctgcc tcattccctg tgaagcgtgg aagggagggg tggtctgtgt 68580
gtagtcatca gcccatgtgc aagtcagcag gcaggactct tgtttgcccc agggctgtgg 68640
cagaataatc taaaggtcgc tagtctacag tggtacatca ccaagaaaag tgattcttaa 68700
aaatctcact gatttagtgc tttaagatgt tggttacttt gtccttgtac tctttctatt 68760
ctctgtttac aaatgaatat tagagggtca tggtcacaaa tgagcatcat cagttacatg 68820
ctgttagtgt ttctatccta tagcaagtac tttttttttt ttttgagatg gagtcttgct 68880
ctgtcaccca ggctggggtg caatggcacg atctcgcctc actacatcct ctgcctcccg 68940
ggttcaagtg attctcctgc ctcagcctcc caagtagctg ggattacagg ctcccaccac 69000
cactcctggc tattttttgt atttttagta gagataggcg tttcaccatg ttggccaggc 69060
tggtctcgaa ctcctgacct caggtgatct gcccgccttg gtctcccaaa gtgctaggat 69120
tacaggcatg agccaccatg cccagccctg tagcaagtac ttagatacta ttattcattt 69180
gtacatgtct tacaatttaa gtataagggg agaaccattc attacctata gtttactttt 69240
ttttaatagc ttactcttaa aatagaaaat taagtatgtt gtatatctct accaaatttt 69300
ataatgtaag gaccaattta tgcccctctt aatgcttaga tctgttgctg atacaggaat 69360
tcattgaaaa tacaatttc tttttcagaa atatcctgta ttgccatact tggttttagt 69420
attgaaacaa ttcctattgc agagggacct taatgaagta tttacaggtg gaattggttc 69480
ttatagtctc tttttaatgg cagtcagttt ccttcaggta agtcatatgg gtatagcatg 69540
ctagtgcaca ctaaaagcaa aagtgatcaa tcagctggga aacattttgg aaaaaatcga 69600
aatcaacctg taattgcatt gctttccttg attacttaac ggcttttccc tttaaactgg 69660
gtacatttta tcatttagca aatatgtatt tttaaattcc tatgaaagaa tatttttggt 69720
tttaaatccc atacattcta gtatttttga gacttttcac tgcaaatttt aacatgcaaa 69780
atgtacggcc tggtttccat aagcataaat agtataaatg ccaacaataa gaatgtcttc 69840
taagcagcta aatcttgtaa gtttagttgg aattgagacc agctatttgg gtaagcgaat 69900
tagagtctta gtattgtaag tgggtatgtt tatgtggcac agggttgcca actgcctgag 69960
tctattcgtg agtcagaacg actttgctga tgtgttgggc caagccagcc ctggttggca 70020
gcctggtgca gccgtaaaat tcagccttac aaacagtctc ccgccattcc cgcaccatgg 70080
gactttagtg ttgtgtgtaa caacagtata acctgctgtt agcccattat caactgactg 70140
ctatgctaaa ccaaaattat aataatattg cttgtagaag ttagaatata atttattccc 70200
cctctccttg ataatttagc aaaaatccaa tataatttct tcttttctgc ttttagttac 70260
atcccaggga agatgcttgc atccccaata caaactatgg tgttctctta atagaatttt 70320
ttgaattata tggacgacac ttcaattatt taaagactgg catccggata aaggatggtg 70380
gttcatatgt ggccaaagat gaagtacaga aaaatatgct agatggctac aggccatcaa 70440
tgctttatat cgaagatcct ttacaaccag gtattgaaat taggtaaatt tgtgggcatt 70500
caaagagagg gcactgtcag tcaccttatt atactttaaa ttctctttag atgaaaaatg 70560
aaggaacaac ttctaattgt tattcttttt tcatcgaaat atttcatgag caaacatact 70620
aaaataaaca gacacagaca atagaaaaac accttggaga cttccagata agtagggagt 70680
agaatctgtt taaccctaaa agcatagtag aaaaggcatt cacttatttg gatgggttca 70740
tgtttggtgg ctgtttctcc ttcttgggtc cttattgcct tgattacaac caattgtcag 70800
caattaatga ggctttaatg agatgattct gaagtcctga gaggcagcaa gcatagtaat 70860
atatctttga attcatgagc agaagggtgc aaggagacaa tgtattttct ttttgaattt 70920
ctcctttcct gtttgatttt gcatgtctct ttgtgctttt tccagcttca tgtgggcttg 70980
aaagtaagca gaaagtaaat tccttccatg cttttctgaa gttctgtttg cttgcttgtg 71040
tcctgatttt tgtgagcaat attttttctt gatataattg taaaatagat tctgcgttat 71100
tggacttcag tggaagtgct tttagtcatt tgctttaatg tgtaaacttt gaaaatgagt 71160
aaggaaaggg ggtgaagaga tagagtagtt gcctaggaac cattttctgg cttattgagc 71220
tgccttataa acattaatag ttctatgtgt ttattcattg aggaaacatt acattgattg 71280
ggagcctgct ctgttcaaaa gtattgggcc aaaggacacg aagactttc agcaagacga 71340
tccttgcttt ttaggggctc ataatttaga gtgagaaata gatatatagc taatataaac 71400

```
ccaaaaaata tagaagtatt tctgatgtaa cttggggttt cactcttagg agtgaacagg  71460
gcactatttc ttttgtttgc ataactgttt atgtatggaa tgggataatt cttgatgggc  71520
cagaatacat tccggcaact gatacaccat aatgaagtac caactgcatg attcacatat  71580
tcagagactg gggagctttg gggacagctc acagctcagc ttccaggcac aactctggtg  71640
ggataactat ggcccttgct ctcctggaag agagtcatca acatttagtg catattaagc  71700
acagtcaggc ttactatgtt acgtatattt cttttaaagg taacgatgtt ggaaggagtt  71760
catatggggc catgcaagtg aagcaggcct ttgattatgc ctacgttgtt ttgagtcatg  71820
ctgtatcacc aatagcaaag tactatccca acaatgaaac agaaaggtaa aagttcatct  71880
ataaccagcc cattgtgtca aaattagttg tggcttctta tcttcaaatt aatgttattc  71940
cctccctctc cctttctttt taaacacatg cagcatacta ggtagaataa ttagagtaac  72000
agatgaagtt gccacatata gagattggat atcaaagcag tggggcttga agaatagacc  72060
tgagccttca tgcaatggta agatattttc cttggtcgat tgactgagta ttagaggctt  72120
ttctgtgttg tgtgcgttta atgggaagaa acgttttcca atcttttgcc actctttcag  72180
gaaatggtgt taccttgata gtagatactc agcagttaga taaatgtaat aataatctat  72240
ctgaagaaaa tgaagccctt ggaaaatgta gaagtaaaac ctcggaatct cttagtaaac  72300
actcttcaaa ctcttcatca ggtccagtgt cgtcctcttc tgccacacag tccagctcta  72360
gtgatgtagt aagtatgaaa gcctcggctc ttctgaactc agatgcatgc acgttctctt  72420
gctggggtta acactgtctc gaaggctaag gctacttcct ttgcttacat gttactggga  72480
tattttaata actttcatgc ttgtacattt tctcaacatt ttgttatgaa aaagttcaag  72540
catatagtaa aagtgaacaa attttagtga gcattcatgt actcaccagt agattctgct  72600
attaaccttt tacttgctta tgtcatacct gtctatccat cactctatcc attaattcat  72660
cttattcttt gatccatttc aaagtagatt acagacatca gttcccctag agtactgtag  72720
cttgtgcatc cttgtagcca gactccagta tttgtttatt gttttttcct ttttttttt   72780
tttgagacgg gatctccctc tgtcacccag gctggagtgc agtggtatga tctcggctca  72840
ctgcaacctc cgcctcccat gttcaaacga ttctcctgcc tcaacctcct gagtagctgg  72900
gattacaggt gcgtaccacc atacccagct aattttttgt atttttagta gagacggggt  72960
ttcaccatgt tggtcaggct ggtcctgaac tcctgatctt gtgatccacc cgcctcaacc  73020
tcctaaattg ctgggattac aggcatgagc caccacacct ggcctttaac gtttttcttt  73080
tcttttcttt tcttttttt  gagacggagt cttgctctgt cacccaggct ggaatgtaat  73140
ggcatgatct tcactcacct caaccttcgc ctcctgggtt caagcgattc tcctgcctca  73200
gcctcctgag tatctaggat tacaggcatg tgccaccaca cccagctaat tttttgtatt  73260
tttagtagag atggggtttc accatgttgg ccaggctggt ctcgaattcc tgacctcaag  73320
agatccaccc gcctcagcct cccaaagtgc tgggattaca ggcgtgagcc cagctgttat  73380
gactttttaa caccatagtt agttttgcct gtttcagaat ttcatacaaa tggaaccaca  73440
tagaatatag tcttgtgtaa ggcttctttc actcaatttt ttttcagctt tctggttgaa  73500
tttttgttg ttgttgtttt gttttgtttt ttgagacgga gtctcgctct gtcgcccagg  73560
ctggagtgca gtggcgcgat cttggctcac tgcaagctcc gcctcccggg ttcatgccat  73620
tctgcctcag cctcccaagt agctgggact acaggtgccc gccaccacac ccggctaatt  73680
ttttgtattt ttagtagagc cagggtttca ccgtggtctt gatcgcctga cctcatgatc  73740
cgactgcctc ggcctcccaa agtgctggga ttacaggcgt gagccaccac gcctggccaa  73800
attttttttt agttgagata tagttaacat aaaattcagc attaaaaatg tacaattcag  73860
tggtttttag aacatattca caatgttgtg cagccatctc cagtaattct agaacatttc  73920
catcacccca agaagaaacc ctgcatttag cagtagtttc ttctaattct tccttccctc  73980
ccttaacctc tggtaacctc taatctactt tctctttcta tcctgataga attttttttg  74040
ttccccccatc ctgatagaat ttatgtgtca attataatgt aagttacctt ttaaaatcaa  74100
agtgaatttg tagtgtactg atttgagatc taaagcaggc ttacctgttt gagtttaact  74160
ttattaagtg taggacatga aaagtaatct aaatattgta tgttgttgat gatgaccatg  74220
tgtcaatatg gaatcataaa tcctcctgtg cagaatctcc ctgtgtgctt ttttggttcc  74280
tagagcagta tgctttggag gacagaagcc aagctagatg tcacagacac agggagatgg  74340
agtgttgggg actgagagaa tgtgactctg acatgctggg tagagtgcca gggccagggt  74400
ggagacctgc agagagacgt agcattgtca tggcccatgc agcccagaaa taggtggagc  74460
tcagcccact gtcgcgggaa gtccaccccc acccacacca gtatgtttgg ttagaatgat  74520
cactgatttg tcatcacaga ctctcagaga ttgaacccct taaacccatc atcttgtgtc  74580
tggctgaagc cagggactag gacctaggtt cctcactctt taccatactc tttcattttc  74640
tataaataaa aaaacaaata aacttagacc tctgtgagct ccttcaaggt cagatgtggg  74700
cagtggattt aacaatgaac agaagctctc tgataaaatc agtcatttta aatgtttgga  74760
ggaaaattta aacaaacagt taattttttg tgtgcttctt ttaactccca aatgtttaaa  74820
tttagtccag agagtacttt aaccaaaatt gtttttcttt ctgaatattg agtatctaaa  74880
ttactaatat gtcacattat aactcacgtg acttgtgtta ggattccgat gcaacaccat  74940
gcaaaacccc gaaacagctg ctttgccgtc cgtccactgg gaaccgagta gggtcgcaag  75000
atgtatcctt ggagtcctct caggcagttg ggaaaatgca aagcacccaa accactaaca  75060
catccaacag caccaacaaa tctcaggtgt gtggaacgtg ggtttttaat tgttagtatt  75120
tgatacaaaa tatttagaat ttcccacatg taaataatat gcagcatggg tttgaagaaa  75180
acgctagatt gaagaacaaa cttattttat tctaagaggt tccaacacat gacagtgctt  75240
ctaggaacag gatgtcctaa ggatccttgt gagacaccat tgtaacataa atctcttcag  75300
gaatctattg actggtcctt ataagatgtt ccagccaaac taccatataa aaagtgtctc  75360
agttgtacat gaaataagct ggcatgaagg ttttgtgagg cctcatggca gtgtgcatat  75420
ctgggaataa tgtatccttt tctaatattt taatgttcaa taccttgttg ctggtgttga  75480
aatgatcagc tggctgtcag gcgtggtcag ttgattaaca ttagcttgga cttaaaaggc  75540
cacagagata ctctagttta agtttttttg ttgcctagaa ttgtcattaa ctgagtaatg  75600
actcagagtg aggggaggaa gccattgata tggggctctg gcctaaggct gggtcactcc  75660
tcactatagc tgggaacctg ggaataggcc tcttggctgt aaccttgtgt ctgatttgac  75720
tcactgagtt cactttacct acgcggcctt agccatgtat gccagacaca gacttatcac  75780
aaaataccag ttcaagtgac agggttgaca gaagggactg aggtcacgag aaagccacag  75840
gccatgagta gcaggaaggg agtagccacc tgtgctgacc caaacctacc agtgtgcctg  75900
tcatgcccaa gagcctcttc ccgctctgtc acttatgatg tggtgtttgg gttggtaagt  75960
ttcttaagaa aacctttgca tcccacacac tgttaagaag gcgggcgagt ggtctatgct  76020
tttcattatt tccattaaaa taaagtaagg gttttagagc taaaaagaac ccctgtaaca  76080
gctttttctg cccactagat aagtcagtga tcagtaaggt aacaatctag ccagcatatt  76140
```

-continued

```
cctagttttg aaagcttccc caaatccagg tgtttgagaa cactctgctt ttctgcaata  76200
ctgatgtctt tgtggtcgtt ttctgtttct gcagcatgga tcagcaaggc tctttcgttc  76260
ttccagcaaa ggcttccaag gtacaactca aacaagccat ggttccttga tgacaaacaa  76320
acaacatcaa ggcaaatcca ataatcagta ttaccatggc aaaaagagga aacacaagag  76380
ggacgcgccc ctctcagacc tctgtagata gtcagcgctg cgcggtggac tgtcttctct  76440
gtgcaatgat ctcatgctca ggacagttgc gcagggactc ctgggagata ttcaggagcc  76500
tcacactgtt cagacgttga cttagcaact gcgtttttc ccagctcgcc acagaatgga  76560
tcatgaagac tgacaactgc aaaaaaaaca aaacaaaaca aaaaaaaaag caagcaaaaa  76620
agagggaaaa aaaaggctgc ttatttgata agtcatatgc tacaacaggg tcattttaag  76680
atttaaagct tgaatgtaaa ataaatatat ttctcattgg ctttatgcag agttataggg  76740
aatagtattc agtgttggta gggtgataga aacaaaaaac agtatcagag gatgaggtgg  76800
ggaaggaaaa caaaggtatc tgataggaag tccagattcc aaaggggaaa gtgatctgtg  76860
catgtttttt ttttaaatat ttttgcatat atttaccatt ttattgtgtg tatatataga  76920
agaccatata ggagattgat atttgtaata gtggatttgt taataatact ttttacataa  76980
cattactgtt taaattgtaa acagattttt tctcaggatt agtttgaaaa ataatctaaa  77040
ttgtcatctt aacatccata tatagggaag tgattagttc tattactcaa tttgtttttc  77100
tcagcattga aatgacttaa tagaaccctt gtgtcctgct gcaaaaattt ttcctctcta  77160
aagaaaaggt ttatggtggc aaatgatgtt tattttattt tgtaaaaaaa aaaaaatgta  77220
ctatgtactt ttgtgtaaac actgaaaaat ctctggtcat ctccgagaat taacttgcaa  77280
ctgttttcta tagtgctgtc gtcttgggca atgggcaatt acatgacttt gtgtttgctt  77340
cctttgcagt cttttttttt tccccccatt tcttcctaat aggaaaaaaa aaaaaaaaaa  77400
ggtcacccat gtctggtctc attcctgttg cagtgaaact tcgagttcca cagactttgc  77460
atgctggctt ctctaaccct gtgtgctgcg tgtgcctgtt tctcatctct tattcttttt  77520
aaaattcatg cttaactact gtgggagaat aactgtaaac agctttaatt aaatcatact  77580
tataaaaaac tattttctta tattccactc tatgcttttg gtattgttga tctttacaaa  77640
ttaaatggtc tttgataatg gatctatttt gtattgcctt attaagacca aatacttctt  77700
gtcatcccat tctttatcct cttctttcat ggaattgtta tcgttaatta aaactttttt  77760
aaacattggc ttgtttcaat catactgtaa attttggttg tagtcagctt tgagtgcaat  77820
gagatgtata attctgttat cattacctgt tgagtttgaa actcagttgg gaatatttaa  77880
tataatagaa tgtaagtgac atttctgaaa atgctttctt tcagggtgaa agctcttatg  77940
tttagcatca atgtgtatgg ctctgttaaa tgcagccatt tctgagacga gattctttta  78000
tatatatata catataaagt actattggct tttaggagtt tcttttatat acatttatga  78060
aatactgaag accaatcaga ccattaatgg acacttagtg taacttttta taaagaaaat  78120
aatgctaaag taagaccaaa actgatgtca tcactgaaat taacaatttt caatatgttc  78180
atattttaat tcacaatgga aaaatgtgtt ccaaaactgg aaactcatag tactcgtgta  78240
aactgtggaa gatttcaaat gtgatgttat tttgacaatg ttttaaattt tagagtcaca  78300
ttttattctg atcagaattt ttattgagat gttgagcttt tgtttttgaa actagtttgt  78360
cataacattg tgcataatca cagtatttat tttctaggac aattgtgaat gtgtagactt  78420
atgtttactg ctaagggaac aattatttat aaaataaatat taaatccagt attagctgcc  78480
tatttcagac acttaatact tgcagagatc tatgttacat ttaccacact gaagtttttt  78540
ttgttgtttt ttgtttgttt ttaaagaatc accctcattg ttgaaagtaa atgtactctt  78600
agggtgcgaa tattagtgtt ccaataagca tgtgattata ttaaggtggt ggtagcggga  78660
agataattct gattccattg ggaatcttag gttttcgtaa atttattggg aaaatagttt  78720
ttcctgtact gctgaagttt ctttttggta aacagtatct ttctaaaaga aaaaagcatg  78780
aaggagaaat tgaggtgtgt atacatttcc tcaaatgacc agcattgtat tcgtgaatac  78840
tgtgtatctt gcagtgaaca gtgtggaagc tgttcatttt tcaatctgaa gtaaaatact  78900
ttcaagaact tttagtttgc ctgctcattt gttttataca tttcatctat ttgactccta  78960
tcttatttct tttttgagtt ttaatacttc ctatattttg tgaatatatc agaaatgtgt  79020
catttatata ttagagtcca ttcatatcca tgaatcataa ccttcctttg ctaatacttg  79080
ttgaatggga ttttacaaat tctccctcac tctggtgaca tttctcaggc agtcatgtat  79140
gtgtacctgg ccattagaaa tattaatatt taaagactgt tttttagagg agctgatggg  79200
ttggtgaggt gtcagcacaa aatcttactg gttatgtttt gatgataaaa gtatatccat  79260
tttttccctc cagctttaag gtgactgtga aggtgcctgg ttttgaatgt ctttgtttgg  79320
tttggagatg tcgcactcag ttttcaaatc tagcttggat ctgtaggacc tatgtttttt  79380
acaagtaatt gccctccagt cttcaacagt tgattctgtt ttatttttat cctgttttga  79440
gtgtacttta cctttacttg cattttgagc ctcattaata tttaggttat ttgatttggc  79500
tccagatatt cctagatctg cacagggcaa aacatgggct atagggtgag catttttaat  79560
tgtctttttc tgctggaacc ttatatctct ccatgtgttt tctgctcctt ccctccccca  79620
tgaaatggta agtgtgactt gtgtttgcct gaacctgtgg actagtgttt ggggtttctg  79680
gaaacactag agggtcagaa aagagtaatg accaccgtga cgtgcaggat tctcttgctg  79740
tgacatgttc attgcaaagc cctctccagt gactaggagg tgtagttatt aaggttgatc  79800
tgttagaaat caccattatt aggtattagt ggtagatgtt gctgatactt ttattggtca  79860
tgactacatc tcagttttac tttaatattg atctatagtt tgatcagttc cttgaattct  79920
aatatgttga tttctcagtg tttctgtcac taaccaagaa tgtttctagg cagttggttg  79980
cttcacagtc aaaactaaat ggtaaactat caaaaataca ttcccaattt tgctgtgata  80040
aatattgaaa tgttaaaatt aatgaacaga agaatttatt cttacccatc tattcttgtt  80100
ctcctagttc attaaacttt cagttattgg aaaggcacat tctcaaagta ttttatgagc  80160
aaaatattct ataaatgcgt ctaacaaacc taattgaata taaaagttat atttagtagt  80220
tactgttgat agtaatttc atcagggtca tagttcatct agtaaaatat ttagagaatg  80280
atgttaacat tccagcatta aagtgggaac aaagatttat atatgaaatt ccttaaaaga  80340
gttcatcttg ccttggtttc tgaccctcaa gactctagct acctgccatc ttgtcaaaac  80400
atttgtgggt agaataagtg ttaaagatca aattttaata tgcttctcga tatttaacat  80460
agctaagaag ccagatttta ctgtagaagt tatttacatg atttgaaaac ttgacctaac  80520
tggaagcctt tttctcagtc atcttgttct aagccatctt gacttcacac ccttagcgac  80580
ttttcttttt tttttggtca aagataatga gctaaatata tatagacgtt gaatgttgac  80640
aaaattatta accagaaaaa ttgcttataa aggctgctga tctatttgat acctagaatt  80700
aaatatttga ggacagtttt tagttaataa actgctaatg tttattttac tgtctctcag  80760
gtttttggtt tttttaaaaa aaatgtgttt ggcctttaca ttttctactt aagtgtgtac  80820
tttattgagt ttaaccttgt ctgtagccta gtagcctgaa agaaaaggag acagaaccag  80880
```

```
agagatggat gtagtgcatt ccctttggtt attacacatt tgtggtagct cctggattta  80940
ctgagagata ttttagctat gtcaataaga acagctaatg atgtggaaat caggtgttct  81000
cttgtgtatt tcagtgaaca tttttattag tagttgcata tcatctctag ttccacattt  81060
taacttaacg tctttgtggc ttcaccactg agctaccttt cactacacca gcttctgtgt  81120
ggcctggtaa catggaaggt ctctcctaag gacagtctgg acgtattttg gggaatgtt  81180
atttatctta aagatgccta gaaacaaaac gcatatagta ccagtgagaa actatgaagt  81240
aaacaagttg ctcaggccgg gcatggtggc tcacgcctgt aatcccagca ctttgggagg  81300
ccgaagcggg aggatggctt gaggctggga gtttgagacc ttcatctctt aaaaaaacaa  81360
acaaaaacct gaatggtgag gtgtggtgga attgggtagg ggagggaaag gaggacttgg  81420
aaaagcattc tccaaagcca gcaacttggt gaagttcagt acttgcctct tagaggttag  81480
gccatgcctt tcaaagagag tgaaatgatg ggttatcagc cacattcttg gagttaatat  81540
ttttcttcat ctttcagttt gggttctgtg ctattcatag ttcttcccta agaccatttc  81600
attattacct tttatattta gttgcaattt attataatat gttgttttgt ccctgaactt  81660
aatctcctaa ttttaagatc ctctctgatt tttgcatatt gaaacttaca gaagtcactt  81720
taaaaaagtc ttttgaaagt cctacaatcc taaaataaat cacaagcttg tttgttagac  81780
gtgtcaagag tctccagtct ttactactaa aaagcagcac tgccttaaca cacattgtta  81840
tgggtgaaaa gtgagggacg accagtgtag tttctggata taaagtgtga aggactgttg  81900
agttaaacat ttttagtgga atatacatag ataacgtgta tttagaaact ttggtgaagc  81960
cagtatttgt ttttagtaac ctttttatgt atttccttct ttgattagca ttgtcttcag  82020
tgttaagaaa tgtggactcc tgtgaggtgc tggaggtttg aatcatcttg aaaactttcc  82080
aatcttgtct agttaccact gcagagacac taaggaattt accagaaaaa gatatttgat  82140
acaagtgatt taagaaatct caacatttcc tgaggccgta tcactgggca accagtgatg  82200
aaaactatga atgaattgca cacctggaag attttttaag ctaatgacag tttcttcaaa  82260
gatgtcaatt atttgccttg gaaattttat aaattgcatt tctatgcaca tcggcctcta  82320
gtgcttacca ctcggtttat tattcataat ctgcaattca ataaaggctt tgtgttttca  82380
tttatcttca aaa                                                     82393

SEQ ID NO: 2           moltype = DNA  length = 44042
FEATURE                Location/Qualifiers
source                 1..44042
                       mol_type = unassigned DNA
                       organism = Homo sapiens
SEQUENCE: 2
ccacgctgcc ctgcgcacgc gcagcgcggc tcaggcggca gcccggtgac accggcccta  60
gcgcgcatgt ctgcacgccg gggtctgcgc gccgcggcgg gccgagggcg gcgtgcgggc  120
cttccagccg ctgcctattc cacccaacgc cggcctagtc agtaatggct caacgccacc  180
gcctctccct ccagcccctc ccagtcgcgt agcttctgac gccgtcctca ccccgcccgc  240
ggccgacggg gccccaacgc gcaggcgcgg taaccacggc ggcagtgtct agtgaggatt  300
tgaaatcggt cgcgcgtgcg caccggcgac acggcccggc gaccgaggcc gcgcttcctc  360
ctgccgcccc cgtccccgcc ccctccccg cccctcattg gagcggacgc ggcggcggcc  420
ccctccttcc cccgcgctgt cgccgccgag agtgtctttt caccgccgcc gccgccgccg  480
ccgcaggagc gccgagccag cggcgcgagc gtgactgagg gctagccgca cgggcggcgg  540
cgcctcccgc gggtccttca gccgctcggc gcctgggccc gccccctcgg ccccgccgcc  600
cgcccttctc cgatggcctc tccccgcggc ccgagtggaa cgccgccgcc gccgcggccc  660
ccgcgcccgc cccgcgccgc gtgaagcggg agcccggaga ccgcagccgc ccgctgggac  720
gcgccaagcg ccggagccgc ccgccgcggc ctgccggggc ccatcaccgc cgccgccgcc  780
ccacgccgga gcccgacggg agcgcggcta gagcaggagg ccggggctcg gcccgcccgc  840
cgccgccgcc gccgccgccg ccaccggccc aggcccgtcc gtccgtccgt gcgcgcgcgg  900
ccgggcctcg gggcgcggcg ggggcggggc cgcgtcgggg cgggcgggcg cgcgggcccc  960
gcgggggcgg cgcgtggatg gatccgcgcg tggcctggat ccagcccgag cagaagggcgc  1020
cggccaatgc cctgtggatg cagatctggg agacctcgca gggcgtgggc cgcggcggct  1080
cgggcttcgc gtcctatttc tgcctcaact cgccggcgct ggacacggcg gccgcggcgg  1140
gggcggccgg gcggggcagt ggcggcctgg gccccgcgct gcccgccgcg tcgccccccgc  1200
cgcccggccc caccgcgccc gccgcgctgc cccccgcgct gctgacggcg ctggggcccg  1260
cggccgaggg cgcgcggcgc ttgcacaagt cgccgtcgct gtcgtcctcg tcgtcgtcct  1320
cctcgtccaa cgcggagtcg ggcaccgaga gccccggctg ctcgtcgtcg tcctccagca  1380
gcgcctcgct gggccggccg ggcggcggcc gcggcggcgc cttcttcaac ttcgccgacg  1440
gcgcgcccag cgcccctggc acagccaacg ggcaccccgg gccgcgcggc cccgcgcccg  1500
ccggctcccc gtcgcagcac cagttccacc cgggtcgccg gaaacgcgag aacaaggcca  1560
gcacctacgg cctcaactac ctgctgtccg gcagccgcgc ggccgctctc agcggagggg  1620
gcggccccgg ggcccaggcg ccgcggcccg gcaccccgtg gaagagccgc gcgtacagcc  1680
cgggcatcca ggggtgagtg cgcggggagg ccgcgggggc gggggcgggg cccatggtcc  1740
tggccggcgc ccgcggtgca gacacccgtc ccaggcgccc gggcttttgg aggatggatg  1800
ttgaaggcta aggccaaggc ccgactctgc actgaaagtt ttttttttaa acatcagact  1860
catttatcgt ggagtgactt gcccagatcc tacaagtaac agtccaagaa aaggggctgc  1920
tgggtaggac ctgcaggtat ttgtcttttt tactcttgag attggaacgg gaaatcgact  1980
ctctacccct ccaccccgcc tccgggcaag tgaggaaccc cttgtcaaag tggggcgtag  2040
ataagtgtgg agtttcacgt aagttaagtt gcagaataat ttagcattgc caggaactcg  2100
aatcacgtcg aaggtaaata ttaacctttt taatttcatt ttttaaaaaa atttaactgt  2160
caacttagag gtgattcatt ttttgggggg tgttgtgtcc tttaattttg tgctgcaatt  2220
accataagca tcgcctatgg tttataaaca ttggcttaat tcaaagaaaa aaccagattt  2280
gtcatatatg tctattcttt ggaaggtgcc atttttattt taaatatttc tacatccgcc  2340
tagagggaat tagaggctct acttaaattt agtgcactta cagacggcaa ggaatgaaac  2400
gaaaggtggt gtgtgtttcg gggttggaat tgtcccaggt gaggctgttc aggtgtgatg  2460
ctgttgacgc agccccttttg ccattttggg cttttctgag cgtctggaag caatttatgt  2520
gtaggttgta tgtcagtatt ttaagactta aatgataatt tttccttgca caatttttcc  2580
ccccaattta aaaaacaatt aaggatttgc tggggtatga gggttgttgc atgcagtaga  2640
gtcctacaaa taaccacaat tgctaggtgt tgggagttct tatagtaaac ttttgcttgt  2700
aactcttttt ctcatttgaa gtatgttggg aaacacgagt tgatacttct ttaaagcgtg  2760
```

-continued

```
tgatacactg taatagctgc atgttctgta acttatttca cctggcttgg gctacaagcg  2820
ataccttcta aatttcccga agtgtaaaca tgcagtgcag acgccggcag gagcgcagac  2880
tcctcttctc tccctccagt tcttacctgt agaactttct gagagcaggt ggttgggagc  2940
agtttcttct tgatgaatag caatatatac ctaagggctc gcttggggag gacctttagg  3000
tttccagcct gttatgtaac tggaatggac tccgtttctc ttagcactag aaaaaacagg  3060
aagacacgtg gtctctgcca gtcttgggtt gtacctctgc tcttagaaag tggtagcgca  3120
tcaggtccca tgcacctcac ttgggctccc cgagctgttt cctccaggta actctagtca  3180
ggctcagtag gtggtgttgc ttttgttagt gaatgagccc actaggatca ggtgctgtgc  3240
taggatctgg ggatctgggg cagggacggc atgggagaca cagtctcatg atcttgaccc  3300
accctgaaac ctgcctgcaa gtgccccctg cctagagcac aagagtaccc tgctcagttg  3360
tgcaggtccc ctctcacgct cttcgtcacc cacgtccagt ctctcatcac atgctgttcg  3420
tttggccctt ttaatctctc cacacctcat cctccctcat gcaggctctt gttacttctg  3480
tggagattgc tcaagcagcc ggaggtgcct ttgatgcact ctggtcctgc ttgagtcctt  3540
tcccatcaca ggtaatgggg caatcttctc tgccagcagg tctggtcaga ttccccttca  3600
ccctgtgatg tcacctcccc catctccaat cccccacatt aaagactaaa gcctaaaact  3660
cagcaacacc tccagggctc tgctgctcag atgcccctag gtcctggctc ctggccccac  3720
cccttgccaa cccgttagaa cctagctgta aggcagtatg gtgtagggca tgagagggct  3780
ctgaagccca ccaggaggtc tggtttgata ctgcagtcat gctcttggaa ctttcctttt  3840
cccctttgct ggagacctct ccttgcctgt ctctgggtgg tgtgtaccat gcctccagta  3900
tggccttggg tgcatccgct tcctgccgtc tctgcccaaa ggggcctgtg aggaccacct  3960
gctctgtgcc cagaagggca cggtgacctc tgcttgggct gctattccag ctactctttc  4020
agaagcaaac ctaagctgtg gtagagttgg gcctgtggct agaggaggta aggtcccccc  4080
tgtgatcatt tccacatggc ctgttggtcc tatataaact aaccttttttg tatcaataaa  4140
tagttctgtc tagaacttgc ttctggccat cagcttaccc agagtgttga gaaaggccac  4200
caaaaagtct ttcggttgtg gcttagctaa ggaaataact gagttttaaa ggctcacctg  4260
ggctggccaa tagtaaagga ccttgttgct gagaagctgc ttggggttgt gatatagtcc  4320
caggacatgc acttctgaaa atgcagtgtg tattcctcat gggaggatga gcctgctgtg  4380
gagcattggc tgaacccagt tggtctttg cctggtagcc catgtggcaa ccctcactgt  4440
ttgtcctttt ctggggagga gtttctgcc cttggacact ttgcctggtg gcttggcctt  4500
gtgagactgc cagtctgcct tctgcttcaa gtaggatgaa gaaaaagcag gtgaaagagg  4560
acagggattg gtgcaagaac cttcagagga gaggaggtga aatgcttctt ttggctctgg  4620
ttcttgaatc attgtttgat tgaaatctca agcctttgtt ttgggagtgg tgtgcttagc  4680
gtgagctgtg ctatctacct gggcttctga cctagagatg ttgggcaggt gtttggacag  4740
gccctgggcc ctttgcatcc cagcctctgg ctgctgtcac ttgcaagtgc tctcatcccc  4800
tgacccagca gggctttggg ctgttgttac tttgtcatgg tcgttctagc agctttggaa  4860
acctcttcag gttaagagtc ttgcataagt gagagtggga gcatggccct cagatatttg  4920
gccacatcct tactggtgtg ttacagagac ccaggaagaa tgtagttgaa cgaggacaca  4980
tgcaggtgtc ccgggccctg aacagcttct attcagagtt tggcctttcg aaggctgtgc  5040
catctcaggt gtgcctgcag tgtgcagcag gtgtatgcag cttcctcttt gcaggtttct  5100
tggtatttaa tctcatcctt taatatcttc tattaactca aaggaaattc tgttcttagt  5160
ttgaagtctg agagagaccg acgactgtcg gcataggaca tggtcagcca tgccccgcaa  5220
ggcgtctggt gagagtcgtt tccaacttgg tgcatgtttt tctcaattct ttcttgcgaa  5280
ggagtcacag cttggaggcg caaccaggat ccccccctctc cctctagcct gacctcactg  5340
acataaagta gagcaggtgt gacctgtccg gaacatcctt gtgatgctca gcagggcctg  5400
ctgcagagca cgggaggcat cactctaggg gcctttccct cccatacttt cctgtgagtg  5460
tccaggatgc atgagagagg ttgttgtgag acctgcctta aagggtggcg gtggcacgtg  5520
tggaccttgc tttctgagtt tcactctccg agtcccagag gtataagctt gtgaagagaa  5580
gcgtgtatgt atgatcacac taagcagata cttgctcctg cactgttgga ggaggaagag  5640
gagttaattt catcaattaa ctcttccaac actccttcca tttagtaata gcatcacttg  5700
ttcctgtctt ttgttccatg gccaagctcc acaaggtgaa attgaaaatc gagtgcaaga  5760
cactggctgt gctggagttg aggaaagttt tgctggagac ctgcttgcac catatgtctg  5820
gtcactgata gatgaggact ggccaggtca ggacagctga cacttggaga aggggctgcc  5880
caggagggca tgacagactc tggaaaagga gggtcggagt attaaactgg ctgggaatga  5940
gaggcctcca atcttttcgc aggaaaaaaa aaaaaaggct taatgctcgt gctgtggaag  6000
tcagaatgga gcaaagtggg ttctgtctgt cttgctgctg tgagcgtgtg atggaacaac  6060
agtgtcattt gctttttctc agaaatattt aatgcatgtt tgtgacataa tttttcaaag  6120
taattttaag taaatatttt aaagtaaaaa gttctaagat ttgtgtctca aggtaaagtc  6180
tcaaacgttc tttggtcact atttaatatg agattttgtc ctcattttaa atggattcat  6240
gtaagcgtcc tgtggaagaa gagttaatag ttatccttgg aaaataagaa ctttttatgc  6300
ctcagttagg tcatatggtt taggatctga ttttgtagtt gtggagtaaa ggttaagaaa  6360
aaaaaacagc aaaccttgat attcaaattc agaaacttga tttttgagga tgcaaccaga  6420
atttggacta aaggtacaga ggggtggcag agtcagacca cccagacttg cagaagattg  6480
aagaagccgc agtgctgcca tgaagaggcc ctttctagga ggtgtggctg gcttgtcagt  6540
gctttgtctt ctctgcagtg aattggatgg caagcctcgc cctcttcgaa agctgccact  6600
ctgaacctgc cttgagaagc acctcaggga gggcaggcag gtggtctcag tcagcgctga  6660
caggtgtcca agttacctga cctgttggga acatgtgcct gagtgaggtg gccaggatgc  6720
cttttctccc aacactgggg atgcacactc gtcagcatcc tatttttgag atttctatgt  6780
tgtggtagtt ctctgttgct gtgtagcaaa ttaacataaa ctcagaggct tagaagaaca  6840
ctcacttatg gtcttaagga ttttgtgtgt cagatcaggg atggcggggc tgggttctct  6900
gcttaggctt ttgcaaggct gaagtcaagg tgttggccag ctgtgttctc agctggcact  6960
cagggtcctc ttaccagcac attcctgtta ttgtcagaat tcagttcctt gcaggatgga  7020
agtccttgat tgcttgctag ctgccagcag gggaattggg tagggcgctg tcagcttctt  7080
aaggccacct gcattccatc tgcaaagcaa ggtactttga atttctctga tgttttccgc  7140
cagctggagg aagccccctg tttctatggg cttgtgttat tgagtcaggc tcctgcagat  7200
aacctgccta cctgaaggtc atgtagtagt acaacatgat catggtgtga taacctcatc  7260
agagccacag gttccaagga gtagggtgta ggaccttgag gggaggaggt tcttctgtgg  7320
gtagacttcc cctggcatag aatccgttga tgagcaggtt gtggttcttc ttgtccaaca  7380
cttttcccct gactggactc cagcccatcg caatgactct tgcagattgc cagttccgtc  7440
ctctggcttg gtggttacta ctgaactcag gcagccacta taaccaggag aacctttctg  7500
```

-continued

```
tgctgcactc agatgaacat tctttaaaat atgtcattta agaaaagttt gcaggactac  7560
tcgggaggca gaggcaggag aatcctttga actggagagt tggaggttgc agtgagccga  7620
gatcgcacca cagcactcta gcctggtgac agagcgagac tctgtctcaa aataaataaa  7680
taaataaata aataaataaa taaataaata aataaaagtt tgcaggaaag ccgtgtgaat  7740
atatgaaaat acagtgattg aaaagtcctg ttcacgaggt gtcctgcatt ggctagttta  7800
ggaaaggggt ctttcctatg caggtggggg ttgatgactt acccaagagt cacctctgga  7860
acccagttct cttaagttga tagcagtcta tctttgcttt gcagaagatg tggggaacac  7920
ttgtcctgca agcccaggtt cgtagcaatg ttggcttccc cagaaccttg gcttcagagc  7980
actgtgcctc ctttaggagg cacaagaaaa ctcccacacg gttcttccct ctgtcccttc  8040
ctgagccccc tgagtgtttg gctcttgtgg agttgctgct attactaagt tgatcccact  8100
gccctcctga gtctcctcag ggaaggaggg gctgtattgt agcccgcatt cttagtgcca  8160
agcacacggt agccactaag taagtatctc ccaagaaaga agagcaggag gaggatctgc  8220
caactcagga gagcaggtgg gggatggcaa gtcttcggag tattcataaa ccaaatgcta  8280
agggaaactt ttgttgtttg tcttagaatt ttaaaaaata aagtctgttg cagtttatct  8340
gctttccttc ctggagagtg gctaaactag tgttctgttt tacaatgtag aatgcaaaag  8400
cagaaaacat tcaagaaaat tctatactgt atttgaaaaa catcaccatt tagttttaac  8460
tgctctttgt ttcttattat aaaaattaat acctaactat gaaaagttag aaagcctgga  8520
gaagtatgga ggtgagttgt ccaccattgg gccactagag agtgccctat gagcctgtcc  8580
ctggtgtcct ggactctggt ggtgtgcact gcatttgctg gcagtgagcc agggggtggg  8640
ccacatctgg gcccgggcgg ggtggatctc tgcagaagtt tatccatctc ttggctgaca  8700
gggtgggcga gatgggagca gctctgaggg tccctgttgg cagagaatgt ctttgattat  8760
caacaacatg ccttttttgtt gtgggcttgt gatccttttc tttcctaaat cagctgccgt  8820
gcataaccag ttaggctctc ctgtggcttc agattggagt tagtttccca agtgctagga  8880
tgtgggtgtt aggtgatttc tgtctttccg tttgaaagag atttcagatc attgtaacat  8940
ttctggaatc ctgtcgatct gaaggaatgg ctaggatgta gtagtttaag ggaaatgaaa  9000
agtcgaatgt atttgatgt ttctgcatca gacctgctcg gtggagtcca tttctcagct  9060
tcgggagcca cgtgcttggc tcttgagagc ctagctccat cagcccatgt cacacactca  9120
caggtctggc tttagctggt ttcgccatgg tttctaactt gagcctcagt ttcccccccct  9180
gtgaagcaga gcctgtggca cccacctcag agagtacatg aaagacttgg aagcactctg  9240
tgagttgtca tgcgagagat taaaaaggcc accgctgccc ttttctcctc tctttaagga  9300
aattgaaacc aaaaattaag tccttcttgc cagctggaca ggaaaagcct ttttcttggt  9360
ttttgaaaat acaacttcca ctttcagacc aaagtgaaaa ctgctaaaga ctgaatattc  9420
tgagtcttgg gagtgggggg ctagaggggt gttgtgaatt gaaagatacc tttctatttt  9480
taaaacattt taacaatgcc ttaatgatga ataatgtctg ttctagtttt gcatttgtta  9540
gtttttttttt tttttttttt ttaactgttc tgaaggtaca tcagcactgt tctacagctt  9600
taaataagaa tctcatctcc ccagaggcaa gggtactctt gatgtatttg ctcagggctg  9660
tatgtgctgc tccgtgtaac tcatttaaag ttggttaagg tttttttatt tcttgcacat  9720
agtagaagga gtggatgaag tgttttctga actctttgca gcttctaaca tagtgttctg  9780
tgtatagtga aggaaaacaa aattaagggc cagggaacat taagtaggca actagaacag  9840
cactgtccag tagaacttcc tgtggagatg gaataattct atttttgcac taatacagta  9900
gccactggcc atatgtgact tttgagcact tgaaatgtga caaatgcaac tgaggagctg  9960
aattttaatt ttatttactt ttaattaaaa tttaaatggc catgtattta gacagctctg  10020
aactgcagta actttaggct ctatttgaaa cagtgtttga ttcagtaact gttgctgaaa  10080
taaattgaaa ctcatacaac agtaaaagct gtgttactca gcaagttatc actgtgaaag  10140
ctctagaaat tgtttgagtt tccaatgcaa atccttttca aaaagccgct gttttaatag  10200
cacatgaagc ataaaatagg ttcatagcag agcgcagcac agagcaacat ggagcaactg  10260
ttatgacctg gagtgtctcc agtccagcat gcaggtgata ggtctcagca tttttgcacg  10320
caggttaatg atggtgcaga cggtcacttc cttctctcaa cagtcttcct ggtcacgagc  10380
accattgtgg ctcgtgtgtg gggctctttt ggcttagctc tctgcacgag tttgctcctt  10440
tagttcccag agctgaccct tgaaatgagt gatattactc ctgttttgta gacagaaaac  10500
tgaagccttg acagtctgac gtgacctggc aagaggtgct gcagttggaa atgtgaattc  10560
acggctgaca tctgggcact ttactcctaa cagtgttcag tgaacaagac gtcgctaaca  10620
tgcgggggat ggaacctagc aactcattct acaaacatgg ttcaaatatg ttggtgcagg  10680
gccttttgct ttgttttcct aaagagatta gattcagatg tggtggggtg ctttgacagc  10740
caccgcagga caaagttgat agctgtgggg ttgcggagtg ttgaggattt catagggaag  10800
ccagtcctgc gcagtagtac gctcaggttc gtgctttctt gaggtgttcc agaactggcc  10860
tggagggagg ctgcagtgtg gaagcgggat ttctgtcacc tggagtattc ttagaagttg  10920
cattctatga agagtggagc atctgatgag ctgtttactc gctgtttcat ctgacggcag  10980
ttgaaagaca aggcaggact ggcagcgcag ctgcctcagt cagcactgct gcactggggg  11040
cttgacctgc agtctcgcaa tcctggacta taactcattt tgaagagaga aaaattaagc  11100
attaagtgat tcaagcgtct tgcccaaggc gctactagaa aataaaggca ctggtgccca  11160
gatgcaggtc tgcatggtat gcaagcctgg gcttcttccc acctccccca cagagagggc  11220
actggtatgt tggagtgaag agccacgcaa gacctctgtg aatgggcaga gatgggccag  11280
tgacgcaaca cagtaaagtg tattttggtt ataggcatcg tctctaaact tatgtaaaac  11340
attattaaaa aatggaagga caacgatgaa atgatggcca aaaatataga aaaggatacc  11400
ttgcatgtcc tgtgaaatgc aaaggaattc taaagtgtca ttatgagtta cctcatggaa  11460
gaaagcaaaa ggtgaatcta tctagagttt gtggttctga ctcacaagag actgatgttc  11520
atgctgaagg acgagtgtga caggtggaag gatagagcac cgagaccaca ctctaaaggg  11580
taggaatcta tgggaactat tcagggagat gaaagcatgg aatgaactga agcttgcaga  11640
ctcgttgagt aaaaagcgcg ttttaggatt ggttttagaa taaaataaca aggcctgtgg  11700
ttggggaaga tgacttgctg ttcacagagc ctcccttaat aggtggggac ctcagctttt  11760
cctctgctgc catcaggtga gtggtgtaca gtcctagcca cagtagtaat caccactggc  11820
ctgactgagc cctcacccctt tatacagtgt ctcctgccac cctcctggga gaggctgttc  11880
tcggcacagc tggcctgggg tcacacagct ggtaggtgta aagcaggcat tggagtccag  11940
gtagtctcac tccgtagcct gtctctttag ccactggaaa tgtagagcaa agcgagaatt  12000
gtccaaagag ataagctaat aaagaggaaa acaggctggg tgcaatggct cacgcctgta  12060
atcccagcac tttgggaggc caaggagggc ggatcacaag ttcaggagat cgagaccatc  12120
ctggctaaca cagtaaaacc ccatctctac taaaaataca aaaaattatc cgggcgtgat  12180
ggcacgcacc tgtagtccca gctacttggg aggctgaggc aggagaatct cttgaatcca  12240
```

-continued

```
ggaggcggag gttgcagtga gccgagatca cactactgca ctccagcctg cgtgacagag  12300
cgagactccg tctcaaaaaa agaaaaaaaa aagaaaacaa ttatgctgag ttccagagaa  12360
gtgatgtctg tcttctcagg agagatgccg atgctgtctg agggcctgcc cagtctccac  12420
atgattcaga gactccagag atggacagct agtgccctga ttttcccaag aggattctga  12480
gggtgacttc tgtcaaccaa acaggaggac ctggtgctgt catcaccagt tgtagagagg  12540
ctgcggacca cctgctgtgt gtgccatctt acactgccat ttgctgattg cttcaaagct  12600
agaggttgtt tctaagagtg cttcgtgcta actaactaaa acataatgac attgtttttg  12660
taaaactgat ccgtggtttg ttttttaaag cagaaagctc taaagtcact cagtcccacc  12720
acccagaagc acaagcaggt ggctgccact gtaggacctc tctctctagg ctcgtgtaga  12780
tggacacatg gattggtcag tagaaatact tttattaaaa gtcttatctt tacataaatt  12840
tgccaaatta ttaattttgc ttgaaaggga aaggtgtcca acttcagttg gaaatactag  12900
tttctaagag atactgctga gactaagagc ataaaacatg atgaaaacct taagtggcta  12960
agtgcagcaa cgtcagagta aaagctttga tgaagtcttg gtttgcttgg gctgtgtagg  13020
ttggaggctc agcctttgtt tctccctcct ctggtgccca gtggtggtgt ttgtgtccgt  13080
gaattttcaa cctctgtagt ttgtttgtag ttatgaccac tgttgcaccg aacccttacc  13140
gagggccagg ccctgtgcta agcacttgcc agtgtggatt tattaagtct tcatgacagc  13200
accatgtagg gggagctgcg tccctgtgtt gtacttggga cgcgatctga cctcaggcac  13260
ttcaggctcc tgaagggtct gcagtctcgt ctctgcctgg gaaaccacga tttgcagcat  13320
attccacaga cctcatgctc atcatcagga ggcttcccgg gactgctgcc tgagatttct  13380
aagttcctaa tgtggttcat gcttctggtg agtttctttg aggcgacgcc ccctgcgttg  13440
cctctggtca gctcagtcct gtggtcctgc agggcatcct acagtgtcct ctgtctgtga  13500
cttgtgccgt gccaccttga cctggcatcc actgtcctct accgcgtttg cagataggag  13560
ccactgttgg tgcctttttg tcgtgtgtgt tgaatggtca gggtcccaaa tagctgattg  13620
ggagcactct ccttgaatct gccatgtgcc tgggtctcag gtgactgggc ccctccttgc  13680
ttcagaaccc acgtgcgttg cctgtcctct ctggcttgga gggttgtgtg gaatcagagg  13740
tgagacccag tccccaggga tgggcagttg cctttgattg cccagctgtc ctcagcgccc  13800
tccctcctgc gcccaactgc tgtctcagtt gcttgcttga ggatccggat atagactgag  13860
gtcggcctta gcgtggcggg gggtttttctc ttgagtcttg gatactttgt taccggtccc  13920
atcttcctgt gggtgggagt gtctgtcttg cttggcccag cctcccagag accttagctc  13980
tcttagtaca tgggctctgc ctaccttgat ccccagctca ccaccctagt gcagttgctt  14040
cttcgctctt gttccactcc ttgtcgccat ccaccctgtg ctttctcgat gtgtccttac  14100
tcggtgtttc tgtggagcag ggcatcctgg gcttcctttc tgatccctgg ctcctgtgat  14160
cttccgtgct gggctccctc ttcccttccc ttttccactg tgttgccctc acacagctgg  14220
catgccatgg atgtcgctca cccaagccct tcctaatgtt gctcaccaaa acccctccca  14280
ccttgcccct gggaccttct ccccttccag gctgcatgca ggccgagggc ctggcgtctc  14340
agcaggaggc agtggggcct ttgctggcac ctgggctctg catcctgacc ttctgagggc  14400
ttggtccttt aggtccatct tgaatctcct ccaggcttcg gactctctgc tctgtagctg  14460
gcccatggag acgggtacac tcaggcctgg tcttagactc cgctgcttgg gctgtgctgg  14520
tgcctttggt gccctcttag tccatcccac ctgggggccc tgtcctgctg tccattgtgc  14580
cagagtgctg tccccttgtc tttccgtaac tggctgctcg ttacctttcc catctcagcc  14640
tcagtaccag ccacttggta tcagggaggc tctccctgac caacctaaag ttcacagccg  14700
tggttgccag tttaaatttc tgcatagcaa ctttttggtt tattttggct acttatcttc  14760
cccatcatgc cccctgtccc tcccatataa actcagtgag agtaggggcc acatctcatc  14820
atcctgccca cagctctgct gtctgtatca gccagggtat gctgtgcaga ggctcacggt  14880
aaatagctgc agaccacgaa tcccatctgc ttgctgtgct ttaatattgg cttacatctt  14940
tggatccagt gagttctttt ctctgtctcc ctctctctca ctcgctcata cttactttgt  15000
gtaattggtg atttccagcc ttttgtatag tcctttctcg aatagttgtt ttctgtcatc  15060
ttggcggggg cctcaagggg ttgactgtac ggagggcagg ggctgcagag ctgcagctgc  15120
tgcctggggt ctcacggcgc ccgtgaggtg taggcaggtg ctttgcctct gagctgtctg  15180
tagaatgggg tgacggcggt ttcatcagac tcagtgaagc atgtcataca gtgagtgtct  15240
ggtcacagca ggaagatggt gaatgtcagc taatgagtat tcatcaccaa tgaatagtaa  15300
cagttttttt tactaaggct atgtaatgta gcctcagaat tccactcagc acagcccccct  15360
ggcagcggtg cctctgagag ctggcatgat ggagagagcc tggttggcct tactggtgtg  15420
gttggggcac ttgggagaac gccttcctca caaagctcat ctggagggtt ttcggacttg  15480
taggatagct ttttcagggg ccttgccttt ggcagggcag ggacgtgtac tgctgcagtc  15540
tagggtatgg gataactttc taaaccagac ccagaacttc atggccgcag gggcctttta  15600
gccatgcggg gctaggagct gacacagcgt cagcagcatg agggcctgtg gtgctgggcg  15660
gcagagccca gagggagccc ctgctggtgt gactttagtg taaaggctgg gggataccag  15720
attcttacag aagacttaag acgggcacag tgatgtctgc tctttgaccc ttgcagtatg  15780
aattagtaaa actgaaatta ttacatttcc tttattagga ttataaaagc aatgatgact  15840
tattgaagaa aatttggaaa atacagaaac tacctataat ttttccattg ttaacatttg  15900
agcatatttc ttgtcacttt taatggtgct ttaaatatgt agcaaatgta tcatttcgta  15960
ttttaaaaaa atgctaggta agcatttcct cctgtcctta aaaagctctt ttaaacaact  16020
ttaaaatatt gtatagatag atgtacacaa ttttctgaat aattggagtt atatttacat  16080
cttttcactc tttaggaaag gactggcctg tttctgtgtt gggttccttc ctgagtgtgg  16140
cttccagctc agtggctcag acttcaagat gaagacttca gtcctggttg tgtatggtct  16200
tgggccagtt accatatgtc taatgaatac ttagttttgt catctacaaa atgaaaatag  16260
taatatttgc ctcaaagact attatttggg aggatctagt gcaaatgtta gtaatgtgga  16320
tattgtgtag tgtcccagga tattaatgtt tttagcctct tggcttttat tctgtattgt  16380
tgcccccaaaa gatgatgctc acttatcttt catccagtgt aaggatatct ggaaagacaa  16440
cagaaagtat agctgttttc atttcaaaag tgatcagctg cttgagctag caagcaaggc  16500
ttgcactagc ttccaggcgc agtcacgcag tttcacagca ggcgcggttc cctcggagca  16560
cccagagctg ccctgcggta gtcagcagtt gtgctgtggc tgcactgcca ggctgggtgg  16620
caggtggatc ggagccagca gatgtggctc aggaagtgcc ttcttggcct ctccttaatc  16680
tctttcagag tctgtgggcc cttgattgca ctgtgggttg tttcagactc cagtattagg  16740
agactgaacc ccttggtggt ttttttgtgt gtgtgtgctg agctgggttg aggacatgtt  16800
aagcaggtgg ggtgcctccc ctgggtttgc tccgggtggt acctgtggtg tggggtggtt  16860
ctgagtagtt ctggccccac tgctggagta tctgcccact cagtttgtga gatggcaggg  16920
cttcatcctg gtctggtgcc tcattttctt ctttagcagt gggcttagaa ccaatgcaga  16980
```

-continued

```
ttcccaagtt aagtattttt tctgtagctt aattattaca ggcttctggt acctaagccc  17040
tttcttactt tctgttctga ggggaagaga agataatgtt gtttctccgc cccccccccgg  17100
agtggcccca ggaccttgca tggcatttgc agcatttgca gcgtgcttgg gtttgcttta  17160
ctagggtgaa agtgttgcac cccccagcac ccacaaaggc acctctgctc acactccggt  17220
gaggttctga ctggccctgg gacatcacct gctccaggat cctatgtggc tcatcccagg  17280
agagatgtgg gagggaaggg gaaaaaaggc ttacatttgc tgagtggaat tcatgtagat  17340
ctgagttccg cattgattcc taagctgcag agcccttatg ccttggctgt tttgtgaatg  17400
ttagtcggtc ttaacctttt tcaccgagtt agcattggct gtctcaggag gctcacagct  17460
cctgctcctc ctccagggga gtgcgccctc ctcctctgtc ggtagctgtc aggtgcccct  17520
ttcctctgca gcagactgtc ctgggtcctt gcctggcctt cccccttacac gtgagcctgc  17580
agcttcattc acagcccctg tgtagaaaga taggcacatc gataggtccc tccctgccca  17640
gagtgggcgg aactgaggca ggcactaaaa gcagctgact ggcagcccta gaaacatgaa  17700
gggtttcatt tatagtttca gtccttttcc ttctttcgag ccttaattta aaaaaaaaaa  17760
aaaaaaaagc cttgaagtcc tgcttctgag ttttctaatt tgtgcaggta ttagttgcct  17820
tgtaacataa tcaaaaataa ataaaaatga tttataatta gcttattaac tgtatcagta  17880
aatggatact ttaaagagga tcattgatcc ctcaaaatag aagcaatgca gtcattccct  17940
cattatgctt tacttgtgat ttgcttacaa cccactcttc ctagttaaag ttaaatatta  18000
atccagaccc tatcagtgcg atgtagtagt gtctgaatca gttgttgttt tggtgtaatc  18060
gtatcaaagc atgttataaa atctacaaaa ttgcagggtt aactccaaat attttcacta  18120
aggtattgtt tttttgggca aaaatgcata gtgaacattg tggagctgaa gtgagggaac  18180
ttcgatttct gagaaaccac tagttttaag ggtttttgaag gaagagttgg aggaggagag  18240
gaagagaata aattcacagt taatgagttt ccagtatttt ctgtcgcatt ttacgttgta  18300
atggaaaaga ctgggaactg aactcacatg cagtttgtca aatcactttt tccctagaat  18360
tcaggattga tgagattaac ggggtgttaa aggtaaactg aggcacataa ttaacatgga  18420
cagaactgta gacctgagtg ttgagagttg ggaaatttca gtgagttggg aagactggaa  18480
gcacctgttc ttcagagtgc aggtcctcat attcagtggg tttaaggtgc tgaaactttt  18540
tttttttttt tgagatgggg tcttgcactg ttgcccagac tagagtgcag tggtgtaatc  18600
accactcact gtagcttcga atcctgggct gtcagcctat cctcccacat cagcctcctg  18660
actagctgga ctgcaggcct gggccaaaac tcctggcttg aaacttcttg taaccagatt  18720
ggaggaggag ggcatgttca ttttcgtgac gtttcctttc ccttaaacat ccagtgaaat  18780
ctgacctttg accatcactt tgcttaaaag aagctactgg atttaaagtc taggagaatg  18840
tcctagacaa gcccatagta tgttcctgta tgttccccac ccagagacct gcgttatgaa  18900
gtgtttggtg tgcttcttcc agccccactg ttctttctaa agtgttttat tttacatacg  18960
ctgtcctggc ttctgggcta tgacctttgc ctttttttgcc ctttagttcc tttgcccttt  19020
acctactgca gtgcagctgc ctgtccttgg gttgactaca aagaagtcac ctttgaacaa  19080
cttagaaatt gtgactttttg gggaaggcag ggcagagcct tggggctgag atgggggagg  19140
agccagctct gccctgggag agatacaaag cgcctgcctg ggtgaggcag tgcacgggtg  19200
ggcttgcttc acctctttgg ccccagcttc aaaaccagcc agtcctccct ggctttggct  19260
ttaattcaca tttacaagct tgaaaaccag ttaatcccat tagctcagct tctaaagctg  19320
aaaatcgtcc cctaaatggg tcacctgttg tcatcaatag ctttattagc tatggaataa  19380
tatagttttg ttctctaact gtaggatcct tcttttgctc ttaaaatagc tcagtaagtt  19440
gggtctcata aatacataca gcaagcatat accagatact aaaatacaaa aacattgctg  19500
atcttgcttt tcagtactaa aagcagaaaa tcgggaattt actaaattga gaagtcagtc  19560
attacctttc gatgggtttg gactcttgca aggcagtgat tgtaaacgag agtgatcttt  19620
tgttgttttt caatgaactt tattctctaa tttttagtaa agcacactag gaaataatgc  19680
ttcagaattc tgttttcgag tagtttcctg actaaaataa aaattcacta aaaaaaacct  19740
ctgctgtcac catttccttt tttcttaaga taactaggaa atgaatcatt aagagtttgc  19800
tccgtggcaa tggatcggga agctgaccct gctctctgtg gggctggagc cttgctaatg  19860
tcccaggatt tcacttcaca gagacaagca tcagaggctt gcttcattta tagatcctac  19920
ttcttttcta caccacagcc aactcaaaat ggtgacagaa tctaagacga ggctagaagt  19980
caccacggag cagttggaag ctctgcttcc ggttctgggg gcagtgttcc tggcgttgtg  20040
tcctttggcc ccacctcagt ttgtccgttt agctcctcag ctgagaatga gatgtgtatc  20100
atataggagt ttcctgggcc actcacagcc ccaagctgga gagtgccagc ctaatgtgtc  20160
aggagtaggg ggtgaggcca gagggctgtg tgccaactcc tccctaagaa gcctcctggg  20220
aaagccctcc caggcacttc ccaggtctca ctggccgcct gaggctgcag gggaggatgg  20280
tcaggccgcc tcttggctgg cactgcttcc cggcgtgccg ccagcctttc tcatggggag  20340
gggaatgatg gcatgcctgg ggggcagcag ggccccaggg ctgcctaggg ctctcactgt  20400
gtcctcctgg ttctgagatg ccacctttgt gatccactgt agagggattt attctattat  20460
gatcaatgca tagaaatttc ttcgatttgg agactgaaca ctagtgagca gaactgaaat  20520
tgagctttaa aagatattga tgacgggtct gtggatagga gactttagtg tggtttttat  20580
gcagacgtcc tgccagctgt aaattccctg gaggtttggt atgtgagaac ataagactaa  20640
acttatttct attttgttga ggagaaatga ttaaaacttt tcattgatgt acttctgtgg  20700
cagactttttt ggagaattga accagcgggc atattcagta tttgaagtca tagatgagta  20760
aaggaggtat gttgtagttt gcgctggcgg cgtggcctgt ggtcggcagg gcttatctgt  20820
gaaggtatgt gcacagcttc ctaaggcagt gaaaagtcct ggcagtgtta gtattgaatg  20880
agataatcca aaaaatgtaa aaatgtttac atttttaaag ggatagttgg cgatttaaat  20940
ggtttctgct aacaaatcaa attattcatt gcagaggtaa aatattttca gaatgttaat  21000
tttagatgtc gtagagagtg tacatcagca atgacaaggt cagcaaaata tcttagcaaa  21060
acttgattga ttgattccat gcacaggcaa gcgctgttct gggcaccgga gacggagcag  21120
tgcgctgttg cgtccatcca cagatggcct ccagagtcat gcggttgcag ggaggccgaa  21180
gggccaggga ggccgctggg tgggcacggc tgggcggtgc cctcacgtgg gttttgttgg  21240
gctactctta ctgtgcactt tttctcagtt tggtcagtgt tccgccttgc tgcctggccc  21300
ccaaccctcg ccctctgagg gcctcacaaa gagccaagca gaaggcaggc tgggggcttt  21360
tcaggccagc ccagaggatg taatgatgat ggttggcact gtcccacggc cgccaccagt  21420
ctcacactgc ctcgtgggca gtcctggagt cgtgcggcac cttgctggtc cctgctctcc  21480
ttgaagaagg gccagtgggg cacttcgcca gagccttctt gtctgactcc gtcatccaag  21540
aggcatggat ggccgggccc ccggcagttt ccattctatt ctgagaaggc aaaacaaaat  21600
tattcctgtc tcttattatc taatatttgt tacagcagtt gctcactttt aggtgcattt  21660
tattacagat ttcagacagg tgtggttatt agtgcagctt actgtttgga cacaatgcca  21720
```

-continued

```
aggtcaggag gacagtgttc ccctgagcac cacttctgct aggagcatgg gcaggccatg  21780
cctcgccatt aatctctcct gatttagggg aggaatacca ggccaccccc tcttctccct  21840
gtgcaaggga acagacattt gacaaaaacg gatgccatgt tacgctgatt ttgtgtgtct  21900
aaggcagact gcagcaggtg ttatctccgt gctcttcctt tcctggagtg ttgagcatct  21960
cttgatagta ggggatgccc ctgagggtgg tgaatgtggc tgcacaggtc ctgaaagcta  22020
tttgatgttg ccgttacttc aggtagaact taaagttgac agtacattct actctgcagg  22080
tggaaatgtg gagtgccatt ttgacaaatt ggaatgccct gtttacaata tgctttaatg  22140
agttaaatct gggggatgtg gatagaattt tagtatccta gctttggcat tcttccatga  22200
ctttgggcca attatttaat aattccaagc ctgcatcttt gttagaatct ctaaatttct  22260
ctactcctgt tattatcctc agaacaggac tgtgaggtgc agtaggccac atggtgtagt  22320
ggtttaggtg gacagacttg ccagtgctgt tctcatggat agcctaggac tgtccctagc  22380
tctctgcagt gacagtgata gtgactggtg aaggtgaagg gatccaccca gacgttcttc  22440
ctgatggaga gaggctggcc tgtggctctt ccctggggtg gatgttaacc tgctaacgtg  22500
acatatctag tcctgcttac attactaagt ggtaggaaat tttaggtaac acctcagact  22560
ttaaagtggc ctactgagct ggtagaaaag tgtgtagttg gtgctcagta attgttgaaa  22620
agatagaagc tttacttcaa agctcttgta gtttgatcag tttggaaaaa atattttaat  22680
gttgggctct gttaacagct ggactggtgg ctgtctgaat tgggaccatg cttggggtga  22740
ggtttttctt tacttttttt ttttttttttg gtgagacaga gtcttgctct gtcgcccagg  22800
ctggagtaca gtggtgcaat ctcggcccac tgcagcctct gcctcctggg ttcaagcgat  22860
tctcctgcct cagttttctg agtagctggg actacaagca tgtgccacca cgcctggcta  22920
atttttttct atttttagca gagatggggt ttcaccattt tagtcaggat ggtcttgatc  22980
tcctgaactt gtgatccatc cacctcagcc tcccaaagtg ctgggattac aggcgtgagc  23040
caccgcatct ggccacatat ttttttaaat taaatgtgat acataaaatt aggctgcagg  23100
catggcctga tttgcaggtg cttcatgagc aagcgtgcac agcatttatt tgctgctcct  23160
ggagtctctc gtgtgtgctt gtagcctagc cttaagccct ctgtggacgg cttggaatgc  23220
gtactccaaa tgactctttt ggcggggtgg gaagtggcaa tactttaggt gactgacagt  23280
tgaaattaac cttacacaag agccaaactg taggctgatg cagggccact cacctttgta  23340
ctcacccctg gcaggtcctg taagaggtgc tacttgcttc cactttgcca gctgttcgtt  23400
ggccctgttt tgtcttctgc tgtttgcctt atttatgaaa cagaatggaa acaggcgagt  23460
ttgatttgtt ataattccta ggagtcatag aatggaagca ggtgagtttg atttgttata  23520
attcctagga ttggataatt tgccttcccc tctctccatc tttaattaat cccttaaagg  23580
aaaagaggac gacagcactt ttcctgcagt catctgtgta ggcctcagcc ttaactcatg  23640
acataggctg gtgccactgg ccacagggct gacctcagct cttggagccc atggggtgac  23700
aggagatcag cacctttgag gtggcggcgt gaggcgtctt ccaggccttg ctcatggtgc  23760
ttgaaaacac tgctttagag ctttgttaag agagagaggc cctacttact cctgtcccac  23820
aggcatttgg gtgttgacct ccttgttggc ctcttaagga gagaatactt gagtattgaa  23880
ttcgatcagc ttttctgcct ccagggaccc tgtttctctc tgctgagact gtggcggatg  23940
aaaccaggat ttagtggatg gtcaccaggt agcttgggca gacctgggcc gcggggcccc  24000
tgaggactca tacgtctttt tcctgttcac atgttccttc cccacacctt ggcccattct  24060
cagtccctcc catgctcctt agcgtgaggc actcagggag gtgcccatgg ggccttgggg  24120
cctgtgctgg agctggttcc cagcctcaga agtgtgccta actgtgccac attcattgga  24180
aagctgcttt cacacttcct ggatggaatt ctctcatttt ttcaatataa agtcactgag  24240
atgatttttt tggagaagtc tttaaaggcc agttatacat ttattgatac ttggtattga  24300
caaagttcag ttgtttagtg ttgctaagtc atactgtgta agtttgttga gcacagagtt  24360
ttcattttat actttcagag gagaaatgaa actgaatttc gtggccagaa atatgtttga  24420
gcgtcatcct gatgtaagaa cagaacagaa aatgtggtga catttcattg taactctagt  24480
atgtttctt ttttgtccat tagactacat gaggaaataa ttgactttta taacttcatg  24540
tccccttgtc ctgaagaagc agctatgaga agagaggtgg tgaaacggat cgaaactgtg  24600
gtgaaagacc tttggccgac ggctgatgtg agtatgttct ttggagttct gtgtcgcacg  24660
tcacgtgcga gtaaatttaa ataccctgtg atgatgatgt gtcggctaga tccacacaga  24720
ccttttctcg ttggcccgag gcagcagttc tccaagtgtg ctttgagaag gcctccgttg  24780
cctggaatgc atggcccccg gcgcacctgc acctgctgtc ttagacacct gcggtggccg  24840
cacatcttcg tgatgctggc gcgcactcaa gtgcgaagac catcggctga gggatttgtt  24900
gggttttttt tttttttttt tggaaggggg agaatggtgt gattgtttct cttaagttca  24960
ccttaaaatt tagaaatttc accctgtcac ccaccccctgc ttccccacca ccacacatag  25020
tagcatataa tgtgctcatt tttgtaaaac ttggaagtgt tccctcatca cacaccactc  25080
ttgcagtgaa ggaacaagtg ttttttgaca tgtggagtgg ggccttctgg aatgcttggt  25140
gcaggtggcg tgaagcctgc ccctggccgg ctctattcag cagccttccc tactgctgac  25200
tgggctcagt ggaccagcag ggctggccgt gccccagctg tgaggggcat gtgtgctctt  25260
ggtgggcaag ggcaacccag ttttctgcgc ctcttttaaa atgatacaga tttttggctt  25320
taaacttcag agtcctagga caaagccctg ccccagtgcc ttagctgtgg gtttaagaag  25380
aggttgaagg gtttgaagct agctctgaaa agtcctcagc tttgaagggt tatagggtga  25440
ggacaaaact tgtttcacct cttaatttg agtttttaaa cattcctttt ttgggcatgt  25500
ctttaactta aagggaattt tctggttgat tgttatacgg tcccctccat cagtttccaa  25560
ggtagtttta ttttttaccc aagggtatag tgagggcttt cttttagtaa gaaataatgg  25620
tagtgtgact gcttggtttg tggtatacat tttaaggcaa ccactctttc tttcaggtac  25680
agatatttgg cagctttagt acaggtcttt atcttccaac taggtgagta ccagactgca  25740
tggcatgggc tagtgggggg ctgggatggt gtctatgcaa tattaagggc tacaaataga  25800
ttctttgtaa ttgagtctaa ggcgagaaat gccagctaaa ggaaaagact gtggttacag  25860
agggaaattg gcagaaagat ttaatttagt gttatgatga attcattgct ttgcattttt  25920
cctctcacac ttaatttgtt ggggtgcaaa aatgcttcat gctggaaata tgaagaagac  25980
aggtgggagg actgtgggaa gtaaacgcaa tagaagacat tctgctgata ttttaggaca  26040
tgtgtttgaa aaattgatct tatgttttga tgaagattca agcaaaattc tctttaaata  26100
gtattttcta agtattttta cctgatagga aaatgtcaaa caagtttgca ttctaaaata  26160
caaactagta ttttctcatt aaggattctt gatagccaaa taaatttcct gtgcactgtc  26220
tcattaaaag cttaccttct attaacccac tgctagttag catttggagg ccgaagaggc  26280
tataatctca ggatttgggg gttgacatta gcagggccag tgggtaattg aacaggtttg  26340
ggtatccagg aatctctggg tccgcaggag tgatccagcg taggcagtgc cggagtaggt  26400
gctgggagag cggggcctca gcctggtttg ggggcaggca ttttcatttg aatcccctca  26460
```

-continued

```
catacctagt gctgttggga gaatgattta accttcttgc tttccatctt atgctacaaa  26520
tatggaagtc ttcccttaag ttcagcgagg acttgctgta gttcatgaac tgcacttcac  26580
ctccttaggg gccataggct agtgggattg tgtcttggcc tttgtgggag acacaggcac  26640
atgtgccttg gtgcttatcc tccccacacg agtgtgtagg ctgtggcgag gggagcagtg  26700
gctgacgtgc gttttcttct gtcagcgaca tagacctggt ggtcttcggg aaatgggagc  26760
gtcctccttt acagctgctg gagcaagccc tgcggaagca caacgtggct gagccgtgtt  26820
ccatcaaagt ccttgacaag gctacggtga gtgcctggct ttggcccctc tgaccgggca  26880
ggagccttgt cacatcccag gtggtcacag gatacgcctg cgtcacgagc ttgtggtatt  26940
ttacacagtt attggctaca gttttgaaga ttaatctgct tctggtatag acatgtgttt  27000
tatgtttttg tttcatagtc gtgatcacca actgagaaca tgtttagtga cagtctgaac  27060
ttttgggact tgtgagccca ttaaactgtt cttggaatga aaatatatga ttgtgtctac  27120
ttgtgttagg atgaatagga aaggagagtc atctgaaacc ggacactgac attcaggtgc  27180
tgcccattat ggagagtgtg gctcaatgat taaaccatgg tttttatgat taccatttgc  27240
tatgttatgt taaagaggaa caacttagct gttcctttcg tggttccaaa aaatatacat  27300
atatgaaaag ccttttatct ttgggggaag tttgaagatg agactgtttc tggtgtgtac  27360
ttgctaaggt ttatgtcagt tcaagattat aagcccccca gggactatga ggtacttgcc  27420
tgttgtatga cagttcttag ctcacctgtg cgaccggcta gcatttcatt tttaaatttg  27480
tgtgtcaact tgtgtgtgat tcacatcctt atagtgttta gcagaatgta agttaaggca  27540
ggagcttcct cctgcctgtg tggtgatagg ggagggggca ttcacatgtt tctcattgtc  27600
aggtgctttt gattgaggct gggggcaagt tttaaaacat gatatatgca ctgaaaagtg  27660
cacatgtacc aggtgcacct cttggtgaga gttaacgaag tgcacatgct catgtcactg  27720
tcatgtggac cagagcgagc aggcagcacc agaggttccc tccaggccca ggttccagaa  27780
ggggctgttg gctcttctca ttagcacgag acaagccctg gccggccact ttctcaaatg  27840
cttacgggcc ttattgcact tagctctccc agccactctc atcagcagat gctgttgctg  27900
ttcacatttt acaggtgagg aaactgagat gcggagaggt gaggtcatta gcccaaggtg  27960
ggtcagcggc atagtccagg ccgctgttgt ctgctgctcc tctgtgtgtg ccaaggggca  28020
gcggggaggt gggtgggaat cctgaccagg cgaccacctt tggagtagag gaactaaggc  28080
gcggctgtcc tgaggccaca cagtaggttg agcagttaca gtaactgctt agtcccagtg  28140
acctcgttac tgtcgcatat tggctactaa gtatcttttc ctctgttacc tgagggccag  28200
tgtagactgt agggagagcc tggagcctgc cactgctcat ttctggggag cactgtgcag  28260
ccggccagtc atgggcacaa gagacccagg gcgagggctg agtttaaggt gaaatcttgt  28320
ctatttggaa caacaaccca aaactgtgtt acagtgttaa ctcctcacct ccaggatttg  28380
gggttcctgc cgtgagtgag tgtgtgcaag agtagggcag gagagtgcca ggagtgattg  28440
tgggaaggag tctatgagat ggaaaggaag ctgcttccta aactgtgggt gtcagggagg  28500
catagccatt gagtgttggc ttcttccaaa gcagtttctg atgagttctt tgggaaagta  28560
tttctttctc tgccttctta agaacatact ggcctcaggg cttaccctgc ctggtggtcg  28620
cagtggtgtc caggtgactc tggcccccact ggcatgtcct cacacgctga gtccttggtt  28680
ggttgccctc aagtgtagac attaaagccc agaataggtg tgtactgaat gcactgtccc  28740
tacgttgcct atcactggca tttgaacttt tcgttagaca ctgattgttt tggttaaagg  28800
aattcctttt tttaatcctt caaggctgaa ggaaacaaaa cattgccttt tcttctggaa  28860
gaattcagtt ttactggtgg ggtggagggt ggggcatgag tgtggtctgg acagttgctc  28920
aggcagattt tgaatgccat tcggtgacag ttcttgttgg tgagaatatt tctaaaatag  28980
ccttttattt gctgaatttt ttaggggaaa aattttttta gtaaagttgt cttaaagagt  29040
gaaaacccaa agtagagaaa caatatcagt ataacataca atttaaaaaa tggcttcgaa  29100
gttacattaa atgatttcaa aaattctgcc aaataaaagt ctggggccaa gcacctctct  29160
ccatcccagc acatagggtg ggcgtggcag agactaactc ctgttccctg ttggctccct  29220
cccctcacgt ctctttgatg cttggtcacc tctggtgctg atccagggct acaggggctg  29280
ggcagaatgt gggtcctgct gtgaggggct ggggcctggg agtcgtcctg ggttcaggga  29340
ctactgatgc tgacagtgtt ctctgacccc ctttcattac taagaaaaaa caccaaacct  29400
ctgtacagct ttggcagcat tttgatgcct ggctgtggag agtcctgcat gttaaagcag  29460
tttttaaaat gaaatcttta caggtaccaa taataaagct cacagatcag gagactgaag  29520
tgaaagttga catcagcttt aacatggaga cgggcgtccg ggcagcggag ttcatcaaga  29580
attacatgaa ggtactgtgc ttggtgaccc agcgcggcga gagtgcagga ctggagtgct  29640
tgtgcttggt ggcatcctac gatgtttaca gctgtcagct gcacacacaa gtctttcgta  29700
acacagacta cacttacatt atttctccta caatattatt tctagagata ctttgaaatt  29760
acatagctgt ttttaaaatt tgcttttcct gagtaaccat tttataaagt tgacaattat  29820
tttagagagc tttgttaaaa tgttctttct agttattaca gactttgctt ctagctcagt  29880
gtgcctcatt cgcaggtttt acccaggtgg aagttgataa atcatgaggt gccttaaata  29940
tactcacttt gggaggtctc agtgcctgag gatgggcaga gagacttggt tgagctgaca  30000
tgtttgggac tctgaccatg tgcctggtct taaacgggtg gtcatgacct cctgttacag  30060
tagaggccgt gcagtcctta gcaggggcag acgcacctcc gggtggtcgt gacctcctgt  30120
tgcagtagag gctgttgcaa tccttagcag gggcaaatcc acccctgcaa tctggtccca  30180
tcttgttcca ttttcaaggg ccttgctctt caggttcccc cttccccctt gtcatctggt  30240
ctgagggagc atgtccaccc caagcgcaac acgaacagca gcagccaggc tttccctccc  30300
tcctgccatc tcctgccgct ctgccttcct tgccagcctc actctgctct cctgctccgg  30360
aggcccccac tgtcctcatg gcctgtgtag caagcacata aacactccag tgaacgcgct  30420
ggtctcttcc tgagttcctt tgtgcctgtg gactcgtcat ggtaggggtg caccccctgct  30480
gagtcgtaac ccagggagag ctccacagtc tcgattttca caagcccctc aggaaattaa  30540
ttcttagcgt cccccaacca aagtttgaga cttaatgact gagagccttc agatgggcaa  30600
gaggatcgag gaaactttcc tttctgtctt gtgtgatttg ctatgtgaaa tctctttgaa  30660
agtatggtaa ttactcagta aatctttttc ttttggaatt tacagaaata ttcattgctg  30720
ccttacttga ttttagtatt gaaacagttc cttctgcaga gggacctgaa tgaagttttt  30780
acaggtggaa ttagctcata cagcctaatt ttaatggcca ttagctttct acaggtatgt  30840
atgctttctt gagactgttt ctgttgagac atgtgtaaga gtagactctt ccaaccagtt  30900
gcctagtggg ttccagcagc ctttgctctc cttttactgt attgtttcaa tttggtagag  30960
gctgatttct gattcttaca atcaaaccct cttgattaat gcacctttct ggatgctcat  31020
tttgtactgg gtgtaactgt tggtgcaggg gtgcccgtct ggttctgtga gtccagtgca  31080
catcagtcca agctcaggga attctctgta ttcagaaatg tccatttcat ggtaaacaat  31140
aaacatttct tggtgcttgt ctgtgattta tattgaaaaa aatttgtctc agaataaagt  31200
```

-continued

```
tgagtaccac atatgagaaa aggatttaca agagagcttt ctcagactga tgaaacatca  31260
ttattttgtc ttaaattata tgtggtcctt attttgctga gtaacatgga aaatctatca  31320
atagaaaacc tacgtgtttt aaaaagtatt gttaaatgct gtgatgtatt gataaactgt  31380
aattatactt tttaaacata taaaatcatc tctaattgga acagtaatta ttccgtttat  31440
atttcttga gtgaagaatt ctgtccttta caaaatcttg cctatataat ttagccgcac  31500
ggctgtattt ctccagtgtt taccattaat ttggtctttg tgattgtgct gagattaccg  31560
aatctgtcca tgatttggta atgttctcac tgtcatgaat gctatgatag tagaatcact  31620
gggtaactac ctgtgatgat cgcagcttcc ttggtctgtc tctgccaaga tgctttaaaa  31680
gtagtgaaaa tggaattcca tgtctgtttt cttacagttc tagtcacact gtcctgtctt  31740
cactttcccc tctgagatgt ggcccttata tatagccttt cttccatagt ttttggacat  31800
tattttgaat taaacatggg cctctgttct ttactgatat actcctgact tgcactattt  31860
tcatggcctt gtagtaacaa cagctactta atactttgat catgcatgtg ccatgtgcca  31920
ggcctgggtc cagggcctcc tccacccccct caggggggtcc tttcagtgat cctgtgaccc  31980
cacaggaggc caccacagca tgagtgggat tcctgtgttc actgccacat ccctgtgcct  32040
tgtccagtgc ccagagcttg tcctgcctca gcggtgtgac tgtggcagca tctgagtttc  32100
ttgactaagt gaggggagga ggcccaccct ggcaccggcc aggctcttgg atatgtgatt  32160
ttggctaaaa gacaaggaat aaggaaggga ataaaggtca ggccagaatc ggaatcctcc  32220
tcttgtgtgg tggaaatatg cagagaactc cggaattctt ctgaacccta aaaacatttg  32280
tatgctttct agctgcagct cctcctggca ctctgtgtta taaatagttt caagcaccgt  32340
gcttctctga gggctttctc tcatgtgccc tcgtccatcc ctttcgagtt ggcactgtcc  32400
gatagaattc tgtgatggtg atggccactt ctgcatggtc cggcaagggg cagggcgcca  32460
catgtggcta ctgagtattg cagtgtggct ggtgagagca acaagctgga tttttaatta  32520
atttgtttta attcatttaa atagacatgt gggcaatgca ggtctggaca gctgagaatt  32580
atgaccctca ggaggtgtgg tggacagtgg tttacttccg aacaagccca gtgcctgctt  32640
ttgaagacga tatggcactg aactgagagt ggtgctcatc tgtgtgacaa gcaggatgga  32700
agcttgctat aaatattgtg atataatgct aatgaccttt acacagctaa aatcaatcct  32760
ttcacttttc cggttttatg tgatactgcc atactagtca gtctaacact gacccctgtt  32820
ggttgtgctt cagcataacg aaattaggat gacgagaatc tgaaattaca tctaccatcc  32880
aggtgactaa gttatgcaga atatagtcca acttatttgc ccatatttgg ttaatcagat  32940
atctgtgttt gcaggaagtt tgctgtatgg attaccaatt tcaaaaatca aactacacta  33000
aaattcagat gagtccgttg tgttcctttt gaacactcct cgttgaagag gctgctgttc  33060
aggcttcctc gtggtgctgg tgagtgagcg agtgccactc actggtattg ccttgaagag  33120
gctgctggac agcagacttc gtcgcgtgct attttcttta gaacatgcca tgaatccata  33180
caaattgtgg gtgcattgct tttacagttg catccaagaa ttgatgcccg gagagctgat  33240
gaaaaccttg gaatgcttct tgtagaattt tttgaactct atgggagaaa ttttaattac  33300
ttgaaaaccg gtattagaat caaagaagga ggtgcctata tcgccaaaga ggagatcatg  33360
aaagccatga ccagcgggta cagaccgtcg atgctgtgca ttgaggaccc cctgctgcca  33420
ggtaagggcg ccctgatctc cactgctgag agctgggcca gcctcgggga cgtgctggtg  33480
acagggcctg tgttggggct ctgagagccc cgggcagttc atttgctctt gatgcaggtt  33540
tctcttatac taaccagtta ataatcacac tttgagaaat ccttatttaa tgcttctaat  33600
taacttttgt ctttctaact gtttacattc tataataaag aagaattaag gaaaatcttt  33660
tctttttctg attattgaag tataacatat ccaccctaaa ccatttgttt ctctgaagta  33720
tgtaatatag aaaaaccatg gatgccataa tccccttta tttggacatg tatttctcca  33780
ctttttccct atatggatat taatgtttat tattgttatc ttgttgaaca catcccacaa  33840
cgcaaacacg tttgtcactt ggcttttgac ttaacgctta cccttgaccc tttcctatgt  33900
gtgtaggttg tgttttgtcg tgaggattgc cgcattgaag agtctaaggc tgggctagag  33960
gtttcccggt tttattccca ttggcgtatt caggggtatt tatgtcctca ttcctttggt  34020
gacagtcttt taaaatcttt gccaatctga taaaaccatg tgttaacgct tttaaattta  34080
tatttcttta atgattagtg gggttaaaca cattgctatt tatgaattcc acaaattttg  34140
attgagcgtc tgttaggtga gataccattc ttactgttgg tgataaaatc gttggcggac  34200
gggtgacaga acaggtggtg gagagcccag ctccaggcgc gtgtccctgg gccttctcct  34260
ctgtgtggct ctgtgtgctg tccgcccggt tgctggctgc cctcctctgc tgtgtgcaag  34320
gcctgtgtgt gtcggggaag cctttcttgt cacacatgtc atactttttc caatttgttt  34380
tttgcatttg tattttttta ttcagctcct atacatttaa aaaaacacct cagatttaat  34440
ggttgttttt gttttatggc ttctgggatg tgagctttat ttatttccta aagatcgtct  34500
caaggaaaac acattggctg atgtgttttg ttgttgttta tagatggcat gatttgtgca  34560
ggctcttgag tggttttctt ggtagcacgg tatggcagtg tatcatccat ttttgtccgt  34620
tggatgagtc acattggaga cattggcatt gtcttcaagt gtctgctgaa atgtactcaa  34680
aaaacaaaga cccacataat cgttgagtta taatataaat ctagaaaaga taaaactcca  34740
gtacttagaa catatatcct ttaaaagaaa tccacactta acctgattgt gaagaatgag  34800
ttgtttgtag attaaaatta gaaacagtgc ttttcttatg aaaattaagc ttctcctgac  34860
tggcttcctt ggtgactgct gtgacagatt cctttgattt gctgtcccag ttttccacac  34920
gtgagaattc acattccatt ctaaaggatt tacttcctgt aggttccatt agcgttgact  34980
gagttgtgat gcacttgggg tgagctgccc ttctacctgc cctgttgggg cactgtgagg  35040
cctcctgatt gtcagatcag cgatcacagt gggtcggtgc tgctggtctg cacaatggta  35100
gtctttggct tcctcatgtt tctgccacct ggagaggtgg ctttttgtgg gctgtcactc  35160
cgtctgtgaa tggcagccgc ctccgtgagg tgggccatga gcacaggggc actgatgatg  35220
cagaccagtc ctctcggcac tcacagactg tgccctgtgc atggtgattg acagggcctt  35280
tgccagtgcc aagtgccacc cgtgcccatt gtgttcgcct gtctgggctt tgctggtagg  35340
gtctggaaga gtttcagtgg tgagggcctg cttcagagtc acttgtatga gaagatccaa  35400
aacatgtgga cgatggtgtg catgtgggga gggtctgaca tagccttttt gctgcaggga  35460
atgacgttgg ccggagctcc tatggcgcca tgcaggtgaa gcaggtcttc gattatgcct  35520
acatagtgct cagccatgct gtgtcaccgc tggccaggtc ctatccaaac agagacgccg  35580
aaaggtaatg ggttgtgtgt ctgcgtctgg gctcagcgtg cctgtgggat ggtacttatc  35640
cctttcctgt gtcatttacc tccatgaaat ttatgaaggg atgttctgcc gtatttcagt  35700
agaatctaga tatgttggtg aaggaaggcc ttctaggaat atgggatggc tgtgtgggat  35760
tcatccatgg ttgagagttg aaaatttctt tcttggagat ttgacatttt cttcagggtc  35820
ttttgttttg gggaggtgat ttctggcttt taaaattcag tccctaccat cttctcttat  35880
gtacactcgt cccttgttct acattttggg gcatttttac agtcccaaaa tgtagtcaga  35940
```

-continued

```
agtatttact tctcacccag atcattctgt ggtagtggaa agggtggtat ttgaaggggt  36000
gggagatgag ataggaatgg gaaggaagag taacgtggtc gtcaagagtg gaattcgaaa  36060
cagtttgata gatctgttct gtggtggatg atggaataaa caggtttcga ggcctggctc  36120
agcagccgct gcaggtgctg gtggtgctgg agctctgtgt gttcctgagc cgctgtctgc  36180
tcggtgtttt caggcggagc tctgggcccc atgtagggca ctcgtctcgg taccgtctcc  36240
attctcgtcc gtgcagtggg aagtgaaatg tcagcactgt atgatcatcg tgggtgggaa  36300
ggccccgctc ccctacttgg agctgcattt cacagtggtc ttctgtaggt agatgtactg  36360
cgatcccagg gtatgcttga gctgaatcat taaaagtcag agatatttgt caacgtattt  36420
tagctccttt cctactgtcc ttcacctagc gagatgatct gttaggggta taaggtagct  36480
gttcgagagg ggttctcagc tccctgacac ctgttgtact ctgttgatct ccaacaatgt  36540
ccctttgcag tactttagga agaatcatca aagtaactca ggaggtgatt gactaccgga  36600
ggtggatcaa agagaagtgg ggcagcaaag cccacccgtc gccaggcatg ggtgagagat  36660
taattcattt gtgttcatcc taaccactgg ctggcatgtt catgcagaag tgtctctatt  36720
cctttgtggt aaattggtca aattaagaaa atagctagtt tttctgatga gcattaatta  36780
agaagacaat aagatctaga gcagcactgt ccagtagaag caatataatg catgccacac  36840
atagaatttc aaagtttcta ggctgtgtca aatgtgaaaa gaaacaggtg aaataatttt  36900
gatagatttt attccactca agtcaaaata ttaacatttc aacatgtaat caacataaaa  36960
ataattaaga tattttatag ctgtttcttg tactgtctga aatccggtgt gtatttattc  37020
gtacttatag tacatcctaa ttaggatgct aaattttcgt aaaaaatact tgatctatat  37080
ttagatttta gaaagttcac agttgaagat gatttgcata cccaagttat tacaaacatg  37140
tttaatgttt tccaacaact aattgaatgt aatttttaaa attaaattag gcaaaaccta  37200
atgttgggtt tgttagtcac attagcagcg ttcccggctc agcagagccc gtgactgatg  37260
ctgccggggc ggctccacgc cgcagttctc aggagttatt aaccaaggct ttttccctcc  37320
acagacagca ggatcaagat caaagagcga atagccacat gcaatgggga gcagacgcag  37380
aaccgagagc ccgagtctcc ctatggccag cgcttgactt tgtcgctgtc cagcccccag  37440
ctcctgtctt caggctcctc ggcctcttct gtgtcttcac tttctgggag tgacgttgta  37500
agtgccctcc cctcctccgt gtgtctgttg gacagtttgt gtctctggta aatgtccata  37560
gccgcgagct taaaatctcc cccttggttt tgctcaggtt ttgtttcctt gtatgtgtgt  37620
ggaggtgggt ggggggcagc cccgtgatgt gggcaccagg cttcctttcc cctgccgtga  37680
accttcagaa cctgtctgtg cgactcatgc ggctgtcgag ggcagtaatc ctctaaatgg  37740
ttgaactaca gtggacttcc ttgagtagtt tttaaaaatt tatttgaaga ttaaaaaaaa  37800
aattaaatcc aagtatctct tctgtatttc ctttaacatt ctttttcagt tgtgatgaaa  37860
ttacttgaag gaagcctggg taggtttggg ctgcctgttc agaagttaga cttaatttga  37920
ataacctttc atagccagcc tggatgcagg cgtttctttt catagcttta aggaagtagt  37980
agtgcacctt tgtggtacag ctgtcctttt tgttttttgt accgggttca aggattcaga  38040
cacaccgccc tgcacaacgc ccagtgttta ccagttcagt ctgcaagcgc cagctcctct  38100
catggccggc ttacccaccg ccttgccaat gcccagtggc aaacctcagc ccaccacttc  38160
cagaacactg atcatgacaa ccaacaatca ggtacgtggc cctctggcac ccttcccgct  38220
ggtggcccct gggaacagca tccgagctgt gatatgcact agaggagatt gatggtcctt  38280
tgaattagaa gagtaacttt ttgagtattt ggccattggt gtgttgttct aggaaatcct  38340
ctcttttttg tggtgttgag gtcccccatg tatagtttca gcagcgagga cactgtggtt  38400
cttgagtgct gccgtggctt ttcacggggg ccaggttgac tgccttcctg caagtttcct  38460
cactgcccca gcatgagact gctgtcgagg gtcatcttga gagagcgact cagtcacgac  38520
ccacttagct gggcgccaag ccgtgccaga cacttgtccc tacttcctct cagaatctca  38580
atgaaagttt taatgtgaac ttattagact tttttcatgt ttgaaattag gcataatttc  38640
taaggctttt tctgttggaa tatactgttt ttaaaattta gataaaatta gaaatctaaa  38700
ggataatttt ataaatacta aattttgtat ctacttgcga ttatacatca cttgaatatg  38760
tgtgggtata aaacccaaca tgttaattga cttaaaacca ttttctgaaa tgtggggtat  38820
aatttgagca taaagctatg taggtacatg caaaagtgtt ttgactcatt tcttggagtt  38880
ttgcactctg ctctggggaa gacattctca caggatccac cgtgattctg gcggagcttc  38940
tgggatgctg gctctgtaat gacccacaga gctgatgagc agagccatgg cccagccgga  39000
caccgtaacg tgtctaattg cagcataagt gtaaaattca ggggcaatta tttacactct  39060
taaaatgaat tataccacag ataaacttgg tcgccttttt atggtcatca cagtggccct  39120
gacgtcctgg ccatgtgtca caaaggtgtt tgttttaacc acccacaagc cttggggccc  39180
ttgagagccc agtgcggctg ctgagctaca gagccacact ctgcggctgc ttgtgtggtt  39240
cgagtgtgaa gtccagggac gctgagggtt tataggtttt tatctaagaa gactcttggc  39300
cacagtcaat ctccagaggt tgttggggta aatgcacggg atgccaagat gcaaccaggt  39360
cagtattgca agtctgagaa aaggggttct cgttagcgca cttctgctgc tgacagtaac  39420
gggtgatgct gacatagaag cagcctggga cctggacagc aggcaaggaa ggaactgcca  39480
gccgtcccac ggcctctcag gccaccagtt gggccagcct tgggctgtga cccctgagtt  39540
cagcgtgtga gtaggggggtt caccacgggg gtgacggttg ttcttctgat gactctaatg  39600
tcttgatcgt ttgatcttca atgagtttca aactttatga cttggattac tgggcatact  39660
ttatatgcca gttgctgttt tagaatacga agtatttcca attcaaagca caatattgtt  39720
aggtaatagt aaaacagact gctctatgga gcccacatgc aactgtgcca tttatcagct  39780
gccctttggt ggtgctgagc ttagaagccg gatggttttc ctctgattgc tttggtaccc  39840
atggccgtct ctcattttgt tcctagacca ggtttactat acctccaccg accctagggg  39900
ttgctcctgt tccttgcaga caagctggtg tagaaggaac tgcgtctttg aaagccgtcc  39960
accacatgtc ttccccggcc attccctcag cgtcccccaa cccgctctcg agccctcatc  40020
tgtatcataa ggtatagctc tgtcctggtg cattcaccta cctgttcaag ctgccatgtg  40080
agaggcggtg ctaaatgttt tctcctccag agagaattcc agagagatca tttgaaaacg  40140
gaatttgctt tgttgtcatt cagcctgttt gcttgtcttt ccaaacaaaa cttaaaaaag  40200
ttaaattatt ttaagatgta atatatagtt taattggttg ccacaaacat ctcttaattc  40260
ctctgttgaa ctgattagca taaaactgaa gtttgaaata aggctcaaaa tgaagacttt  40320
tcccatttac ataattcatt tatatgctaa ataccttggt tttcaagaag caaatgataa  40380
aaccaagagc agatcttgcc atgatgtccc gtgtatgctg ctgtcattcc cacgttgcct  40440
gatccccgcc tggggcagga gcaagcgtca gggctggcag agctgtgtgc tgggcctcag  40500
cagggccctg gcatgcgtgc ccttgtggct cctctcaagt ccagctgtgt gcatggagga  40560
aacaggtcac gttaagtctc tatattcttg aagtacctga atgattggga gagccatggc  40620
gaggatcttc caggtcagcc cccgtcgtgt gtgatgttcc ttgggctctg cggatgctcg  40680
```

-continued

```
gtgctttcat cggtgtccac acctctttat tccgctcctc ctttgcttgt ctaatcctat  40740
tttgccagta agttttttat tcttgaggct ttgttggccc tgtgttgtat gatgattgtt  40800
tttaggagtt aagtaataga acatttcctc ttggatttat ccatccccga tagacacatt  40860
cagggtgaaa gaacaacttc gcacaccggc ctcttctttg cattttggct ttgctttccc  40920
agtctcctcc tgctgttttt cttgctctga gactttcctg aagccggcgt gtgttccctc  40980
tcagtctgct tggccgcgac tttgcagtgc agggaatgtg ctttgggtgt agcccaagca  41040
caggctgctg catgctggga tcgacaggct gctgagggcg agagcgccag gtcctggcac  41100
gtgtgacttg cttggttctt tctagaaggt cacagctggg ggaagaacat gacagggacc  41160
ttcttacttc tgttttttttg gagacagaat ctcactccat cacccaggct ggagtgcagt  41220
ggtgtgatct cagctcactg caacctccgc ctcccgggtt caagcaattc ttgtgcctca  41280
gcttcttgag tagctggaat tacaggtgtg tgccaccaca cccagccaat ttttgtattt  41340
ttagtagaga cggggtttca ccatgttggt caggctggtc tcaagctcct gacctcaagt  41400
gacatgcctg cctcggcctc ccaaagtggt ggaattacag gtgcaagcca ttggcacctg  41460
gctagggacc ttcttatttc tatggataag tggaacaagt tagaagtgag gttctgctga  41520
atttgtgtgg tttgatcctg gtacatggtt cttgccttta gtcattcacg gaatgggaag  41580
aatgcttttc tctcagatgg aggagttggg aagtcccaga gggcaggtgt ccatccctgc  41640
tctctatgta acatcacgtc ggtgcttagt gtggtcactg cccgaggacg tgggcattgt  41700
gcctgctgtc tggctccaac actgctgtct ctctctttct ccagcagcac aacggcatga  41760
aactgtccat gaagggctct cacggccaca cccaaggcgg cggctacagc tctgtgggta  41820
gcggaggtgt gcggcccccct gtgggcaaca ggggacacca ccagtataac cgcaccggct  41880
ggaggaggaa aaaacacaca cacacacggg acagtctgcc cgtgagcctc agcagataat  41940
ggctcctggc tgcgtcagcc tcccccaccc ctctgcagac tgccccgcgg cctcggccac  42000
cggcagggga accgagacca gcaccccgca cgtcagccgg gctcgcggca cgcccgccgc  42060
tgatcactct gcatgtttct tcgtgtggtg gtcgcgtcca tcttcaagaa cagctcgttg  42120
tgctcatctg tgaagcctta ttaaacgtgg acgttgtttt ctgccttccc aggattcttc  42180
cttcagtgct gaggcaggtc gggctcagga actgcaggga cgtgaacatg cgcttgcggt  42240
ttgaggtagc cgtgtctgtt ccttcgcggt ttgctatttt catttcctgt tcgtcaaagc  42300
agcagaggag atcaaacccc gttcgtgtgt ctttcctcca cggataagct tgggaggtca  42360
ttgttttact gccctcacat tttgtttgaa atttcagaac tgtttttcta tgtaaatatt  42420
gaaaacttat gatttgtgca ataactcaga tattttttat ttaatttcct attttcacat  42480
aagttatatt taagggagga gggaattttt tttaaacaag cttaggtcct ttcccgagct  42540
gcattttcta agttgggtca tcgtgtcggc tggttgtctg acgagcatcg ttacaaacac  42600
catgatgagg ggtttggggt tttattttga tgtcttttct tttggtcgga agtgagtgaa  42660
ggagccaggt cgccctgaag gttttccaaa gggcttggct ccagagccac ctggcagact  42720
gcccgtggcc ctgctgtcgg gccccaggcc gttgtcctgc tctgaccaca gagttttaat  42780
gttttggttt tcacttcttt taaactggac aacaaatcca gcatttcaag tgccagaagt  42840
ataactttct aaggagagaa gggttgtcac attataaaat ctttaggaaa atgtgaactg  42900
gaaaacgctt cggtcagttt tagtgacata gcctgtgatg atgggtctgg tgactattat  42960
tgcggaccgt ggtacccagt tttaggaatg tggagaaagg aattctgttg attccgttga  43020
ggaatctgta gcgtatgcat tcgttctgtt aagagcaaat ctaggagaag tgcttcagct  43080
gcccagtgcg ccgtggggag tgttttaacg gatcgtgtcg caggagagca cagcccagcg  43140
ttggggccgg gaccgctggc gcccgacgtc ggaagcatac aggtatacta tgcaagtgta  43200
ttctgccaca acaaccactg tctttgttac cttttttga acaagaatat atccatcctg  43260
cctaaccctg agtttttgga gcaccacagt tgtcctggga gttggttgca tcttgtaggc  43320
catctgactt cctgttttta aaacgggggt ctggtcttgc taaacactac aggtaggttg  43380
gtctttgaag tccactagtg gagaatgtca agacaagata cttattacca tgacatctga  43440
tgcatgtgca gcagtgggga gttctagatt gatctctgaa tgtgatcgac gcccagcaag  43500
gacaagcttt aaaatgtctg cggtctgccc ttttgaagca ggactggctc actctgtcat  43560
tgggagctgt cagctgcgac tgcaggttct ctaggaggca ttccagaata gagtagcaca  43620
ctgtgtctgc agttctcgat gaccgaaagt tatcaaaaat atttaaaata tttaaattgt  43680
gaacctattg ataaagaata tttataaaaa ctgatctgta ggcctgtact aatctctacg  43740
cattagcaat attgactgta aacccacatt aaggaaacca ctacgggtct ggcagtgcgt  43800
gtcccgtggg gtgtgcattt taaaactcga ttcatagaca caggtaccat gttccatttc  43860
cgtcatggtg aagcaaatga attggcctgg ctaccactgt ggtcgcgtgc tacaggtttg  43920
acaaaaagat atcatgtttc gatttttttg tgtgtggaca acaatatgga agctaaaatt  43980
gacatatttt tatgtaaagt ttttctattc tttgattttt aataaacttt ggaaaccagt  44040
tt                                                                 44042
```

```
SEQ ID NO: 3            moltype = DNA  length = 86750
FEATURE                 Location/Qualifiers
misc_feature            23430..24809
                        note = n is a, c, g, or t
misc_feature            70678..70758
                        note = n is a, c, g, or t
misc_feature            71318..71417
                        note = n is a, c, g, or t
source                  1..86750
                        mol_type = unassigned DNA
                        organism = Macaca fascicularis
SEQUENCE: 3
ggcggcgcgg cctcggcccc ggccccggcc ccggccccgg ccggcatgta ccgctccggg  60
gagcgcctgc tgggcagcca cgcgctgccc gcggagcagc gggacttcct gcccctagag  120
acgaccaaca acaacaacaa ccaccaccag cccggggcct gggcccgccg ggcgggctcc  180
tcggcgtcct cgtccccctc ggcgtcctcg tccccgcacc cttcggccgc cgtgcccgcc  240
gccgatcccg ccgactcggc ctcaggcagc agcaacaaga ggaagcgcga caacaaggcc  300
agcacgtatg gactcaacta cagcctgctg cagcccagcg gagggcgggc cgcgggggc  360
ggccgagcag acggcggcgg ggtcgtgtac agcggtaccc cgtggaaacg gaggaactac  420
aaccagggag tcgtggggtg agtgctggcc ctgcggcccg atggcctggc cggtgcgaaa  480
gcgcagccga gcacacgccc acagtggggg gttgtgaggg tctgggagcg gccaccccca  540
```

-continued

```
cggcctgcct ttgcttctgg tgcacggggg tgctgctggc catccccacc cccctagtcg  600
tccacacctt tccccagcct ccttaaccgt ccccaccctc cgctctcctg tcctccctta  660
gtcgtccaca ccttcctccc ctccctctta accgtccaca ccttccccag gtcccccctt  720
tatccattca ctctcctccc atccccctta gtcaaacaca tctacccctg accaccaccc  780
cgcctccagc cctccacacc tttttccccg tcatcacaac tcaagatgag accgcttaac  840
acgggcatat cattcattcc ctgagaacat tggtgtgtga gtgtttttttg atggtgcagg  900
acccggaggt gctttccttg ccaagaatag aaacatccag aatgctcctc cccctccccc  960
agtcccagac agcaatcatg tcagccctgt aaggcattgc ctgctcttga ccctttggcc  1020
aatcttttta tttttaaaa attcgcatat cacagatgcc ctgtctgtgg agagggtggc  1080
gtgggatggg tgaccgctaa gtttaggctg gcgaaggtgg tgagctcttc tgaggccctg  1140
atagaacttt ccaggagttc atggtccgcg gctccagctt ctcactgtaa agttgtcatc  1200
ctggcagagg cagccaatgc ttttcattct agggggtaga gatttatgct aatgagtgaa  1260
tattgcacca ctagtgactg tttaaagttc agctgttaga aaatggaatc ttacctgacc  1320
cctagtgaat tatgtacata agcagggaat gtttccagct agatcaccct tcagaagagt  1380
ccctgtgttg gaataggtta ctgagtctta tttgttttgc aaaacaaagc ttttggtctc  1440
gtgtgtgtgt gtgtgtgtgt gtgtgtgtgt gtgtgtgtgt gtgtgtagct tgagtatgga  1500
gaacgggctt tcaaattgct tttcattttt caggttctgt tttacactga gggctttggc  1560
atgcaaatga aattaccaat tagtaatctc atgtgaacct tttcctggat ttattcattc  1620
agatctgtcc tgctttggct gagagagaga gttctgtgta cctttttgaa ggtctggata  1680
aaatgagttg gtgggttcca tctgcttcca gtgggctggt gtctgctcta tgctactatt  1740
acaactccta ccttttgtgg aaaatgcagt caagcgtttt aggactggtg ctgtggtaca  1800
tgtcaaacct gccctcacat tccagaaagg gaaccctttt agggttgagt cctctgttgc  1860
taagcttcaa gggcgctctc catggtcatc acgttttatt aaaggcttgt ggttccatcc  1920
tgttagcatt tccaagtcta agcgtaaacc tgtggtttag tgacaagcaa attgatgttg  1980
agggtttctg gtagtttcat ttcacaggag taagctccag ttaagtaatc actgtcaacg  2040
aaaaccttga agttccttaa ttgcatttta ttgaagcctc cttgcatgtg tctagcaaaa  2100
gatataagtc caagatgctt attttttttt gataaattag aaattgtcct ttcctctgct  2160
tgctatttaa tgcagaagat actctaaaag gttcatattt gtacctagta gaagcaagat  2220
gttcttgttc ctaattcaaa tatattgccc tcaaagggat taggagagga attttcattt  2280
cccagaggga ttactgtttt aaaactgatt gtaaacctct ttaaaaactg cttatcactt  2340
caccagtttt tccattcttt tgcctcctcc cttagaggat gtcagcagtt aatttttttaa  2400
aaaaaaaatt gaaaaaagaa tttcaattct gagtcctcct agtttcaaaa aatacgttaa  2460
acaattccca ggagtgttaa gagtgtcggg gtgcttagaa attcttgctt tgattcatgt  2520
atcctgattt cttttttttt tttttttttt tgagatgaag tttcactctt gttgcccagg  2580
gtggagtgca gtagcacaat ctcagctcgc cacaacctct gcctcccagg ttcaagcgat  2640
tctgctacct cagcctcctg agtagctggg attacaggtg cttgccacca tgcctggcta  2700
ctttttttatt tgtagtagag acggggtttc tccatgttgg tcaggctggt ctcgaactcc  2760
cgatctcagg tgatctgccc gccttggcct cccagagtac tgggattata ggcatgagcc  2820
accgtgcccg gcctcattat cctgatttct tttttttttt tttttttttt tttttttttt  2880
tttttgagac tggtctcac tctgctgcct aggctggagt ggagtgatgt gatcatagct  2940
catggtatcc tctaactctt aggctcaagt gatcctcctg cctcagcttc ctggagtacg  3000
tgggactaca ggcacatgtc accacacctg cctaattttt ttatttttac tttttgtaga  3060
gatggggcct ccatttgttg cccgggctgg tcttcaactg gcctcaagca ctcctcctgc  3120
cttggcctca cagagtactg ggattatagg catgagccac cattcttgcc agtgtcctta  3180
tttcttaagg aagttttctt gtttttgata caggtatttc aaaatatctg aattcagagt  3240
gcacctcgat gttttgctgt tctgagattt aatatactaa aactattacc attgttgtct  3300
gaattcttaa gatgtgactg atagttagct aataggttaa cacgttgtgt tggttcttgg  3360
cctctgaact gatagtccag atagggagag gacaccagaa agcatgtgaa aaatggacta  3420
gaactatgga acagctatat agtctctcac agctgtcttt tgtgttctct gcttcaacca  3480
aactggttga cttatttaga attctgacct cttgcattgc ctaagtcctt gatgtttttg  3540
gtttcttctc tgaactctca aaggtactca cttcatgctc ttggtatagc ccacttatgt  3600
ttaactttcc ttttattatg tcttccctct tacacatgac atggacattt cttttaatat  3660
gtagagtaag atattggatt tcatctaaag tcttcaaaat aaaactcttg ggctcaccat  3720
ctcagacttc ttcatgtatt tacagaccag ggattttgtc tgcttttttaa aaaaatttta  3780
tattttttat tatttttaaa ttttaattta attttatgga gacagggtct cgctctcttg  3840
cccaggctgg agtgcagtgg tgtgatcttg actcactgca acctttgcct gggctcaacc  3900
catccacatg ccttggcctc ccagagtgct gggattacag gtgtgagcca ctgtgcctgg  3960
cctaaattta tttttttaat tttttttgag acagggtctt gctctgtcac tcaggctgga  4020
gtgcagtggc atgatcatgg gtctcagcag ccttggcctc ccaagctgaa gtgatcttcc  4080
cacctcagcc tcctgagtag ttgggattac aggtgagtac caccacgcct ggctcatttt  4140
ggtatttttt gtaaagatgg ggtcttgcca tgttgcccat gcaggtctcc aactcctggc  4200
ccaagtgatc ctcccacctc accctcgcaa aatgttggga ttacaggtgt gagccactgt  4260
gcctggcctt atgtatttat ttaattatga atgaatgaat gagagggagt cttgctctct  4320
cgcccaggct ggagtgcggt ggcacaatct tggctcactg caacctctgc ctcccaggtt  4380
caagcagttc tcctgcctca gcctcccgag taactgggat tataggcgcc tgccaccatg  4440
cccagctaat ttttgtattt ttagtggaga tggggtctca ctatgttggc cacactggtt  4500
ttgaacttct gacctgccca cctcggcttc ttaaagtgtc aggattacag gcatgagcca  4560
ccgcgcctgg cctggccttt tatgttttaa gttgcttcca ctgattctct ttcttgggct  4620
ttgctgccct ccagaactgg ctatggtgta ggatgctgtc cacctgctgc tgcttgtcca  4680
tgaaaacgag ccataaaccc ttttatttgg aaagacttag ttgttgatcg ctatggagaa  4740
agaggggatg gcaagaagta gcaactacag agaatttgca gaacttggtc ttgagccctg  4800
ggtccagaaa cttcttgtgg aaggtgcttg gtgtttgtcc aagctcatga ggataggttt  4860
ctgttggctg tactgccaga tctgtagatg cttttttaag gcttggatga cttgttcaaa  4920
acaacgtttt ggagtacaaa tttggcttgg ggacatcaag accttgttgg gaaacttggg  4980
tttaagatat aatttcttaa actaggatgg tgggaatggg gatgtgaagg gagaatgaat  5040
gtgagaggca ttacagggta aggatggaga ggattcagat tccttaagtg gatttaataa  5100
tcacactgta gctttgaact tcagtgactg gggaaatgtt tgtggtgttt ttggaaataa  5160
gggccagaag gactattggt ttggggaaga agatagtagg gggatatata ggtagacccg  5220
ctagtggggt gctgagattt ggagggcaga gatgtagtgc tcttcactgc tgtagggcag  5280
```

-continued

```
tatcgtcctg tatgtgccat cctctagtgc cctttttca ccatattgta gtaagcccga 5340
gatgttcatt cctttcttca gtactgcatt aaggcttatc tctgcttgtt tctttgtttc 5400
tgtgtttttt tttttttttt aagatggagt tttgcttttg gtgcccaggt tggagtgcaa 5460
tggcgcgatc ttggctcacc gcaacctctg cctcccggtt tcaagcgatt cccctgcctc 5520
agcctcccac gtagctggga ttacgggcat gcgccaccat gcccgactaa ttttgtatct 5580
ttggtagaga tggggtttct ccttgttggt caggctggtc tcaaactcct gacatcaggt 5640
gatctacccg cctcggccgc ccaaagtgct gggattacag gcatgagcca ccacgcccgg 5700
cctatctctg cttatttctg cacagtatta tcagtgagat tggtgttact gctgggctcc 5760
aaagcaatca gacatagtaa agtagattga atatgaaata atttagaggc cttgttccaa 5820
gtgatttgtg ctttgtttaa tttctgtgca tttgtaaata tagcccacag taattcttag 5880
tgaactggaa ccttcaggtt attgcatttt actgatttgg gtactgaaat gtgcttttaa 5940
gaagacatta ggttttctat agtgtagatt gtacactaac aatataattc atatttaaga 6000
atgtctcaaa atttagtatg ctgtgttcag ctaacttaac tttatttgtt tttttgtttt 6060
gttttgtttt tttctttgag atggagtctt gctgtgccac ccaggctgga gtgcagtggc 6120
atgatcttgg ctcactgcaa cttcaacact cctgggttca agtgattctc ctgcctcagc 6180
ctcctgagta gctgggatta caggcacccg ccaccacacc agctaatttt tgtattttta 6240
gtagagatgg agttttgcca cgttggccag gctggtctcg gactcctgag tcaaatgatc 6300
tgcccgcctt ggcctcccac agggctagga ttacagacat gagccactgc gcccggccac 6360
taacttaact ttcattccac aacttccatc ttttatccaa aatctgtgat cagtgaacac 6420
tgtcaccatt aaccattgac atttcagtgt ttggactttt ttttttcttt tcccccttg 6480
tctttgtgga ctctttttta acactcataa agttttaact attgaaaagc acaaagaaac 6540
agtgagtgac tttttggaat ttgtttaccc agtgttcaca taaaaggctt actacattac 6600
aggaaagata ggatgagaaa gggatactag aaaattctaa gtcagggacg ggggtgtgta 6660
ttagaaaaat tctgatcctg gcatgccaga tggccttaca tctcaacttc ttctgtgaaa 6720
ttcctgccaa caaatcatag tgttggaagt acagaagggt ccatgggaac agaatttaag 6780
ggctcccttg gtgatactga actgatcaga tggttctcac ttgttctcag ataacctgca 6840
tactgaatat cacaggaagg gtatagacat catggctatg gttagatatt cttgcacctg 6900
ctgaagctga gaaaattaaa gtcatttttt tttctgtgga aagtagaaaa tcaagctttt 6960
atatgatttc acacagcttt ctattctctc ttctgttgac tctgttaaga gtaacattta 7020
gtggtggaaa ctatttcagg atcacaccca caacactaga gactgtatta atcactcaca 7080
cacacatagg tatagagtaa tcttgaaggg gctgtaggcc agagataatg cttttttgaa 7140
gaattagaga ctagttacca gcacctggta tttgctgttt cctacagacc tgactggaca 7200
gcttagagtc tgctgaggaa ttcagaggat ggccagtaga atgttcttc taccccagag 7260
tatttggtag ggactcagct gctatggaat gccaaaaagg ctttaagttt ctttcactat 7320
tcttaagatt acatgtaatt gttttttgt aagagattat atatattcaa attgaggatg 7380
gctttgagct agacttttcc ttaatttgga accacacagc agatgataca tttatttcca 7440
tctgataagt tacttgatga tgtaaaagac atttgagtta aagatttttg ggaaaaaagc 7500
tgaatgttga gccatttatg ttgtgtactg gttccctatt cacttagaca attttaagtc 7560
tgaaaacaat cttatcatat gcacaagaga tttcatgtag tatttggtaa ttaagttgag 7620
gaattctagc tcaagtcatg ctttttgctg aaataggtgt atatatttag tgcaaaaacc 7680
tgtgttttca aaaaaaatta atgtaataaa agtttcaaca aaatggaagc ctttataacc 7740
atgtttcaaa tgctatacta aacctttcc atttgttatt atattaacct cctcatacat 7800
agccctacta tttttttttt tttttacttt ctattttgaa ataattgtag atttatggga 7860
agttgtgaaa aatagtacag agcccatgtt cccttcacca agtttcacct ggtggtgata 7920
gctcacataa ctatagttta atgtcaagaa ccaggaaatt gtcattgtta caatccataa 7980
ggcttttta gatttcacca gtttcacatg tatttgtgtg tatgtgtgta tataatagta 8040
tgcaatttta tcatgtgtag atctgggtag ccactctaac agtctatagt tctatataca 8100
gaactactcc atcacctcag ggctccccat gctaccgctt tgtagccgca tgcacccttc 8160
caacaaccac taatctgttc tgcatctctg taattttgcc attttgagaa tgttatataa 8220
atggaatcat acagaatgta actttggctt ttttctttta ccataattcc tttgagagcc 8280
atccaaattg ctgcatgcat cagtagttca tttcttttta ctattgagta gtagtccata 8340
gtatggctga accacacaat ttgtttaacc atttacttgt tgaaggacat accagaaggg 8400
tggtttccag ttttttgact attacagata aagctgctat aaacattcat gtatataaat 8460
atttttatat gaattaaagt tttcattttg ggggaataaa tgcccaaatg tttggatcat 8520
ctggtaaatg catgtttggt ttttagagaa actgctgaac tatttatttt ctagaatgac 8580
tatatcctct tgtattccta tcaacaacgt atgagatatc cagtttctct gcatccttgc 8640
tagcatttag tgttaccatt tttttatttg agcggttcta atatgtgtag taatagcctg 8700
ttttgcgtta tattaatcaa taaaaatagc ctcatctaat tttaactttt taattttaaa 8760
atatcttggt ggtattgaac tttctcagtg agaaatatct aaaattgtga cttgaaaggc 8820
tttaatttc aagtttttct ttggttttac tcttagcagt aacattttaa tttttttttgt 8880
ctttgaagta attttcagtg tttcctttac atgttgcttt ttcttagaaa ctagttatta 8940
gcatgaagta gatctttagt ctcgttttct aaaaacataa aaaagtaaaa ctgcgggatt 9000
tatttcaaaa ttgagagtct tgtcttttca tatgaggata ttttatagtc tgttggcttg 9060
gctatatttt agggagtaaa cctgtggcta gtggtttgtt ggtgatggtg gtggtaaagt 9120
tttcttacag aatttttatt tttttttta tttttattt tttatttatt tatttttttt 9180
gagacggagt ctcgctctgt cacccaggct ggagtgcagt ggccggatct cagctcactg 9240
caagctccgc ctcccgggtt catgccattc tcctgcctca gcctcccgag tagctgggac 9300
tacaggcgcc tgccacctcg cccggctaag tttttgtatt tttagtagag acggggtttc 9360
actgtgttac ccaggatggt ctcgatctcc tgacctcgtg atccgcccgt ctcagcctcc 9420
caaagtgctg ggattacagg cttgagccac cgcgcccggc caagaatttt tatacctgaa 9480
tgatacettt agactctata gaatagatac ttgatttcaa atctatccta gaataaattg 9540
tttcatctaa acagctttgt gacctgagaa ttgggactta gtgccttagt tttcccttac 9600
tggccctttg tagtcactgt tttgatttag tcaaagtaac ctaactctta gcactgtcag 9660
gtattgtaca ttcctgccaa agcaagaata ataatacata ggattgtgtt ttaattctat 9720
aattaggtga cttagctaat ttccaggaac ttggacttaa tacagtacta gtgataaggc 9780
ttgaaatttt agtgcctttg ttctttgaag ttattcaccc tttagtttcg tgtttgtttg 9840
gggtgtttat accactgtcc ctaaatatag ctgaaataac ggaggaaaac ccctgtaatg 9900
tcactagcag gatataattt ctgttaatag tttgatgtaa atattttttg acttttaat 9960
tttttatat atatatatat tttctttcat caatatggac tcttactgtg agcataattt 10020
```

-continued

```
taatgtcttt aaagagttgg gttttgttta tttgtttatt ttattttata gaaatgggat  10080
ctcactgggt gcggtggctc acgcctgtaa tcccagtact ttgggaggcc aaggcaggcg  10140
catcacctca ggtcagtgag gttggtcacc agcctgacca acatggagaa accccgtctc  10200
taccaaaaac acaaaattag ctggacgtgg tgacatgcgc ctgtaattcc agctacttgg  10260
gagcctgagg caggagaatc acttgaaccc aggaggtgga ggttgcggtg agtcaagatt  10320
gcaccattgc attccagcct gggcaacaag agtgaaactt tgtctcaaaa aaaaaaaaaa  10380
aaaaagaaag aaagaaagaa agaaagaaat ggggtctcac cattttgatg ggttttgaac  10440
ttgtggtctc aagcagtctt cccacttcag catcccaaag tattgggatt acaggtgtga  10500
gcccatcctg gtttttgtt gttgtcgttg tttgcttgtt ttttgtttgc caccgtaccc  10560
ggctaatttt tgtattttta gtagagacag ggtttcacca tattggccag gctggtcttg  10620
agctcctcac ctcgtgatct tcccacctcg gcctcccaaa gtgctgggat tacaggcgtg  10680
agccactgtg cccagcctat tgttgtttaa ataaaagaat gttgtttaaa taaaataaat  10740
ttattctctt atagtctgga ggccagaact tagaactggt tttcagtcta attttttttt  10800
tcttctttgg gagaagggca tcagaatatt gtgaatatac ttttttgact aaaaaaagtt  10860
ttctctgggc atggtggctc acctggaatt gcctgtaatc ctggtacttt ggaggaggct  10920
gaggcaggtg gatcgcttga gtccaggagt tggagagcag cttgggtgac atggtgaaac  10980
ccagtctcta ccaaaaaaaa aaaaaaaaat tagccaggca tgatggtggc gtgcccttgt  11040
agtcccagct acttgggagg cttagctggg aggatcactt gagaccaaga ggcagaggtt  11100
gcagtgagct aaattcatac cactgcactc cagcctggat gacagagcaa gacctcgtct  11160
gaaaaaaaaa ttttttttt tactagcatg acaaacatct tttcatttca aatatatttc  11220
tttttttttt tttttttgag acggagtctc gctctgtcgc ccaggctgga gtgcagtggc  11280
cggatctcgg ctcactagtt ttttgtattt tttagtagag acggggtttc accgtgttag  11340
ccaggatggt ctcgatctcc tgacctcgtg atccgcccac ctcggcctcc caaagtgctg  11400
ggattacagg cttgagccac cgcgcccggc ctcatttcaa atatatttct ataccatttt  11460
taatatctca ttgcctttag aatgaccttg tattcatagt acatatgtat gtgatattcg  11520
atttatttat ttttcgtttg tcttattttt ggttatattc cattgattta atgtaccata  11580
atttatctta ccaatttctt gctgaccatt ttgtttccag tcttttgttt ttttatcaga  11640
catggattaa gctgaggctt tgtcccagac aacattattt cttttttatc agcaaaatat  11700
gcatgtaatg aaattaaaat taaaaggcaa aaaacgttat cctttatttt cttcttattt  11760
ttgttgagat aataattcac ataccataaa tttaaccctt ttaaagtgta caattcagtg  11820
gttttgtata ttagaaggtt gtaccatcac aactaattcc agaacagttt caagaaactc  11880
tgaacccatt atcactcccc actccctcac acgccctaat cctggcagcc acatagagac  11940
tgtctgtctc tgtgtatttg tctattctgg acctttcata taagtggaat cataacaatt  12000
tgtggccttt tgtgcttggc ttctcaaact tagcacaatg tttgcaaagg ttatctgtgt  12060
cgtagcatgt gtcatacttc attccttttt gtgactgaat attttattgc atatatatgt  12120
cacattttgt ttatccattc acctgtagaa ggatttttag gttgtttcca ttttttagct  12180
gttatgaata ttactgctgt agacgttcat gtacaagttt ttatgtgaat gtgttttcat  12240
ttttcttgggg tatatactta ggtaagaaat tctgggtctt atgttaactc tctgtttaac  12300
attttgagga actgtcaact tgttttttaa agtggctgtg acattttata ttctaccagc  12360
agtgaattaa atttccaatt tctccacata cttgacagca ttttttgttt tgttttttt  12420
tttgttttgt ttttttgag acgaagtctc gctttatcgc ccaggctgga gtgcagtcgc  12480
acgatcttgg ctcactgcaa cctccgcctc ctgggttcaa gtgattcttg tgcctctcag  12540
cctcccaagt agctgagatt acaggcacgt gtcaccacac ctggctaatt tttgtatttt  12600
tttttttttt tgagacggag tctcactctg tcgcccaggc tagagtgcag tggcatgatc  12660
tcaggtcact gcaagctccg cctcccggga tcacaccatt ctcctgcctc agcctcccga  12720
gtagctggga ctacaggcgc ccgccaccac cccgggttaa ttttttttat atatttttag  12780
tagagacggg attttaccgt gttagccagg atggtctcga tctcctgacc tcgtgatctg  12840
cctgccttgg cctcccaaag tgctgggatt acaggcgtga gccactgtac ccggcctaat  12900
ttttgtattt tttttagag acaggatttt gccatgttgg tcaggctggt cttgaactac  12960
tgacttcaag tgatccacct gccttagcct cccaaagtgc tgggattata ggcgtgagcc  13020
actgtgcccg gcctacactt tttaaattat ctgtcttctt tattatagcc aacctagtga  13080
gtatgaagta agtgtctcat ttgtgatttt gattgttagt ggtgactaac aatattgaat  13140
atctttacat gagcttgttg gccatgtaca catctttgga gaaatatcta ttcaaatctt  13200
ttgaccattt taaaattggg ttatttatct ttttattgtt gagctatagg agttctattt  13260
tattttattt tattttattt tattttattt tactgagaca gggtcttgct ttgtcaccca  13320
ggctggagtg tagtgatgcc atcttgactc actgcagcct ctgcccccac cccaggctca  13380
agcaatcctc ccacctcagc atcccacagc tgggaccaca ggcgcatgcc actgtgcctg  13440
gctaattttt tttttttgt atttagtat agacggagcc tcaccatatt gcccaggctg  13500
gtctcaaact actaagctga agcagtctgc ccatctcagc ttcccaaagt gctggaatta  13560
gaggcatgag ccactgtgcc tggtctattt tatttttaag atgagacttt actttgtcac  13620
ccaggttgga gtgcagtagc atgatcatag ttcactgcca ttttgccctc ctgggctcaa  13680
atgatcctcc cggcttatct tactgagtag gtaggactgc aggcatgtcg ctaccacgcc  13740
cagctaaaag agttctttat attctagatc ggggtatcca atcttttgac ttccatgggc  13800
cacattggaa gaaaaattgt cttgggccac acataaaata cactaacagt aatgacagct  13860
gatgagctaa aaaagaatta ccaaaaaatc tcataatgtt ataagaaagt ttacaagttt  13920
gtgttgggcc acattcaaag ccatcgtggg cctcatggct gtgggttgga tgagcttgtt  13980
ctaaatgcta gacccttatc agatggatgg tttgtagcta tttatctcat gctgtggatt  14040
ttttttactt tcttttttt cttttaggtt tttttttctt aaataattca actgattata  14100
agctttaatc gttttgtttt cttgatagtg tcttttaaag cacaaagttt tatttcgatg  14160
gtgtctaatt tgtctgcttt ttctttggtt gcttgtcata tgtaagaaac tgttgctaaa  14220
tccagaatgc tgaagattta cttgtgaact ttgtttcctt ctatgtgttt tatagtttta  14280
gctcttacat ttaggtcttt gatcattttg ggggtttttt tttttttttt ttttttttt  14340
gacagagtcc tgttctgtat cccaggctgg agtgcagtgg tgtgatcttg gctcactgca  14400
ccctctgcct cctcggttca agcaattctc atgcttcagc acccgagtag ctgggattac  14460
aggcatgtac caccaagcct ggctaagttt tgcattttta gtaaagagag agtttcacca  14520
tgtttgtcag gctggtctcg aactcctggg ctcaagcagt cctctaacct tgacctctgc  14580
aagtgctagg attacagggt gtgagctacc gcgcccagtc catttggagt tcatttttaa  14640
aatacggtgt gaggtagagg tcccatttca ttcctttgcc tgtgggtatc cagttgtccc  14700
agaaccattt gttgaaaaga ctgttgtttc tccattgagc aatgttgtga ggccctatct  14760
```

-continued

```
ccataaaaaa aaaaaaaaaa aaaaagaatg cagaaggaag cagtttttgc caattttgta 14820
gtatttactg acaatttgca tatatctgta cattctttag ctatttattt ttcttttgag 14880
ttattgcctt tgttcatttt tcttttggag gtgtttgtct ttttcttatt aatttgtaag 14940
agattttgca aatgtataca atttcttttt tttttttttt tttttttttt tttgagacgg 15000
agtctcgctc tgtcacccag gctggagtgc agtggcgcaa tctcggctca ctgcaagctc 15060
cgcctcctgg gttcacgcca ttctccggcc tcagcctccc gagtagctgg gactacaggc 15120
gcccgcccct gcgcccggct aatttttttct attttttagta gagacggggt ttcaccatgg 15180
tctcgatctc ctgaccttgt gatccgccca cctcggcctc ccaaagtgct gggattacag 15240
gcgtgagcca ccacgcccgg ctaatttctt ttcttgtttg ttttgagata gagttttgct 15300
cttgttgcct aggctggagt gcaatggcat gaccttggct cactgcagcc tctgcctcct 15360
ggtttcaaga gattctcctg cctcgacctt ccgagtagct gggattacag gtgcccacca 15420
ccacacccag ctaatttttt tttttttttt tttttgtatt tttagtagag attcgtttca 15480
tcatgttggc caggctggtc tcaaactcct cacctcaggc gatccaccca ctttggcctc 15540
ccaaagtgct ggaattacag gtgtgagcca ccgtgcctgg acctcccacc ttattttgaa 15600
acaaatttct ttctttttttt ttcttctttt tttgttttga gaccaagtct cgctctgtca 15660
cccaggctgg agtgcagtgg catgatctgt gcttgctgta ccttctgcct cccaggttca 15720
agtgattctc ctgcctcagt ctcctgagta gctgggattg caggcatgta ccaccacacc 15780
tggctaattt ttatattttt agtagagacg gggtttcaac atgttggcca ggctggtctt 15840
gaactcctgg cctcaggtga tccacccgct ttggcctccc aaagtgctgg gattacagac 15900
ttgagccatt gcgcctggcc agtatcacat aatttcatat aaatatttct ttgtgtatct 15960
ttagataagg acttaaaaga aggcataatc ataacaccat tattaatacc taaaagaaat 16020
gaataataaa taattcattt gttgtatcaa atatccaatg ttcatatttc ctcaattgtc 16080
ccataataat ttttaaaagt ttgcttaaat caaaatcgaa acaagattct ttcattgcta 16140
ttgtttgaga tacatttgaa atcttaattt atagatttct ctgccatttc ttttccccca 16200
tatttatttg ttgaagaaat caagtgttgt ttcctatgga ctttcttact atctggattt 16260
tgctggttat attcttctgg cgtcagttta ctatgatccc ttttcccctg tattttctat 16320
aaatttgtaa ttaggtctag agatttgtta agattttgtg gtgttttttt tttttttttt 16380
ccaaaaatgc atcataaatg gtggtgtgta gatatcgcag aagacacgta tcttaatgtc 16440
tttttgtggt attagtagtt attaatgatt actacctata tttattaatt cattatttgg 16500
actataagtt tataatattc tcattctctt gatccttttt ctgttgttag ctgtaatgct 16560
tctaaaagga gaaacctttc ctcttcaagc tacttggttg tcttaagggt tcacttctaa 16620
tagggaaaac gggctaaggg tgaaaaagga aatagttttt aactgaatct gttaatgagc 16680
tgtcacccca ggcaaagaga agcaaggcag gccctaggaa actgaagtgg gtttgggatg 16740
attggtgccc catgcgtgca tgcatgaagg gaagttaatc ctccctgtag tgaactctac 16800
ttggcttttt gtcagtggcc aggactgtca aggaagacct ttgtccaaag tcatacctgg 16860
cctttgcttt tagctcttgg tagctgaagg aaaccaaaac agacctatga cctgcaaact 16920
tctgcttagt agacaaagtt ctcacagcct caattcagta agcaggagta agatgcttgc 16980
tttcccttga agtgaaatgt gaattacatg tttcttcaac ttgtgctaat attctctttt 17040
ttaatattta tttatttatt tatttattga gatggagtct cacactgtcg ccgaggctgg 17100
agtgcagtgg tgcaatctcc gctcactgca acctcagtct cccgagtagc tgggattaca 17160
ggtgcctgcc atcatgcccg gctaattttt tgtattttta gtagagatgg ggtttcacta 17220
tgttggccag gctggaattg aactcctgac ttcgtgatct gcctgcctca gtctcccaaa 17280
gtgctgggat tacaggcgtg agccaccaca cccgggcaac ttgtgctaat attcttaaca 17340
gggtgtgaat cattcctgcc ctcaggctaa cataacccat acagccttcc ttataggaag 17400
atttcctact gggagtgaat ttgtccagtg attcccccaa aatgtccccc aatcaaatat 17460
tttaaaactc agcatttaca tgtaaaaact aacaagcatg gtagcagcag tataaagaaa 17520
cagcagtatg gcccttgtaa gggaaggctc cggaagatga gctgcactca gcctctaggt 17580
cacagctacc ttaggagttt gcagtagttc ctggggaagt cagtagacag gccatctctc 17640
aggcctgggc aagataggga cttttttttt tttttctttt gagatagagt ctcaccctgt 17700
cgtccaggct gaagtgcagt ggcatgatct cggttcacca caacctccac ctcctgggtt 17760
caagtgattc tcctgcctca gcctcctgag tagctgggac tacaggcgcg gacaaccatg 17820
cctggcccat ttttgtagag atggggtttc atcatgttgg ccaagctggt ctcaaactcc 17880
tgacctcagg tgatccaccc ccctcccaaa gtgctgggat tacaggcatg agccactatg 17940
cccagtgttg tttttttttt ttttgaattg tagtgatagg atctcacttt gtttgatggg 18000
ctattcccaa actccaggcc tcaagccgtc ctcccgcctt ggcctcccag aatgctgggg 18060
ttacaggttt gacccactgt gcctggtccc agaattcatg tttttaaaag tcactctgtg 18120
ccaggctcat gcctgtaatc ctaatacttt gggaggctga agcaggagga ttgcttgagc 18180
ccgggagttt gagaccagcc tggacaacat agcaaaaccc taactctaca aaaatacaaa 18240
aactagccag gtgtggtggc atgtgcctgt agtcccggtt gctttggagg ctgaagtgga 18300
aagatcgctt gagtctagga agttgaggtt tcagtgagct gtgattgtgc ctgggcaaca 18360
gagtgagaaa agtcactctg attgtggtgg ggaaagtgga ttaatggaga atggaagctg 18420
ggaaacatgg tggttcttgc taagtcagta tcaagggttc acagatgagg gggctgtttc 18480
ttcctagtaa gggccttggc caaatagtca tggatctttc tctttggaag aagctcctca 18540
atttttcttc cccaaggcat atatggttga tgcttgaaca acacaggctg ggtctgtatg 18600
ggttcactta tatgtggatt ttttttcaac caaacttgga ttaaaaatat agttgtaggc 18660
cagggtcagt gactcatgcc tgtaagccta gcactttggg agcccaaggc aggtggatca 18720
cctgaggtcg ggagtttgag acgagcctgg ccaacatagt gaaaccatgt gcctactaaa 18780
aatacaaaaa atagctgggc ttggtggcgt gcgcttgtaa tcccagctac tcaggaggct 18840
gcagctggag aattgcttga acctgggagg tggaggttgc agtgagccaa cggggtggag 18900
gttgcagtga gctgagattg caccaccaca ctctagcctg tgtgacagag caagactctg 18960
tctcaaaaat aaataaataa aaatacagtg taggccaggt acagtggctc atgcctataa 19020
tcccagaact ttgagaggcc aaggcaggca gatcagttga agccaggagt ttaagaccaa 19080
tctggctaac atggtagaac ccccacttcta ctaaacagaa gtacagaaat taaccaggca 19140
tggtggtaca cgcctgtaat cccagctact tgctaaactg aggcaggaga attgtaatcc 19200
cagctgcttg ggaagcttga ggcaggggaa ttgggaggcg gaggttacag tgagctgtga 19260
tggtgccact ggactccaga ctgggtgaca gagcgagact ctctctccaa gagaaaaaaa 19320
aaaaattgta tttacaggac atgaaacctg cctgtatgat gtgctgactg ggagactaga 19380
gtatgcacag attttggtaa acaaggggat tcctgaaacc aatcccctga gtatatggag 19440
gattgactat atattttaat agaatttatt tattattatt tttagcagtt ttaggtttgt 19500
```

-continued

```
ggaaaaattg agcaggagta catagtttct ctctctccct cacatttccc cgttactaac  19560
gtcttgaaat agtgtggtac atttgttaaa actgaagagc caagtattga tacatcactg  19620
ttaaccaagg tccatagttt agagttcatt cttggtgttg ccgtttctat gagtgttggc  19680
aaatatataa tgacatgtat ctaccattat agtatcatat tgagtagttt cactgcccta  19740
aaaatccccc tcgttctacc ttttcatccc tccctctatc tacctgaacc cctggcatcc  19800
attgatcctt ttactgtctc catagtttta ccttttacag aatgtcaaat agttggaatc  19860
atatagattg gcttctttcc atgttccttc tggcttgata gctcttttct tttctttttt  19920
tttgagacag agtctcgctc tcgcccaggc tggagtgcag tggtgcaatc tcagctcact  19980
gcaaactctc tgcctcctgg gttcaagcaa ttctcctgtc tcagcctccc aagtagcttg  20040
gactacaggt gcctacctcc ctgcctggct aatgtttgta tttttggtag agacggggtt  20100
ttaccatatt ggtcaggctg gtctcaaact cctgtcttca ggtgatccac ccacctcagc  20160
ctcccaaagt gctgcgatta caggtgtgag ccaccctgcc ctgccagctc ttttctctgt  20220
actgctgact aatactctat tgtataggtg tatgagttta ttcaccttct gaaggacatt  20280
ttggttgctc ctaagtttgg gcaattatgc atgaagttac tataaacgtc tgtgtgtagg  20340
tttttgtgtg gtcatgtttt tagctcattt ggataaacac caaggagcac gattgctgga  20400
ttgtatggta agagtatgtt tagttctgta agaaactgcc aaactgtctt tcagggtgac  20460
tgtaccattt tacattccca ccagcaatga atgaagttcc tgtcgctcca catcctcgtt  20520
agcatttggt gttgtcagtg ttttggcttt tcaccattct aatagatgtg tagtgatatc  20580
ttgttttagt ttgcaattct ctagtgatgt atgatgttga gcatcttttc atctgcttat  20640
ttgttgttgt tgttgttgtt gttttttatt gagatggagt ctcgctctat tgcccaggct  20700
ggagtgcagt ggtacaatct tggctcactg caacctctgc ctcccgggtt caagtgattc  20760
tcctgcctca gctccccaag gagctgggtt tacaggcgcc cgccgccatg cccagctaat  20820
ttttgtattt ttagtagaga tggggtttca ccatgttgcc caggctggtc ttgaacttct  20880
gacctcgtga tctgcctgag ctcaagcaat ccgcctgcct cagcctcaca aagtgctggg  20940
tttacaggcg tgagccaccg cgccctgtct tcatctgctt atttgatatg tgtatatgtt  21000
atttggtgga gtgtctgttc tgatcttttg cccattttaa aatcagattg ttttattgtt  21060
tctgcggttc ttttagtttg tttttttgag acaaactctc gctctgtcac ccagtctgga  21120
gtgcagtggc gtgatctcag ctcattgcga cctctgcttc ctgggttcaa gcgattctcg  21180
tgcgttagcc tcccaaatag ctgggattac aagcatgtgc cactgcacct ggctaatttt  21240
tgtatttata gtagggacag ggttttgcca tgctggccag gctggtcttg gactcctggc  21300
cttcagtgat ccacccactt ttgcctccca aagtaatgag attacaggtg tgagccacta  21360
tgcccggctt attgttaagt tttaagagtt ctttgtatgt gtgtattttt tgtgattctt  21420
ttaaagttaa tgcttaataa aataattgta catatttatg ggatgcatgt gatattttga  21480
tacatgcata caatgtggat caaatcaagg taattagagt atcacctcaa acatttttca  21540
tttctttatg ttggaaacat ttcaaatctt ctagctattt tgaaatatat agtaaattat  21600
taactataag tcacctcatt gtgctatcaa acattagaac ttattctttc tacctgactt  21660
tatttttttt acccattaac caaccattct tcatcagctc cccatctccc ctactctttt  21720
tttttttttg agatggagtc gctctgtcac ccaggcggga gtgcagtggc gcgatctggg  21780
ctcactgcaa cttccgcctc ccgggtttaa gcagttctct gcctcagcct cctgagtagc  21840
tgggattaca ggcgaatgcc accatacctg gctaattttt gtatttttag tagagatggg  21900
gtttcaccat cttgtccagg ctggtcttga actcctgacc tcctgatcac ctgcttcggc  21960
ctcccgaagt gctgggatta caggggtgag ccaccacgcc tggcccctct tactctttgc  22020
ttagcctccg atatctatca ttctattctc tacttctatg agatcaactt ttttttagc  22080
tcccacatat gagtaagaca tgtaatattc ctctttccgt gtctgatttc tttgtatatt  22140
ttggataata gtcttttatt agatacgtgt tttgcaaata ttttttccca gtccctgact  22200
tatcttttca ttctcttaag tagtgtcttt tgcagagcac acattttaca ttttagcaca  22260
gtccagttta ccaattcctt ctttcatgga ttttgctttt ggtattgtgt ctaaaaagtc  22320
tttgccaaac cacagtcagc tagagttccc cttaccttac aggattttta agtttttgtt  22380
ttacatttat gtctgtgatt cattttaagt taacttttat gtgaaagatg taagatctat  22440
gtctggaatt tctctttttt tttgagatgc agtctcgctc tgtcgccagg ctagagtgca  22500
gtggcgtgtg atctcggctc actgcaacct ctgactccct ggttcaaatg attctcctgc  22560
ctcagcctcc tgagtagcac acgccaccat gcccagctaa gttttgtttt ttagtagaga  22620
cgggatttca ccatgttgac ctggatggtc ttgatctcct gacctcgtga tccgcccgcc  22680
tcagcctccc aaagtgctgg gattacaggc atgagccacc acgccctgcc gggcttaacc  22740
atttttaagt gtacagttca gtagtgttaa gcacattcac attgcaaaca atctctacaa  22800
gtttttcaaa aaaactgaaa aacttgcaaa actgaaactt tatacccact aagtggtaac  22860
tccccattct agtggttacc ctagcccctg gtaaccacca ttctcctttc tgtttctatg  22920
aatttgacta ctctgggaac cttagataag ggaaatcata cagttcttgt ttttttgtgg  22980
ctagcttctt tcacagcatg atgtctaagg ttcatcccca tagtaccatg tgatcctaat  23040
gtttttaaac ctccacagca acactttcaa gttagatttc acattttaca ggtgagaaaa  23100
tggagactca aaaagaaaaa gcaattgtcc ataggtagtg tcatgggttg acactagctt  23160
tgaaggttgg tccccacctc caaagacatg cccaagtccc aagtcccagt accgtgaatg  23220
tggtgttatg tggaaatagg tctttgcaga tgtaattaag ttatggatct cgatatgaaa  23280
tcttcctgag tttggggtgg actctaaatt ttacgactga tgtcctcata agagaaggga  23340
gggggaggtc aggcgcagtg gctcacacct gtaatcccag cactttggga ggctgaggcg  23400
ggcagatcac ctgaggtcgg gagtttgagn nnnnnnnnnn nnnnnnnnnn nnnnnnnnnn  23460
nnnnnnnnnn nnnnnnnnnn nnnnnnnnnn nnnnnnnnnn nnnnnnnnnn nnnnnnnnnn  23520
nnnnnnnnnn nnnnnnnnnn nnnnnnnnnn nnnnnnnnnn nnnnnnnnnn nnnnnnnnnn  23580
nnnnnnnnnn nnnnnnnnnn nnnnnnnnnn nnnnnnnnnn nnnnnnnnnn nnnnnnnnnn  23640
nnnnnnnnnn nnnnnnnnnn nnnnnnnnnn nnnnnnnnnn nnnnnnnnnn nnnnnnnnnn  23700
nnnnnnnnnn nnnnnnnnnn nnnnnnnnnn nnnnnnnnnn nnnnnnnnnn nnnnnnnnnn  23760
nnnnnnnnnn nnnnnnnnnn nnnnnnnnnn nnnnnnnnnn nnnnnnnnnn nnnnnnnnnn  23820
nnnnnnnnnn nnnnnnnnnn nnnnnnnnnn nnnnnnnnnn nnnnnnnnnn nnnnnnnnnn  23880
nnnnnnnnnn nnnnnnnnnn nnnnnnnnnn nnnnnnnnnn nnnnnnnnnn nnnnnnnnnn  23940
nnnnnnnnnn nnnnnnnnnn nnnnnnnnnn nnnnnnnnnn nnnnnnnnnn nnnnnnnnnn  24000
nnnnnnnnnn nnnnnnnnnn nnnnnnnnnn nnnnnnnnnn nnnnnnnnnn nnnnnnnnnn  24060
nnnnnnnnnn nnnnnnnnnn nnnnnnnnnn nnnnnnnnnn nnnnnnnnnn nnnnnnnnnn  24120
nnnnnnnnnn nnnnnnnnnn nnnnnnnnnn nnnnnnnnnn nnnnnnnnnn nnnnnnnnnn  24180
nnnnnnnnnn nnnnnnnnnn nnnnnnnnnn nnnnnnnnnn nnnnnnnnnn nnnnnnnnnn  24240
```

-continued

```
nnnnnnnnnn nnnnnnnnnn nnnnnnnnnn nnnnnnnnnn nnnnnnnnnn nnnnnnnnnn  24300
nnnnnnnnnn nnnnnnnnnn nnnnnnnnnn nnnnnnnnnn nnnnnnnnnn nnnnnnnnnn  24360
nnnnnnnnnn nnnnnnnnnn nnnnnnnnnn nnnnnnnnnn nnnnnnnnnn nnnnnnnnnn  24420
nnnnnnnnnn nnnnnnnnnn nnnnnnnnnn nnnnnnnnnn nnnnnnnnnn nnnnnnnnnn  24480
nnnnnnnnnn nnnnnnnnnn nnnnnnnnnn nnnnnnnnnn nnnnnnnnnn nnnnnnnnnn  24540
nnnnnnnnnn nnnnnnnnnn nnnnnnnnnn nnnnnnnnnn nnnnnnnnnn nnnnnnnnnn  24600
nnnnnnnnnn nnnnnnnnnn nnnnnnnnnn nnnnnnnnnn nnnnnnnnnn nnnnnnnnnn  24660
nnnnnnnnnn nnnnnnnnnn nnnnnnnnnn nnnnnnnnnn nnnnnnnnnn nnnnnnnnnn  24720
nnnnnnnnnn nnnnnnnnnn nnnnnnnnnn nnnnnnnnnn nnnnnnnnnn nnnnnnnnnn  24780
nnnnnnnnnn nnnnnnnnnn nnnnnnnnng atggagtctt gctctgtcac ccaggctgga  24840
gtgcagtggt gcaatctcat ctcactgcaa cctccacctc ctgggttcaa gcgattcttc  24900
tccctcagcc tcctgagcag ctggagctac aggcatgcgc caccacgctc agctaatttt  24960
tgtatttttt gtagagatgg agtttcacca tattggccag gctggtctca aactcctgac  25020
ctcaagtgat ccacccacct tggcctccct aagtgttggg attacatcca tgagccgctg  25080
cgcccggcct ataattcttt atgtacattg ttagattcag tttgctagta ttttatttag  25140
catttgtctg tgttcatgag aggtattgtt ctgtagtttt ctttggtttc ttttctgtct  25200
agtttagggt aatgctggcc tcatagaata ggttaggaag tacttcctct gcttctgttt  25260
ctgaaagaga attgagataa tatctttttt tttgagatgg aatcttgctc tgtcatctag  25320
gctggagtat agtggtgcca tcttggctca ctgcaacctc tgcctcccag gttcaagtgc  25380
ttctcctgcc tcagtctcct gagtaggtgg aattacaggc atgcaccacc atgcctggct  25440
aatttttgta tttttagtag agatggggtt tcactgtgtg ggccaggctg gccttgaact  25500
tctgatctca ggtgatccgc ctgccttgtc ctcccaatgt gctaggatta caggcatgag  25560
tcactgcgcc tggcctgaga taatatctaa aacagtttgg tagaattcac cagtgaaccc  25620
atctgggcct ggtgcctttt gctttagaag attattgatt attgattcaa tttccttaat  25680
agataaaggt acattgagat tgtcttttct tcttgggtaa gttttaatac attgtgtctt  25740
tcaagaaatt gttccatttc atctaggtta tcaaatttgt ggattagagt ccttcataat  25800
atttctttgt tttgcttttg atgtccacag gtttagaagt gatggccctt tttcattttt  25860
tctattagca atttgtgtct ttgccttttt tttttcttc ttaatctggc tagaagctta  25920
tcaattttgt tgatcttttc aaagaaccag tttttggttt cactgatttt tctctgttaa  25980
ttttgttttc agtttaattg atttctgttg taattggttt tcttctgctc actttggatt  26040
ttttttagt tttcctagaa aactaagttt ttaagtgaaa actgagatta ttgattttta  26100
gatcttttt gtaatgttta tagttaatgc tatacaattt cctgtaagca ctgctttctc  26160
tgtatcttac aaattttgat aagtcatatt ttcattttca tttagttaga catatctctt  26220
gagacttctt tgatccatct gttatttaga agtgtggtgt ttaatctcca agtatgtatt  26280
ttgggatttt ctggctatct ttctgctatt gatttctagt ttaattacat gtggtcttag  26340
agcatacctt gtttgctttc tattcttttc aatttgttaa ggtgttcttt gtggctcaga  26400
agttggtcta cttttttttt tttttttttt tttttaaaga aaaactggct agatgcagtg  26460
gcttatgcct gtactcccag cactttggga ggcctaaatg ggaggatcac ttgaggtcag  26520
gagtttgaga ccagcctggg caaaattttt aaaagattag ttgggtatgg tggcatatac  26580
ctgtgtatgg ctgaagtggg aggattgctt gagccctgga ggttgagact acattgaact  26640
atgatcacat cactgtactt cagcctgggc aacagagtga aactttgttc tctcttgaaa  26700
agaaaaaaat agttgatgac ataaagttca ttcatctttt ttgtatgtga cttcaaaata  26760
actactgatg gttaaaaaaa aaatcagaat gatgcagccc aagtgtccat caatggatga  26820
atagataaac aatatgtggt gtgtgaatac aatggactac tattattcag ccttaaaaaa  26880
taagaaaatt ctgacactgc tgtaacatgg atgaaccttc agctcgttat gctaaatgaa  26940
aaaaaccaga cgcaaaagga caaatattgc atgattgcac ttatatgagg tgtctggagt  27000
ataaaagtca tagaaacagt aattcaataa ttagaataat gattgccagg ggctctgggg  27060
aggagggaat gaggaattca tgtttaatgc atacagagtt tcatttggaa aagattaaaa  27120
agttacggag gtggatggtg gtgagggttg cacaacagtg tgaatgtact taataccact  27180
gaattgtaca cttaaaaatg attaaaatgg tacattttat gttacatata ttttacaaca  27240
acttttacag atggaaaaaa tttattaaaa aacatcagga tggtgttgac agtgaaaagg  27300
ttaaagagtt actttaaaaa tttactttat tccggccagg tgccgtgact cacacctgta  27360
atcccagcat tttgggaggc cgaggtggac agatcacctg aggtcgggag ttcgagacca  27420
gcctgaccaa catggagaaa ccccatctct actaaaaata caaaattagc cgggcgtggt  27480
ggtgcatgcc tgcagtccca gctactcggg aggctgaggc aggagaattg cttgaactcg  27540
agtggcggag gttgcagtga gccaagatct cgccattaca ctccagcctg ggcaacaaga  27600
gcgcaactcc atctcaaaaa aaaaaatttt ttttaatttt attccaaata tttatattta  27660
ctttggggct tatgtgacca gtttaatttt catttgtaat tgacttgata gaatacacta  27720
tgttcagtta agattcctta tggtgtgatg aggaatagga attttatgta agtaagccca  27780
aaattgtatc agattaatct gatatttgca gaagatattc atgcattaat gtaaggacca  27840
ctctgcttat tcatttgact gatttgtagc aacatggtta gaaatcatca aggtgtttga  27900
gatcaaagga tcatcagagg tcatttactc taatcctttc tttaaaaaat taataacttg  27960
agcctcagag aagttaaatg atattaccaa gttctgctgt tagtatagtg actttatctt  28020
tacctgaagc cagggcttct tagccctagt ctgtaatgtg tcctagtatg cctgtggaat  28080
ctggtcctat cagcccaagt ctgttaaatc aaataaaacc agggcttggt gcttcacctt  28140
gtcttctacc ataccactgg gtttcctgtg gaccatgcag ataacgatga tgggctcagt  28200
tggcttgata gtgataactc ctaaagcagc tgcttctaag tgtggttctc aatctgagga  28260
agttaaaaaa aattttagtg actagaaccc acttctcagc tactcttact aaataaatct  28320
gtaggggagt gatagtttc aattttttt tttttttttt ttttttgag atggagtctc  28380
actctgttgc ccaggctgga gtgcaatggt gcgatctcag ctccctgcaa cctctgcctc  28440
ccagcctcaa gcgattcttc tgcctcaacc tcctgagtag ctgggattac aggtgcgtgc  28500
caccatgcct ggctaatttt tgtattttta gtagagatgg ggtttcaccg tgttggtcag  28560
gctggtctcg agctcctaac cttgtgatct gcctgcctca gcctcccaaa gtgctgggat  28620
tacaggcatg agccactgcg cccggccttc acatattttt tgaaataata ggccagttgc  28680
ggtggttcgt gcctgtaatc tcagcacttt gggaggccga ggtgggtggg tcacttgagg  28740
ccaagaattc aaggccactc tggccaacgt ggtgaaaccc tgtttctact gaaaatacaa  28800
aaaattagcc gggtatgatg gcatgtgctt gtggtcccag ctactctgga agctgaagcg  28860
tgagaatcgc tttaacttag gaggcagagg ttgcagtgag gcgagattgc gcccctgcgc  28920
tccagcctgg gtgacagagc aagactccat ctcatttaaa aaaaaaaaaa aaaaatcata  28980
```

```
ggcagtaaag gttgagaact gctgcccaaa ggacctatta aactatagat tcccaaacct  29040
ggccaattat caaaatccct caagaagggg caatggggtc taagggaccc cactggaaga  29100
gattagtagt ccaagagtga gatgaactgt tggaagtcct cagacttcca aactattaga  29160
atagttttgc ttcctcaaaa tagagtagtt ttgcttcctc actaattttt ctgtattgat  29220
tagaaccgta acaagtgaat taaacaacta caaaatagtt atgtgggcaa cagacattat  29280
tgtaatgaag tgaagtttgg ctcaggcctt ggaacacaat tgcgttttgg attaaaagta  29340
aaaatattta ttaaatcatg tgagatttatg tgtaagtttt aaaaaattgg tcttatacaa  29400
aagtgttggg ggtttttttt tttttttttg gctgaatttg tttttaagca agacagaata  29460
tttatattgt tggagagtca cagaggaggt gtgtttgtgg atttaaatgt ggagacagtg  29520
tgccttgagt gccctttatc agtctgattc gagccactga taatcatgga tttgaactac  29580
cgccccccac cccctgcgcc tagatagggt ctccctctgt tgcctaggct gcggtgcagt  29640
ggtgggatct cggctcgctg caacctctgg cttagcctct tggagtagct gggactacag  29700
gcacacaaca ccatacccag ctattgtttt ttttgtttgt tttctttgtt tttttttttt  29760
tttttttttt atagagacag ggtttcacca tgttgctcag gctggtcttg aactcctgag  29820
ctcaagcaac ccacctgtct cggccttcca gagtgctggg attacaaggc ctgagctacc  29880
atgcccagct ttcacttcat ttaaaaacca tagtttttaa aatccacagt cctactgacg  29940
aacacagagg ttgtttccag tgttttcatt tgcagtattg cagtgattgt ttttgcacat  30000
gcctccttat gcacatgtgc tgtggcttct gggacagaga atggacatat taagtgtttt  30060
attgatcctg ctaaattgtc cttcagccaa actgctgcag aggtgataga gatgaggtgg  30120
gtactcagga gaattgtgcc cagtgcttgt gtgctggttg ctgacctgga aacattttat  30180
taaaaatgct cgattaggtt agtgatgtaa agatgattac caggtgatag taaccagaat  30240
aattgtgtca aaacatcaag aattatcaag agatgccagg catggtggct cacgcctgta  30300
atcgcagcac tttaggaggc caaggtgggc agattgcttg agctcaggag ttcaagacca  30360
gcctgggcaa catggtgaaa ccctgtctct accaaaaata caaaaatttg ctggatgcag  30420
tggtatgtgc atgtggtctc agctattcag taggctgaga cgggatgatc acttgagcct  30480
ggaaggcaga ggttgcagtg agccgagaca atactgcagc ccgggcaaca gagtgaaacc  30540
ctgccttaaa aaaaaaagag aaaaagaatc atcaagagaa aacttaattt gatgtgttct  30600
gtgttttctt tggtgcttcc tgtcagtgtt agaaactgta ggttatatat ttaataattt  30660
ttctcctgta tttgttcaac ttgactataa aatattaact ccaaatgcct agaatttcaa  30720
aacacctctt cattataaag tatcagctat ttctgagtcc ccttaagctc atagtattgt  30780
gtcattgtaa aagatctgtt gtgaaaaata atttttgtca acatgaaagg tcttaatgtg  30840
tctcccagtt tacattttac atggtctttt ccgtgtattt ttatagttga catatatagc  30900
ttttttgta aatatacttt cctatatgaa catgccaagg tttacttaag cattctctta  30960
ttcttggaca tctaaattgc ttcttatttt ctattgtaaa taaagtgcta gaagcttcct  31020
tcctgaaaag ttatttactg ttcagctagt atttccatct gtgttcctca aaataagatt  31080
actgagattc atgtatgttg ccagaaagat tgtgaggttt aacagtgaat gaggaaaact  31140
tttaacactt aaggtctctc aagtacagca agttttatca ttttactttt tttttgagat  31200
aaggtcttgc taagttgcct aggccagtct caaactgctg ggctcaagca atccttctgc  31260
ttcagactcc ggagtagctg ggattatagg tgtgcagcac cacacccggc tttcttgtat  31320
tattattatt attatttatt tatttatttt tgaggtggag tttcactctt gtcacccagg  31380
ctgtagtgca atgacccgat gtcggctcac tgcagcctcc atctcccagg ttcaaatgat  31440
tctcctgcct cagcctccca agtagctggg attataggca tgcgccacca cacccaccta  31500
atttttctat ttttagtaga gacagggttc ctccatgttg gtcaggctgg tctcgaactc  31560
ccgacctcaa gtgatatacc cgcctgagcc tcccaaagtg ctgggattac aggtgtgtgc  31620
caccgcgcct gtccgctttc ttgtattatt tttatcttgc tgtagtggtt gtaggatttt  31680
tgcctggtgt gttcattgga gtgtgtgtgt gtgtgtgtgt gtgtgtgtgt gtgtgtgtgt  31740
gtgttttgag atgtatgact gtgttggttg tgttgtcatg ctttgaaggt tcattcatgt  31800
gctcatctat ttttctcatt atacttagtc acttaaaaac ctcttttatt tggatttcta  31860
atttttacag ttcctgtttt attaatcacc ttcttatctg aaagtgaagt attgaattag  31920
aaatttgtgt gtccctgatc agaagatcac gtacacagga acaagataag ttgagggatt  31980
tagcagttcc agaaatgggc atttgtgtct tccagtggag aagcatctgc aaaagaattg  32040
tgcagatttg gccgggcacg gtagctcatg cctgtaatcc cagcactttg ggaggccgag  32100
gcgggcagat cacctgacgt caggagtttg agaccagcct ggccaacatg gtgaaacccc  32160
gtctccacta aaaatacaaa attagccagg cgtggtggcg ggcgcctgta atcccagctg  32220
cttgggagga tgaggcagga aaatcacttg aacccatgat gcggtggttg cagtgagcca  32280
agatcgcacc attgcacacc attgcactcc agcctgggca acagagtgag actccatctc  32340
aaaagaaaaa aaaaaaaaat catgcagatc tatttaactt tccataaagt gagacagaac  32400
tccgtaagtt agggtaaatt taaggacatg taatgtgctc attatgttat taggaaatta  32460
atggtgaaaa gggtgtttg gcctcgtgtg gcttcttgaa gatgacctgt gaaaacagca  32520
aggcctggaa gggaactgaa ttgggcagat gcagatttgt ggactctagt gaactatgga  32580
gaaacaatta ggactccagg atgagatctt cttaggttgg tgcagaagta attacagttt  32640
tggactgtga attttaaatc attataacta ggcttaaaca catctttatt aatcaaaata  32700
ggaaccatta cagtcaacac attttcacca acaagaaata agtttgtttc ttcctgcagc  32760
acaaaaatcc gtgcttcagg attcaacaaa ctgttggaaa gcatttctg catcctgctg  32820
gttgtggaaa tgttttccct gcaaaaagtt gttgagatgc ttcaagaagt ggtagttggt  32880
tggcaagagg tcagatgagt atggtgaatg aagcaaaatt ttgtagccca attcattcaa  32940
cttttgaaac gttgtgtgac gtgaggccaa acgttgtcat ggagaagaat tgggcccttt  33000
ctgttgacca atgccggctg caggtgtagc agtttccgga gcatctcatt gatttgctaa  33060
gcatacttct cagaggtaat ggttttgcca ggattcagaa agccgtactg gatcagacca  33120
gcagcagacc agcagcagac caccaaacag tgaccatgac cttttttttt tttggtgcaa  33180
atttggcttt gggaagtgtt ttagagctgc ttcttggtcc agccactgaa ctggtcatcg  33240
ccagttgttg tataaaatct actttttgtc gcacatcaca atccaattga gaaatggttc  33300
gttgttgtgt agaataagag aagacaacac ttcaaagtga tgattttttt ttttaaattt  33360
ttgctcagct cctgaggcac ctacttttca agctttaaat aagtagtgac cctgggattc  33420
ctagatccct tgtgggtcct gatgtaatgt ggtctgcaga tgttttcagt attcataaag  33480
gtgaacaatt tgcctgttaa ctaaaatatg aagttgtgtt ttgggtttgt gtgggtcatc  33540
cattatcata acgtctgagt cttcttttta ttgacttaga gtcttccagt cctcttattt  33600
tgcttggtgg tagcatgtac aagatagaag tttaggcaca ataatctatt cagtggctgt  33660
aatagcagct tgtcctgcct ggtttttttt gtttttgttt ttttgtaata gcattgagga  33720
```

```
gatataattc acccatttaa agcaggtgaa ttatatattt tatgttttaa tgtattccta  33780
gagttgtgca accatcacca gagtaagtta tagaacattt tcatcaaccc aaaaagaaac  33840
tttgttttca ttaatcgttc ctcctcattt ctcccctaaa ctcccagcac taggcaacca  33900
tcagaatact ttttgtctcc acagatttga ctgttttgga catttcatat taatggaatg  33960
tacgatacag tagtataata cattaatttt ggaaggccaa agttaatggc cttcgatgtc  34020
tcccttttt cacttagagt aatgtcttcc aggtccatct gtgttgtagc ctgtatcatt  34080
actttatcct ttatgtggct gagtaatatt ccattgtatg gttgtaccat gttttgttta  34140
ttcatcagct gatggacatt taggttgttt tccattgact attaagaata atgctgccat  34200
catgcttgag tttttttttt tttattttag gggtgggtgg tgggcagagg gcacagtctc  34260
gctctgttac gcaggctggc gtgcagtggt gcgatctcgg ctcaccgcag cctcctctac  34320
cccctgggtt ctagtgattc ttgtgcctca ggctcctgag tattatgctg cagtttttat  34380
gcgagcatac attttcagtt cttttgggtc aatatctagg agtatcccca cttttggatc  34440
tgagtgttaa ttgagcctgt tgtgttctca cattccctgt acttacatgg aaatagtgct  34500
ttgcctaaaa agaaaaacaa aagacctaat tgcgcaggcg agtgagagag aaagagagag  34560
agagagaaag agagagagag agagagagag agagagagag agagacacgc tagggttatt  34620
tccaccctga tactctttgt gtagtcttgg tatgactagc aaagaagcaa gctccaagtt  34680
gtaatttgct tccaagtttc tggcttctgt gggaatttct gcatcttagt aatgacaatt  34740
ttcagttact tgcagtaagt aaattatcag ccagtcttac tctgtattac tagtctagga  34800
ggagtttact tgtatattga gagaaatgct gcagctttta ccttacttct aatggggatt  34860
aatgcttact taacttaccg tttcggaggc aaataaaaag tgtaggacca attatggtct  34920
tgaagtgaga gagaagtctg gctagtgaat ggtgattggc aactccagtt gactgttcat  34980
ggcatcttag atctgtgagg agagaggagg gaaggaaagt tcaagctggt ctttatggta  35040
agttctggaa catttccctg tgtcagtggg tcatctgttc attcactgtg taaaatggct  35100
gaggaaagtt ttcattttca tacttcttca ttgtgtaaac ctttgatttt tagtgatttc  35160
agagtttgtt tttataatta tttaaacatg tgaagaggat acagagtaac atatcgaacc  35220
tctggttatc ttccactggg atttgacata tttgagttcc ttttcttcct tcttccttcc  35280
ctccctccct ctctcttttc ttaaggaatg caactactca gattcacctg cataccgttg  35340
gcatacctct cacttcctca gaggtgacca gtcctcagag caaatgtgtg ccctttccat  35400
ccgcgctttt atgctctcat ctatgtttac atctattagt acactattgt ctatattttt  35460
aaacattaca taaatggtgt aatttttact tttaattctg tagtggtatt tctcaaatta  35520
agttctgcat aaaacatttt tatagatatc cagtgttagc ttaacgtttt tcttattgtg  35580
gtaaaatata cataagataa aatttaccat ttttgccatt tttaagtata caagtcagca  35640
gcattaagta cattcacagt gtagtataac catcaccatt gtccattgct ggaacttttc  35700
ctcatcctaa acagaaactc tatactcatt aaacaatagt ttatcactcc ttccctgcaa  35760
ctagatgctg gcagtcacca ttctactttc tgtctctatc aatttgcctg ttccatctaa  35820
gtggaatcct acatatttgt cgctttgttt ctggcttttt ttttcttctt gtgatgcttt  35880
gttttaatta tgtttctggc tttcttcatc tagcaggctg attccaaggt tcgtccatgt  35940
ggtagcttgt atcactttaa ttcttttaga gataattaat attatgttgt ctgtatatgc  36000
cacattttgt tttttcattc aaccttgatg gacatttgga ttgtttcccc cctttaacta  36060
ttgtgaataa tactgctatg aacattgatg gccaaatatt tgtttgaatc tctgatttca  36120
gttcttttgg ttctatacct aggagtggaa ttgctggatc atatgataat tctatgttta  36180
actctttgag ggatggccag acttttccac catagctaaa tcattttacc ttcccacaag  36240
caaagttcaa gggctctagt ctctccccat catgtccttt gcactttttt tttttttttt  36300
ttgaggcaga gtctcactct gttgcccagg ctggagagta gtggcacgat ctttcctgac  36360
ctcaagtggc ccctgctttg gcctcccaaa gtgctaggat tataggtgtg ggccactgca  36420
ctctgccaat ttttaaattt taattttcat ttatttttcg ttttttcatt tttagttttt  36480
tttatttttt gaagggataa ggtctcattt tgttgcccag gctggtcttg aactcctgac  36540
ttcaagcaat cctcctacct cggcctctca gagtgctgag attgtaggtg taagcccctg  36600
cacctggcct ttactctctt gatagtgtcc tttgatgcac aaaagctttc aattttgatg  36660
aagtctattt tttctcttgt tacctgtaca tttggtgtca tatatctaag agaccattgc  36720
caaatgcaat gtcgtgaagc tttccctcag tgttttcttt ccatagtttt atgattttag  36780
ctcctaagtt taggtctttg atccattttg agttaatttt tgtatacagt ttaagagtca  36840
gacttgagac tctgggcgca gtggctcact tctgtaatcc cagtactttg ggaggccgag  36900
gtgggtggat cacctgaggt caggagtttg agaccagcct ggccaacatg ccaaaacccc  36960
gtctctagta aaaatacaat aattagccag gcatggtgat gcatacctgt ggtcccagct  37020
actcgggagg ctgggcagga gaatcgcttg aacccgggag gtggtggttg cagtgagctg  37080
agattgtgcc actgcactct agcctgggcg acaaaagcga gtctccatct ggggaaaaaa  37140
caaaaaaaaa gtcaaacttg agtcttttgc ctatggatat ccagttttcc catcactatt  37200
tgttgaaaag actatccttt ctcaactgtg aatggtcttg gtatcctagc tgaagttatt  37260
tttattacta tgttacttag gaatgcacat aaggccgggc acagtggctc atgcttgtaa  37320
ttgcagcact ttaggaggtc aaggtgggag gattccctga gccgaggagt ttgagaccag  37380
cctgggcaat atagcagcaa gaccccatct ctatatttta aaaaaagaag aagaaaaaaa  37440
aaacccactc tgacacataa ttatttaaac ttgtatgcat tcttttcttt ctttattttt  37500
aaaaaattga gatagcagct tactctgttg cccaggctgg tctcgaactc ctgggctcaa  37560
gcagttcctc ttaccttggc ctgaagtgct gagatgacag gtgtgagcca ctacatctgg  37620
cctgcttaca gattataaaa agaaaataag tttacaaatt aaagacagat aaaatgacag  37680
aatcagtaaa attaaaattt cttttatgga gctgatgatg tttatcccaa ttggtcctct  37740
cattgtgaat atggtattgt tgctgtggca gatttggagg ctttggcaat ggcttctatt  37800
accttgccat gaggtaactc agttccctca ttacttttct ctgagaactg taaaaccttg  37860
gaggggtgcc ctctgccctt cgcttggcat gtgtattatg cggggatcag gtcttactct  37920
gttcttgatt gttagtacaa acgagttaaa atcctgttgt ttggccttag cctgatggta  37980
aacacaacag cacacatggg ctgtgaaatc cctgggcagc tctgtgtttc tagggaagca  38040
tctcgatgat ccagaacagg cttatactga tgttttagtg taattttgaa atgaaaacac  38100
tgcatttaaa aaattctcat agagaatgta tagacctgga gaagtgttag cagacccagt  38160
ttaagacatg tctcaatatt acggaacatt gctttattcc ctgtcctgct tgtacattta  38220
attttttcac ccactttaa acaacttggg tactgtggcc tgtgcctgta ttcccagcta  38280
ctagggaggc tgaggcagga agattgcttg agcacaggac ttcgagggct atagtgagct  38340
gtgtttgtgc ctgtgaatag ccattgtgct ccagcctggg caacatagca agaccctgat  38400
accctgggtt tttaaaaaac aaaacaagat acatgctgac atttctagtt tggcaggcag  38460
```

-continued

```
agcttgttct gctccccacc ctccctttc ctatagtaac catttatagg acatctcact  38520
gttgtctact ctgtgttgcc tctgcttccc tacgtggtag atctaggaat cttaggattt  38580
cttagtttta gctggtgatc catatatttt tcttaattcc attgtaactt cagcttttct  38640
tattgcttgt aagaaggctg tttccattga atacaaacaa aataaaagct tttatttgta  38700
atcttagaga taggatgttt gtatttaaaa ataattgtgc tgtcaaaatt ctgtcaagtt  38760
ggcttctacc atattagttt tttttttttt ttatgtgatt tatatgaccc tggagtacct  38820
tgtcttctca ctgttaaatt ctcaactgag ttgtccctat ttaaagtgtg agactgtgcc  38880
agtttgattt taaaatattg caagtgcgtt atggcaagat aaagctgcaa agaaagaacc  38940
ttcatgttcc tttgattata aatgcttttg gcacttgttt ctactggaag ataacttttt  39000
cctgatgtgt ttttgaggaa agaacctcca acgctctaga caggtctggg ggcaaatgac  39060
taaaacatca actgaggccc tgggctgtct ccatgaggat atcccctcta ttgtctctga  39120
aatgtcccag catgtggtgc atttcttgtt agtgtggact cctctgtata taacacccat  39180
tatttatgtt ctgtgcataa catgaaatag tgccctaatg caattccagg atgtaattca  39240
acatttctat aaaaatacaa tgtttttgta catttgcatc aaacaataac cagataatta  39300
tatttgttaa gaaaatagta tttttggctg ggtttgatag ctcacgtaat cccagcactt  39360
tgggaggctg aggcgggtgg atcacttgag gtcaggagtt caagaccagc ctggccaaca  39420
tggtgaaacc ccatctctac taaaaatgca aaattagcca ggcatagtgg tgcatgcctg  39480
taatcctggc tgctcaggag actgaggcag gagaattgct tgaactcagg aaggggagat  39540
tgcagtgagc tgagattgtg ccactgctct gtagcctagg caacagagtg agactctgtt  39600
tcaaaaaaaa gaaaaaagaa agaaagaaag aaaatagtat ttttggtatt tgttttcaca  39660
aactagagca tttatgtgaa ataacattgc tagtattgat attataccat agtataatac  39720
ttagttcttc aaatgatgta tctctgctga tcagctacat gatatctacg tgagttgttg  39780
cgtgtttttt ctctttttttt aaagagcagt gcatttttga atgcttttga aaaattgcag  39840
taaaatacat aaacgtaaca tttaccttgt aaccatttta attggtacaa ttcagtgaca  39900
ttaagtacag tcccagtgtt gtgcaaccac tgttactgtc tagtttcaga atgttttagc  39960
tccaaatggg taccctgtac ctgttgaaca ttcagtccta gtggcccaat aatcttcttt  40020
atgtctgtat agatttgcct gttctgcatg ttttatataa atggaatcat gtcttttttg  40080
tctggcttct tttacttagc atagtatttt caaggttcat ctacgttgca gcatgtttca  40140
atacttcgtt ccttttttatg tccattatga atataccaca tttcgttaat gacagttctt  40200
tggggtagct acattttaaa acattatagt aaaatacaca tggcatacga tttactatct  40260
taaccacgta agcctgcagt tcagtggcat taaatacatt cacattattg tacaattatc  40320
accaccatct gtttccagaa atttttcatc tcctccaatt gaaactctgt atacattaaa  40380
catgaactct ccattctccc cttcctccag cccttagcag ccaccattct acatttctat  40440
ctttctgaca gattttacta ctctaggtac ctgacataag ttaaatcaac cagtatttat  40500
ccttttgtga ccagcttatt tcattagctt aatgtcctca agattcatcc atgttgtagc  40560
atatatcaga attactttcc ttttaaggtt gaataatatt ccattgtatg tatatgtcac  40620
aattcgtttc tccatttatc catcactgga catttgggtt gcttccacgt atcgcctatc  40680
ttgagtcatg ttgctatagc tgtacgagta tctatttgag tccccgctat caattctttg  40740
agtatatgcc cagaagtgga attgctggat catatggtaa ttccgtgtct ggtgtttttg  40800
aggaactgcc atgctgtttt ccacacagct gtatcattat atgttccctc cggcaatgta  40860
tgagggctct aagttcttca catctttgct aacacttagt atttttttttt ttatggaata  40920
gccatcctaa tggctacttt aaaaatatat ttaactttat ttatttattt ttaaattttt  40980
ttatagagat gccatcttac tatgttgccc aggctggtca tgaactcctg ggctcaagca  41040
atcctcctgc ctcagcctcc caaagtgttc agattacagg aatgagccac catgcccagc  41100
ccaaatttaa atatgtaact aaacacatag cagctaacac caagccttta aaaatatcat  41160
taataggctg ggtgcagtgg ctcatgcctg taatcccagc actttgggag gccgaggtgg  41220
gcagatcacc tgaggttggg agttcaagac cagcctgacc aacatggaga aaccctgtct  41280
ctactactaa aagtacaaaa ttagctgggc atggtggcac atgcctgtaa tcccagctac  41340
tagggaggct gaggcaggag aattgcttga acctgggagg cagaggttgt ggtgagccga  41400
gattgcgcca ttgcactcta gcctgggcaa caagagcaaa actccatctc gcaaaataaa  41460
tatctgtatc tatatctata tatcgaactt cttaccccag tgatccaccc acctcggcct  41520
cccaaagcac tggaattaca ggcatgagcc accacacccg gcctattaat tatatatgca  41580
cctataatcc caactactcg ggaagctgag gctggagagt ggcttgaacc tgggaggtgg  41640
aggctacagt gagctgagct cacactccag cctgggtgac agagcaagac tctgtctcag  41700
aaaaaaaagt cattaataaa tgtgatcttt ttttttcctg tacaagttgt caaggaagta  41760
tgaccttctt aattgaccct ttgacatgaa ctgggatgag atcgtggagg atgttgagga  41820
gacagttgtt accatagtgc gcttctaaaa actaattcta tagatttctt tacaaaaatt  41880
tgtttaaatt attatgagta cacaataggt gcatctatag atttcattac cctcaaataa  41940
atgtacaagg caatgcagag aaatacatag tgtaacttgg tagacttgac ctatcaagtt  42000
actcttgaat atgttatgaa gcctgtgtat tactgggggc agcaaacttc tcctgttatg  42060
atagttgttt tcagctttgt tgaatctgtg gtctctgtct taactacaac tgagaaagca  42120
gccatcgaca atatgtagat gaatgtacat gactctattg taataaaact gtgtacactg  42180
taatttgaat tgcacataat tttcatgtgt cccctgtata attcttcttt tgacttcttt  42240
tcaaccatta aaaaatgtaa aaacaggcat ggtggctcat gcttgtaatc ccagcacttt  42300
gggaggctgg gtggattgct tgagcccagg agcttgagat cagctttagc aatgtgacga  42360
aaccctgtct ctacaaaaaa ttagctgggc atggtggcat gtgcctgtgg tcgcacctac  42420
tcgggaggct gaggtgggag gattgcctga gcccgagaaa gtcaaggcta cagtgatttg  42480
tgccactgca ctctagccta ggtgacagag tgagaccctg tctcagtgaa tgaatgaata  42540
cattattagc ttgtggacta tacaaaaatt agaggctgga ggtgagctgg gtatggccat  42600
tgggcatggt ttactgacct ctggtagaga ggaattagta tatgttaaag gtggtggaac  42660
tgtctgatac ttgcgttctt ttagaaatac tttggagtta gctttttggt tcaggcaaag  42720
gaccaaagag ttaggagagt caggctggta aagaggagtg gtgggcccat agcaacaggt  42780
cctggagtct ttaagaggag gtgtgtctca tgtgacattg gttggttgga caaaagcctg  42840
gcatgttgtc accttccata ataagtgttt gtgggaatgt aggtaatgag aaggaggagt  42900
aaagggttcc tgaaggatga ggaggagggc tggtggctgc cataggaagt gatcaccatt  42960
ttggcggacc tgtcttagag taatgaccat catactctct cactccttgt gaactcatga  43020
agtcccatgg ctgctaaagc taaaggtcaa gtggggactt ctctgggcac tgggcttggc  43080
accccacaga gctgtggagt gggcattaat gtccctgtta tatagatgca gagactgaga  43140
atgaggactg ttggtaactt ttgagagggc actcagctag aaaagtctga gccaggatgt  43200
```

-continued

```
caagtcccat ggctttacct ctgtggtcct aatggttggt gtgttcaagt gagatccgtt  43260
ttttcatatt tggttttgat tattgatttt catgcatttt ttttcttttt tgagttagta  43320
tattctctct cttttctttt tttcttttct ttctttcttt ctttctttct ttctttttct  43380
ttctttcttt ctttctttct ttctttcttt ctttctttct ttctttcttt cttttctttc  43440
ttttctttct tttctttctt tcttttttt ttttttttt gtgagacaga atctcgctct  43500
gtcacccaga ctggagtgtg cagtggtaca atctcagttc actgcaacct ccacctctcg  43560
ggttcaagtg attctcccat ctcagcctcc gaagttgctg agattacagg cacctgccat  43620
catgcctggc tagtttttat atttttgtag agacagggtt tcaccgcgtt ggccaggctg  43680
gtcttgaact cctgacctca ggtgaaccac ctgcctctgc ctcccaaagt gctgtgattt  43740
ataggcatga gccactgtgc ctagccagta tttttttctt tctttctttt tcttttttttc  43800
aggttcattg aatttgcttt gagacaggat cttgctctgt tgcgcaggct gaagcacagt  43860
ggtgcaatca tggctcactg gagcctcaat ttcctgggct caagcaatcc ttgcacctca  43920
gcacccctcc acccccacct actcctttcc cccaccagta gctggaacta caggcgccag  43980
ctaccgtgct tggctaattt tttaaatgtt tttatagact gggtttccct atgctgccca  44040
ggcttattaa ttgattttct gtgtgatctt agggaaatcg attatttccc ataaacattt  44100
tttaaattag aagttaaatt ctgcctagtt tgcctcacat gattattgtg gatgactgaa  44160
tcagagaaga ggtaagagct ctttgaaaaa tatgaagtac catacagaag ttagatgctt  44220
tgtcctggtg agacccctcc aaagcacagc taaggaagtg tggaaggcac tcttatcaca  44280
tcatatagct ttgaaagcct agcattgaaa gtatgaactt gattcttttg gagaaatcct  44340
ttggctctca gtgagtttac tttctattaa tgactatatt aagcggaatg gaaactgaaa  44400
gaggaaagag gaggaagtca gaattaaata ggaagagtaa gcccatagca gagtccagat  44460
ttagacccca agctacttgg aatgatactg gacaattatg ggtgtgttta atgattgccc  44520
tgagtcatga aaacaaaagg aggctttaaa ttatgtctgg cttagtaata tagcatattt  44580
tatcattatt caagttttag catgtaaaga ggaaaagtgt gcagtactta cacataccat  44640
tttctattag cgaaactaaa tgaggccgct ttaaaattat cagtgttcac agtatcttcc  44700
aaaagacatg taaatgtata aatgtataaa aaatatacat ataaatttta cagtttggtg  44760
agctatatag tagatctctt attttgtcca taggtcgtaa agatcttata ctgtatttag  44820
gaacaaatat aacttaagtg ggagtccttt acagggctaa taagtaagca ttattttgat  44880
aaagtgctgt gttgtctaca ctaggtatag tagaaatact cttggaatag taatcatccc  44940
aggccctact ttggagtgga agaaatagtc aatgtagaac tttatagtac attgtacgta  45000
gatgtgcctg ctaataactt ctgtagacag caaagtttaa gagaaattag gtggtaaata  45060
caacatatgt atctaaataa atttggtctg agagatttga taagatgaaa cagtacatag  45120
tccagaaaat ttttatactc aaagaattgt agaaaatatc ttaaatgttt tcagttttgt  45180
gtatatccag agaatatcat cctgtaatct gctggttggc aacccaatgg cagtattaga  45240
tgtatgtttt tattttgttt cgtttgctat ttgtttggtt aagagagtta cctaattagg  45300
agtgtggaaa aaaaaaaaag atttattata gtagtgggct tttgtttgac ttcagacatt  45360
tttgttgtta caacaatatt agtgtcttgt ttgtgaaatt tgtttaccgg gaagccaaat  45420
acttagaata actttagtt tatcattatc atcatcatca tcatcatcat ctccatcatg  45480
aaaggaagaa gctaccaatg ttgctttatt ctgcaaacaa tataatagat gcttgttgaa  45540
agtatggagt gaaatcttaa atatatctgt taaaaagagt acaactggcc aggtgtggtg  45600
cctcatgcct gtaatccaag cactttggga ggccaaggcg ggcgaattgc ttgagccagg  45660
agtttgagac cagcctgggc aacatagtga aaccctgtct ctacaaaaaa aatagacaaa  45720
aattagctgg gtgtgatggc atacacctgt agtcccagct acagtggggc tgaggcaggg  45780
ggtattgcat gagcccagga agtaaaggct gcagtgagct atggtcgtgc cactgcactc  45840
cagtgtgggt aacagaatga gaccctgtct caaaaaaaaa aaaaaaatag tacaacttta  45900
agcaggatgt gggtacatga ctgtagtctc agctacttgg gaggctaagg caagagggtt  45960
acttgagccc agaagcttga tgctgcagtg agatgtgatt gtgccactgc cctccagcct  46020
ggggaccata gaaagatccc atctcttaaa gaaaaaaaaa acagagtaca acaactttgg  46080
taaacttgga atataaagat atttccttaa cctattaaag agctgataaa gagtggtact  46140
ttcaaaccag tacacattat gtgaaacact agaggcactt cccatttgtt aaaagaaaaa  46200
ccttagccaa attaaattta agttttgttt ttttttttt tgttttttttg ttttttttgtt  46260
tcttgagaca gagtcttgct ttgtcaccca ggctggagtg cagtggtgca agcacagctc  46320
actgcaacct ccgccttctg ggttcaagtg attttcttgc ctcagcctcc tgagtagttg  46380
ggactacagg tgtgcaccac cacgcctggc taatttttgt attttttgta gacacgtggt  46440
tttgccatgt tgcccaggct ggtcttgaac tcctgggctc aaggaatctg cctgcctggg  46500
cctctgaaag tgctgggatt acagatgtga gccactatgc catttaacgg tttaattgag  46560
caaagaatga tttgcaaatt gggcagcctc ccgagccaga gtaggttcag agagactcca  46620
gcacagccat gtggtggaag aagatttatg gatggaaaaa ggaaagtgat gtatagaaaa  46680
gagaagtgag gtacagaaac agccggattg gttacagctc agaatttgcc tttttagaac  46740
acaagtagag gtttgaacag ttggccacct ttgattggcc aaaacccggt gattggcaca  46800
agagcaggtt ccagtctctt tacatctcca tttaggttat agttcactat ggatggaaaa  46860
acctgtagat caaacttaaa atacgtaagg agacagtttt aggctaaact tgatttaaca  46920
cattaaatcc ataacaagac aggatgcctg ccctcaccat gttatttgat cttattttag  46980
taattctagc caatgtagta gggcaagaaa actgcctgct tggttacaaa ataaacatgc  47040
aaaagtcaat atttgtaata tgtgacagaa aatataattt aaaaaagaag aagccgggca  47100
cggtggcccg tggctgtaat cctagcactt tgggaggcca acacaggtgg atctcttgaa  47160
ctcaggagtt caagaccatc ctaggcaaca tggaaaaccc cgtctccaca aaaaaattag  47220
ccaggtgcgg tggtgcgcgc ctgtagttcc agctgctttg gaggctgagg ttggaggatt  47280
gtttgagcct aggaagcaca ggttgtagtg agctgagatc atgccactgc actccagcct  47340
gggtgacaaa gtaagactct atctaaaaaa aaaaaaaaga aagaaagaaa aggaaagaaa  47400
aagaaaaaag aatttcactt actagagcat caaatcccta agataattta gaacaaagcc  47460
agaaaagtga agaaaataca aaaatcttta cagtgagttg cataaaaaaa aacaacttga  47520
agatgtcaga tcaactcatt aatgtgttga ttaatgtaat taaaatccca ctgtttttttt  47580
tgtggggagg gtgggagagt cacttgttaa aatgattcta aagagcatct ggaagaataa  47640
acaggcaaga atagccaaga acattttgaa aactaaagat gagtttggaa gacgattggt  47700
tttgtactat caactactta tagattttac atgaatttta aagggtaatc tgagtcctcg  47760
aatagacaga aatagccata gatctgaaag aacacttaag acctgatcta gctatccgtg  47820
agagtatgta taatcaaagt ctttgtgtgt gaatcaggag tctttcaggt gcaaggtaaa  47880
taagctcata attgcttaag caaaggtggt atttgcttta gtgactccag agaaagctca  47940
```

-continued

```
agtgcctgtc tccccctgac tttgattctt tttggggttg gctccattct ctcctgttgc  48000
taatggcttc ctttgtgcag ccagaggaaa ggaggtgtgg ttttttgata cttccagtct  48060
tctattttta tagcttgaga tcaaagaggg aagtgacctt ccttagagtc agtgtgtaaa  48120
gtcctaagga agataccacg tggggtgctg gggccatgtg cccatccctg gcccatgacg  48180
atggggatgc tacactaact gggggccacc catggctgtt cctgccttga actgccaact  48240
ggctttgcag tgcagcttca ccagaatcac atggaatagt agggatagga attgtttccc  48300
aaagagagtg tgtggggtgg taaaattact agtgggggag taaggggaca ggccattggg  48360
cagactggag cagcatttac ttactcagtc attgagaaaa ggatggaaca ttcaataaag  48420
ggtgctggac acagtttgtg ctctaaaaat tttgtgtttc acctattaat ttatccctcc  48480
ccttagcccc tggcaaacac tggtctgttt actgtctcca tagttttgcc tttcccagaa  48540
cgtcatgccc ttggaatcat acagcaggta accttttcca gttggcttct tttatctagt  48600
aatgtgcatt taagattcct tcatgtcttt tcctggattg ataacccatt tctttttagt  48660
cctgaataat attccattgt atggttgtac cacagttgat ccattcacct actgaaggtc  48720
attttggctg cttccaagtt ttgataattt gaaaaaaaaa ttttgagaca gggtgtgatt  48780
gtgtttaaga tactggtctc ctgaacaact gagctcacgt gaacccctct cctcagcctc  48840
ctgggtaact gggattacag ctatacacca ccgtgcccag tgtgacaatt atgaataaag  48900
ctgctataaa cttctatgta ggttttttg tgtttggaca ttggttttca gttcattatg  48960
gtgaatacca aggagtgcaa ttgctggatt atatggtaaa agtatgttta gtttgctaag  49020
aaactgccag ctgggtgtgg tggctcacgc ctgtaatcct agcataatgg gaggctgaga  49080
caggaggatc ccttgaagcc aggagtttga gactagcctg ggcaacatag tgagacctca  49140
tctctacaga aaatttaaaa attagctggt cgtggtctta tgtgtctata gtcctaactg  49200
cttgggaaac tgaggtggga ggatcacttg agcccaggag ctggaggtgg cagtaaactg  49260
tgatcatacc actgcactgc agcctgggtg acaaagcaag accctgactt taaaaaaaaa  49320
aaaaaaaaaa aatgagtcag agggtaagga agcaaaaata agtaaataaa taaatagaag  49380
ataaaagaaa aatctatctt tcaaagtggc cgtgccattt tgcattccta ccagcaatga  49440
atgagagtct ctgttgttgc acatcctcac cagcatttgg tggtgtcagt gttctggatt  49500
ttgaatattc tattaagtat ataatgctgt ctcacttgtt ttaatttcca attctttagt  49560
gatgtatgtc attaagcgtc tttttaatat gtttacttat catatatgta tcttctttag  49620
tgaggccttt gtttaggtct tctgcccatt tttaaaaatg ggtttatttt cttattgttg  49680
aatagtatga gttctttgtc tattttgaat acttgtcttt tgctttattt ttgtgttttt  49740
tttttatttt tatctttttg agacaagttc tcactctgtt gcccaggctg gagtgcagtg  49800
gcatgaacat ggctcactgc agcctcaact tcttccaggc tcaagcaatc ctcttgcctc  49860
agccttccga gtagctggga ccataggcgc acaccaccac accctgctaa tttgaaaaaa  49920
tttttgcag aggcggggtc tcaccatatt acccaggctg gtcttgaact cctggcctca  49980
gtcaatcttc cagccctcag cctcccaaag tgctgattat aggcctgagc cacttagcct  50040
agcccagaat ttattttttt atttcttagt tttgaaaaaa tataggacct cataaaagtc  50100
agtctagatt tgtacacatt atgtttttgg tgtatatgta aatggattct ttgtgaatca  50160
atttggtttt gtttttttgc ttttaaaaat accagcactg ggctgggtgc tgttgctcat  50220
acctgtaatc ccagcacttt gggaggctga ggcaggtgga tcacctgagg tcaggagttt  50280
gagatcagcc tggccgacat ggtgaaacgc tgtctctact aaaaatacaa aaattagctg  50340
ggcgtggtgg cacatgtcag taatcccagc tactcaggag gctgaggcag gagaattgat  50400
tgaacttggg aggcggaggt tgcagtgctc caagattgcg ccactgcact ccagccttgg  50460
cgatagagca agactttgtc tcaaaaaaaa aaaaaaagaa aaaaaccgca gcagtggctg  50520
gccaaggtgg ctcacacctg taatcccagc actttgggag gccaaggcag gtagatctct  50580
tgcggtcagg aattcaagac cagcctagcg aacatggcga aaccccatct ctaccaaaaa  50640
tactaaaatt agccagatgt ggtagtgcac acctgtaatt ccagctgcct gggagactga  50700
ggcatgagaa tcacttgaac cctggaggca gaggttggag tgagccactg tattccagcc  50760
tgggtgacag agggagactc tatttaaaaa aaaaagaaaa aaaaggctgg atacagtggt  50820
gcacgcctgt aaccccagca ctttgggagg ctgaggtgct cagattgctt gagctcagga  50880
gtttgagacc agcctggaca acatagtgag acatcatctc ttaaaaaaaa aaaaaaatac  50940
ctgcacttgg tcaaaagatt tcaacagtgc agaaaaagaa agttgctata tcttttctcc  51000
aaattagtct tgtttctagt ttcattatcc aaataatcac tactaatagt taaaacattt  51060
taaatacaca ttgggagttt gtcctattta atataaatta tttattgagc aaataatcac  51120
tgctagtata ttttggatac tggaattttc atatgtaggg gtccttgaat gtaaggtgcc  51180
cctttggtag ttctgtgctt cttttacctg tactgtaaca tagggaaaga tgttacaaat  51240
ggttagtatc tattcttaaa caccagccct tccactaaag gtaaacaaca aataaatata  51300
taaatgaagt tttggtattg ggattacacg ggttaaacac atccatattt cattattaat  51360
atttaagaat ataacaaact tcttattggc atttggacct tgtagctagg gaaagattaa  51420
gctttgttta tttgtgcttt gtttttttc ttcactcaga tatttgaggg tttcccattt  51480
gaggaataca tttattaatc aagctttagt tgcaagatat ttgatcttag agaataccat  51540
caaccattct tctttaagct tcctaacttt acccaaatgt ggttggatct actcaagagt  51600
agtttgggta gttcagaaat tttattggaa ggggaaataa tttttgaccc aaatttgata  51660
aagcaactct tgagtaatga tttcttttct tgttctctct ttataatcag ttgaaagtag  51720
tagtaaggct gggtggcaaa agaaagaggc ctggggagaa tcgggtggtt ttcattatct  51780
cttttcatag cagctaagtg ggaagggacc aagaggaaat caactgaaaa accatccttc  51840
tgaaacattg gcctaaaaaa gtgtagtcca gaaattgagt gcaactggca gtggcattta  51900
aaaggaatgc tctaatttct aggaaagcag gcacgagtac ctcttaaaag aagaaaaaaa  51960
tgaaaactgt aatttaggac acacagacga gtatccattc cctgtacttt tttactctcg  52020
tgtcctaacc aaggaagggt taccatagca aatatggcat tccttagcca tgattcactg  52080
ttgtaaatgc ctgcagcatt cataaaagta agatatatgg gctctttctt tttccttttg  52140
aatccgtatt tctgtattta aatctgtatg tcaacatctg tattttctgt ctctcttgtt  52200
tttttaaatc ttgggagatg gtacaaatta tttaggggag tgaataagtt tcttgtctac  52260
aaatagagga gagagaaggc tttttgtctt tctgctttgg aactggagag cttcctattt  52320
aggcacggcc tttttcaagt gaccttgtat tgttatcagt actgtagaag gtaggcacat  52380
tgtacagact ttaaaatgta aagcttttag gcattccact tgtaaacctt ggctttttaa  52440
agaaaattac atgttcattg tgaatatttt cttatcgccc tatctctgtg cacatgcaga  52500
cttcctttgg ctacattctg aaaggtgtaa ttgtcttctt taaggacagt ggacatctat  52560
agttcttagg tcaaattgtc ctccttctgg ttttgtcagt tctcagccac actgtgtgag  52620
catccatttt cttggatcct ggtttggagc tcattttaag gaacatcacg tccctttttga  52680
```

-continued

```
gactatgtgg acatcagggt gggtagatgt tcccctgtga acagaaggtt cctccctaag  52740
gaggtgcttc tctgtgttga gtcttgcatc tgggcacaca gagcccaaag caggaagagt  52800
tgagtctgaa tagggaggcc tgtaagcctc actgctctgc cacggctagg cctggttggc  52860
catgctctag gagccctcag gaggctctga agtgattctg cctctgggaa ttttacagag  52920
gagctaatat ttgagatctc caaagctgag tgagagggtg attcttgaaa aggcaaggca  52980
tgcctcggtc cagttctgtg gggctgtcat agaagagggc tcggaagctc ttgtaagtga  53040
ggctggaaag gtaggcagtg ttaccataag gaggatggaa atgacacaga taggctaagg  53100
aaggggacct ctgtaatcat gcagcgatgg cctagaaaag ggacaggctc atggcaggga  53160
gaccagtttg gaggctgcca cagtgttcta ctgagagaga aaaagaatta aactcaaagc  53220
acggtcaggg aaggtggagg ggcaggatct gatttggaag tgttttgttt tttggtttcg  53280
ggtacaagga tttggaaacc tcttgactcc gtagatgaaa gaatatgaac caaggaagac  53340
tgaagtttcc actcagggaa gaaaacacag gagtaggaat cgatttaaga gaatggcagg  53400
cagttgtgtt ttgaacttgt ttagtgtgag gtgacatctt tgtagggatg tctagctggt  53460
agctgcaagt acaggaggct agatgtgtgc atgagtttct tggtaaagat ccatctgcag  53520
tctcctgaag atgtcactca gattgcactg ccatcacccc agggcccaag agaagacact  53580
cgcttctctt ggtgtctagg cgggtttgaa aaaaatcaaa cagtacaaaa tcatgcaaat  53640
tcagacctct actccacccc agaggaaagt cctgctagca gtttttgtgt attcttccag  53700
aaatctgcct tgcaacatgt ttgagtatat aaataatccc agaaaggatg ggccagacac  53760
tagcagaaac tcaccacaca cactgcgctg ggcatgcaga aacttcgcga aatatactgg  53820
tgtgtgctgt cactgcattc ctggatttgg gggtcttctg tgtccccagg tatcagtatt  53880
gcccacaggc tgaccactga gctccttcca cagccgactc acgtcaccct ctttcgaagt  53940
gtgtctgcaa agctagatta ttagattgtt tctgctttgt gtttcttta atgaattttt  54000
taatgatgaa gttcttgttt taaaaatata cagtggtaat taacatgtat gcatttttct  54060
taaaatgacc cccccagtcc ctcttcagat gtaatcactg ttaacagtat cgtatataga  54120
ccctgttctg tgtggggtgg gcagagggcc ggttagcggg tggaacatgc atactcacaa  54180
ccatattttt cacatgggaa aatataaagg tgacaacaaa tctcctggtc tgtaatctca  54240
tcaagcagac aataatcact atttgaaaag cggacaaata catgctgatt tttaaaaaaa  54300
attatagtag tacagaaaga tacaaaaaaa aaacaaagtt aaagtcttcc taactctcct  54360
gcctgtaccc tccactgggc aaaagtccct gtccctaagg taatatctgt tgacagttct  54420
ccttgcaata cagataggag catgttgtgt atctgcctct gtgtgtatgt gtttacatgt  54480
cttttttttt tttttttttt tgagacggag tcttgctctg tcatccaggc tggagtgcag  54540
tggcgtgatt tcagcatgct gtgacctccg cctcccgggt tcaagtgatt ctcatgcctc  54600
agcctcccga gtagctggga ttacaggcaa ccaccaccac acccagctaa tttttgtatt  54660
ttttgtagag atggggtttc accatgttgg ccaggctggt ctgaagctcc tgacgtcaag  54720
taatccaccc gcctcagcct cccaaagtgc tgggattaca ggcatgagcc acaactcctg  54780
cccctgcaca tgtctaacgc acacaaaggg gattctgctg aacacatttt tttgtgcttt  54840
ttctttccaa cttaacatat ttgacatctt tatcagctta tatagcttta cttcattctt  54900
ttaaagaggt tattggctat aaagagaaag tcagagaaag tcagtcaatg ggtgcttcta  54960
tgattattta attagatcct gttgatggac attgatacaa tttctaaatt ttttagtatc  55020
ctaaataatc ctgtggtaaa catccttata cagatgtcct tgttcgctca tgaaaatatt  55080
tctggaggat ggtgagaagg gaaattttaa aaattattta tataaacatt atcatttgtt  55140
agtagaatga cctcgggaga ggttgtagta atttatgctt ccccacatgc atatgaacgc  55200
cttttcaata tattgtttca aaattggata tcatgaacct aaagatatat atatatgtat  55260
gtattttttt tttttttttg ggggtggggg gatgtcctgt tattttcagt tatcgaatag  55320
aactttgtta gttccttcat gtaaggatga agttggtaat tattattttt tttgtgtgtg  55380
tgtgttactt tcttttttttt ttttttttgaa gttggtaatt aaagggatct gacttcagtt  55440
atggaactgg gaaaacagga ccttgatgtg gaggtgggct tagacatgct atgtctgggc  55500
aggtatctct tgggaagcag tgtcacccct gaacagaagc atggatgagc cgcaggggac  55560
ggtgctgagc agaggggctg gccgtgggtc atctgcggct gttgacctgg aaggcacaag  55620
ggagtttcc acctttcctt tggttttgag agtgcagaag ctactaagca actcacaacg  55680
tgcccagggt ggtggtccaa ctgaaggatg tgaaacggtt cttcctttcc cagccaaaga  55740
acttgaacct cccaccctgt gacaagcatt ataaaattca cataattttg ataggctgga  55800
ttccctttct gtagcagatc tttcctcaga acagaagtgg tttttttgttt tttggttttt  55860
ttttaaccta aattacctgt gagttttatt ttttaaatat ggaatatgtt ttttggacac  55920
ctccttgtca tattaaatgt tgttattaaa tttgagattt taatataaat tttaccccag  55980
caaattaatt ttgtttctct tactctcttg tttttggcat cttttcccgt tatatagtgg  56040
tgctcatgtc atcatattgc tcttatgtga cttttccttt gtgaacaggg atcttgttca  56100
cttttccttt tttaactttt tttttgtttt ttcgagacgg agtcttgctc tgttgcccag  56160
gctggagaac agaggcacag tctcagccca ctgcaacctt tgtctcccgg gctcaagcga  56220
ttctcccacc ttagcctctt gagtagctgg gattacaggc atgcaccatc acgcctggct  56280
aattttttgt atttttgtag agatggggtt tcaccatgtc atcgaggctg gtctcgaact  56340
cctggactca agcgatccac ctgcctcagc ctcccaaaat gctagggtta caggcatgag  56400
ccactatgcc tgagtcactt ttccttttaa cataaaaaca ctggtatcct agagagggca  56460
ctatattttg ggtacatatg agttcagatc acagaagagt tgtattctat acttcttttt  56520
tcatcattct tacttcagta tgatgtattt tataatttta tatgagaaac tataacactg  56580
ggcatgtgtc atcaagcagt acctactcat aaatcatatt aaattttgat ccaaacatgg  56640
gacaaactga agtttctctt gtgtacttga atgctttcag aggcataaaa ttatattacc  56700
atgtgaaagc aagcctacaa aattcctcag gcgtccactc tgccactcaa atgagagcca  56760
gacttacagt gcacactcta caaacaaact tccagcccgt cagggtattt taagtgcctg  56820
aatatgcaag gcactgtgcc agtaaaatta ctcagtccca aggatagagc ctgttagaat  56880
tattttaaaa tctgtacttg aagtttattt cctcagtgtt ccaagatatt ttatctggtt  56940
gttctctgag tatttcacat gtagctagtt acatataggt gagatagtga tgcttgtgcc  57000
tggtgtggat gagaaactga gcctggcaga cctgagattg gatttccttt tctgactttg  57060
caagtgtggc ttggctttaa tagccctcct ctttttccgt attcctcttt ccccccttcca  57120
ttttgcaaat atgcatcaat caaaatacaa attgattgca aatatgtgtc aatcaaattg  57180
tattgtattt tgattgtgca catatgcact gatagttaca catatgcatc aatcaaaata  57240
caataacctg tggaaccatt tttttctgaa ataggaaggt ggtgccatgg gctattgatt  57300
gttgaaggta gtcttcagag cttgtcttac aaatctataa taattttccc ccaaattaat  57360
gtgctagtta gaacactaga ttgcatcact gaaagtgaat tttagaatct tttccaactt  57420
```

-continued

```
tttaccaagt tcagaaaacc gttttattgg acctttattt gcctcatggt catctggttt  57480
ctttatgctg ataatgacag ggaccttact aacctacaag gcaacccagt ccatcctggg  57540
cagctatgat cattggaaag ctctgaatca ttcatctgga agctgcctat ggcagaatag  57600
tgcagaacat atgcattgca ctatgttcta caaaactaca ttaaataagt gttccttttc  57660
attgttagat ggaagtgacc cagggcaagg atcatgtttg atgagccagt tttctcctag  57720
tgccttgaac ataggcactt ggtaatgttt aaagaatgaa ttcttttttt ttggagacaa  57780
aatctcactc caccacccag gctggagtgc agtggcacgg tgtcagctca ctgcaacctc  57840
tacctcccaa gttcaagtga tttttgtgcc tcagcctcct aaggaactgg aattacaggc  57900
atacgccacc acgcccagct aatttttata tttttagtag agaaggggtt tcgccatgtt  57960
ggccagatgg tctccaactc ctggcctcag gcagtctgcc tgcctcagcc tcccaaagtg  58020
ctgggattac aggcatgagc catttgcctg gccagagaat gaattcttaa tcagtttctt  58080
atgacttcat attgactgac agttgtgcta aatacttttt gcctttattt gaattagaaa  58140
atttgtaagg gggccttcag aatagatgca gtcacattta ggagttttct tccccccatt  58200
agttaaaatg cagtttttct atggatctgt tttagaacta cgaataaact ctgatcagtc  58260
actgcagact acgcagtaag ataagaagca gtccatttgt tctgtcgttt attcatggcc  58320
ctcatctttg ccagctgact tgtgcagaag agcacagcaa actgtaagct tcctaacagc  58380
tattcccatt cagctgctgt cttcaagaag cagaagagga tagatagacc ttagagaaca  58440
taatcaaacc tgggaaactc aaatcaaaac aaaacacaac ttcaaaacag aagttgaagg  58500
tcctgaaggt acccagaggc atagcaagga aaatggcccc actgggatat cttttggatt  58560
cacctacaga cctctctgga gttttaagat ccactttttg tgacatattg catagcaaac  58620
aggccgaacg ctgttgtaaa tcatcctctg cgaaaggccc aggttttgaa actgaaggcc  58680
tgaaaaggct cctgcttacc agctgtgtgc tgtacctgac acactgaagc ctgagagtgc  58740
cagtcacctg tcagagggaa cacagctgcc ctcaggcaga acctgagtct agaactcaag  58800
gtttttgact cttaggctaa aaataaaaaa tcagaaggag gaactatgga ttgcttaatc  58860
agtcacattt tcactttcca gagtttcttg tagcacaagt tatagccttt ggggattagg  58920
atgtaaacac tttttttcc ttccctaaag cgatttttgg tctgtcagtt tttccagctt  58980
cctgctctgg gccctgaagg tgccacacag ttgcaggcat gctcctactt caaggctctg  59040
ttaagctgtg gctgcccttc cttcccactg ctgtgcccca ggccaacccc tctgcccctt  59100
ccttcccctg aggcgctttg cacctgttgc tccgagcctc ctggtctatc ccagttagta  59160
gagtccctgt gcttacctcc gtggctcagt cctcatgggt ggtcagtgct ctagggaagg  59220
tgagctgacc tcttcacttt cccttcccag ccatttatag ctcttcatag cctcaccaac  59280
ttagaaaggg atgctgcttt tctctctgtc ccccatcctg actacattca agtcattgct  59340
cagcccagtg agtttgtcct ttcttccaga ccagtagttt tcccccaggc cctcaggctt  59400
cagcccttga aggcatcctt agcccccccc ccacactatg atagccaggc gctgtgcctg  59460
gccatggggt gtgggtatgt gtgtgtgttt tgtttctgga gcccattcct ttccttccac  59520
catcttctag gccttcatcc aatcctcctg caacttgatt catgactttt ccctgcatct  59580
agtctagtct ctttgctggt ctgttgtttg catagttgcc agtttaatct tcttaaaatg  59640
ctgcattttt gaagtcagtc tctctctagt ccctgtcaga aacatttaaa tagctctgtt  59700
gccacagggg gaaagcttga acctcttagc cagtcagtca ttcagagcct gccctctact  59760
ggggcctgct ttcctctcca gatgcttctc ccactctgcc tgccacagcc cttgtagctg  59820
gctgattgcc ctgtacctcg caggctctgg aagtcttcag ctccttcatg gagcctttgt  59880
ctaccagcca ttcttttcaa gactttgctg ttgttcactg cctgatttgt tcatttgaca  59940
cttaattcac tgagcaaaca ttatgaaaga tgtactgttt gctactgtga ggaatggatc  60000
cccaagaggt aagagggtca gtccctactg ccaggaaatt tgcctggatt cagtatcttc  60060
ttgtgtctat tagatcagaa gtggaaaggc agaggccagg ctgtatgctt tttaaatttt  60120
attttatttt atttaaatca ccagcacctc agcaagtgtt ttgcacagga aatttcttaa  60180
tgttatttaa ttattttggt ttttttgatt aaattctgta cattcccatt ttagcttatc  60240
ttgagttata acattaaaat taaggtagtc atcaactgaa ttataagacc taattaaata  60300
agattattta agatagtgat tttctcattag attggcccta ttcatattaa cttttctgct  60360
tttttcttca gtctgcatga agaaatcagt gatttttatg aatacatgtc tccaagacct  60420
gaggaagaga agatgcggat ggaggtggtg aacaggatcg agagtgtaat taaggagctc  60480
tggcccagcg ctgacgtgag tcccttcctg ggtagcctat gcttgggaca gtccttgtcc  60540
acgggccaga ggcctatctg ctagtatctc atgctagtcc tcacatgcaa gtagaagtgc  60600
actgtagagt tgtggtctaa ttaaatttta aaggcaaaga attttctgca gtctttagaa  60660
tttgaggctt actaattatt ttcattggat tggatgacta acaacctttt tttttttttt  60720
tttgtagtgc taatagcaac tactaaaggc aagctattgt tagaaattat tagtgtaaag  60780
agaagaaaga caaatcaaac ctcattgttg tagtggtctg ttattggata tgatatatca  60840
aaacctcatt actacttagt tccagcctgc cagagtaaac attatataat tgtttacagc  60900
tgaatgaaaa tgtcaagtac gaaattttgt cacttgtggc taatgcaggc ataagtcttt  60960
tcttatttct ttcctgaaat tgccattttc atctctctca gaccagctaa ttgcctttta  61020
gacagctccc agtcagtgaa caaaatgatt gcttgggatt tcttcttggc ttatttgttg  61080
tttttgttac tggtaccaag tcttttgttt tttttttttt ttttttttga gataggggtc  61140
tcactctgtt gctgaggctg gagtgcagta gtgcgatcac gactcattgc agccttgatt  61200
tcctgggctc aagtgatcca tctcagcatc ccgagtagct gggaccgcag gtgcacgtca  61260
ccacacctag ctgattttcg tattttttg tagagactga gtctcactgt gttgcccagg  61320
ctggtcttga actcctgggc tcaagcagtc tgcccgcctt ggcctcccaa agtgctagga  61380
ttataggcgt gagccaccac acttggcctg ttactggtac taagttaata cttcactttt  61440
tagggcactt tgagggcctg ttttatgatt ttgtgtatgc aaagaagtaa caaaataata  61500
gaatccatta ctttgtgttc tgtaactttt ctttaggcac tgtcctgggt ggtgtttttg  61560
tccaattggc aaaacaagga agtttcactg tatgtaaaac ttgcatgtat atgacagtat  61620
atatatgacg ctgtaggtaa agggaaaagg ggaggatact aatattttat gaacagtgac  61680
catatgtcac attctttctc ctatgtgatc caaatcagtg gttcttagct ggtggttatt  61740
ttgctctcca ggggggcgtt tggcaatgtc cgagacattt ttgattgtcc tggctgggta  61800
tgcactgcta gtacctagtg ggtagaggcc atggatgccg ccagccattc tgtgatgagc  61860
agtataggcc cttacaacaa agaattatcc actcccaaat gccaatgttg agaagccctg  61920
gtctaattta acccttatct ttcttaggtg gaggttgact ctctctctct ctctctctcc  61980
agccagccag ccagccatca tctgtctacc tacagatgag gaacatgagc ttgtggttag  62040
gttcccaggt ccatctcgcc tcagaggttg aacttgtttc actgtttatc cttttccccc  62100
gccctgagat ggagtcttgc tctgttgccc aggctggagt gcagtgacac agtgacatga  62160
```

-continued

```
tctcagctca ctgcagcctc tgcctcccag gttcaagcaa ttctcctgtc tcagcctcct  62220
gagtagctgg gattacaggt acccgtcacc acacctggct gatttttgtg tttttagtag  62280
agatggggtt tcatcatgtt ggccaggctg gtcgtgaact cctgacctca ggtgatccac  62340
ctgcctcggc ctcccaaagt gctgggatta aaggcgtgag ccactgtgcc cggcctatcc  62400
tttttatta caattacctg catacgtatt tctgcctgag ttcccctgtt ctccatgggt  62460
tgaggtggaa tgcatcccag ttttatgcca cagcacgatg ttataaaatg atggtgcctg  62520
gtgttctctg tggaattgac ctgaaggccc acacttgccc tacagttagt ctgatcccaa  62580
tttagtaatc tattcgaaga ctcctgctca gagaacaaaa attaaggatt tgtgattgtg  62640
tctctggata atgagggaac attattgatc tgaactactt ctggaagttt cctgtggttg  62700
gctttctgta tccttaagta ccatacctcc atattaaacc aacagtggat tgaaaatatt  62760
cagaaaaaaa ctattaaaat aacaatgcac taataaaaac aatacaaatt atttttaaaa  62820
tatagtataa tgactattta gatagcattt acattgtact aggtattata agtaatctaa  62880
agatgatgta aagtatatgg gaggactcgc atagttatat gcaaatactc caccatttta  62940
tagcagtgac tcgaacatct tcagattttg gcatagtggg actggaacca gtctcctgcc  63000
gataccaagg gacaactgta ttttggtctc tgtgtttcat atttgaacca ggtaagttga  63060
aattatattc agaatgtctg cttgtgaaac agaatgccca cttcatgaag aatggggtta  63120
gaaaaaaaaa tactcttgtc atactgaaaa gtaccagtag agggtagcaa aaactgacat  63180
ttctccatat cttggtgact ttatctgata cctcaatata ataacttctt tttctgtttc  63240
aggtccagat atttggaagt tttaaaactg gactatattt acctactagg ttagtacact  63300
catgaatctt ttaaaggact gtaccttttc ctagagtgta ttcgttttgg ctgtcaaatt  63360
tgtaaggagt agaaacaaaa caaatttata aaacaaaaat gggactgggc atggtggctc  63420
acgcctgtaa tcctagcaat tcaggaggcc gaggagggcg gatcacttga agtcaggagt  63480
tcaagaccag cctggccaac atggtgaaac tccatctcta ctaaaaatac aagaattagc  63540
tgggtgtagc ggcacgcgcc tataatccca gctactccgg aggttgaggc aggagaattg  63600
cttaaactcg ggaggtggag gttgcagtga gctgagattg tactccaggc tgggcaacag  63660
agcgagactc tgtctcaaaa aaataaataa ataaaaataa aaaataaaaa agtaaaggat  63720
ttaccagcat ttaatttgat ttaccttgaa gtagaatatc acttcacatc tccaagacgt  63780
agatggtaca gagagatgga aaagggatca tgttgcagtg gaatcagtta gttactaatt  63840
ttagaaattg actacctggc agagtattgc tcagtcccat aacttaaccc actgacacag  63900
atgttaatgt agtctcatga taaaatgtct gattgtatat cctctagaat gtgagttccc  63960
actgtctcac tcactcactc actctctctc tcactctcac tttcaaatta agaactcatt  64020
ctactagtta tggctccagc atcctgatcc agaaattcag gtacagatct cttctctgag  64080
aaagatcttg gcctttcagg actcttgttc agtttcagtc ttctcaaatg agacctctct  64140
tgatgcacag ccttggaggc tttcttttgg aaatgatgtt tctctgaagg gtgaatactt  64200
gctctctaag aattgaaatt gtttgaacat tccgtcatgg ttattactat tattacttaa  64260
tctctccaga ataaagtcag cgtcatgttt ttccatttga gcttgatttg gtacacttta  64320
gcccaactta aagtgtgctg aagtgggtgg accctggcaa tttccattct tcccatagat  64380
gtccttggcc tgcaaaagtc ataaaatact caacttcgag ttcatatttc ttacttaggt  64440
tctcagcctc agtaaaacat gaaaaatcac tctttcttaa aaaatttaat taaattttat  64500
gaataggtag tacattcaca tagttcacat ttggaaaagg cacaaaaatc aatacaggga  64560
aaagtctcag tcccacctct gccccctggt tctccgtgga acagccactt gtttttttgt  64620
tttgttttgt tttgttttg agatggagtc tggctctgtc gcccaggctg gagtgcagtg  64680
gcgcgatctc ggctcactgc aagctccgcc tcccgggttc acggcgttct cctgcctcag  64740
cctcctgagt agctgggact acaggcgcct gccattgtgc ccggctaatt tttttgtatt  64800
ttttagtaga gatagggttt caccgtgtta gccaggatgg tctcaatttc ctgacctcgt  64860
gatctgccca cctcggcctc ccaaagcgct gggattacag gtgtgagcca ccacgcccag  64920
ccagaacagc cacttttacc agtttctcac atatcctttc agagatacct gtgcatataa  64980
aaggacatgt gtgtgtatta acacaaatgg tagcatgctg gatacttgtt ctgcatccag  65040
tttaaagtac ttcataatat ttctgagttg caattaatct catccagata ggaaaatcat  65100
tatgtctagt accggaagcc tttattaagg aaaggacgtt aagtgccttt tttttttttc  65160
ttttttttt ttttgaggtt ttacttcttt caaaattacc ctatttcctg agacctgaat  65220
tctgtgaaat gactgggagg aggagtttgt taaaatcaac aactactatt tcccctctcc  65280
acaaaaccat tatcactaac acatttagtc tttgttggcc agggtggaaa ataggtttta  65340
attgtactaa tgaagtctgt aagcatgagt gtcagttaaa acaagtttcc agcttcttca  65400
gaccctcttg tatatgtatt ctgtgttcag tgacatcgac ctagtggtgt ttgggaagtg  65460
ggagaaccta cccctctgga ctctggaaga agctcttcgg aaacacaaag tcgcagatga  65520
ggattcggtg aaagttttag acaaagcaac tgtaagttct gcagcatttc atattaaacc  65580
ttggttattt acctatgaaa cttgaattaa aattaaagtt tggtgagcac agttacattg  65640
caagtgagtg attctttcat tttgttaatg tcaccgtgct tgcacataaa aagttttctg  65700
gttgtccacg ctggattgtg accacacaat cttgggtcac tgcaacctgt acctcctcgg  65760
ctcaagtgat ccttctactt cagcatctcg aggagctgga ctacagacac agcctgccat  65820
gcctggctaa ttttttttgta aattttgtag agacggggtt tcaccgtgtt gcccagactg  65880
atctccaact cctgggttca agtgatccac ccacctctgc ctcccaaagt gctgggatta  65940
caggtgtgag cctctgcacc tggcctgcat ttcttttaac aacagcagaa tacccaattt  66000
tatcacacac agtactcact gtagagatgt ttgttttatt catttgcatt attatttttt  66060
ttttgagaca gagtcttgct ctgtcaccca ggctggagtg catggcgcga tctcggctca  66120
ctgcaagctc cgcctcccgg gttcacacca ttctcctgcc tcagcctcct gagtagctgg  66180
gactacaggc gcctgccacc actcccggct catgttttgt atttttaata gagacggggt  66240
ttcactgtgt taggcaggat ggtctcaatc tcctgacctc gtaagccgcc ccgcctcagc  66300
ctcccaaagt gctgggatta caggcgtgag ccactgcgcc cagcaatatt ttattcattt  66360
ttttagagag agatacagtc tcactatgtt gcccaggctg ttccctaact cctggactca  66420
agtgatcccc ccacctcagc cttatgtgta gctgggacta caggctcacc ctaccacgcc  66480
ttgtttattt aaaaaaaaat tttttttgta gagatagggt ctccctgtgt tgcccaagtt  66540
ggagcatttt ttgaaaagaa ctcctgatag ctcatgtaaa taatcatgtc agtttttgag  66600
aataattttt atatcttatc ttgtcaggtc gctttttggg ctatttgcaa aactgaccag  66660
taatgcaagg gggttgtagt gtatacctta agaatccagc aattttcttt tttttttttt  66720
ttttttttt ttttttttt ttttttttt ttttttttt tttgagacgg agtctcgctc  66780
tgtcgcccgg gctggagtgc agtggccgga tctcggctca ctgcaagctc cgcctcccgg  66840
gttcacgcca ttctcctgcc tcagcctccc gagtagctgg gactacaggc gcccgccacc  66900
```

```
tcgcccggct agttttttgt attttttttag tagagacggg gtttcaccgt gttagccagg  66960
atggtcttga tctcctgacc tcgtgatccg cccgtctcgg cctcccaaag tgctgggatt  67020
acaggcgtga gccactgcgc ccagcaatat tttattcatt ttcttagaga gagatacagt  67080
ctcactatgt tgcccaggct gttccctaac tcctggactc aagtgatccc cccacctcag  67140
ccttatgtgt agctgggact acaggctcac cctaccacgc cttgtttatt taaaaaaaaa  67200
ttttttttgt agagataggg tctccctgtg ttgcccaagt tggagcattt tttgaaaaga  67260
actcctgata gctcatgtaa ataatcatgt cagtttttga gaataatttt tatatcttat  67320
cttgtcaggt tgctttttgg gctatttgca aaactgacca gtaatgcgag ggggttgtag  67380
tgtataccctt aagaatccag caattttctt attagaaaca gtttgatgat acaaaacatt  67440
taatacctag tattcattgt tcttcatctt atactcagaa agtgttctcc aaagtattga  67500
ggaaggtttt tgttagataa tttaaaaatt attataacta tatgtcaact aataaacgag  67560
atgatgggca tattaattta cttaactgtg gtaatcactt cagtatgtat atcaagataa  67620
gtatatcaaa acatgtatgc cttaaatata aacaataaaa ataaataatc aaaaattgga  67680
caccaaacaa aattctcaat ttatagaaat tacaaaatat attgtatggg gcccaatgct  67740
aaatatgcaa catgatattt gtagcagtcc agggttactg gggtgtgcca tatttagaat  67800
actcagtgtt cttatgctcg catgagatga tggagacctc atgtctagta accctccatc  67860
ccctgatttt gtcatttaat ctggttaaag catttacatt ttacctttct tctctttata  67920
ggtacctatt attaaactaa cagattcttt tactgaagtg aaagttgata tcagctttaa  67980
tgtacagaat ggcgtgagag cagctgacct catcaaagat tttaccaagg tcagagaatt  68040
tagtgtttat acaataaaac tattagaaac gtaattttaa gattctgttg tggtggtggt  68100
ctaatatttt tatatgcgtg ttgctgacaa acacctctct ctctctctct ctctttctct  68160
ctttttaaaa tggagctagg gtctcactct gtcacctaag ctggagttca gtggctggat  68220
catgacccac tacagcctca aactcctggg ttcaagtgat catctcacct cagcctccca  68280
agtagctggg actacaggcg tgagccacta cacctggctt ttttttttt ttttttttt  68340
tgagacggag tcttgctctg tcacccaggc tggagtgcag tggccggatc tcagctcact  68400
gcaagctccg cctcccgggt ttacgccgtt ctcctgcctc agcctcccga gtagctggga  68460
ctacaggcgc ccgccacctc gcccggctag tttttttgta ttttttagta gagacggggt  68520
ttcaccgtgt tagccaggat cgtctcttga tctcctggcc tcgtgatccg cccgtctcgg  68580
cctcccaaag tgctgggatt acaggcttga gccactgcgc ccagcctttt ttttttttt  68640
ttttaagtgt tggggatctc gctgtgttgg ccaggctggt ctctaactcc tagcctcaag  68700
caatcctcct gcctcagcct cccaaagcac tgggattata ggcatgagcc accatgctca  68760
gcctgcacct tacttttgta tgcaatggtt ttgctttctt tgaatctgct tgtaatgatc  68820
agtgattaac ttataatgtg acctcaagta agaattaaaa gttgagaaag cttttgaaga  68880
aattgtctgc tctagatcct tccttgtaga gacagaagag atggaattct gctacacagt  68940
tgattccatc tgtttttaac cttcaggagt tcagattaag aacctttcct ttaacccatt  69000
tcctgtttgc cccaagaata ctgcgtgggc agtgagctgc actttctttt ttttcttttt  69060
ttgaggcaga gtctcgctct gtcacccagg ctggagtgca gtggtgcgat cttggttcac  69120
tgccacctcc acctcccagg ttcaagcaat tcttctgcct cgatctcaca agtacctggg  69180
actacaggca cccgccgcca tgcctggcta atttttgtat ttttagtaga gatggggttt  69240
caccgtattg gccaggctgg tcctgaactc ctgaccttgc aatctgctca cctcagcctc  69300
ccaaactgct gggattacag gcgtgagcca ccgtgcccgg ctgtactttt tttttctaa  69360
acgggaaata ggttaagagt tttaagagca ttttctagat ttcaatccct aaattacctt  69420
taaggtgttt cctacaggct tccttacttc tattttgaaa tgatttaagt ttatttctat  69480
tctattttct tccaagatag agaagaattt gtcaccatta tctgtggaac attttacata  69540
cttagatagt tgtcagcttt ctcctctcta acctaaacca ttaactcctt tggcttctgt  69600
tagaatattc acaatttttt tttctcaagc agctctaaag tttctatttc ttctttgttt  69660
tttaagaaaa aatgttaact acttgatgtt gcaagcatta tcatcttgca taaatatatg  69720
gaagacagaa aagcagaaaa ttaaagaaat attatccata atctcactat attgggtgtg  69780
tgtatgtgtg tgtgcatgtg cgcctgtcta atatttttct ggaaaaaagc ttttaaaaat  69840
tgaaattcgt atgcatgata acattcatca gtatgaagag atggtgtaaa gtgagtcacc  69900
cttacaccat agatacttag atcattttta tagaatttct cattgccagt tattattttt  69960
tgtgttgctt ttttatgttc tttaaaatta taagcaaagg agtagcacat tgtacacaca  70020
ttgtctcata cctttgtaaa aacttaatgt tttggaggtt tcttccatat tgacgcatag  70080
aggcttgctt tattcttttt gttggttaca caggcagtag tcttttgtaa gactgtggct  70140
gcttgattta gcagttcttc agtgttgttc cagtttttct tttgctgtta gaaaaaggga  70200
ttgacgaata tacttccatg catgcatctt gctttacacg tgcaaaatgt ttgtaggaag  70260
agtcccagaa gcaaaatttt gaggtcgaag ggtatatcca ggtaaaactg cgttagatat  70320
ttccctaatt atttattctt tcacattctc attttctctc tctccctccc cctttcttc  70380
tccctctccc tatccctctc tctcttcctc tgtccctccc tttctctttt ctctcttttt  70440
ctttcccttc ctcttctttt cttttctttt ctccttttct tccttcccct ttccctttc  70500
cttccttctt ccttttcttc ctttctttca tttttgaca ccgggtctca ctctggtacc  70560
caggctagag tgcagtgatc atggctcact gcagcctcag cctcttgggc tcaagtgatc  70620
ctcccacctt agcatgagta tctgggatca caggcgggcc taccacacct ggctaccnnn  70680
nnnnnnnnnn nnnnnnnnnn nnnnnnnnnn nnnnnnnnnn nnnnnnnnnn nnnnnnnnnn  70740
nnnnnnnnnn nnnnnnnntt ttttttttt tttttttaat ggagtctcac tctgttgccc  70800
aggctagata gagtgcaggg gcgtgatctc ggctcactgc aacctccgcc tcctgggttc  70860
aagcgatttt cctgcctcat cctcctgagt agttgggatt acaggtgctc accaccacgc  70920
tcagctaatt tttgtatttt tagtagagat gtagtttcat catgttggcc agggtggtct  70980
caaacgccga cctcaggtga tccgccctcc tcagcctctc gaagtgctgg gattataggc  71040
gtgagccacc aagcccggcc actttttttt ttttcaaagt agagatgagg tcttgctatg  71100
tggccccccc cttttttttt tccttttttt taaatagaga tgaggtcttg ctatgttgcc  71160
caggctgttc ttaaactcct gggctcaagc agtcctcctt gcttgacctc ccaaaatgtt  71220
gggattacag gcatgagcca ccaaacctga cccccttattg ttctttggaa gggaactgta  71280
tctagactga cttaactaca atgttttttt tttttttnnn nnnnnnnnnn nnnnnnnnnn  71340
nnnnnnnnnn nnnnnnnnnn nnnnnnnnnn nnnnnnnnnn nnnnnnnnnn nnnnnnnnnn  71400
nnnnnnnnnn nnnnnnntga gacagagtct tgctctgtca ctcaggctgg agtgcagtgg  71460
tgcgatcttg gctcattgta ccctccacct cccgagttca aatgattctt gtgcctcagc  71520
ctctagaata gctggatcta catacgtgtg ccaccacgcc cggctaattt ttgtattttt  71580
agtagagatg ggtttttcc atgttggcca ggctggtctc gaactcccta cctcaagtga  71640
```

-continued

```
tctgcccacc tcggcctccc aaagtgctga gattacaggc gtgagccacc atgcccagcc  71700
cacaatgttt aaaaatactt acttctccat atttttgttc tttcctatgc ttgcttagtt  71760
tgatacaatt tgcaaaagta taagcttttt tttttttttc tttttatag aagccatgcg  71820
tgttcactgt aggacatcta gaaaacagag ataagagtaa agaaaaaaat agaaatcact  71880
ggccaggtgc tatggttcac acctgtaatc ccaacacttt gggaggccca ggcaggcaga  71940
tcacttgagc tcaggagttc aagaccagtg gtaaaaccct gtctctacaa aaatacaaaa  72000
attagctggg tgtcgtgggc tgaggtggga gaatcacttg agcccaggag ctggagattg  72060
cagtgagcca agattgtgct actgtactcc agcctgggtg acagagtgag ggggagaaaa  72120
atggaaataa ctagtaattt taccacccta agtaataata gctgttaaga cttctttgaa  72180
gatgttgtgc ctgctttgtt ttcctcagtg gcctcagcct atggcatggc ttacagagag  72240
gagtgaatga atatgtgcac agcaaaaggt ggactcattc tgtacatact tgtccgttca  72300
ggtgttctct aggatagccc tgcctcattc cctgtaaagc atggaaggga ggggtggtct  72360
gtttgtagtc atcagcccat gtgtaagtca gcaggccgga ttcttgtttg ccccaggact  72420
gtggcagaat aatctaaagg tccctagtct acagtggcgc gccaccaaga aaagtgattc  72480
ttaaaaatct cactgattta gtgctttaag atgttggtga ctttgtcctt gtactctttc  72540
tattatctgt ttacaaatga atattagagg gtcatggtca caaatgagca tcatcagtta  72600
catgctgttt gtgtttctat cctatagcaa gtactctttt tttttttttt tttttgaga  72660
tggattcttg ctctgtcgcc caggctggag tgcaatggca cgatctcgcc tcactacatc  72720
ctctgcctcc cgggttcaag tgattctcct gcctcagcct cccaagtagc tgggattaca  72780
ggctcctgcc accactcctg gctgtttttt gtatttttag tagacacagg gtttcatcat  72840
gttggccagg ctggtctctg actcctgacc tcaggtaatc tgcctgcctt ggtctcccaa  72900
agtgctggga ttacaggcat gagccaccat gcccagccct gtagcaaata cttagatgct  72960
attattcctg tgtacatgtc ttacatttta gatataaggg gagaaccatt cattacctat  73020
agtttacttt tttttaatag cttactctta gaatggaaaa ttaagtatgt tgtatatcgc  73080
taccaaattt tataatgtaa ggaccaattt atgcccctct taatgcttag atctgttgct  73140
gatacaggaa ttcattgaaa atacaatttt ctttttcaga aatatcctgt attgccatac  73200
ttggttttag tattgaaaca attcctattg cagagggacc ttaatgaagt atttacaggt  73260
ggaattggtt cttatagtct ctttttaatg gcagtcagtt tccttcaggt aagtcatatg  73320
ggtataccat gctagtgcac actaaaagca aaagtgatca atcagctggg aaacattttg  73380
gaaaaaatca aaatcaacct gtaattgcat tgctttcctt gattccttac ggtttttccc  73440
tttaaactgg gtacattttt atcatttagc aaatacatat ttttaaattc ctgtgaaaga  73500
atatttttgg ttttaaatcc catatattct agtatttttg agacttttca ctgcaaattt  73560
taacatgcag aatgtacggc ctggtttcca taagcgtaaa tagtataagt gccagcaata  73620
agaatgtctt ctaagcagct aaatcttgta agtttagttg gaattgagat ttgctatttg  73680
gatgagcaaa ttcgagtctt agtattgtaa atgggtgtgt ttatgtggcg cagggttgcc  73740
aactgcctga gtctattcgt gagtcagaac gactttgctg atgtcttggg ccaagccagc  73800
cctggtcggc agcctggtgc acctgtaaaa ttcagcctta caaacagtct cccaccattc  73860
ccgcaccatg ggactttagt gttgtgtgta acagcggtat aggctgctgt tatcccatta  73920
tcaattgact gctatgctaa accaaaatta taataatatt gcttgtagaa gttagaatat  73980
aatttattcc ccctctcctt gataatttag caaaaatcca atataatttc ttcttttctg  74040
cttttagtta catcccaggg aagatgcttg catccccaat acaaactatg gtgttctctt  74100
aatagaattt tttgaattat atggacgaca cttcaattat ttaaagactg gcatccggat  74160
aaaggatggt ggttcatatg tggccaaaga tgaagtacag aaaaatatgc tagatggcta  74220
caggccatca atgctttata tcgaagatcc tttacaacca ggtattgaaa ttaggtaaat  74280
ttttgggcat tcaaagagag ggcactgtca gtcaccttat tatactttaa attctcttta  74340
gatgaaaaat gaaggaacaa cttctaattg ttactctttt ttcatcaaaa tatttcatga  74400
gcaaacatac taaaataaac agacacagac aatagaaaaa caccttggag acttccagat  74460
aagtagggag tagaatctgt ttaaccctaa aagcatagta gaaaaggcat tacttatttg  74520
gatggattca tgtttggtgg ctgcttctcc tttttcttgg gtccttattg ccttgattat  74580
aaccagttgt cagcaattaa tgaggcttta atgagatgat tctgaagtcc ttagaggcag  74640
caagcacagt aatatatctt tgaattcatg agcagaagga tgcaaggaga caatgtattt  74700
tctttttgaa tttctccttt cctctttgat tttgcatgtc tctttgtgct ttttccagct  74760
tcgtgtgggc ttgaaagtaa gcagaaagta aattccttcc atgctttttt gaagttctgt  74820
ttgcttgctt gtgtcctgat ttttctgagc aatatttttt cttgatataa ttgtaaaata  74880
tttagattca gcgttgttgg acttcagtgg aagtgctttt agtcatttgc tttaatgtgt  74940
aaactttgaa aatgagtaag gaaagggagt gaaaagatac agtagttgcc taggaaccat  75000
ttctggctta ttgagctgcc ttataaacat taatagttct atgtgtttat tcactgagaa  75060
aacattacat tgattgggag cctgctgtgt tcaaaagcat tgggccaaag gacacgaaga  75120
cttttcagca agatgatcct tgctttttag gggctcataa tttagagtga taaatagata  75180
tatagctaat ataaacccca aaaatataga agtatttcta atgtaacttg gggtttcact  75240
cttaggagtg aacagggcgc tatttctttt gtttgcataa ctgtttatgt atggaatggg  75300
atagttcttg atgggccaga atacatttcg acaactgata caccataatg aagtaccaac  75360
tgcatgatgc acatattcag agactgggga gctttgggaa cagctcacag ctcagcttcc  75420
aggcacaact ctggtgggat agctatggcc cttgctctcc tggaagaggg tcgtcaacat  75480
ttagtgcaca ttaagcacag tcaagcttac tatgttacct atatttcttt taaaggtaat  75540
gatgttggaa ggagttcata tggggccatg caagtgaagc aggcctttga ttatgcctac  75600
gttgttttga gtcatgctgt atcaccaata gcaaagtact atcccaacaa tgaaacagaa  75660
aggtaaaagt tcatgtgtaa ccagcccatt gtgtcaaaat tggttgtggc ttcttatctt  75720
caaattaatg ttattccctc cctctccctt tcttttaaa cacgtgcagc atactaggta  75780
gaataattag agtaacagat gaagtcgcca catacagaga ttggatatca aagcagtggg  75840
gcttgaagaa tagacctgag ccttcatgca atggtaagat attttccttg gtcgattgac  75900
tgagtattag aggcttttct gtgttgtgtg cgtttaatgg gaagaaacgt tttccaatct  75960
tttgccactc tttcaggaaa tggtgttacc ttgatagtag atactcagca gttagataaa  76020
tgtaataata atctatctga agaaaatgaa gcccttggaa aatgtagaag taaaacctcg  76080
gaatctctta gtaaacactc ttcaaactct tcatcaggtc cagtgtcgtc ctcttctgcc  76140
acacagtcca gctctagcga tgtagtaagt atgatagcct cagcccttct gaactcagac  76200
gcatgcacgt tctcttgctg gggttaacgc tgtcttgaag gctaaggcta cttcctttgc  76260
ttacatttta ctgggatatt ttaataactt ccatgcttgt actttttctc aacattttat  76320
tatgaaaaat ttcaagcata cagcaaaagt gaacaaattt tagtgagcat tcatgtactc  76380
```

-continued

```
accaatagat tctgccatta accttttact tgcttatctc atacctgtct atccatcact  76440
ctatccatta attcatctta ttctttgatc tatttcaaag tagattacag acatcagttc  76500
ccctagagta ctgtagcttg tgcatccttg tagccagact ccaatatttg tttattgttt  76560
tttccctttt ttttcttttg agacggggtc tccctctgtc gcccaggctg gagtgcagtg  76620
gtatgatctc agctcactgc aacctccgcc tcccatgttc aaacgattct cctgtctcag  76680
cctcctgggt agctgggatt acaggcgcct gctaccacac aggactaatt tttttgtatt  76740
tttagtagag acggggttta accttgttgg ccaggctggt ctcaaactcc tgaactcaag  76800
tgatccacct gccaccctcc caaagtgctg ggattacagg cgtgagccac cgtgcccagc  76860
ctattttttc cttttgatat gaaattgaca tataaggaaa tcttaattgt acatttacta  76920
aatttttttt tttaatttcc ctaattgttt tactttcagg gtctaggtta cttgctcata  76980
tgttcactaa attttatcaa atacatacat acacatgtat agcccaaaat cctaataagg  77040
tacaaatatt accgtcaacc caaagagcaa gctcatgatt ctttcatcaa tccctaaccc  77100
caccctcaga gggaaccact gttacgattt tttttttttt ttttgagatg gagtctcgcc  77160
ctgtcgccaa ggctggagtg cagtggtgtg atcttggctc actgcagcct ctgcctcccg  77220
ggttcaagcg attctcctgc ctcagcctcc tgagtagctg ggattacagg tgcacaccac  77280
cgtgcctggc taattttttt tatttttagt agagacgggg tttcactatg ttggtcaggc  77340
tggtcttgaa ctcctgatct cgtgatccac ccgcctcaac ctcctaagtt gctgggatta  77400
caagcatgag ccaccccacc tggcctttaa cattttttctt tctttctttt tttttttttt  77460
tttgagacgg agtcttgctg tgtcacccag gctggaatgt aatggcatga tcttcgctca  77520
ccacaagctc cacctcctgg gttcaagcaa ttctcctgcc tcagcctcct gagtatctga  77580
gattacaggc acgtgccacc acaccgagct aatttttttct atttttagta gagatggggt  77640
ttcaccatgt tggccaggct ggtcgcgagc tcctgacctt gtgatctgcc caccttggcc  77700
tcccaaagtg ctgggattac aggtgtgagc ccagctgtta tgactttttg acaccatagt  77760
tagttttgcc tgtttcagaa tttcatatat atggaaccac atagaatata cttttgtgta  77820
aggcttcttt cactcaattt ttttcagctt cctggttgaa ttttgtttgt ttttttgttt  77880
tttttgtttt ttgagacgga gtctcgctct gttgcccagg ctggagtgca gtggcgtgat  77940
cttggcccac tgcaagctcc accacccggg ttcccgccat tctcctgtct cagcctcccg  78000
agtagctggg actacaggtg cccgccaccg cacctggcta attttttgta tttttagtag  78060
agacggggtt tcaccatgat ctcgatctcc tgacctcgtg atccacccgc ctaggcctcc  78120
caaagtgctg ggattagagg tgtgagccac tgtacccagc caaatttttt ttaattgagg  78180
tataattaac ataaaattca gcattaaaaa tgtacaattc agtggttttt agaacatatt  78240
cacaatgttg tgcagccgtc tccagtaatt ctagaacatt tccatacccc aagaagaaac  78300
cctgcattta gtagtagttt ctcctaattc ttccttccct cccttatcct ctggtaattt  78360
ctaatctact ttctctttct accctgatag aatttttttt cttcccccat cctgatagaa  78420
tttatgtgtc aattataacg taagttacct tttaaaatca aggttaattt gtagtttact  78480
gatttgatat ctaaagcagg cttacctgtt tgattttaac tttattaagt gtaggtcatg  78540
aaaagtaatc taaatattgt atgttgttga tgaccgtgtg tcaatatgga atcataaatc  78600
ctcctgtgca aaatctcccc gtgtgccttt ttggttccta gagcagtatg ctctggagga  78660
cagaatgcca agctagatgt cacagacaca gggagatgga gtcttgggaa gtgagagact  78720
gcgactctga gatactgggt aaagtgccag ggccagggtg gagacctgca gagagacgta  78780
gcattgtcat ggcccaagca gcccagaaac aggtggggct cagcccactg tcgctgggaa  78840
gtctgcaccc acccacacca gtatgtttgg ttggaatgat cattgatttg tcattacaga  78900
caaatgacat cttgtgtctg gctgaagcca gggactagga cctaggttcc tcactcttta  78960
ccatactctt tcattttcta taaataaaaa aacaaataaa ctcagacctc tgtgagctcc  79020
ttcaaggtaa gatgtgggca gtggatttaa caatgaacag aagctctctg ataaaatcag  79080
tcactttaaa tgtttagagg aaaatttaaa caaacaatta attttgtaaa ttcctcagtg  79140
tgcttctttt aactcccaaa tgtttaaatt tagtctagag agtactttaa ccaaaattgt  79200
ttttctttct gaatattgag tatctaaatt actaatatgt cacattataa ctcatgtgac  79260
ttgtgttagg attccgatgc aacaccatgc aaaaccccga aacagctgct ttgccgtccg  79320
tccactggga accgagtagg gtcgcaagat gtatccctgg agtcctctca ggcagttggc  79380
aaaatgcaaa atacccaaac cactaacaca tccaacagca ccaacaaatc tcaggtatgt  79440
ggaacgtggg tttttaattg ttagtgtttg atacaaaata tttagagttt cctacatgtg  79500
aataatatgc agcatgggtt tgaagaaaac gctagattga agaacaaact tactttattc  79560
taagagattc caacacatga cagtgcttct aggaacagga tgtcctaagg atctttgtga  79620
gacaccattg taacataaac ctcttcagaa atctattgac tggtccttat aagatgttcc  79680
agccaaacta ccatataaaa aatgtttcaa ttgtacatga aataagctgg catgaaggtg  79740
ttgtgaggcc tcatggcagt gtgcatgtct gggaataatg tatccttttc taatatttta  79800
atgttcaata gcttgttgcc cgtgttgaaa tgatcagctg gctgtcaggc atggtcagtt  79860
gattaacatt agcctggact taaaaggcca cagagatact ctagtttaag ttttttttgtt  79920
gcctagaatt gtcattaact gagtaatgac tcagagtgag gggaggaagc cattgatatg  79980
gggctctggc ctgaggctgg gtcactccta actataactg ggaacctggg aagaggcctc  80040
ttggctgtta ccttgtgtct gatttgactc actgagttca ttttacctcc gtggctttta  80100
gccatgtatg ccagacacag actcaaaata ccagttcaag tgacagggtt gacagaaggg  80160
actggggtca tgagaaagcc acaggccatg aatagcagga agggagcggc cacctgtgct  80220
gaccccaacc tacccgtgtg cctgtcatgt ccaagagcct cttcccgcta tgtgacttat  80280
gatgtggtat ttgggttggt aggtttctta agaaaacctt tacatcccac acacactgtt  80340
aagaaggtaa gcgagtggtc tatgcttttc aatatttcca ttaaaataaa gtaagggttt  80400
cagagctaaa aagagttaac ccctgtaaca gctttttctg cccactagat aagtcagtgg  80460
tcagtaaggt aactctctag ccagcatatt cctagtttg aaagctgccc caaatccaga  80520
tgcttttctg caatactgat gtctttgtgg tcgttttctg tttctgcagc atggatcagc  80580
aaggctcttt cgttcttcca gcaaaggctt ccaaggtaca actcaaacaa gccatggttc  80640
cttgatgaca aacaaacaac atcaaggcaa atccaataat cagtattacc atggcaaaaa  80700
gaggaaacac aagagggacg cgcccctctc agacctctgt agatagtcgg cgctgcgcgg  80760
tggactgtct tctctgtgca atgatctcat gctcaggaca gttgcgcagg gactcctggg  80820
agacattcag gagcctcaca ctgttcagac gttgatttag caactgcgtt ttttcccagc  80880
tcgccacaga atggatcatg aagactgaca actgcaaaaa aaaaaaaaaa aaaaaaaaaa  80940
aaaaaaaaaa aaaaaaaaaa agggggaaaa aaaggctgct tatttgataa gtcatatgct  81000
acaacagggt cattttaaga tttaaagctt gaatgtaaaa taaatatatt tctcattggc  81060
tttatgcaga gttataggga atagtattca gtgttggtag ggtgatagaa acaatatcag  81120
```

```
aggatggggt ggggaaggaa aacaaaggta tctgatagga agtccagatt ccaaagggga  81180
aagtgatctg tgcatgtttt gttttttttt tttttaatat ttttgcatat atttaccatt  81240
ttattgtgtg tatgtataga agaccatata ggaaattgat atttgtaata gtggatttgt  81300
taataatact ttttacataa cattactgtt taaattgtaa acagattttt tctcaggatt  81360
agtttgaaaa ataatctaaa ttgtcatctt aacatccata tatagggaag tgattagttc  81420
tattactcaa tttgtttttc tcagcattga aatgacttaa tagaaccctt gtgtcctgct  81480
gcaaaaaattt ctcctctcta aagaaaaggt ttatggtggc aaatgatgtt tattttattt  81540
tgtaaaaaaa aaaaaaaaaa aaatactatg tactttgtgt aaacactgaa aaatctctgg  81600
tcatctctga gaattaactt gcaactgttt tctatagtgc tgtcgtcttg ggcaatgggc  81660
aattacatga ctttgtgttt gctgcctttg cagtcttttt ttttcccccc catttcttcc  81720
taataggaaa aaaaaacccc aaaaaaacaa accaaaaaaa aaaacggcca cccatgtctg  81780
gtctcattcc tgttgcagtg aaacttcgag ttccacagac tttgcatgct ggcttctcta  81840
accctgtgtg ctgcgtgtgc ctgtttctca tctcttattc tttttaaaat tcatgcttaa  81900
ctactgtggg agaataactg taaacagctt taattaaatc atacttataa aaaactattt  81960
tcttatattc cactttatgc ttttggtatt gttgatcttt ccaaattaaa tggtctttga  82020
taatggatct attttgtatt gccttattaa gaccaaatac ttcttgtcat cccattcttt  82080
atcctcttct ttcatggaat tgttatcatt aattaaaact tttttaagca ttggcttgtt  82140
tcaatcatac tgtaaatttt ggttgtagtc agctttgagt gcaatgagat gtataattct  82200
gttatcatta cctgttgagt ttgaaactca gttgggaata tttaatataa tagaatgtaa  82260
gtgacatttc tgaaaatgct ttctttcagg gtgaaagctc ttatgtttag catcagtgtg  82320
tatggctctg ttaaatacag ccatttctga gacaagattc ttttatatat atatacatat  82380
aaagtactat tggcttttag gagtttcttt tatatacatt tatgaaatac tgaagaccaa  82440
tcagaccatt aatggacact tagtgtaact ttttataaag aaaataatgc taaagtaaga  82500
ccaaaactga tgtcatcact gaaattaaca attttcaata tgttcatatt ttaattcaca  82560
atggaaaaat gtgttccgaa actggaaact catagtactc gtgtaaactg tggaagattt  82620
taaatgtgat gttattttga caatgtttta aattttgag tcacattctg atcagaattt  82680
ttatcgagat gttgagcttt tgtttttgaa actagtttgt cataacattg tgcataatca  82740
cagtatttat tttctaggac aattgtgaat gtgtagactt atgtttactg ctaagggaac  82800
aattatttat aaaataatat taaatccagt attagctgcc tatttcagac acttaatact  82860
tgcagagatc tatgttacat ttaccacact gaagtttttt ttgttgtttt ttgtttgttt  82920
gtttttaaag aatcaccctc attgttgaaa gtaaatgtac tcttagggtg cgaatattag  82980
tgttccaata agcatgtgat tatattaagg tggtggtagc gggaagataa tcttgattcc  83040
attgggaatc ttaggttttc gtaaatttat tgggaaaata gtttttcctg tactgctgaa  83100
gtttcttttt ggtaaacagt atctttctaa aagaaaaaag catgaaggag aaattgaggt  83160
gtgtatacat ttcctcaaat gaccagcatt gtattcgtga atactgtgta tcttgcagtg  83220
aacagtgtgg aagctgttca tttttcaatc tgaagtaaaa tactttcaat aacttttagt  83280
ttgcctgctc atttgtttta tacatttcat ctctctattt gactcctatc ttacttcttt  83340
tttgagtttt aatactttct ataaagattt tgtgaatata tcagaaatgt gtcatttata  83400
tattatagtc cattcatatc catgaatcat aaccttcctt tgctaatact tgtagaatgg  83460
gattttacaa attctgcctc actctggtga catttctctg gcagtcatgt atgtgtacct  83520
ggccattaga aatattaata tttaaatact gtttttaga ggtgctgatg ggttggtgag  83580
gtgtcagcac aaaatcttat gggttatgtt ttatgataaa agtatatcca ttttttccct  83640
ccagctttaa ggtgactgtg aaggtgcctg gttttgaacg tctttgtttg gtttggagat  83700
gttgcactca gttttcaaat ctagcttgga tctgtaggac ctatgttttt tataagtaat  83760
tgccctccag tcttcaacag ttgattctgt tatatttttg gcctgttttg agtgtacttt  83820
acttgcattt tgagccttat taatatttag cttatttgat ttggctccag tattcctaga  83880
tgaaatctgc acagggcaaa acatgggcaa tagggtgagc atttttaatt gtctttttcc  83940
actggaacct tatatatctc catgtgtttt ctgctcattc cctcccccat gaaatggtaa  84000
gtgtacttgt gtttgcctga acctatggac tagtgtttgg ggtttctgga aacactagag  84060
ggtcagaaaa gagtaataac cacgtgaagt gcaggattct cttgctgtga cgtgttcgtt  84120
gcaaagccct ctccagcgac tgggaggtgt agttgttaag gttgatctgt tagaaatcac  84180
cattatgagg tattagtggt aaatgttgct gatattttta ttggtcatga ctacatctca  84240
gttttacttt aatattgatc tatagtttga tcagttcctt gaattctaac atgttgattt  84300
ctcaatgttt ctgtcactaa ccaagaatgt ttctagacag ttggttgctt cacagtcaaa  84360
attaaatggt aaactatcaa aaagacattc ccaattttgc tgtgataaat attgaaacat  84420
taaaattaat gaacagaaga atttattctt acccatctat tcttcttctc ctagttcatt  84480
acactttttc agttactgga aaggcacatt ctctaagtat ttggtgagca aaatattcta  84540
taaatgcctc taacaaacct aattgaatat aaaagttaca tttagtagtt actgttgata  84600
gtaattttca tcagggtcat agttcatcta gtaaaatatt tagagaatga cgttaacatt  84660
ccagcattaa agtgggaaca aagatttgta tgtgaaattc cttgaaagag ttcatcttgc  84720
cttggtttct gaccctcaag actagctacc tgccatcttg tcagaacatt tgtgggtaga  84780
ataagtgtta aagatcaaat tttaatgtgc tccttgatat ttaacatagc taagaagcca  84840
gattttactg cagaagttat ttacatgatt tgaaaactcg acctaactgg aagccttttt  84900
ctcagtcatc ttgttctgag ccatcttgac ttcacaccat tagcaacttt tcttttttt  84960
tggtcaaaga taatgagcta aatatatgta gatattgaat gttgacaaaa ttattaacca  85020
gaaaaattgc ttataaagtc tgctgatcta tttgatatct agaattaaat atttgaggac  85080
agtttttagt tagtaaactg ctaatgttta ttttactgtc tctcaggttt ttggtttttt  85140
aaaaaaaatg tttggccttt acattttcta tttaagtgtg tactttattg agtttaacct  85200
tgtccatagc ctagtagcct gaaagaaaag gaggcggaac cagagagatg gatgtagtgc  85260
attcactttg gttattataa atttgtggta gctcctggat ttactgagag atattttagt  85320
tatgtcaata agaacagcta atgatgtgga aatcaggtgt tctcttgtgt atttcagtga  85380
acgtttttat tagtatttgc atatcatctc tagttctacg ttttaactta acgtccttgt  85440
ggcttcacca ctgaggtacc tttcactaca ccagcttctg tgtggcctgg taacatggaa  85500
ggtctctcct aaggacagtc tggacatatt ttgggggaat gttatttatc ttaaagatgc  85560
ctagaaacaa cgcatatagt accagtgaga aagtatgaag taaacaagtt gctcaggctg  85620
ggcatggtgg ctcacgcctg taatcccagc actttgggag gctgcagtgg gaggattgct  85680
tgaggccagg agttcaagac ctttgtctct taaaaacaaa caaaaacctg aatggtgagg  85740
tggggtagaa ttgggtaggg gagggaaagg gggacttgga aaagcattcc ccaaagccag  85800
tgacttggtg aagttcagta cttgcctctt agaagttagc ccatgccttt caaagagagt  85860
```

```
gaaatgatgg gttatcagcc acattcttgg agttaatatg tttcttcatc tttcaatttg  85920
gattctgtgc tattcatagc tcttccctaa gaccatttca ttattacctc ttatatttag  85980
ttgcaattta tcataatatg ttgttttgtc cctaaactta atctcctaat tttaagatcc  86040
tctctgattt ttgcatattg aaatttgcag aagtcacttt taagaagtct tttgaaagtc  86100
ttgcaatcct aaaataaatc aagcttgttt gttagaagtg tcatgagtct ccagtcttta  86160
ctattaaaaa gcagccctgc cttaacgcac attgttatgg gtgacaagtg acggacaaca  86220
agtgtagttt ctggatataa agagtgaagg actattgggt taaacatttt tagtggaata  86280
tacatagata tgtatattta gaaactttgg tgaagccagt atttgttttt aataaccttt  86340
tcatttattt ccttctttga ttagcattgt cttctgtgtt aagaaatgtg gactcctgtg  86400
aggtgctgga ggtttgaatc atcttgaaaa ctttccagtc ttgtctagtt accactgcag  86460
agacactaag gaatttacca gaaaaagata tttgatacaa atgatttaag aaatctcaac  86520
atttcctgag gccatatcac tgggcaacca gtgatgaaaa ctatgaatga attgcacacc  86580
tggaagattt tttaagctaa cgacagtttc ttcaaagatg tcaattattt gccttggaaa  86640
ttttataaat tgcatttcta tgcacatctg cccctagtgc ttaccacttg gtttattatt  86700
cataatctgc aattcaataa aggctttgtg ctttcattta tcttcaaaac             86750

SEQ ID NO: 4            moltype = DNA  length = 49960
FEATURE                 Location/Qualifiers
source                  1..49960
                        mol_type = unassigned DNA
                        organism = Macaca fascicularis
SEQUENCE: 4
aactacctgc tgtccggcag ccgcgcggct gctctcagcg gagggggcgg ccccggggcc  60
caggcgccgc ggcccggcac cccgtggaag agccgcgcgt acagccccgg catccagggg  120
tgagtgcacg gggcggccgc gggggcgggg gcggggacca tggtcctggc cggcgcccgc  180
gttgcagaca ccggttacag gcgcccgggc ttcttttgga ggatgcatgt tgaaggccaa  240
ggcccgactc tgctctgaaa gttttttttg tttttttttt ttcttgctaa tatgaaactc  300
ctttataatg gagtgacttg cccagatcct gcaagtaaca atgcaagaaa ggggctgctg  360
aataggacct gtaggtattt gtcttttttta ctcttgagac tggaaaggga aatcgactct  420
ccccctgcac cccgcctccg ggcaagtgag gaaccccttg ttaaagtggg gcgtagataa  480
gtgtggagtt tcattaagtt aagttgcaga ataatttagc attaccagga actcagatca  540
cgtcgaaggt aaatattaac cgtttttatt tcatttaaaa caaaaattta actgtcaatt  600
tagaggtgat tcattggggg gggttgtgtg ctttaatttc gtgctgcagt taacataagc  660
atagtatata catattggct taattcaaag aaaaaaacag atatgtcata tatatctgtt  720
ctttggaaga tgccattatt attttaaata cttccacatc cgcctggagg gaattagagg  780
ctctacttat atttagtgca cctacagacg gcaaggaatg aaagcaaagg tggtgtgtgt  840
ggggttggaa ttgccccagg tgaggctgtt caggtgtgat gctgttgacg cagctctttg  900
gccattttgg gcttttctga gcgtctggaa ataatttatg tgtgggttgt atgtcagtat  960
tttaagactt aaacgataaa ttttccttgc acgatttttt tccccccaat ttaaaaaaga  1020
aggatttgcc ggggtatgag ggttgttaca tgcagtagag tcctacgaat aaccacaatt  1080
gctaggcgtt gggagttgtt acagtgcact ttttcttgta actctgtttc tcatgtgaag  1140
tatgttggga aacagagttg atacttcttt aaagcgtgtg atacactgta atagccgcat  1200
gttgtgtaac ttttttcacc tggcttgggc tacaagtgat gccttctaaa ttccctgaag  1260
gtgtaaacat gcattgcaga cactggcggg agggcagact cctctccctc cagttcttac  1320
ctgtagaact ttctgagagc aggtggttgg aagcggtttc ttcttgatgt atagtaatgt  1380
atacctcagg gctcgcttgg gaggaccttt aggtttccag cctgttatgg aactggcatg  1440
ggctctttct agtgtctctt agcactagaa aaaacagaca cgtcgtctct gcaagtcttg  1500
ggttgtacct ctgctcttag cggtagcgca tcaggcccca cgcatctcac ttggactccc  1560
caagctgttt cctcctggta actagtaagc ctcagtaggt cgtgttgctt ttgttagtga  1620
atgagcccac tagggtcagg tgctgtgttg ggatctgggg atctggtgca gagacgatat  1680
ggagacaatc tcatgatctt gacccaccct gaaacctgcc tacaagtgcc ccctgcctag  1740
agcacaagag taccctgctc agttgtgcag gtcccctctc acgctcttcg tcacccacgc  1800
ccaatcaatc atcagatgct gttcgtttgg cccttttaat ctctccacac ctcatcctca  1860
ggcagtctct tgttacctct gtggagatcg ctcaagcagc cggaggtgcc ttcgatgcac  1920
tctcgtcctg cttgagtcct ttcccatcac tgctaatggg gtgatcttct ctgccggcag  1980
gtctggtcag gttccccttc accctctgat gtcacctcct ccatctccaa tcccccacat  2040
taaagtctaa agcctaaaac tcagcaacac ctccagggtt ctgctactca gatgaccctg  2100
ggtcctggcc cctggcccca cgccccaccc cttgccaacc tgttagaacc cagctgtaag  2160
gcagtatggt gtagggcata agagagggct ctgaagcccg tcaggaggtc tggtttgatg  2220
ctacagtcat gctcttggaa ccttcctttt cacctttgct ggagacctct ccttgcctgt  2280
ctccaggtgg cgtgtaccat gcctccagta tggccctggt gcatccactt cctgctgtct  2340
ctgcccaaag gggcccgtga ggactacctg ctatgagcct agaagggcac gttgacctct  2400
gcttgggctg ctactcaagc tgctctttca gaagtaaacc taagcggtgg tagagttggg  2460
cctatgacta gaggaggtaa ggtcccccca gtgatcattt ccacatggcc cgttggtcct  2520
acatgaacta accttttcgt gtcaagaaat agttccgtct agaactttct tctggccatc  2580
agcttaccca gagtgttgag aaaggccacc aaaaagtctt tcagttgtgc cttagagaag  2640
gaaataactg agttttaaag gcacacctga gctgaccaat agtaaaggat cttgttgctg  2700
ggaagctgct tggggttgtg atatagtccc aggacgtgca cttctgaaaa tgcagtgtgc  2760
gttcctcatg ggaggatgag cctgctgcgg agcactggct gaacccagtt gggtctttgc  2820
ctggtagccc atgtggcaac ccgcactatt tgtccttttc tggggaggag ttttctgtcc  2880
ttggacactt tgcctggtgg cttggccttg tgagactgcc agtctgcctt ctgctcaagt  2940
aggatgaaga aaaagcaggt gaaagaggac agggattggt gcaagaacct tcagaggaga  3000
ggaggtgaaa tgctcctttt gactctggtt cttactccat tgtttgattg aaatcccaag  3060
cctttgtttt gggaatggtg tgcttagcgt gaactctgct gttgacctgg gcttctgacc  3120
ttgagatgtt gggcaggtgt gtggacaggc cctgggcccg ttgcatccca gcctctggct  3180
gctgttactt gcacgtgctc tcatgccctg acccagcagg gctttgagct gttgttactt  3240
tgccatggtc attctagcag ctttggaaac ctctccaggt taaaagtctt gcgtaagtga  3300
gagtgggagc atggccttca gatatttggc cacatccttc ctggtgtgtt acagagaccc  3360
aggaagagtg tagttgaacg aagacatgtg caggtgtccc gggccttgaa cagcttctat  3420
```

-continued

```
tcagagtttg gccttgcgaa ggctgtgcca tctcaggtgt gcctgcagtg tgcagcaggt  3480
gtttgcagct tcctctctgc aggtttcttg atatttaatt tcatctttta atatcttctg  3540
ttaactcaaa ggaaattctt agtttgacgt atgagagaga ctgaccactg tcagcatagg  3600
acatggtcag ccgtatctca caaggcccct ggtgagagtc gtttccaact tggtgcatgt  3660
ttttttcgat tctttcttgc aaaggagtca gagcttggag gcgcaaccag gatcccctcc  3720
tctccctcta gcctggcctc actgacataa agtagagcag gtgtgacctg tctggaacgt  3780
ccttgtgatg ctcagcaggg cctgctgcag agcacgggag gcatcactct aggggccttt  3840
ccctcccata ccttcctgtg agtgtccagg atacatagaa aggctgtcgt gagacctgcc  3900
gtaaaggatg gcggtggcac gtgtggacct tgctttctga gtttcactgt ctgagtccca  3960
gaggtataag cttgtggaga gaagtgtaca tgatcacact aagcagatac ttgctcctgc  4020
actgttggag gaggaggagg gattaatttc ataatttcat aaatcaactc ttccaacact  4080
cctcctgttt agtaatagca tcacttgttc ctgtcttttg ttccattgcc aagctcccca  4140
aggtgaaatt gaaaatagag tgcaagacac aggctgtgtt ggagttgagg aaagttttgc  4200
tggagaactg cttgcaccac gtgtctggtc actgatagat gaggactggc caggtcagga  4260
cagctgacac tgggagaagg ggctgcccgg gggggcatga cagactctgg aaaaggaggg  4320
ttggagtatt aaactggctg ggaatgagag gcctctaatc ttttctccaa aaagaaaaaa  4380
aaaaaaaaaa aaaaggctta atgctcatgc ggtggaagtc agagtgaagc aaagtgagtt  4440
ctgtctgtct tgctgctatg agcgtgtgat ggaacaacag tgtcatttgc tttttctcaa  4500
atatttaatg catgtttgtg acataatttt tttaagtaat ttcaaataaa tattttaaag  4560
taaaaagttc taagattttt gtgtctccag gtaaagtctc aaactgtctt tggtcactaa  4620
tatgagattt tgtcttcatt ttaaatggat tcatgtaagt gtcctgtggg agaagagtta  4680
atggttatcc ttggaaaata agaacttttt atgcctcagt taggtcatat ggtttaggat  4740
ctgattttgt agttgtggag taaaaaaggt tgtttaagaa aaaaaaaaca aaaaaccttg  4800
atattcaaat tcagaaactt gatttttgag gatgcaacca gaatttggac taacggtgga  4860
gagggctggc ggagtcagac cacccagact cgcagaagat tgaagaagct gcagtgctcc  4920
tgtggagagg ccctttctag gaggtgtggc tggcttgtca gtgctttctc ttctctgcag  4980
tgaattggat ggcaagcctc gccctctttg aaagctgcca ctctgagcct gccttgagag  5040
catctcaggg agggcagaga ggtggcctcg gtcagcgctg acaggtgccc aaattacctg  5100
acctgttgtg aacatgtgcc tgagtgaggt ggccaggatg ccttttctcc caacactggg  5160
gatgtacact catgcaacat cctatttttg agatttctat gttgtggtag ttctctgttg  5220
ctgtgtagca aattagcgta aactcagagg catagaagaa cactcattta tggtcttgtg  5280
gattctgtgt gtcaaatcag ggatggctgg gctgggttct ctgctcaggc ttttgcaaag  5340
ctgaagggtg ttggccagct gtgttctcag ctggcactca gggtcctctt accagcgcat  5400
tcctgttatt gttagaattc agctccttgc aggatcgaag tccttgattg cttgctagct  5460
gccagcaggg gaattgggta gggctctctc agcttcttaa ggccacctgc attccatctg  5520
caaagcaagg tactttgaat ttctctgacg tttcccgcca gctgcttaga agcccatgga  5580
agccccctgc ttctatgggc ttgtgtgatt gagtcaggct cctgcgaata acctccctac  5640
ctgaaggtca tgtagtaata caacatgatc atggtgtgat aacctcatca gagccacagg  5700
ttccaaggag tagggtgtag gaccttgagg ggaggaggtt cttctgtggg tagacttccc  5760
ctggcgtgga atcggttgat gaggaggttg tggttcttct tgtccaacac ttttcccctg  5820
actggactcc agcccatcgc aatgactctt gcagattgcc ggttctgtcc tctggcttgg  5880
tggttactgc tgaactcagg cagccaccat aaccaggaga acctttctgt gctgcagtca  5940
gatggacatt ctttaaaata tgtcgtttaa gaaaagtttg caggaaagcc gtgtgaatat  6000
atgaaactac ggtgattgaa aagtcctgtt tgtgaggtgt cctgcattgg ctggattagg  6060
aaaggggtca ttcctatgca ggtgggggtc gatgacttac ccaagagtca cctctggaac  6120
attctcgtat gttcatagca gtccatcttt gcagaaggtg tgggggacac ttgtcctgca  6180
agcccaggtt cgtaggaatg ttagcttccc cagacccttg gccgcagagc accgtgcctc  6240
ctttaggagg gacaagaaaa ctcccatatg gttcttccct ctgtcccttc ctgagcccct  6300
ctgagtgttt ggctcttgtg gagttactgc tgctataaca aagctgaccc gactgccctc  6360
ctgagtctcc tcagggaagg aggagctgta ttgtagcctg cattcttagt gccaagcaca  6420
cggtagccac taagtatgta tctcccaaga aagaagagca gaaagaggat ctgccagctc  6480
aggagggcag gtgggggatg gcaagtctgc ggagtgttca taaaccaaat gctaagggaa  6540
acttttgttg gttgtcttag aattttaaaa aataaagtct gttgcagttt atctgctttc  6600
cttcctggag agtggctaaa ctaatgttct cttttacaat atagaatgcg agagcagaaa  6660
acattcagga aaattctata ctgtatttga aaaacatcac catttagttt taactgctcg  6720
ctcttattat aaaaattaat acctaactat gaaaagttag aaagcctgga gaagtatgga  6780
gatgagttgt ccaccattgg gccacctaga gagtgcactg tgagcctgtc cctggtgtcc  6840
tgtactctgg tgatgtgcac tgcatttgct ggcagtgagc cagggagtgg accacatccg  6900
ggcctgggcc gggtggatct ctgcagaagt ttatctctcg gctgacaggg tgggctagat  6960
aggagcagct ctgagggtcc ctattggcag ggaatgtttt tgattatcaa tgacatgcct  7020
ttttgttgtg ggcttgtgat ctttttcttt cctaaatcag ctgctgtgca taaccagtta  7080
ggctctcccg tggcttaaga ttggaattgg tttcccaatg ctaggatgtg ggtgttaggt  7140
ggtttctatc tttccgtttg aaagaggttt cagatcagtg taacatttct agaatcctgt  7200
tgatctgaag gaatggtaga atgtagtagt ttaagggaaa tgaaaagttg aattattttg  7260
atgtttctgc tttaaacctg ctgggtggag tccatttctg agcactggga gccacgtgct  7320
tggctcttga gagcctagct cgatcagccc atgtcacaca ctcacaggtc tggctttgcc  7380
tggtttcgcc acggtttcta acttgagcct cagtttcccc aactgtgaag cggagcctgt  7440
ggcacccacc ttagagcaca tgaaagactt ggaagaggcc gggtagcctg taatcccagc  7500
actttggagg tcaggagatc gagaccatcc tggctaacac ggtgaaaccc catctctact  7560
aaaaaaatac aaaaattagc cgggcacggt ggcgggcgcc agtagtccca gctacacggg  7620
aggctgaggc aggagaatgg cttgaacccg ggaggcggag cttgcagtga gtggagatcg  7680
cgccactgca ctccagcctg ggtgacagag cgagactccc tctcaaaaaa aaaaaagact  7740
tggaagcact ctgtgagttg tcatgcaaga gattaaaaag gccaccactg ccctttttctc  7800
ctctctttaa ggaaattgaa accaaaaatt aagtccttct tcttgccagc tggacaggaa  7860
aagccttttt cttggttttt tgaaaataca gctttcactt tcagatcaaa gtgaaaactg  7920
ctaaagactg aatgttctga gttgtgggag tggggggctg gaggggtgtt atgaattgaa  7980
agatactttt ctatttttaa aacattttaa caatgcctta ataatatctg ttctagtttt  8040
gtgttttttt tttttttttt tttaactgtt ctgaaggtac atcagcactg ttctacagct  8100
ttaaataaga atctcatctc cctagaggca agggtactct cgatgtattt ggtcaggggt  8160
```

-continued

```
gaatgtgctg ctctgtgtaa ctcgtttaaa gttggttaag gtttttttta ttttgtgcac  8220
atagtagaag gagtgaatga agtgttttct gaactcttcc agcttttaac atagtattct  8280
gtgtatagcg aaagaaaaca aaattaaggg ccagggaaca ttaagaaggc aactagaaca  8340
gcactgtcca gtagagcttc ctgtggagat ggaataattc tagttttgca ctaatacagt  8400
agccactggc catatgtgac ttttgagcac ttgaaatgtg acaaatgcaa ctgaggagct  8460
gaattttaat tttatttact tttaattaaa atttaaatgg ccatatattt agacagctct  8520
gaactgcagt aactttagac tctatttgaa acagcgtttg attcagtaac tgttgctgaa  8580
ataaattgaa actcatacaa cagtaaaaac tgtgttactc agcaagttac cactgtgaaa  8640
gctctagaaa ttgtttgaat ttccaatgca aatccttttc aaacagccgc tgttttaata  8700
gcacatgaag cataaaatag gtgcatagca gcgcaacaca gagcaacacg gagaaactat  8760
tgtgacctgg agtgtctcca gtccagcatg caggtgatag gtctctcagc gtttttgcac  8820
acaggttaat gatggtgcag acggtcactt ccttctctga acagccttcc tggtcaccag  8880
caccactgtg gctcatgtgt gtgaggctct tttggcttag ctctctacgt gagtttgctc  8940
cttgagttcc cagagctgac ccatgaaatg agtgatatta ctcctgtttt gtagatagaa  9000
aactgaagcc ttgacaggct gacatgacct ggcaaaaggt gctgcacttg gaaatgtcaa  9060
ttcacggctg acatctggac actttactcc taactgttca gtgaacaaga cgttgctaac  9120
atgcggggga tggaacctag caactcattc tacaagtatg gttcaaatat gttggtacag  9180
ggccttttgc tttgttttcc taaagagatt agattgagat gtggcggagt gctttgacag  9240
ccaccgcagg acaaagttga cagctctggg gttggggagt gttgaggatt tcggagggaa  9300
gccagtcctg ggcagtagtg cgctctgggt tcgtgctttc tcgaggtgtt ccagagctgg  9360
cctggaggga ggctgcggtg cggcagcggg atttctgtca cctggagtat tcttagaagt  9420
tgcattctat gaaaagtgga gcatctgatg agctgtttac tcgctgttgt atctgacggc  9480
agttgaaaga caaagcagga ctggcagcgc agccgcctca gtcagcactg ctgcgttggg  9540
ggcttgacct gcagtctcgc aatcctgggc aataactcat tttcaagaaa gaaaaattaa  9600
acattaagtg attgaagcgt cttgcccaag ccgctactag aaaataaagg tgctggtgct  9660
caggtgcagg tctgcatggt gtgcaaacct gggctccttc ccacaccccc tcagagaggg  9720
cactggtatg ttggagtgaa gagccacgca agacctctgt gaatgggcag agatgggccc  9780
gtggcgcaac acagtaaaat gtattttggt tatgggcatt gtctctaaac ttatgtaaaa  9840
cattataaaa aatggaagga caatgatgaa atgatggcca aaaacataga aaaggatacc  9900
ttgcatgtac tgtgaaatgc aaagaaattc taaagtgtca ttacgagtta cctcatggaa  9960
gaaagcaaaa ggtgaatcta tctagagttt gtggttctga ctcacaagag actgatgttc  10020
atgctgaagg acaagtgtga tgggtggaag gatagagcgc caagaccaca ctctaaagat  10080
gggaacctat gggaactgtc cagggagatg aaagcatgga atgaactgaa gcttgtggac  10140
ttgttgagta gaaagagcct tttaggattg gttttagaat aaaataataa ggcctgtggt  10200
tggggaagat gacttgctgt tcacagagcc tcccttaaca ggtggggacc tcagcttttc  10260
ctttgctgcc atcaagtgag tggtgtacag tcctagccac agtagtaatc tctactggcc  10320
tgactgagcc ctcacccttt atgcagtgtc tcctgccacc ctcctgggag aggctgttct  10380
cagcatagct ggcctggggt cacacagctg gtaggtgtaa agctggcgtc ggagtccagg  10440
tagtctcact ccatagcctg cctctttagc caccgcagat gtagagcaaa gcaagaattg  10500
tccaaagagg taagctaata aagaggaaaa caggctgggt gcagtggctc atgcctgtaa  10560
tcccagcact ttgggatgcc gagaggggtg gatcacgagt tcaggagatc gagaccattc  10620
tggccaattc tctgggcgtg atggcacgca cttgtagtcc cagttacttg ggaggctgag  10680
gcaggagaat ccccttgaact caggaggcgg aggttgcagt gagccgggat cacgcaactg  10740
cactccagcc tgggtgacag agtgagactc catctcaaaa aaaaaaaaaa aaaaaaaagg  10800
aaaacaatta tgctgagttc cagtaatctc tgggtccaga gaagtgatat ctgacttctc  10860
aggagagatg ctgatgctgt ctgagggcct gcccagtctc cgaatgattc agacactcca  10920
gggatggaca gttagtgccc taattttccc aagaggattc tgagggtgac ttctctcaac  10980
ccaacaggag gacctggtgc tgtcatcacc agttggagag aggctgtttt gtgaggctgg  11040
ggaccacctg ctgtgtgtgc cgtcttacac tgccatttgc tgatcgcttt agagctagag  11100
gttgtttcta agagtacttc gtgctaacta aaaaatgacg acattgtttt tataaaactg  11160
attcatggtt tgttttttga agcagaaagc tctgaagtca ctcagtccca ccacccagaa  11220
ggacaattag gtgactgtca ctataggacc tctctaggct cgtgtagatg gacacatgga  11280
ttggtcagta gaaatactta cattaaaagt cttatcttta cataaatttg ccaaattatt  11340
aattttgctt gaaagggaaa gatgtctaac ttcagttgga aatactggtt tctgagagat  11400
agtgctgagg ctaagaacat aaaacatgaa aaccgtaagt ggctaagtgc agaaacatca  11460
gagtaaaatc tttgatgaag tcttggtttg cttgggctgt gtaggttgga ggctcagcct  11520
ttgtttctcc ctcctgtggt gcccagtggt ggtgtttctg tgtccatgaa ttttcagcat  11580
ctgtagtttg tagttatgac cactactgca cctagccctt actgagggcc agggcctgtg  11640
ctaagcactt cccagtgtgg attcattaag tcctcataac agcaccatgt gggggcagct  11700
gcgtccctat gtcgtacttg ggacgcgatc tgaccccagt cacttcgggc tcctaaaggg  11760
tctgcagtct cgcctctgcc tgggaaacca cgatttgcag catattccac agacctcatg  11820
cttatcacca ggaggcttcc tgggactgct gtctgaggtt tctaagttcc taacgtggtt  11880
catgcttctg gtgagtttct ttgaggcgac atacccagca ttgcctctgg tcagctcagc  11940
cctgtggtcc cgcgtggcat cctgcagtgt cctctggctg tgactcgtgc cgcgccacct  12000
tgacctggca tccactgtcc tccactgcgt ttgcaggtgg gagccactgt tggtgccttt  12060
tgtcatgtgt gttgaatggt cagggtccca aataagagct gattggggtc attctccttg  12120
aatctgccat gtgcctggac cactctttgc ttcagaactc acacatgttg cctgtcctct  12180
ctggcttgga gggttgtgtg gaatcaaagg tgagacccag tccccaggga tgggcgtttg  12240
cctttgattg cccagctgtc ctgagcgccc tcgcttccgc gcccagctgc tgcctcggtt  12300
gcttgcttga ggatccggat gtagactgag gttggcctta atgtggcagg gggtttctct  12360
tgagccttgg atactttgct actggtccca tcttcctgtg agtgggagcg tcccgcctgg  12420
cccagcctcc cagcggtgac cttagctctc ttagtatatg ggctctgcct gccttggtcc  12480
ccagcttgcc accctagtgc agttgctgct tcgctcttgt tccgctcctt gtctctgtcc  12540
accctgtgct ttattgatgt gtccttactc ggtgttttct gtggagcagg gcatcctggg  12600
cttcctctct gatccctggc tcctgtgctc ttccctgctg ggctccctct tcctttccgt  12660
tttctgctgt gttgccctca cacagctggc atgccacgga tgtcgctcac ccaagccctt  12720
cctagtgttg ctcaccaaac acctcccacc ttgcccccgg gaccttctcc ccttccaggc  12780
tgcaggcagg ctgagggcct ggcatctcag gagtgccgag gctcagcggg aggcagtggg  12840
gcctttgctg gcagctgggc tctgcatcct gactttctga gggcttagtc cttttggtcc  12900
```

-continued

```
atcttgaatc tcctccaggc ttttggactc tctgctctgt agctggccca tgggaacagg  12960
tacactcagg cctggtctta gactccacta cttgggctgt gccggtgccc ttggtgtcct  13020
cttagtccgt cccacctggg ggccccatcc tgctgtccct tgtgccagag tgctgtcctc  13080
ttgtctttcc acaactggct gctcattgcc tttcccatct cagactcagt tccagcccct  13140
tggtatcagg gaggctctcc ttgagcaccc aacctaaagt tcacagctgt ggttaccagt  13200
ttaaatttct gcctagcacc tttttggttt attttggcta cttatctccc ccatcatgcc  13260
ccctgtccct cccatataaa ctcagtgagt agggaccgca tcatcatcct gcccacagct  13320
ctactgtctg tatcaaccgg gtgcgctacg cagaggctca tggtaaataa ctgcagacca  13380
cgaatcccat ctacttgctg tgctttaata ttggcttaca tctttggatc cagtgagttc  13440
ttttctctct ccctctctct cgctcagtca tacttacttt gtgtaattgg tgatttccag  13500
ccttttgtat agtcctttct tgaatagttg ttttctgtca tcttggcggg gcctcagggg  13560
gttgactgtg tggagggcag gggctgcaga gctgcagctg ctgcctgggc tctcatggcg  13620
cctgcgaagt ataggcaggt gctttgcctc tgagccatct gtagaatggg gtgacggtgg  13680
tttcatcaga ctcagtgaag cgtgtcatac agtgagcgcc tggtcacagc aggcagatga  13740
tgaatgtcag ctaatgagta ttcatcacca atgaatagta acaatttttt ctactaaggc  13800
tatgtaatgt agcctcggaa tcccactcag cacagccccc tggcagcagt gcctttgaga  13860
gctggcatgg tcgagagacc ctggttggcc ttactagtgt ggttggggta cttgagagaa  13920
ctccttcctc acatagctct tccggtgttt agtctttgca tctggaggtt tttcgcgatt  13980
gtgggatagc tttttcaggg gccttgcctt tggcagggca gggacgtgta ctgctgcaat  14040
ctggggtatg ggataacttt ctaaaccaga cccagaactt gacggccgaa ggggcctctt  14100
agccatgcgg ggctaggagc tgacacaggg tcagcagcac gaggtcctgt ggtgctgggt  14160
ggcagagccc ggagggagcc cctgctggtg tgactttagt gtaaaggctg cgggatccca  14220
aattcttaca gaagacttaa gacgggcaca gtgatgtctg ctctttgacc tttgcagtat  14280
gaattagtaa aactgaaatg attacgcttc atttattagg attatgaaaa caataatgta  14340
cttattgaag aaaatgtgga aaatacagaa actacctata atttttctat tgttaacatt  14400
tgagcatatt tcttgtcact tttaatgctg ctttaaatat gtagcaaatg tatcattttg  14460
cattaaaaaa aaatgctgct agcatttcct cctgtcttta aaaagctctt ttaaacaact  14520
ttaaaatatt gtatagatag atgtacacaa ttttctcaat aattggagtt atatttacat  14580
cttgtcactc tttaggaaag gactggccta cttctgtgtt gggttccttc ctgagtgtgc  14640
tttccagctc agtggctcgg acttcaagat ggagacttga gtcctggttc tgtatagtct  14700
tgggccagtt accatatgtc tgatgaatac ttagttttgt catctgtaaa atgaaaatag  14760
cagtacttgc ctcaaagact atttgggagg atctagtgtg aatgttggta atgcggatat  14820
tgtgtagtgt cccagaatat taatgttttt agcctcttgg ctcttactct gtattgttgc  14880
cccaaaagat gatgttcgct tcttattttt catccagtgt aaggatatct ggaaagacaa  14940
agtatagctg ctttcatttc aaaagtgatc agctgcttga gctagcaagc aagctagctt  15000
ccaggcgcag ttatgcagtt tcacagcagg cgcggttccc tcggagcacc cagaggtgct  15060
ctgtggtcgt cagcagtgat gctgtggctg cactgccaga cggggtggca ggtggaccag  15120
agcagatgtg gctcaggaag tgccgtcttc ttcgcctctc cttaatctct ttcagagtct  15180
gtgggttctt gattgcgctg tgggttgctt cagactccag tattaggaga ttgaacccct  15240
tgggtttttg tgtgtgtgtg tgtgtgtgtg tgtgctgagc tgggttgagg acatgttaag  15300
caggtggggt gcctcccctg ggtttgctcc tggtggttcc tgtagtgtgg ggtggttctg  15360
agtagttctg gccccactgc tggggtatct gccgactcag tttgtgagat gtggagcttc  15420
atcctggtct ggtgcctcat tttcttcttt agcagtgggc ttagaaccaa tgcagattcc  15480
caagttaagt atttttcctg tggcttaatt attacaagtt tctggtacct aagccctttc  15540
ttactttctg ttctgagggg aagaggagat tatggtgttt ctccccactc cgagtggccc  15600
caggaccttt gcatggcatt tgccgtgtgc ttgggtttgc tctactgggg tgaaagagta  15660
tcatgccccc cagcactcac aaaggcacct ctgctcaccc tccggtgagg ttctgactgg  15720
ccctgggaca tcacctgctc caggatcctc tgtggctcat cccaggagag atgtgggaga  15780
gggaagggga aaaaaggctt acacttgtcg agtggaattc ctgtaggtct gagttccaca  15840
ttgattccta agctgcagaa cccttctgcc ctggctgttt tgtgaatggt agtcagtctt  15900
aacctttta accaagttaa cattggctgt ctcaggaggc tcacagctcc tgctcctcct  15960
ccaggggagt gcgccctcct cctctgtcgg tagctgtcag gcgcccctc cccccgcagc  16020
agattctcct gggtccttgc ctggccttct ccttacacgt gagcctgcag cttcattcac  16080
agccgctgtg tagaaagaca ggcacatcga taggtccctc cctgcccaga gtgggtggaa  16140
ctgaggcaga cactaaaagc agctgactgg cagccctaga aacacgaagg gtttcattta  16200
tagtttcagt ccttttcctt ctttcgagcc ttgatttaaa aaagaaagga aaaaaaaaaa  16260
gccttgaaat cctgcttctg gattttctaa tttgtgcagg tattagttgc cttgtaatgt  16320
aattaaaaat aaataaaaat gatttataat tagctcatta actgtatcag taaatggatg  16380
ctttaaagag gatcattgat ccctcaaaac agaagcaatg cagtcgttcc ctcattatgc  16440
tgtacttgag atttgctcta gcaacccact cttcctaaag ttaaatatta atccagaccc  16500
tatcagtgca acgtagtagt gtctgaatca gttgtggttt tggtgtaata gcatcaaagc  16560
atgttataaa atctacaaaa ttgtagtggt taactccaaa tatttcactg agacattatt  16620
tttttgggca aaaatgcata gtgaacattg tggagctgag gtgaggaact tcgatttctg  16680
agaaaccacc cgttttaagg gttttgaagg aagagttgga ggagaagagg gagagaataa  16740
attaacagtg agtttccagt attttctgtc gcattttacg ttttagtgga aaaaactggg  16800
aactgaactc acatgcagtt tgtaaaatca ctttttccct agcattcagg attgatgaga  16860
tttaacgggg tgttaaaggt aaactgaggc acataattaa catggacaga actgtatacc  16920
tgagtgtcga gagctgtgag atttcagtga gttgggagac tggaagcgcc cattcttcag  16980
agtgcatctc ctcatgttca gtgggtttaa ggtgctgaag ccttttttt tttttttttt  17040
gaaatggggt cttgcactgg tgcccagact ggagtgcagt ggtgcaatca ccactcactg  17100
tagctttgaa tcctgggctc agcctatcct cccacatcag cctcctgact agctgggact  17160
gcagacctgg gccaacactc ctggcttgaa acaacttgta tccagattgg aggagggcgt  17220
gtttgttttt gtgacctttc ctttccctta aacattgaat aatatcagac ctttgaccat  17280
cactttgctt aaaagaagct actggattta aagtctagga gaacgtcctg gacaagcaaa  17340
cccatagtat gttcctgtat gttccccacc cagagacctg gattataaag tgtttggtgt  17400
gcttcttctg gccccactgt tctttctaaa gtgtttcatt ttacataggc tatcctggct  17460
tcagggttgt cacctctgcc tttgtgcccc ttagtacctt tgtcctttac ctactgcagt  17520
gcagctgcct gttcttcggt agactacaaa gaagtcactt ttgaacaact tagaaattgt  17580
gccttgtggg gaaggcaggg cagagccttg ggctgagat ggaggaggag ccagctctgc  17640
```

-continued cctgggaggg atacgaagct cgtgaggcag gggacgggtg gagttgcttc acctctttgg 17700
ccccagcttc aaaaccagcc agtcctccct ggctttggct ttaattcaag tttggacaaa 17760
ctggaaaacc agttaatccc attagctcag cttctaaagc cgaaaatcat gccctgaaat 17820
gggtcatctg ttttcatcaa tagctttatt agctatggaa taatatagtt ttgttctcta 17880
actgtaggat ccttcttttg ctcttaaaat agctcagtaa gttgggtctc ataaatacat 17940
gcagcaagca tataccagat aaatacgaaa acattgctga tcttgctttt tagtactaaa 18000
agcagaaaat cgggaattta ctaaatggag aagtcagtcg ttaccttttg atgggtttgg 18060
actcttgcaa ggtagtgatt gtaaacaaga gtgatctttt gttgtttttc aatgaacttt 18120
attctctaat ttttagtaaa gcacactagg aaataatgct tcagaattct gttttctagt 18180
agtttcttga ttaaaatgaa aattcactaa aaaaaaaaac tctgctgtca ccgtttcctt 18240
ttttcttaag ataaccagga aatgaatcat tcagggtttg ctccatggtg atgggtcagg 18300
aagctgcccc tgctgtgtgt ggggcaggag gcttgctgat gtcccaggat ttcacttcgc 18360
ggagacaagc atcagaggct tgcttcattt atagatccta cttcttttct acaccacagc 18420
caactcaaaa tggtgacaaa atctaagacg aggctggaag tcaccgcaga gcagttggaa 18480
gctctgcccc cggttctggg ggcagtgttc ctggagttgt gtccttcggc cccacctcag 18540
tttgtccatt cagctcctcc actgagaatg agatttgtat cataaaggag tttcctgggc 18600
cactcgcagc ccccagctgg agagtgccag cctaatgtgt caggagtagg gggcgaggcc 18660
agagggctat gtgccagctc cttccctaag aagcctcctg ggaaagccct cccaggcact 18720
tcccaggtct cactggccgc ctgagggtgc tcaggccgcc tctccgctgg cactgcttcc 18780
cgacgtgccg ccagcctttc tcatggggac ggggatgatg gcatgcttgg ggggcagcag 18840
ggccttgggg ctgcctcggg ctgtcagtgt gtcctactgg ttctgagatg ccacctctgt 18900
gatccactgt agagagatat attctattat ggtcaatgca tagaaatttc ttcgatttag 18960
agactgaaca ctagtgagca gaactgaaat tgagctctta aaagattttg atgactggtc 19020
tgtggatagc agactttagt gtggttatta tgcggacatc ctgccagttg taaattccct 19080
ggaggtttgg tatgtgcgaa cataagacta aacttatttc tgttttgttg agaagaaatg 19140
attaaaactt ttcattgatg tacttctgta acagactttt ggagaattga agcagtgggt 19200
atattcagta tttgaagtca tagatgaata aaggaggtat gtcgtagttg gcactggtgg 19260
catggcctgt ggtcagcaag gcttttctgt gaaggtatgt gcacagcttt ctaaggcagt 19320
gaaaagtcct ggcaatgtta gtattgagat aatccaaaac acttagtgac tgtttacatt 19380
tttaaaggga tagttggcca tttaaatggt ttctgctaac agatcaaatt attcagtgca 19440
gaggtaaaat attttcagaa tgttaatttt agatgtcatt ttatagagaa tgtatatgag 19500
caatgacaag gtcagcaaaa tatcttagca aaacttgatt gattcattcc atgcacaggc 19560
aagcactgtt ctgggcaccg gagatggagc agtgagccat tgcgtccatc cacagatggc 19620
ctccaggatc gtgcgggttg cagggaggcc gctgggtggg cacggctggg cagtgccctc 19680
atgtgggttt tgttgggctg ctcttactgc gcactgtttc tcagtttggt cggtgttcca 19740
cctcgctgcc tggcccccac ccctcgcctt ctgagggcct cacaaagagc caagcggaag 19800
gcaggctggg gactttgcag gtcagcccag aggcttcatg atgatggttg gtactgtccc 19860
gcggccacca tcagtctcac gctctgcctc gtgcgcagtc ctggcgtcgt gcggcacctc 19920
gctggtccct gctctcctgg aaggaagggc ccagtggggc gcttcgccag agccttcttg 19980
tctgactccc ttacccaaga ggcatggatg gcagggccgc cggctgtgtc ctttctgttc 20040
tgaaaaggca aaacaaaatt gttcttggct cttattatct aatatttgtt acaatagttg 20100
ctcactttta ggtccatttt attacagatt tcagacaggt gtggttatta gtgcccctca 20160
ttgtttggac acaatgccaa tgtcaggagg ccccgtgttc ccctgagccc cctttctgct 20220
aggagcacgg gcaggccacg cctcgccatt aatctctcct gttttagggg aggaatacca 20280
ggccaccccc tcttctctct gtgcaaggga acagacattt gacaaaaacg gatgccatgt 20340
taacgctaat tttgtttgtc tgaggcagat tgcagcaggt gttatctcca tactcttcct 20400
ttcctggagt gttgagcatg tcctgatagt aggggatgcc ccggagggtg gtgaatgtgg 20460
ctgcacaggg cctgaaagct atttgatgtt gctgttactt caggtagaac ttaaagttga 20520
cagtacattc tactctgcag gcagaaacct ggagtggcat tttgacaaat tggaatgccc 20580
tgtttatagt atgctttaat gagttaaatc tgggggatgt ggatagaatt ttagcatcct 20640
agccttggta ttcttccatg actttgggcc aattatttaa taattccaag cctgcatctt 20700
tgttagaatc tctctaagtt tctcctgttg ttatcctcag aacgggactg tgaggtacag 20760
gaggccacgt ggtgtagtgg tttaggtgga cagacttccc agtgctgttc tcatggagag 20820
cccaggcctg tgcctagctc tgcagtgaca gtgatagtga ctggtgaagg taaaggggtc 20880
cacccagacg ctcttgctga tggagagagg ctggcctgtg gctcttccct ggggtggata 20940
ttaacctgct aacgtgccgt atctagtcct gcttacatta ctaagtggta ggaaatttta 21000
ggtaacatct cagactttaa agtggcctac tgagcgggta gaaaagatag ttaaatgcct 21060
agtatgtagt tggtgctcag taattgttga aaagatagaa gctttacttc aaagctcttg 21120
tagtttgttc agtttggaaa aaatatttta atgttgggat gtattaacag ctggactggt 21180
ggctgtctga attgggacca tggttagggt gacgtgtttt cttacttttt tttttttttt 21240
tgggtgagac agtcttgctc tgttgcccag gctggagtgc agtggcagaa tctcggccca 21300
ctgcagcttc tgcctcccgg gttcaagtga ttctcctgcc tcagtctccc gggtagctgg 21360
gactacaagc tcgtgccacc atgcctagct aatttttttt ctatttttac tagagatggg 21420
gtttcaccat tttagccagg atggtcttga tttcctgaac tcgtgatcca cccacctcag 21480
ccacccaaag tgctgggatt acaggcgtga gccaccgcat ccagacacat gttttttttaa 21540
attaaatgtg atagataaaa ttaggctgca gggatggcct gatttgcagg tgcttcatga 21600
gcaagggtgc ccagcattta tttgctgcta ctggagtctc atgtgtgctt gcagcctagc 21660
cttaaaccct ctgtgggcgg tttggaatac ttcctccaaa tgactttttt ggcagggtgg 21720
gaagtggcga tacttcaggt gagagacagt tgaaattaac tttacacaag agccaaactg 21780
taggctgacg tggggccact cacctttgga ctcacccctg gcgggtcctg taagaggtgc 21840
tatatgcttc cactttgcca gctgttcgtt ggccctgttt tgtcttctgc tctttgcttg 21900
attagtgaaa cttagaatgg aaacaggcaa gtttgatttg ttataattcc taggagttct 21960
agcattaagg aagcagatga gtttgatttg ttataattcc ggggactgga taatttgctt 22020
tctcctctct ccatctttaa ttaatctctt aaaggaaagg aggacgacag cacttttcct 22080
gcagtcatcg gtgtaggctt cagccttaac tcatgacata ggctggtgcc actgaccaca 22140
gggctgacct cagctcttgg agcccatggg gtgacaggac atcagcacct ttgaggtggc 22200
ggcatgaggc gtcttccagg ccttgctcct agtgcttgaa aacactgctt tagttttttg 22260
ttaagagaga cagaggccct acttactcct atcccacagg catctggctg ttgacctcct 22320
tgttggcctc ttaaggagag aatacttgag tattgaatta gatcaacttt tctgcctcca 22380

```
gggaccctgt ttctctctgc tgagactggc agatggaacc tggatttagt ggatggtcac  22440
caggtagctt gggcgacctg ggccgctggg cccctgagga ctcacatatc ttttttcctg  22500
ttcatgtgtt ccttccccac accttggccc attctcagtc cctcccatcc tccttagctg  22560
aagcactcag ggaggtgctg atggggcctt gggacatgca ctggagctgg gtcccaccct  22620
cagacctgtg cccgactgtg ccacattcat tggaaagctg ctttcacact tcctggatgg  22680
aattctctca ttttttcag tgcagaatca ctgagatgat ttttttgga taaatcttta  22740
aaggccagtt gtaaatttat tgatacttgg aattgacaaa attcacttgt ttagtgttgc  22800
taagtcatac tgtgtaagtt tgttgaacac agagttttca ttttatactt tcagaggaga  22860
aatgaaactg aatttcatgg ccagaaatat gtttgagtgt catcctaatg taagaacaga  22920
acagaaagcg tggtgacgtt tcattgtaac tctagtatgt ttctctttt gtccattaga  22980
ctacatgagg aaataattga cttttataac ttcatgtccc cttgtcctga agaagcagct  23040
atgagaagag aggtggtgaa acggatcgaa actgttgtta aagacctttg gccgacggct  23100
gatgtgagta tgttctttgg ggttctgtgc cgcaagtcat gtgcgagtaa atttaaacgc  23160
cctgtggtga tgggtcggct ggatccacac agaccttttc ccatttgccc gagaaagcag  23220
ttctccaagt gtgctttgag agggccaggt cgcctgcaat gctaggaatg cacggccccc  23280
ggcccacctg cacctgatgc cttcgacacc tgcggtggcc acgggtctgt gtgacactgg  23340
cgcacactca agtgcgagga ccattggctg agggattttt tttttttttg gagcggggag  23400
aatgatgtga ttgtttctct taagttcacc ttaaatttag aaatttcacc ctgtcaccca  23460
cccctgcttc cccaccacca cacatggtag catataatgt gttcattttt gtaaaacttg  23520
gaagtgttcc ctcatcacac accactcttg cggtgaagga acaagtgttt ttgacatgtg  23580
gagaggggcc ttctggaatg cttggtgcag gcggtgtgaa gcctgcccct ggctggctct  23640
gctcagcagc cttccctgct gctggctggg ctcaggggac cggcagggct ggccgtgctc  23700
tagctgtgag gggcatgtgt gctcttggtg ggcggtgggc aaggacgacc cagttttctg  23760
ctcctcttta aaaatgatac atatttttgg ctttaaactt cagagcccta ggacaaagcc  23820
ctgccccagt gccttagctg tgggtttaag aagaggttga agggttcaaa gctagctctg  23880
gaaagtcctc agctttgaag ggttgtaggg tgaagacaaa acttgtttca cttcttaact  23940
tagagttttt aaacattcct ttttggggca cgtctttaac ttatagggaa ttttctggtt  24000
aattgttaca cagtcccctc catcagtttc caaggtagtt ttattttttta cccaagggta  24060
tagtgagggc tttcttggag taagaagtaa tggtagtgtg gctgcttggt ctgtggtata  24120
cattttaaag caacctccct ttctttcagg tacagatatt tggcagcttt agtacaggtc  24180
tctatcttcc aactaggtga gtaccagact gcatggcatg ggctagtgtc tgtgcttatt  24240
tagaggctgg gatggtgtct gggcgatatt aagggctaca aatagattct ttgtaattga  24300
gtctaagggg aaaaaggcca gctgaaggaa aagactgtgg ttacagaagg aaattggcag  24360
aaagatttaa tttagtgtta tgaattcatt gctttgcatt ttgcctcaca cttaatttgt  24420
tggggtgcaa aaatgctggg tgctggaaac gtgaagaaga caggtgggag gactgtggga  24480
agtaaacgca atagaaaaca ttctgctgat actttagaac atgtgtttga aaaattgatc  24540
ttatgtttta atgaagattc aagcaaaatt ctctttaaat agtattttct aagggttttt  24600
acctgataag aaaatgtcaa acaagtttgc attctaaaat gtaaactggt attttctcat  24660
taaggattct tgatatcaaa ataaatttca gtgcactatc tcattaaaag tttaccttct  24720
gttaacccac tgctagttag catttggagg ctgaagaggc tctaatctca ggatttgggg  24780
gttgatgtta gcagggccaa tgggtaattg aacaggttcg ggtatccagg aatccctgag  24840
tctgcaggag tgatccagtg taggtagtgc tggagtaggt gctgggagag cggggcctca  24900
gcctgctttg ggggcaggcg ttttcatctg aatcccctca catacctagt gctgttggga  24960
gaatcattta acctttgctt tccatcttat ggaagtcttc ccttcagttc agcgaggatt  25020
tgctgtagtt tatgaactgc atttcacttc cttaggggcc atagcctagt gggattgtgt  25080
cttggccttt gggggagacg caggcacatg tgcggtggtg cttatcctgc ccacacgagt  25140
gtgtaggctg tggtaagggg agcagtggct gacgtgcatt ttcttctgtc agcgacatag  25200
acctggtggt cttcgggaaa tgggagcgtc ctcctttaca gctgctggag caagccctgc  25260
ggaagcacaa tgtggctgag ccgtgttcca tcaaagtcct tgacaaggct acggtgagtg  25320
cctggctttg gcccctctga ctgggcagga gcctcgtcac atcccaggtg gttacaggat  25380
acgcctgtgt cacgagctcg tggtatttta cacagttatt ggccacggtt tcgatgatta  25440
atctgcttct ggtatagaca agtgttttat gtttttgttt tatagtcatg atcaccaact  25500
gagaacgtgt ttagtgagtc tgaacttttg ggatttgtga gcccattaaa ctgttcttgg  25560
aatgaaaata tatgattgtg tctactcatg ttaggatgaa taggaaagga gagtcatatc  25620
tgaaagcgga cactgacgtt caggtgctgc ccattttgga gtgtttggct caatgattaa  25680
accatggttt ttatgattac catttgctac gttaaattca agaggaacaa cttagctgtt  25740
ccttcgttgt tccaaaatat atacatatat gaaaagcctc ttctctttgg gggaagtgtg  25800
gagatgagac tgtgtctggt gtgtacttgt taaagtttat gtcagttcaa gattctaagc  25860
ccccagtgac tgggaggtac ttgcctgtcg tatgacagtt cttagctcac ctgtgcgact  25920
ggctagcatt tcatttttaa atttgtctgt caacttatgt agtgtgtgat tcacatcctc  25980
ctagtgttta gcagagcgtc agttaaggcg ggagcttcct cctgcctgtg cggtggtagg  26040
ggagggggca ttcacatgct tctcaggtga ttccttgtca ggtgcttttg attgggactg  26100
ggggcaaatt ttaaaacgtg atatatgcac tgaaaagtgc acatgtacca ggtgcacctc  26160
ttggtgaaag ttaacgaagt acatgtgctc acgtcattgt catgtggacc agagagagca  26220
ggcagcacca gaggcttcct ccaggcccag gttccaaaag gggctgttgg ctcttctcat  26280
gagcatgaga cgagccctgg ctggccactt tctcaaatgc ttatgggcct tattgcactt  26340
agctctccca gccactctca ccagcagaca ctgttgctct tctcatttta caggtgagga  26400
aacaggtgca gagaggtgag gtagtaagcc caaggtgggt tggcggcagt gcgaggcagc  26460
acctgcgttt agcccaggcc gctgttgtct gctgctcctc tgtgtgtgcc aaggggcagc  26520
ggggaggtgg atgggaatcc tgaccaggcg accacctttg gagtagagaa ctaaggtgcg  26580
gttgtcctga ggacacacag taggttgagc agttgttgca gtaactgctt cgtcccagtg  26640
acctcattac tgtcgcatat tggctactaa gtacctcttc ctctgttgcc tgaaggccag  26700
tgtagactgc agggagatcc tggagcctgc cactgctcct ttccagggac cgtcctcacc  26760
atgcagccgg tctgtcatgg gcacaagagc cccggggcga gggccgagtt taaggtgaaa  26820
gcttgtctgt ttggaaggac aacccaaaac tgaatgttcc agtgttactc ctcacctcag  26880
gatttggggt tgctgcggtg agtgagtgtg tgcaagagta gggcaggaga gtgccaggag  26940
tgactgtggg gaggagtcca tgagatggaa aggaagctgc ttcctgaact ctgggtgtcg  27000
gggaaggcat agccatcgag tgttgacttc ttccaaagca gtttctgatg agttctttgg  27060
gaaagtgttt tgtttctctg ccttcttaga atgtgctggc cccagagct taccgtgtct  27120
```

-continued

```
ggtggttgca gtggcgtcca ggtgactctg gccccactgg cctgtcctca cacgctgagt  27180
ccttggtggt ttgccctcaa gtgtagacat taaagcccag aataggtgtg tactgaatgc  27240
cccgtccctg tgttgccttt cactggtgtt taaacctttc atcagaccct gattgttttg  27300
gttaaaggaa ctccgttttt aatgcttcac ggctgaagga aaccaaacat tgcctttttt  27360
cctggaagaa cacagtttca ctggtggggt gggcggtggg gcgtgagtgt ggcctggaca  27420
gttgctcagg caggttttga gtgccatttg gtgacagttc ttgttgggga gagtatttct  27480
aaaatagccc tttatttgct gaatctttta ggggaaaggt ttttttggta aaattatctt  27540
aaagagtgaa aacccaaagt agataaacaa taccagtatt gtttggagaa acagtatcag  27600
tataacgtac aatttaaaaa atggctttga agttacatta aattatttca aaaattcgac  27660
caaatagaag ttgggggcca ggcacctctc cccatcccag cacgtagggt gggcgtggca  27720
gagactaact catcatgttc cctgttagct ccctcccctc agtcctcttt gatgcttggt  27780
cacctccggt gctgatccag ggctgcaggg gcgggacaga acgtgggcct tgctgtgagg  27840
ggctggggcc tgggagttgt cctggattca gggactactg atgctgacaa tgttctctga  27900
ccccctttca ttactaagaa aaaacaccaa acctctgtac agctttggca gcattttgat  27960
gcctggctgt ggagagtcca gcatattaaa gcagttctta aaatgaaatc tttacaggta  28020
ccaataataa agctcacaga tcaggagact gaagtgaaag ttgacatcag ctttaacatg  28080
gagacgggtg tccgggcagc ggagttcatc aagaattaca tgaaggtact gtgcttggtg  28140
acctcgcgca gcgaaagtgc aggactggag tgcttatgct cggcggcatt tctcctacag  28200
atgtttacag ctgtcagctg cacacagggg tctttcgtaa tacagactac acttacatta  28260
tttctcctac aatactattt ctagagatac tttgaaatta catagctgtt tttaaaattt  28320
gcttttcttg agtaaccgtt ttatgaagtt gacaactatt ttagagggct ttgttaaaat  28380
gttgtttcca gttattacaa agagactgct tctagctcag cgtgcctcat tggcaggttt  28440
tgcgcagggg tccagtggaa gttgataaat catgaggtgt cttagatata ctcactttgg  28500
gtggtctcag tgcctgagga tggcagagga gatttggttg agctgatgta tttgggactc  28560
tgaccatgtt cacgaccccc gggtggtcgt gacttccttc ctgttactgt agagactgtg  28620
cagtccttag caggggcaaa tcctgttaca gtagaggcca ttgtagtcct tagcaggggc  28680
aaatccaccc ctgcaatctg gtcccgtctt gttccatttt caagggcctt gcccttcagg  28740
ttccccctc ccccttgtca tctggtctga aggagcacgt ctgcccccag cacaacacgg  28800
acagcagcag ccaggctttc cctccctcct gtcatctcct gccgctctgc cttccttgcc  28860
accctcactc tgctctcctg ctccggaggc ccccactgtc ctcacggcct gcgtagcaag  28920
cacataaaca ctccagcgaa cgcactggtc tctccttgag ttcctttgtg cctgtggact  28980
cttcatggtg ggggtgcacc cctgctgagt cataaccgag ggagagctcc acagtctcga  29040
ttttcacaag cccctcagga aattaattct tagcgtctcc caaccagttt gagacttact  29100
gagagtcttc agatgggcaa gaggatggag gaaacgttcc tttctgtctt gtgtaatttg  29160
ctatgtgaaa tctctttgaa agtatggtaa ttactcaata aatctttttc ttttggaatt  29220
tacagaaata ttcattgctg ccttacttga ttttagtatt gaaacagttc cttctgcaga  29280
gggacctgaa tgaagttttt acaggtggaa ttagctcata cagcctaatt ttaatggcca  29340
ttagctttct acaggtacgt atgctttctt gcgaccgttt ctgttgagac atgtgtaaga  29400
gtagactttt ccaaccagtt gtcctgtagg ttccagcagc ctttgctctc cttttactat  29460
attgtttcaa tttgttagag gctgatttct gattcttata ttaaaaccct cttgatcaat  29520
gcacctttct ggaggctcct ttgtagctca ttttgtactg ggtgtaacgg ttagtgcggg  29580
gtgcccatct ggttctgtgg gtccagtgca catcagtgca agctcaagga gttctctata  29640
ttcagaaatg tccatttcat ggtaaacaat aaacatttgt tggtgcttgc ctgtgattta  29700
tattgaaaaa aaattgtctc agaataaagt ttggtaccac atatgagaaa aggatttaca  29760
agattgcttt ctcaattgat gaaacctcat tattttgtct gaaattatat gtggtcctta  29820
ttttgttgag taacatggaa aatctatcag tagaaaacag atgtgtttta aaaaatattg  29880
ttaaatgctg tgatgtattg ataaactgta cttacacttt ttaaacattt aaaatcatct  29940
ctaattgaaa cagtattgtg tttatatttt cttgagtgaa gaattctgtt ctttacagaa  30000
tctttcctgt ataatttagc tgcacaactg gatttgtcca tgtttaccat taatgttgta  30060
cttgtgattg tgctgagtga gccgtttctg ttcatgattt ggtaatgttc tcactgtcgt  30120
gaatgctatg atagtagaac cactgggtaa ccacctgtga tgatcgcagc ttccttggtc  30180
tgtctctgca gagatgcttt aagagtagtg aaaatggaat tccatgtctg ttttcttaca  30240
gttcaagtca cactgtcctg ttttcacttt cccctctgag atgtggccgt tagtgtatag  30300
cctttcttcc atagtttttg gacattattt tgaactaaac atgggcctat gttctttact  30360
aatatactcc tgacttgcac tattttcatg gccttgtagt aacaacagct acttaatact  30420
ttgatcatgc atgtgccatg tgtgcctggg cccagggcct cctgccaccc cctcaggggg  30480
tcctttcagt gatcctgtga ccccacagga ggccaccata gcatgagtcg gattcctggg  30540
ttcactgcca catccctgtg cctgtccagt gcccagagct tgtcctgcct cagcggtgtg  30600
actgtggcaa catttgagtt tcttgactga gtgaggggag gaggcccacc ctgccactgg  30660
ccaggctctt ggatatgtga ttttggctaa aagacaagga ataaggaagg gaataaaggt  30720
gaggccagaa ttggaatcct cctcttgtgt ggtggaaata cgcagagaac tccgggattc  30780
ttctgaacct taaaaacatt tgtatgcttt cgagctgcag ctcctcctgg cactctgtgt  30840
tataaatagt ttcaagcacc gtgcttctct gagggatttc tctcatgtgc ccttgtccat  30900
ccctttctag ttggcactgt ccgatagaat tctctgtgat ggtgacggcc acttctgcat  30960
ggtccggcaa ggggcttggt gccacatgtg gctactgagt attgcagtgt ggctggtgag  31020
agcaacaagc tggatttttta attaatttgt tttagttcat ttaaatagac atgtgggcaa  31080
tgcaggtctg gacagctgag aattatgacc gtcaggaggt gtggtggaca gtggtttagt  31140
tcagaacaag cccaatgcct gcttttgaag acgatatggc actgaactga gagtggtgct  31200
catctgtgtg caagcaggat ggaagcttgc tatagatatt atgatgcaat actgatggcc  31260
tatactcagc tgaaatcagt catttcactt tctggtttta tgtgataccg ccatactgtt  31320
cagtctaaca ctgacccctg ttggttgtac ttcagcataa caaaattagg atggtgagaa  31380
tctgaaatta catctaccat ccacacaact aagttatgca gaatatagtc aacttatttg  31440
ccaatatttg gttaatcaag tatctgtgtt tgcaggaagt ttgctgtatg gattaacaat  31500
tccaaaaatt aaacgacaat aaaattgaga ttagtacatt gtattccttt tgaacactcc  31560
tcattgaaga ggctgctgtt caggcttcct cgtggtgctg gtgagtgagc gagtgcctct  31620
cactggtatt gccttgaaga ggctgctgga cggcagactt cgttgcatcc tattttcttt  31680
agaacatgcc ctgaatccat acaaattgtg gatgcattgc ttttacagtt gcatccaaga  31740
attgatgccc ggagagctga tgaaaacctt ggaatgcttc ttgtagaatt ttttgaactc  31800
tatgggagaa attttaatta cttgaaaacc ggtattagaa tcaaagaagg aggtgcctat  31860
```

```
attgccaaag aggagatcat gaaagccatg accagcgggt acagaccgtc gatgctgtgc  31920
attgaggacc ccctgctgcc aggtaagggc tccccgacct ccactgctgg gagctaggcc  31980
agcttcgggg ggtggggggg aggtgtgggg gctatgttgg ggctctgaaa gcctcgggca  32040
attcatttgc tcttgatgca ggtttctctt tttttttttt tttttgaga cagtctcgtt  32100
ctgtcgccca ggttggagtg cagtgacgtg atctcggctc actgcaagct ccgcctcccg  32160
ggttcacgcc attctcctgc ctcagcctcc tgagtagctg ggactacagg cacccaccac  32220
cactcccagc taattttttg tatttttagt agagatgggg tttcaccatg ttagccagga  32280
tggtctcgat ctcctgacct tgtgatctac ctgcctcggc cttccagagt gctgggatta  32340
caggcgtgag ccaccatgcc cagccacagg tttctcttat actaaccagt taataatgac  32400
actttgagaa atccttattt aatgcttcta attaactttt gtctttccaa ctgtttacat  32460
tctataataa agcagaatta aggaaaatct ttttttttct gattatagaa gtattccgta  32520
ttcatcctaa atcatttgtt tcccagaagt atgtaatata gaaaaacagt agatgccata  32580
atccctttat ttggacatgt atttctccac ttttttcgta tatggatatt aatgtttatt  32640
attgttatct tgttgaacac atcccacaac gcaaacctgt tagtcacttg gcttttgact  32700
ttatttccta aagatcatct cagggaaaac acattggctg atgtgttttg tttttgcttg  32760
tagatggcgt gatttatgca ggctcttgag tggttttttt ggtagcacgg tgtggcagtg  32820
tatcatccat ctttttgtct gttggatcag tcacattgga gacattgcca ttgtcttcaa  32880
gtgtctactg aaatgtactc aaaaaaacaa agacccacat aatcattgag atatataata  32940
taaacctaga aaagataaaa ttccggtact tagaatatat gtcctttaaa aaaaatctac  33000
acttaacctg attgtgaaga atgagttgta tgtagattaa aattcgaaac agtgcttttc  33060
tgatgaaaag taagctcctc ttgactgact tccttggtga cttctgtgac agatttcttt  33120
gatttgctgt cccagtttc cacacatgag aattcacatt ccattctaaa ggattcactt  33180
cctgcaggtt ccgttagtgt tgactgagtt ggggtgcact ttgggctagc tgcccttctg  33240
actgccttgt gaggcctcct gattgtcaga tcggctatca cactgggtcg gtgctccggt  33300
ctgcacaatg gtagcttttg gcttccttgt gtgtctgcca cctggagagc gggctttttg  33360
tgagctgttg ctccgtctgt gaatggcagc tgccttcatg aggtgggccg tgagcacgtg  33420
ggcaatgatg atgcagacca ggcccctcgg cactcacaga ccgtgccctg tgtatggtga  33480
ttgacagggc ctttgctagt gccaactgcc atgcgtgccc attgtgttcg cctgtctggg  33540
ctttgctggt gagggcctgc ttcagagtca cttgtatgac aagatctgaa atgtggacga  33600
tggtgtgcgt gtggggagag tctgacatag cctttttgct gcagggaatg atgttggccg  33660
gagctcctat ggcgccatgc aggtgaagca ggtcttcgac tacgcctaca tagtgctcag  33720
ccatgccgtg tcaccgctgg ccaggtccta tccaaacaga gacgccgaaa ggtaatgggt  33780
tgcgtgtctg tgtctgggct cagcatgcct gtgggatggt agttacccct ttcctgtgtc  33840
atttacctcc atgaaattta tgaagggatg ttctgtcgta tttcagtaga atttggatat  33900
gttggtgaag gaaggccttc taggaatgtg ggatggctgt atgggattca tccatggttg  33960
agagttgaaa atttctttct tggagatttg acattttctt cagggtcttt tgttttggag  34020
aggtgatttc tagctttcaa aactttggaa catgatgctt tttctccagc cttgaaagca  34080
taaacattca ctttctaagt gaatgtatct gatcacccaa tccctaccat cttctcttat  34140
gtacactcgt cccttgttct acattttggg ccatttttac agtcccaaaa tgtagtcaga  34200
tgtatttact tctgacccag atgatgctgt ggtggtggta gtggtgggat tggagggggt  34260
gggagatgag ataggaatgg gaaggaagag taacgtggtc gtcaagagtg gaatttgaaa  34320
cagtttgata aatctgttcc atggtggatg atggaataaa cagatttcga ggcctggctc  34380
agcagctgct gcaggcgctg gtggtgctgg agctctgtgt gttcctgagc cgctgtctgc  34440
tcggtgtttt caggcggagc tctgggcccc gtgtagggca ctcatctcag taccatctcc  34500
attctcgcct gtgcagtggg aggtgaaatg tcagcactgt gtgaccatcg agggtgggaa  34560
ggccacgctc ccctacttgg agctgccttt cacagtggtc ttctgtaggt agatgtactg  34620
cgatccaggg tgtgctggag ctgaatcatt agaagtcata tatatttgta aatgtatttt  34680
agctcccttc ctactgtcct tcacctagtg agatgatctg ttaggggtat aaggtaactg  34740
ctcaagaggg gttctaactc cctgatacct gttgtactct gttgatctcc aacaatgtcc  34800
ctttgcagta ctttaggaag aatcatcaaa gtaactcagg aggtaattga ctaccggagg  34860
tggatcaaag agaagtgggg cagcaaagcc cacccgtcgc cggggatggg tgagagatta  34920
attcatttgt gttcatccta accactggct ggcgtgttca tgcagaagtg tctctattcc  34980
tttgtggtaa attggtcaaa ttaagaagat agctagtttt tctgatgagc attaattaaa  35040
aacacaataa gatctagagc agcactgtcc agtagaaaca atgccacaca tagaatttca  35100
aatgcatgcc acacatagaa tttcaaagtt tctagggccg tgtcaaatgt gaaaagaaac  35160
aggtgaaata attttggtag attttattca actgaagtca aaatgttaac atttcaacat  35220
gtaatcaaca taaaaatgat tgagatattt tatagccatt ttttgtacta agtctttgaa  35280
atccagtgtg tatttatttg tacttacagt acatccttat atgggtgcca aattttcata  35340
aaaaatactt gatctatatt tagattttag aaagttcaca tttgaagatg atttgcatac  35400
ccaagttgtt acaagcatgt ttaatgtttt ccaataacta attgactata atttttaaaa  35460
ttaagcaaaa cctaatgttg ggtttgtcag tcacattagc agcattcccg gctcagcaga  35520
acccatgact gatgctgccg gggcggctcc acgccacagt tctcaggagt tattaaccaa  35580
gactttttcc ctccacagac aacaggatca agattaaaga gcgaatagcc acatgcaatg  35640
gggagcagac gcagaaccga gagcccgagt ctccctacgg ccagcgcttg actttgtcgc  35700
tgtccagccc ccagctcctg tcttcaggct cctcagcctc atctgtgtct tcactttctg  35760
ggagtgacgt tgtgagtgcc ctcccctcct ccgtgtgtct gttggacagt ttgtgtctct  35820
ggtaaatgtc catagctgtg agcttaaaat ctccccctta ggtttgctca ggttttgttt  35880
ccttttatgt gtgtggagtg ggtgggaggg tagccccgtg atgtcggcac caggcttcct  35940
ttcccccact gtgaaccttc tgaacctgtc tggctcatgc ggctgtcgag ggcagtaatc  36000
ctcttcacag atttaaaaaa aaattaaatc caagtatctc ttctgtattt cctttaacat  36060
tctgtttcag ttttgatgaa attacttgaa ggaagcctgg gtagatttgg gctgcccgtt  36120
cagaagttag acttaattca aataaccttt catagccagc ctggaggcag gagtttcttt  36180
tcatagcttg aaggaagtag tagtgcacct ttgtggtaca gctgtccttg ttgtttttg  36240
taccgggttc aaggattcag acacaccgcc ctgcacaacg cctagtgttt accagttcag  36300
tctgcaagcg ccagctcctc tcatggccgg cttacccacc gccttgccaa tgcccagtgg  36360
caaacctcag cccaccactt ccagaacact gatcatgaca accaacagcc aggtacgtgg  36420
ccctctggtg cccttcccgg tggtggcccc gggaagggca tctgagctgt gatatgcgct  36480
agagattcat ggtcctttga attcgaagag taacttttg agtctttggc cattgctgtc  36540
ttattctagg aaatcctgtc tttttgtgg tgttgaggcc caccatgtag agtttcagca  36600
```

```
gtgaggagac tggttctcga gtgctgccgt ggcttttcac gggggccagg tcgactgcct  36660
tcctataagt ttcctcactg ccccagcatg agactgctgt cgaggatcat cttgagagag  36720
cgactcagtc gcgacccact tagccgggca ccaggcagcg ccagacactt gtccctactt  36780
cctctcagaa tctcagtgtt gagacttttt taaaagtttt aatgtgaact tattggactt  36840
ttttcatgtt tcaaattagg catactttct aaggcttttt ctgttagaat gtactgtctg  36900
tttctaaaat ttagataaaa ttagaaatct aaaggagaat tttataaata ctaaattttg  36960
tatctacttc cgattataca tcactggaat atgtgtgggt ataaaaccca acatgttaat  37020
tgacttaaaa ccattttctg aaatgtgggg tgtaatttga gcataaaact atgtaggtat  37080
atgcaaaagt atcttgactc attacttgga gttttgcagt atgctctggg gaagacatgc  37140
tcacaggatc caccctgatt ctggcagagc ttctggaatg ctggctctgt aatgacccac  37200
agagttgatg agcagagcca tggcccagcc agacaccata acgtgtctaa ttactgcata  37260
aatgtaaaat tctgaggcaa ttatttacac tcttaaaatg aattatacca cagataaact  37320
tggttgcctt tttatggtca tcacactggc cctgacgtcc tgggccatgt gtcacaaagg  37380
tgtttgtttt aaccacccac aagccttggg gcccttgaga gcccagtgcg gctgctgagc  37440
tccagagcca cactctgcgg ctgcttgtgt ggttcgagcg tgaagtctag ggacgctgag  37500
ggtttctagg ttcttatcta agaagactct tgtccacagt cgatctccag aggtggttgg  37560
ggtaaatgca tgggatgcca agatgcaacg aggtcagtgt tgcaagtctg agaaaagggg  37620
ttcttgttag tgtgcttctg ctgctgacag taatgggtga tgctgacgta gaagcagccc  37680
gggacctgga cagcaggcaa ggatggatct gccggccgtc ccacggcccc ttgggccacc  37740
agtcaggcca gtctcggtct ctgaccccga gttcagtgtg tgagtcgtgg attcatcacg  37800
ggggtgacag ttgttattct gatgatgcta atgttttgag tcatttgatc ttcaatgagt  37860
tttaaacttt atgacttgga ttactgggca tactttatat tctaattgct gtttcagaat  37920
atgaggtatt tctaattcaa agcacaatat tgttaggtta tagtgaaaca aactgcttta  37980
tggagcccac atgcaactgt gccatttatg agctgccctg tggcggtgct gagctttaga  38040
agccggatgg ttttcctgtg attgatttgg tacccatggc cgtctctgtc gttttcttcc  38100
tagaccaggt ttactatacc tccaccgacc ctaggggttg ctcctgttcc ttgcagacaa  38160
gctggtgtag aaggaactgc gtctttgaag gccgtccacc acatgtcttc cccggccatt  38220
ccctcagcgt cccccaaccc gctctcgagc cctcatctgt atcataaggt atagctcttt  38280
cctggtgcgt tcacctgttc aagctgccat gtgagaggtg gtgctgaatg ttttctcctc  38340
caaagagaat tccagagaga tcatttgaaa acggaatttg ctttcttgtc attcagcctc  38400
atgtttgctt gtctttccaa acaaaacttt aaaaagttaa actattttaa gatgtaagat  38460
acagtttaat tggttgccac aaacatctct taattcctct gttgaactga ttagcataaa  38520
actaaaagtt gaaataaggc tcaaaatgaa gacttttctt ttcccattta tataattcat  38580
ttatatgcta aatacctcgg tttctaagaa gcaaatgata aaaccaagag cagatcttgc  38640
catgatgtcc catgtatgct gctgtcattc ccacgttgcc tgatccccac ctggggtagg  38700
agcaagcatc agggtgggca gagctgtgtg ctgggcctca gcaggatcct ggcatgcctg  38760
cccgtatggc tcctcacaag tgcagctgtg tgcacggaaa aaacaggtca cattaggttc  38820
ctatgttctt gaagtacctg aatgattggg agagccatga cgaggatctt ccaggtcagc  38880
ctctatcatg cgtgatgttc ccttgggctg tgcggatgct cggtactttc atcggtgtcc  38940
acacctctta ctctactcca ctcctccttt gcttgtctaa tcctactttg ccaggaagtt  39000
ttattcttga ggcttgcgtc tttggccctg tgttgtatga tggttgtttt taggagttaa  39060
gtcatagaac atttcctctt ggatttatgc atcccccata gacacattca gggtgaaaga  39120
acaacttcgc acagcagctc cttcgttgca ttttggcttt gctttcccag cctcctcctg  39180
ctgtttgtcc tgctctgaga cttccctaaa gccggcgtgt gtttcctctc agtctgcttg  39240
gccgggacct tgcagtgcgg agaatgtgct ttgggtgcag cccaagcaca ggctgctgca  39300
tgccgggatc gacaggctgc tgagggcgag agtaccaggc cctggcatgt gtgactcgct  39360
tgtttctaga aggtcacagt tgggggaaga acatgaccgg gaccttctta tttctttttt  39420
tttgggacag aatctcactc catcccccag gctggagtgc agtggtgtga tctcagctca  39480
ctgcaacctc cgcctcccgg gttcaagcaa ttcttgtgcc tcagcctctc gagtagctgg  39540
aattataggt gtgtgccgcc acacccagcc aatttttgta tttttagtag agacggggtt  39600
tcaccatgtt ggtcaggctg gtctcgagct cctgacctca agtgagctgc ctgcttcagc  39660
ctcccaaagt gctggaatta caggcgcaag gcactggcac ctggccaggg accttcttat  39720
ttctatggat aagtagaaca agttagaagt gaggttctgc tgaatttgtg tggtttgatc  39780
ctggtatatg gttgttgcct tcagtcagtc acggaatggg aagaatactt ttctgtcaaa  39840
tggaagagtt ggaaagtccc agagggcagg tgtccatccc tcctccctac gtaacatcac  39900
gtcggcgctt agtgtggtca ctgccggagg acgtgggcat tgtgcctgtt gtctggctcc  39960
aacattgctg tctctctctt tctccagcag cacaacggca tgaaactgtc catgaagggc  40020
tctcatggcc acacccaagg cggcggctac agctctgtgg gtagcggagg tgtgcggccc  40080
cctgtgggca acaggggaca ccaccagtat aaccgcaccg gatggaggag gaaaaaacac  40140
acacacacgc gggacagtct gcccgtgagc ctcagcagat aatggctcct ggctgcgtcg  40200
gcctccccca cccctccgca gactgccccg cggcctcggc caccggcagg ggaaccgaga  40260
ccagcacccc gcacgtcagc cgggctcacg gcacgcccgc cgctgatcac tctgcatgtt  40320
tctttgtgtg gtggtcgcgt ccatcttcaa gaacagctcg ttgtgctcat ctgtgaagcc  40380
ttattaaacg tggacgttgt tttctgcctt cccaggattc ttccttcagt gctgaggcag  40440
gtcaggctca ggaactgcag ggacgtgaac atgcgcttgc ggtttgcggt agccgtgtct  40500
gttccttcgc ggtttgctat tttcatttcc tgtttgtcaa agcagcagag gagatcaaac  40560
cccgttcgtg tgtctttcct ccatggatag gcttgggagg tcattgtttt actgccctca  40620
cattttgttt gaaatttcag aactgttttt ctatgtaaat attgaaaacc tatgatttgt  40680
gcaataactc agatattttt tatttaattt cctattttca cataagttat atttaaggga  40740
ggagggaatt ttttttaaac aagcttaggt cctttcccga gctgcatttt ctaagttggg  40800
tcatcgtgtc ggctggttgt ctgacgagca tcgttacaaa caccatgatg aggggtttgg  40860
ggttttattt tgattctttt cttttggtcg gagtgagtga aggagtcagg tcgccctgac  40920
ggttttccag agggctcggc tccagagcca cctgacggac tgcccgtggc cctgctgtcg  40980
ggccccaggc cgttgtcttg ctctgaccac agagttttaa tgttttggtt ttcagttctt  41040
ttaaactgga caacaaatcc agcatttcaa gtgccagaag tataactttc taaggagaga  41100
agggttgtca cgttataaaa tctttaggaa aatgtgaact ggaaaatgtt tcagtcagtt  41160
ttagtgacat agcctgtgat gatgggtctg gtgactatta ttgcggaccg tggtacccag  41220
ttttaggaat gtggagaaag gaattctgtt gattccattg aggaatctgt agcgtatgca  41280
ttcgttctgt taagagcaaa tctaggagaa gtgcttcagc tgcccagtgc gccgtgggga  41340
```

```
gtgttttaat ggatcatgtc gcaggagagc acagcccagc gttggggccg ggaccgctgg  41400
cgcccgacgt cggaagcata caggtatact atgcaagtgt attctgccac aacaaccact  41460
gtctttgtta cctttttttg aacaagaata tatccatcct gcctaaccct gagtttttgg  41520
agcaccacag ttgtcctggg agttggttgc atcttgtagg ccatctgact tcctgttgtt  41580
aaaacagggg tctggtcttg ctaaacacta caggtaggtt ggtctttgaa gtccactagt  41640
ggagaatgtc gagacaagat acttattacc atgacatctg atggatgtgc agcagtgggg  41700
agttctagat tgatctctga atgtgatgga cgcccagcaa ggacaagctt taaaatgtct  41760
gcggtctgcc cttttgaagc aggactggct cactctgtca ttgggagctg tcggctgcga  41820
ctgcaggttc tctaggaggc attccagaat agagtagcac actgtgtctg cagttctcga  41880
tgaccgaaag ttatcaaaaa tatttaaaat atttaaattg tgaacctatt gataaagaat  41940
atttataaaa actgatctgt aggcctgtac taatctctac gcattagcaa tattgactgt  42000
aaacccacat taaggaaacc actacggggc cggcagtgag tgtcccgtgg ggtgtgcatt  42060
ttaaagctcg attcatagac acaggtacca tgttccattt ccgtcatggt gaagcagatg  42120
aattggcctg gctaccactg tggttgtgtg ctacaggttt gacaaaagat atcatgtttc  42180
gatttttttg tgtgtggaca acaatatgga agctaaaatt gacatatttt tatgtaaagt  42240
ttttctattc tttgattttt aataaacttt ggaaaccagt tttgtgtttg tgttcaagtg  42300
tatgctttca agggtaagag cggcttccac attttcagtt ttgaatttct aaattagggc  42360
aatacgttaa ccagttattc taaataagat tcaaaagaag gcagatgatc ccagtcctat  42420
aaagcaagtt gcggcaggga gattatgttg tcactggtcc attaaagtag gaggaggtga  42480
aaatacaaaa attagccggg catggtgact cactgagtag ctgtaatccc agctactcgg  42540
gagggtgagg catgagaaat gcttgaaccc gggaggcaga gattgcagtc aatcgagacc  42600
gtgctactgc actccagcct gggcgacaca gtgagaccct ttctccaaaa caaaaaacaa  42660
aaagtgggtg gaggttctag gctttgcaca aggcctatat aacagtaaca gaaacgtgct  42720
ctctgtcctc acattctgat gctaacaaat tcagtaaaac tgtttaaatg gttcttacat  42780
gcagtttctg gcaagctgct atgtgatatt gtgtacttag actgcccagg ggcaacattt  42840
tactttcttc atttctttta ggtcaacatt gcatcacttg caaacaagac attacaaacc  42900
aaacaatcat agtgtagctt aaaatgcaac ggacatttgg gatttatttg agaactgacg  42960
tttgggattt atttgagaca gagtctcgga gtctcgctct gttgcccagg ccggaataca  43020
gtggtgcaat ctcggctcac tgcaggctct gccttccagg ttcaaatgat gcttctgcct  43080
cagcctgccg agtagctggg attagaggca cccaccacca tgcctggctg atttttgtat  43140
ttttagtaga gatggggttt caccatgtcg gccaggctgg tcttgaactc ctgacctcag  43200
gtgatctgcc cacctcggcc tcccaaagtg ctgggattac aggtgtgagc caccatgcgc  43260
tgccgacatt tagaatttat aaggaaaggt ataagaattc ttctaggcca gtaagtgaca  43320
gaactgcatg tcccagcctg tgcagctgta gaactatcaa ctgagtgcat gttgtagaac  43380
tatcaactct agagttcttc cagttgtcaa ggtgggtgtt gtgggtaaaa cacgttcctt  43440
ccacccaaag aacagagtag ccctgtcctc ttggcacctg gttcctgagg gggtgcagaa  43500
gctgctcaca gcactgccta gtggtgctgt ggggaagatg gcaggcagct gggtgggact  43560
cgaaagcctc tccagggggc cgagccctgt gcagggtctg catgagctgc catggtcagg  43620
gtggggctgg caggagctga gctgggcctc cgagggaact ggagggcttg tagccagggg  43680
catctggagg aggagcccac gacagtgctg aggtacaggg cactggagtg gggagatgtg  43740
gctgagttag cctctgttgg aggcgggact ggtgggtgtt gtgggggggc actctcggcc  43800
tgccccggat ttccccgtgg gtggtgatgc tgcctactga gccactggtg cctgtaggag  43860
agctgtcttt aggaggcttc caggagcagc cactggagca gccacgttac cagggagcct  43920
gaggccccac agaggcatct gaggtgtcag atttgggtcc cgctctcctc ggaagctgcg  43980
agtactggaa ggtaagggct ttctgggggc agagtgaacc tgtccaggcc actgcgtgaa  44040
catcagtaag cccaccacgt catctcggga ccccgtggac tggatttcat ggtaacaggt  44100
aacccccctca tgaccggctt ttgtacatgc cttttgattt gtccggggtc tcgagtgcca  44160
cctctttacc ccgtgagata cccagagatc tctgtaaatg ctgtgcccag catgcctcgg  44220
cctgggcatg aaccgtacgc aggggaggtg gcgacatttg taatcgagat atggtttcgt  44280
tgtgactggg tcacctgtga tgccctaagc cttgagaact tgtcatgtgt gtgtcattat  44340
cctcttgctg tctaacttgt gagattcttg ccaagcctta ggtgactttg actacctttg  44400
gtccaaggta atcgcctaga atggacggtg gctcctgtta aacacacaca catcccagac  44460
accacgccgg gggctatgcc tgttgtttaa gaatggcccc aaaatatgtt gcctgcactg  44520
tgtctccagg gcctgtgtgg gaggggtagc ttgggagggc cgggtcccgc tagccctggg  44580
ttgcaagggt aaaccgcctg gtgtcattca tggtgagatt tacttacccc atgacttgat  44640
cctagagaag gccagctaag gacttcagag gtcttggagt gagttccagg caagggcaag  44700
aaaccaaggc ttttcatggg ttcttaggta aaggaagggg gtgtggacca gtcgcactgg  44760
gaggtcgagt cctgtctcct aggaagccac atggctgtgg ggtgagcttg cccagggttc  44820
cttcctgcca gtgtggatat ggcgtcctct gcccaggcct cttgagatgg aacgcttgga  44880
gctcagccaa tgctcaggtc gtcataggtg ctgtggggtc actcacactt ggttgagagg  44940
tatgtgactc gaggcagatt cctgtcattc ctgcttgtat ttcatcaagt cctgagcgag  45000
gtttgtggta atgagtgcag gtggctgtga ccgaatccag gtctcctcaa cagataggag  45060
acctccgcac atcctgccat gtcactgttg gaattttcaa gttgggagga atcttaagaa  45120
tcagctagag cagctcagcc ccaaaaatga gaaactgaag tcctgtgatg ggaagggctt  45180
ctaaaggtca cgtggcacat ccgccaggcc cccgagagcg tcctgggcct ggctcccacg  45240
ctgctgctct ttgcaaaggc ctgtggcccc tttttgttgt ctgacgacat gtagagaaat  45300
tgctgtgagt ttacgcagaa cactggtgct tacgctataa ttgagtctca ccaggttctg  45360
aagatgcgtc ttgtgcccat ggctcacatc tgtgggagcc tttcagggac agcggcatca  45420
ccagcctggc cctgtgtgtt gaaatggtta tggtggaact acgtgggctc atgaaacgtg  45480
ggaggcttcc agttggactt tttgtggcca atattgatag gatcctgcca gcggagagcc  45540
cgggcctagg gccaaacggc tggagttagg agctggggtg cgcagagccc tggaaggatt  45600
tggcagggca ggggagaagg gagtaacagc ctcactgtgc ttcaggcttt tccttgctgg  45660
ttcaagtgtc cgctgaaagc agctaacata atcagtacag cttctctgtt ttgggaaatc  45720
aaaccccaaa tctttaattt gatttaaaaa gctttccagg atcttgcctt tgcctccctt  45780
tccaatcttg ccgctcggca gttatttctg ctagaaaata ggtatttccc tctcagtgtc  45840
tccaaatgtg aaagaaaaat catcgtcatc aatagtcggg tataagagag gcagccttct  45900
ccggaagggg accagtgagc aggcagttca cagagcagaa gggagggtgg atctccaggg  45960
accgtcactg gcttcaagtc tcgcttctgt tgcttcctgg ctgtgtgtcc ctgggcatgt  46020
cactcaactc ctgtgctcca gtttcctcag cctcgcaatg ggccattgta cagactaaac  46080
```

```
gagtaaacgc acataaagca cctggagccg tgccaggccc gatgtgagca tttgggccgc  46140
atcgactcat gtgattagtc ctggtaggcc cggcgcaggg aaccaagcct gtcaatttaa  46200
aggggagtgg caggaagaac tcatttttaa tgacaggcaa aaagggaaaa tattgtaata  46260
catggcttcc tattttcctt ttcccttttt cttgcctttg aatttataat gttgcttatt  46320
tggtatttaa gattcttgct ctggagcttc aaacattttg aaagaaaaag tagtgtcatt  46380
taataaatgc tgtcatttga cgctctggtt actattttag ggcagcatgg taggtagata  46440
ctgctagtta cttacccaat atccattttt ctttattact tgcaggattg ccaggtttag  46500
aaaatgaaaa cgcaaaactc caagttaaat ttgaatttaa gtagacaatg aatacttttt  46560
tggtggatgt tccaatattg catgggcaat ttaactaggt gtcctgtatt ttatctggct  46620
caactttgtt tagacagcag ggtgcacagc tgaaaagata acttgtataa catccttgca  46680
gctaggggtg gttgcaacag agtgctttcc tttggaatga aacttttctg ggataaagta  46740
ctttgcttcc ctccttggat tctggctgga attcaagtgc aatgcctggt gacacagcag  46800
ccatgttgta atcatgaagc ggctagctgt gtagtaaggc tgacagagca ggaagctgga  46860
aaggacccag agtcgtgagg ctttgggcct tctttatatg ttcatatata acatttgcat  46920
gaagaagaca cccgcatctg tttatgccac tgatattcag ggctctcagc tgaatacaat  46980
tttaactgat atatacagga aacgcacatt tcaaacaaaa tctcatgtga aactccatat  47040
gggtggttct ggttaaagca gtctggtagg gaggaaaaag gggacatcgc ttcattgctt  47100
gaatttcggc tccactccct ttcccttctc ccagattttg ggggatgccc tgtggaaccc  47160
ctcactttct atggaacaca tctttaagcc aggaaaccac ccattctttc ccgctcttat  47220
tctcattttt attttctcaa ctcttttggg caggggttga ggagggtgtc ctgtggtttg  47280
catagatgcc tgctggactg atcagagccc tggatcccat acctggagtc gggagcttcc  47340
cccagagccc tgcaactccc accctggttg ctgtgcacgg cggaaagggc ccgtcaggaa  47400
acaggaaggg agcctgctcc actcaggtca tttgtcctaa tccagctaag gcacaggctg  47460
gagatctcag gggagtccct tccctgtgcc cttaggaacg ctggccccac ctgggtgctg  47520
gtttcaccac tttgttacca aagtctttgt cacagacagg tatcgggtga gcttacagct  47580
cagcctgcag acatagcccc agggcagcat ggctggactg gttgtgcaca gatgcctgct  47640
gcgggctgtg gctcccctgc gggtggaagt cttggcccct ggacctggta ttcgaggtct  47700
tctgagacat tctgccctcg gaatgcttgc ctccctattg atctgtcctg agtggcttgt  47760
tactattttt taatagtcat gtatcagtag ttatgtaaaa tgtggcaaaa atgaatgact  47820
gaagaaaaat gagatggaaa aagaaaaaat ctgaaaatat acaaaataaa agcccacact  47880
gttttgctat tggattcaaa gacctggaac tatccttgca ggagcccctc ggtgcccacc  47940
cgtaggccac actcaccaac tgcacccggg gctgtgcttc caggacccaa aagctccctc  48000
cttgagcggc acccaggcct gctcccacta acctcaccag ccgcacccgt ttctcccacg  48060
gcccgcccag gggaccattg atcctttagt cctcttcggc cagtgtaccc ccaatggccc  48120
aggacagccc ctagtacaca atggctgttt cttgtggaca acgcgtggag gcacacatca  48180
gggccctgct tttaagaagg aagtgctgag acctgggtgc cacctcttcc aggagccatg  48240
gatgccgggg ctcacctcca gagactgaat taaacggtca ggagggagcc tgcacaccgg  48300
agagctctga gcaccgggcg agtctcccgt gtggccaggt tgggagccat cgctgttcac  48360
gtggccaggg ctgccttgcc agaggagctc atcttacttt gccactgtgt aactgttcat  48420
gtttatcaag tcatgacctc ccttgctaca gtcactcttg tctttcgtgt tctatttaat  48480
ttttttaaaa tgctggtggc ctcactcacg aaattttttt caccaccact catggacagg  48540
acctgtcacg tgagacatgc accaaagcac ggatagggat ggccacgatc ctgcctggaa  48600
cgggacttca gaactgggca gagcatggct ccttccggtg ggggccccag aactcttttt  48660
caaaggcaat ggcaggacgg gatccacagt gcttgaccct ttgataagga gacatcctct  48720
ggccaaaggt gacaccacag ggataaggtc cacgtgctgc ttaacactgt tttgggtgca  48780
gaacaaaggg cagctgggac atttcttgtc tggtctcccc ctctacgtgt cctgaatttc  48840
tagcttgttc aaagtggtca aagacccaag gctggtctgg cacagaaggg gtcgtgccta  48900
catgtaggga ggcactgagg cttctgtctc ccgttgtatg tccccaggga caggacagcc  48960
ccctgcctgt tgttccgagt gtcctctgtg aatggggacc atctgtcctc cgggtaactc  49020
cctcctcctt cacctctgtc cacccgctct ggtagccacc ccttccacgt gcagtgcggc  49080
tctgcatccc ggagagcctc gaggactcct tttctcttct ctagtgttgg ctcccatatc  49140
tgtcagttaa ttacctattc attatatgaa catgtttctc ttgggtcatt atttaacttt  49200
tcaaatttat cttctttact caatatattg tgagcgtgga tgtctgttcc ttatgggatc  49260
accactgcca ggcatgtaga aattgcttga tgtagtttca ctggcttgtg gagaggcagt  49320
catgcttctc tgtgcttcta tgccaaagaa agtcagtagc aagcaaatag cagagcttta  49380
gtgaataaga acaatatttt accttgaaaa aggcagcagg aaggagagtt aagactcaag  49440
tttcctttat taaggaaaat tgaaatctag gtacctacag atgctctttg acttatggtt  49500
aggtcttagt aaacccattg taagtcaaaa atgcgtttaa tacacctaac ctaccgaatg  49560
tctatcttac atgtgcttag agcacttata ttagcataca gtcgggcaaa atcatctaac  49620
acaagccgat tctattaata ttaaaattga tgtaatatat gtacatattt tagtacatat  49680
gatagtttaa tatgttcata taatgtatac aggtcaaatc agagtaattg ggagatccat  49740
cgccttaaat atttctttat gctaaaaaca ttggaattat tctatctatt ttgaaatata  49800
caatagactg ttgtgaactt cagtgtccct actgatctag aactaccatg tgatccagaa  49860
atctcactgt tgggtatata tccaaaagga aaaattattg aagagatatc tgcactccat  49920
gtttattgca gcactattga caatagccaa gatgtggaat                        49960

SEQ ID NO: 5            moltype = DNA  length = 60510
FEATURE                 Location/Qualifiers
source                  1..60510
                        mol_type = unassigned DNA
                        organism = Mus musculus
SEQUENCE: 5
actttccgcg gagtcggcag ccgcctcgtg tgcctcggcg gcgcttgagc ggcaacagag  60
tcctgcggcg gcgcgcgcgt ccgaggtgcc cggaggccca ggtacgtgcg accccagcta  120
agctagcgcg ggacggttga ccaggcggtt gcggccccgc tgcctgcagc ctgccgcggc  180
ctctgtgacg cgcggtgcgg cctcggggaa cccgcggacg gctggcagca gggacggggc  240
ggggcgagcg cggcggcggg gcaggcggag cggagcgagg ggcggagccg gcggaggccc  300
cgccccgggg ccgagcagca cggacgctac ggagcaggcg cgtcccgctg ccgccgccgc  360
tgccgccgcc gccgccgctg ctgctgccgc cgccgccacc accgccgccg ccgctcgccc  420
```

-continued

```
ttctcgggat ccgccgccgc catttgcacg ggaaccccgg tgacaggggc tcggcggagg  480
ggcggaggga ggggggaggg cctgcgagcc ccgagggcgg gagcgacgcc gccggcgccg  540
gccaggctcc ctgcgctacc gcgccgcccg tggcggaacc cgggtggcag cggcggcggc  600
ggccgagggc gggcgtgcgc ctgaggcagc ggcggcggcg gcggccctgc gggcggccgg  660
gaggggcggg ggcagcggcc gccgccgttt gatggatccg aggatcgcct ggttccagcc  720
agagcagctc ggaccgtcca atagtctgtg gatgcagatc tgggagacga cccaggggct  780
gaggaacctc tacttcaacc accactgtca cagcagcggc gcgagcagcg cgagcggcgg  840
gagcggcagc ggccccggca gccccggcgg cacggccccg gccccggccg gcatgttccg  900
ctcgggggag cgcccactgg gcggcctcgc cgtgcccgcg gagcagcggg acttcctgcc  960
cctggagacg accaacaaca acaacaatca ccaccagccg gcggcctggg cacggcgggc  1020
atcggcgggc ccctcggcgt cgccggtccc atcggctccc tcgtccccgc gaccggcggc  1080
cgcactcccc gcctccgagt ctaccgaccc ggcctcgggc agcagcaaca agaggaaacg  1140
tgacaacaag gccagcacct acggactcaa ctacagcctg ctgcagccca gcggagggcg  1200
cgcggccgga ggcggacggg cggacggcgg cgggggcgtg tacagcggga ccccgtggaa  1260
gcgacggaac tacaaccagg gagtcgtggg gtgagtgctg gcgtcgtggc ctgcgtcttg  1320
gagggtcggc acacccgcac agcggggaac acgcccacag gcgggagggg gggatgatgg  1380
gtgggggatg gggagcccca gtggggcctc cagagcatcg gtggccattc attccttcat  1440
agcttgacca gtctcggtgg acctttcttt ggaattcctt tggaaaaagt ggagctatcc  1500
tctccttttc gtagtcatct ctaccttcct cctctcctaa ctgtccacac cttcccgatg  1560
cattcttgct tgtccttctc ctggatcttt ctatgctcta gaattcagcc tgccctctga  1620
tccctttctg tcctccacac cttgctcccc accaccacac cccaagatga agccccttag  1680
catcgggcta gttaacttcc tgagaacgtt tctgccttag cgtctttaga tgttaggacc  1740
aggaggtgct cttcttgcca agaatagaaa catccagaat gctccttccc ctcccccagt  1800
ccacgacgaa aatctcctca gccctgaaag acactgcctg ctcttgatcc tttggcccat  1860
cttttatatt tacttaagga aaaaaaaaaa aaaagccagt gtttgccatg tctgtcgtga  1920
gcagaaagca ctgagtgaca gctagcttga agttgtcata gatggtgagc ttttctgagc  1980
cctgacagaa ctttgcagga gttcatggtc ggcagcttct cactgtgagg ttgtcactgt  2040
ggcagaggta gcagtggttt tcatttaggg gtgctggtgt tagtgtgtga atgttgcacc  2100
accggtgact ttgtgtttaa agttcagctc ttacaaaatg gaatcttacc tgagccctag  2160
tgaattatgt acataagctg ggaatgtttc cagcctgctt ttcctttggg aagagcccct  2220
gtgttggctg gattaggtta ctgagtcttt tcttctcgtt cttttttttt cccttttcat  2280
aaacttatgc ttttggattt tggtgtagtg tgtgtgtgag aagtgtagag tgtggtttgt  2340
gtagctccag tatggaaaac cagctctgaa ggtttttgag ggcagtttct cgttttcagg  2400
tactgatctg tagttaggcc tcaggaaatc aatcagtaat cccgtgtgaa ctttcttaga  2460
ctcacccagt cagctctgcc ctggttttgg caaggagaga tagttgtgtg taccttttg  2520
aaggtttggt aaaatgagtt ggtgggttcc atctgctgta gtgggctggt gtctgctcag  2580
tacactacta ttacaactcc caccttttat ggaaaaatgc agtcatgtgg ttcaggagtg  2640
atgctgggga atgcctcata gctgccctcg ttttccagag gagatccttc ctggctcagg  2700
catttttgcc agcttcaagg gcgctctcca tggtcatcac cttacattaa agatttgtgg  2760
ttccatcctg ttagccttcc catggcaaac ataaacctgt ggtttagtgg caacaactta  2820
atgctgaggg ttctggtggt cttgtcttcc tcgagtgagc tctgcttagg taatcactgt  2880
caaataatac ctggaaggtc cctagctgca tttcactgat gcctctggtc tgtttctaga  2940
aaagatatgc tataaatcca aagtgctggc tgccccttaa tcctgaaaaa gttcccacgc  3000
agaagcttcg gatactgcct tgccctcaga aggatcaggg aggaatgttc acttccctga  3060
gggattactg cttaaaaact gattgtaaac ttgctaagcg gcttatcact ccatcagact  3120
tgtattctta ccctgaagaa gacggcagca gttaggagtg gccctcctag tgtgagagat  3180
gcagtgaata gttcctaagg tttgttaaga gactctgggt tttcagtgat tccattcctt  3240
tccgatcttc gtggtccagt ttcttagctt ttaagggagt ttagttatta aaattttcat  3300
ttacttattg tgtgtgtgtg tatatgcatg tgttcacatg catgtgtgca catatgtgcc  3360
aaagtaagcg agtggaagta acaggacagc atattgggag ttggcattct tcttcagggt  3420
cttgtagatt gaactcagtt caccagtgct tgatggcaaa cagctttttc tgatgagcca  3480
tcttgccagc ctagttttgc tttttttgt ttttgttttt gtttttgttt ttgtttttgt  3540
ttttaagaga cagggtttct ctgtgtagcc ctggctgtcc tggaactcac tgactggcct  3600
tgaactcaga aatctgcctg cctctgcctc cccaagagct gggattaaag gtgtgcgcca  3660
ccaccgcctg acagttttgc tattttagtt acaggtattt aaacagtagg acttctgagt  3720
gtacctcagt atggtgctat tcattatgtg acagaacttt ccctggggag acataacata  3780
catgtctact cactttagat agggaactca aaacagactt aagtgtgaat accataaaag  3840
ccaaaacttg gtgaaatctg actttttggg gggttactta aaggaatatg ggtgaaaggt  3900
tacttaaagg agccagaaat gactcagaca tctgcatcac caaagcctat ccagctctca  3960
aagctaggga cctggagcac atggcacaga ccgcaggcag ctaaataggt agacagtgtc  4020
ctttctaggt gcctcagttt gtctaaaact cctccaggtt ttttctgctt ccaggtatcc  4080
agctggtccc tgagttgtca ttgcagctga gctctgctct tctgagtggg tctctcagct  4140
ttgtttgttt gtttgtttgt ttgtttactt ttgcatggag tggcacagtg aatctggtta  4200
gtttcaggga tatccaagct gttttgagtt gtttacctcc ctgtttaagg agcttctttg  4260
tagaataaag atttcagtct cagaatacag cactgttcag aggtccagca ctgttcggac  4320
attaaatgta gtgtgactct tagcagtatc tcccacgtcc tgaggtttaa ctggtaccct  4380
gctggtagaa gaacaaattc tcgtgcctgc attcttgagt ggactctcca ggtagggact  4440
caggacatgg cagtagaact ctgtccttta tgcctttggg ctagtggctg acaaactcct  4500
gagttttcat taagagtttg aagccaactc ttaaaggtgt ccaggctctt gagtcttttg  4560
gtttccccta acatgcttca tgttcttgca agtgcaagat cctgtttaac cctctttatg  4620
tacgtatccc cttgtattca ctggatagac actctcagta gcccagtggg gcatcacttg  4680
tatggtacct taggtttcat ctctagtaat cccacaaaag gggaaaaagg tggaagagga  4740
ggaggaggag gaagatgaag aagaaaggaa ggaaggaaag aaacaaatat ttggatttca  4800
tcctaaagtc tctctctctc tctctctccc tctctctctc ttttttaaat gaaattactc  4860
tggatttagt tactgtctct caacctttgc cccctgaagc cgtaaaccca agtctagaga  4920
gggtatttgc attgtctgtt atttatttca gagattcaat ccagggcctt gtgtatgtta  4980
taaaaggacc tctgaccaat gggctatttt ctcttgtgct ttttcctttt tttactgttt  5040
gagacagagt ctcagtaagt tacccaggct tgaacatact ctgtagccca ggtgggtttt  5100
gatactatga tcttcctgga tcagtctcct gaatggcagg aataacaccg gacccaccag  5160
```

-continued

```
gcccagcttg cttgcttgct tgcttccttc cttccttcct tccttccttc cttcctttat  5220
ttatttattt atacaactgt tttcatgtac ccttttgcta gggctggctg tgttgaagga  5280
tgctgtccgc cagcactttc ttgtccgtag aaatgagcca gatgcccttt tcttggaggt  5340
ttagcagtat ttgtggtaga gaaggaagga tacatagagc tacaagcatg ggaacttagt  5400
gaatcggagc cctcactcct gacctggttt tgagaaactt ctgtggaagg tgcctgatac  5460
tttccaacct cctgaggatg agacactgtg gctgccctga gaggtctctg tttgtcaagg  5520
ctaaatgact ttaacaatat agatatcaaa gagacttggg aaataacctc acttttggat  5580
atttgggttg ctctaggaat tggacctggg ctcccacatt tgtgctagag agtgaagctg  5640
taccccagcc ccctgaaaac acaagtttaa gtaattggtt tttgagctaa ggaggtaaga  5700
atgagtggaa ggaagggcag gttaggaaag gatcctggct gagtggtggg cttagtgact  5760
acagctttga aggtcagggg ctaagaggct gtgctctcct gcagaggggc cgcccattct  5820
ccattgtagt gctctccttt ggctgtcagt gctggtggct ttctttagtg ctgctgttgt  5880
gacatgtttc tttagcctaa ccacgcatgg gtttgctgac cctgctggat acctgctcag  5940
cccagcagat gagcacaggt tggtaggaaa gaagttagaa gactttactc tgcctttggt  6000
gctcacttta atttctgtgt gtttgaacat gcagcttact gtaattcttc agtgaaccga  6060
actcttccgg ctcttttgtt ttaccgattg ggatactgaa atgtattttc aagaagacat  6120
catattgtgg attctatgct acctgtaaat taatagttga gaattgctga attaattcca  6180
actgagattc gttccttctg agacctcatg tgagagttag tttgactggt gggtgagtgg  6240
tgtttctttt ggagtcattg gcacaggtag gcctttacaa ttcctgttat ggctctagct  6300
gttgagatgc aaagggaagc atcacccaga gcattttaga atctgccctg tgcttacacg  6360
ggagattagg acaccagaag gaagaaagga aggaaaagga agatgtgaga cgggtgagag  6420
agaggtcagg atcctggtgc actgggtggc cctcatctca gctgctttca ggaaatagct  6480
acctgcccta gtgttgggcc cagaaaggtt cttggtagga atgttatggg tttcttggtg  6540
cactggactg ggcagataga tggcagtctt ccttgatgag ttctttctca gacaatctga  6600
gaattgtaga aatgaggtag acatgagagc agtgaatagt aggcattctt gtttgttttt  6660
gtttttgttt ttttttgaga cagggtttct ctgtatagcc ctggctgtcc tggaactcac  6720
tctgtagaca aggctggcct cgaactcaga aatccacctg cctctgcctc ccgagtgctg  6780
ggattaaagg cgtgtgccac cacgcccggc atagtaggca ttcttatacc tgccgaagct  6840
gaggaaaatc atgggcacct tccctgtggg acacagagac gctgctcttg tctgacttca  6900
cacagctctc tctcctgctc tctgatgata gtgtttagtg gcggacacta gtccaggatc  6960
acacccacaa acactagact aaatcacata cacacggagt gccgtgttct caatgggtaa  7020
tgggccggga aagctgctgc ttttgaagac tctttgttgg tccactgatt agcatatatg  7080
catgtttctg cagagctgac tggacggctc ggagcctcct caggagctga gaggccagta  7140
gactgctctt tcagtttttg ctaaggactc agcacctgtg gaacatcaaa aaggcttcac  7200
atttgtcata ctgtatatat ttgttacaca taatgacttt tttttaaatg attgtatatt  7260
gaatttgaag atggctttaa gctaggcttt ttattaattt acaatcacct ttaaattctg  7320
agaaatttct tgatgatata agtaagactc gaatactaag aactttggtc ctaaaaagtt  7380
gaatgtgggg ccgtttatga tgtctattgc ccagagatta cacattagta tttaatgaca  7440
aaacatagga attctcgctt aggcccttcc tgaaatagtg gtttgtaatt agtgcagaag  7500
tgcttgcttt cctatcagct tagtaagtag aagtgcgcat gaaaatagaa accgttatta  7560
ccacattcca aaaaaaaaaa aaacctgtcg tacttgttac cataatcaac ctcttcatat  7620
gtagttatgt ttcttctttc ttttgagata atcgaaaggt tagtaggaca ttatagaaat  7680
tagtgattga tcattgtagt cttacttcac tgtcgtaaca tctcaatgac tagtttaatt  7740
cagaaccagg caactaatat tttcataatt tgtaacattt tgtattttgt caggtttaca  7800
agcaaatgtg tgttgagtac agctttatga catttgtaaa ttcatacaca ccaccacaat  7860
gaactttcag aactaggtta agttcatctt ggatactcat tatgtttccc tcatggggaa  7920
ccacaaaaaa aaaaaaaaga tacaactatt gtattaactt ggagatctct gatgcccgta  7980
gttagacaca tccttcttgg cactaaacct taacaagcac tagtctgtcc tcctctctgt  8040
agctttgccc ttttgagaat gtgatgtaaa tggaatcctg tcttctgtaa ctttggctgt  8100
tttcctgttg ctgaaatgtc tcggcgagtc attcagcttg tcttatgtgt cagtagttgt  8160
tctgttaccc agtagtgttc cattgtatgg aggcactagt tgaagaatat tccagaagag  8220
tgctttccag tttttgactg ttacaaataa agctgctata aacatttatg tacatatttt  8280
tatgtgaaca taaggcttca ttttggggga ataaatgccc aaaagcacca tatggtaagt  8340
acatgtttaa agaagtcgct aaccagtttt tatacttcct tcttttgtgt gtgtacatgt  8400
ggtataatca catgcatttg caggtcagag gttcacacca cgtcttcctt tttgctctct  8460
accttatttt tgaaacatga tttctctgaa cctggagtcc actgttttgg ttagactgat  8520
tggccatttg gcccccagga tccacctgtc ttcgtcaatc tccggcatca cattgtgatt  8580
acagacaggc actgccacca tccaccttgt cttcaggagt catatctaaa ctcaggtctt  8640
catgcttgca tagcaatcac tgtactcact aggacatctt cctagactcc ttccactttc  8700
tacacttgat tttaggaggc tgagaatcaa aactaagcca ttttctacag tggctgcatc  8760
atgccaagtt cctgtatgaa ggggtccaga atctatctct ccagtacttg ccgtggccaa  8820
tgtactgtag tacagctctt ttcttctaat aggtgatacc aggcagctcc tgtgctgtgg  8880
tcataccaga ctgattggag taaccctgcc taataagtca tgcccttact ttccatctca  8940
atcatatctg ggattgcagc tcggtggtag aatctttttt ttaatcctat atgcacaaag  9000
tccctgtttt ctagccttgc attgaaaaaa aaatctgaat tcccaaggct tatgtttttc  9060
tggggaaagg gagtgtgttc ttgaaatact cctctttctc ccctcagcgg tgtcttacta  9120
tatttgtcta ccggattggt cttgaactag ggctggtggt ctctgcacct cagattcctg  9180
actagctgga acttcagttg tatgccacaa tactaccctt agtggttgtg gtgtcttgtc  9240
ttgtaataaa taaatgtaat agcaagagaa agaaaaataa attaagtaga tagagtctca  9300
ctatgtagct cactgtgtct tgaatactgg caatcctcct gcctcagcat gccgaatgtt  9360
ggaggacttg ccagtgatgg ctaccgtgcc tgcttgtagt tgttgagtgg aatgaaacat  9420
ccactgtttg tctcccagtt gtcctataat aacctcttaa aaacagcttg ttcaaagcat  9480
gatccaaata tggttctttc cctgctattt aaatcttttg atctataggt ttctctgcca  9540
tctgtttccc tctctattaa atttgttgaa gaaattaggt tacttttttc tttgttttag  9600
ttgagatttt tggatgtggt gtgtgtgtgt gtgtgtgtgt gtgtgtgtgt gtgtgtgtgt  9660
gtgtgtgtat gtgtttagac atgtgtgcct gtgtgtgcac atgcggcagc cagagaggac  9720
acgtgtggtg gtgccctgct cttttgcttt gcatttaatc cctttgagat gggcgctctc  9780
tctgtgtgtt tttggttagt ctggctggcg gacaaactct gggatctgtc tgtcttttcc  9840
cctgtcagca caggggttgc agacatgcat gtagggtcac atgtggcttt cacatgtgtg  9900
```

```
ctaggggtct gagttcagat tctcatgctt aggcagtaac tgagccatct cctcagctct  9960
ctgtaaactt ccctgctctc tcctttctcg aatcatggct ctattacgtc actttacttt  10020
gtctctttgg ttagatatta aattcataat tggaactaga gactgttctg atattttttt  10080
tcatgaatat tcttaccaat ggattataca tatttttaaa aggaaaatag ccagagggat  10140
ggctcagtgg ttaagagcat tggttgctct tctagagacc taggtataat tcccagaacc  10200
cacatggttt ataattggtg gtaactccag tcctagtggg gatccaacac cagctgagtg  10260
tggtgttatg tgccttagat ccactgtgga tggaggcagg cagtggatct ctctgagttc  10320
aagaccagtc tggtttatac atgtcctgat ttcaggaaag ctagggctat gttgagagac  10380
cctgtctcaa taaactacaa caaccactta aaggtcaaat ctgaatagct tttgtgatgt  10440
aggtagccat taatgatgtt tgtctgatgg tattaatgca ctaggatttt aacctcatat  10500
ttggcttgga tccttcccct tgttagttgg tacttctaag agaaggtctc cttccttggc  10560
tccctctggt catgaggact cagttgtctc tctattggag tagagcttga gtgaggattg  10620
gggtgggaag acttacaggc acgagggaga agtaagggcc accgtgggaa ggggaaatgg  10680
gctttgggta gcttggggtg tgtacactcg tgtgcatgag tctgtgtgca tctatgtgtg  10740
tgtgtgtctt tctgtctgtc tgtgcgaaaa gagaaggaag ttctcacaat gaattgtact  10800
aggcctttgg tctctggtta gaaattgcat gagagccctt tgcccattgc caccctgtct  10860
tggctttttga tctgtggcag ccaagggaag ccatatgaga tctgtgacct gttagcctct  10920
gctcaggaga caaagttcac tcagccgtaa ttcagtattc aggaacagta tttttggtt  10980
ttgttttgtt tttcctttca gattagcctt agattatttt tccttgtctg ttttttttt  11040
ttttttttt ttttttttt taaagattta tttatttatt atatgtaagt acactgtagc  11100
tgtcttcaga cactccagaa gagggagtca gatcttgtta cggatggttg ttagccacca  11160
tgtggttgct gggatttgaa ctctggacct tcggaagagc agtcgggtgc tctaacccac  11220
tgagccatct caccagccct ccttgtctgt ttttaatatt ggagccaatc attcttgttt  11280
tcaggctgat agagataagg ttgtaaggtg actccttccc cctcagacac tttaaaggga  11340
accacttata acagtagagc aagatcattg agggcatggt ggcctggaga gcaagactgt  11400
gaggactctg gaccctagcc ctaggtcagc tttagctttc tcaggagttc tttgtggagg  11460
cagcagtcag ttgtgggtaa gatggctgtc acaccctctt tttttggttt tctgagacag  11520
ggtttctctg tgtagccctg gctgtcctgg aactcactct gtaggccagg ctggccttga  11580
actctgcccg gtggctgtca cacacagtct aaataaagag ggtcttaaga tgggcagtgg  11640
tggtgcacgc ctttaatcct agcacttggg gagcagaggc aggcagatta ctaagttcga  11700
ggcctgcctg gtctacagag tgagttccag aacagccagg gctacacaga gaaaccctgt  11760
ctggaaaaaa agaaaaaaag aaaaaaagaa aaaaaagttc tcttcctttt tgtgtcctcc  11820
tcaaagtata tgaacttggt tgagttttga caagcagttt aggtttatgg aaaagtgagt  11880
gggcagttag tccagtttcc atgtgtcctc tgcgcccagt ttcccatact aagatcttgg  11940
tgtacggtga tgaacttgat gggcctgatg ccgttaagtt cctggagctc aggaaacatg  12000
tgacaagatg gttctgttga ccacccaatt ctcttttatc cacctagtca cccccccccc  12060
cccttttttct tcctgttcct gaacacctgg caaacacctg tcctttcttt gtctcttccg  12120
tttgccatac cctgggctgt attctaagtc gccatcacta agtcttttcc tgttaccttt  12180
cgctcggcag cctgcttttg agatcctttta tgtattttcc tggcttggtt tagctgattt  12240
atgtagtgct aagtaatact gcatggtata gatatgttgg tctgtttatc cactcaccta  12300
ctggagaata gagtgttgct tccaagtttg gcattggtgc acaaagctgc tgtaaatatc  12360
cacgtgtgag ttcttgtgtg gccatacttc tagcactttg aataaacacc agggaacaca  12420
actgctgcat tatatggtaa gaatactgcc aagagggtct tccaaagtgg ctgtgtcatt  12480
ttttgcattc ataaaacaga aaatagggtt tcttgttatt tcacttcttc ccctgggtta  12540
ttgttttggc tttttgccat tctagtatat gaatagtgat agcaatttaa tttgtggttc  12600
tgatttcctt catgtgctgg aagtatctga atgcatcaat gttgagtgtt ggggcggctg  12660
agacaggaag gtggtgcatt caaagccagt ctgggcttca tggcaagaca ctgcctttta  12720
gggcttttag tggccaaacc taggatctca tacatgttag gggtgcacac ttgtcactga  12780
gatacatcca agcccaaggc cctgcctcaa gatgaagtaa attagtaata aatgttaggt  12840
tatgagagct ctgccctcat gactagattg atattattct tgttcttttt ctccctttct  12900
ccattttcat atgtattgta tgcatgcata tgtatgtgtg cctatgatgt gtgtgtgtgc  12960
atgcacatgt atacacatgt atatggaggc ctgaggctga tgtggagact caccctcagt  13020
tgctcttcca ttactggtgc aggatctctc aagcccctag cttgctgatg tgcctatagt  13080
atcactagcc agcttgcttg gggggatccc ttgcctctgg cgtctctgta attataggca  13140
ggccactatg cctttttcttt ttttttttta agttttgttt attattatac ataagtacac  13200
agtagctgtc ttcagacact ccagaagagg gtctcagatc tcattacata tggttgtgag  13260
ccaccatgtg gttgctggga tttgaactca ggaccttcgg aaggtgcttt taaccgctga  13320
gccatctctc cagccccact tccttccttt ttaaagaatt atttatatat tatgtgagta  13380
tactgttgct gtcttcagac acacaggaag agggcatcag atcctattac aggtagttgt  13440
gagccatcat gtcgttgctg cgagttgaac tcaggatctc tggaagagca gtcagtgctg  13500
ttaaaccacc aaggcatttt ccagcccttc tcttactttc ttacattgct gccttgtgtg  13560
tcggtgttga catttctctt tcatatgctt cccaccatgt cgtgcctgtc atgagggagc  13620
agaaaggctc acaagtgagg gatagttatt ttcttccttg tttttccctt tggtgaatta  13680
agatctgttt ttgctgtgta gcccaggctg gccttgaact tgagttctgc ttcagcttgt  13740
ctagcactgg ggttacagac atggctaaat catctttatc cttccagctg ctagaactat  13800
gggccaaata aagttttgtc cattgtaagc tacctggtct gataaagtct attgtagttg  13860
tataaacaca gacaaagagc accagtgtag caaaaagcta cacctccacc cccatacaat  13920
tactaaagta tctgttctga tagtttgcgt attatttatt tgggatattt ttcttgttga  13980
aatttaagac ttcttggtat gttttatttg agatattttt cttgttgaat tttaagactt  14040
cttagtatgt tttagaatca gcctatcaga taaggacttg cagatacttt cttgcagtct  14100
gtggcttaca ttatcccatc tccccacccc cgaaaagttt aatttcagag tagtcaaata  14160
attataatct ttcagagttt gtgcttttgg taatatgtct accaaaacca agaacactta  14220
cccttttttct taatatttag aagttgctcc atttattgat tgtttagaga caagtcttgc  14280
tatttagctc aggatagtcc aggttagcct tgaagccaca gtcttatctc aaggttgtag  14340
gtatgagaca ttgattgttt ttctttcctt tcctttcctt tcctttcctt tcctttcctt  14400
tcctttcctt tcctttcctt ttctttattt atttttttgg tttttcgaga cagggtttct  14460
ctgtgtagcc ctggctatcc tggaactcat tttgtagacc aggttggcct tgaactcaga  14520
aatccgcctg cctctgcctc ccaagtgctg ggattaaagg tgtgcgccac cattgcctgg  14580
ccaattgttt gctaagctgg agtcttactg cattgtccag gttgctctct atatcctcaa  14640
```

-continued

```
gtgacccgtt cccttctctt cctgagcccc cggcaatact gcccacttca ctgtctccac  14700
aattttgttt ttccagaaag tcacatatga tgatgtagtg tcttggtttg gcctcactta  14760
gcaggagctt tttaagattc taccatgtct tttttgtttt tttgtttttt ccttctattc  14820
tttttttttt ttttcttcct ttccctgcct ctgcctccta agtgctggga ttaaaggcat  14880
gccccaccac ggactggtac ttccatgact tgatagtctt ccttccattt agaatgactg  14940
gcatgtgcca ccagacccat atttttttgg agttttataa ttttgtgttt tacattttag  15000
tttgtggccc attttaagtg tgtgtgtgtg tgtgtgtgtg tgtgtggtat agtatctgtg  15060
tctagaattg tttcatttgt ttaggtttat ttatttaatt tatatgtgtg agtgtttagt  15120
ctaaatgtct gtatgccaac catgtgtgtg agaagtcaag agagggtgca gattccctgg  15180
tactggagtc atggatactt gtgagtttcc gtgtggctgc tgtgaatcaa acctagggcc  15240
taaggttaat aagggctcta aattgccgag ctatctcttc agcctctaga atctgtgccc  15300
cgccccccac ctttgtatag ctctgattgt ttgggaattc tgtctgtaga ccaggctggc  15360
cttgaactca cagatatctc tacctgcttc tgcctctcaa ataatgggat taaaagcgtg  15420
caccactgtt gtgggaaata tttaagaagt taacccacca tctctctgct ccactggtcc  15480
gtgctcctgc tccagtaccg gtactggcct gccacaacac tatgtcctgg cgcgtcccac  15540
tttggcctgt tctcaccgct gagctactct ctcccagcta gcgggttgat cccgctttca  15600
tgcaacaccc tacacacccc atgatcagcc atctcaacac ctagttaccc agtagaaaac  15660
tgacacttaa agcttaataa tccaatcaga tgtatataac aataagatca caagttacaa  15720
gatgccaata caataatttc agagccaact gataaggata aagctttacc ccaattattc  15780
taatctttgt gacaatctta gctacttgtg gctgttcaaa accatgtggg atcaggatca  15840
tcttcctgtt tgtctgcctc catgttggct tctcccctcc tcctacctct ctctccctgt  15900
cccccaaact cttagctcca actccccttt cctgaagtag caatgaaata atgttatggc  15960
tcggggtcac tccagcacga ggaactgtac taaaggtcac accgcattag gagggctggg  16020
aaccactggg atccttgttt ctttcattaa agtttcagag tctccttcat atagggcctt  16080
tgcatatttt gttagagttc agagttagat tgtttgtttg tacgtgtgct agtataaatg  16140
atattatgct tcaagtttca aattctagac ttatttaata ccttgtatct ttaatcccaa  16200
gtgctgggct taaagcatgt gccaccactg ccctgctctg gccttgttct taatcggagt  16260
gggtgggaaa acatctccct tctcgctgtt ggctttttga agattgtttt gaaaatcagg  16320
ttgaactttc cttttctaat tgctgaggtt ttttgtgaaa gtagttaaaa gtttaaccct  16380
tttttgccta ttaatatgat tatagaattt ttcttctctg gttgcagtaa tggatattat  16440
ttttgaactt tgaactaatc ttgcatatct ggagcaagtt cattcggtta tgtttattta  16500
ttaatcatcc tgcttcagcc tctttaagtg ctgatatacc agctgtgcac caccaagccc  16560
agcgtcttat ttaagtcttg gtagttatat cttcatgcat tggtatgtct catttaggtt  16620
aacagatctg agggatattg ttcttcatga cacttattaa tggctgtaag atcagtagtg  16680
attatttgcc tttcattttt tgtttgttta tttatttatt tttgattttt cgagacaggg  16740
tttctctgta tatccctggc tgttctggaa ctcactttgt agaccaggct ggcctcgaac  16800
tcagaaatct gcctgcctct gcctcccaag tgctgggatt aaaggcttgc gccaccaccg  16860
cccagtttgc ttacttattt ataagttgta tgtttttagc caggtggtga cccatgcctt  16920
taataatccc agcttttggg aggcagaggc aggcagatcc ctaaaattcg aggccagatt  16980
ggtccaagga atggcttcca gggcagccaa agctacatag gaaaatcctg tctcaaaatc  17040
caaacaaata aacaaaaaaa ttgtatgtat gagtgtgtac ttctatattg gctttgtgaa  17100
tatgggtgta gtgtctgcag aagccagaag agagcattct gttcccagga gctgcgggta  17160
ctggggactg aatgctcaga atcgctgagc tgtctctcca gcctcctttc actgctagta  17220
ctagtaactt aatatttgta tgtgtatttg cctgggagta tgtttgtgca ctagataggt  17280
gcttggccag aaggcatcag gtctcctgga actggagtca caggtggttg tgagccacca  17340
tgtaggtact gggagcagaa ccgggttcct ctgcaaaagc aactggtgtg cccttaacca  17400
cttataattc tccagccctg atattggcag tttttatatg ttcttcacta atctggctac  17460
aagttgacca gtttttggtt tttttgttg tttttttaag aatttattta tttattttat  17520
atatatgatg agtatgctgt agctgtcttc agacacacca gaagagggca tcagatccca  17580
ttacacatgg ctgtgagaca ccatgaggtt gctggaaaac agtcagtgct cttaactgct  17640
gagccatctc ttcaacaccc tgttagtttt tttgtttttt tgttttttaa ataaaagtat  17700
acatatacat tttaaatttt atatttattt tatgtttca tttttctgc ctgtaattct  17760
gtgccccatt cccattcagt gtttgcaggt gccaaaggaa ggtgtcagat cttttggaac  17820
tggagttaag ggtggtggtg agctaccaca taggtgcagg gaaatgaacc cttggtcctt  17880
tgcaagaaca gccagtacat gtaacctgtg aaccatctct ctagcctatt aaggttttat  17940
agctgaaaat atgcccttct ccctttaaaa aaaaaaaagt gctggatata tcagtttctc  18000
tttttttgtc tgtgtgactt caaagtgcca aatatgtaaa acaaccagag gccagctatg  18060
gtggcacagg cctttaatcc cagcacttgg gaggcagagg caggtaaatc tcttgagttc  18120
gaggacagcc tggtctacag agtgagttcc aggacagtta gggctctgtt acccagagaa  18180
cccggtcttg aaaaagcaaa gcaaagcaaa ccaaaaaaaa aaaaaaaaaa aaaaaaaaaa  18240
tccctaaacc aacaaaccaa agaacaacaa caggaaagaa ctaatgagaa tgctatatcc  18300
atggtccatt gatggtgaag tgataaacaa catggtgtag ctctacacag taggctgctg  18360
tttactgtta agaggagaaa ttctgctgtg tgaaaagcag gcacagagga caagtattat  18420
acagtgttgc atattatagg aaccacctag gcagtggaac atacagaggc agaaatcatg  18480
atggttattg ccaaaggctg ggggaaagag gaaatcgggt accatgaacc ctaacagttt  18540
caactgagaa tgttaaaaac ttgaggagag ccggggagtg gtggcgcatg cctttaatcc  18600
cagcacttgg gagacagagg caggcagatt tctgagtttg aggacagcct ggtctaaaaa  18660
atgagttcca ggacagccag ggctatacag agaaacgctg tctcaaaaaa caaacaaaca  18720
aacaaaaaaa ccaaaacaaa acaaaaaaaa aaacttcagg agaacaggta gtggcaatag  18780
ttaaacacta aggtgagtga atgtactaat gacatagatt gtgtaattaa aagtggctga  18840
aagcacacta ctacttggtg agcataccta gggtcctggg tttgagccct atattgggag  18900
gaaaacaata gttgtaatgt taaattatgt attatatata ttttaccata atttgtgaaa  18960
atgagaaaaa aatttaaaat tattttattg tgtcttatgt gtgtcttatt tgtgttggca  19020
cccatcatgt tacagaaagg tgcgagccag ctggtgtgag ttttgggaac agaccttggg  19080
ttctctgtcc tgggtgctta taactgcaga gccacttctc cagcctggat gatttattta  19140
tttttaaaa aatctgtgtg gtattgataa tggaaagggt ttaaaggaag ctatttgaaa  19200
tgtttaattt tcatggtggg aggtgactgg ggatattttg agcctctgct actgagctac  19260
atttccagct ttcaaaattt taacttaatg ctagtattag cattatttaa ttttcattg  19320
ttactgtttt gatagaattg ttatatatag ttaggatgtt ttatgatgag taaatcagca  19380
```

-continued

```
caaaatcgtt tatttgtgtt gagtcttgta agggtctaag aatcgctgaa agaagacccc  19440
agactcaata gtattcaaag acaaagagtg ttctgtagaa acagccagca tgagtgggtg  19500
gaggatgggt gggggactga agggggtggt caaccatcca agcaaaatgg caaccatggg  19560
ggaggggtct cacagaccca ttttaaagcc agttacggat tttccagttg tggttgggtc  19620
atcttcaatc aggattggtt gagcttatgg tatgggatat ttgtacactt ctgattggtt  19680
cctacctgga gggagagagg gttaccttat agggactatt tctgtatctg ttataagccc  19740
ctggccagat gtcagagcag ttgctgattg gttgctcttt ttcttcgttt tttccaagaa  19800
gcctgggatg tcctgggaaa ttgaggctta aggcctaaca tggctgccta ttattctaaa  19860
atggagtgag ttaggtcctt tcagtttgat actgtagaac atatggatgc cttcactgct  19920
ctgcttattt gtagccagat tctgagattt gggttttgag attgaaggat cttcaggggt  19980
cagtggagca tagctgtgtt tagagtgttt gctcaccatt caaaggtccc tatgtttgat  20040
ccaacaactc ttcaaatcaa cagaacacca aaataaatta cttaagcctc agagattcta  20100
cctggttttt ccttactaag tgcagaagct gatactgccc ttccctggag ctgagcccgt  20160
ttgcccagca tgctgggtcc ctgtgaacac ctgaatctgg tcctgtcaac ccaggcccgt  20220
gataacataa aacctggggc ctctgtccat gcctgctgcc tcttttcaca gctttgcagg  20280
taacagagca tgcgtggtgg gcttgacact tctttattta ttttatgtat atgagtacac  20340
tgtagctgtg tagatggttg tgagccttca tgtggttgtt gggaattgaa tttaggacct  20400
ctgcttgttc tggccaaccc tgctcgcatc agaagagggc gtccgatttc attatgggtg  20460
gttgtgagcc accatgtagt tgctggaatt tgaactcagg accttcagaa gagcagtcag  20520
tgttgagcca tctcgacagc tcttcttcat gccttttaag tcctgattgg taactgggat  20580
tgaggactgg aaccttctcc tgggggactg acctaacagg tggtgtagtg tgtggtggtt  20640
ttgacaccat atttataaat gatcatgcgg cacaaattca gaactaccat tcaaggatct  20700
attgacggga tcccagagct ggccggttgt cagaacacat ggaccattag atgcctcaga  20760
ctcattgctg tgaccagagc tagtgtggaa gtggggggct gagaattcca ctcaggatgc  20820
agtatctctt cctcactact cactcttctg aattaaggcc aggccaagtg aggtcaacct  20880
taaaacttaa catgggccgg gtgtggtggc acattccttt aatcccagca ctcgggaggc  20940
agaggcaggt ggatttctga gttcgaggcc agtctggtct acaaagtaag ttccaggaca  21000
gccagggaaa cagagaaacc ctgtcttgaa aaaccaaaaa aaaaaaaaaa aaaaaacctt  21060
aacatgagca agtggattgg tttaggcctt aacaccatgc tttttaaagt taaaagtgaa  21120
aatgcttatt aaggaatctg aggttatatt gcaaggtttc tcttattaaa ctttttggtc  21180
tttaggcagg ccagcttgtg acaggcagag gtaggcagag ttttgaggcc agactggtct  21240
acaaagcacg tcctaagcca gccagaacta tatagtaaga ctttgccttt gaaaaaacag  21300
aaaagacgag aaattggtct tgcagtgaaa gtgttgggtc tttttgtttc cttttggctg  21360
ggtttacttt taagtgagac agtgagttag aggaagaggg tgtacctgtt tacatgtgaa  21420
cattgtgtgc cgggagctcc ttactaagtt ttgaattttc cttaatggaa tcttagataa  21480
attacctata ctttttgatc tggaattttt ttcttaaagt ttatctttgt aacaacttaa  21540
aacaggaaaa agaggggtta gagtcgtaca taactaccat tctgagttct gaccttgtct  21600
tgggaggtgt aattgtttct agtgttctga ggagtcttgc aaacctgcca ggtaaactgg  21660
acaggaacca aagaagtcat tatttagtaa tttatatgtg gtattttttaa acttattcac  21720
atgtaacctc tcttagtctc cccctcgccc tctttgtgga agtcatgtga atgttctgta  21780
gacttcagtt gtagggctgt gcagttgttc ctgctatgga gattgaacac ttgctgctct  21840
ctcttttttt ttttttttga gacagggttt ctctgtgtag tcctggctgt cctggaactc  21900
actctgtaga ccagactagc ctcaaactca gaaatccgcc tgtttctgcc tcccaagtgc  21960
tgagattaaa ggcctgcgcc accacgcccg gcacacttgc tgctcttgta gaagacctga  22020
gtcctgagtt tggttcccag tacctatgta gggtgactca caaccacatg taactctagc  22080
tccaggggga tccaatatct ctggcctcat caggcacctg catatataac ccctatgcat  22140
taatgttgtt ttgttttgtt ttgttttgag atagcacatc tgcttgtctc ttagttcact  22200
atagagaatg acactggcta cgtaggatgc caagtaattt aaaagttatg agctgtgtat  22260
tcctggaatt tcctgtgtag ttttgaaact gtagttgagc atggataact gaaaccacta  22320
aaaggaaaac ggaggtaagg ggtaggagtg ggcggggcct gctttacagt gctctgctga  22380
gccactggcc cagggatgag tgctgaagtg ctttctgtgt ttcctaacct gctgctgctg  22440
cgagcattct ctgtgcctgc tggagtctct ctgcttgtag aacagagctg agcagttcac  22500
tgtccaacag gatctgccta aggatctgga gctggccctg ttgctgagat gataagaggt  22560
aaagcgacac tcaggagatt gctggaaccg ggcagcggtg gcgcacacct ttactcctag  22620
cacttgggag gcggatttct gagtttgagt ccagcctggt ctacagagtg agttccagga  22680
cagccaggcc agggctacac aaagaaaccc tgtctagaaa aaaaaaaaag gagattgctg  22740
gatctcactg acactgctcc acaactcctg ggaaggtgga cagggcaggg ccggtctgct  22800
gggcgccact atagaaatat ttgttaaaat gctaggatgg tgatatgaag gtggttggca  22860
gatgttggtg gttggactga ttgtgtcaaa acatcaagca tcaagagaag gcttaaaaaa  22920
tctaatatct aaagtctttg tcttctacta cttgaataca gcatgcttca agcatccctt  22980
acagttggac atctaaattg tttccttttt gtctgttgga aatgaagctc tagaaacatg  23040
cccagcattg gctttgcagc tattgtcttc gtctgcgttg cttagaatac gcttcttaaa  23100
tgttgccagg gatcttgtga ggcccagcag tgagggaggg agcctggcac tcagcttgga  23160
gcctcttctc cacccatgaa gagtagagat ccactctttt gtttgttggg atggtgcttg  23220
tcaaattttt gcctttcaga ctcttggggt gtgtgtttca caatggaaat gagttacttg  23280
ctgttgacta tggagtttga ctagtgtgtt aggtttttag gggaagaact gggggtactt  23340
cgcatcacca aagtggaaag gtgtttgtcc ttggctataa gatcctgcac gtaggactta  23400
ggtagggtgg atacaggtcg gtgctagagt gcttgcttat tactgtatcc caggaacttg  23460
ggcttggtcc tcagtgatgt tgagcgaaca agcagattaa tgggaacttg ttagttcagc  23520
agcagctctg tctgccagtg agtgatctgt cataaaatga agcggggctc ctcggtcagg  23580
gtcagtgtaa gtgcgtgccg taggtgcttt ttggtgaaga agttaaggta ggaaggggct  23640
ttgagtttgt gaggattatt gaatattatc ctgtgaaaac agcagaccag gagagagaga  23700
gagcttagct gggtacacgc cacaggttga aaactgctga tgtagaatga ctcaggagag  23760
ttttattttt acatttcatt gatttgtctt tcctgttttc ctttccattt tgtttattgt  23820
gttctacatt tttttctaag gacagtttta attcctttg tgggcttgat agctagtcat  23880
atttttaaga tttgttttac tttatgtata tggatgcttt gcctgaatgt atataaatgt  23940
actatgtctg tgcctgatgt ttttagagac cagagacatc tttaactgga tttacaagtg  24000
tgggccatca tttgggtgct gggacaggat ctcagtctat acagtgacag ccagtgctct  24060
taaccagtga gacatctcat caatcatttt taaattattc ttcttttaac tgtgtgtgtt  24120
```

-continued

```
ttagtgtctt tgtttatctg atgaatgtat ggagatgaga aaacaggttc tgaactcagt  24180
tctttttact tttttttttt ttttttgaga caagtgtctc acaatgtagc tctggctacc  24240
ctggaatttg ctatgtagac caggccttga ttcacaggca tccttctgcc tctgctgccc  24300
acgtgctggg attacaggtg taaaccacac atcagacctc atttacaatt ttacttgtgt  24360
tatttcaagt atgtggtaag gaatacagag taacatcgaa tctttgagca tctacccctg  24420
aatttaagaa actctaattc tattttaaac ttattttctc cttcccttcc ctccttaagg  24480
acaacagctt ttcagatgta ttacacacta cgtggtgccc ctcctgcttt ccaggtgatt  24540
gttgccacag gcaggacagg accttccctg ttcttcccaa gtaatgcgcc atagtctgta  24600
cttacatcca tgagcaatgt gcactgtatt ctgtacttac aaacattgta ttagtgggtt  24660
atctttctta ctttagaaaa ctatacgtgt gagcattcat atatacatat ggcacagctc  24720
tgtagttcag aagataactt ggaatttgtt tatgtgcacc aacacttcag tgtctttgtg  24780
ttttaggaga gcttaatttg agaaacatgg ctgcagaata gaaatttaaa acccatgtat  24840
tgccaggcct ggtggaatgt gcatggagct cgaggtgctt acaagaccat ttgcaggttg  24900
tgtcaggatg ctaacatttg ccacctgttt tcaagccatg taacctcttt ctagtggaca  24960
ggtgtcatta tgtccacttg atagatgaag aaaatgaggc tgaaggaagt atagggaccg  25020
gtatataaat gtgtgtcaga agcaggtata gaatctataa ggcaaggctc cttttgcagt  25080
gatcaaggga ctatagtcag tgatcttggt gcttccagga agcctgtggt agagtaggac  25140
caccgaagtc tcagcgagca cttacgtggg tgctggggag tctgaactgg ttctcatgct  25200
tgcatggata gcatgggctt tacctactga gctttagctt gttaaatatg tcatccagtg  25260
gcattcagca cgtttacatc attatgcaag cctttgtttt tgttttttaa ctttttttatt  25320
tattttatgt gtgtgagtgt tctgcctgtg cgccatgtgt ttgcattgcc tgcagaggga  25380
ctggagttac agatggttat gagggaattg aacctgggtt ctctgggaaa gcagtcaagg  25440
gctgttaggc tgtttagtgc tatagattga acccttgaat gcaaatatcc taccaaagcc  25500
ctgctattat ccattccttt ttaagcagtt aaatatttgg gttgtttgct tattttgtct  25560
tttgtggccc tggttgttct ggaactcact ttgaccaggc tggcctcaaa ttcacagaca  25620
tccacctgcc tctgtccccc aagtgctggg atttacgaat ctctgctttc agctccttta  25680
tatttatatc tgggagggaa attgttaggc cagatggcaa ctctgtgttt aagtttgaaa  25740
tgacatttta tattttttat tatttttagg tagggccttt gttgcctagg accttgagtt  25800
cccaagccta ctggatggat tgctagaaga gacttaaaga cttaaagatt tgtgttagac  25860
ttcagaagcc agagccaggg ctagtcgtgt aagcctgtga atttgatccc tggggcctgt  25920
gtgaggttgg aaggaggaca accatagagt tgtcctctca cctccactta ggtgatgtgg  25980
cacaggttgg acatgggatt gcataagtgt gtgcatgtac acatgtgcat tcatgcacac  26040
atacactcac acacacagaa taaaaaattg tttttaaaga taagcatcta gaaacatgac  26100
taagccacag gttggtggtt cgccatatgc tttccactga actgggagtg ttagcagctt  26160
ggttggtcag cattgtgaac ggcagcaggc agcagcagca ggagcttctt acaggtctta  26220
gacagcctca gctcctggga cccctgccct gaagcggcag cccttgagag tgacacatgt  26280
cacagtcctc tgacctaggt gccaggatct ccatcctttg agagaagcta gtgttgcgtg  26340
tcttaggcct gtaggagcgc tccctggaga gagaagcttc tgctgcgtct agagcccagg  26400
cctacattgt cttcagctcc tcacagccct cattgtttct gctgcctctt ttgtttctgc  26460
cctgacaccc tagctgccct tgtgtattta ttgtcactgt ctctacaatg gctgcttcca  26520
ccctctcttt tttatggcag cagcctagcc agctctgcta attatatagt tagaagcaaa  26580
gaaaaaggca caagaatcct tttattggtc ccagtgttgc agtaccagcc caggagcccc  26640
tctccagcgt ggttaacaga gagctgagca gccttcagtg tgaccagaaa tggaccagaa  26700
atggacatct ctatctcaga atttcatgaa aaagaacaac tgtctgaacc aaaaaaaatgg  26760
cacagtccct tatgcaaatg aagaactctc cttacactaa ttgtaggctt tctgtttccc  26820
cttgtttggg tgaaaatgcc tgcaaggtaa actgtcatct ggacctcact gagtctttca  26880
tggtaaaatg tctagggcaa tgcgtttcac acaggccagc cccctgcttt ctggagctgc  26940
agttactact ctcgggtagc aagcagcagt ggcagctgag gaacttcatc tgatacctca  27000
gtgcagtatt cacagccaga cctatgtgag gatagtcctg cagctgatgg atggcagcct  27060
gggtgccagg gagagctctg atagctgtca gttaggcagg tggcccttag aaggatgctt  27120
atagaaaaga caagccttcc tgctgcagcc ttcatatcat agtgggtttg ttttctgttt  27180
tgtttgtttt gttttaatgt tttttaaaat ggggaatgtg ggagggggat gtatgctgca  27240
tgtatggagg gaggtcagag gacaacttgt ggaagttact tctctatttt cactatgtgg  27300
atcttaggga ttggacacag gcagcaagta cctttaccct ctgagccacc caatagcaac  27360
tctgtttgtt ttaatgtagt tatcctctta gatgtaaatt gatgtctgat tgtggttttc  27420
attagttaaa ctgtggtggt ttgaataggt atgtctccca tagacttctg tgtttgaatg  27480
cttggcacta ttgagagatg tggccttact ggagtaggtg tgggcttatg ggagggagtt  27540
tgtcactgtg ggggcaggct ttgagatctc ctatgctcaa tctctagccg gtatggaatt  27600
cagtctcctt gctagctaag gatttagatg tagaactctc agttatctca tctctgtgct  27660
gccatggact gaacctctga acatgtaagc cagcctcaga taaatgctgt cttttataag  27720
agttgccttg gtcatggtgt ctctgcacag aaataaagcc ctatctaata taatggctaa  27780
cagtgcattt ttatgtgtct attgcaatct gtctttcttc tttggagaaa tgtctgttta  27840
gacctttctt ttttcccttt tgcattgttg aatcatgctt cttacataat ctgtcaggat  27900
agtatttctt tatcaaatat ataacttgca aatatactct cccattctgg ggattttctt  27960
tttactttca gtttttttaaa aattggcttt aaaaattttt atgtgtatga gtgttttcct  28020
gcatgcatgt ctgtgcacca tgcctggtgc ccttggtggt cagacgagag cattcggtat  28080
cctgaaactg gagttacaga tgttgtgagc cagcatgtgg gtgctaggaa ttgaaccctg  28140
agtactctgg aagaccagca ggctctccta aacatgagcc atctctccag cccagtcctt  28200
tactctctta atactttact cttttgcaca aaggtttaca atttttgatt aaattcaatt  28260
ggttcttcct tttatatgtg tgtttagtgt catgtcttaa gaagtcagtg ccaaatgtag  28320
tgtttcctac agtgtgcttt ccagagtttg aggttttaag tgtggctttt tggcactctg  28380
agtgaattat tgaatattgt tgaaggtaag tgtctggcct tattcttttg tatgcggata  28440
tccagttccc tcagcaccat ttgttgcatg atctattgaa cagtctttgc tcactagttt  28500
gagttatttt tattatgtta actaagagtg cacagaaata gaaacttctt gtgttcaagg  28560
atgatttaaa aggaaacaaa tttacgagtt agagatgcta ttgaaatcgt ataagatgtt  28620
aattttcatg gcatctcatg ataccactcg aagtgaacat tggtggtgtt gtgtgatgtg  28680
gaagtgtatt taggtcctgg ccagagtgac acccttcggt tatgaaaatt tggcccttgc  28740
agcagtgtca cctgctctta cttggcatgc atgcatgcat gggtcaccaa gttgtgcttt  28800
gctcttggct gttaatacag accaggtaaa tctcttgcgt ggcctgagcc ggacaagcag  28860
```

-continued

```
gtgcagcagt atgtatgtgc tgggacacag ggcagccctg tgctcccaag gaaggctagc  28920
ccttagccca aacagaaacc atgtgagact tcctgtggca ccgtccactt tctcttgtgc  28980
tcctgaaggg ttaattcccc ccacccctga gagttagccg ggaagaggga attatttaca  29040
cctcgtctga caaagggagc ttgttttgct tttcccagag gaattattta caggatcctt  29100
gcttctgtgc tccttctgtg gttggttagg gtgcttcctc atggctagtg accccacctt  29160
tgcctcagtt ccactgtaac cacagctttt cattgactgc aactagattc aaagcttgtg  29220
ctcccagtct tagatgggat taggatgttt gctcttaaca ctgattttac tgccaagatt  29280
ctgtcaagtt gaagattcac tacatcagtt ttgtttgcat gaccatagag ttcttcacag  29340
ctaaattctt aactgggttg tccctccctg tttaaagtgc tagactaccc atttgatttt  29400
taactattga aaatgagtga tgctgagata agcttccggg tgaggacctc atgcccctgg  29460
ggcagagagg ttctttagct gttttctgct tggatacagt ttggtttaga tattcagttt  29520
ggttttggtt gtttggttgt ttgttttgag acagggtttc tctgtgtcat cctggctgtc  29580
ctggaactca ctctgtagac caggctggcc tcaaactcag agagatctcc tgcctgtgcc  29640
tcctgagtgc tgacattaaa ggtgtgtgcc accaccacct ggctagaaga tggagtcttt  29700
ttatgctgtt ctgagcaaag agtctccact ttgtaggctg tgaaggcaag tggctgaaac  29760
tggaagtgaa gctctgccta gctgctggaa ggagtggctc tccccccccc cccccccagg  29820
cggaagtgtt ccttgtcttg tatgcatgtc aggaagtgta gtaatcttgt atgacttcag  29880
gatgggattc atttagtatg atagtataca acatttttct aagtttgtat caagtcatag  29940
ctaagcagat tatatatata tatgtgtgtg tgtgtgtgtg tgtgtgtgtg tgtgtgtgta  30000
tattttttttt tttaaataac caaaacaaga gtgttatgtg aattaacaca ttatgggcta  30060
ggtatggtgc cacacccacc agtgagagtt tgaccatgct ctagtgaata tatagacaat  30120
acaaactggg ctttttccct ttgattttta cttattattt taatctatct atccatctgt  30180
ctatctgttt attttgatgg gggggaataa caagggcaag gtggtcatgg aaagactggg  30240
aagtgagtgt gatgggttgc ataatgtgag tcccagagga tcactgaaaa tactacatgg  30300
aaaaaaaaag agaatttcaa catatgaacc agggaaatgg cctaggatgg agagagctga  30360
gtggcagagc acttgtctgt gtgcaaggct tcgggtgtga ccccagcact gcaaataaat  30420
aataacaaaa gggaaagggt tcactgatcc agcaatgtag gtagatatca aaatattgac  30480
actgaaagac taaatgagta accctacaag tattttctgc ataatttgct ttatatgctt  30540
tttataaaat tatatataac tatacgagat gcaaaactaa agtagtaaaa aggacatatt  30600
aattgttgct gacgatgggt aaaaataaaa gcaggctgaa ttatagagac ccaagaaagc  30660
ttgggaaggt gtcagtgtgt tcactattac gattataaag atagtctgac atccactggc  30720
caaaatcaag ttttaatgtg tagcttatta ttatacttaa gtgttatgga gctaaaataa  30780
taccggtaaa aacctcagct tcactgggtg gtggtacaca cctttaatcc caacactcaa  30840
gaggcagagg cagggaggca gagaggcaga ggcagaatct gtgagttcaa ggccagcctg  30900
atctgcacag agaattctag tacagccagg gccaaataat acagaataag acaagtcctt  30960
attctcatcg atgtgtatcc tcattagctg ggtaatagca cacgagctga tagttctggg  31020
gacttgggcc caggcctcac atgctaagaa agagcactat cactaagcta catgtctatt  31080
cagtgttttg agatagggtc ttgctgcata gtttagacag gcctagaact catgatcttt  31140
ctgtctcagc ttcctgagtg ctagaattac aaacatgcac accactttgg ctgatagagt  31200
agtttattct aaaatgcttt taaaattgga accatgtaaa acaatcaatt ttagtaatat  31260
aatctcttgt tcatttttaa agttttaatt atgagggatt tattttcttt ttaagattga  31320
ttttatttta cgtgtgtgtt ttgcctgtgt cctgtggagc tcagtagtgg ttgactactg  31380
gagctggagt taaggatggg tgtgaagtac atgtgggtcc tgggaacaca acctgggtcc  31440
tctgcaagag cagcaagtgc tcttaactgc tggatcactt ttattagttt aaaaaaaatg  31500
tgtatattat ttttctgcat acatatctgt gcacctcttg catgtctggt gcttgcagaa  31560
accagaatag agcatctaat ctcctggagt gaactacagt tggaagccaa tatgttggtt  31620
cggagacttg aactgggccc cctggaagag cagcaagttt tttcttaacc agtgagtgag  31680
ccatttctcc aaccctaatg tgattctctt cattagttta tctatttact tatttgagga  31740
aaagcctcac tatgtagctc tagctggcct ggagctggcc ttgaactcac aaagatctgc  31800
ttcctgaacg ttgggattaa agttatgctc cagcatacct tgactctcaa gtacaccata  31860
gtttatggca ttaagtatag tcacaatgta ttgtggcaat tgtcactatt aagttccaga  31920
acattcatca ccaaatagga attctgtttc tttccagccc ctggcaacca agaggctctg  31980
gattttctta ttcttcatgt gtcatgtaat agactcatac tgtatggggc tggttttata  32040
gcttcagggg tttagtgcat ggttctcatg ctgggacaca tggtgggatg taggcagaca  32100
gggtgctgaa ggtaagttta gaattctaca tctagattag taagctgtag gaagacatgc  32160
acgcacacat gcatgcacac tgagcctgat ttgagcattt gaaaccccaa agcccatctc  32220
caagtgacat acttcctcca acaaagccac acctcctaat tcctgtcaag tagtgccact  32280
ccctaaagac caagcatcca cataaacgaa cctgtagtgg ccactcctct tcaaaccacc  32340
gtgtgtgtgt gcgtgcgtgc gtgcgtgcgt gcgtgcgtgc gtgcgtgcgt gcgtgcgtgc  32400
gtgtgtgtgt gtgtgtgtgt gtaacttaat atcaaccatt tgaaagcata caatttatgt  32460
tgttgtcatt gcccgtctcc agaaattttt atcctcccca actgaagctg aaaatactgc  32520
tatattttct cttccatcct tgccccctata gccatgattg tctattatgt caggattatt  32580
cctgggattt gacttctcta gagacctcat aaaaatggga tcaaacagta tccttttgag  32640
tccagctgat ttcactctgc gtaacagtat tctcaaggtc cactcacttt ttatccacca  32700
ttcctcgccc atagactcct tcacttggct ctgcctcagg ctagcatgaa taacactgca  32760
gtgaacaggt ctcttctgga gacctgctct cagttctttg gggatgcac ccatgtgata  32820
attctgtgtg tgtttgttag tttttcttta acaaattgcc atgattctct ccccatgctg  32880
tccattttat attcccggaa gcagagacaa gggtcctcca gctgtgtcac gtgcttgtct  32940
gcacacgaca acgtgtttcc ttttgtttgt tttatagaaa tcaccctaat agctactata  33000
aaattttcat acactttaca ttttaatgta taaccaagtc ttaatgtact gctggacagc  33060
agttacccct aaacccttgt ggaagtgtgg aggactctga caactgtcag tctcctcctc  33120
agccttactt actcccaaat atcaaggcgg cccagggaag tacacagtgt accttggtct  33180
ggcatgtaac ttttgaagac tttatggaac ctacagatgg cagaggtcag caggtgttcc  33240
ctgtagagac aatacgtact ccttattggg tctgtggtct ctgtctcagc cgctgcactc  33300
tggtgtgctg gtgacaagca gctggagtca acgtggaaag gagtgagggg tgttgattgt  33360
attctagaat agttattcat atgtgcttga atttgaatta tatatacttt ttaaaaattt  33420
attttgctat tttatgtgta tgagtgtttt gcctccatgt atgtgcgtgt gccacactca  33480
tgcttggtgc cggaggaggt ggtgagcctc tatgtgggtg ctgggaaccg agccctcctt  33540
tgcaacaaca gtactcttaa gcactgagcc aactctctag cccattatat atgcttatcg  33600
```

```
tgtgtcgcag tataattctg acttcttttc aaccatttaa aaatgaaact ataaaagcac  33660
ttttaacttg tggagtgtat acaaatggcc tttgttttgc tctttgggca tgaactctgt  33720
taagagagag ctgagtagat gtcgggggag gggggacgaa tgtggtttgt tagaactttt  33780
ggaaattcca ttttctggtt aaggcaaagg gtacagtact tagctgatgg caagaagtgc  33840
tatgctcaga gtagaagacc ctagaattac agatggggta ggtgtgtcta taacaactta  33900
catgaagaga ccaggacctg gcacagtgct cagcatgttg tctactgtta agtgttttat  33960
gggacatagg tgggaggagt gtctataaga acaagaagga tggttagtgg ctaccattgc  34020
taaatgatta ttttattggt ggacctgtct cagagacaca tggtcattgc tctgtgcctg  34080
agagagtcca tgaagagctg agagagctga ggtctgggag tcatatcagg acttggacgc  34140
atatggaggg acaggcagta ggtgaagcct cctagcttgt tacacacaca catggactga  34200
aaatgaagga aggtgccatc ttcctgtttc tgctgtaatg aaacaccaga gacagttttt  34260
tttttttttt tgaacagagg ttgcttttat ttagctgaag ctgagaagcc caaagtcaaa  34320
gggcccatgc cagattcaga gctgcttgct gcacatgtct tcctagcccc tcactagaat  34380
tgttcttacc ccatgcctcc aaactctgcc agcccctgcc caatacctgc ctccagatgt  34440
ttcagcacct cggatagtta tagcagcaac cccactctga gtgccaaatc ggtagtagaa  34500
ttttgacaga agcagaaaca atagggatgt agacagacag accagtgatt tattaggaaa  34560
atcagcttgt gtggttatgg agggacagaa atccctaagc aggctgtcta gaagtggaag  34620
gtgctgggac gccagtactc tgtaactctt gtttctgtcc agaggtctca gagttaggga  34680
gccagcaggt ggtgtttctg tcagtttgag accaaaggcc ttacagattc agggatgggc  34740
tgctataaat tctggagttc aaaggccaga gaacctaggc ttctgatggc cagagaggcc  34800
tcatagttgt gtcgctatga ggaaatctct agatgtattt ctctttgatt ctctctgtta  34860
atgaaatgga ctggtttcca taaaagttct taaaattaga aattaacttt tttagaatct  34920
atctgatgtt aatagcatta tggatacttg gaccagagat taagtaagag cctatggaca  34980
caataaaagt ccctcttcaa agctagaggc acggctttgc acagcacagg aaggaatatg  35040
gaagatggcc attctccatg tgactctcca agccagcacc agaattacag gttttattct  35100
tatgtgagaa cttcagatgc tctgtgagtt tgttgtctct agtgactgta ttaagcagaa  35160
cagaagctaa agatggatgg agagaagtca gaatgatatc atcaaaaggg accaattgca  35220
gagcccaaat atagacccct aagctgctct gaatgaatga tgggtgttgg ctttaagtta  35280
ggtcaaccct agtcacaggc ttttttttt ttttatgata gggtttcatg tcattcaggc  35340
tggctttgaa ctcactgttg ttgctgaagg tgaccttaaa ctcctggtaa ccccacctgc  35400
aattcttgaa ttgtaggcat gcgttgcagg aaatattaaa aaaggaacag gcacattcct  35460
gtgcttgtgt cggcaactct ctgccctggt ggcatggctg gccatgcact ggtgacctgt  35520
ttttatcaag tggaggctct aactcacaac tccaagatct ctccacccaa cttgctaggt  35580
tccctctggc aggtcgctac cacgccaatc ccatgattca aatcccccac accgctgtgg  35640
tgcacctcag gcagacccac actttgctgc catacctttc tctcttgaac ctggaggaga  35700
cgggagggaa agcatcacat aaacttagtt cacgatagtc gcaagtaagt gttagttttt  35760
aaaaaaaaca gggctggaga gatgatggct cagaggttaa gagcactgac tgctcttcca  35820
gaggtcctga gttcaaatcc cagcaaccac atggtagctc acaaccatcc gtaacgagat  35880
ctgactccct catctggagt ctctgaagac agcaacagtg tacttacata taataaataa  35940
ataaatcttt taaaaaaaaa gttgaagccg ggcgtggtgg tgcacgcctt taatcccagc  36000
actccggagg cagaggcagg tggatttctg agtttgaggc cagcctggtc tacagagtga  36060
gttccaggac agccagggct aaacagagaa accctgtctc gaaaaaaaaa aaaagttgaa  36120
aaaatatagc ttaatgtttt ttgtttttgt ttttgttttt ttcgagacag ggtttctctg  36180
tgtagctctg tagatcaggc tggccatgaa ctcagaaatc cggctgcctc tgcctcccaa  36240
gtgctgggat taataaaggc atgagccacc actgcccggc aaatttttt ctgtagaact  36300
tatatttagc tttacaaagt ttatagcaga attgagtgga aggtacaggg attccctgta  36360
tagccccggc actcccttga gtccccttat atgacgttct gcccagagca gtatagttgt  36420
tcagttagtt aatcttcatt ggcttgttgt tagcgagtgg tccctgatgt gtattggtgt  36480
tgtagtaaat agttaatctc agttgatcat tcagttgatc attcaacttg atcattcagt  36540
tcccagagaa aagacacaca accttttat ttatttattt atttatttat ttatttattt  36600
atttttaaag atttatttat tatgtgtaag tacactgtag ctgtcttgag acactccaga  36660
agagggagtc agatctcgtt acggatggtt gtgagccacc atggttgctg ggatttgaac  36720
tcgggacctt tggaagagca gtcgggtgct cttacccact gagccatctc actagccccc  36780
aacctttata tttataataa gccttaatca gctctagagc tgggcagtta tctaccctct  36840
atggctatta tgtctactac tctatcaata actacgagtt ataacttgcc atgttgcctc  36900
tggacagctt ttaactccag ttggccagcc ctcatggcca tgttttttatt tctcacccat  36960
cgagtcttct ctccaccttc tccctctcct agaagtcctt gcctccagcc ccagcccaaa  37020
tcaaactccc acttctctgt cttctgtcca gctataggct gtaggcatct ttattcacct  37080
atggggataa cttgggggtc aaggttacat agcattactt gggtcaaccc aagaatctgc  37140
tccctgggac aactagggct gtatttagca ttacaacaca tagaacagac taaacatcaa  37200
catatcagta ttgctggaac ttcttactta gtggaatgat ggatccaaga tgcatcacat  37260
agaattggtt ttattgcccc aaaattcttt gctctgtctc ccaactcttg gcaaccactg  37320
agccttcttc ccccatcttc agtttgactt tccccaagat gtcttacagt tggaatcaca  37380
cagtttacag cctttgaatt tggcttcttt cactcagcag ccagcattta aggcccttta  37440
aatttgtcct ggcttggtag ctctcctcgt tctcatgctg tgtgatcttc ctttgtacag  37500
atgcactaga ccacatttcc tctgctgaag gccatgttgg gtgcttccat ctgggcagcc  37560
atgaaaggcc tgttctatat gtcctggtgt aagcttttga gagcatgttt ttagcttcct  37620
ggattgctgg attataaact ttgagaatgt ttgtttgtct attgattgat tggcagacag  37680
gttctcactg tgtagtccta gcacggaact caaagagatg tgctggcctc tgttgggatt  37740
agaggcatac accaccactt ctggcctcta gcttatgttt tcattctcac ttaaattttt  37800
tttcttcccc aaaacctttta aaacacacaa acaaacaaaa agatagaaag tatgtggaag  37860
ctggggccat ggcttagtgg ttaagagcac tcgcagtttt atttccagca cccacgtgtt  37920
ggctcctaac tgtcttatgc cctctctggc ctctgagtac acagacatgc aggcaaaata  37980
ccgtacacat aaaatgtaat aattaataat gacaagaaca acacagattg tgagtggtga  38040
ccccgtgact gggatcagac ctgcacacac attaaattat gcctgtattg aattgtcttg  38100
taaaattaat tatctgataa tggtgcttat ttcccgaggg tttgctttgt gcttggtaaa  38160
cagtaaacct tgtagagata cagatagaag ctgcctgtat ctgcactcct gctctcccca  38220
ctcagcaagt gggaaggagg ctgtctgtgt aaaatgcttc ccccagcaca ggctggctgt  38280
gtaaagctca ggttttgttt ttgtttttgt tttgtttttg cttgtttgtt tgtttattgc  38340
```

-continued

```
tactttaagg aagaaaggga acctgggaca tgtggcccag ggtgcttgga ccggagtgcc  38400
tctgcgtgtg tgcctttggt tggttttgag cagaaagaat ttggtaagct atcagatcag  38460
catgagaaga aaggtggacc tgggaagcag agagcagagg aggaagtcct ggtgaccgtt  38520
gggactggga gtaagatgat ctttggttct ggtcttgtgg catttgaggt gacagcctgg  38580
caagaggtct ctggcattga gctggaatgc tgaactggct aactatgttt ctgtttctac  38640
catgaattct ggaaccttct ggagccactt acattgcttt gtggttttgt agggcttgat  38700
tgctcacttc ccttagtgtc ttggtatagt tgagaaaaat taagtggtat agaaagttgt  38760
aagtgcctgg ccttccctgg aggaaaatac caccagctgt tatagctact ttggaagttt  38820
gtctcaaatt tgaatacgta attctgacac cagcagacac tccttgaatg tgtatgaaac  38880
cgaccatgac ttgttagtgc tctgtaccaa agtgctgaca ctgagtcctg ggcttggggt  38940
cctccttgct ccctggtggc cgtgctgccc cacatttgac cacagaatcc cttctacagt  39000
tgctcaggct ccctagttac gcaggtagaa cctttgctct acagggtaag attattaaaa  39060
taattttctc tagttgatat atttccttgt tacaaagatt tagtttttaa aaaaatacat  39120
gccattaaca tacattttat aaaatgggtc agtaaaagta tacatttcaa aacagtaaat  39180
ccctctcttt catgtcactg cttaaactta atcactgctg atagtaagtt ccagatcttg  39240
ctttgtggga acagggaaat gtacagctat ccaagccaag cgcattcatg tgtacatagc  39300
atgtatcacg tgggacacca actgtggaga agacgactct taggaccggt atgtcactaa  39360
gcagactgta atcctcactg gaagggtaga caacagattc ttgccggtga tggaaatcct  39420
tctgggttct gttgttgact gtaagttttt agcatttcct gatcatgagt tctgtgctgt  39480
gcatccttgt acccatgcct ttatattaat ccttatggaa tatttctgaa ggatagggtt  39540
agggagtttg gaaattacat gaacctcttg agatatttgg taacttatac ttccacctgt  39600
agcatctatg cttttttcat catccttttc aaaaagtgtc cgctcttagc tacactaaga  39660
cttaactaag actagttact aatagttctt gggtgaatat agtcagtgct tttgtgtagc  39720
attagatcct tgtgttaaaa agcctggatg gtggttgtaa cagaccttgt tttacctttg  39780
tgtttgtgtt tgcatattcc atgcccttat aagagaattg tgattctttg cctactttaa  39840
cttttagaag gaaagtacta ttatccaaat ggaggacact tgggtacaac aatcaaatcc  39900
agcttctctt gttctctcaa aacacagacc actgttgtgt ccaagtgtgt aggggtttcc  39960
agtctgtacc tgggaagcta ccaattctgt agcagacgcc agctgggtgt ctatcgttct  40020
agttctgtag tcccctggtc tagttcatgc taaccttact tacccaggga tagcaacaga  40080
gcttttatca ctggtgtccc cagcccaatt gcaagcccca ggttgttggg gtagtatgca  40140
acacttttac tagattatct tagaaaagct gccttcgagg aataaatggc agagatgcag  40200
aaacacagga tggtctggag gctccccagc ttctgtgcca gtggagttga gatgtgcccc  40260
cgcctggctc ttgctccccc gcagggaagc gccagcatgt tctgtcagta agtaagctct  40320
gctagaccag gccttttggg caggtgtggg aagctttttc ctgtaaacat gatcaactcg  40380
gatcttctcc ctgatgtcaa ggtggcaggg aagaacagga agcccagagc ttcttctctt  40440
accctggtct tcacagcatc atcccgatgc agtccaccat cagccagtta tcagtggaca  40500
gaaaagcatg gagtgcctaa atggttccaa agattacaag gctgtatttc aggaatcaga  40560
agtctcacaa tcagggcagt gttgcatagt gtagtcacag agctcagttc tcaagatctg  40620
caatttataa tttcatctga gcttcacggg ggtgggggat gggggtgggt ggggggtgat  40680
gtttcacaga acttcctggt gttactatga tccagaccct ggagaaactg ttttctgtgc  40740
atagttagat ggttctagag gcatacagct gcattggtgt gtgaaagaca gcctacagaa  40800
cttgtctctg tcctaattta ttctatcatg atatcaagct tatactcagc caagagtggg  40860
cacttcagac acagacttta gtctgtgcag tacttagtca ataagcactt agattcactg  40920
tgattctatg ttagcaaagt catgtaggcc aggctggaga gatggtttac tggttaagag  40980
cgttggctgc tcttccagag gtcctgagtt caattcccag caaccacatg gtggctcaca  41040
accatctgta atgggatctg atgctctctt ctgatgtgtc taagtgtact catatacata  41100
aaataaataa gtaaagtcta aaaaaaaagt tttaagaaaa agaaaaaagt ctaacaagcc  41160
aaagagactc aaaagtactg aagtctgctt tgaatgttta tgaagaatgt accaagattt  41220
attactgctt gcattgtgca tgccactagt tgcatagaga aagaaagggt gtgtttggca  41280
tgactaagag gaccctaccc ggcctgacat gggtctcctt ttcttactga tgaaaggcat  41340
tttgctttat tagcttggcc ttctaccttc ttcacacaga tggttgtgtt ggcatatgat  41400
catctaaaac cctagcaccg gggacaggaa gacagcaggc ctgcctgagc tgcataacaa  41460
gaccctggtt taaaaaaata aaataaaata aaataaaatt gtgggggctg gagagatggc  41520
tcagtggcta agagcactgt ctgctctttg aaaggtcctg agttcaattc tcagcaacca  41580
catggtggct cacaaccatt tataaaggga tctgatgccc tcttctggtg tgtctggaaa  41640
cagctacagt gtattcataa ataaaacaaa tctttaggaa aaaaaaatag agaatccttt  41700
aaaaaataat aaataaataa aactgtggcg gggattctct tgacaagcac tcacacggcc  41760
ccaggttctt ctagcaactt aaggagctaa agaaatacag taacttctgg gagcagaagg  41820
gagatgatag ttcatagact attaagtatc tgcatagtcc tttcttttat agtgctgggt  41880
atccaatccc gggctccaca tcacatgcta ggcaaatact tttacggcta aactgcaacc  41940
tagcccttag gggaatcctg tcttaaaact tgtagaaccc tgaataactt gctgtcaaat  42000
taatgtgctg acagaaagcc caggatcaca gcactgaaag cagattttag aatcttccct  42060
accttaccat tgtgttcaga aaatcccttc tgtagggtct ttgctttatg atagtctagt  42120
ttgttttcat gtatagtaac aagaacctgt ggtccctttc tgaagcctgt ctgtggtgaa  42180
gcagtgcaga acagaccact agcacccttt acaaaccctg ctttgatgaa tttttttctc  42240
tgttcttgga tagagatggc tcagtttgac aagttctgtt catactatac acattcccag  42300
cgtgcacatt cagagaacag actctcttga ctggtgtctt ctgacataaa ctttaactgg  42360
caggtggact ctatacttct gtctgcattg aatcagaaac catgtaagga aaccttcata  42420
tggtagaggt agtcaagttt tcagttcttc cctcgctagg atgctttatc tggaagctac  42480
agataaactc tcaaaatgca cccctgacct cttcacctgc ccagtcccag aagtgcctta  42540
cctcaggcag ggcctcagct agaactcaga gggtttttta ggcagcagaa gaggcaagaa  42600
caaaaggttg cttgctccca ctggttccat tttttaagac atcagtgcct catgaggtag  42660
aagttgcagc cagtgaaagt gaaaaagaaa ggattttttcc cttcttcaaa actagttttg  42720
gtctacttga gtttctgtct tcccactcca tggccagtgg attttctaat tgcagacact  42780
ccctctaggg taccccctgac ttcttcacct tccaatccta gggagagttt aatgcgtgct  42840
tctcttcagt ctcttttcac ttcctctttc cacggtaact ccccagggtc tcagggactt  42900
ggaagcaagg agtgtctttg gttctgccca aggcccagtt gtcttgttcc cagccagctg  42960
tctgtgtgta cagtgtttcc gagcttctgt cctaggtctt ctgtgatgat gtgttctagg  43020
ccttgctgct ctgtccatct gatacgatct tcttaaatgc tcacattgta gtctctccaa  43080
```

-continued

```
ccctcccttt taatttcccc ttttcttttc tttcccttcc ttctctcttt tgcttttttt  43140
tcaagacagg gtttctctgt atagccctgg ctgtcctgga actcactctg tagaccaggc  43200
tggcctcgaa ctcagaaatc cacttgcctc tgcctcccga gtgctgggaa taaaggtgtg  43260
tgccaccaag cccggctccc tctctttctc tccccttctc ttttcattga acataccagg  43320
gcgcatgctc taccaccaag ccacaccttc agcctagcct gaccttctta gctttgtcgt  43380
tatcctgagc ctgtattccc ttcctgacgg gcctgtctac atgagatgct ttggtttcat  43440
gccttgccca ctgtagtctc tggaagcctg cagctttctc agagcccttc tctgcctgac  43500
attcttctca gggcactgct gggtcactga ctagcttgtt catttgacag ttaattcatt  43560
aagcaagtgc catactgttt tgctccttgt ggcgaggtgg gatagtcagg aagctctgct  43620
gcctgggctc agggcctgcc ttcctggtct atgcctgcag agtatgagac ctggcctgta  43680
tgactttaaa aagaaaaagg aaggcaaaaa ctcacctaca gcttagtaga ggaacacaca  43740
agggatttct tactttcttt taattaaatt ctgtatatta cctctttaac ttgtatgatt  43800
ataatattaa aatgaaggca aaaattgcaa gtataaattc atcagctgaa ttataagact  43860
tttttttact atttttttat tacgtatttt cctcaattac attttcaatg cgatcccaaa  43920
agtccctcat accctccccc cgaattataa gacttttaag attattcatg aaactgactt  43980
catattggat cggcccgcct cacatttgct ttctgctttt ttcttcagtc tgcatgaaga  44040
aatcagtgat ttttatgagt acatgtctcc cagacccgag gaagagaaga tgcggatgga  44100
ggtagtgagc aggatcgaga gtgtgattaa agagctctgg cccagtgctg atgtgagtac  44160
ttgtcctgga cctgggcttg aggcagagcc tgccccagac tgtctctcat agagactcac  44220
tcacactgta agtgctttgg tagaggtagt ctactttatt ttgcagcagg gtcttacgat  44280
gtcataccca tggctagccc tgaactcaag cctccttaag cttcccagac atgtgccaca  44340
cccagctttg gtcaaatcac atcttaaagg caaacaggga cctgcagcct gtagactttg  44400
gggtttgttg atgacttctc tccactcaga tgctttactc taaacctctt cctctcagtt  44460
ctgagtagca cccaataaag tggacagaac ttaggcttat taatgcaagg aaaagagagg  44520
tccagcctca gtacagtagt tagttgctgg aagggattta tcaaggcttc atctttgttt  44580
ttactctagc ccgtcagtgt aaacattgca gttggcttgt agctgacggc atttcttttg  44640
ctacttgaag ttgactgtct tgggcaaatg caggcgagtg tatgcctctc attgcaaacc  44700
actctttgtt ccccgggcca acttcttttg attactcagt cagtgagcag atttgttgcc  44760
ttagtctcca ctttgtgtgt atctcttttt tttttttttt tttttttaa gattatttat  44820
ttatttattt tatgtatgtg agtacacagt agccgtcttc agatacacca gaagagggca  44880
tcagatctca ttacagatgg ttgtgagcca ccatgtggtt gctgggaatt gaactcagca  44940
cctctggaag agcagtcagt gctcttaacc gctgagccat ccctccagcc ccgtgtgtat  45000
ctcttattat tggcattaat acttaatttt ttagggattc tttcaggtct gctgtagaat  45060
cctccctgag caaagagtaa ctgactttgt tgcatagatt ccttagacct tcctgaagtg  45120
atgtaaggga agccagggcc aggtttgtcc atttggcaaa agaaagaagt tcaaatatag  45180
gtaaagaata gaagggaagg cacaggtgcc cttcactgca ctggggcaca gcagagatgg  45240
ctccgcctgg catgcctctg taagcactgc tgacatctag tggctagaaa gggaagctgc  45300
tggcagtgcc atgacctgca cagaccctat agcaagggag aacctgcccc aggttaagat  45360
gcctccatct ttccgaaacc tttctgaggt aggcaattgt attcatacaa atagaagtgc  45420
agagatacgg ctaggttccc ggaacttttt tttttttttt tttttttttt ttaccagaat  45480
ggtttagcat tttcctgact tggcttacag acacatgtat aattgcctgg gtgcctctgt  45540
cctcagtgga ccaagattct cagttgatag cacatcagga tcttgtatag actgctcctg  45600
gtactctctc gcactgacct acacatcagc acatggtcag cagctaaata ttctgaattc  45660
atgagagaac tcctgcagag aggacagaat taaggatttg tgacattcct tatcttgtaa  45720
aagaatacta actagccttt gaaacataac ttgtgaaact tctgtataat gtgtacacat  45780
gtatattatt atatgtatat gtaggcatgt gtgtagaagt cagaggacag ttttttttttc  45840
ccatttttta ttaggtattt agctcattta catttccaat gctataccaa aagtccccca  45900
tagccaccca cccccactcc cctacccacc cactcccctt tttttggccc tggcgttccc  45960
ctgtactggg gcatataaag tttgcgtgtc taatgggcct ctctttccag tgatggccgc  46020
ctaggccatc ttttgataca tatgcagcta gagtcaagag ctccggggta ctggttagtt  46080
cataatgttg ttccacctat agggtgagga cagtttttat agtcaggttt tgtctacctc  46140
tatatgtggt ctgggcatca ggcttgcata gcgagcatct tcaactgctg agccatctca  46200
atggcctcaa cgtctctgat ttagattata agccatgctc tgagtgaatg cccgtgaggc  46260
atggtgtccc tactttagga aagccttgta tttggacctg tccattctaa aacaccagta  46320
gaggacaaaa gggacgtgca tttctctgta ggcaccttaa tgtgattttt cttccccttgt  46380
tctaggtcca gatatttgga agttttaaaa ctggcctgta tttacctacc aggttagtat  46440
gttgatgaag ttttgaagga ttattatttt gaagggatta ttgtccactg gggctattga  46500
atatgtctga gtagaaatgg ggcttgtttg tttattgttt ttgagatagg gtctctgtgt  46560
agtctgggct gtcctaaagc ttggtgagaa cagttgtcat aggtgagata tggaaaaggc  46620
acataaataa tgagattgga agtaaatgcg tgtatttaca cactgagagc cagcatgatg  46680
ctctggcttt atgcagctta atagtcaggt cacatctcat tgaggcagca cacgtgaagt  46740
ttaataccag aaggctctag gaaaaaccaa acaaaccaaa aaaccattca ctaatagaat  46800
ttaatatgtt tgaggttttg tttctgtcag cattatctca tgtcctgggg cctgagatct  46860
gtgaaatacc tgagggtatg aggttgctaa aattgacact ccctgcttct cctctcctct  46920
cctctcctct cccctcctct cccctcccct cccctcccct cccctcacct cccctcccct  46980
cccctcccct ctcctctgct tcccttccaa aacttaccat cagcacactg atgctctgaa  47040
gcagagaggg aaagggattc ttgttaccct aacttaaagt tggtaagcat aattgtcagc  47100
tacaatagag acctgattga tgcttcttga aacctcacac gtgtccctac agtgacatcg  47160
atcttgtggt gtttgggaag tgggagaacc tgcctctctg gaccctggaa gaagcccttc  47220
ggaaacacaa agtcgctgac gaggattccg tgaaagttct agacaaagca acggtaagtt  47280
cttagcattg tgtctttgtg agccttatta cctgcaggag aaacttggac tctaatctcg  47340
aatagcacag ttggaatgtg actcagtgaa tcattttttg aatgtcacag tgactatgca  47400
taaagactgt cattggagaa tcaaagtaac ttgtccaggc tatacatttc tttaagaata  47460
atacccaatt tttcatgcgt aatgaaatat aaaaatagat tactagctgg gcattggtgg  47520
cgcaggcctg taatcccagc acttgggagg cagaggcagg tgatcttagt ttgaggccag  47580
cctggtctac agtgtgagtt tgtttctgtt aaatagcccc tagttataac aaaagatatt  47640
gttctcttat tttgcacttg agatcttgtc aaggcctttt tttttttttt aattaaaaag  47700
gatatgtttt tattttgtgt gtgtgttttg gggctacagc agagggcttt ggatcctcta  47760
gagctgagct gcaagcagat tgagccacaa tgtgggtgct aggaattgaa cttaaactca  47820
```

-continued

```
ctaagtgatg actcttagcc attgagccat ctctatagcc tctgaagtca tgctttctat  47880
agagaagtcc tgtcgcaaac aatgttttaa atagaatata ttgtattttt atgaatttat  47940
tgctttttag aatttttaga atttattgcc ttctatgaac tttttcattt tacttatgtg  48000
cgtgcacaca caccccccac gctcccccctc cccccatgcc ctgtgtaggt ctgtgcgtga  48060
gaggacagta tggtgcagtt tctccactct gagctggagg tccagctcag gttatcaagc  48120
ttggcagcag acgcctttgc ccgctgtgtt ggctggtgcc tggtcctcag agcacttcat  48180
ggttttgtgg tctcgtgaga agtgtagagg tcacaggtct agctagtaac cttgtgtcct  48240
gattctgcca cttactttgg gagactattt taaactttta tgtcttcttt ttctaggttc  48300
ctattattaa attaacagat tcttttactg aagtgaaagt tgatatcagc tttaatgtcc  48360
agaatggcgt gagagcagca gacctcatta aagattttac taaggtcaga tacagtctat  48420
attgtgaagc tattaagttt gtctcgagcg actgctgtgc tgtgctgtct tctgcccagc  48480
ttatgtatgc gtgcggctga cacatgactg catttcgtgt gcttcctgtg gacgggtttc  48540
tgaaaggttg tggacacttg tgaagaccac tctgttcctt aggctgagtg gcatgggagc  48600
tgagattgta caacaagctg actctggcca gtttttaatc tccaagttta gattagaatc  48660
tttcccaggg agcctttttt tttaatccca aattctctgt caggagatac ttgctacttt  48720
atcttgaggt aatgttagtt tatttcaatt ggtttcaaaa taaagaagtt gccagcatta  48780
tatatactca gaacatttta cagccccaga cctgaaagca ttctgtccaa tgcagtcacc  48840
tttcttaagc agttctccag tttctagaca tttcagtttt tgtattttgg tgtttttagt  48900
ttttcaaaca ggatttctta tgtagccctg gctgtcctgg aactaactct gtagaccagg  48960
atggccttga actcacagag atcctcctgc ctctgcctcc cacatgctgg gattaaaggc  49020
atgctccacc actgccctgc tttttgcttg ttattttgag gcagagtctc actatgtggt  49080
tggcctcaag cttttaatct ttctagcaca gtatctggga ttgctgggat catagttgtg  49140
tcctactgcg gcttctgcct gctgtacctt gcttcctttt tcctatcagg catgaaagaa  49200
tatagaagat agaaagaaaa agaaaaatat ctcttttgca ggggctatgt atatgtgtat  49260
agcttttcat aaaaagaaac taaacgttcc aaattgtttg cttactaaca aacaatagaa  49320
gatgacatga aaagccatgg ccatcctctg tagcggacct tgtgttctgt gcctggagcg  49380
ttaacagttc tggagggtta tatctgtcag ctctaagagc cctgctcatc ttctgtaaag  49440
caggaagtga tctgggtggt gacctgtcca ctgggtgaca gcgggcaaga ctgtgtgtgc  49500
tcgggcagct gcagaatgga ataggggacc ttgctgtaca gcagaaggcc acacacaaat  49560
gatttcttga ctttcttact ggattagtgc cttaaatgtt gaggtgcttt ggcctttgtg  49620
ctatttctgt tgtctgtttt aagagacctt tctgtgatca taataatatg gttagatagt  49680
tagtatgtct gttcagacag catgtggccg ccattattta cgtcaccatg aggagaaagc  49740
cttttattac ttagaagggt gactttgaaa ttgaatatat tacatatatc taccaaattt  49800
tgtattataa ggaccaattt atgcccctgg tgatgctttg ggctattaaa atataggaat  49860
tcattgaaaa tgtaatttca tttctctttc agaaatatcc tgtattgcca tacttggttt  49920
tagtattgaa acagttctta ttacagaggg accttaatga agtatttaca ggtggaattg  49980
gttcttatag tctcttttta atggcagtca gtttccttca ggtaagttgt gtgggtgtgc  50040
tatatcagtg tgcactggaa aaaagataaa ctacttgcag agacatttgg ggagaaaatt  50100
taaatcagga atttttacag tacttctcct ttaaactggg taccttttat atagtttagc  50160
aaattagtat ttaaacattc ctaggagaga gattgagact ttactaggta tgttaacatg  50220
taatgtttgg cctggtttct gtaaatgtga atgcaataac agccaaaaca cagggctgtc  50280
tggagctcac tggtcagtca tcaagctctg ggttcagtaa aagaccttat ttcagatgga  50340
aagtgattat ggaagacagc tgatgtcagc agcagacctt tggctcctgc atgcctctct  50400
acttacactt agacattcat ttgtacatac aagtacacat accacttgaa catacacaca  50460
cacacagcag cagtgcgcgc gcacacacac acacacacac acacagcagc agcatttgta  50520
catacaagta cacataccac ttgaacatac acacacacac acacagcagc agcagcagca  50580
gcacacagag ggactgggaa atggctcagt cagtaaagta cttgccattg caagcatgag  50640
aatctgagtg tagatcgcta aagcccacta acaagctgga cacagcagca ggtgcttata  50700
gtcccagcac tggagaggga gagacaagag gatccctggg gctagctggc ccaccagtct  50760
agcccactgg gttcagtact tcagtgacag acactctttc acttgcctat catgcataaa  50820
gtctaggttc cattccttag caccgttatc tgaaaaacaa caagtatggt ggccagatgt  50880
ggcaggtaga tctccatgag ttcaaggcca gcctggtcta cacagtgaat gccaggacag  50940
ccagaactac atagtgagac cctgtgttga taaacctaaa tatatatatt ataatatatt  51000
gtgggcagtg acttaggaag acacctctca tcaactgctg tctttgatat acatgtacac  51060
acacacacac cagaaataag agtacattta aagcagttac ccatggaagc tcagctataa  51120
ctgacacatg ttctttggat aagagcttta gttttgcctg tttggcagtg gttgccagta  51180
accagactgc taagtgagat gaattccctg atgtggctca cactcagcct tacctacctg  51240
gtctataccc atggtgcatt gcatgagctt tgtagcatag ctgtcaactg gtccaagatg  51300
atgatgatga tgatgatgat gatgatagcg agtgctcgta gaagttggga tctcacttat  51360
accccctcct tcataacaga gaaaatccaa aataatttct tccttttttt tttttttttct  51420
gttttagtta catcccaggg aagatgcttg catccccaat acaaactatg gtgttctctt  51480
aatagagttt tttgaattat atggacggca cttcaattac ttaaagactg gcatccggat  51540
aaaggatggt ggttcctatg tggccaaaga tgaagtacag aaaaatatgc ttgatggcta  51600
ccggccgtca atgctttata tcgaagatcc tttacaacca ggtactgcga ttcggtgtct  51660
gtaggcttca gaggggcgtc acagtccacc catgctttac tctgttcaga tgaaaatgct  51720
tatttctaag tagcacttgt tcagaatatt cttatcatac taaaagagac acatactcca  51780
gaaaaaccac ctgctagact tgcacataag ttgaggtagt gtccatttga ctttcaaagc  51840
caagcagaga ggaattcact gtggggtggg tttgcagcca tctctcctcc tgtgggctgc  51900
catttccagc tagttgtcag cagggcttta gtgaggtaag atgggggctg gagagatggc  51960
tcagccgtta agagcactga atgctcttcc aggggtcctg agttcaatac ccagcaacca  52020
cgtggtggct cacaaccatc tgtaatggga tctgatgccc tcttctggtg tgtctgaaga  52080
cagtggcagt gggcagtgta ctcacataca taaaataagt aaatctttaa aaaaaaagaa  52140
agaaagaaag aaagaaagaa agaaagaaag aaagaaagaa agaaagaaag aaagaaaaga  52200
aaagaaaaga aaagaaagaa aggaggaaag gtggaagtcc tcagacagca gggagcatgg  52260
gcagaaaagc tccaggagac cgctcttact catgttctga ctgctgcttt ctttttgtgt  52320
gccctctctg tatggctcta gctttgggag tggcttgaga gtgaacggag tgcaagtttc  52380
tgcctcactt tcacaacgtt aaatgtattt gcttatgatg tgcagatgta tgttcatagc  52440
taattcagac aaagaccagg cagcaccctt ccttccttac tgttttcaat gtagcttggc  52500
tttattccga ggagaaaata gccagctgtt tgtttgtatg tgataggaga atccttgctg  52560
```

```
ggctaaagtt gtatgcaggc agtgggtggg tgtaccatag caaagcactg tgcaggtctt  52620
ccaaggctga cagcccactc atgagcagct gtcacccttg ttcctgggca agggctcatc  52680
agcctttatt cataataacc agcagccagg tttacttgtc ttcgtatcca tttcttttaa  52740
aggtaatgat gttggaagga gttcctatgg ggccatgcag gtgaaacagg cctttgatta  52800
tgcctatgtg gtattgagtc atgcagtgtc accgattgca aagtactatc ccaacaatga  52860
aacagagagg taaaagtcta gcccaggcca gcctgtgtgt tgagagtggt tggtacttct  52920
tatcttcaac ttaatgtaca cctcttttgt tttttttaa cctgtgcagc atattaggta  52980
gaataattag agtgacggat gaagttgcca cgtatagaga ttggatatca aaacagtggg  53040
gcttgcagaa taggcccgag ccatcatgca acggtaagac ctccttgatg gtggactggg  53100
tcttagaggc tttttctatg ttttgtgtat ttaatgggaa gaaacgtttt ccaatctttt  53160
gccacttttt caggaaatgg tgttaccttg atagtagata ctcagcagtt agataagtgt  53220
aataataatc tgtctgaaga aaaggaagcc cttggaaaat gtagaagtaa cgcctcggaa  53280
cctcttagta aacactcttc aaactcttca tcaggtccag tgtcctcctc ctctgccacg  53340
cagtccagct ctagtgacgt cgtaagtatg acacatgctg ccccagcctg ctctttggag  53400
ggccctcaca ggcaccaggg atatttccaa tacctttcat tcttgtactt tttccctaac  53460
attttttttt aaagaaattt gaaaatctag tgaaggtaga acccgtcagt ggctgtagca  53520
ttccatactc cattagcatt gacctgctta ttatattcct gacactctgt cccgtaggca  53580
gctcctcttc ctctttgatc tgcttcaaag atggcagatg tcacacttca ccccagcctc  53640
catagcatgc atcctggatt tagatggctt gcttattctt tattcctcac taagttttat  53700
gaccatgctc aggtcactca gagctctagt aagagaatgt cctctcacta acccacagtc  53760
cccagtctcg cctccagagg gcatccttgt ccttgtaaag gattttctac atcacatatt  53820
ggttttccat gtcggggttc ctagagcttt gatctcatgc tatagaatat tatttgtaaa  53880
gcagctttca ctttcttttt tttttttctt tttttctttt ttgtttgttt gtttttttgt  53940
tgttgttatt gttgttgttt tcgagacagg gtttctcttt ataaccctgg ctgtcctgga  54000
actcactttg tagaccaggc tggcctcgaa ctcagaaatc cgcctgcccc tgcctcccaa  54060
gtgctgggat taaaggcgtg caccaccacc gcctggctgc ttttacttc ttaagctttt  54120
ttttttcttt acttgttttt gagatcccta attgaaattg ttaattgata aaacttgcat  54180
ttaataaaag tataattcag ggttcccagc aatgatatca ggcagctctc aactgcctgt  54240
atgtaactct aggagtgtgt gtgtgtgtgt gtgtgtgtgt gtgtgtgtgt gtgtgtttgt  54300
gtttgtgttt tctggaactc actatgtaga ctaagctggc ctcaaactca gattcaactg  54360
cttctgtctc ccaagttcta ggattaaagg ctcagttttg agtttctaat gtattcagta  54420
ttacacagct actttcactc ttaatttaag gatgtttcca gctaggcatg gtggcacatg  54480
ccttcagtcc tggcactcgg gaggcagagg gagacagtcc tccaccaggg ccatatagag  54540
agatggtgtc tcaatccccc tgccttcccc ccaatatcca tgttatttag taacctctcc  54600
cagctcccct ttcccataac ctttggtcta cttcctgtct ctatcatgat gaataacatc  54660
tcacattaaa ttttcgttgt aaaaaatttg agtctactta attaaagttt aaggtagatt  54720
tgtctttcct ttgaattttg actttaatat gtgattgcaa aatgtcctat tagggtcatg  54780
gaggtactag catgtgccct gggtttagtc ctctgcactg cataaatcag gcttggtagt  54840
acatatctat aatcccaata atagggaggg tggaagcagg agactcagga gcaggagtta  54900
aagacatgct ctgttgcaga gtgagttgga gcccagcctg cattaaatga gactgtgtct  54960
caaagaaaaa ggaagaaaga aagaaccaat tttccacata gcaatatgat ggcatattgt  55020
tatggagtca taaatactga tatactggat ccttgtgtct gggttctgga gtggtgcttt  55080
ggaaggtgga atgaatgcta agctagatgt ccctgtagag actgccttga aaagaagaat  55140
ttagctatgc cgctgacgtg tcaggcagtg taccaacata aagcagccaa gagagcagat  55200
ggagcttaga acaagcatcc ctgtcctaga cactcagttg tgccacttga acctgccatc  55260
ttgcaataag gtccctccct ctttatggtg atcttccatt gtttatatga cttgctattt  55320
taaaaagttc acatcaactg gaactcacaa tgattgacat tcacaactga tttaaaaatc  55380
agctagatgt ggtcagtgac ttggcaataa ctagaagcat acagtagaat agatcacctc  55440
acatgtctgc agaaggggct gggaaatgac tcaatggggt agaggtgcaa gctgtgcaag  55500
caaaaggacc tgagtgtgaa caccccatgt cctctgactt gagtgtgaat accctgtgtc  55560
ccctgacctg agtgtgaccc gaatcccttt gaaacagtca tgactgtgtt tgcctgcagc  55620
tgtactgttg ggagcagaag ctctcattca gtgagggacc ctgtctcaga aaataaagtg  55680
gaggggtaga ggaagacaga agctgttgtc tggtctctga ctgcatgctt tggatgcgca  55740
cacacacctt ccttcacaca gcatttgaag taaagcctcc tcaggtccca gatgtgtctg  55800
tttagactag aaagtactta gccgaaattg ttgcccctct gagttctgaa tatgaaaatt  55860
actaatatat tgctttaccc atgtgacttg tgttaggatt ctgatgcaac gccatgcaaa  55920
acccccaaac agctgctctg ccgtccaccc actgtcaccc gggtaggctc acaggatgtc  55980
tccttggagg tctctcaggc agttgggaaa atgcagagca ctcaaaccac taacacaccc  56040
aacaacgcca acaaatcaca ggtgggtaga atctgtgctt gttactctta gcgttcagtt  56100
ttagatagtt agaagttctt ttttcgcttc taattttaaa atgtgtattt attaaagcat  56160
ttataacaag tatgaatagc ctatccttat ttactagagt tgataaaaat gtccacggca  56220
tttgttgctt ctttccatgt ttataagctc catcaaaccc acacattctc acgcctctac  56280
taaacactaa tatttcacag gggtaaattt tttcagtact ttctaaagta ttgagaaaat  56340
acattatttt gttgtactta ctgttgttgg acagatcaga taacagttgt gtttttatag  56400
attgaaaatc acataaaatt atccaattag aattaaattt caattcttgt ctcatactat  56460
tattggaaga ataaataatg aaacacagcc tgagaaagca gaagtcataa agtggcagca  56520
tggatagtgt cccgttgact agcacgggct caggtgtgtt ccttcctgtt ctcagcagtg  56580
ggaagtgtgg ccttgaaaag cccatctggc ccctctgttt ttctcatctg ctagacagac  56640
ttaattatgt acctcccttt tctataaaat gatgacaaga atagtctacc ttcaaattta  56700
tagtgaatac tatgttaata attatagaaa tgcttagaac aattagaaaa tgttgagcat  56760
atattaagca tcatatagtt agaatttctt acatgtgcac agttgctaca cataaagaac  56820
tctcttagtt aaagaatgaa ctgttttgtc aaaccagatg tcctgaagct ccttttaaga  56880
tagggttgta acatagtaac atagatctta gtgctagcca agcccattga gcattggggc  56940
tgaggatgta gctgagtgta gagcaggctg atgagtggtc tccgtggctg tgcttgaggt  57000
gcactggcat ggaatgtctg cagcatccct agaaacagct agttctttgt tcttatttga  57060
tacttgttgc tgaggacaat taccaggtac ctgggagaca ggttcagttg attaacatca  57120
gctttgactt acttaagtat ttttagttgc caaatagtat tactaatttg ccatgaataa  57180
ctaatcaggc aagagaagaa gcttttgata ctgatctgtg gtaaaaattt tctttcccat  57240
cctcagatgt agcaggttcc ataggaaaag gtctgtcttc ttggaagttg tgatttgatt  57300
```

-continued

```
ctcccggttc actgtacctc cacagtctta gcatgggcac caaatgcagg tgcagggagg  57360
ggcaggacta accagagact ggtgccagta ggcaccacaa gagctgtcac tgggaacagg  57420
aaagaaacac ctaaactgtt taggtctctt gacctcctcc ggtagtgcac acaacatgat  57480
aaggaggagg taaggtagac ctcctcctta tcatgttgtg tgagcagtag gatccttgag  57540
gaagctttca tgttgtacac atgctgtcag gaaggggagc tatagagttc accccctgtta  57600
gtcctcgttt tctagcctct agaacagtgt gtgatagctg ggtgtgatgg cacaccccctt  57660
taatcccagc acttgggagg ggaggtaggc ggatctctga gtgtttgagg ccagcttgaa  57720
ctgcatagga aggaagggcc agactggcca gagtgacagt gtgggagttg tcagtggggg  57780
accatgttaa gtgcgcgcct gccccttttct agtctgggag cggccctgca tgcggtttgc  57840
cagggggcag ctctgctccg attctcactg ctttcttctt ctgcagcatg gatcagcaag  57900
gctcttccgt tcttccagca aaggcttcca aggtacagct caaaccagcc atggggcctt  57960
gatgacaagc aaacagcatc aaggcaaatc caatactcag tattaccatg gcaaaaagag  58020
gagacacaag agggacgcgc ccctctcaga gctttgtaga tagtcggcgc tctgcgacag  58080
actgtcttct gtgtgcaatg atctcgtgct caggacagtt gcacagggac tcctgggacg  58140
gcaggagcct cacactgttc agacgttgat ttagcaactg cgtttttttcc cagctcgcca  58200
cggaatggat catgaagact gacaactgca aaaacaaaaa gcaagcaaaa aaaagggggga  58260
aaggctgctt atgtgataag tcatgtgcta caacagggtc attttaagat ttaaagcttg  58320
aatgtaaaat aaatatattt ctcattggct ttatgcagag ttataggggc tagtgctcag  58380
tgtgggtagc tgacaggaag agagcagtgt caaggagatg ggtgggcagg tcagcaggag  58440
catctcatgg gaagtcagac tccgagggaa aggagtttgt gcatggtttt ttttaaaaaa  58500
taattttgca tatatttgcc attttattgt gtgtatatat agaagaccat ataggaaatt  58560
gatatttgta atagtggatt tgttaatact ttttacataa cattactatt tgaattgtaa  58620
acagattttt ttctcaggat tagtttgaag aataattgag ttgtcactct taacacatgc  58680
agggaagtga ttagctctgg tcctgtctgt tttcttcagc attgaaatga cttcatagaa  58740
cccttgtgac ctgcttcaaa attctttcct ctctaagcaa aaggtttatg gtggcaaatg  58800
atgtttattt tattttgtaa aaaagagaaa aatgtactgt gtacttgtgt atacactgaa  58860
caacctctag ctgtctctcc gaatgaacac acctgctctg gatccagtgc tgttgtcttc  58920
ctgggcactg ggccgtagca ggccttgtgt gtgtttccta gcagtctttt cttcccctcc  58980
ctcctcttct tcctcaaagg aaacgaaagg cctccctggg cctgggctgt tcctgtcaca  59040
gtgtggctga cctctagctc cacagccctt gttagctcgc atgctggttc ctctgaccct  59100
gcgttccatg tgcttgtggc gtcctctcat tctttctagg ttcctgctta ctgctgtggg  59160
agagagtaac tgtaaacagc tttaatgaaa tcatacttat aaaaactatt ttcttatact  59220
ccactttatg cttttggtat tgtcgatctt taaaaattaa atggtctttg ataatggatc  59280
gatttttgta ttgccttatt aagaccaaat acttcttgtc atcccattct ttatcctctc  59340
ctttaatgga attgctgtct ttaattaaaa ctttgtaaac actggcttgt tttaatcatc  59400
ctgtaactta ggctgtggtc agctacaagc gcagatgtgt aatcctgtta ctcattgcca  59460
gctgagtctt gagactcggg tggggtactt aacacaatgc atcgtacacg ctctgctcgc  59520
tcgctcgtca gcagagtggt cttggaggtg aaagccctcg tgtctagcat cagtgtgtgt  59580
gtgtgactct gttcagtacg gccgtttccg agatgggatt cttttatatg tgtatgtgtg  59640
aagtactgtt ggcatttagg catttctttt ctatacactt aggaaatact gaagaccaat  59700
cagaccatta atggacactt agtgcaactt tttataatga gaataatgct ataaagtaag  59760
accaaaaccg gtgtcatcac tgaaattaac aattttcaat atgttcatat tttaatttac  59820
aatgggaaaa aatgtgttcc acaactggaa actcacagta ctgtgtaaac tgtgtaagat  59880
tttaaatgtg atgttatttt gactgttctc aattttagag tcacatttta ttctgatcag  59940
aatttttatc aagatgttga agttttgttg ttttgaaact agtttgtcat aacatattgt  60000
gcataatcac agtatttatt ttgtagggct tgtggatgtg tagacttatg tttactgcta  60060
agggaacaat tatttataaa aaaaatatta aatccagtat tagctgccta tttcagacac  60120
ttaacacctg cagagatctg tgttacattt accacactga agttttttta aagaatcacc  60180
ctcattgttg aaagtaaatg tactcttagg tgggttatta gtgtccaata agcatgtgat  60240
tatattaagg tggtggtagc gggaagataa tcttgattcc attgggaatc ttaggttttc  60300
gtaaatttat tgggaaaata gtttttcctg tactgctgat gtttcttttt ggtaaacagt  60360
atctttctaa aagaaaaagc atgaaggaga attgaggtgt gtatacattt ccccagatga  60420
ccagcattgt attcgtgaat actgtgtatc tggaatgagc agtgtgcaag ctgttcattt  60480
ttcaatctga agtaaaatac tttcaagaac                                    60510

SEQ ID NO: 6            moltype = DNA  length = 36659
FEATURE                 Location/Qualifiers
source                  1..36659
                        mol_type = unassigned DNA
                        organism = Mus musculus
SEQUENCE: 6
ccgccgcccc cgcgccgcct ccccgcccct cattggagct gaggcggcgg cccccatccc  60
tctccgttcc cggccgccgc cgagggcgtc tttccgccgc cgcgccgcag gagcgccgtg  120
actgactgac ggcccgacgc tctgggcccg ccccctcggc cggtcaccgc cccttcgatg  180
gcctctccct gccgcccgca cgctacgccg ccgccgccgc ggccccctcg ccctccccgc  240
gccgcctgag ccaccgggac cgcagctgcg ccgcgcgccc caccgagcgc cgcccgcgcc  300
catccgcgcg caccggagcg cggcccaggc ccgtccgtcc gtccgtccgc gcggccggcc  360
cggggcgcgg cggggcgggg cgcggcgggg gcggggcgcg gcgggcgacg cgggcccgc  420
gggggcggcg cgtggatgga tccgcgcgtg gcctggatcc agccggagca gaaggggccg  480
gccaatgccc tgtggatgca gatctgggag acctcgcagg gcgtgggccg tggcggctcc  540
ggcttcgcgt cctacttctg cctcaactcg ccggcgctgg acacggcggc cgcgcccggg  600
gcggcggggc gcgcagcacc agcagcagga ggcccggggc cggcgcccgc cgcctcgtcc  660
ccgccgccgg cgcccggccc cgccgcgctg cccccggcgc tgcttaccgc gctagggccc  720
gcggcggaca gcgcaagacg cttgcacaag tccccgtcgc tgtcgtcgtc gtcgtcctcg  780
tcgtcgtcca acgccgagtc gggcaccgag agtcccggct gctcgtcgtc gtcctccagc  840
agcacctcgc tcggccgcgc cggcagcggc cgcaccttct tcagcttcgc cgacggtgct  900
gcccacgcac acccgggccc acgcggctcc acgcccgccg gctcgccgcc gcagcaccag  960
ttccacccgg gtcggcggaa acgcgagaac aaggccagca cgtatggcct caactacctg  1020
ctgtcgggca gccgcgcggc cacgctgagc ggagggggcg gccccggggc ccaggcggcg  1080
```

-continued

```
cggcccggca cgccgtggaa gagccgcgcg tacagcccgg gcatccaggg gtgagtgcgc  1140
ccgagccgcg gggctgccag cggcgcgggc actttaaaaa ctccgttgga tcgagatcca  1200
ccaggcaggg gggattgaca gttcgggatg gaggcctagg gctagactag aaagtggttc  1260
ctttctttcc tctgctccag ggcagggaag caagggctgg ctgtcagagt gggaagcgtt  1320
tacgcgtgtt ctttcctgta ggctaaatcc tgtatcttag tgtagtgagg ttgaatgtaa  1380
aaaatttttg ttcccttttt ttgagacagt aggtttttgg tattggtgca gtttagccat  1440
caagtgaggt ttagaagtgg agtcttgtgt gtgttgaggt tacctcgtac gttttaattt  1500
tgggcagacg ttcacagaaa gaccgtcacc tggggtttct gaaaaccacc taatagtact  1560
caggtttttt tcctgtgaac tcacaggaag gtgttttcat ttaaaaattt ttccataagg  1620
ctcagaggac cttagcggtt taatgtcccc aatgacagca aggtgggggt gttggtctgg  1680
aattgcccca ggtgagactt ttctagtatg aagctcttca ttcaacctat tggttgaatt  1740
tctgaacatc tagaaacaaa atagtggttg tgtagtctca agactggtga gcttgatttg  1800
cctcagttcc tgccgctctt aaagggcgtc taacctcccc ccctccccct cactccaggg  1860
agcgacatcc ccagttcaag tccacccggg tggttgctag gccctgggac tcctttgagg  1920
taacttctta gggggctgtt tgcggtttga ggtctgtggg gaacacggat actctttaag  1980
gggttggggg tgttacatag aaacagttgt cccctctgca acttgtttca cctgccttgg  2040
atctttgggt cgggattctc cagcatgcac tacaaatcca ggaggagcct ggtttcttct  2100
gccagttccc ccgcagtgct tgcttgtaga actttgtgag acaggtgtgg ccgtggacct  2160
acgggaggtt tctggattgt tacataactg taatggacat ggtgtctgcc gggagacgga  2220
tcctagcctc tgacagagtt ccacttgggt acttaggcat cagcagcatg atctgcccct  2280
cggtgagagt tgtgtccctt gatgtggtct ctctggtggt ctgtaaagct ggtcagcctc  2340
tgtgtgttct tctgtggcgt tttgttagta tgtgtgcctc tgtgggctag gtgtgctttt  2400
agagtctagc atgggtgcag ttggcatggg tggcatgtat ttctattgat cccacaagca  2460
tggtcccttc tttaaatacc ctcccttcct ggtacagatg aacattgcca cctgggtatt  2520
catacttggc tcctgtcacc ctactcccaa gtctgtagtt cttgattagc cgctgtcccc  2580
caagtctggg tctctcttcc tatgtcaagc acattgtaac cactctctgg aggaggatgc  2640
tcaggcagtc caagactggg gtcttctgtg cactgtggcc tagcctgtgt ccttggtcag  2700
cagggtcagt gggatgaggt tctaccagcc cccaactttc acgagagcct ccattacttc  2760
ccccacccac ccaagagaga tgaaggcctg actcggtggt gcttgggctc tgccactctt  2820
cttgcctgag ccctgcctca gagccccact tgctcacttt agggttcaaa acccagctag  2880
agtttagcgt tggatgctgc ctggtgactc ttccttttct gtctaggtgg catgtgttga  2940
atggtgactc ctggaggagg agcttgctaa ctggcttggc atgtgtgcgt gagagagtgc  3000
ctcctgagag ggtaccttgt ctgtttccta ctgtgactga cctctcgagg gggtgggaag  3060
gaattagtga acgggcacca gtagagctga gccctatatg ttaacagtaa aggtggctcc  3120
aactattgct ggttgctctc acgtgagctg atcttggatg gcaaaaaaag gacctgtctg  3180
aagctagtct tgtgctgtgt ggggccagca ccaagcctgg cttagcaaga gacacaagta  3240
aggttaagtg ttggcttgag cgtggcccag ttaacagtga gggggcctgt tatgttagtg  3300
agaggctgct gagcttgctt tctgctgctg gggacgtgcc tttgggggac tccgcagacc  3360
tccagaaagg gtgagtggtt ttctggtggg gtgagagtct gggtctctgc ccaggtggac  3420
acggggcact tgcacctttc agctctctgg gtggagtttg cccttggaaa ctgctagact  3480
gctttcgatc ccgggtagga tgaagaaagc ggacagggct tagtgtaatg agcttgggga  3540
ggagagaagg tgagccctgc tatgggagct cccctgagcc cagctctgaa accttccttg  3600
ggacatggca ggcataatgt cagatgtgcc tctgcatgag tttcttgctt aggatggagg  3660
caggcatggg caggctctct gggtcctccc tccccccttt aactaactca ctgtgccttc  3720
tgagtcctta actctgaccc acagtgtgat tccttagtcc tgggcagtct cagtggcttt  3780
agaagctgct ttgggttaaa agtaaagagc attcccctgg aagtgaggat tggagtgtgg  3840
tcctgacctc cctggtgtct tgcaggagtg cagatggaca ggggaggccc cagcccttgc  3900
atacacctgc agccccatga cttgagttga ctctgaaggt tgtgtcctcc caggtgtgcc  3960
tacagtgggc agcttctctg caactctctt caccatagtt agtctttgaa tgtgtcctgt  4020
gcccttggcg acaggagtcc cgttgtccgt ctgaagccgg agaagcctcc agtgtcagca  4080
gttacagctt ggctgtgact gatggtgctc tcagggctgt ggggtgattc cctcccagct  4140
ccatgactgc tctttttgct gttctcctgt gagggagtca gagctcggtg gagcagccag  4200
gttccctctc ctgcagcaca gctcctggct gttctgacag aagcagatgg cctttcctca  4260
gaaggctcca ttgggaaggc acaggtgagg gcccagtggg ttgtgctgtg gaacacaagt  4320
gtagtcactg ctatctccct ccctgtcttc cagtgagcat caggggatgc acgggaggga  4380
agagggaatc agggaagctg taaaccccgc ctgtgcaggt gacagtggca taagaggttt  4440
ctttcacaga gatgctcaag gttgaagagg gagatgagaa cagtatacta cacagagctt  4500
gttgtcatat ggacagtgtt acctcctgtg caaccttctc caactaaaca gcaccactct  4560
cttgtcatgg ccagtctcca tacagaactg gaaaggctag tgagatgctg tcccgggcag  4620
ctgaggggag tcccggagaa ctgctgcacc acggcttgct caggatggag agctgatgct  4680
ggggaaggct gcccaggagg acaaggccag tcttctctta gactagaata ttaagcaggc  4740
tggcgcagtc ctttggaaaa gaggccctag ggttggggag gccttgggtt tggttcctaa  4800
caccaaggag aaaagcaata gaaacaaaga aacaaacaac cataaaaata aaaatggagt  4860
ccctgagtaa ttttgaagaa aaaccatcta atgctcatgc tgtgtaagtt aaggagggcg  4920
ggcatccggg tgtcctggcg tctgggtgtc ctggcgtcct gtggctggga tatttggatg  4980
aagaagcagg gctgcttccc ccttagaagc aacacacctg tggcttaaaa gtaattttta  5040
agtaaaaaaa tttttttaga tttttttttca tactgttatt tacatatttg attcttgtgt  5100
atgtgcttat gtgagtttat gtgcatcaca tttacaaatg tctgcggtcg ccagaagagg  5160
gcattggatt cctctggacg tgtaatgaca ggcagctgtg ggcagccaga tgtgggtgct  5220
gggaacaatc tggattctct gcacgtgctc ccaactgctg gacagcccat ctagctcttt  5280
aagtagacat ttaaaaggaa aaaaagaaaa tatgacttta agacttgtgc ttcaaagtct  5340
tggttatttt tgatgacaga tgtgagcttt tgggcatcac cttgaaagat ttcataccaa  5400
gtatcctttg ggagcaggga taccagtcag tgcaccatgg acagaaagga tgctgtgcct  5460
tggtaaggtg gtatacctaa gaaagtaaac ccggatgctc acattcagag acatggtttt  5520
gatgatgcag acagaactca agctgcaggg gtgcccgccc tttccaggaa ccatctctag  5580
tgcttgctat ggctggtatt gctgtgatga ggctaggcca gaggctctgc ccagcctgtc  5640
agggttgctt taaccttaaa taaagttgga tggtatgcta accccataag gctgcccagg  5700
agagtgtggc ttacagcaaa gtgaagttgg tgatgccctc tgcatgcctc tgagtggggc  5760
agccatgtcg tcttcccatt tggcatgtgc acggactcag acagcattga actcttgata  5820
```

-continued

```
cgtctccatt gttcactgtt tctgtggtca ggtagcaaag tccagtgcac taggcttgga  5880
ccggttatct catcagtcac atccttccgg tcacttgagg atggcttggg tgagttctct  5940
attcagcagg gcagagggct gagtgtcagc tgcttgttgt cacatctgtc tccagagccg  6000
gctcataagc acattcctgt agtttcagca cttggggaga ctcctcagag ggctcacatg  6060
attgcatagg ccaattcgga tggtctgtct tcaggccatg caatgcagtg tggtctatag  6120
actattccat cagaaccaca agtttgggca tgggttgctg tctgccacac actggcattg  6180
tttagtagga agacagcatt gatgtgggaa gaggaggcca tggttgtctt gtccaacact  6240
cttgtcctct gcttggacat cagcttatca caagtgactc ttttatattg ccagtcccgt  6300
cttctggctt gattgtcacc cctgaagctg ggctaattga tgacaagaac agtgtgcact  6360
tttctctgcc tctcacagat gaaccattct ttagtgtgcc atttaacaaa gtctatacaa  6420
gagccacgtg attgcacaaa aactgtttca gccatgaggg cacctgcatt catcagattg  6480
tcaccgtggc ccatttaagt tgccacttga taatgacaaa acagcccatg gttgctctgt  6540
gtaagatgtg gcccacaccg gatctgcatg ctccgttgat ggggatggtg gtttgcccat  6600
ggcctcagct gcagaacatg tgcctctccc tggaggagca aaaagacccc ccacaattct  6660
tgccttgtct cttcctgagc tcccatctga atctttagtt tctacggagt tagcttttac  6720
tgtcccctgc ctacctacac tcccagaacc aaagacgtgc atactaagaa agatgcaaaa  6780
gacaaatagg ttttgtatgc aaaagtaaac tttagttttt tgtcttaggc attttaacat  6840
agattgtgag ctttgcagtg attttttgtt gttgttgttg ttgttgtttt gtacatgcaa  6900
aacagtatgt tagtttctct ctgagtgtag ctaagacccc tagtgcagga tgaaaacatt  6960
aacatacaca caggatgaaa aacatgtaga gaagtctcat gccacatctg aaaggtattc  7020
ctatttgctg gcatcctttt ctttttaaat actggataac aaccaaaaag tcagagaacc  7080
tctgattgga ccacctgccg agagtctctg tcatctgtgt tgcctgttgg cctcccgcat  7140
gagctggctg ggctgtggca agacttctgc acaggcttat cttttcccag atgacaggcc  7200
caactagatg ggatgtcccg gacatccttg agtcagtggc ttgtgacact catttgcctt  7260
ttagaaaatt ttttatttta tttatttaca ttccaaatgt tatccccttc ctgttagctc  7320
cagatttctt tgcccccatcc cctcttccct ttgcctctga gcaggtgctc tcccccaaac  7380
ctcacctctt accccccccc cccagcatcc cccttccctg aggcatcaag tctttacaga  7440
atttaggcac atcctctccc actgaggcca gacagggcag tcctctgcta catatgtgct  7500
gggggccaca gagaagccca tgtttgctct ttggttggta gcttagtctc tgggagctat  7560
gtggagtctg ggttagttga tactgttggt cttcctatgg ggttgctgct ttgcacaact  7620
ctagcttttc ctggtgtttg ttttctgaga tacagcagtg ggcatgattg ggacacagag  7680
tcaaattagt ccctttttttt cttttttttt aaacctcatt ttttttctca tattgggaag  7740
catgcacttg gtttggagtt gactttgtgc aactttatgt tttacttgaa atagtttaac  7800
ttggtaagtt actgaaataa attgaaactc aacttcatta gcccagccac atacttgggg  7860
gtctggttct ggctggtttt acctgtgctc taactcccac acctcagttt ccccacctga  7920
gaagtagggc ctgtgacata actcagtcag tttctgagct ggtcagcatg tgtgagaaag  7980
gctactcctt ctcccttttcc tcctctcagg aaatggaaac caaaaatgag cttcttgttg  8040
ccaacaggaa agccttcctc ttcttccttt tcttaaatga cgaagctaca gactcaaagc  8100
tccacatctt agagagggga gagggactca gactcagctg ggagttctgg aatccccctg  8160
ccccctagtc cttgtatttt aaatgcagac gacactttag cccattgtca cagcgtgtgt  8220
gtgtgtgtgt gtgtgtgtgt gtgtgtgtgt gtgtgtgtac accgtgtgcc tgctgtgctg  8280
cagctggagt taggttgggt tcagttctta gcctctgctc cgaggggagg tttgagtggc  8340
cgtggatgac gatgaccctt actctgagtt ctttgccact tcctacacag agttagtggg  8400
tttagaggga agagagcagt gtgctgggga gccacgacag tgcagggtgg cacagtcctg  8460
tgcagaggag gagatgcagt gtctgtcctg agtagtggcc acacttcatg tgtcctagct  8520
agcacttgga gggtggccag tgcaggtgaa aagctaagtt gaactttaat gtgttgactt  8580
gttttgtggc attgggaatc aagctgagct ctttgagcat gccaggcgga ccgtctacca  8640
gtgaggaccc tcccgagctc ttacttaatt ttagttaaaa tttaaatggc cctgtgtttg  8700
aacagtgctg actttgtgca actttatgtt ttacttgaaa tagtttaact tggtaagtta  8760
ctgaaataaa ttgaaactca actgcagtaa aaagagtgtt gcttagtaag ttgctatgga  8820
gaaagctcta gagttcatgt ttctgagttt ccaatgcaag tcctttatga aaggctgata  8880
tctttgtgcc ggaggcagca gggaacgggg cagtgcagcc cagagcattc tgaggagggg  8940
agcatttctg gtcagcatgc aggagcgagc gagtaggcag gcaggctgct ggtggtgtgg  9000
cgaatgggtt gccttcaggt ctctgcaggt gtcacagctt cccgccacat ctcctagcag  9060
ctctgtgctc aggattcctg gaggctagtg agccctgctc cactgtactc tttgacgtcc  9120
tggttcaaag ccacacagag gcaatatttc ttgtgtttta caggcacaaa cccagtctag  9180
attagctaaa atagtctgac caagaggtct gcacttgtgc atattgctgt tgctgaggga  9240
aatagctacc acagactgag gatttagcac agcactaggc agagccaaag gtaagttcat  9300
gcggagcctt tcctaatgag aacaggcaaa tacagagcct gcctgtgctg tgcttcctct  9360
gtgcagccgc gtcctgcaga ggggcgcagg gagccctttg gggtggatct ggcttcctgg  9420
gctgtttaga ggttgaattt tgggagaggt gaagaagctg tgagttctga catgtcctgg  9480
aagggccagg cttccctgca gtcccaaaac agctcgtttg aacgagatga gagcaatttt  9540
caggagatgt tctgattttg tccaagagtc acctaggaag tgatagaact aggctcagat  9600
gcaggcttct tgcctggcaa gtccatgcac ttgaccagtg ctttccagag agtgagaggg  9660
aacacgagtt gagagtcaga agcatgactt ggtgaaatgg cagagacaag ttgaagcata  9720
agaaagagta ctttggtcac aggcatcttc tctcaattga agtaacattt tagaaagtga  9780
agagcagcta tgatatggta tccaaaagta aagagagcac ttggcatgat aaagaaacaa  9840
aggaattcgg aatataacta ctagttatct tgtgaatgag tcatgagaca ctagtgtggg  9900
catggaagga aggtcactgt gttggcatga cactctgaac tacagggtgg gctactgaac  9960
agtttgaagc ttgtgggggg ctgcttgggg ctggaagaaa gctcactgtg catgagactt  10020
tccttagcag tgagctctgc ctctttcccc tttttcccac ctggctgtag ccggctgtac  10080
tagctagcta gagccttact ggctccactg acccacacct gggccaggcc tctctttttt  10140
atccctttat acagtgtttc cggctgccct ccaggatgct ccaggaggta tggcactgag  10200
agaaacagtc cacccacaca ccacaacaca gcacagggct gtcagtggag ctcaggcctc  10260
gtgattccct agctcactca ttacctagga actaggtaga gggacttgcc aaagaggtga  10320
ggttggtagg agcaatgctt gtgaattcca ggctctgact cctctggaga gaggccagat  10380
gctgccagaa ttctttgctt ctgaggacag gtctttgaac atcccagagg aatgtgagtg  10440
acacttctca ctaatctagc agcagcagga cagggagctc tgtcctactt gagaggggct  10500
cttctccttt ctgtaagaca gtttataggt gactcttcag agcattgatg cctatcgttt  10560
```

-continued

```
attcactgtt tcttacataa gggtaccccc tgctgatgta aacttaaggc tgttctgtct  10620
cagcctccca gcttccaaga ttacaaacgt gagccatcat ttctggcacc aattctaaaa  10680
tactgatgaa tcggtaaaac tggctcatat ttttaaaagt ggaagcttta aagtatctca  10740
gtcctatcac ccagaaatcg ccaggataat tagatgacca cagctgcaga tggtattctc  10800
caagatcctg gagatagtac ttggagccac caacagaaaa actcactaga atcatcttca  10860
tgaaaactct agtaaattat ttattttgct tcagtaagaa acgtgcagtt tcaaatagaa  10920
acccgggctc ctgagagcga gtgctgtggc tgagaatgta aactgacaaa gcccgagtgc  10980
agaaggtcgt gctaacaagg caccaaccgg tttgctctca gtttatgggc tgagaagtcc  11040
gcccttctgc atcttccctc ctgactgaac atgaggcgtt gctgtgagtt tgctattttg  11100
ttgtgtggtt tcattcacta gtatttgttg attgagccct tactgagcca gtgtcgcagg  11160
cggtgttttc aggaggttca ttgctggccg tgctgctcct ctgtgctgtc ctgtgctctc  11220
agtagctctg cagggccagc cctgcatccc tgggctctgg gttgctctgc tctgaccctg  11280
tgtgtgtagt ttttgcctga gatgtggttt ggttcttcat actgcatagt ggctgctgcc  11340
agtgtctttt tatgaaggga ctggatagat gcatttttttg tagagtggat aagggctcta  11400
ctccctgaag cctgttgtgg ccctgtaggg ttgcttggct ttcttctccc atggcagaac  11460
agtgccacca ccacctgtcc tccgagacag gaccttgtct cctctggtct gaagattgat  11520
actaattgct gacctgtcta gacatctctg tctaagctgg cctctttgtg aggcagactt  11580
ttctggacct cagatgcttg tgcactgcag gctgaagttg gcctgcagtc taggggggagg  11640
ctctgtcagg tccttgctcc tgtgttgctg gctttgcctt cctggggtga caagtgtctg  11700
aatgtctgtc catctttgga tgctgcttgc cttggctctg tcactgacac ccagcagctt  11760
cttcctgact cctgactttt ctcaacatta gggacacgct ctgatttttt ttctgtggaa  11820
ctggcagtga ggtagctttc tcttctgggt tcactgtttt tgtgatacac tgtgtccctt  11880
atgccatccc tcttactcta cctgtgcaca gcatatttcc cccctgctca ttttaatact  11940
caataagtct taatactgac ttgctgtgga tatttcccta tggaagcagc cgccaccccc  12000
aatccatctg cagatctgaa agtctgcctg ttccatggga tgactattct ctggccttct  12060
ggtaccagat tgtgggcagc agagattcag gctgagctag ggcattacct tgttgggacc  12120
tggactctgc tttgagttgt ttcagctttc cagggtcagt gctcttggct taccccctggg  12180
cttcctagaa ggccttctgg cctcttgttt acagtcagcc cctggggaca ggagtggccc  12240
tgggctccag tgctcagtgc tgctgtgtag ggatgctgcc ttctctccag ggtttccttg  12300
cctgggggcc tgctgtttca atccagctgc tgctgctgct tcctttctca gccttagcac  12360
cagctccttg gaaggcagtc cctgacaact gtcctgtgcc acatgaaacc agtttggatt  12420
tcttcactgt ttattcattt cccctagccc cagggaggac ccttctagtg tgagcaaggg  12480
cctcagtttc tcctgtctgg ctcactggtc tgcagaacga gccacacagg agtaaactac  12540
tggagtatgc aggtcacttc tgctttctct actggtgtac tgagagaaac ctttgcacct  12600
gttgggttat tttctctccc tctgtcttaa ttcctgcctt ttctttctat atttttggta  12660
aatttccact gttagggtct cccttttctc ataaggtcct ttttgtcatc ttgagtgagg  12720
gcagaaacta ctgccctggt cccagtttcc gtatgtgggg ctgtgtgcag agtggttgac  12780
agtggtacca ggactctact cagtggccag tgtcacacag gagaggccca agcacctgtc  12840
acatgcaggt gcagccgtga tgcttccttc cagtctgaat gcagcagcag agctctctgc  12900
atagtgcctg ggcttgtgtc tctaaggagg ctgagtggct ggtctgctga gagggaggga  12960
gtggctgttc agggactaag tcattgagaa tcacacaccc tccatgtgga agggtttcct  13020
aagcaaggag gtatttctga gcaagatggg tgtctgtgtc tgagtttgtt gctcatggca  13080
tgaaggggat ctgggatgtg tcccttatat ccagtgcaaa gtggctcagt cctgctctct  13140
gctgcatttc agtatgctca gtgcctaagt actggcactg cttcatctgg tccagcgctt  13200
accagacttc cctctataga gaccaagggg ctgtagtagg tagccatgtc agaggcattg  13260
ctagcactgc ggcaggaagt gcgtactcta gttaacgctt tgttcatggc ctacctgctg  13320
ttgagaagtg atgctcttgc tttgcctgaa agtggcttct cggtgccctt ggggcttgct  13380
ctgcctgggg catagtcttg agtcttggag catgcacata gagcctctta gaacccctcc  13440
ctcgttaggc tctggaaggc tcttagacat ctatctgttc agagtccaga ttggtaatgt  13500
tgatcagaaa gttgaggagc cctccctttt tttttttttt ttttggtttt ttcgagacag  13560
ggtttctctg tatggccctg gctgtcctgg aactcactct gtagaccagg ctggcctcga  13620
attcagaaat cgcctgcctc tgcctcccaa gtgctgggat taaaggcatg cgccaccacg  13680
ctcggctcga gccctccctc tcttatcttg tgtattaacc tgttgtaatt agcttttact  13740
gtaaacttga ccagactggt cagtgggctt gtctgtggag acttggcttc ttgttaatta  13800
tgtgagaggg accccactct gtacaagaca aacactgtta tctgggcagg tggtcctggg  13860
ctatatgaga agtctaccta agcgtgagcc tcagtgaacc agcaagcacc attcccctgc  13920
ttcaggtctg ctgagttctt gctgttggat gtccttcaat gatagactgc aacctggaga  13980
ggtgcaggcc acatagtgat gggctgcgac ctagaagtat agccacataa accccttttct  14040
ccccaggctg cttttgatga gggttttatc acagcaacac cattttaacc ctagcctctc  14100
ctgactgccc agggagtagc tgctgcacag agatcttcct tctctcttca gctttctcag  14160
gccaagcttg tcctatgcgg tagagcagtc atgtgcaccc cactccacct tccttcagag  14220
ccgtgctctc tataccattt agagccctgt gtagaagata ggtaccagaa agattcttgt  14280
agctattcag aacatctagt gggagtcccc taaacaccca taggctccgt tccagcctac  14340
agccttccac ttattttgag actgcagggt tttcttgttt tttgtgtttt ttttgttttt  14400
tgtttttttt taaaaagcac gtttgatagt ctgaggcaag gttttctaat ttgttcagat  14460
actagttacc ttgtgacata attaaataaa agtgatttat aattagttca ttaaccatgc  14520
catttaatga tgctttaaag aagattaccc gccctcagag ttgtggaagc agctcactta  14580
ttcttctata ggtacttgtg cttgccttgc tcagcagctc attccttctg atgaataaag  14640
aggcccctac agctcagcac agtgggtcag ttgtacttgt gtcaaagaaa gctgcaagac  14700
cctcctgtcc tggctgctct gtgtatgcta cttggtccta ctaacctgct gctgttagct  14760
ttaactgtta gcttggcatg tgtgtgtgtg tggggggggg ggagaattgt tttattttct  14820
ggcaaaaatg gttcctgaag tgaagggttt tggtctcaga aacttactga ttttaaagtt  14880
ttttgagact gggtgtagtg ggccacacct ttaacgctag cactagggag gcaaaggcag  14940
gtgcatctat gtgagttcaa gtccagcctg gccagcatag caagtttcag gtcagcacag  15000
ctatggagta agatcatgtc tgaaagcagc aacagtaacc actgaagaag ttggtagagg  15060
ggaaagaata acttaacagc tgaggaactg aggaggtttc agagttttga tcaacagtct  15120
ggaaagggaa atcagtgcct gaagtcaatg caggtcctag catcactttc cagtagaagt  15180
gggaactgat gggatgaatg ggcagctctg cgggtaaagg gggtgagggt aacagttaca  15240
gagccctagg tctgtgggca gcagagaagc cacgtgctag cagctcacag ttggtgaatt  15300
```

-continued

```
acatgctgtg gcaacaccca gggagggcca ctggttcttc ctgtgcgtgc gttctcactt  15360
gtgcgcgtcc tccctctccc cctctccccc ctttttagtt tatgtatatg agtgttttgc  15420
ctgcttgtgt ctgtgcacca gctgagatcc tggtgctctg gggaggttgg aaaaatatgt  15480
tgggtctcct ggaattggag tacaaatggt taggagcctc catgtgggtg ctaggagcag  15540
aacctgggtc ctctgaactc ctgaaccatg tctctagcac cagacctctt tttctttgga  15600
taaaggtgcg tcatgaagcc taatgtcaca tttgggtgtt tctctgcctg ttgttgtgtg  15660
gttcttgtgc ctccgtcatg cttgctgcag gccaaggctc tgtttctgct ctgtttctgc  15720
tctgtttcct tgtgctgatg cagtgcagtt gctggctgag gttgaaaaca gcaccttcca  15780
acagtttaca gcttgtgctt gtttcgagtg gggatcccaa gcctgaaggt ctgcgatctt  15840
gggagtagag aaggagccag ctttgcccag gtaggaactg gaaggaatag gaaccaggaa  15900
cctaaggtcg gggctgcact agccagcttg gatttgcttg gattacctgg gacagcactt  15960
cggaagtgaa aaccattctc gcaggatgac catctctttc cttggtagct agatttggta  16020
tggagagagt tggtttggct taatagctgg gatcctttat tcttaagact agcccagaga  16080
tccaagctcc atgtccctga cttgggcatt aaagacagaa actgatggaa tatacaaaaa  16140
ataggagaaa atctgtcgta ttttcctctg gtgttctgag atggtctctt gtggtccagg  16200
ctggcaccaa ctccccattc tcatgcctcc acctcccaag tgctgggtta tagacatgga  16260
ctgccacact cctcctgcag ttggagactt ataggcccca gggtatgaaa gagtagctct  16320
gacacagtga gcatgcaggc ctctagcacc ctctttgcct gcttccttca tctgccccta  16380
ttggaggctc caggatctag gaaagtatag gagtagggct ccctccaggc ttccaggcca  16440
cctgaagcaa gaggtttctc agcattgtcc cttacctggc aggtacctta cctgcacagg  16500
tgtggctttt agtgctaaca gcaggcctag tggacagcag cagagtaatt tttgactccc  16560
acaggctttt gcgtgtgccc agacaggagg tggtgctctg ctacctcttc ccatggctgc  16620
taacagctat tgtcaatcat caagctgcct gtctttgctg actacagttt ggtggtgacc  16680
ctgctttttg gggagggcca ataggaggct tggctttttt tctaaccccc tcatctcaaa  16740
ggcttaaagg caattcctgt gcagtgtcct gttctgagaa cacaaagcac attctttcct  16800
gatttttccc cccagatcag tttgtaatat ttatatcccg tttgtaatga cttcagaacg  16860
atgcgtgcct tgctgatagg accacagcac agcactggat ttaggacacc tgtgtttgac  16920
tgcgcaccac ttcttactct gggcacttac aggccatggc cttactcctg gaggaatgcc  16980
agccacttcc ttcttggccc caagtgagtg atcagtatga ttgcacactg tgctttactg  17040
atggcagggg ttttgctgtg gatcagagga ccctttccag ctttcttctc tggagtatca  17100
gggaaggccc taagggtaaa gtgcacctga gtgaggaagc ccagcatgag acccgaggag  17160
cgggtgtgtg tgtgtgtgtg tgtgtgtgtg tgtgtgtgtg tgtgtgtgtg tgtgtgtgtg  17220
agactgtctc atgctgttgg tatttcagat agagcttgaa agcttggcca tatgtactgc  17280
tttgcaagtg aagaccttga gtcatgtttt ggctattgga cctctctgtc tacaggatgt  17340
ttgagtgtgg ctagtttgag ctatgcatga gatttttgta agctagcctc agtgttctgt  17400
tgtgaccggg ccagttattt aatttttctt tttgtctttg aaacctgctg ctctgaggct  17460
ttaaactctg ctgttctcat cttgagctcc tcccctctgg acctagtgga cagccagcag  17520
gacctcctgt ggatttgtat gtctttcctg tctcaggctg tgtgttacct atcatgaggt  17580
atgcagtgag ctgcctgtgt gactcaggat gtcttggcta gggcttgaac ctttggctgg  17640
gtactgtgct gcactgcagt tcattgaaaa atgtctgtcg tgagtgtagc tttccgactg  17700
gcattgtttt gaatgcatct ttaaaggtta gttataaata cattaatgct tgggactgac  17760
aagaattcat ctgtggaact ataccatcct gtgagatttt atttcattat atatgttcac  17820
agaaaagaaa cagggagggt agggtgggct ggaaagaccc tcagcaatta agagcactgc  17880
gtgtgctttc agaggacttg gggttggttc ccagtactca cgtgggaggg acctctctac  17940
tgtgcataac tggttccaag ggatctgata ccctcttatg gcctctgagg gcactctgtg  18000
tgcaaatggt atgcagacat acgtgcaggc aaaactccca tacacttaca gtagatacta  18060
ataaataagc tggacttaaa ttttcatttt atgtgtatga atatttggta tatatcagtg  18120
taatgtgtgt gctatgcctt cagaatccag aagagggcat tagatccttt agaactagtc  18180
ttacaaaggc ttttgagcca cattatggct gctgggaatt gaacctgggt cctctggaag  18240
accccagagg agcaagtact tctaataaca gagacatcac tccagtccca gaagctgggt  18300
tctgagtggc tccaatataa tttgaactat agcaaaaggt agaattctgt ttaattgtaa  18360
ctctccttct tcttcttctt cttcttcttc ttcttcttct tcttcttctt cttcttcttc  18420
ttcttcttct tctcctcctc ctcctcctcc tcctcctcct cctcctcctc ctcctcctcc  18480
tcctcctcct cttcttcctt cttcttcttc tttcttcttc tttcttcttc ttcttctttt  18540
cttttttttgg ttttttgaga cagggtttct ctgtatagcc ctggctgtcc tggaactcac  18600
tttgtagacc aggcaggcct caaactcaga aatccgcctg cctctgcctt ccaagtgctg  18660
ggattaaagg catgcgccac cacgcccagc ttcctttttc tctttttttcc acagacttca  18720
tgaggagata atcgactttt ataacttcat gtccccttgt cctgaagaag cagccatgag  18780
aagggaggtg gtgaaacgga tcgaaactgt ggtgaaagac ctctggccca cagctgatgt  18840
gagtatcttg ttcacgtacc agtccatgag gttgtgtcag ctttatccac atgtgcccac  18900
gcttcctatt cccacagtag agcagctccc caggcctagt cccgggagca tcgcctggga  18960
gggaacggct tagacgagca ctctccccctc tactgcgtct agccctggtg tagtccagcc  19020
tctggttagc ctgtgaaacc cataaatagg aatatttata ttcttatggt ccttcattcc  19080
cctccctctt cattcttgtt taaaaattgc gttaaggtta gaaatctccc tcctgctcca  19140
cccacacttg cagtcactgc agttcacagc atggaacatg tttgcgtcat tagaaattgc  19200
aagtggcagc agagcatggt ggcacatgcc tttcatccca gccctcaggc agcaaaggct  19260
ggaagtttga ggctcaagtg ggctacgtag ggaaactctg tcttaaaaca taacagaata  19320
caagtgttcc tggtgtagca ctcacatgaa tgagtgtgtg tctgtggaaa tgaggtactt  19380
gcctatttgt agtccttggt gcaggcagcc tgtggtatgt cagctgacca gggagctaac  19440
cgcctggcct ggattttgat gtaaataaat gtacaaagag ttttctagtt tgttgcacca  19500
tttcatctgc ttcttcccct aatgtccaag ctggttttgt ttgtcctcgt gtttttcaag  19560
gcatggtggg ggtctgctgg cttgaactct gggacttctc tttcaggtgc agatatttgg  19620
cagctttagt acaggcctct atcttccaac aaggtgagtg tcaaggctga cggcacactt  19680
gggtgttggc ttatggagtg gcagtgtctt tgcttctaag gcttgaatag ccagctaagg  19740
ggaaggattg tggaacacag gggaaatagg cagaaagttg catttattag tttagtatta  19800
aggcaggaga ttgcttgctt ggcattttttc ttcttgcatt taatttcttt cttttttttt  19860
gggggggggt atatttggat aatagtttat tggttaaaag aatatatttc cacaaagatt  19920
tttttgattt gtttacagag ctacccatat tttatagaat acctgaagaa gctggaaagc  19980
tgttcagatt tcatgtgcta aaaaaagaat attcttaatt aaattgtaag aaaaacacta  20040
```

-continued

```
aaatacacag gacaaataag cctcaagaga aaatatggct gaacaaaaat aatcagcaac  20100
tacatcactt tataacacag gaattataat gaaatgaagt tctctctgga cgactccagc  20160
tatacatgaa atgaaaagta ttttcaacat acatccaatt tccaaagtac aacataatga  20220
aacatttaaa acttcagtgt attttgatta gttcttaaag ccccttcccc caaacatttt  20280
ggcaccaaac aaactttgc tacaaatggg gatttttttc ctttgagatt tcctgcatga  20340
ccagtgttga taaaataagg aaaggggaaa ggctgattga caagaacagc tacataaact  20400
attagaagac cattcctaat cgagaaatga attggtacta accactgtgt gcatacactt  20460
agatcaatgc ctgtcagagc cttacaacaa cgaatggcag tcttaatcaa cacagaggga  20520
tctttttctg ggtttggtcc atccagcgaa ggagaccagt ggcctccaat ggccatggct  20580
tcatccttgc ctttcattcc cactagaaac taattcaaac caaagaatca tttatatata  20640
tataacacag cccatcaaat tataatagat acttagaaaa ttaggaaggt acaaaccttc  20700
ccaatactac ttttactacc tctgatatct gtcagtcaag gacgagttca gttcagcatt  20760
taatttctta agcacagaaa tgttgggtgt cagacagaaa atggatggga actgccttgg  20820
tctcctgctg ccatagaaca ggaccccggg ttggctgaac tgtaaactgt agaagcttcg  20880
ttagctctca gttctgggga ccgagaagtc ttaagattca gaggcttatc tgggtctaac  20940
tcaccccgta gcagaggtct tgatccattt agaaaacatt gccccagagc ctactcacct  21000
caggaaggag aaaggcctga cctgttggtt ggggggggcca catttcagtg ggagtctttg  21060
gggttttgat agtgaataga aaatgttagc gaaccttcaa gcacacttct gttagaacag  21120
tattttatga agctctttat gtagaagtgt cagatttaca tcctaaaatt gtcttctggg  21180
ttcatattgt catatatata atgtataggt ggtttttgtt gtacatgctg gttagcattt  21240
ggaactagcc tgctagtata gcatttggct gtgatgtcag gacttaggaa ctgacatggg  21300
caaaggctct ggaagccaag tagattaaaa gtcttcaggg atctccagac cttgaagcaa  21360
gagccagtga cgatagaata gactgctgaa aacagtttat cctgtcacct gttggttcct  21420
gggactctga ggccctttc actctggctt tatatactta gatgactcaa gagctgcatt  21480
cagggctcat ggcttaggta cttaggggac cttgttgata agaggcaaca tgctgtggtg  21540
ctggccttcc catgggaggc cacctggtga ggtttgttgt gactgacaca gtttctcttc  21600
tgtccagtga catagacctg gttgtctttg gaaagtggga acgccctcca ttacagttgt  21660
tggaacaagc cctccggaag cacaacgtgg ctgagccgtg ctccatcaaa gttcttgaca  21720
aagctacagt gagtattggg ggacagatac cttcacctga agtccccaca tggggtcagt  21780
gtcctctggt tttcttacag tggttactgg ttatattttg attgtcctct tgtggtataa  21840
ccataccagt gaccatcttc atgatttacc agctgagaac ctgtttggtg ataagtggat  21900
ttgttctcat tgtgagatct tagattttca ctcttggcct taaaagactt gtgtctgtct  21960
gtgtctgtag agtaaagcaa ggcagaggat cactacggag gaactagcac tccacctgct  22020
gttgtcctgg tttgcagctt agagatctgt gtggcagtgg tgtgtgtgtg tgtgtgtgtg  22080
tgtgtgtgtg tgtgtgtgtg tgtgtgtaag accgcacact aacttacgct gaaggaggaa  22140
aacctggagt tccctttgtt gctcagccct gtgtcttctt aggaaaggca ctgtctcagg  22200
ggaaactgaa agataagatt gcttctaaga agttcctggg acgattcatt gaaatggttt  22260
atgttagaca gcttatgatc tcagtctgtg gccctggtat gcaccagaca ccagctctgc  22320
tgccatggac tggtgtttca gttttgagtt ggtgtgttac ctcgtctgta gggtttttgg  22380
ggaaagtgtg agtttcaatc cagtggctgc aagctttgtt ggtactttg cctggggtgg  22440
gtgagtgttt agatggaagc atgcccactg tggattggat cttcacaaag tgtctagact  22500
gtcccttccc agtggttgtc cctccaggcc tggctaccat actgcctttt attttattca  22560
ccggaactct gcttagtcat gaaccttggg taagatgcag aaggccatgt tgtactcagt  22620
cagtcctcca actcaccggc aggcacatga ggaaacaccc acaatgaata gcaagggaaa  22680
ggctttgagc tcctttaaac acagtgggca gaggtgacac cttgctatga ccagggtcct  22740
gctgtggtcc agggtcctgt tgtgatccag ggaaggtcct gctgtgatcc agggaaggtc  22800
ctgctgtggt ctggggtcct gctgtggccc catctgtgcc atggttgttc tttttgtctt  22860
taattcttca tccagggaga aatccagctg tcttaggcac tctgaccact cagtcttgca  22920
cagttagtga agtgaggccc tttgacaatg tggaggcaat ggggacttgc tgttggtggt  22980
ggtattcaga tgtaggagag cttatgggtg gcctgaggtt cctgagttgt tgaacttttc  23040
aagatccaga cagagcattt gaggattgtt gggtataact gcttagtcct cccagactcc  23100
ctgctccagc atgttgaaaa atatatacct caattacttg aaggcatccc atcctggctg  23160
gtgtgtgtgt gtgtgtgtgt gtgtgtgtgt gtgtgtgtgt gtgtgtgtgt gtgtgtgtgt  23220
gtgtgtgtgc gctcttctct tctcttctct tctcttctct tctcttctct tctcttctct  23280
tctcttctct tctcttctct tctcttctct tctcttctct tctcttctct tctcttctct  23340
tctcttctct tctcttctct tctcttctct tctcttctct tctcttctct tctcttctct  23400
tctcttctct tctcttctct tctcttctct tctcttctct tcttctcttc ctctccctcc  23460
tgctcgtcct gtgatgataa ccatggatct ggatcttgaa gtgcaagggc tttgtgctgc  23520
tgtgtatttc tcagtgtctg gtctaacaga gcagctgtgg tgctctcacc cttgggtgtg  23580
tagtgtgact ttgtagggtg catgtgcagg tcaggcctct cacctgagtc ctctctcagg  23640
ctcccattcc cctcttgctg tcccacttca gagttggcct gtaggagatg gtagagtggg  23700
agtcctgcta ggagaagaca ggtcatggac gttgtgtgga gcttcatgac cactgatttt  23760
aactcctgac agagccctc tctttaaaac tgacatcctt gaccaccaat tcccttttgt  23820
gaagagagaa cggtgagtga ctgtctggag atgtagatgt cacagcagtt tgtcaactac  23880
atcctcatag gtgcccatca taaagctcac agatcaggag actgaagtta aagtcgacat  23940
cagctttaac atggagactg gcgtgcgggc ggcagagttc atcaagaatt acatgaaggt  24000
actgttgtct caggtgccca gtaggacaga ggtgtgagac cttgttactc atttttctca  24060
tgaatgttaa aaaccttagg atgggtcatg ggtagcaata cagacagtgc aatttccagg  24120
ttctgtcatg gggtctgtgg gggcactcag gaagtgtgta gttgctttct gattggcttt  24180
gagtgactgc ttcttttaga gcactctggg gaaatgttct gtgttagtgc acagcctcgc  24240
tcctgctccc ggctttgtgc tactctccca acctactttc tcacttgcca gactccgtct  24300
aggttggctt agtttagagg cctcagtgct tgtgaatgtg agagtggctg gtgcctgagc  24360
tgctgctttc tggagctttg agtgttggca ctcaggccac acagccaagc ctgtggtctc  24420
tttcctctgt cagttcccct tgtctgtcat tgatctgcag gagcatttgc ccacttccct  24480
cgctctctgt ccctgctttc cctagttctg ttcagggctg agccacctgc ttactgagtg  24540
ctgggattct tgtgtcccac tgatggggtc atggcttggg cctgggggtg tgggggcagt  24600
accctcagct agtgtgaatc cttaagccta aaattggagt caagagtttt tgggggggagg  24660
gagcaggaga atgggtgagg agttcttttt ctcccaggaa gcttgtctag agtcccttca  24720
aaagtacatc agctacgggg ctggagagag agctcagagg ttttaagagt tttttcaatt  24780
```

-continued

```
caattcccag caaccgccca gtagcttata gctatctata atgagatcta gtgccctctt  24840
ctggcctgca ggtgtacatg caggcataat taaaacaata acaaaaaaaa tatcagctga  24900
cctgtatgcc tcttcttggg tttcagaagt actcgctact gccatacttg attttagtgc  24960
tgaaacagtt cctgctgcag agggacctga atgaggtctt cacaggcggg atcagctcct  25020
acagcctcat cctaatggcc atcagctttc tgcaggtgag cggcctccgc actgtgctct  25080
cctcaccctc actgggctga ggaggcgccc ttttctgctt ctcctcacaa tgctttcttg  25140
gtcagccccc gtcctgtagg ttgattctgt gggtgtaggt ttcagaccct gggtgatgcc  25200
tgcctgtgct tcaggaagct ccaactttta ctatactgag aactgtggat tgtcagtttg  25260
gagcaggaga gcaagaattg gtttattcct atataaatca taaaaagcct tttccactgg  25320
cgcttatctg taaattactc ccaaataccc tgagagtaaa gggtagttac caacatgggg  25380
atgagatgga gacatttcct tttgtgtttt tgagataaag tcactctagt cctggatgac  25440
ctagaactca tgtgcagccc agcctggctt tggacccatg gcagtcctct tgactcagtt  25500
tccctggcac tgagactgca catgtgagcc actctgcctg gcaagccctc tgtgattatt  25560
ggtcttaaat tcggtgtcat ctctgctttg cgagtagagc actaggagct gccctgtcag  25620
cagctggcct cccaagcaag gcgctcctct ccttgctggt tggttggttg gtgatgttga  25680
gccagaacct cttacatact gacctggaat tcactttgta gcccaggctg gccttgaact  25740
agtagcaagt cttctgtctt aggctcctga gcactgagat tatagatgtg agctcttaca  25800
cctgctaact catatacaaa atagcacctg tgttaaagtt ttattgcatt tctattggct  25860
tgagaaaaca tttgcctgtg tgtgttagtc acctgagtgt atgtccccat gtatatcact  25920
gagagtgtat gtatgtcccc atgtatatca ctgagagtgt atgtatgtcc ccatgtatat  25980
cactgagagt gtatgtatgt ccccatgtat atcactgaga gtgtatgtat gtccccatgt  26040
atatcactga gagtgtatgt ccccatgtat atcactgaga gtgtatgtat gtccccatgt  26100
atatcactga gagtgtatac atgtccccac gtatatcact gagagtgtac gtatgtcccc  26160
atggctgccc aagtctcttt ccccacgtat atcactggtt ctcctttgtg agtgcttgct  26220
gagggtttgt tattcccaat gacactgcta gcctgcaagt cagactgtag ctcggactgt  26280
ggtgagcttt gatgcagacg tgttgcccct gaagcattag tccccaggtg tgacagcgga  26340
gaggcttaca gtgctgagcc atcacagtgg gtgacattac tgttagcgac atggcctctg  26400
tttatatctt gagtacccct gatttgaggt aatgtgtttg gatatcttgt caggacaggt  26460
gacgttacct tgagtggggt ttcccaaggc ttcctggtgt gctgttacta ggatccttct  26520
ggctgtcaga cctcacagag ctatatagat gggatagccc tccttctgtg cctgtgttgg  26580
agaccaccca cctgaggctg gacctggtgt agcattctgc ttatctcact gctgctgcct  26640
gagggaagaa ggccaggccc tgtactgggc tgccttgagt atttgatttg gctcaaaagc  26700
aaggacataa aggcttggca agaggactgc cctgttatgt agaggaggga agaactctga  26760
cattatgagg gattattcct ggaaggccac attcatgctt cagccctgtg ctaccaggac  26820
ttggacacta gggaggcttg accgtcacca tctagaattg tgcaaaggac aagttctctg  26880
tgtgaccatg gaagcgatga gccacacgct actcttggat gctgagagta actggcatgc  26940
ccacactcat tctgtagtgg gcagctcagg tctataaagt tgctggcacc tgggagttag  27000
ttatcaggga ccgtgggcaa gcgtcacaga gaggctgtgg cttgctagaa caaagtgtgc  27060
aggtgaaata gcctgacagt gatgtgtgaa agctggaagt gagttcccag gcagagttag  27120
ctctgtccac tcacatcctg gtccaatgat tgtgatactg ttcagtctca tcctgctccc  27180
tcctggtagc atgtcaggat gatgacattg atgtgaacca tgcagccacc atccagatga  27240
caatgtggaa aacttaccat tgcagcatga gggtaactag atgtgtgtgc ttggatgtcg  27300
tggtctgaat ggatgttgag atgtgttctt tctttcaagc ctcccaccaa cagaggctgt  27360
ccattgtctt gtgttttctc aggtgctatc gagtggggac ccctcagtgg gttcctggag  27420
agctgctagg tgagtgttgt tggagtgtag cttgaattca tatgctggtg gctctcttgc  27480
ttttacagtt acatccaaga atcgatgccc ggagagctga tgaaaacctg ggaatgcttc  27540
ttgtagaatt ttttgaactt tatggaagaa attttaatta cttaaaaact ggtattagaa  27600
taaaagaagg aggtgcctat atcgccaaag aagagatcat gaaagccatg accagtgggt  27660
accgaccatc gatgctgtgc attgaggacc ccttactgcc tggtgagctt gcccctctgg  27720
ctggaagcac agtgctggct tatctctacc agcagaactc agtgggaaca ctttcaggtt  27780
tctaacgagt ttactgcact ttaaaatgtt tacattctgg aaatatcata actaggaaag  27840
gctaatcagg gaatcctcac aggaaacatt cacttcagga aggaagcatg ggccaggaag  27900
tgaagaatgg ggactcctgc aggtgattct cctggctttc ctatgtcact gcaaatgttg  27960
ctcttgcagt atgtggtggc tgagctagga ctccaagccc cactccattg gcacgtgtaa  28020
gggtgcttat ctcacccacc gtggtaacac ttggtcttta agtccttgcc aatctgataa  28080
ctgctgcaca ttcttattta gttatagtcc ttcctggtgc ttgctcttca actctgcata  28140
tgcctgttga gcctgtcttg ggtgataggc taagtgcatg atgggatcag ggcaggctgt  28200
gacaacagga cgacgggagg ctgcaaacgc cttggctttg ttcttctttc gtggaactgt  28260
gcgctgcgct gcagccatgg tctcctgagc tggccacgtt ggtgttctgt gctaggggag  28320
ccttgtccac atgactctca gatcccagct tgtgctttca tttgtattca gtcgcttatt  28380
attctgctcc tattccttat ttatttacta tcctcatttt tttaaataat gtttttatta  28440
aatattttct ttatttacat ttcaaatgtt atcccctttc ctggtttccc ctccgaaaac  28500
cccctatcct catccccact tcccccctgct caccaaccca ccccactccca cttccctgtc  28560
ctgttattcc cctatactgg gccttcgagc cttcacaaga ccaagaggcc tctcctctca  28620
ttgatgtcct acaaggccat cctctgctac atatgtggct ggagccatgg gtccctccat  28680
gtgtactagc tggttggtgg tttagtccct gggagctctg gggggttctg gttggttgat  28740
attattattc cttctatggg gctgcaaacc tcttcagctc cttcagtcca ttctctagct  28800
tctccattgg ggactctgtg cagtggttgg ctgtgagcat tcacttctgt atttgtcagg  28860
ttctggcaga gcctctcagg agacagctat atcaggctcc agtcagcaaa cacttgttgg  28920
catccacaat agtgtctggg tttgttgtct gtatttggga tagatcccca ggtgggacag  28980
tctctggatg gcctttcttt cagtttctgc tctatacttt gtctccgtat ctcctcccat  29040
ggatattttc ttccccctac tgtcctcaaa tttaatgatt atttttaaac tgttcgttct  29100
agggtgagac taatttcttt aaaaatcttt tgaaaggaaa atagacaatt ctagtgagct  29160
gtcttcaagt ggctaacgga tcccataaat ggggaggtgg ggttttcgtg gaaacgtcct  29220
gacagtgtgt catctacttg agtgtcccat gtcttcaggt tctatttcag tgtgcctgca  29280
ttactcctgg actgtagctg tgtctaggaa gatgaaattc ccatatcctc cctaaaatcc  29340
catacttgag atgactgagc agtgaatcta tgtaggagtt acagttcctc ttgatgctag  29400
tggtagcttc atttgctttg ctctgtgagt ttgtaataca gcattcttcc cttaaagggc  29460
ttccttccag ttctgatact ctgttcagtg tgagcgaccc cgttacactg tgtgccactc  29520
```

-continued

```
agggcttatc atgacattga tcatgccaag tccacactgc tggttggtgt gttggatatt  29580
ctggatttcc ttgtggtgtg ggcttccctt tttttttctt tttccctttt ctgctacctg  29640
gggtcttagc agactctgtg aactgtcaga cacttgtggc tgcccccttt ccattgttag  29700
gaatagactg gtcacagagt ctgaagcact gaacctgtgt gcaattatat accatgcact  29760
tgcagcagct cgctcgggtc tgtgtttaca tgcctgttgc ttgagctgct gtagttggga  29820
ggcatttggt ggtgagcccc tattcacagt accttgtatg agagacaggt gcctttgtgt  29880
tgcaggaaat gatgttggac ggagttccta tggggccatg caggtgaagc aggtgtttga  29940
ctacgcttac attgtgctca gccacgctgt gtcaccgctc gccaggtctt accccaacag  30000
ggattctgaa aggtaatggg tcttgtgcct gggttctagg ctcctctttc ctgtagagta  30060
gcaggtgtac tttttcatgt gcttctgtgg catggatgga tacactgtca tacttgagtg  30120
gaccttgagg aaagcttttt tgggggcaac aagatggctt ttgggtagcc cgtggcctag  30180
gacagcattt cttagtgggg tggtattgta cttgggacat tctgtattag agcagattcc  30240
tgactttgaa aacctcggtt ggtgcctgtc cagcagctgt caggtgtgct tgcttaggtt  30300
gtgagtgggt tcagatctga acacactgct ctgcctctac agctgtttag ccgtccttca  30360
ctttacagtt gaggatagtc tacagtgtct cctttagtgg ttgtcaggca tatttatttc  30420
cagttcagct tagctgctat agtatgtgca catggggagc aggaggagac aagagtggaa  30480
ggggagaaat gggctgaaca gactgctgtc agcagtgtgt gaatgtctgt tccagagctg  30540
gctgcctcag gaaactgtta ggaatgggcc tggctttcca tgattgtcca cacacagtgt  30600
tgcaggccag cccctagcct gtaatgggcg cctgggtatc tctccacacc tgtgcagtgg  30660
aaacaaagtg tcaggacttc atggctaccg cttaaactgg attgaagcca tcatttgtag  30720
acagatcttg gttaaggact tctacatagt gaacctacct ttatctgtac cgtgatctca  30780
tggtactatg aatgtaaaca tgtcagacct catgctctct cctgtcttta atgagcctca  30840
catctgacac ctagtgctta tgtccaaccc tgttctctgc agtactttag gaagaatcat  30900
caaagtcacc caggaagtga tcgactaccg gaggtggatc aaagaaaagt ggggtagcag  30960
aatcctcccg tctccagacc ttggtgagag actgacagtg tgaggcgtgg cctctcacca  31020
tagcacagaa gcatctctgc cctcttgtag ggttggccaa gctgtgaaag tagttccttt  31080
tctacttttt ctgataggct atccgttctg taagctctgg accctataga aatacagtcg  31140
tagctgcagt aaacgaaggg aaggagcaga tggaagtggt tgctaatgtt gcatttgatt  31200
aaacgaaggt atactccaac acagtggcaa gaaatcactg agatgcagat aggttttgtt  31260
ccaaatctta gaaatccagt atgtatttgt ttcagaattc tacattctac attgacattg  31320
gacatatttg ttttatgttt atagtttatg acagctacag gttaagactt acacagcact  31380
ggacaaatta tagtgttttc tggtgactag tttgattcac atttaaaatt agattaactc  31440
agatacaagg tttggtttgt taacattcag agttcagcag ccttgtgctt cgagcacatt  31500
gtactaatca ctaacctgga ctttgctttc ctgccccaga caacaggatt aagataaagg  31560
agagaattac cacgtgcaat ggggagcaga tgcagagccg ggagcccagc tccccttaca  31620
cccagcgcct gactctgtcc ctgtccagtc cccagctgct gtcttcaggc tcttctgctt  31680
cttctgtgtc ctcactttct ggaagtgaca ttgtgagtgg gcttttgctc ttgactcgtc  31740
cttctcatgg ggtggggtgg ccactgtcct tgttatctgt agcagggagt tcaagaccta  31800
ttcctcctcc atctcagtcc cttgctgggg tgtgaggatg tgtgtgtgtg tgagagatgt  31860
atgtgtgtgt gtgagatgta tttgtgtgga tatctatgga gtatatgtga ggtacgtgtg  31920
ggtgggaggt tggggtgtgt gtgtgtggtg tcgtgtctgt ctttgttggg tgttctttga  31980
cataggcttt aagaacccct ggctgtgttg ctccgatgac ccatcaatag cactcagcca  32040
aactttggac tttgagtggt ttttttgag aaatggttta gagatttacc ggttaggtcc  32100
atgtgcctca tctgcatttt ctgcagccta gtctttctcg tgctgcagtg actgaggaag  32160
gataggtttg ctgtaatggc ctttcctagc ttcctcctta aaggcgcctg gctcacactt  32220
cagctgcgct gtgcttatga ctctccttgt ctctgtgctg cgctctagga ctccgacaca  32280
ccgccctgca ccacacccag tgtttatcag ttcagcctgc aagcacccac taccctgatg  32340
gccagcctgc ccacagcctt gccaatgccc agcagcaaac cccagcctgc tgcttccaga  32400
acgttgatca tgacaacaaa caaccaggta caggcttcct ccccggggac ggcatccggg  32460
ccaagcagga ccctagatca gcgttcttgt ggacgactgg gtctagtgct gtctcccggc  32520
agtcatcgtg ctttggtggc tgcagttgtt actcagcctg ttgtgtaacg cagtctctga  32580
cctggagtct gatgttgttc tggagcactg gatgcctctg acaggtgctc tctcagtgcc  32640
gctttgcatg cagtagtgtc cagggcacgc actgctggct gcgtagacac ttgctctctc  32700
tctccagaaa ctcagtgtca gcatgggctt agactctctg ttagtcagtc agtactcggg  32760
acttctcttt ttaaatttta tataaagtga atcaaaagaa aagtatagaa attcagtatt  32820
gtgttgggtt tgtacaaact cagtgcatta ttaactggga aggagaagca gcatttgacg  32880
tgggagttga gtgggaaaca gaacagaagc atgtagatgg ctttcctgga gtcctttggc  32940
cctgctgaga tccattccca cacagctgct ttgaagctga gctctacgaa agcatgtgac  33000
tctgatgttg gtgagcgttg gacacccttc ccccagtgta gcccagacta cagacctcaa  33060
cgagtgcacg cgaggaactt tccaaggcag ttgttgaagc tattaaattc taccccactt  33120
caacttgact gtcagcttcc ggaaaggaca ctgcccaccc ttccactctg gaggcctctt  33180
tgtcactcgc caggacagtg tcttggagag cccgatgcag ggccagcttc agtttcctgc  33240
cggaggtgtt ttggacctgt ggtgtctaag aaagtatagg tgtggatccc agttggttgt  33300
cacagttgta tgattatcct gtgtgagtgt gagtcaggct gagcttgaaa ccaaagtttg  33360
ctgtaatggc ctggagcaga gtgctggcat ccgattctcc accatgtgct ttctacagag  33420
gtagccaggc tgctgcctct cccagcagct gctatccccc tatggagctc tgctgtcaaa  33480
ggttagctcc tactgtagca agtctctctg caagtgctgg gtaaagcagc gatacctgca  33540
gtgtcaggct gagagtggca cttaccagct ttcttttgct ttgggtggga cagataatgc  33600
ggtggccaga aagagccgcc ctctttgact cttcttgtgt tcctctgttc ctctggggtc  33660
tgagggttgt tcactttggg gctcattcta gggactaaag tgacagttgc tgttttggtg  33720
gctctaattg ttttgaattt ggtttgatct ttggagaatg ttagatttta tgacctagtg  33780
actgttataa cttggtattg taattgctat ttgagaagat gagatgattg taattccaag  33840
gccacagtgt ccttaggtca caacagaagc tgtgctccgt gggcatgtgt gtgagtggat  33900
tcgcacagcc agccccacac tgctttcact tggtgtgaag tttcacttgt gggaagctca  33960
tgtttctctt ttccttctag accagggtta ctatccctcc accaaccctc ggagtcgccc  34020
ctgttccttg cagacaggct ggtgtcgacg gaaccacatc tttgaaggct gttcacagtg  34080
taacttcccc agccattccc tcggcatccc ccaacccact gtctagtcct catctgtatc  34140
acaaggtaag tgtcgtctgc tgctgggcta ctttactgca gccgcttgct cactcggggc  34200
cctgcacccc ttggaactga attcccctgc atgctctctg gttggtggtt cagtctctgt  34260
```

-continued

```
gagcccccat gggcccgggt ttgttgactc tgaccctgca gggaccttct cacacccatg  34320
aagaggcaga gcagattaaa agcctgtagg ctctgagtgg agccatagtc tgttcagagg  34380
gaagggttcc ctcagcttac tgcacgccgc agcagggatt atgtggctat gggttcctgt  34440
tgtacattgt gtcttttcac ctcatggtct gtgtgctgca ctccagccct gctttctctc  34500
tctccagcag cacaatggca tgaaactgtc catgaaaggc tcccacaacc acactcaggg  34560
tggcggctac agctctgtgg gcagtggagc tgtgaggcct cctgtaggca accgaggaca  34620
tcatcagtac aaccgcaccg gctggaggag aaaaaagcac gcacacacaa gggacagcct  34680
gcccgtgagt ctcagcagat aatggtcctg actgactgcc caaaggcctc gctcgggcac  34740
cacaggggag ccgagaccag catccagcac ctccaccgct gtctgccaag cgcagcccag  34800
cactggtcac tctgcatgtt tgtgtggtgg ccgcatccat cttacagaac agctccttgt  34860
gctcatctgt gaagccttac tacatgtgga tgtgcgtctg cctgcctaga agtcttcatc  34920
tgtgcccagc agggcggcct aggagtgtca gggactggat gtgcggctgt gcagccgggt  34980
cagctaggtg gccatttggg gttctcatcg tgtctgtcac aggcagagac gccaagccct  35040
gctccgtgtc ttctgacgga gtgggcaggc tgctgtttta ctgccctcat gtcttgtttg  35100
aaaatttggg actgttttc tatgtaaata ttgaaaactt atgatttgtg caataactca  35160
gatatttttt atttaatttc atattttcac ataagttata tttaagggag gagggaattt  35220
tttttaaaac acgcttaaat cctttcccaa tttgcatttt ctaagttggg ttcctcgtgt  35280
tggctggtta tctgatagca tcctgacatg aacaccgtga ggagggaggg gcctgtgggc  35340
tttgttttta tgtcttttct tttggtcaga tgcagtgaag gagccaagtc aacttgatag  35400
ttctgtgagg ccagtgtgta cctggcagcc tggctgtcgg ccttgggcct ttgtcctctc  35460
tgaccacgag ttctgacatt ttggtttggg tttttaaaaa ctagacacca aatccagcat  35520
ttaaagtgcc agaagtaaga acctctaaga ggagaagagg ttgtcacgtc gtataaatcg  35580
taaagaatcg tgactctggg cgtgcttcgg tcattaagtg acgtggtcta gagtcacggg  35640
cctggtgagt atcgttacag acaatggcac ccagatttag gaatgtggag aaagggattt  35700
tgttgattcc attgaggaat ctgcataggt atgcactcgt tctgttaaga gcaaatatct  35760
gaaaaggacc tccgttgtcc aggcacatgg gggtatttta atgtatcaca ggagagcaca  35820
gccccagtgt gggcccagga gcggctggtg cctggcgtca gaagcataca ggtatactat  35880
gcaagtgtat tctgccacaa ccactgtctt tgttactttt tttgaacaag aatccatcca  35940
ttgcctgacc ctgattctca agcaccacgg ttgtcctgga gtgcttgcag ttgtaggccc  36000
tctgacttct gcttctaaaa cgggggtctg gacctgctgc acaccacagg caggttgctt  36060
cttgtccacc agtacagagt gtcaagccga gtgctgtgcc acctgattga catgcagcag  36120
tggaaattct gaatggatgt ctgagtgaca ttggacacct cgccaaggac aagctctgtg  36180
tgtctgggtc tgcctcctgc tgccgtggtg aggctgttga ctctgggagg cattccagag  36240
cagaggagca catgggtctg cagctcatga ggattggagt catccagaat atttaaaatt  36300
atttaaattg tgaagcctgt tgctaaagaa tatttatgaa cactggtcca tagcctgtac  36360
taatttacac attagcaata ttgactgtat ctgcattaag gagccaccgt ggggccgttc  36420
gagtgacccg cagatgtgcg ttttaaagtt ctgtcatcca caggcacagg tatgtgtccg  36480
tctccgtcat ggtgaaccag atgaattggc ctggcgacca ctgtggccat atgctacagt  36540
ttacaaaatg ataccatgtt taaattttct gtgcggacaa caatgtggac actaaaatta  36600
acatattttt atgtaaagtt tttctattct ttgatcttta ataaacttta gatgctaga   36659

SEQ ID NO: 7            moltype = DNA  length = 16
FEATURE                 Location/Qualifiers
misc_feature            1..16
                        note = oligonucleotide motif
source                  1..16
                        mol_type = other DNA
                        organism = synthetic construct
SEQUENCE: 7
agatctgcat ccacag                                                   16

SEQ ID NO: 8            moltype = DNA  length = 17
FEATURE                 Location/Qualifiers
misc_feature            1..17
                        note = oligonucleotide motif
source                  1..17
                        mol_type = other DNA
                        organism = synthetic construct
SEQUENCE: 8
cagatctgca tccacag                                                  17

SEQ ID NO: 9            moltype = DNA  length = 18
FEATURE                 Location/Qualifiers
misc_feature            1..18
                        note = oligonucleotide motif
source                  1..18
                        mol_type = other DNA
                        organism = synthetic construct
SEQUENCE: 9
ccagatctgc atccacag                                                 18

SEQ ID NO: 10           moltype = DNA  length = 17
FEATURE                 Location/Qualifiers
misc_feature            1..17
                        note = oligonucleotide motif
source                  1..17
                        mol_type = other DNA
                        organism = synthetic construct
SEQUENCE: 10
```

```
ccagatctgc atccaca                                                17

SEQ ID NO: 11          moltype = DNA  length = 17
FEATURE                Location/Qualifiers
misc_feature           1..17
                       note = oligonucleotide motif
source                 1..17
                       mol_type = other DNA
                       organism = synthetic construct
SEQUENCE: 11
cccagatctg catccac                                                17

SEQ ID NO: 12          moltype = DNA  length = 16
FEATURE                Location/Qualifiers
misc_feature           1..16
                       note = oligonucleotide motif
source                 1..16
                       mol_type = other DNA
                       organism = synthetic construct
SEQUENCE: 12
cccagatctg catcca                                                 16

SEQ ID NO: 13          moltype = DNA  length = 17
FEATURE                Location/Qualifiers
misc_feature           1..17
                       note = oligonucleotide motif
source                 1..17
                       mol_type = other DNA
                       organism = synthetic construct
SEQUENCE: 13
tcccagatct gcatcca                                                17

SEQ ID NO: 14          moltype = DNA  length = 17
FEATURE                Location/Qualifiers
misc_feature           1..17
                       note = oligonucleotide motif
source                 1..17
                       mol_type = other DNA
                       organism = synthetic construct
SEQUENCE: 14
gtctcccaga tctgcat                                                17

SEQ ID NO: 15          moltype = DNA  length = 16
FEATURE                Location/Qualifiers
misc_feature           1..16
                       note = oligonucleotide motif
source                 1..16
                       mol_type = other DNA
                       organism = synthetic construct
SEQUENCE: 15
tctcccagat ctgcat                                                 16

SEQ ID NO: 16          moltype = DNA  length = 16
FEATURE                Location/Qualifiers
misc_feature           1..16
                       note = oligonucleotide motif
source                 1..16
                       mol_type = other DNA
                       organism = synthetic construct
SEQUENCE: 16
gtctcccaga tctgca                                                 16

SEQ ID NO: 17          moltype = DNA  length = 17
FEATURE                Location/Qualifiers
misc_feature           1..17
                       note = oligonucleotide motif
source                 1..17
                       mol_type = other DNA
                       organism = synthetic construct
SEQUENCE: 17
tcaactttca cttcagt                                                17

SEQ ID NO: 18          moltype = DNA  length = 16
FEATURE                Location/Qualifiers
misc_feature           1..16
                       note = oligonucleotide motif
source                 1..16
                       mol_type = other DNA
                       organism = synthetic construct
```

-continued

```
SEQUENCE: 18
tcaactttca cttcag                                                16

SEQ ID NO: 19          moltype = DNA  length = 16
FEATURE                Location/Qualifiers
misc_feature           1..16
                       note = oligonucleotide motif
source                 1..16
                       mol_type = other DNA
                       organism = synthetic construct
SEQUENCE: 19
tgtttcaata ctaaaa                                                16

SEQ ID NO: 20          moltype = DNA  length = 18
FEATURE                Location/Qualifiers
misc_feature           1..18
                       note = oligonucleotide motif
source                 1..18
                       mol_type = other DNA
                       organism = synthetic construct
SEQUENCE: 20
catcaacttt cacttcag                                              18

SEQ ID NO: 21          moltype = DNA  length = 19
FEATURE                Location/Qualifiers
misc_feature           1..19
                       note = oligonucleotide motif
source                 1..19
                       mol_type = other DNA
                       organism = synthetic construct
SEQUENCE: 21
catcaacttt cacttcagt                                             19

SEQ ID NO: 22          moltype = DNA  length = 20
FEATURE                Location/Qualifiers
misc_feature           1..20
                       note = Oligonucleotide motif
source                 1..20
                       mol_type = other DNA
                       organism = synthetic construct
SEQUENCE: 22
caacataagt ctacacatcc                                            20

SEQ ID NO: 23          moltype = DNA  length = 19
FEATURE                Location/Qualifiers
misc_feature           1..19
                       note = Oligonucleotide motif
source                 1..19
                       mol_type = other DNA
                       organism = synthetic construct
SEQUENCE: 23
cagttttacc gattcatca                                             19

SEQ ID NO: 24          moltype = DNA  length = 19
FEATURE                Location/Qualifiers
misc_feature           1..19
                       note = Primer
source                 1..19
                       mol_type = other DNA
                       organism = synthetic construct
SEQUENCE: 24
ctgtgccttg ggtggcttt                                             19

SEQ ID NO: 25          moltype = DNA  length = 24
FEATURE                Location/Qualifiers
misc_feature           1..24
                       note = Primer
source                 1..24
                       mol_type = other DNA
                       organism = synthetic construct
SEQUENCE: 25
aaggaaagaa gtcagaaggc aaaa                                       24

SEQ ID NO: 26          moltype = DNA  length = 34
FEATURE                Location/Qualifiers
misc_feature           1..34
                       note = Prope
misc_feature           9..10
                       note = ZEN - internal quencher
```

```
source                1..34
                      mol_type = other DNA
                      organism = synthetic construct
SEQUENCE: 26
agctccaaat tctttataag ggtcgatgtc catg                                34

SEQ ID NO: 27         moltype = DNA  length = 16
FEATURE               Location/Qualifiers
misc_feature          1..16
                      note = oligonucleotide motif
source                1..16
                      mol_type = other DNA
                      organism = synthetic construct
SEQUENCE: 27
agcgaagtgc acacgg                                                    16

SEQ ID NO: 28         moltype = DNA  length = 13
FEATURE               Location/Qualifiers
misc_feature          1..13
                      note = oligonucleotide motif
source                1..13
                      mol_type = other DNA
                      organism = synthetic construct
SEQUENCE: 28
gcgtaaagag agg                                                       13

SEQ ID NO: 29         moltype = DNA  length = 18
FEATURE               Location/Qualifiers
misc_feature          1..18
                      note = oligonucleotide motif
source                1..18
                      mol_type = other DNA
                      organism = synthetic construct
SEQUENCE: 29
caagcgaagt gcacacgg                                                  18

SEQ ID NO: 30         moltype = DNA  length = 15
FEATURE               Location/Qualifiers
misc_feature          1..15
                      note = oligonucleotide motif
source                1..15
                      mol_type = other DNA
                      organism = synthetic construct
SEQUENCE: 30
cagcgtaaag agagg                                                     15

SEQ ID NO: 31         moltype = DNA  length = 18
FEATURE               Location/Qualifiers
misc_feature          1..18
                      note = oligonucleotide motif
source                1..18
                      mol_type = other DNA
                      organism = synthetic construct
SEQUENCE: 31
caaaggttgt tgtactct                                                  18

SEQ ID NO: 32         moltype = DNA  length = 17
FEATURE               Location/Qualifiers
misc_feature          1..17
                      note = oligonucleotide motif
source                1..17
                      mol_type = other DNA
                      organism = synthetic construct
SEQUENCE: 32
cagttttatg ctaatca                                                   17

SEQ ID NO: 33         moltype = DNA  length = 17
FEATURE               Location/Qualifiers
misc_feature          1..17
                      note = oligonucleotide motif
source                1..17
                      mol_type = other DNA
                      organism = synthetic construct
SEQUENCE: 33
gtattcttat tcttgct                                                   17

SEQ ID NO: 34         moltype = DNA  length = 19
FEATURE               Location/Qualifiers
misc_feature          1..19
```

-continued

```
                        note = oligonucleotide motif
source                  1..19
                        mol_type = other DNA
                        organism = synthetic construct
SEQUENCE: 34
cattgctttt ataatccta                                            19
```